United States Patent
Li et al.

(10) Patent No.: US 9,265,253 B2
(45) Date of Patent: *Feb. 23, 2016

(54) USE OF MACROCYCLIC PICOLINAMIDES AS FUNGICIDES

(71) Applicant: DOW AGROSCIENCES LLC, Indianapolis, IN (US)

(72) Inventors: Fangzheng Li, Carmel, IN (US); Kevin G. Meyer, Zionsville, IN (US); James M. Renga, Spokane, WA (US); Chenglin Yao, Westfield, IN (US); Jeremy Wilmot, Zionsville, IN (US); Jessica Herrick, Zionsville, IN (US); Karla Bravo-Altamirano, Carmel, IN (US); Timothy Boebel, Indianapplis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,695

(22) Filed: Sep. 29, 2014

(65) Prior Publication Data

US 2015/0094281 A1   Apr. 2, 2015

Related U.S. Application Data

(60) Provisional application No. 61/885,409, filed on Oct. 1, 2013, provisional application No. 61/885,417, filed on Oct. 1, 2013.

(51) Int. Cl.

| | |
|---|---|
| A01N 43/40 | (2006.01) |
| A01N 53/00 | (2006.01) |
| A01N 47/18 | (2006.01) |
| C07D 405/14 | (2006.01) |
| C07D 493/04 | (2006.01) |
| A01N 43/22 | (2006.01) |
| A01N 55/00 | (2006.01) |
| C07D 407/06 | (2006.01) |
| C07D 313/00 | (2006.01) |
| C07D 405/12 | (2006.01) |
| C07F 7/18 | (2006.01) |

(52) U.S. Cl.
CPC .......... *A01N 43/40* (2013.01); *A01N 43/22* (2013.01); *A01N 47/18* (2013.01); *A01N 53/00* (2013.01); *A01N 55/00* (2013.01); *C07D 313/00* (2013.01); *C07D 405/12* (2013.01); *C07D 405/14* (2013.01); *C07D 407/06* (2013.01); *C07D 493/04* (2013.01); *C07F 7/1856* (2013.01)

(58) Field of Classification Search
CPC .............................. A01N 43/40; C07D 405/12
See application file for complete search history.

(56) References Cited

U.S. PATENT DOCUMENTS

| | | |
|---|---|---|
| 6,355,660 B1 | 3/2002 | Ricks |
| 6,521,622 B1 | 2/2003 | Ricks |
| 6,706,740 B2 | 3/2004 | Ricks |
| 6,861,390 B2 | 3/2005 | Meyer |
| 6,927,225 B2 | 8/2005 | Ricks |
| 7,034,035 B2 | 4/2006 | Ricks |
| 7,183,278 B1 | 2/2007 | Imamura et al. |
| 7,250,389 B1 | 7/2007 | Sakanaka et al. |
| 8,785,479 B2 | 7/2014 | Meyer |
| 8,835,462 B2 | 9/2014 | Meyer |
| 8,883,811 B2 | 11/2014 | Owen |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2003/0022903 A1 | 1/2003 | Ricks |
| 2004/0034025 A1 | 2/2004 | Ricks |
| 2004/0048864 A1 | 3/2004 | Ricks et al. |
| 2004/0171838 A1 | 9/2004 | Meyer et al. |
| 2004/0186296 A1 | 9/2004 | Niyaz et al. |
| 2004/0192924 A1 | 9/2004 | Meyer et al. |
| 2005/0239873 A1 | 10/2005 | Hockenbery et al. |
| 2007/0060579 A1 | 3/2007 | Wachendorff-Neumann |
| 2007/0066629 A1 | 3/2007 | Tormo i Blasco et al. |
| 2009/0306142 A1 | 12/2009 | Carson |

(Continued)

FOREIGN PATENT DOCUMENTS

| | | |
|---|---|---|
| EP | 1516874 | 3/2005 |
| WO | 01/14339 A2 | 3/2001 |

(Continued)

OTHER PUBLICATIONS

Koyanagi, T.,"Bioisosterism in agrochemicals." In Synthesis and chemistry of agrochemicals IV., pp. 15-24. American Chemical Society, 1995.*

(Continued)

*Primary Examiner* — Samantha Shterengarts
*Assistant Examiner* — Matt Mauro
(74) *Attorney, Agent, or Firm* — C. W. Arnett; Faegre Baker Daniels LLP

(57) ABSTRACT

The invention relates to macrocyclic picolinamides of Formula I and their use as fungicides.

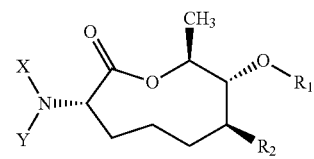

20 Claims, No Drawings

(56) References Cited

U.S. PATENT DOCUMENTS

| | | |
|---|---|---|
| 2013/0296371 A1 | 11/2013 | Meyer |
| 2013/0296373 A1* | 11/2013 | Meyer et al. .................. 514/336 |
| 2014/0187588 A1 | 7/2014 | Lalonde |
| 2014/0275171 A1 | 9/2014 | Meyer |
| 2015/0065529 A1 | 3/2015 | Owen |

FOREIGN PATENT DOCUMENTS

| | | |
|---|---|---|
| WO | 2009040397 | 9/2008 |
| WO | 2012/070015 A1 | 5/2012 |

OTHER PUBLICATIONS

Thomas, S., International Search Report for PCT/US14/58067, Dec. 22, 2014, pp. 1-4, ISA/US.

Thomas, S., International Search Report for PCT/US14/58070, Dec. 15, 2014, pp. 1-4, ISA/US.

Thomas, S., Written Opinion for PCT/US14/58067, Dec. 22, 2014, pp. 1-5, ISA/US.

Thomas, S., Written Opinion for PCT/US14/58070, Dec. 15, 2014, pp. 1-5, ISA/US.

Anonymous, Synergistic Fungicidal Composition of Heterocyclic Aromatic Amides and Trizaoles, IP.COM, Electronic Publication, 2004, 11 pages.

Anonymous, Synergistic Fungicidal Composition of Heterocyclic Aromatic Amides and Triazoles, IP.COM Journal, IP.COM Inc., West Henrietta, NY, US, Dates Jul. 2004, 10 pages.

Z. Hu, et al, Synthesis of Novel Analogues of Antimycin A3, Tetrahedron Letters 49 (2008) pp. 5192-5195.

K. Tani, et al, Journal of Antibiotics, vol. 55, No. 3, Mar. 2002, pp. 315-321.

Y. Usuki, et al, Journal of Antibiotics, vol. 55, No. 6, Jun. 2002, pp. 607-610.

\* cited by examiner

USE OF MACROCYCLIC PICOLINAMIDES AS FUNGICIDES

CROSS REFERENCE TO RELATED APPLICATIONS

This application claims the benefit of U.S. Provisional Patent Application Ser. No. 61/885,409, and U.S. Provisional Patent Application Ser. No. 61/885,417, each filed Oct. 1, 2013, the disclosures of each of which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

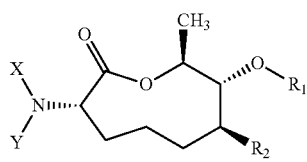

I

X is H, C(O)$R_3$, or CH$_2$O$R_3$;
Y is H, C(O)$R_3$, or Q;
Q is

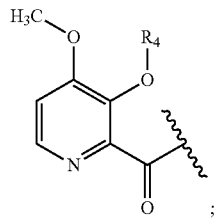

;

$R_1$ is H, alkyl, alkenyl, aryl, —Si($R_5$)$_3$, —C(O)$R_6$, each substituted with 0, 1 or multiple $R_6$;
$R_2$ is CH$_2$$R_8$, aryl, alkyl, alkenyl, each substituted with 0, 1, or multiple $R_6$;
$R_3$ is alkyl, alkoxy, benzyl, benzyloxy, each substituted with 0, 1, or multiple $R_5$;
$R_4$ is H, —C(O)$R_7$ or —CH$_2$OC(O)$R_7$;
$R_5$ is alkyl, halo, alkoxy;
$R_6$ is alkyl, alkenyl, halo, haloalkyl, alkoxy, aryl, heteroaryl, heterocyclyl, thioalkyl, —C(O)$R_5$;
$R_7$ is alkyl or alkoxy, each substituted with 0, 1, or multiple $R_6$;
$R_8$ is H, alkyl, alkenyl, aryl, heteroaryl, thioalkyl each substituted with 0, 1, or multiple $R_6$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" refers to any aromatic, mono- or bi-cyclic, containing 0 heteroatoms.

The term "heterocycle" refers to any aromatic or non-aromatic ring, mono- or bi-cyclic, containing one or more heteroatoms The term "alkoxy" refers to an —OR substituent.
The term "cyano" refers to a —C≡N substituent.
The term "hydroxyl" refers to an —OH substituent.
The term "amino" refers to a —NH$_2$ substituent.
The term "arylalkoxy" refers to —O(CH$_2$)$_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis (dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, flpronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impact stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m²).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.3, where $R_2$ is as originally defined, can be prepared by the method shown in Scheme 1, steps a-b. Compounds of Formula 1.1, where $R_8$ is as originally defined and $R_9$ is alkyl or alkoxy, can be prepared from compounds of Formula 1.0, where $R_8$ is as originally defined, by treatment with an alkoxy borane such as pinacol borane in the presence of a nickel catalyst, such as bis(cyclooctadiene) nickel(0) (Ni(cod)$_2$), as described by Ely, R. J.; Morken, J. P. *J. Am. Chem. Soc.* 2010, 132, 2534-2535, in a solvent such as toluene, and at a temperature between 0 and 23° C. Alternatively, compounds of Formula 1.1, where $R_8$ is as originally defined and $R_9$ is alkyl or alkoxy can be prepared as reported in Brown, H. C.; Bhat, K. S.; Randad, R. S. *J. Org. Chem.* 1989, 54, 1570. Compounds of Formula 1.3, where $R_2$ is as originally defined, can be prepared from compounds of Formula 1.1, where $R_8$ is as originally defined and $R_9$ is as defined above by treatment with a benzyl (Bn) or para-methoxybenzyl (PMB) protected lactate-derived aldehyde such as compound 1.2, prepared as described in Cheng and Brookhart *Angew. Chem. Int. Ed.* 2012, 51, 9422-9424 (see Takai, K.; Heathcock, C. H. *J. Org. Chem.* 1985, 50, 3247-3251 for characterization of Bn aldehyde and Terashima et al. *Bull. Chem. Soc. Jpn.* 1989, 62, 3038-3040 for characterization of PMB aldehyde).

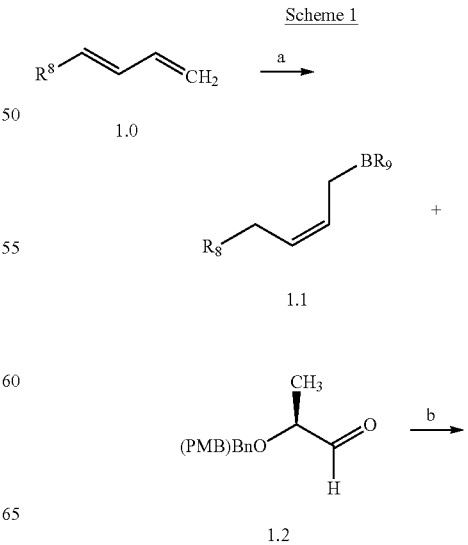

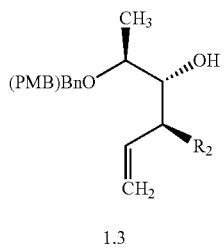

1.3

Compounds of Formulas 2.0, 2.1, and 2.2 can be prepared using the methods shown in Scheme 2, steps a-c. Compounds of Formula 2.0, where $R_1$ is aryl and $R_2$ is as originally defined, can be prepared by the method shown in a, from compounds of Formula 1.3, where $R_2$ is as originally defined, by treatment with a triarylbismuth reagent, prepared according to the methods described by Hassan, A. et. al. *Organometallics* 1996, 15, 5613-5621, Moiseev, D. V. et al. *J. Organomet. Chem.* 2005, 690, 3652-3663, or Sinclair, P. J. et al. *Bioorg. Med. Chem. Lett.* 1995, 5, 1035-1038, in the presence of a copper catalyst, such as diacetoxycopper, and an amine base, such as N,N-dicyclohexyl-methylamine, in an aprotic solvent such as toluene at 20-40° C. Compounds of Formula 2.1, where $R_1$ is alkyl and $R_2$ is as originally defined, can be prepared from compounds of Formula 1.3, where $R_2$ is as originally defined, by treatment with a base, such as sodium hydride (NaH), in an aprotic solvent such as tetrahydrofuran (THF), followed by treatment with an alkyl halide or sulfonate, such as isobutyl toluenesulfonate at 0-22° C., as shown in b. Compounds of Formula 2.2, where $R_1$ is silyl and $R_2$ is as originally defined, can be prepared from compounds of Formula 1.3, where $R_2$ is as originally defined, by treatment with a silyl trifluoromethanesulfonate, such as triisopropyl trifluoromethanesulfonate, in the presence of a base, such as 2,6-lutidine, in a solvent such as dichloromethane (CH$_2$Cl$_2$, DCM) at a reduced temperature, such as 0° C., as shown in c.

Compounds of Formula 3.2, where $R_1$ and $R_2$ are as originally defined and Y is tert-butoxy carbonyl (Boc), can be prepared by the method shown in Scheme 3. Compounds of Formula 3.2 can be prepared from compounds of Formula 3.0, where $R_1$ and $R_2$ are as originally defined, by treatment with an alkylborane reagent, such as 9-borabicyclo[3.3.1]nonane (9-BBN), in a solvent such as THF at 20-50° C., followed by treatment with an aqueous base, such as potassium phosphate (K$_3$PO$_4$), and a bromoacrylate, such as a compound of Formula 3.1 where Y is Boc, prepared as in Singh et al. *Org. Lett.* 2003, 17, 3155-3158, and a catalyst, such as [1,1-bis(diphenylphosphino)ferrocene]dichloropalladium(II) (PdCl$_2$(dppf)) at 20-55° C.

Scheme 3

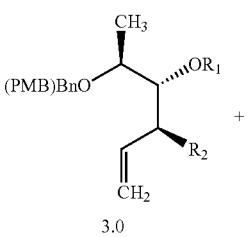

3.0

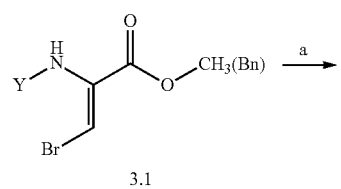

3.1

Scheme 2

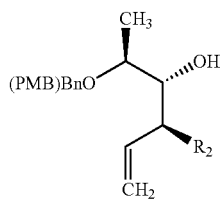

1.3

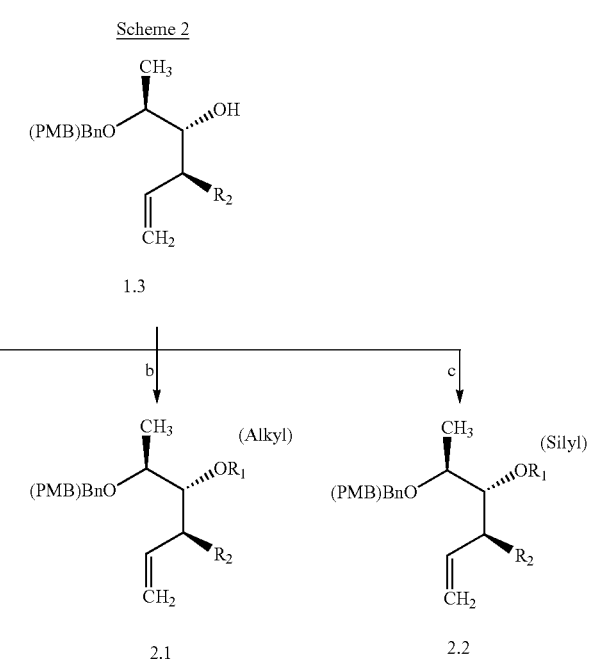

2.0    2.1    2.2

-continued

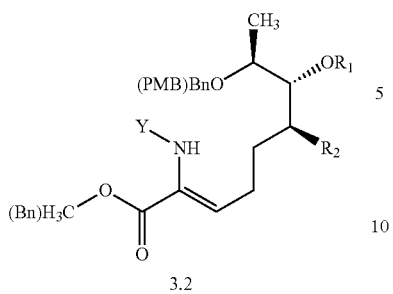

3.2

Compounds of Formula 4.0, where $R_1$ and $R_2$ are as originally defined and Y is Boc, can be prepared by the method shown in Scheme 4. Compounds of Formula 4.0 can be prepared from compounds of Formula 3.2, where $R_1$ and $R_2$ are as originally defined and Y is Boc, by treatment with hydrogen (15-200 psi) in the presence of a catalyst such as 1,2-bis[(2S,5S)-2,5-diethyl-phospholano]benzene(1,5-cyclooctadiene)rhodium(I) trifluoromethanesulfonate ((S,S)-Et-DUPHOS-Rh) in an alcoholic solvent such as methanol (MeOH).

Scheme 4

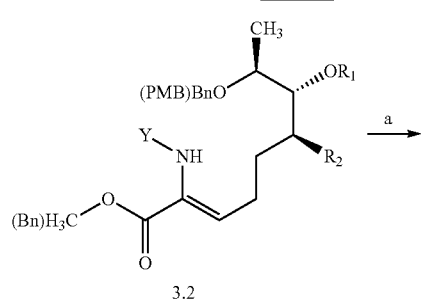

3.2

-continued

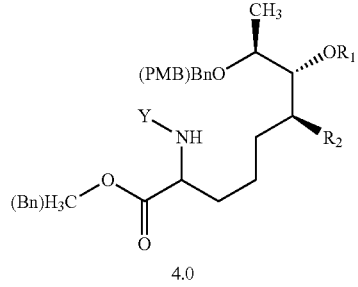

4.0

Compounds of Formula 5.3, where $R_1$ and $R_2$ are as originally defined and Y is Boc can be prepared through a variety of methods, as shown in Scheme 5, steps a-c. Compounds of Formula 5.0 and 5.1, where $R_1$ and $R_2$ are as originally defined and Y is Boc, can be prepared from compounds of Formula 4.0, where $R_1$ and $R_2$ are as originally defined, Y is Boc, and the alcohol is protected as the PMB ether, by treatment with an oxidant, such as 2,3-dichloro-5,6-dicyano-1,4-benzoquinone (DDQ) in an solvent mixture such as DCM and water ($H_2O$), as shown in a. Compounds of Formula 5.2, where $R_1$ and $R_2$ are as originally defined and Y is Boc, can be prepared from compounds of Formula 4.0, where $R_1$ and $R_2$ are as originally defined, Y is Boc, and the alcohol is protected as the Bn ether, by hydrogenolysis, i.e., treatment with hydrogen ($H_2$; 15-500 psi) in the presence of a catalyst, such as 5% or 10% w/w palladium/carbon (Pd/C), in a solvent such as THF, as shown in b. Compounds of Formula 5.3, where $R_1$ and $R_2$ are as originally defined and Y is Boc, can be prepared from compounds of Formulas 5.0 and 5.2, where $R_1$, $R_2$, and Y are as defined above and the acid is protected as methyl (Me) ester, by treatment with a base such as lithium hydroxide (LiOH) in a mixture of $H_2O$ and a solvent such as THF, as shown in c. Compounds of Formula 5.3, where $R_1$ and $R_2$ are as originally defined and Y is Boc, can also be prepared from compounds of Formula 5.1, where $R_1$, $R_2$, and Y are as defined above and the acid is protected as the Bn ester, by hydrogenolysis or saponification, as shown in b and c, respectively. Alternatively, compounds of Formula 5.3, where $R_1$ and $R_2$ are as originally defined and Y is Boc, can be prepared directly from compounds of Formula 4.0, where $R_1$, $R_2$, and Y are as defined above and the alcohol and acid are protected as the Bn ether and Bn ester, respectively, by the hydrogenolysis conditions described in b.

Scheme 5

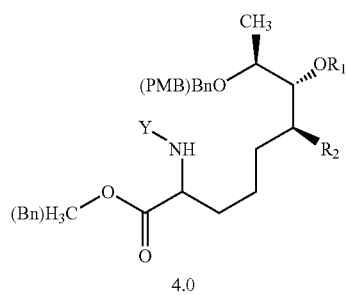

4.0

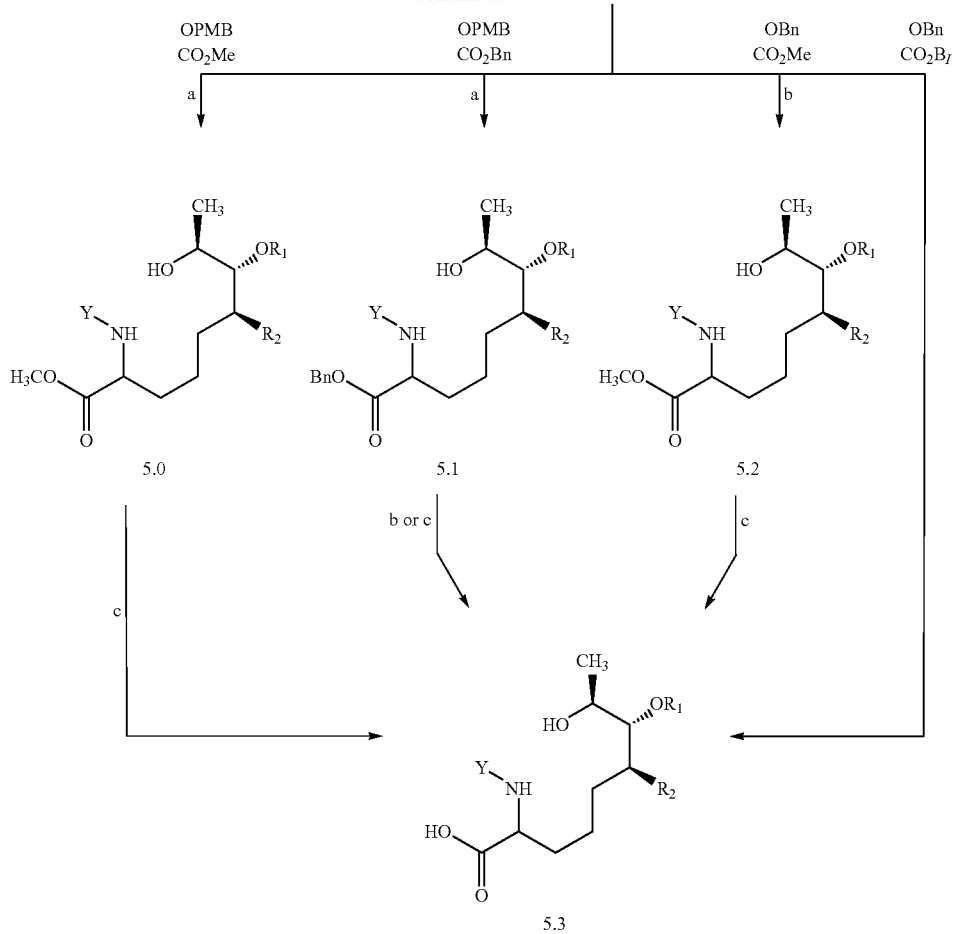

Compounds of Formula 6.0, where $R_1$ and $R_2$ are as originally defined and Y is Boc, can be prepared from compounds of Formula 5.3, where $R_1$ and $R_2$ are as originally defined and Y is Boc, by the addition of a solution of compounds of Formula 5.3 in a halogenated solvent such as DCM or an aromatic solvent such as toluene to a mixture of a base, such as DMAP, and an anhydride, such as 2-methyl-6-nitrobenzoic anhydride (MNBA), in either a halogenated solvent such as DCM or an aromatic solvent such as toluene over a period of 4-12 hours, as shown in Scheme 6.

Scheme 6

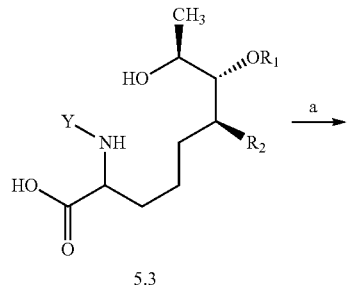

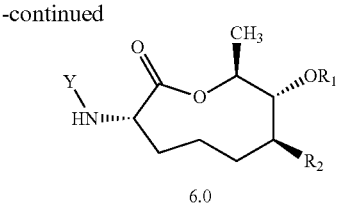

Compounds of Formula 7.1 can be prepared according to the methods shown in Scheme 7, steps a-b. Compounds of Formula 7.0, where $R_1$ is triisopropylsilyl (TIPS), $R_2$ is as originally defined, Y is Boc, and X is methoxymethyl (MOM) can be prepared from compounds of Formula 6.0, where $R_1$, $R_2$, and Y are as defined above, by treatment with an aldehyde, such as paraformaldehyde, in a solvent such as DCM in the presence of a silyl chloride, such as trimethylsilyl chloride, at a reduced temperature such as 0° C., followed by addition of a solution of a base such as triethylamine, in an alcoholic solvent such as methanol, as shown in a. Compounds of Formula 7.1, where $R_1$ is H and $R_2$, X, and Y are as defined above, can be prepared from compounds of Formula 7.0, where $R_1$, $R_2$, X, and Y are as defined above, by treatment with a fluoride salt such as tetra-N-butylammonium fluoride (TBAF), in a solvent such as THF, as shown in b.

Scheme 7

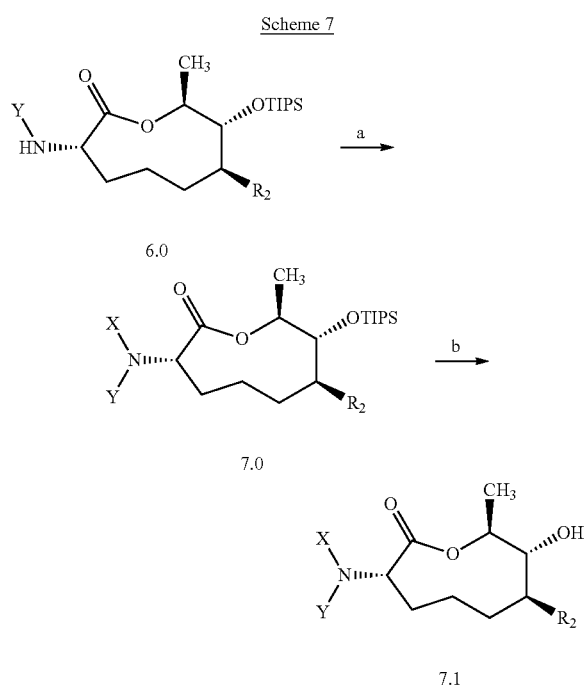

Compounds of Formulas 8.0-8.8 can be prepared through the methods shown in Scheme 8, steps a-g. Compounds of Formula 8.0, where $R_1$ is allyloxy, $R_2$ is as originally defined, X is MOM, and Y is Boc, can be prepared from compounds of Formula 7.1, where $R_1$ is H, $R_2$, X, and Y are as defined above, by treatment with an allyl carbonate, such as a tert-butyl (allyl) carbonate or a symmetric (allyl) carbonate, such as bis(2-methylallyl) carbonate, in the presence of a palladium catalyst and ligand, for example tris(dibenzylideneacetone)-dipalladium(0) ($Pd_2(dba)_3$) and 1,1'-bis(diphenylphosphino) ferrocene (dppf), in a polar aprotic solvent like tetrahydrofuran (THF) at an elevated temperature such as 60° C., as shown in a. Compounds of Formula 8.1, where $R_1$ is alkyl, $R_2$ is as originally defined, X is MOM, and Y is Boc, can be prepared from compounds of Formula 8.0, where $R_1$, $R_2$, X, and Y are defined as above, by treatment with $H_2$ (15-200 psi) in the presence of a catalyst, such as 5% or 10% w/w Pd/C in a solvent such as EtOAc, as shown in b. Compounds of Formula 8.2, where $R_1$ is an aliphatic aldehyde and $R_2$, X, and Y are as defined above, can be prepared from compounds of Formula 8.0, where $R_1$, $R_2$, X, and Y are as defined above, by treatment with ozone in the presence of a base, such as sodium bicarbonate ($NaHCO_3$) in a mixture of a halogenated and an alcoholic solvent, such as DCM and MeOH, as shown in c. Compounds of Formula 8.3, where $R_1$ is fluorinated alkyl and $R_2$, X, and Y are as defined above, can be prepared from compounds of Formula 8.2, where $R_1$, $R_2$, X, and Y are as defined above, by treatment with a fluorinating reagent, such as bis (2-methoxyethyl)aminosulfur trifluoride (Deoxo-Fluor®) in a solvent such as DCM, as shown in d.

Compounds of Formula 8.4, where $R_1$ is an vinylogous ester, $R_2$ is as originally defined, X is MOM, and Y is Boc, can be prepared from compounds of Formula 7.1, where $R_1$ is H, $R_2$, X, and Y are as defined above, by treating solutions of the compounds of Formula 7.1 in a solvent such as DCM with a catalytic amount of 1,4-diazabicyclo[2.2.2]octane (DABCO), followed by addition of a conjugated alkyne, such as but-3-yn-2-one at a reduced temperature, for example 0° C., as shown in e. Compounds of Formula 8.5, where $R_1$ is an aliphatic ketone, $R_2$ is as originally defined, X is MOM, and Y is Boc, can be prepared from compounds of Formula 8.4, where $R_1$, $R_2$, X, and Y are as defined above, by the reductive conditions described in b. Compounds of Formula 8.6, where $R_1$ is fluorinated alkyl, $R_2$ is as originally defined, X is MOM, and Y is Boc, can be prepared from compounds of Formula 8.5, where $R_1$, $R_2$, X, and Y are defined as above, by the fluorination conditions described in d.

Compounds of Formula 8.7, where $R_1$ is acyl, $R_2$ is as originally defined, X is MOM, and Y is Boc, can be prepared from compounds of Formula 7.1, where $R_1$ is H, $R_2$ is as originally defined, X is MOM, and Y is Boc, by treatment with a base such as triethylamine and a catalyst such as (DMAP) in a solvent such as DCM, followed by treatment with an acid chloride, as shown in f.

Compounds of Formula 8.8, where $R_1$ is alkyl, $R_2$ is as originally defined, X is MOM, and Y is Boc, can be prepared from compounds of Formula 7.1, where $R_1$ is H, $R_2$ is as originally defined, X is MOM, and Y is Boc, by treatment with a base, such as 1,8-bis(dimethylamino)naphthalene (Proton Sponge®) and an alkylating agent, such as trimethyloxonium tetrafluoroborate, in a solvent such as DCM, as shown in g.

Scheme 8

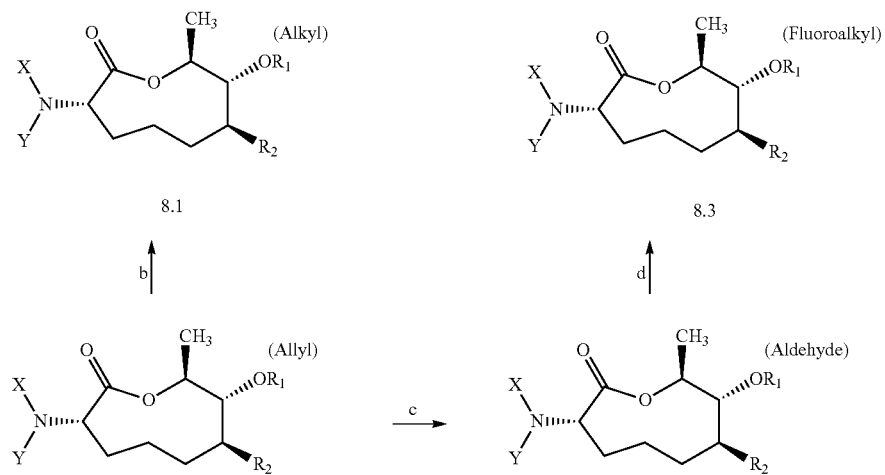

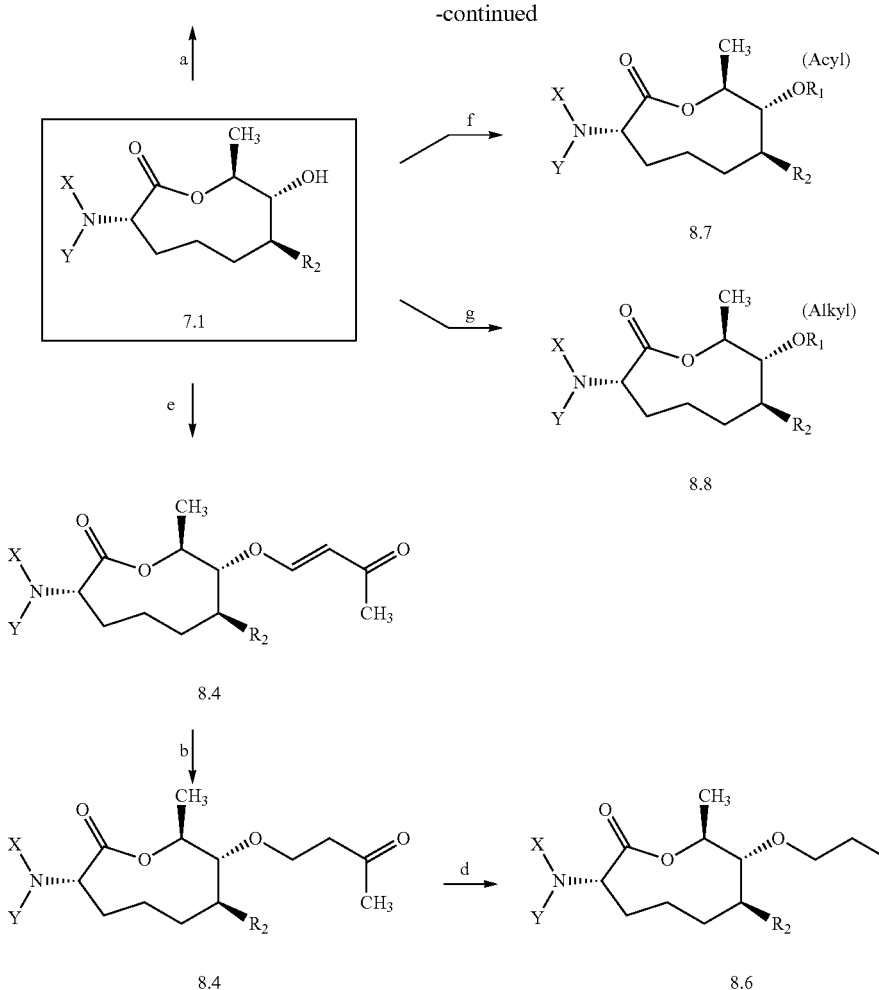

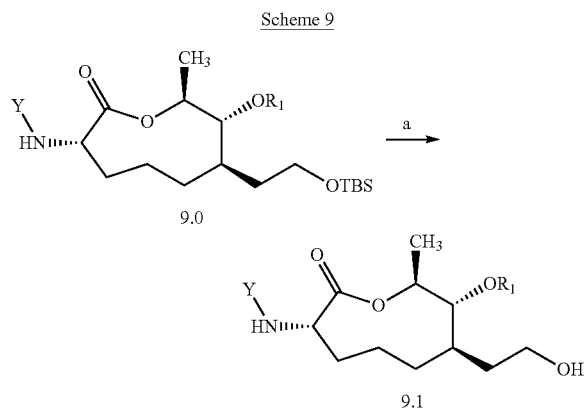

Compounds of Formula 9.1, where $R_1$ is as originally defined and Y is Boc, can be prepared by the method shown in Scheme 9. Compounds of Formula 9.1 can be prepared from compounds of Formula 9.0, where $R_1$ is as originally defined and Y is Boc, by treatment with a fluoride salt, such as TBAF, in a solvent such as THF.

Scheme 9

Compounds of Formulas 10.0-10.7 can be prepared through the methods shown in Scheme 10, steps a-h. Compounds of Formula 10.0, where $R_1$ is as originally defined and Y is Boc, can be prepared from compounds of Formula 9.1, where $R_1$ is as originally defined and Y is Boc, by treatment with a triarylbismuth reagent, prepared according to the methods described by Hassan, A. et. al. *Organometallics* 1996, 15, 5613-5621, Moiseev, D. V. et al. *J. Organomet. Chem.* 2005, 690, 3652-3663, or Sinclair, P. J. et al. *Bioorg. Med. Chem. Lett.* 1995, 5, 1035-1038, in the presence of a copper catalyst, such as diacetoxycopper, and an amine base, such as N,N-dicyclohexyl-methylamine, in an aprotic solvent such as toluene at an elevated temperature of about 50° C., as shown in a. Compounds of Formula 10.1, where $R_1$ is as originally defined and Y is Boc, can be prepared from compounds of Formula 9.1, where $R_1$ and Y are as defined above, by treatment with a base such as Proton Sponge® followed by an alkylating agent, such as trimethyloxonium tetrafluoroborate, in a solvent such as DCM, as shown in b. Compounds of Formula 10.2, where $R_1$ is as originally defined and Y is Boc, can be prepared from compounds of Formula 9.1, where $R_1$ and Y are as defined above, by treatment with an oxidizing reagent, such as Dess-Martin periodinane, in a solvent such as DCM, as shown in c. Compounds of Formula 10.3, where $R_1$ is as originally defined and Y is Boc, can be prepared from compounds of Formula 10.2, where $R_1$ and Y are as defined above, by treatment with a fluorinating reagent, such as Deoxo-Fluor®, in a solvent such as DCM, as shown in d. Compounds of Formula 10.4, where $R_1$ is as originally defined and Y is Boc, can be prepared from compounds of Formula 9.1, where $R_1$ and Y are as defined above, by treatment with a fluorinating reagent, such as Deoxo-Fluor®, in a solvent such as DCM or through halogenation conditions, such as treatment with perhalomethanes in the presence of triphenylphosphine in DCM at a reduced temperature, such as 0° C., as shown in e. Compounds of Formula 10.5, where $R_1$ is as originally defined and Y is Boc, can be prepared from compounds of Formula 10.4, where $R_1$ and Y are as defined above, by treatment with a reducing agent such as tributyltin hydride in the presence of a radical initiator, such as azobisisobutyronitrile (AIBN), in a solvent such as toluene at an elevated temperature, for example 80° C., as shown in f. Compounds of Formula 10.6, where $R_1$ is as originally defined and Y is Boc, can be prepared from compounds of Formula 9.1, where $R_1$ and Y are as defined above, by treatment with a selenocyanate and a phosphine, such as tributylphosphine, in a solvent such as THF at a temperature from about 0° C. to about 23° C., as shown in g. Compounds of Formula 10.7, where $R_1$ is as originally defined and Y is Boc, can be prepared from compounds of Formula 10.6, where $R_1$ and Y are as defined above, by treatment with an oxidizing agent, such as hydrogen peroxide, in a solvent such as THF, as shown in h.

Scheme 10

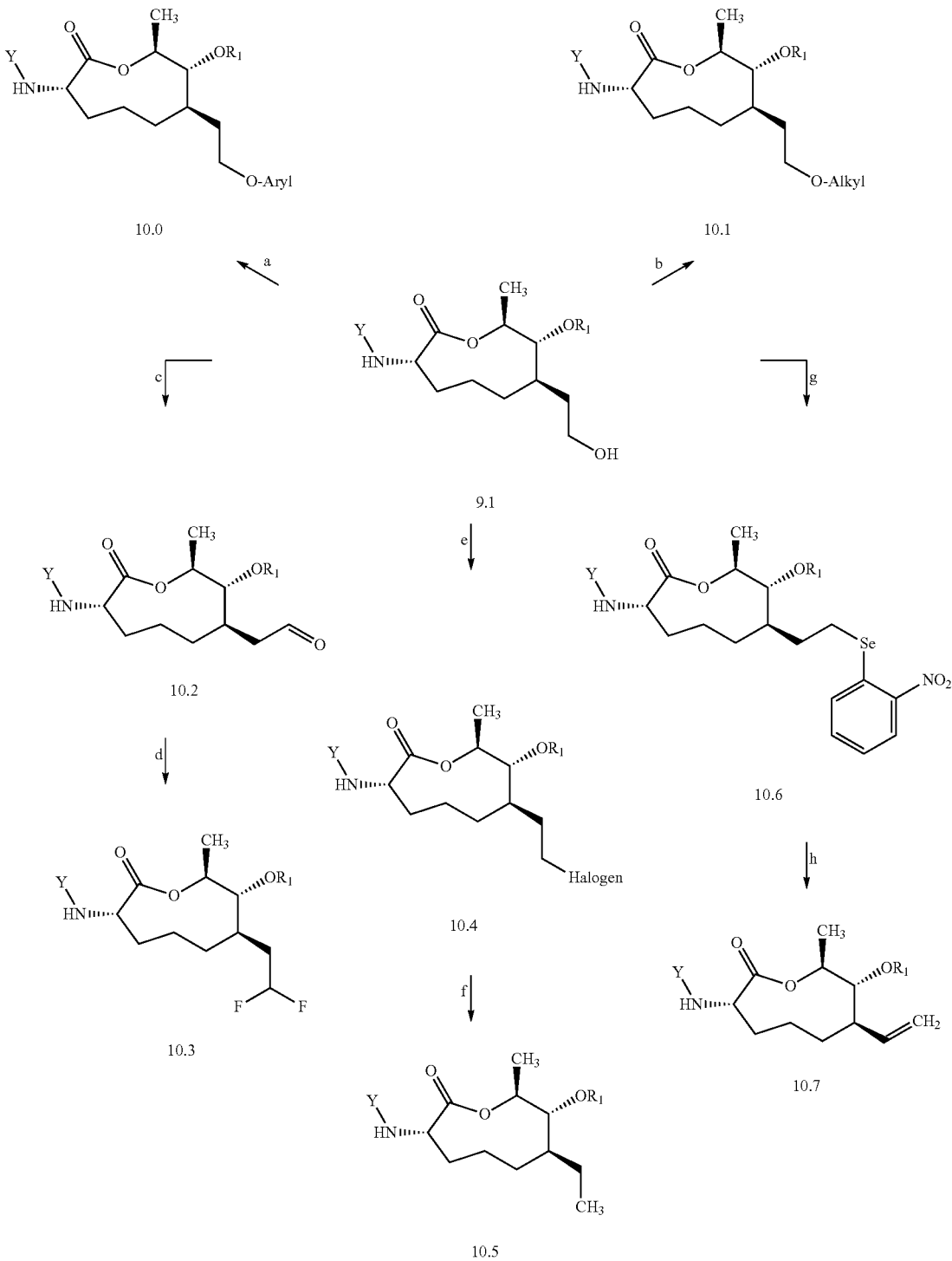

Compounds of Formulas 11.4 and 11.5 can be prepared through the methods shown in Scheme 11, steps a-d. Compounds of Formula 11.4, where $R_1$ and $R_2$ are as originally defined, can be prepared from a variety of precursors, including, but not limited to, compounds of Formulas 11.0, 11.1, 11.2, and 11.3, where $R_1$ and $R_2$ are as originally defined, and Y is Boc (11.0), X and Y are Boc (11.1), X is MOM and Y is Boc (11.2), and Y is CBz (11.3) respectively. Treating compounds of Formulas 11.0-11.2 with an acid, such as a 4.0 M hydrogen chloride (HCl) solution in dioxane, in a solvent such as DCM affords the hydrochloride salt of compounds of Formula 11.4, which may be neutralized in situ in step d or neutralized prior to use to give the free amine, as shown in a. Additionally, compounds of Formula 11.4, where $R_1$ and $R_2$ are as originally defined, can be prepared from compounds of Formulas 11.0 and 11.1, where $R_1$, $R_2$, X, and Y are as originally defined, by treatment with trimethylsilyl trifluoromethanesulfonate in the presence of a base, such 2,6-lutidine, in an aprotic solvent such as DCM, followed by treatment with a protic solvent such as MeOH, as shown in b. Alternatively, compounds of Formula 11.4, where $R_1$ and $R_2$ are as originally defined, can be prepared from compounds of Formula 11.3, where $R_1$ and $R_2$ are as originally defined and Y is CBz, by treatment with hydrogen in the presence of a catalyst, such as 5% or 10% w/w Pd/C, in a solvent such as EtOAc, as shown in c. Compounds of Formula 11.5, where $R_1$ and $R_2$ are as originally defined, can be prepared from compounds of Formula 11.4, where $R_1$ and $R_2$ are as originally defined, by treatment with 3-hydroxy-4-methoxypicolinic acid in the presence of an amine base, such as 4-methylmorpholine or triethylamine (TEA), and a peptide coupling reagent, such as O-(7-azabenzotriazol-1-yl)-N,N,N',R'-tetramethyluronium hexafluorophosphate (HATU) or benzotriazol-1-yl-oxytripyrrolidinophosphonium hexafluorophosphate (PyBOP), in an aprotic solvent such as DCM, as shown in d.

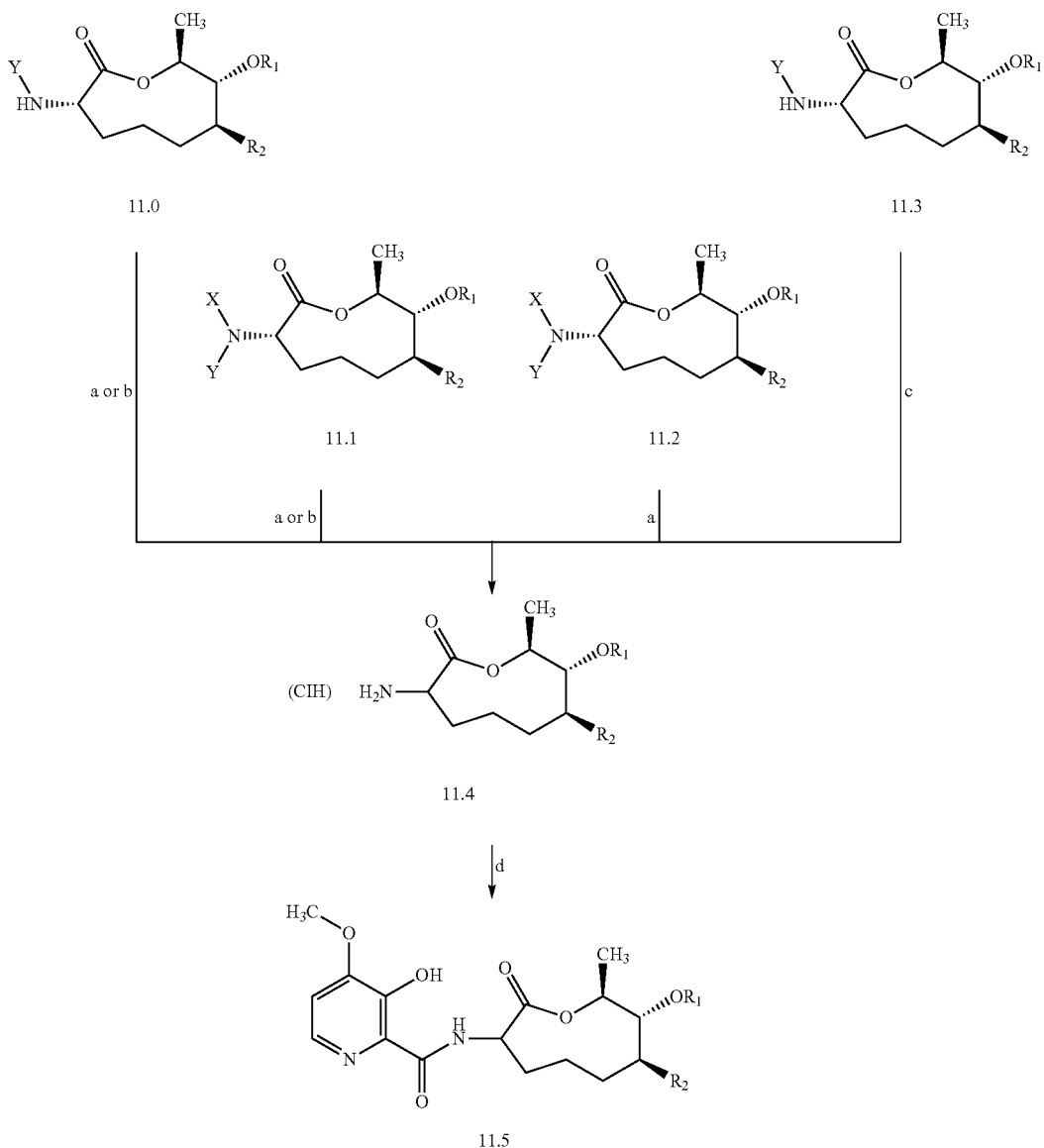

Scheme 11

Compounds of Formula 12.0, where $R_1$, $R_2$ and $R_4$ are as originally defined, can be prepared by the method shown in Scheme 12. Compounds of Formula 12.0 can be prepared from compounds of Formula 11.5, where $R_1$ and $R_2$ are as originally defined, by treatment with the appropriate alkyl halide with or without a reagent such as sodium iodide (NaI) and an alkali carbonate base such as sodium carbonate ($Na_2CO_3$) or potassium carbonate ($K_2CO_3$) in a solvent such as acetone or by treatment with an acyl halide in the presence of an amine base, such as pyridine, triethylamine, DMAP, or mixtures thereof in an aprotic solvent such as DCM, as shown in a.

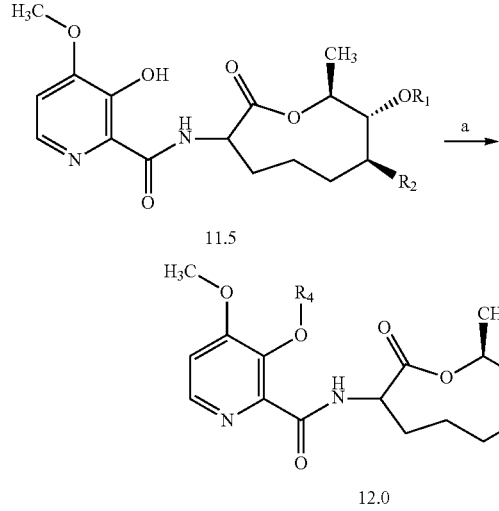

Scheme 12

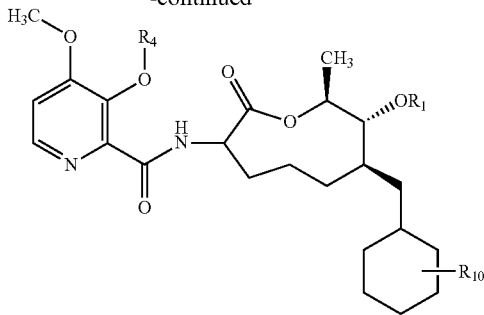

13.0

Compounds of Formula 13.0, where $R_1$ and $R_4$ are as originally defined and $R_2$ is cyclohexyl optionally substituted with one or multiple $R_{10}$, wherein $R_{10}$ is halo or alkyl, can be prepared by the method shown in Scheme 13. Compounds of Formula 13.0 can be prepared from compounds of Formula 12.0, where $R_1$ and $R_4$ are as originally defined and $R_2$ is aryl optionally substituted with one or multiple $R_{10}$, wherein $R_{10}$ is halo or alkyl, by treatment with hydrogen gas in the presence of a catalyst, such as rhodium on carbon (Rh/C), in a solvent such as THF at an elevated temperature such as 70° C., as shown in a.

Scheme 13

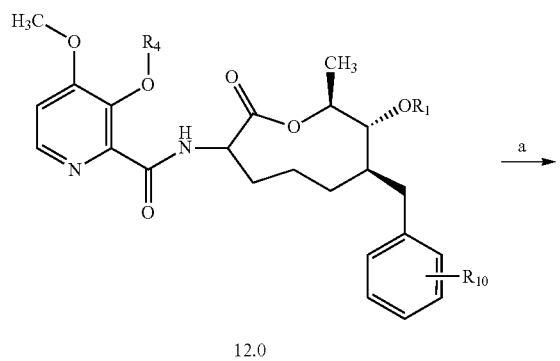

The following examples are presented to illustrate the various aspects of the compounds of the present disclosure and should not be construed as limitations to the claims.

EXAMPLES

Example 1

Step 1: Preparation of (2S,3R,4S)-2-((4-methoxybenzyl)oxy)-7-methyl-4-vinyloctan-3-ol

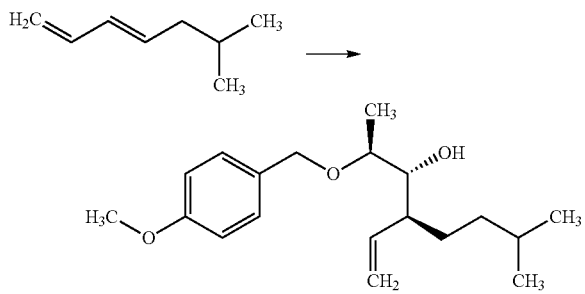

Under a strict nitrogen atmosphere an oven-dried round-bottomed flask with a magnetic stir bar was charged with bis(1,5-cyclooctadiene)nickel(0) (0.297 grams (g), 1.080 millimole (mmol)) and tricyclohexylphosphine (0.379 g, 1.35 mmol). Anhydrous toluene (40 milliliters (mL)) followed by 4,4,5,5-tetramethyl-1,3,2-dioxaborolane (8.34 ml, 57.5 mmol) and (E)-6-methylhepta-1,3-diene (11.9 g, 54.0 mmol), prepared according to the procedure disclosed in Wang, Y.; West, F. G. *Synthesis* 2002, 99-103, were added to the flask and the reaction was allowed to stir at room temperature for 20 hours (h), as described in the diene hydroboration conditions reported in Ely, R. J.; Morken, J. P. *J. Am. Chem. Soc.* 2010, 132, 2534-2535. To the mixture was added a solution of (S)-2-((4-methoxybenzyl)oxy)propanal (10.49 g, 54.0 mmol) in anhydrous toluene (5 mL) at −20° C. The reaction mixture was slowly warmed to room temperature and stirred at room temperature for 40 h, then quenched with MeOH and stirred for an additional 2 h. The crude mixture was concentrated under reduced pressure and purified by column chromatography on silica gel ($SiO_2$; gradient, hexanes/ethyl acetate) to yield the title compound as a colorless oil (11.3 g, 69%): IR (neat) 3467, 2925, 2868, 1513, 1247 cm$^{-1}$; $^1$H NMR (400 MHz, $CDCl_3$) δ 7.27-7.22 (m, 2H), 6.90-6.85 (m, 2H), 5.51-5.38 (m, 1H), 5.08-4.96 (m, 2H), 4.52-4.40 (m, 2H), 3.80 (s, 3H), 3.66 (ddd, J=9.2, 3.1, 2.1 Hz, 1H), 3.59-3.49 (m, 1H), 2.26-2.20 (m, 1H), 2.04-1.95 (m, 1H), 1.90-1.80 (m, 1H), 1.59-1.43 (m, 1H), 1.29-1.14 (m, 2H), 1.13 (d, J=6.2 Hz, 3H), 1.10-0.99 (m, 1H), 0.87 (d, J=6.4 Hz, 3H), 0.86 (d, J=6.4 Hz, 3H); $^{13}$C NMR (101 MHz, $CDCl_3$) δ 159.19, 138.56, 130.59, 129.22, 116.59, 113.82, 75.89, 74.46, 70.11, 55.29, 47.18, 36.05, 28.57, 28.23, 22.98, 22.42, 12.17; ESIMS m/z 329.2 ([M+Na]$^+$).

Example 1

Step 2a: Preparation of 1-methoxy-4-(((((2S,3R,4S)-7-methyl-3-phenoxy-4-vinyloctan-2-yl)oxy)methyl)benzene

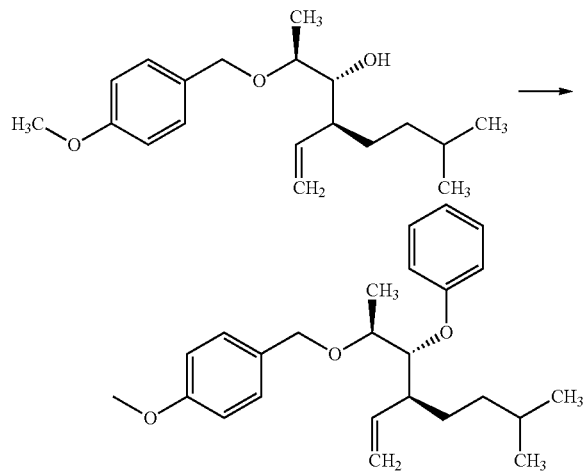

To a solution of (2S,3R,4S)-2-((4-methoxybenzyl)oxy)-7-methyl-4-vinyloctan-3-ol (2.0 g, 6.53 mmol) in anhydrous toluene (30 mL) was added bis(acetato-O)triphenylbismuth (V) (5.47 g, 9.79 mmol), N-cyclohexyl-N-methylcyclohexanamine (2.10 mL, 9.79 mmol) and anhydrous diacetoxycopper (0.237 g, 1.305 mmol) at room temperature. The reaction was heated at 43° C. for 5 h, filtered through a Celite® pad, concentrated and purified by column chromatography on SiO$_2$ (gradient, hexanes/ethyl acetate) to furnish the title product as a colorless oil (2.30 g, 92%): $^1$H NMR (400 MHz, CDCl$_3$) δ 7.27-7.21 (m, 2H), 7.19-7.13 (m, 2H), 7.03-6.97 (m, 2H), 6.94-6.88 (m, 1H), 6.86-6.81 (m, 2H), 5.64-5.51 (m, 1H), 5.07-5.00 (m, 2H), 4.54-4.33 (m, 2H), 4.26 (dd, J=6.5, 4.7 Hz, 1H), 3.79 (s, 3H), 3.79-3.72 (m, 1H), 2.44-2.31 (m, 1H), 1.74-1.61 (m, 1H), 1.52-1.38 (m, 1H), 1.34-1.25 (m, 1H), 1.23 (d, J=6.3 Hz, 3H), 1.22-1.11 (m, 1H), 1.09-0.98 (m, 1H), 0.84 (d, J=6.8 Hz, 3H), 0.82 (d, J=6.8 Hz, 3H); $^{13}$C NMR (101 MHz, CDCl$_3$) δ 160.05, 159.04, 139.48, 129.42, 129.32, 129.19, 121.56, 120.67, 116.46, 113.67, 83.41, 75.26, 70.16, 55.26, 47.15, 36.47, 28.05, 27.64, 22.96, 22.34, 14.83; ESIMS m/z 405.3 ([M+Na]$^+$).

Example 1

Step 2b: Preparation of 1-(((((2S,3R,4S)-3-(cyclopropylmethoxy)-7-methyl-4-vinyloctan-2-yl)oxy)methyl)-4-methoxybenzene

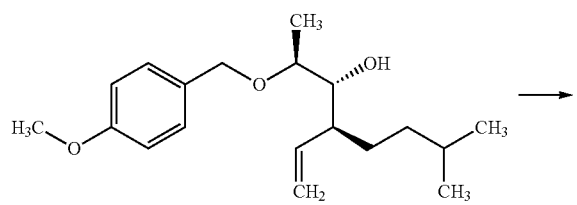

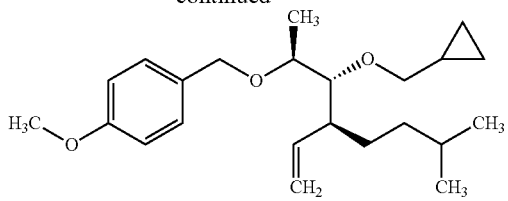

A solution of (2S,3R,4S)-2-((4-methoxybenzyl)oxy)-7-methyl-4-vinyloctan-3-ol (2.0 g, 6.53 mmol) in anhydrous DMF (12 mL) was added at room temperature to a solution of NaH (NaH; 0.326 g, 8.16 mmol, 60% dispersion in mineral oil) in anhydrous DMF (12 ml). The reaction was stirred for 15 minutes (min) at room temperature, treated with (bromomethyl)cyclopropane (0.823 ml, 8.48 mmol) at room temperature, and then was heated to 40° C. for and stirred for 6 h. The reaction was cooled to room temperature and additional NaH (0.131 g, 3.27 mmol) and (bromomethyl)cyclopropane (0.317 mL, 3.27 mmol) were added, and the reaction was heated at 45° C. for 4 h. The reaction was again cooled to room temperature and a third batch of NaH (0.131 g, 3.27 mmol) followed by (bromomethyl)cyclopropane (0.317 mL, 3.27 mmol) was added and the reaction was heated at 45° C. for 2 h. The reaction mixture was quenched with saturated aqueous ammonium chloride (NH$_4$Cl) and the phases were separated. The aqueous phase was extracted with diethyl ether (Et$_2$O), and the combined organic phases were washed with brine, dried over magnesium sulfate (MgSO$_4$), concentrated, and purified by column chromatography on SiO$_2$ (gradient, hexanes/ethyl acetate) to furnish the title product as a colorless oil (1.94 g, 82%): IR (neat) 2953, 2868, 1613, 1513, 1247, 1084 cm$^{-1}$; $^1$H NMR (400 MHz, CDCl$_3$) δ 7.25-7.20 (m, 2H), 6.89-6.81 (m, 2H), 5.52 (dt, J=17.0, 10.0 Hz, 1H), 5.03-4.92 (m, 2H), 4.52-4.32 (m, 2H), 3.78 (s, 3H), 3.65-3.56 (m, 2H), 3.34 (dd, J=10.0, 6.9 Hz, 1H), 3.28-3.22 (m, 1H), 2.09 (tdd, J=10.1, 7.7, 3.1 Hz, 1H), 1.81-1.67 (m, 1H), 1.55-1.42 (m, 1H), 1.28-1.13 (m, 2H), 1.19 (d, J=6.3 Hz, 3H), 1.13-0.95 (m, 2H), 0.87 (d, J=6.4 Hz, 3H), 0.86 (d, J=6.8 Hz, 3H), 0.56-0.45 (m, 2H), 0.25-0.14 (m, 2H); ESIMS m/z 383.4 ([M+Na]$^+$).

Example 1

Step 2b: Preparation of 1-(((((2S,3R,4S)-3-isobutoxy-7-methyl-4-vinyloctan-2-yl)oxy)methyl)-4-methoxybenzene

-continued

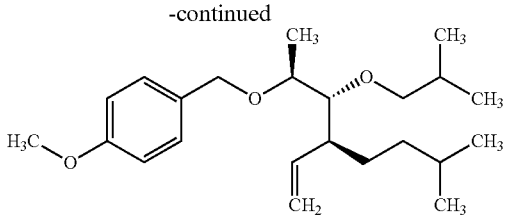

A solution of (2S,3R,4S)-2-((4-methoxybenzyl)oxy)-7-methyl-4-vinyloctan-3-ol (2.0 g, 6.53 mmol) in anhydrous DMF (15 mL) was added at room temperature to a solution of NaH (0.326 g, 8.16 mmol, 60% dispersion in mineral oil) in anhydrous DMF (6.0 mL). The reaction was stirred for 15 min at room temperature, then isobutyl 4-methylbenzenesulfonate (1.66 mL, 8.16 mmol) was added at room temperature and the reaction was heated at 50° C. and stirred for 1 h. The reaction was cooled down to room temperature and NaH (0.261 g, 6.53 mmol) followed by isobutyl 4-methylbenzenesulfonate (1.33 mL, 6.53 mmol) were added and heating continued for 2 h at 50° C., after which the reaction was again cooled down to room temperature and a third batch of NaH (0.131 g, 3.27 mmol) and isobutyl 4-methylbenzenesulfonate (0.67 mL, 3.27 mmol) were added and the reaction was heated at 50° C. for 7 h. The reaction mixture was quenched with saturated NH$_4$Cl and the phases were separated. The aqueous phase was extracted with Et$_2$O, and the combined organic phases were washed with brine, dried over MgSO$_4$, concentrated, and purified by column chromatography on SiO$_2$ (gradient, hexanes/ethyl acetate) to furnish the title product as a colorless oil (2.05 g, 87%): $^1$H NMR (400 MHz, CDCl$_3$) δ 7.29-7.21 (m, 2H), 6.90-6.83 (m, 2H), 5.61-5.49 (m, 1H), 5.04-4.89 (m, 2H), 4.53-4.33 (m, 2H), 3.80 (s, 3H), 3.64-3.51 (m, 2H), 3.28-3.16 (m, 2H), 2.15-2.02 (m, 1H), 1.90-1.77 (m, 1H), 1.76-1.60 (m, 1H), 1.54-1.41 (m, 1H), 1.28-1.11 (m, 2H), 1.17 (d, J=6.3 Hz, 3H), 1.08-0.96 (m, 1H), 0.95-0.88 (m, 6H), 0.86 (d, J=6.4 Hz, 3H), 0.85 (d, J=6.4 Hz, 3H); $^{13}$C NMR (101 MHz, CDCl$_3$) δ 158.97, 140.43, 131.09, 129.06, 115.66, 113.67, 84.26, 79.58, 76.41, 70.05, 55.26, 47.38, 36.46, 29.13, 28.21, 27.85, 22.91, 22.47, 19.66, 19.55, 14.25; ESIMS m/z 385.4 ([M+Na]$^+$).

Example 1

Step 2b: Preparation of 1-((2S,3R,4S)-3-(benzyloxy)-4-((4-methoxy-benzyl)oxy)-2-vinylpentyl)-2,4-difluorobenzene

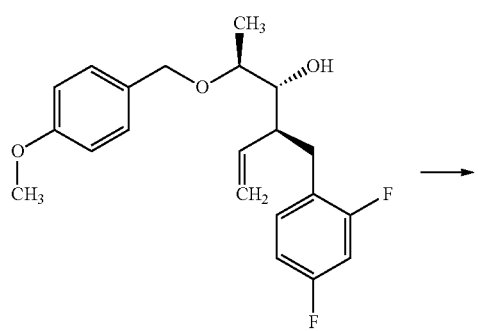

→

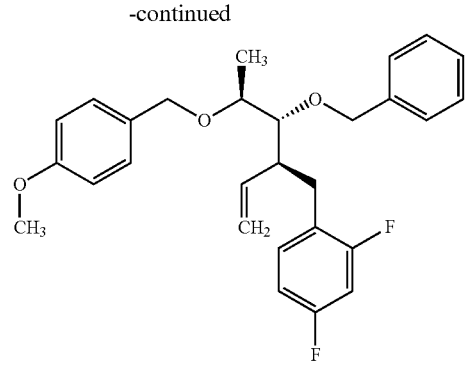

An oven-dried 100 mL Schlenk flask was cooled under nitrogen and was then charged with NaH (60% dispersion in mineral oil, 1.24 g, 31.0 mmol) and anhydrous DMF (50 mL). A solution of (2S,3R,4S)-4-(2,4-difluorobenzyl)-2-((4-methoxybenzyl)oxy)hex-5-en-3-ol (8.06 g, 22.2 mmol) in anhydrous DMF (10 mL) was added via canula over a period of 6 min followed by an anhydrous DMF rinse (5 mL) of the source flask and needle. Gas evolution was observed, and the resulting white suspension was stirred at room temperature for 90 min, at which point the reaction color had turned red. Benzyl bromide (4.23 mL, 35.6 mmol) was added and the reaction was heated to 40° C. After stirring for 3 hours, the heat source was removed and the reaction was cooled to room temperature. Saturated aqueous NH$_4$Cl solution (20 mL) was added, and the mixture was allowed to stir for 30 min, at which point gas evolution had ceased. The crude mixture was then diluted with H$_2$O (50 mL) and extracted with Et$_2$O (100 mL×3). The combined organic extracts were washed with saturated aqueous NH$_4$Cl solution (100 mL), dried over anhydrous MgSO$_4$, filtered, concentrated, and the residue was purified by column chromatography on SiO$_2$ (0%→10% methyl tert-butylether (MTBE)/hexane gradient) to furnish the title product as white solid (90% Pure, 8.47 g, 84%): mp 141-144° C.; $^1$H NMR (400 MHz, CDCl3) δ 7.41-7.30 (m, 4H), 7.30-7.24 (m, 3H), 7.05-6.96 (m, 1H), 6.90-6.84 (m, 2H), 6.76-6.67 (m, 2H), 5.57 (dddd, J=17.1, 10.3, 9.0, 1.3 Hz, 1H), 4.88 (dd, J=10.2, 1.9 Hz, 1H), 4.87 (d, J=11.4 Hz, 1H), 4.72 (ddd, J=17.2, 1.8, 0.5 Hz, 1H), 4.63 (d, J=11.4 Hz, 1H), 4.53 (d, J=11.3 Hz, 1H), 4.40 (d, J=11.3 Hz, 1H), 3.79 (s, 3H), 3.70 (qd, J=6.2, 3.8 Hz, 1H), 3.52 (dd, J=6.9, 3.9 Hz, 1H), 3.09 (d, J=10.4 Hz, 1H), 2.59-2.44 (m, 2H), 1.25 (d, J=6.3 Hz, 3H); $^{13}$C NMR (101 MHz, CDCl3) δ 161.24 (dd, J=245.7, 11.9 Hz), 161.09 (dd, J=247.0, 11.6 Hz), 159.11, 138.90, 138.24, 132.05 (dd, J=9.4, 6.7 Hz), 130.92, 129.17, 128.33, 127.97, 127.53, 123.45 (dd, J=15.9, 3.7 Hz), 116.95, 113.78, 110.59 (dd, J=20.8, 3.7 Hz), 103.33 (dd, J=26.5, 25.0 Hz), 83.67, 76.56, 74.18, 70.41, 55.28, 47.98, 29.75, 14.24; $^{19}$F NMR (376 MHz, CDCl3) δ −113.06 (d, J=6.8 Hz), −113.95 (d, J=6.4 Hz); ESIMS: m/z 475 ([M+Na]+).

Example 1

Step 2b: Preparation of 1-(((((2S,3R,4S)-4-benzyl-3-(2-methoxyethoxy)-hex-5-en-2-yl)oxy)methyl)-4-methoxybenzene

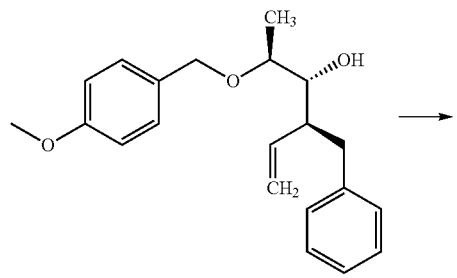

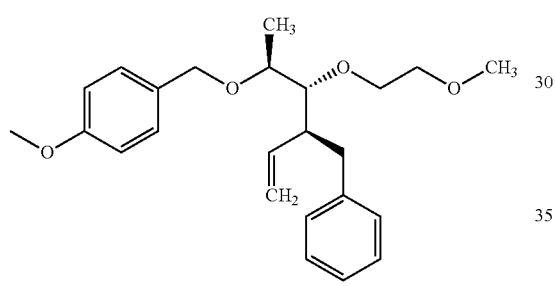

To a suspension of NaH (0.088 g, 3.68 mmol) in DMF (10 mL) was added dropwise a solution of (2S,3R,4S)-4-benzyl-2-((4-methoxybenzyl)oxy)hex-5-en-3-ol (1 g, 3.06 mmol) in DMF (5 mL). The mixture was stirred at room temperature for 20 min and then 1-bromo-2-methoxyethane (0.852 g, 6.13 mmol) was added. The reaction mixture was heated to 60° C. for 5 h. The reaction was cooled to room temperature and another portion of NaH (0.088 g, 3.68 mmol) and 1-bromo-2-methoxyethane (0.852 g, 6.13 mmol) were added, and the reaction mixture was heated to 60° C. and stirred overight. The reaction mixture was quenched with saturated NH4Cl and the phases were separated. The aqueous phase was extracted with EtOAc (2×40 mL), and the combined organic phases were dried over MgSO4, concentrated, and purified by column chromatography on SiO2 (EtOAc/hexanes) to furnish the title product as colorless oil (0.730 g, 62%): $^1$H NMR (400 MHz, CDCl3) δ 7.30-7.06 (m, 7H), 6.86 (dd, J=8.6, 0.9 Hz, 2H), 5.68-5.47 (m, 1H), 4.95-4.69 (m, 2H), 4.60-4.26 (m, 2H), 4.04-3.91 (m, 1H), 3.79 (s, 3H), 3.73-3.69 (m, 1H), 3.68-3.60 (m, 1H), 3.59-3.53 (m, 2H), 3.39 (d, J=0.8 Hz, 3H), 3.38-3.36 (m, 1H), 3.15 (d, J=10.4 Hz, 1H), 2.70-2.42 (m, 2H), 1.30-1.17 (m, 3H); $^{13}$C NMR (101 MHz, CDCl3) δ 159.05, 140.67, 138.83, 130.95, 129.56, 129.11, 127.92, 125.60, 116.61, 113.74, 84.59, 76.46, 72.41, 71.76, 70.26, 58.96, 55.28, 48.55, 36.96, 14.01; ESIMS m/z 407.2 ([M+Na]+).

Example 1

Step 2c: Preparation of triisopropyl(((2S,3R,4S)-2-((4-methoxybenzyl)-oxy)-7-methyl-4-vinyloctan-3-yl)oxy)silane

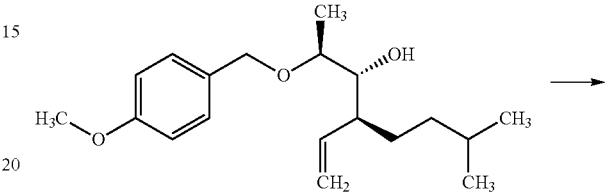

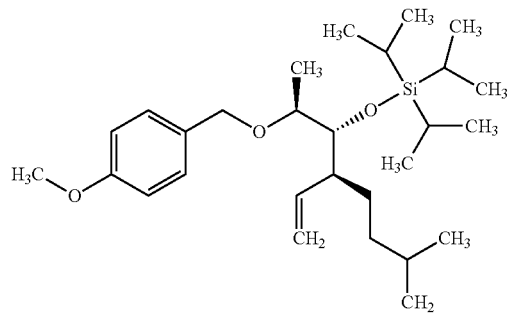

To an ice-cooled solution of (2S,3R,4S)-2-((4-methoxybenzyl)oxy)-7-methyl-4-vinyloctan-3-ol (3.70 g, 12.07 mmol) in anhydrous CH2Cl2 (60.4 ml) were added 2,6-dimethylpyridine (1.97 ml, 16.9 mmol) and triisopropylsilyl trifluoromethanesulfonate (3.89 ml, 14.5 mmol), and the mixture was allowed to warm to room temperature while stirring overnight. The reaction mixture was poured into saturated aqueous sodium bicarbonate (NaHCO3) solution and mixed thoroughly. The phases were separated and the aqueous phase was extracted with CH2Cl2, and the combined organic phases were washed with brine, dried over MgSO4, concentrated, and purified by column chromatography on SiO2 (gradient, hexanes/ethyl acetate) to furnish the title product as a colorless oil (4.76 g, 85%): $^1$H NMR (400 MHz, CDCl3) δ 7.26-7.19 (m, 2H), 6.88-6.81 (m, 2H), 5.63-5.50 (m, 1H), 5.05-4.89 (m, 2H), 4.51-4.29 (m, 2H), 3.84 (dd, J=6.6, 3.0 Hz, 1H), 3.79 (s, 3H), 3.55-3.46 (m, 1H), 2.11-1.98 (m, 1H), 1.75-1.61 (m, 1H), 1.56-1.41 (m, 1H), 1.24-1.17 (m, 1H), 1.15 (d, J=6.2 Hz, 3H), 1.13-0.97 (m, 20H), 0.85 (d, J=6.8 Hz, 3H), 0.84 (d, J=6.4 Hz, 3H); $^{13}$C NMR (101 MHz, CDCl3) δ 158.88, 139.86, 131.19, 129.19, 115.64, 113.50, 78.34, 76.39, 70.08, 55.24, 49.46, 36.94, 28.35, 28.23, 22.83, 22.51, 18.43, 18.41, 13.71, 13.18; ESIMS m/z 485.4 ([M+Na]$^+$).

Example 1

Step 3: Preparation of (6R,7R,8S,Z)-benzyl 2-((tert-butoxycarbonyl)amino)-7-(cyclopropylmethoxy)-6-(4-fluorobenzyl)-8-((4-methoxybenzyl)-oxy)non-2-enoate

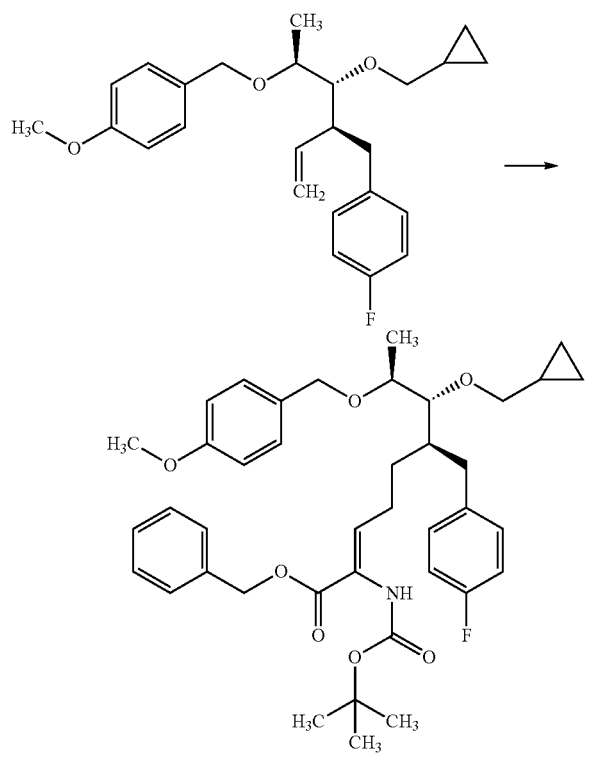

A 0.5 M solution of 9-borabicyclo[3.3.1]nonane in anhydrous THF (7.0 mL, 3.50 mmol) was added to a solution of 1-((2S,3R,4S)-3-(cyclopropylmethoxy)-4-((4-methoxybenzyl)oxy)-2-vinylpentyl)-4-fluorobenzene (960 milligrams (mg), 2.409 mmol) in anhydrous THF (5 mL) at 0° C. The resulting solution was warmed to room temperature and stirred for 1 h, then heated to 50° C. for 2 h. The reaction was cooled to room temperature, a solution of K$_3$PO$_4$ (3 M aqueous, 1.61 mL, 4.82 mmol) was added, and the reaction was stirred for 15 min at room temperature. To the mixture was added a solution of (Z)-benzyl 3-bromo-2-((tert-butoxycarbonyl)amino)acrylate (870 mg, 2.44 mmol), prepared using a similar procedure to that disclosed in Singh, J. et al. *Org. Lett.* 2003, 5, 3155-3158, in degassed DMF (2 mL) and PdCl$_2$(dppf) (88.0 mg, 0.120 mmol). The reaction was heated overnight at 60° C., cooled, diluted with Et$_2$O, and washed with saturated aqueous NaHCO$_3$. The phases were separated and the aqueous phase was extracted with Et$_2$O. The combined organic phases were washed with saturated aqueous NH$_4$Cl and water, dried over MgSO$_4$, concentrated, and purified by column chromatography on SiO$_2$ (gradient, hexanes/ethyl acetate) to furnish the title product as a pale yellow oil (1.43 g, 88%): $^1$H NMR (400 MHz, CDCl$_3$) δ 7.38-7.26 (m, 5H), 7.26-7.19 (m, 2H), 6.97-6.89 (m, 2H), 6.88-6.78 (m, 4H), 6.39 (t, J=7.2 Hz, 1H), 6.29 (s, 1H), 5.24-5.10 (m, 2H), 4.61-4.25 (m, 2H), 3.73 (s, 3H), 3.64-3.53 (m, 1H), 3.45-3.31 (m, 2H), 3.22 (dd, J=7.2, 2.8 Hz, 1H), 2.79 (dd, J=14.0, 4.8 Hz, 1H), 2.37 (dd, J=14.0, 9.5 Hz, 1H), 2.25-2.08 (m, 2H), 1.92-1.79 (m, 1H), 1.57-1.43 (m, 1H), 1.43 (s, 9H), 1.39-1.28 (m, 1H), 1.28 (d, J=6.0 Hz, 3H), 1.09-0.96 (m, 1H), 0.53-0.44 (m, 2H), 0.21-0.13 (m, 2H); $^{13}$C NMR (101 MHz, CDCl$_3$) δ 164.48, 160.91 (d, J=243.2 Hz), 158.99, 153.40, 136.94 (d, J=3.2 Hz), 136.82, 135.55, 130.26, 130.24 (d, J=7.7 Hz), 129.39, 128.31, 128.04, 128.00, 126.23, 114.62 (d, J=20.9 Hz), 113.58, 82.58, 80.01, 76.69, 74.41, 69.70, 66.72, 54.94, 40.81, 34.83, 28.49, 27.99, 25.75, 16.00, 11.01, 2.86, 2.78; $^{19}$F NMR (376 MHz, CDCl$_3$) δ −117.70; ESIMS m/z 676.4 ([M+H]$^+$).

Example 1

Step 4: (2S,6R,7R,8S)-methyl-2-((tert-butoxycarbonyl)amino)-6-(4-methoxybenzyl)-8-((4-methoxybenzyl)oxy)-7-((triisopropylsilyl)oxy)nonanoate

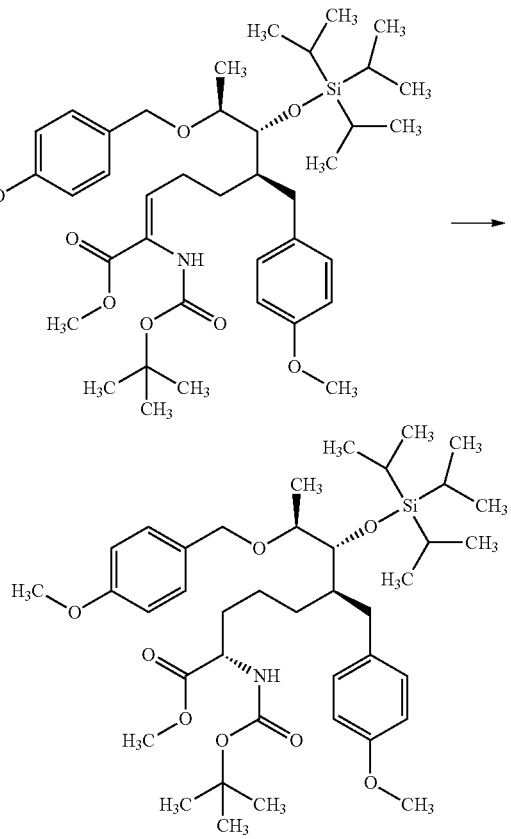

The title compound was prepared using a procedure adapted from Jones et al. *Tetrahedron Lett.* 1999, 40, 1211-1214. A high pressure reactor was charged with (6R,7R,8S,Z)-methyl 7-(benzyloxy)-2-((tert-butoxycarbonyl)amino)-8-((4-methoxybenzyl)oxy)-6-(4-methylbenzyl)non-2-enoate (2.72 g, 3.82 mmol) and anhydrous MeOH (20 mL) and the solution was sparged with nitrogen using a needle for 10 min. To the solution was added (+)-1,2-bis((2S,5S)-2,5-diethylphospholano)benzene-(cyclooctadiene)rhodium(I) trifluoromethanesulfonate (28 mg, 0.038 mmol) and the reactor was sealed, pressurized with H$_2$ (200 psi) and stirred at room temperature for 3 h. The pressure was released and the crude reaction mixture was filtered through a pad of Celite®, concentrated, and purified by column chromatography on SiO$_2$ (0→100% EtOAc/hexanes gradient) to furnish the title product as a colorless oil (2.73 g, 100%): IR (neat) 3377, 2941, 2865, 1744, 1715, 1511, 1245, 1164 cm$^{-1}$; $^1$H NMR (400 MHz, CDCl$_3$) δ 7.31-7.22 (m, 2H), 7.01 (d, J=8.5 Hz, 2H), 6.87 (d, J=8.6 Hz, 2H), 6.77 (d, J=8.6 Hz, 2H), 4.90 (d, J=8.5 Hz, 1H), 4.51 (d, J=11.2 Hz, 1H), 4.33 (d, J=11.3 Hz, 1H), 4.25 (q, J=7.2 Hz, 1H), 3.81 (s, 3H), 3.78 (s, 3H), 3.70 (s, 3H), 3.63-3.52 (m, 1H), 2.77 (dd, J=13.8, 7.2 Hz, 1H), 2.43 (dd, J=13.8, 7.4 Hz, 1H), 1.78 (d, J=7.7 Hz, 1H), 1.70 (s, 1H), 1.52 (d, J=10.7 Hz, 2H), 1.44 (s, 9H), 1.35-1.07 (m, 7H), 1.07-0.93 (m, 21H); $^{13}$C NMR (101 MHz, CDCl$_3$) δ 173.40, 158.94, 157.67, 155.35, 133.91, 131.04, 130.15, 129.21, 113.63, 113.58, 79.80, 76.44, 76.36, 70.18, 55.29, 55.26, 53.37, 52.16, 45.89, 36.12, 33.12, 29.50, 28.32, 23.81, 18.27, 16.23, 13.02; HRMS-ESI (m/z) ([M]$^+$) calcd for C$_{40}$H$_{65}$NO$_8$Si, 715.448; found, 715.4479.

Example 1

Step 5a: Preparation of (2S,6R,7R,8S)-methyl 2-((tert-butoxycarbonyl)-amino)-8-hydroxy-7-isobutoxy-6-(2-(methylthio)ethyl)nonanoate

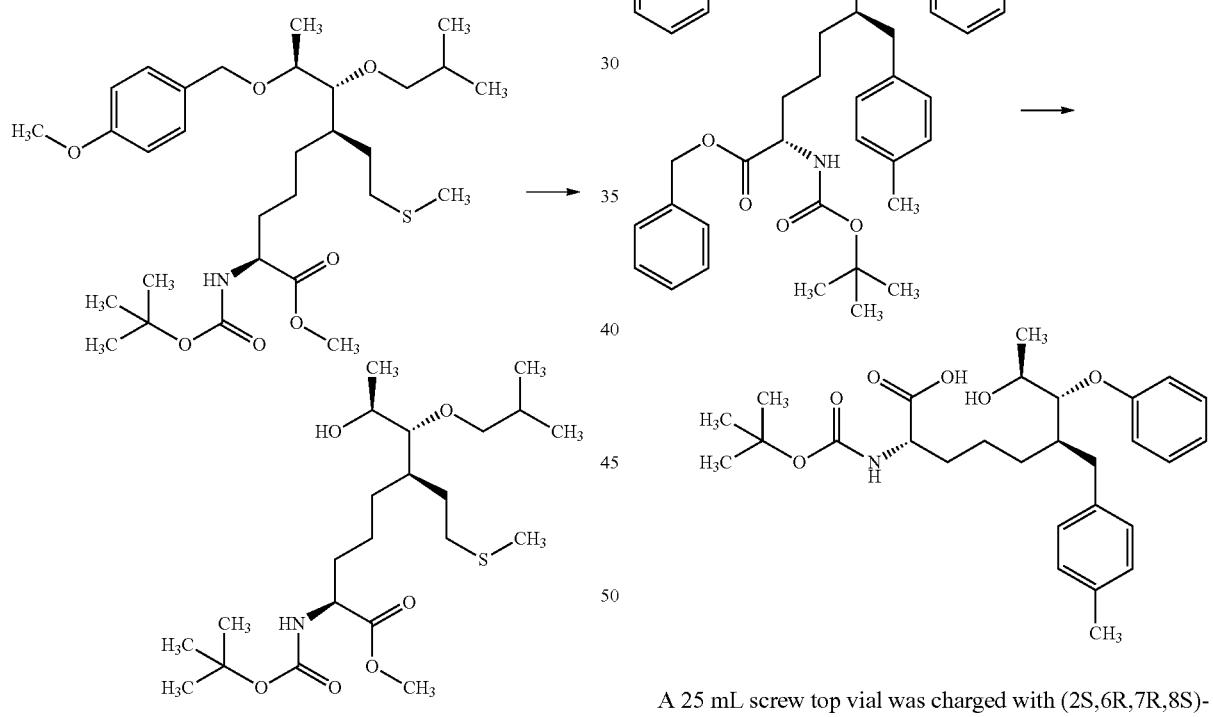

To a mixture of (2S,6R,7R,8S)-methyl 2-((tert-butoxycarbonyl)amino)-7-isobutoxy-8-((4-methoxybenzyl)oxy)-6-(2-(methylthio)ethyl)nonanoate (536 mg, 0.941 mmol) and 0.85 mL H$_2$O in CH$_2$Cl$_2$ (9.4 mL) at 0° C. (icewater bath) was added DDQ (214 mg, 0.941 mmol). The resulting dark mixture was stirred at 0° C. for 3 h, then another portion of DDQ (41 mg, 0.180 mmol) were added and the reaction was stirred for 1 h. The reaction was quenched with sodium hydroxide (NaOH; 1.3 ml of 1M aqueous, 1.3 mmol) and stirred for 10 min. The reaction was then diluted with H$_2$O (20 mL) and extracted with CH$_2$Cl$_2$ (3×20 mL). The combined organic extracts were dried over Na$_2$SO$_4$, filtered, and concentrated to provide a red oil which was purified by column chromatography on SiO$_2$ (5→35% acetone/hexanes gradient) to furnish the title product as a clear, colorless oil (353 mg, 83%): $^1$H NMR (400 MHz, CDCl$_3$) δ 5.02 (d, J=8.0 Hz, 1H), 4.31 (d, J=5.2 Hz, 1H), 3.95-3.83 (m, 1H), 3.74 (d, J=1.6 Hz, 3H), 3.36 (dd, J=8.5, 6.3 Hz, 1H), 3.22 (dd, J=8.5, 6.6 Hz, 1H), 3.05 (dd, J=5.6, 3.9 Hz, 1H), 2.58 (ddd, J=14.0, 8.7, 5.3 Hz, 1H), 2.47 (ddd, J=12.8, 8.3, 7.4 Hz, 1H), 2.10 (s, 3H), 1.96-1.68 (m, 4H), 1.68-1.49 (m, 3H), 1.45 (s, 9H), 1.39 (s, 4H), 1.21 (d, J=6.3 Hz, 3H), 0.91 (dd, J=6.7, 1.9 Hz, 6H); $^{13}$C NMR (101 MHz, CDCl$_3$) δ 173.36, 155.36, 84.83, 79.93, 79.24, 68.10, 53.20, 52.27, 38.01, 33.20, 33.05, 32.76, 30.90, 29.21, 28.83, 28.33, 22.83, 19.52, 19.46, 19.11, 15.43; ESIMS m/z 450.4 ([M+H]+), 472.4 ([M+Na]$^+$).

Example 1

Step 5b: Preparation of (2S,6R,7R,8S)-2-((tert-butoxycarbonyl)amino)-8-hydroxy-6-(4-methylbenzyl)-7-phenoxynonanoic acid

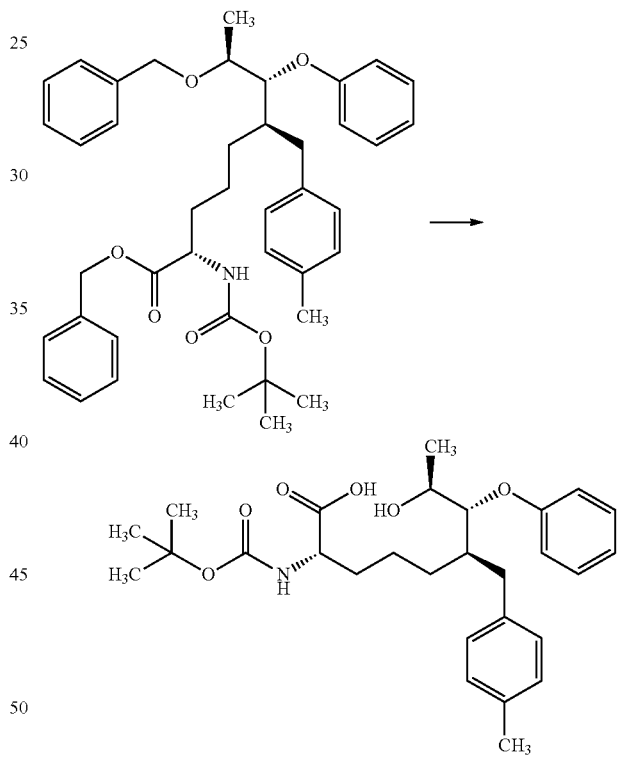

A 25 mL screw top vial was charged with (2S,6R,7R,8S)-benzyl 8-(benzyloxy)-2-((tert-butoxycarbonyl)amino)-6-(4-methylbenzyl)-7-phenoxynonanoate (741 mg, 1.11 mmol), EtOAc (10 mL), and 10% Pd/C (61 mg, 0.057 mmol). The vial was sealed with a septum-cap, and the reaction was briefly degassed under high vacuum, and then repressurized under about 1 atmosphere of H$_2$ (balloon pressure). This process was repeated 2×, and the reaction was stirred at room temperature under balloon pressure of hydrogen. After stirring for 19 h, the solids were removed by filtration through a pad of Celite®, rinsing with excess EtOAc. The filtrate was concentrated and then dried under high vaccuum to afford the title compound as a white solid (516 mg, 91%): mp 48-51° C.; $^1$H NMR (400 MHz, CDCl3) δ 7.30-7.17 (m, 2H), 7.09 (s, 4H), 6.97-6.83 (m, 3H), 6.69-6.02 (m, 2H), 5.00 (d, J=8.3 Hz, 1H), 4.33-3.96 (m, 3H), 3.03 (dd, J=13.8, 5.3 Hz, 1H), 2.49 (dd, J=13.9, 8.9 Hz, 1H), 2.33 (s, 3H), 2.19-2.08 (m, 1H), 1.78-1.62 (m, 1H), 1.59-1.15 (m, 17H); $^{13}$C NMR (101 MHz, CDCl3) δ 176.73, 159.43, 155.73, 138.03, 135.33, 129.57, 129.10, 129.06, 120.88, 115.85, 82.16, 80.24, 68.15, 53.26, 41.47, 35.46, 32.45, 29.53, 28.35, 22.51, 21.05, 20.01; ESIMS: m/z 486 ([M+H]$^+$).

Example 1

Step 5b: Preparation of (2S,6R,7R,8S)-2-((tert-butoxycarbonyl)amino)-8-hydroxy-6-(4-methoxybenzyl)-7-(triisopropylsilyl)oxy)nonanoic acid

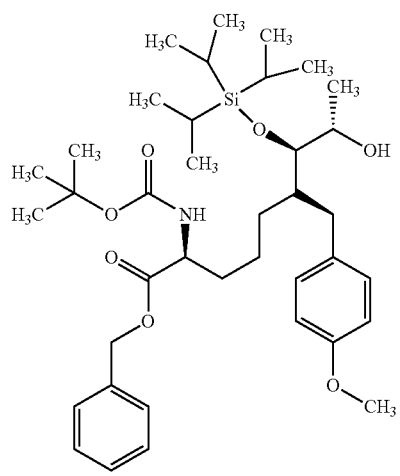

A high pressure reactor was charged with Pd/C (212 mg, 0.199 mmol) and a solution of (2S,6R,7R,8S)-benzyl-2-((tert-butoxycarbonyl)amino)-8-hydroxy-6-(4-methoxybenzyl)-7-((triisopropylsilyl)oxy)nonanoate (2.02 g, 3.01 mmol) in THF (10 mL). The flask was pressurized to 500 psi and stirred for 2 days (d). The reaction mixture was filtered through a pad of Celite® and concentrated to give the title compound as a sticky semi solid (1.730 g, 99%): IR (neat) 3337, 2941, 2865, 1714, 1511, 1462, 1245, 1165 cm$^{-1}$; $^1$H NMR (400 MHz, CDCl$_3$) δ 7.13-6.90 (m, 2H), 6.88-6.67 (m, 2H), 4.87 (d, J=8.0 Hz, 1H), 4.22 (s, 1H), 3.96 (qd, J=6.4, 4.0 Hz, 1H), 3.79 (s, 3H), 3.76-3.62 (m, 1H), 2.93 (dd, J=14.0, 5.9 Hz, 1H), 2.44 (dd, J=13.9, 8.7 Hz, 1H), 1.92-1.65 (m, 2H), 1.62-1.48 (m, 2H), 1.44 (s, 9H), 1.34-1.14 (m, 6H), 1.14-0.71 (m, 21H); $^{13}$C NMR (101 MHz, CDCl$_3$) δ 175.71, 157.74, 155.72, 133.62, 130.02, 113.74, 70.38, 60.42, 55.27, 53.21, 43.79, 35.95, 32.41, 29.79, 28.30, 23.72, 19.11, 18.28, 14.20, 13.03; HRMS-ESI (m/z) ([M]$^+$) calcd for C$_{31}$H$_{55}$NO$_7$Si, 581.3748; found, 581.3744.

Example 1

Step 5b: Preparation of (2S,6R)-2-((tert-butoxycarbonyl)amino)-6-((1R,2S)-2-hydroxy-1-((triisopropylsilyl)oxy)propyl)-9-methyldecanoic acid

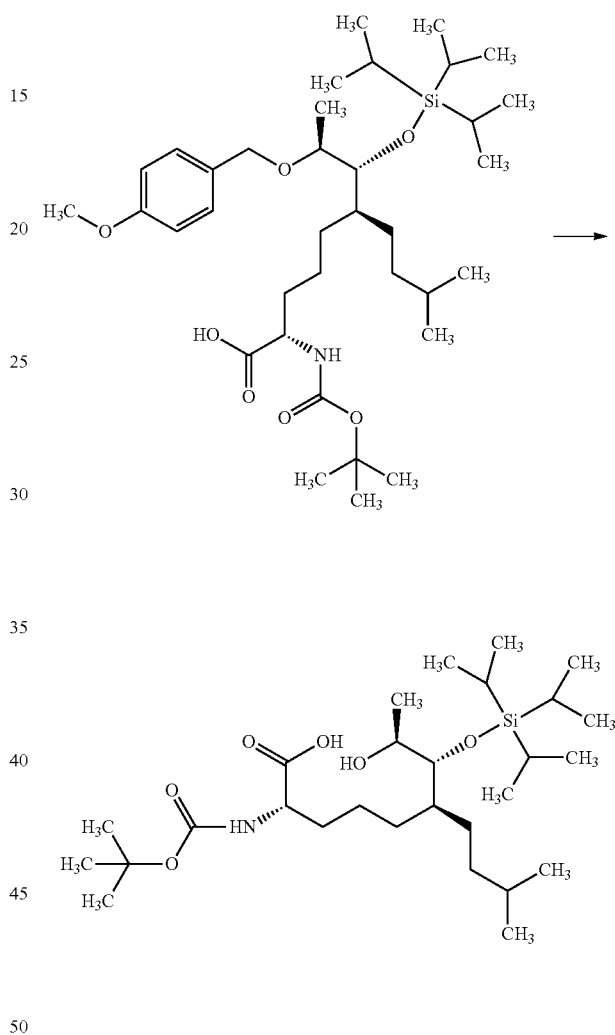

(2S,6R)-2-((tert-Butoxycarbonyl)amino)-6-((1R,2S)-2-((4-methoxybenzyl)oxy)-1-((triisopropylsilyl)oxy)propyl)-9-methyldecanoic acid (8.55 g, 13.1 mmol) was dissolved in THF (40 ml) in a high pressure reactor with a stir bar. To the resulting solution was added 5% Pd/C (1.40 g, 0.656 mmol) was added, the reactor was sealed and purged with H$_2$ (4×), and then charged to 600 psi with H$_2$ at room temperature. The reactor was heated to 50° C. for 12 h and then stirred at room temperature overnight. The reaction mixture was filtered through a pad of Celite® and concentrated to yield the title compound as a colorless oil contaminated with 20% p-methoxytoluene (7.76 g, 89: $^1$H NMR (400 MHz, CDCl$_3$) δ 5.05-4.92 (m, 1H), 4.37-4.22 (m, 1H), 3.89 (qd, J=6.4, 3.5 Hz, 1H), 3.83-3.78 (m, 1H), 1.93-1.77 (m, 2H), 1.74-1.45 (m, 5H), 1.45 (s, 9H), 1.45-1.19 (m, 2H), 1.19 (d, J=5.1 Hz, 3H), 1.14-1.02 (m, 24H), 0.87 (d, J=6.6 Hz, 6H); ESIMS m/z 554.5 ([M+Na]⁺).

Example 1

Step 5c: Preparation of (2S,6R,7R,8S)-7-(benzyloxy)-2-((tert-butoxy-carbonyl)amino)-6-(2,4-difluorobenzyl)-8-hydroxynonanoic acid

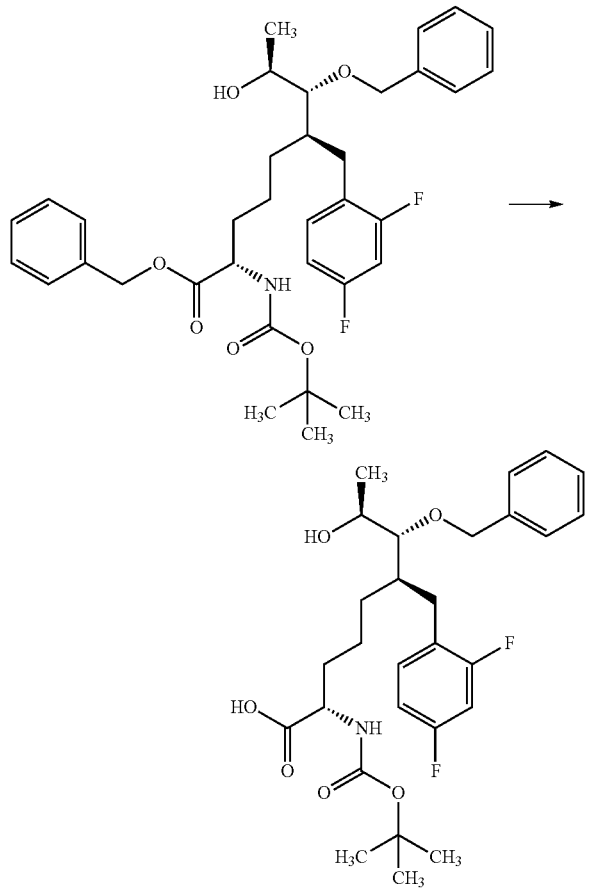

A 250 mL round bottom flask was charged with (2S,6R, 7R,8S)-benzyl 7-(benzyloxy)-2-((tert-butoxycarbonyl) amino)-6-(2,4-difluorobenzyl)-8-hydroxynonanoate (2.10 g, 3.43 mmol), THF (24 mL) and H₂O (6 mL). LiO.H₂O (153 mg, 3.64 mmol) was added, and the resulting mixture was allowed to stir at room temperature. After stirring for 2.5 h, the reaction mixture was heated to 50° C. and was stirred for an additional 17 h at that temperature. Additional portions of water (3 mL) and LiO.H₂O (152 mg, 3.62 mmol) were added and the reaction was stirred at room temperature for 4.5 h. The reaction mixture was diluted with 1.0 M aqueous HCl (50 mL) and extracted with EtOAc (3×50 mL). The combined organic extracts were washed with saturated aqueous sodium chloride solution (NaCl, brine; 50 mL), dried over anhydrous MgSO₄, filtered, concentrated, and dried under high vacuum to obtain the title compound as a colorless oil contaminated with 10% BnOH (1.55 g, 87%): ¹H NMR (400 MHz, CDCl3) δ 7.39-7.26 (m, 5H), 7.15-7.05 (m, 1H), 6.82-6.69 (m, 2H), 5.03 (d, J=8.3 Hz, 1H), 4.64 (d, J=11.5 Hz, 1H), 4.55 (d, J=11.6 Hz, 1H), 4.20 (q, J=7.4 Hz, 1H), 4.03 (p, J=6.2 Hz, 1H), 3.37-3.24 (m, 1H), 2.99 (dd, J=14.0, 4.6 Hz, 1H), 2.51 (dd, J=14.0, 9.9 Hz, 1H), 2.01-1.90 (m, 1H), 1.75-1.60 (m, 1H), 1.56-1.15 (m, 17H); 13C NMR (101 MHz, CDCl3) δ 176.51, 161.26 (dd, J=246.7, 12.7 Hz), 161.07 (dd, J=247.1, 12.0 Hz), 155.60, 138.35, 131.98 (dd, J=9.3, 6.9 Hz), 128.37, 127.77, 126.97, 124.00 (dd, J=15.8, 3.8 Hz), 110.83 (dd, J=20.8, 3.6 Hz), 104.38 102.95 (m), 83.36, 80.11, 73.75, 68.11, 53.17, 39.82, 32.49, 29.71, 28.85, 28.25, 22.55, 19.22; 19F NMR (376 MHz, CDCl3) δ −113.45 (d, J=7.0 Hz), −113.63 (d, J=6.7 Hz); ESIMS: m/z 522 ([M+H]⁺).

Example 1

Step 5c: Preparation of (2S,6R)-2-((tert-butoxycarbonyl)amino)-6-((1R,2S)-2-((4-methoxybenzyl)oxy)-1-((triisopropylsilyl)oxy)propyl)-9-methyldecanoic acid

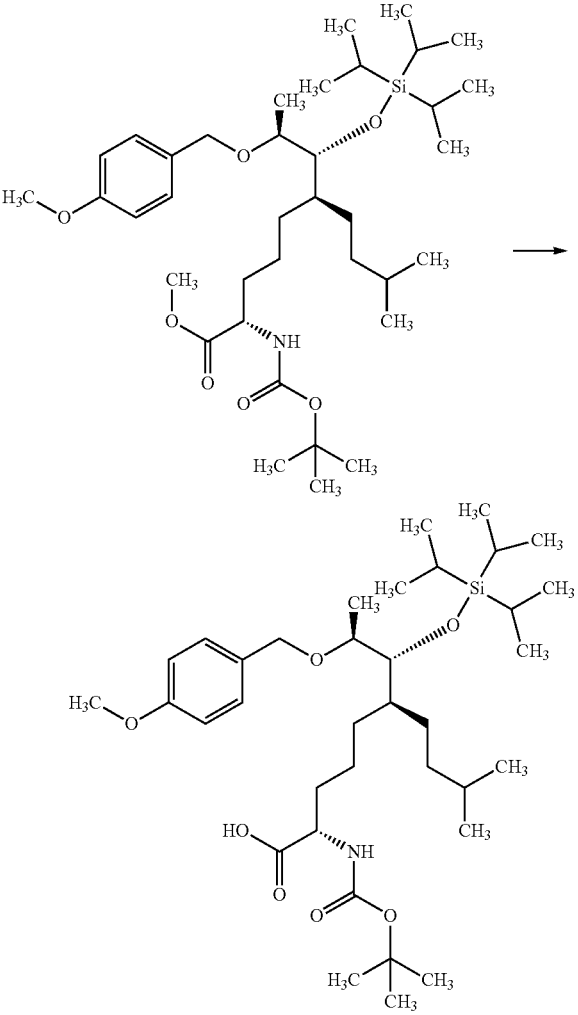

To a solution of (2S,6R)-methyl 2-((tert-butoxycarbonyl) amino)-6-((1R,2S)-2-((4-methoxybenzyl)oxy)-1-((triisopropylsilyl)oxy)propyl)-9-methyldecanoate (8.76 g, 13.2 mmol) in a mixture of THF and H₂O (125 mL/62.5 mL) was added LiOH (2.047 g, 85.0 mmol) and the resulting mixture was stirred for 24 h at 40° C. and then for another 24 h at room temperature. The reaction mixture was diluted with EtOAc and washed with 1.0 M aqueous HCl. The phases were separated and the aqueous phase was extracted with EtOAc. The combined organic phase was washed with brine, dried over MgSO$_4$, and concentrated to furnish the title compound as a pale yellow oil (8.55 g, 100%): IR (neat) 2943, 2866, 1715, 1513, 1392, 1247, 1162, 1038 cm$^{-1}$; $^1$H NMR (400 MHz, CDCl$_3$) δ 7.26-7.20 (m, 2H), 6.88-6.82 (m, 2H), 4.96-4.83 (m, 1H), 4.51-4.31 (m, 2H), 4.31-4.20 (m, 1H), 3.88 (t, J=3.8 Hz, 1H), 3.80 (s, 3H), 3.52-3.43 (m, 1H), 1.91-1.72 (m, 2H), 1.68-1.46 (m, 5H), 1.45 (s, 9H), 1.44-1.19 (m, 2H), 1.18 (d, J=6.2 Hz, 3H), 1.18-0.98 (m, 24H), 0.86-0.80 (m, 6H); ESIMS m/z 674.6 ([M+Na]$^+$).

Example 1

Step 5c: Preparation of (2S,6R,7R,8S)-2-((tert-butoxycarbonyl)amino)-8-hydroxy-7-isobutoxy-6-(2-(methylthio)ethyl)nonanoic acid

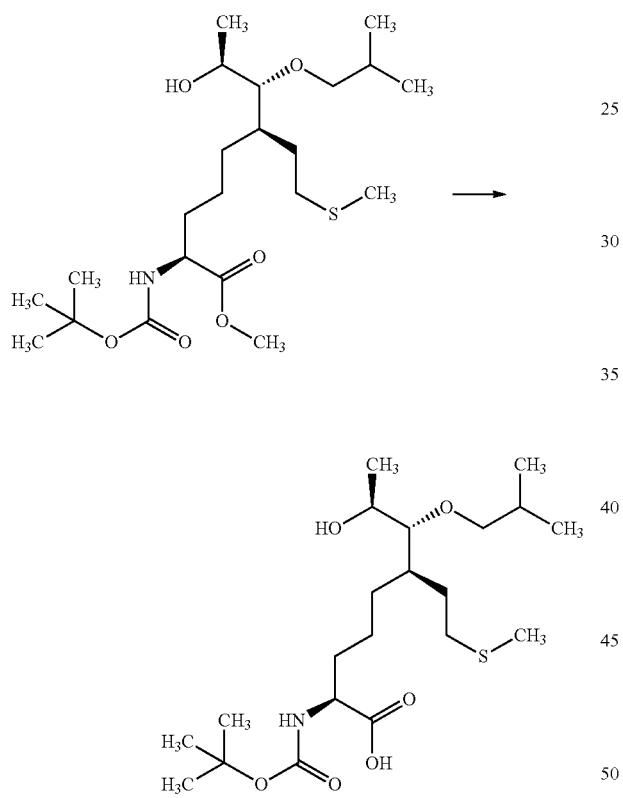

To a mixture of (2S,6R,7R,8S)-methyl 2-((tert-butoxycarbonyl)amino)-8-hydroxy-7-isobutoxy-6-(2-(methylthio)ethyl)nonanoate (326 mg, 0.725 mmol) in THF (2.4 ml) and H$_2$O (1.2 ml) was added LiO.H$_2$O (91 mg, 2.2 mmol). The resulting mixture was stirred at room temperature for 3 h, quenched with 2N HCl (3 mL), diluted with H$_2$O (20 mL), and extracted with EtOAc (3×20 mL). The organic extracts were combined, dried over Na$_2$SO$_4$, filtered, and concentrated to provide the title compound as a sticky colorless oil (307 mg, 97%): $^1$H NMR (400 MHz, CDCl$_3$) δ 5.05 (d, J=7.3 Hz, 1H), 4.31 (s, 1H), 3.88 (p, J=6.3 Hz, 1H), 3.36 (dd, J=8.5, 6.3 Hz, 1H), 3.23 (dd, J=8.6, 6.6 Hz, 1H), 3.07 (dd, J=5.7, 3.9 Hz, 1H), 2.59 (ddd, J=13.9, 8.6, 5.3 Hz, 1H), 2.48 (dt, J=12.8, 7.5 Hz, 1H), 2.10 (s, 3H), 1.84 (tt, J=13.2, 7.1 Hz, 3H), 1.78-1.62 (m, 2H), 1.55 (dd, J=13.6, 5.8 Hz, 1H), 1.46 (s, 12H), 1.22 (d, J=6.3 Hz, 3H), 0.91 (dd, J=6.7, 2.0 Hz, 6H); $^{13}$C NMR (101 MHz, CDCl$_3$) δ 155.81, 99.99, 84.81, 79.35, 68.26, 38.01, 32.80, 30.94, 29.22, 28.80, 28.32, 22.88, 19.51, 19.46, 19.13, 15.44; ESIMS m/z 436.3 ([M+H]$^+$), 458.3 ([M+Na]$^+$).

Example 1

Step 6: Preparation of tert-butyl((3S,7R,8R,9S)-7-isopentyl-9-methyl-2-oxo-8-((triisopropylsilyl)oxy)oxonan-3-yl)carbamate

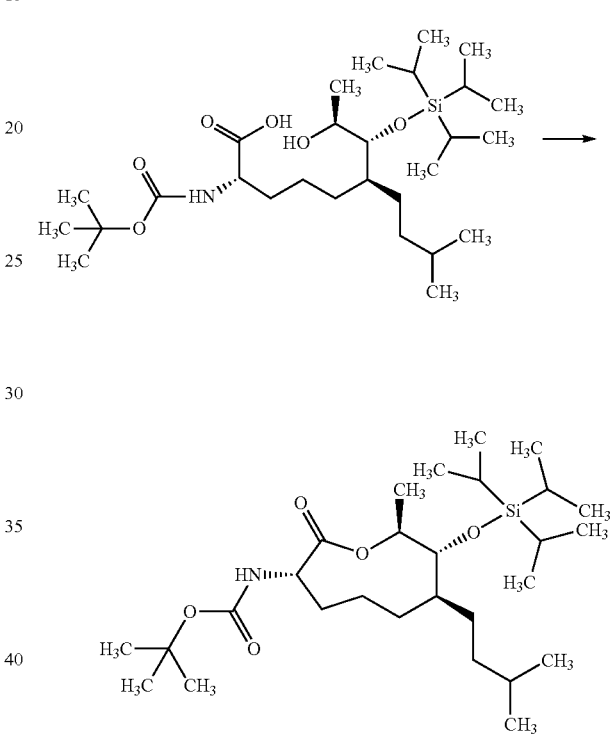

A solution of (2S,6R)-2-((tert-butoxycarbonyl)amino)-6-((1R,2S)-2-hydroxy-1-((triisopropylsilyl)oxy)propyl)-9-methyldecanoic acid (7.76 g, 13.1 mmol) in anhydrous CH$_2$Cl$_2$ (500 mL) was added to a solution of MNBA (9.04 g, 26.3 mmol) and DMAP (12.8 g, 105.0 mmol) in anhydrous CH$_2$Cl$_2$ (2.5 L) at room temperature over the course of 4 h. After the addition was complete, the reaction was stirred for 12 h at room temperature, concentrated and purified by column chromatography on SiO$_2$ (gradient, hexanes/ethyl acetate) to furnish the title product as a sticky pale yellow solid (3.98 g, 59%): $^1$H NMR (400 MHz, CDCl$_3$) δ 5.14 (d, J=8.2 Hz, 1H), 4.90-4.78 (m, 1H), 4.20-4.09 (m, 1H), 3.61 (t, J=7.6 Hz, 1H), 2.26-2.10 (m, 1H), 1.79-1.65 (m, 1H), 1.65-1.40 (m, 3H), 1.44 (s, 9H), 1.37 (d, J=6.5 Hz, 3H), 1.32-0.97 (m, 28H), 0.884 (d, J=6.7 Hz, 3H), 0.878 (d, J=6.7 Hz, 3H); $^{13}$C NMR (101 MHz, CDCl$_3$) δ 173.12, 154.92, 79.62, 78.59, 75.82, 60.33, 53.07, 45.68, 36.92, 34.17, 28.64, 28.58, 28.31, 27.27, 22.82, 22.49, 18.95, 18.86, 18.38, 18.33, 13.75; ESIMS m/z 536.5 ([M+Na]+).

Example 2

Step 1a-1: Preparation of tert-butyl((3S,7R,8R,9S)-7-(4-methoxybenzyl)-9-methyl-2-oxo-8-((triisopropylsilyl)oxy)oxonan-3-yl)(methoxymethyl)carbamate

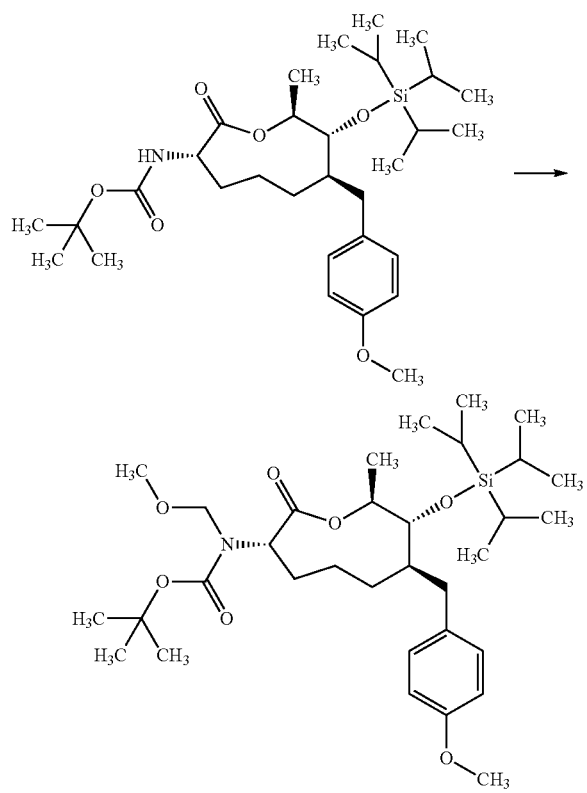

A 4 mL vial was charged with tert-butyl((3S,7R,8R,9S)-7-(4-methoxybenzyl)-9-methyl-2-oxo-8-((triisopropylsilyl)oxy)oxonan-3-yl)carbamate (42.0 mg, 0.074 mmol), paraformaldehyde (3.13 mg, 0.104 mmol) and CH$_2$Cl$_2$ (0.5 mL), then cooled to 0° C. under N$_2$. Chlorotrimethylsilane (0.026 mL, 0.201 mmol) was added to the reaction mixture, which was stirred for 45 min, then quenched by the addition of 9:1 MeOH/Et$_3$N (0.5 mL). The mixture was warmed to room temperature and stirred overnight. The reaction was diluted with H$_2$O (2 mL) and passed through a phase separator cartridge. An additional portion of CH$_2$Cl$_2$ (2 mL) was passed through the separator and the combined organics were concentrated to afford the title compound as a colorless oil: IR (neat) 3445, 2942, 2866, 1747, 1706, 1512, 1464, 1367, 1247, 1175 cm$^{-1}$; $^1$H NMR (400 MHz, CDCl$_3$) δ 7.00 (d, J=8.6 Hz, 2H), 6.76 (d, J=8.6 Hz, 2H), 5.05-4.45 (m, 3H), 4.23-4.03 (m, 1H), 3.72 (s, 4H), 3.68 (t, J=8.2 Hz, 1H), 3.23 (d, J=13.1 Hz, 3H), 3.09-2.97 (m, 2H), 2.23 (td, J=12.9, 5.4 Hz, 1H), 2.01-1.96 (m, 1H), 1.73 (d, J=9.8 Hz, 1H), 1.42-1.32 (m, 3H), 1.13-1.05 (m, 21H), 0.99 (d, J=0.8 Hz, 9H), 0.91-0.77 (m, 3H); $^{13}$C NMR (101 MHz, CDCl$_3$) δ 155.89, 127.66, 111.86, 53.32, 45.75, 43.84, 35.14, 34.42, 26.38, 26.30, 24.77, 22.70, 17.65, 16.86, 16.56, 16.46, 15.89, 15.76, 12.07, 10.72, 10.35, 6.69, 0.00, −1.94 (Note: Peaks missing, likely due to rotamers); HRMS-ESI (m/z) ([M]+) calcd for C$_{33}$H$_{57}$NO$_7$Si, 607.3897; found, 607.3904.

Example 2

Step 1a-2: Preparation of tert-butyl((3S,7R,8R,9S)-8-hydroxy-7-(4-methoxybenzyl)-9-methyl-2-oxooxonan-3-yl)(methoxymethyl)carbamate

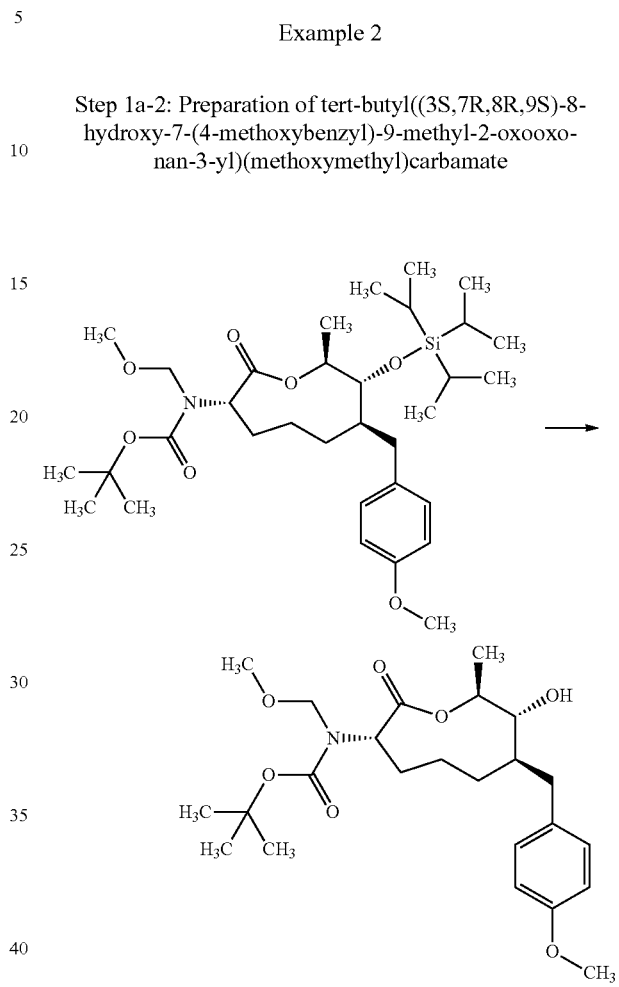

To a round bottom flask were added tert-butyl((3S,7R,8R,9S)-7-(4-methoxybenzyl)-9-methyl-2-oxo-8-((triisopropylsilyl)oxy)oxonan-3-yl)(methoxymethyl)carbamate (1.61 g, 2.65 mmol), THF (26.5 ml) and TBAF (1.0 M, 5.30 ml, 5.30 mmol) at room temperature and an exotherm noted. The reaction was stirred at room temperature until thin layer chromatography (TLC) showed complete consumption of starting material. After approximately 2 h, the reaction was quenched by the addition of NaHCO$_3$ and extracted with EtOAc (3×). The combined organic extracts were washed with brine, dried over MgSO4, concentrated, and purified by column chromatography on SiO$_2$ (0→10%, hold, 10→20%, hold, 20→50% hold EtOAc/hexanes gradient) to furnish the title product as a colorless oil (703 mg, 59%): IR (neat) 3479, 2976, 2936, 1744, 1700, 1512, 1368, 1297, 1246, 1175 cm$^{-1}$; $^1$H NMR (400 MHz, CDCl$_3$) δ 7.15-7.06 (m, 2H), 6.87-6.79 (m, 2H), 4.96-4.87 (m, 1H), 4.85-4.73 (m, 2H), 4.61-4.49 (m, 1H), 4.23-4.18 (m, 1H), 3.79 (s, 3H), 3.51 (td, J=8.8, 5.8 Hz, 1H), 3.32 (d, J=12.9 Hz, 3H), 3.01 (dd, J=13.6, 4.9 Hz, 1H), 2.44 (dd, J=16.2, 7.3 Hz, 1H), 2.07 (d, J=16.5 Hz, 1H), 1.69 (s, 2H), 1.63-1.49 (m, 3H), 1.44 (d, J=5.9 Hz, 9H), 1.40 (d, J=6.3 Hz, 3H), 0.94 (s, 1H); $^{13}$C NMR (101 MHz, CDCl$_3$) δ 173.45, 158.00, 129.72, 113.97, 76.28, 55.25, 37.08, 28.24, 27.29, 19.43, 18.18 (Note: Peaks missing, likely due to rotamers); HRMS-ESI (m/z) ([M]+) calcd for $C_{24}H_{37}NO_7$, 451.2558; found, 451.257.

Example 2

Step 1b: Preparation of tert-butyl N-[(3S,7R,8R,9S)-8-benzyloxy-9-methyl-2-oxo-7-(p-tolylmethyl)oxonan-3-yl]-N-tert-butoxycarbonyl-carbamate (F230)

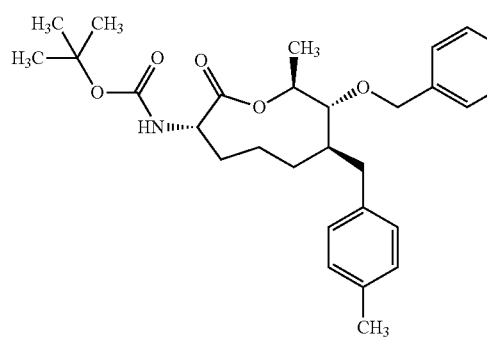

A 25 mL screw top vial was charged with tert-butyl((3S,7R,8R,9S)-8-(benzyloxy)-9-methyl-7-(4-methylbenzyl)-2-oxooxonan-3-yl)carbamate (720 mg, 1.50 mmol), DMAP (91.0 mg, 0.75 mmol), and anhydrous $CH_3CN$ (7.5 mL). To the mixture was added di-tert-butyl dicarbonate (1.30 g, 5.98 mmol) and the reaction was stirred at room temperature for 17 h and then warmed to 50° C. and stirred for an additional 29 h. The reaction mixture was concentrated under a gentle stream of $N_2$ and the crude concentrate was purified by column chromatography on $SiO_2$ (gradient, 020% acetone in hexane) to give tert-butyl((3S,7R,8R,9S)-8-(benzyloxy)-9-methyl-7-(4-methylbenzyl)-2-oxooxonan-3-yl)carbamate as a white solid (167 mg, 19%): mp 164-166° C.; $^1$H NMR (400 MHz, $CDCl_3$) δ 7.41-7.26 (m, 5H), 7.07 (d, J=8.1 Hz, 2H), 7.03 (d, J=8.0 Hz, 2H), 4.88-4.75 (m, 3H), 4.61 (d, J=10.8 Hz, 1H), 3.35 (t, J=9.1 Hz, 1H), 3.10 (dd, J=13.3, 3.3 Hz, 1H), 2.40-2.28 (m, 4H), 2.22 (tt, J=13.5, 7.2 Hz, 1H), 2.02-1.88 (m, 2H), 1.64-1.41 (m, 24H), 0.96-0.84 (m, 1H); $^{13}$C NMR (101 MHz, $CDCl_3$) δ 171.13, 152.83 (2C), 137.98, 137.51, 135.31, 129.01, 128.77, 128.54, 127.89, 127.76, 84.14, 82.64 (2C), 75.44, 75.21, 57.57, 45.77, 36.43, 30.83, 27.97 (6C), 26.84, 21.04, 19.67, 18.49; ESIMS m/z 604 ([M+Na]+).

Example 3

Step 1: Preparation of tert-butyl((3S,7R,8R,9S)-8-(allyloxy)-7-(4-methoxybenzyl)-9-methyl-2-oxooxonan-3-yl)(methoxymethyl)carbamate

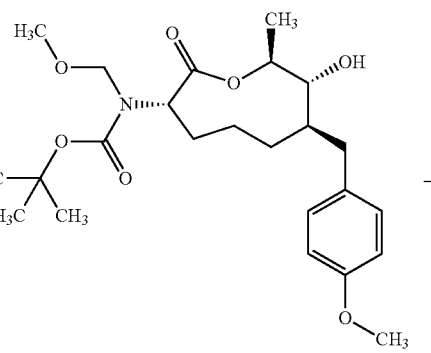

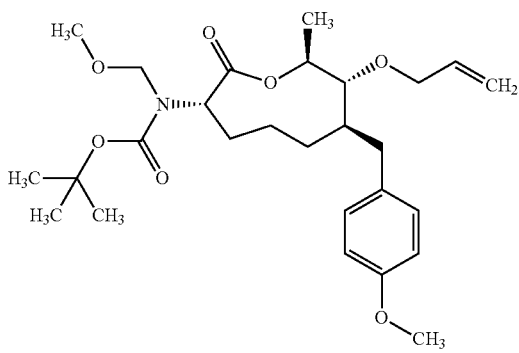

A solution of tert-butyl((3S,7R,8R,9S)-8-hydroxy-7-(4-methoxybenzyl)-9-methyl-2-oxooxonan-3-yl)(methoxymethyl)carbamate (350 mg, 0.775 mmol), palladium tetrakis (triphenylphosphine) (90 mg, 0.078 mmol), and allyl tert-butyl carbonate (758 mg, 4.79 mmol) in degassed THF (3876 μl) was heated to 60° C. and stirred for 4 h. The reaction mixture was cooled to room temperature and purified directly by column chromatography on $SiO_2$ (EtOAc/Hex gradient) to afford the title product as a light yellow oil (200 mg, 52.5%): IR (neat) 2977, 2934, 2836, 1746, 1702, 1511, 1367, 1297, 1246, 1175 cm$^{-1}$; $^1$H NMR (400 MHz, $CDCl_3$) δ 7.07 (d, J=8.5 Hz, 2H), 6.81 (d, J=8.6 Hz, 2H), 6.02-5.88 (m, 1H), 5.33 (dd, J=17.2, 1.6 Hz, 1H), 5.20 (dd, J=10.4, 1.5 Hz, 1H), 4.94-4.81 (m, 2H), 4.76 (t, J=10.3 Hz, 1H), 4.60-4.50 (m, 1H), 4.28 (dd, J=11.8, 5.6 Hz, 1H), 4.22-4.15 (m, 1H), 4.09 (dd, J=11.9, 5.3 Hz, 1H), 3.78 (s, 3H), 3.30 (d, J=14.5 Hz, 3H), 3.21 (t, J=9.0 Hz, 1H), 3.03 (dd, J=13.5, 3.4 Hz, 1H), 2.34-2.22 (m, 1H), 2.15-1.98 (m, 1H), 1.80 (s, 1H), 1.65-1.59 (m, 2H), 1.50-1.39 (m, 13H), 0.90-0.76 (m, 1H); $^{13}$C NMR (101 MHz, $CDCl_3$) δ 173.53, 157.82, 134.40, 134.36, 132.63, 129.69, 117.12, 113.73, 84.28, 84.24, 81.09, 74.62, 58.57, 57.06, 55.24, 55.22, 46.01, 35.97, 28.32, 28.23, 26.57, 19.22, 18.26; HRMS-ESI (m/z) ([M]$^+$) calcd for C$_{27}$H$_{41}$NO$_7$, 491.2883; found, 491.2862.

Example 3

Step 2a: Preparation of tert-butyl((3S,7R,8R,9S)-7-(4-methoxybenzyl)-9-methyl-2-oxo-8-propoxyoxonan-3-yl)(methoxymethyl)carbamate (F221)

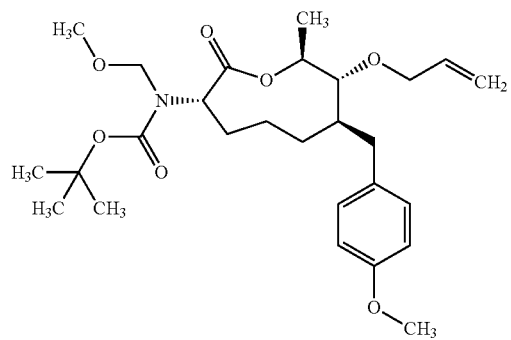

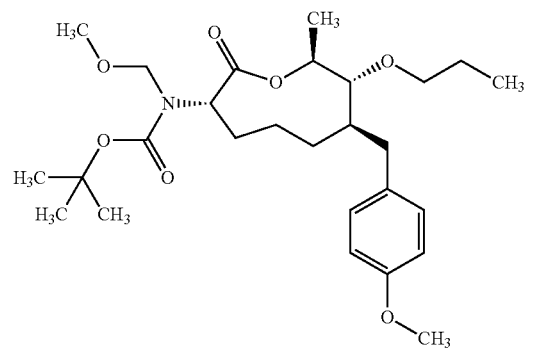

A vial was charged with 5 wt % Pd/C (26.0 mg, 0.012 mmol) and a solution of tert-butyl((3S,7R,8R,9S)-8-(allyloxy)-7-(4-methoxybenzyl)-9-methyl-2-oxooxonan-3-yl)(methoxymethyl)carbamate (200 mg, 0.407 mmol) in EtOAc (1 mL). The vial was evacuated and backfilled with H$_2$ (3×) and then stirred vigorously under one atmosphere of H$_2$ (balloon) at room temperature for 15 h. The reaction mixture was filtered through a plug of Celite® and concentrated to the title compound as a colorless oil (168 mg, 84%) IR (neat) 3368, 2973, 2936, 2877, 1746, 1705, 1511, 1454, 1367, 1175 cm$^{-1}$; $^1$H NMR (400 MHz, CDCl$_3$) δ 7.12-7.03 (m, 2H), 6.87-6.77 (m, 2H), 5.04-4.67 (m, 2H), 4.21-4.09 (m, 1H), 3.78 (s, 3H), 3.71 (dtd, J=8.6, 6.8, 1.9 Hz, 1H), 3.50 (dtd, J=8.4, 6.6, 1.7 Hz, 1H), 3.34-3.25 (m, 3H), 3.12 (td, J=9.3, 3.6 Hz, 1H), 3.07-2.98 (m, 1H), 2.27 (ddd, J=13.4, 11.7, 6.2 Hz, 1H), 2.07 (s, 2H), 1.76 (s, 1H), 1.71-1.54 (m, 4H), 1.55-1.33 (m, 14H), 0.97 (td, J=7.4, 1.0 Hz, 3H), 0.81 (s, 1H); $^{13}$C NMR (101 MHz, CDCl$_3$) δ 173.30, 157.80, 132.75, 129.69, 113.73, 99.98, 84.02, 83.99, 81.11, 75.59, 75.52, 55.25, 55.23, 46.20, 35.86, 35.82, 28.32, 26.56, 23.59, 19.21, 18.19, 18.12, 10.75; HRMS-ESI (m/z) ([M]$^+$) calcd for C$_{27}$H$_{43}$NO$_7$, 493.3040; found, 493.3018.

Example 3

Step 2b-1: Preparation of tert-butyl((3S,7R,8R,9S)-7-(4-fluorobenzyl)-9-methyl-2-oxo-8-(2-oxoethoxyl)oxonan-3-yl)(methoxymethyl)carbamate

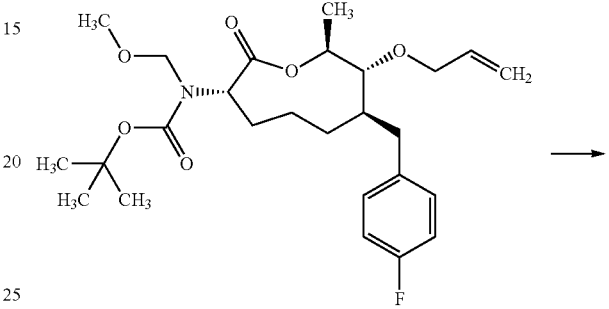

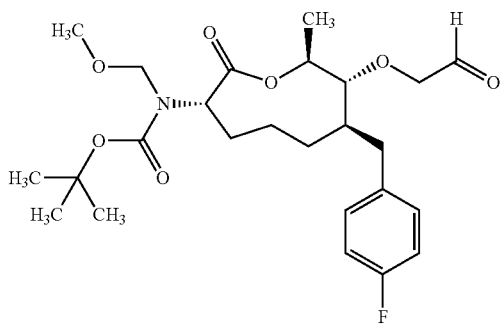

A mixture of tert-butyl((3S,7R,8R,9S)-8-(allyloxy)-7-(4-fluorobenzyl)-9-methyl-2-oxooxonan-3-yl)(methoxymethyl)carbamate (480 mg, 1.001 mmol), NaHCO$_3$ (8.41 mg, 0.10 mmol) and anhydrous MeOH (0.31 mL) in anhydrous CH$_2$Cl$_2$ (9.7 mL) was treated with ozone at −78° C. until the solution became light blue in color. The mixture was purged with nitrogen until colorless and then quenched by addition of dimethyl sulfide (0.148 mL, 2.00 mmol). The reaction mixture was warmed to room temperature and stirred for 20 h, concentrated, and purified by column chromatography on SiO$_2$ (gradient, hexanes/EtOAc) to provide the title compound as a mixture of rotamers in the form of a white solid (461 mg, 96%): mp 51-53° C.; IR (neat) 2935, 1740, 1701, 1509, 1367, 1297, 1173, 1081 cm$^{-1}$; $^1$H NMR (400 MHz, CDCl$_3$) δ 9.68 (s, 1H), 7.17-7.06 (m, 2H), 7.00-6.91 (m, 2H), 4.99-4.16 (m, 6H), 3.87-2.97 (m, 4H), 2.46-2.27 (m, 1H), 2.17-2.01 (m, 1H), 1.97-1.75 (m, 1H), 1.74-1.37 (m, 17H), 0.95-0.78 (m, 1H); HRMS-ESI (m/z) ([M]$^+$) calcd for C$_{25}$H$_{36}$FNO$_7$, 481.2476; found, 481.2481.

Example 3

Step 2b-2: Preparation of tert-butyl((3S,7R,8R,9S)-8-(2,2-difluoro-ethoxy)-7-(4-fluorobenzyl)-9-methyl-2-oxooxonan-3-yl)(methoxymethyl)carbamate (F212)

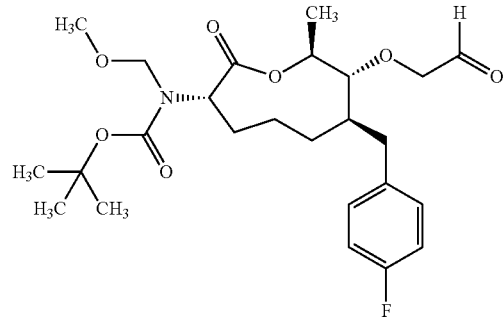

To a solution of tert-butyl((3S,7R,8R,9S)-7-(4-fluorobenzyl)-9-methyl-2-oxo-8-(2-oxoethoxy)oxonan-3-yl)(methoxymethyl)carbamate (461 mg, 0.957 mmol) in anhydrous CH$_2$Cl$_2$ (6.0 mL) at 0° C. was added a ~50% toluene solution of Deoxo-Fluor® (0.710 mL, 1.92 mmol) in anhydrous CH$_2$Cl$_2$ (4 mL) dropwise at 0° C. and the reaction mixture was stirred at 0° C. for 1 h. The reaction mixture was concentrated and purified by column chromatography on SiO$_2$ (gradient, hexanes/EtOAc) to provide the title compound as a mixture of rotamers in the form of a white solid (399 mg, 83%): IR (neat) 2978, 2938, 1747, 1700, 1509, 1368, 1297, 1080 cm$^{-1}$; $^1$H NMR (400 MHz, CDCl$_3$) δ 7.16-7.04 (m, 2H), 7.02-6.89 (m, 2H), 5.86 (tt, J=55.1, 4.0 Hz, 1H), 4.95-4.71 (m, 3H), 4.60-4.46 (m, 0.5H), 4.25-4.13 (m, 0.5H), 4.04-3.89 (m, 1H), 3.84-3.69 (m, 1H), 3.37-3.18 (m, 3H), 3.03 (dd, J=13.3, 3.5 Hz, 1H), 2.41-2.30 (m, 1H), 2.19-1.99 (m, 1H), 1.88-1.75 (m, 1H), 1.72-1.32 (m, 17H), 0.93-0.75 (m, 1H); $^{19}$F NMR (376 MHz, CDCl$_3$) δ −117.16, −117.27, −125.28-− 125.61 (m, 2F); HRMS-ESI (m/z) ([M]$^+$) calcd for C$_{25}$H$_{36}$F$_3$NO$_6$, 503.2495; found, 503.2499.

Example 4

Step 1: tert-butyl((3S,7R,8R,9S)-7-(4-methoxybenzyl)-9-methyl-2-oxo-8-((3-oxobut-1-en-1-yl)oxy)oxonan-3-yl)(methoxymethyl)carbamate

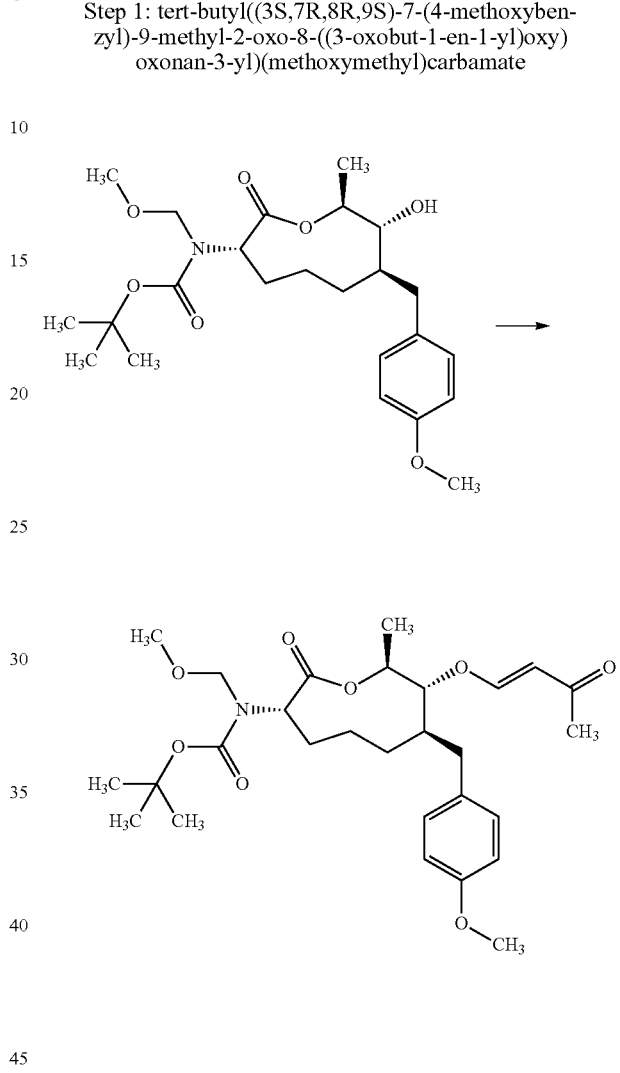

A round bottomed flask was charged with tert-butyl((3S,7R,8R,9S)-8-hydroxy-7-(4-methoxybenzyl)-9-methyl-2-oxooxonan-3-yl)(methoxymethyl)carbamate (400 mg, 0.886 mmol) in CH$_2$Cl$_2$ (4429 μl). To the solution was added DABCO (4.97 mg, 0.044 mmol) and the reaction mixture was cooled to 0° C. under N$_2$. Upon addition of but-3-yn-2-one (83 μl, 1.063 mmol), the colorless solution became dark brown-orange. After stirring for 2 h, the reaction mixture was concentrated and purified directly by column chromatography on SiO$_2$ (0→10%, hold, 10→20%, hold, 20→50% hold EtOAc/hexanes gradient) to afford the title compound as a thick colorless oil (257 mg, 55.8%): $^1$H NMR (400 MHz, CDCl$_3$) δ 7.43 (d, J=12.2 Hz, 1H), 7.03 (d, J=8.6 Hz, 2H), 6.81 (d, J=8.6 Hz, 2H), 5.75 (d, J=12.4 Hz, 1H), 5.06-4.85 (m, 2H), 4.82-4.73 (m, 1H), 4.61-4.50 (m, 1H), 4.26-4.14 (m, 1H), 3.78 (s, 3H), 3.37-3.26 (m, 3H), 2.82 (dd, J=13.6, 4.0 Hz, 1H), 2.41-2.28 (m, 1H), 2.24-2.01 (m, 1H), 2.18 (s, 3H), 1.62-1.39 (m, 12H), 1.34 (d, J=6.4 Hz, 3H), 1.26 (t, J=7.1 Hz, 2H), 0.92 (dt, J=13.6, 4.6 Hz, 1H); $^{13}$C NMR (101 MHz, CDCl$_3$) δ 197.24, 173.18, 163.24, 158.03, 155.34, 131.19, 129.61, 113.83, 108.08, 88.73, 88.61, 81.19, 76.86, 76.23, 75.39, 72.61, 72.49, 58.42, 56.97, 55.41, 55.14, 44.87, 35.82, 30.38, 29.45, 28.43, 28.27, 28.16, 26.38, 26.18, 19.16, 18.24; ESIMS m/z 542.4 ([M+Na]+).

Example 4

Step 2: Preparation of ((3S,7R,8R,9S)-7-(4-methoxybenzyl)-9-methyl-2-oxo-8-(3-oxobutoxy)oxonan-3-yl)(methoxymethyl)carbamate

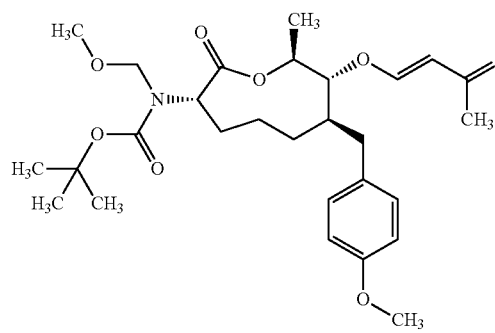

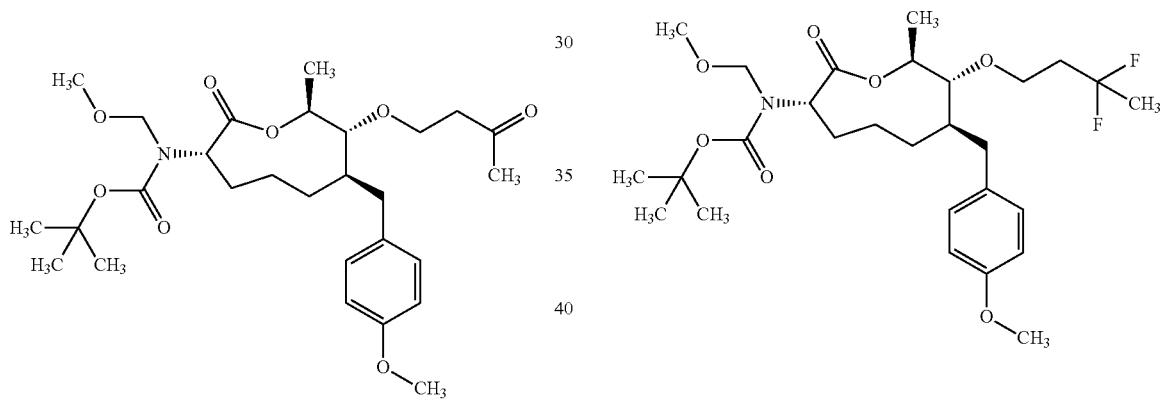

A round bottomed flask was charged with tert-butyl((3S,7R,8R,9S)-7-(4-methoxybenzyl)-9-methyl-2-oxo-8-((3-oxobut-1-en-1-yl)oxy)oxonan-3-yl)(methoxymethyl)-carbamate (257 mg, 0.495 mmol), 5 wt % Pd/C (35 mg, 0.033 mmol) and EtOAc (4 mL). The reaction flask was briefly evacuated under vacuum and backfilled with H₂ (3×) and then stirred vigorously under an H₂ atmosphere at room temperature overnight. The reaction mixture was filtered through a plug of Celite® and concentrated to afford the title compound as a colorless oil (256 mg, 99%): ¹H NMR (400 MHz, CDCl₃) δ 7.14-7.01 (m, 2H), 6.87-6.77 (m, 2H), 4.94-4.73 (m, 3H), 4.08-3.95 (m, 1H), 3.88-3.71 (m, 1H), 3.78 (s, 3H), 3.39-3.25 (m, 3H), 3.21-3.09 (m, 1H), 3.07-2.88 (m, 1H), 2.70 (t, J=6.2 Hz, 1H), 2.37-2.22 (m, 1H), 2.20 (s, 2H), 1.80-1.59 (m, 3H), 1.58-1.35 (m, 16H), 1.32-1.17 (m, 2H), 0.86-0.71 (m, 1H); ¹³C NMR (101 MHz, CDCl₃) δ 206.65, 173.53, 157.82, 132.63, 129.72, 129.68, 113.81, 113.74, 84.56, 68.21, 55.23, 45.95, 43.90, 35.95, 30.73, 28.31, 28.21, 21.05, 19.42, 19.26, 18.17; ESIMS m/z 544.3 ([M+Na]+).

Example 4

Step 3: Preparation of tert-butyl((3S,7R,8R,9S)-8-(3,3-difluorobutoxy)-7-(4-methoxybenzyl)-9-methyl-2-oxooxonan-3-yl)(methoxymethyl)carbamate (F218)

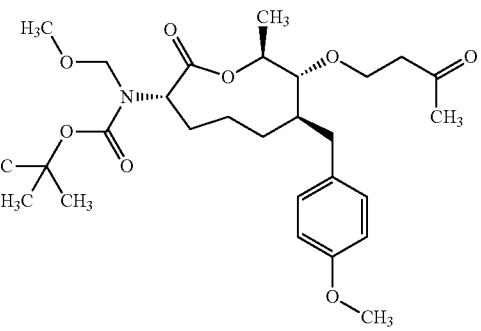

A 20 mL vial was charged with tert-butyl((3S,7R,8R,9S)-7-(4-methoxybenzyl)-9-methyl-2-oxo-8-(3-oxobutoxy)oxonan-3-yl)(methoxymethyl)carbamate (250 mg, 0.479 mmol), CH₂Cl₂ (3 mL) and Deoxo-Fluor® (1.04 g, 2.35 mmol) and the mixture was stirred vigorously at room temperature under N₂ for 12 h. An additional portion of Deoxo-Fluor® (900 mg, 4.07 mmol) was added and reaction was stirred for an additional 48 h. Upon complete consumption of starting material, the reaction mixture was quenched (carefully!) with saturated aqueous NaHCO₃ solution and extracted with CH₂Cl₂ (3×). The mixture was passed through a phase separator and the organic phase was concentrated, and purified by column chromatography on SiO₂ (gradient, hexanes/EtOAc) to provide the title compound as a colorless oil (106.6 mg, 40.9%): ¹H NMR (400 MHz, CDCl₃) δ 7.10-7.00 (m, 2H), 6.88-6.76 (m, 2H), 4.97-4.82 (m, 2H), 4.81-4.71 (m, 1H), 4.55 (s, 1H), 4.19 (t, J=9.6 Hz, 1H), 3.97-3.84 (m, 1H), 3.78 (s, 3H), 3.72 (dt, J=9.1, 6.8 Hz, 1H), 3.37-3.26 (m, 3H), 3.14 (td, J=8.9, 3.2 Hz, 1H), 2.97 (dd, J=13.4, 3.5 Hz, 1H), 2.37-2.24 (m, 1H), 2.26-2.02 (m, 3H), 1.81-1.57 (m, 5H), 1.58-1.23 (m, 14H), 0.89-0.77 (m, 1H); $^{19}$F NMR (376 MHz, CDCl$_3$) δ −89.52, −89.56 (d, J=72.5 Hz); ESIMS m/z 566.3 ([M+Na]$^+$).

Example 5

Preparation of (2S,3R,4R,8S)-8-((tert-butoxycarbonyl)-(methoxymethyl)-amino)-4-(4-methoxybenzyl)-2-methyl-9-oxooxonan-3-yl cyclopentanecarboxylate (F217)

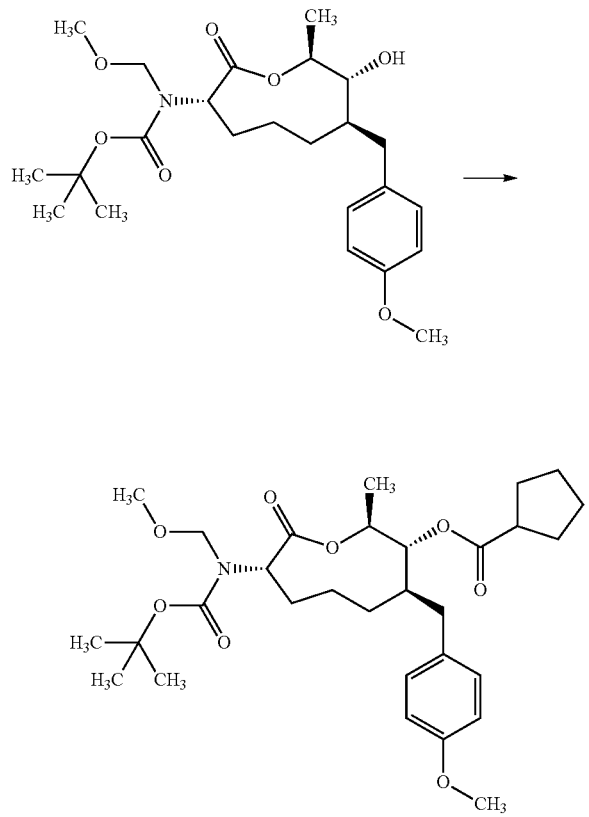

A 20 mL vial was charged with tert-butyl((3S,7R,8R,9S)-8-hydroxy-7-(4-methoxybenzyl)-9-methyl-2-oxooxonan-3-yl)(methoxymethyl)carbamate (200 mg, 0.443 mmol), CH$_2$Cl$_2$ (2215 µl), NEt$_3$ (185 µl, 1.329 mmol) and DMAP (5.41 mg, 0.044 mmol). The reaction mixture was cooled to 0° C. in an ice bath under N$_2$ and cyclopentanecarbonyl chloride (76 mg, 0.576 mmol) was added in one portion. The reaction became dark brownish-yellow. After stirring for 2 h, the reaction mixture was quenched by the addition of saturated aqueous NaHCO$_3$. The mixture was extracted with CH$_2$Cl$_2$ (3×) and the combined organic layers were washed with brine, dried over MgSO4, concentrated, and purified by column chromatography on SiO$_2$ (0→100% EtAOx/hexanes) to provide the title compound as a yellow solid (85 mg, 35.0%): $^1$H NMR (400 MHz, CDCl$_3$) δ 7.01 (d, J=8.5 Hz, 4H), 6.81 (d, J=8.4 Hz, 4H), 5.06-4.85 (m, 3H), 4.77 (d, J=11.6 Hz, 1H), 4.57 (dd, J=10.7, 6.0 Hz, 0H), 4.29-4.17 (m, 1H), 3.78 (s, 3H), 3.38-3.26 (m, 3H), 2.74 (p, J=8.0 Hz, 1H), 2.61 (dd, J=13.7, 3.7 Hz, 1H), 2.31 (dd, J=13.7, 11.1 Hz, 1H), 2.20-2.07 (m, 1H), 1.99-1.52 (m, 8H), 1.51-1.40 (m, 9H), 1.27 (d, J=5.8 Hz, 3H), 1.15-0.96 (m, 1H), 0.97-0.87 (m, 1H); $^{13}$C NMR (101 MHz, CDCl$_3$) δ 176.26, 173.56, 157.94, 155.49, 131.94, 129.59, 113.80, 81.21, 75.54, 72.72, 58.52, 55.43, 55.22, 44.32, 44.04, 35.77, 30.09, 30.00, 29.58, 28.20, 26.48, 25.72, 25.70, 19.09, 17.56; ESIMS m/z 570.5 ([M+Na]$^+$).

Example 6

Preparation of tert-butyl((3S,7R,8R,9S)-7-isopentyl-8-methoxy-9-methyl-2-oxooxonan-3-yl)(methoxymethyl)carbamate (F205)

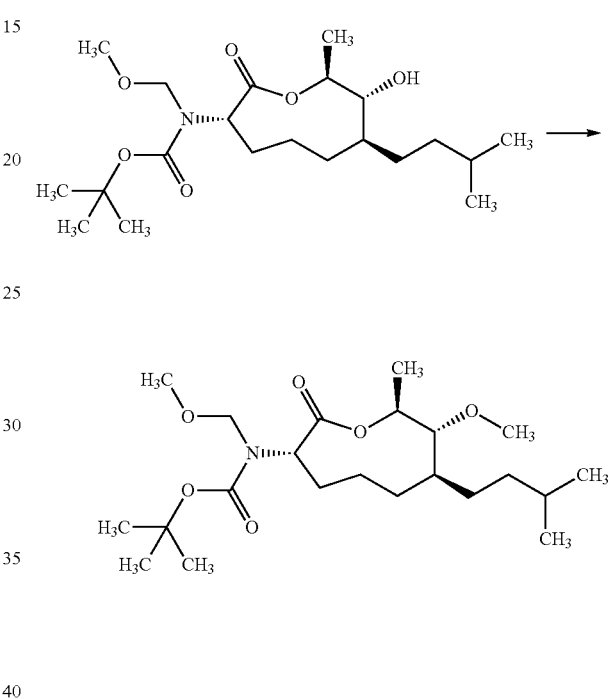

To an oven-dried vial were added N1,N1,N8,N8-tetramethylnaphthalene-1,8-diamine (Proton Sponge®; 1.63 g, 7.60 mmol), tert-butyl((3S,7R,8R,9S)-8-hydroxy-7-isopentyl-9-methyl-2-oxooxonan-3-yl)(methoxymethyl)carbamate (436 mg, 1.086 mmol), anhydrous Na$_2$SO$_4$ (1.15 g, 8.10 mmol), and trimethyloxonium tetrafluoroborate (723 mg, 4.89 mmol) in anhydrous CH$_2$Cl$_2$ (11 mL) at 0° C. The reaction mixture was slowly warmed to room temperature and stirred for 5 h. The reaction mixture was diluted with EtOAc, filtered, and the filtrate was washed with water. The phases were separated and the aqueous phase was extracted with additional EtOAc, and the combined organic phases were washed with 1.0 M aqueous sodium bisulfate (NaHSO$_4$), washed with saturated aqueous NaHCO$_3$, dried over MgSO$_4$, concentrated, and purified by column chromatography on SiO$_2$ (gradient, hexanes/EtOAc) to provide the title compound as a mixture of rotamers in the form of a white solid (320 mg, 71%): IR (neat) 2934, 1747, 1705, 1454, 1366, 1296, 1170, 1080 cm$^{-1}$; $^1$H NMR (400 MHz, CDCl$_3$) δ 4.97-4.70 (m, 3H), 4.60-4.47 (m, 0.5H), 4.25-4.11 (m, 0.5H), 3.49 (s, 3H), 3.40-3.28 (m, 3H), 2.97-2.86 (m, 1H), 2.17-2.01 (m, 1H), 1.79-1.42 (m, 16H), 1.42 (d, J=6.4 Hz, 3H), 1.31-1.07 (m, 3H), 0.99-0.82 (m, 7H); $^{13}$C NMR (101 MHz, CDCl$_3$) δ 173.54, 155.56, 155.39, 86.39, 81.02, 80.98, 76.34, 75.50, 74.70, 74.43, 61.04, 58.62, 57.11, 55.45, 55.36, 43.42, 36.40, 30.67, 29.62, 28.20, 28.15, 28.09, 27.31, 27.04, 23.05, 22.12, 19.19, 18.10; HRMS-ESI (m/z) ([M]+) calcd for $C_{22}H_{41}NO_6$, 415.2934; found, 415.2943.

Example 7

Step 1: Preparation of tert-butyl((3S,7R,8R,9S)-7-(2-hydroxyethyl)-9-methyl-2-oxo-8-phenoxyoxonan-3-yl)carbamate

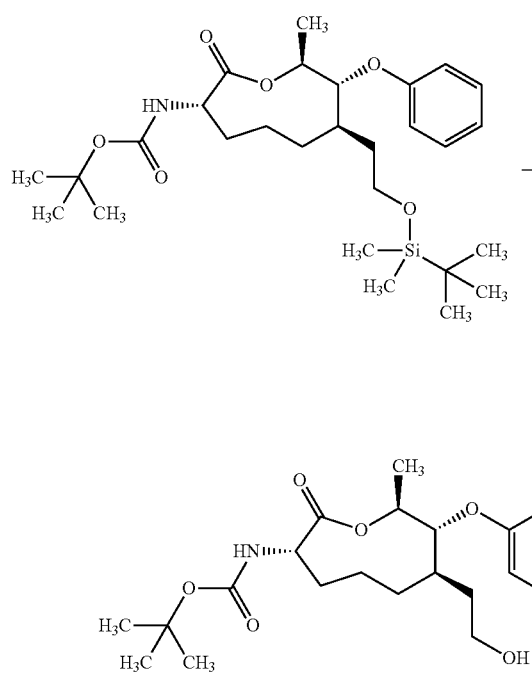

To a solution of tert-butyl((3S,7R,8R,9S)-7-(2-((tert-butyldimethylsilyl)-oxy)ethyl)-9-methyl-2-oxo-8-phenoxy-oxonan-3-yl)carbamate (3.01 g, 5.77 mmol) in anhydrous THF (58 mL) was added a 1M solution of TBAF in THF (8.65 ml, 8.65 mmol). The resulting yellow solution was stirred at room temperature for 4 h, poured into 100 mL ½ saturated NaCl solution, and extracted with EtOAc (3×50 mL). The organic extracts were combined, dried over MgSO$_4$, filtered, and concentrated to provide a light yellow oil, which was purified by column chromatography on SiO$_2$ (5→25% acetone/hexanes) to provide the title compound as a hard white foam (1.95 g, 83%): $^1$H NMR (400 MHz, CDCl$_3$) δ 7.44-7.17 (m, 2H), 6.95 (t, J=8.2 Hz, 3H), 5.17-4.98 (m, 2H), 4.29-4.11 (m, 2H), 3.75-3.53 (m, 2H), 2.28 (dt, J=13.4, 6.7 Hz, 1H), 2.03-1.88 (m, 1H), 1.88-1.74 (m, 2H), 1.74-1.62 (m, 1H), 1.62-1.48 (m, 2H), 1.44 (s, 10H), 1.28 (d, J=6.5 Hz, 3H), 1.26-1.19 (m, 1H), 1.14 (ddd, J=15.1, 7.5, 3.6 Hz, 1H); $^{13}$C NMR (101 MHz, CDCl$_3$) δ 173.30, 159.23, 154.90, 129.69, 121.20, 115.33, 80.99, 79.92, 74.68, 60.96, 52.99, 39.55, 34.07, 28.56, 28.33, 19.13, 18.36; ESIMS m/z 408.3 ([M+H]+), 430.3 ([M+Na]+).

Example 7

Step 2a: Preparation of tert-butyl((3S,7R,8R,9S)-9-methyl-2-oxo-8-phenoxy-7-(2-phenoxyethyl)oxonan-3-yl)carbamate (F240)

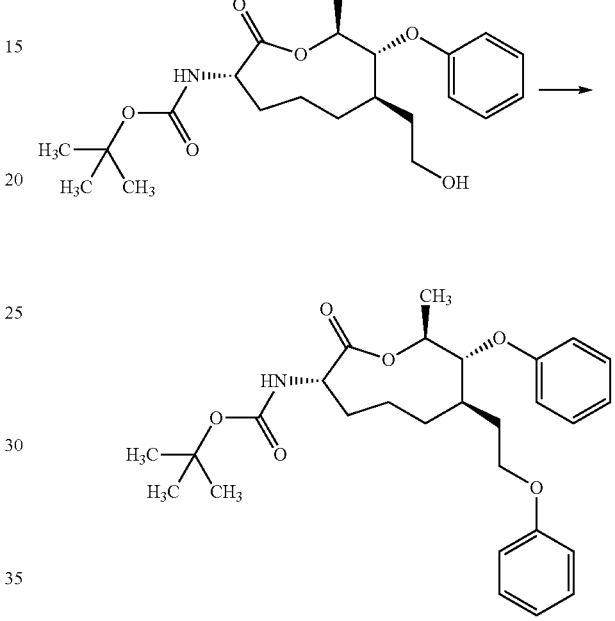

To a solution of tert-butyl((3S,7R,8R,9S)-7-(2-hydroxyethyl)-9-methyl-2-oxo-8-phenoxyoxonan-3-yl)carbamate (215 mg, 0.528 mmol) in anhydrous toluene (5.3 mL) were added Ph$_3$Bi(OAc)$_2$ (354 mg, 0.633 mmol), diacetoxycopper (19.17 mg, 0.106 mmol), and N-cyclohexyl-N-methylcyclohexanamine (224 μl, 1.055 mmol). The resulting mixture was heated to 50° C. for 20 h, cooled to room temperature, filtered through a plug of Celite®, and rinsed the plug with toluene. The filtrate was concentrated and purified by column chromatography on SiO$_2$ (2→20% acetone/hexanes) to provide the title compound as a sticky oil (253 mg). $^1$H NMR gives the desired product, but it is contaminated with Cy$_2$NMe. The oil was dissolved in CH$_2$Cl$_2$ (25 mL) and the solution was washed with 0.2 M HCl (25 mL), dried over Na$_2$SO$_4$, decanted, and concentrated to provide 234 mg of the desired product as a hard white foam. The product was repurified by column chromatography on SiO$_2$ (5→20% acetone/hexanes) to provide the title compound as a hard white foam (199 mg, 78%): $^1$H NMR (400 MHz, CDCl$_3$) δ 7.33-7.20 (m, 4H), 6.93 (p, J=7.4 Hz, 4H), 6.86-6.75 (m, 2H), 5.21-4.97 (m, 2H), 4.32-4.11 (m, 2H), 3.94 (t, J=6.6 Hz, 2H), 2.34-2.22 (m, 1H), 2.06 (dd, J=16.4, 4.9 Hz, 2H), 1.93 (d, J=12.6 Hz, 1H), 1.89-1.78 (m, 1H), 1.78-1.65 (m, 2H), 1.44 (s, 9H), 1.31 (d, J=6.5 Hz, 3H), 1.19 (dd, J=25.8, 13.7 Hz, 2H); $^{13}$C NMR (101 MHz, CDCl$_3$) δ 173.28, 159.34, 158.76, 154.89, 129.68, 129.39, 121.17, 120.61, 115.40, 114.42, 99.98, 81.14, 79.92, 74.68, 66.01, 53.01, 40.14, 34.11, 30.49, 19.20, 18.35; ESIMS m/z 484.3 ([M+H]+).

Example 7

Step 2b: Preparation of tert-butyl((3S,7R,8R,9S)-7-(2-methoxyethyl)-9-methyl-2-oxo-8-phenoxyoxonan-3-yl)carbamate (F242)

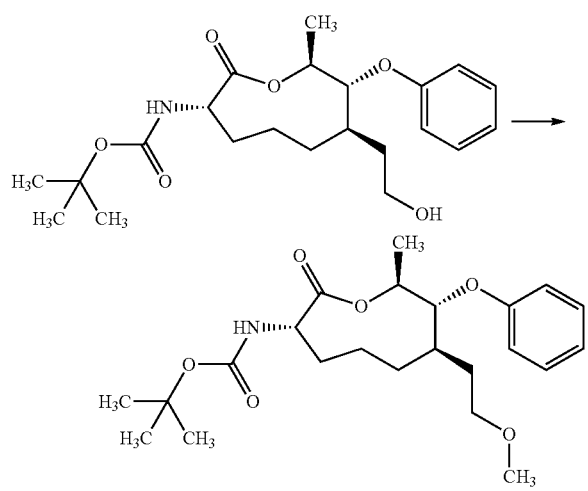

To a solution of tert-butyl((3S,7R,8R,9S)-7-(2-hydroxyethyl)-9-methyl-2-oxo-8-phenoxyoxonan-3-yl)carbamate (400 mg, 0.982 mmol) and Proton Sponge® (841 mg, 3.93 mmol) in anhydrous $CH_2Cl_2$ (10 mL) at 0° C. (icewater bath) was added trimethyloxonium tetrafluoroborate (290 mg, 1.963 mmol; weighed under $N_2$), and the resulting mixture was stirred at 0° C. for 3 h, quenched with 1N HCl (20 mL), and extracted with $CH_2Cl_2$ (3×20 mL). The organic extracts were combined, dried over $Na_2SO_4$, filtered, and concentrated to provide an oily white solid, which was purified by column chromatography on $SiO_2$ (5→20% acetone/hexanes) to provide the title compound as a white, crystalline solid (321 mg, 78%): $^1$H NMR (400 MHz, $CDCl_3$) δ 7.27 (t, J=8.0 Hz, 2H), 6.94 (dd, J=7.7, 3.3 Hz, 3H), 5.10 (d, J=8.1 Hz, 1H), 5.08-4.98 (m, 1H), 4.20 (q, J=7.9, 6.9 Hz, 2H), 3.36 (t, J=6.5 Hz, 2H), 3.25 (s, 3H), 2.27 (dt, J=13.3, 6.8 Hz, 1H), 1.88 (ddt, J=10.8, 6.9, 3.9 Hz, 2H), 1.83-1.71 (m, 1H), 1.70-1.61 (m, 1H), 1.60-1.52 (m, 1H), 1.44 (s, 10H), 1.28 (d, J=6.5 Hz, 3H), 1.25-1.16 (m, 1H), 1.16-1.05 (m, 1H); $^{13}$C NMR (101 MHz, $CDCl_3$) δ 173.28, 159.46, 154.90, 129.61, 121.05, 115.38, 81.12, 79.86, 74.71, 70.79, 58.42, 52.99, 40.09, 34.12, 30.53, 28.33, 28.15, 19.07, 18.36; ESIMS m/z 422.3 ([M+H]$^+$), 444.3 ([M+Na]$^+$).

Example 7

Step 2c-1: Preparation of tert-butyl((3S,7R,8R,9S)-9-methyl-2-oxo-7-(2-oxoethyl)-8-phenoxyoxonan-3-yl)carbamate

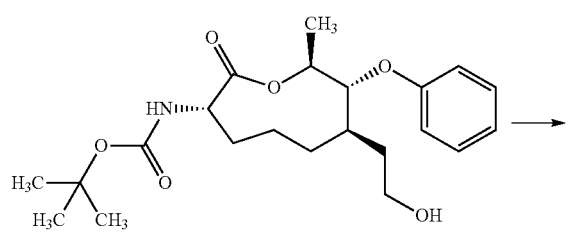

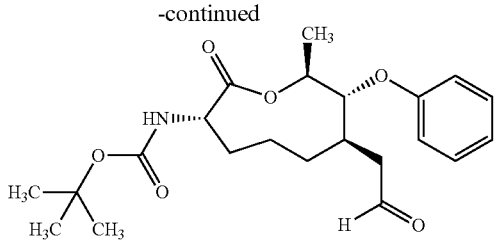

To a solution of tert-butyl((3S,7R,8R,9S)-7-(2-hydroxyethyl)-9-methyl-2-oxo-8-phenoxyoxonan-3-yl)carbamate (250 mg, 0.613 mmol) in $CH_2Cl_2$ (6.1 mL) at 0° C. was added Dess-Martin periodinane (286 mg, 0.675 mmol). The resulting mixture was stirred at 0° C. for 2 h, quenched with sat. aqueous sodium thiosulfate ($Na_2S_2O_3$; 3 mL) and sat. aqueous $NaHCO_3$ (3 mL) solution, and then removed from the cold bath and stirred vigorously for 10 min. The phases were separated and the aqueous phase was extracted with $CH_2Cl_2$ (2×6 mL) and the combined organic extracts were dried over $Na_2SO_4$, filtered, and concentrated to provide the title compound as a fluffy white foam (255.4 mg, 98%): $^1$H NMR (400 MHz, $CDCl_3$) δ 9.65 (t, J=1.7 Hz, 1H), 7.29 (dd, J=8.7, 7.4 Hz, 2H), 7.02-6.93 (m, 1H), 6.88 (d, J=7.9 Hz, 2H), 5.23-5.08 (m, 2H), 4.30-4.10 (m, 2H), 2.60 (dd, J=16.0, 5.4 Hz, 1H), 2.44 (d, J=6.4 Hz, 1H), 2.38-2.21 (m, 2H), 1.73 (ddd, J=19.5, 13.8, 9.2 Hz, 3H), 1.44 (s, 9H), 1.37-1.22 (m, 5H); $^{13}$C NMR (101 MHz, $CDCl_3$) δ 200.78, 173.29, 158.65, 154.90, 129.80, 129.73, 121.59, 115.23, 80.63, 79.98, 74.23, 53.28, 46.09, 36.71, 33.64, 31.78, 28.33, 19.72, 18.18; ESIMS m/z 428.2 ([M+Na]$^+$).

Example 7

Step 2c-2: Preparation of tert-butyl((3S,7R,8R,9S)-7-(2,2-difluoroethyl)-9-methyl-2-oxo-8-phenoxyoxonan-3-yl)carbamate

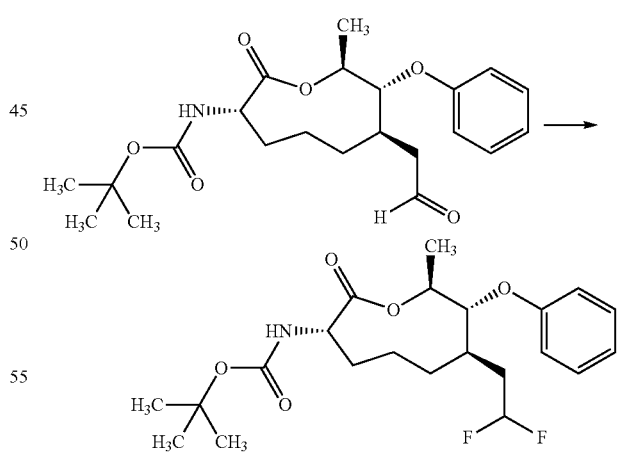

To a solution of tert-butyl((3S,7R,8R,9S)-9-methyl-2-oxo-7-(2-oxoethyl)-8-phenoxyoxonan-3-yl)carbamate (241 mg, 0.594 mmol) in anhydrous $CH_2Cl_2$ (6 mL) at 0° C. (icewater bath) was added Deoxo-Fluor® (230 µl, 1.248 mmol). The reaction was stirred for 2.5 h, concentrated, and purified by column chromatography on $SiO_2$ (220% acetone/hexanes) to provide the title compound as a white crystalline solid (153.2 mg, 60.3%): $^1$H NMR (400 MHz, $CDCl_3$) δ 7.29 (dtd, J=10.1, 4.8, 2.5 Hz, 2H), 7.01-6.95 (m, 1H), 6.93 (d, J=8.0 Hz, 2H), 5.83 (tt, J=57.0, 4.6 Hz, 1H), 5.18-5.00 (m, 2H), 4.21 (q, J=8.7 Hz, 2H), 2.29 (dt, J=13.4, 6.8 Hz, 1H), 2.12-1.94 (m, 2H), 1.91-1.77 (m, 2H), 1.77-1.70 (m, 1H), 1.66-1.54 (m, 1H), 1.44 (s, 9H), 1.30 (d, J=6.5 Hz, 3H), 1.27-1.16 (m, 2H); $^{13}$C NMR (101 MHz, CDCl$_3$) δ 173.21, 158.93, 154.89, 129.83, 121.55, 116.74 (t, J=239.4 Hz), 115.25, 80.57, 79.97, 74.39, 53.02, 37.53, 35.74 (t, J=21.1 Hz), 33.86, 29.44, 28.32, 19.21, 18.27; ESIMS m/z 450.3 ([M+Na]$^+$).

Example 7

Step 2d-1: Preparation of tert-butyl((3S,7R,8R,9S)-7-(2-bromoethyl)-9-methyl-2-oxo-8-phenoxyoxonan-3-yl)carbamate (F249)

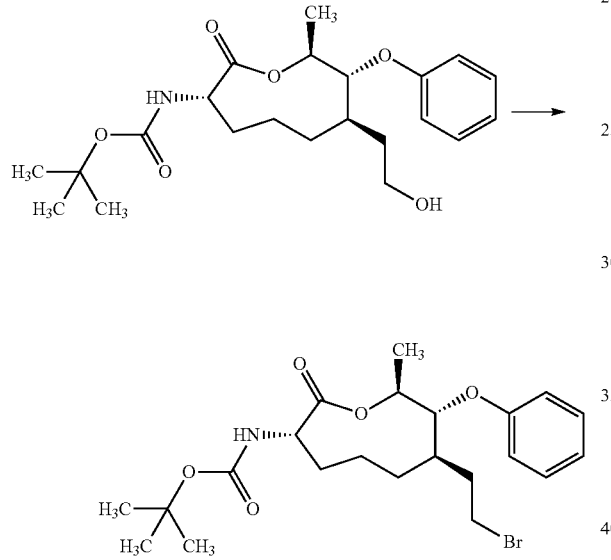

To a solution of tert-butyl((3S,7R,8R,9S)-7-(2-hydroxyethyl)-9-methyl-2-oxo-8-phenoxyoxonan-3-yl)carbamate (700 mg, 1.718 mmol) in CH$_2$Cl$_2$ (17 mL) at 0° C. (icewater bath) were added perbromomethane (627 mg, 1.890 mmol) and triphenylphosphine (541 mg, 2.061 mmol). After 70 min, TLC (2:1 hexanes:acetone) showed incomplete conversion so additional CBr$_4$ and Ph$_3$P (64 mg and 54 mg, respectively) were added and the reaction was stirred for an additional 20 min. The reaction was concentrated and purified by column chromatography on SiO$_2$ (5→20% acetone/hexanes) to provide the title compound as a hard white foam (712 mg, 88%): $^1$H NMR (400 MHz, CDCl$_3$) δ 7.39-7.27 (m, 2H), 7.03-6.82 (m, 3H), 5.18-4.99 (m, 2H), 4.21 (q, J=8.7 Hz, 2H), 3.44 (ddd, J=10.0, 7.4, 5.0 Hz, 1H), 3.33 (ddd, J=9.9, 8.4, 6.9 Hz, 1H), 2.28 (dt, J=13.0, 6.6 Hz, 1H), 2.10 (dtd, J=12.6, 7.9, 4.5 Hz, 1H), 2.05-1.96 (m, 1H), 1.85-1.73 (m, 2H), 1.73-1.61 (m, 1H), 1.44 (s, 10H), 1.30 (d, J=6.5 Hz, 3H), 1.28-1.20 (m, 1H), 1.20-1.09 (m, 1H); $^{13}$C NMR (101 MHz, CDCl$_3$) δ 173.20, 159.18, 154.89, 129.74, 121.33, 115.37, 80.94, 79.95, 74.57, 53.02, 41.18, 34.13, 33.95, 31.54, 28.33, 19.13, 18.29; HRMS-ESI (m/z) ([M+Na]$^+$) calcd for C$_{22}$H$_{32}$BrNNaO$_5$, 492.1356; found, 492.1352.

Example 7

Step 2d-2: Preparation of tert-butyl((3S,7S,8R,9S)-7-ethyl-9-methyl-2-oxo-8-phenoxyoxonan-3-yl)carbamate (F250)

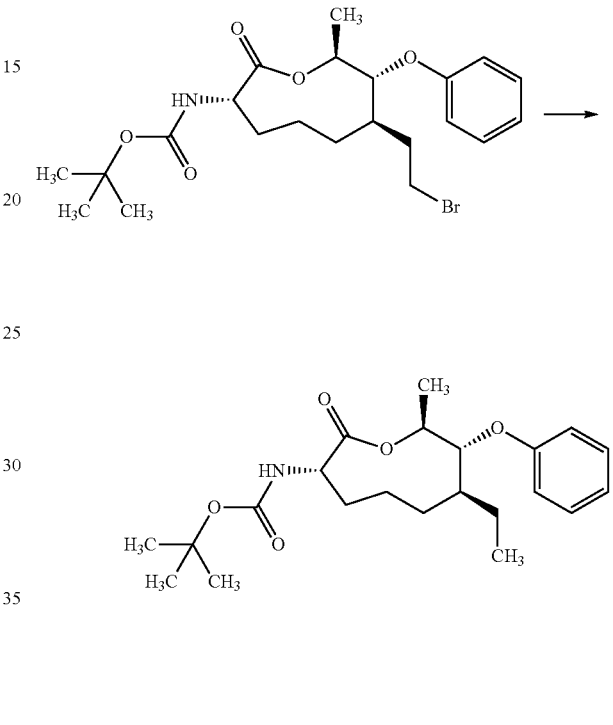

To a solution of tert-butyl((3S,7R,8R,9S)-7-(2-bromoethyl)-9-methyl-2-oxo-8-phenoxyoxonan-3-yl)carbamate (408 mg, 0.867 mmol) and AIBN (14.24 mg, 0.087 mmol) in anhydrous toluene (8.7 mL) was added Bu$_3$SnH (257 μl, 0.954 mmol), and the reaction was heated to 80° C. After 1 h, TLC (4:1 hexanes: acetone) still showed starting material. An additional 0.5 equivalents of Bu$_3$SnH and 0.05 equiv AIBN were added and the reaction was stirred for an additional 1 h at 80° C. The reaction was cooled to room temperature, stirred with 10% aqueous potassium fluoride (KF) solution (7 mL) for 20 h, and partitioned between Et$_2$O (20 mL) and sat. NaCl solution (20 mL). The phases were separated and the aqueous phase was extracted with Et$_2$O (2×20 mL). The organic extracts were combined, dried over MgSO$_4$, filtered and concentrated to provide a white solid, which was purified by column chromatography on SiO$_2$ (5→20% acetone/hexanes) to provide the title compound as a white solid (295 mg, 87%): $^1$H NMR (400 MHz, CDCl$_3$) δ 7.38-7.16 (m, 2H), 7.00-6.87 (m, 3H), 5.19-4.97 (m, 2H), 4.18 (t, J=8.8 Hz, 2H), 2.27 (dt, J=13.1, 6.7 Hz, 1H), 1.91-1.77 (m, 1H), 1.70-1.58 (m, 3H), 1.58-1.48 (m, 1H), 1.44 (s, 9H), 1.28 (d, J=6.5 Hz, 3H), 1.25-1.14 (m, 2H), 1.12-1.01 (m, 1H), 0.86 (t, J=7.3 Hz, 3H); $^{13}$C NMR (101 MHz, CDCl$_3$) δ 173.34, 159.68, 154.91, 129.58, 120.95, 115.40, 81.44, 79.86, 74.74, 53.00, 44.96, 34.20, 28.34, 27.85, 27.03, 26.85, 23.50, 18.74, 18.40, 17.53, 13.61, 11.86; ESIMS m/z 392.3 ([M+H]$^+$), 414.3 ([M+Na]$^+$).

Example 7

Step 2e: Preparation of ((3S,7R,8R,9S)-7-(2-fluoroethyl)-8-isobutoxy-9-methyl-2-oxooxonan-3-yl)carbamate (F235)

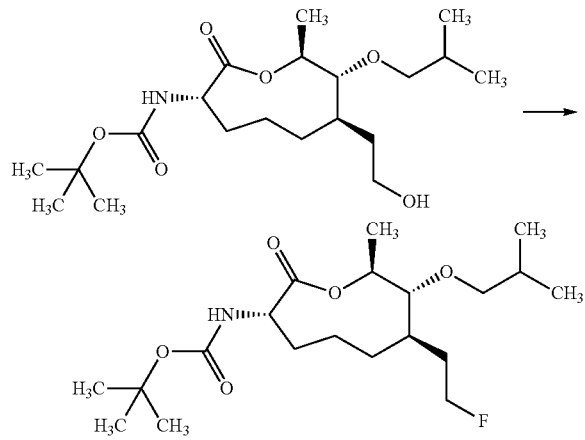

To a solution of tert-butyl((3S,7R,8R,9S)-7-(2-hydroxyethyl)-8-isobutoxy-9-methyl-2-oxooxonan-3-yl)carbamate (200 mg, 0.516 mmol) in anhydrous chloroform (CHCl$_3$; 5.1 mL) at 0° C. (icewater bath) was added Deoxo-Fluor® (114 µl, 0.619 mmol). The resulting solution was stirred at 0° C. for 4 h, poured into H$_2$O (20 mL) and extracted with CH$_2$Cl$_2$ (3×20 mL). The organic extracts were combined, dried over Na$_2$SO$_4$, filtered, and concentrated to provide a yellow solid, which was purified by column chromatography on SiO$_2$ (2→25% acetone/hexanes) to provide the title compound as a white solid (177 mg, 88%) as a white solid: $^1$H NMR (400 MHz, CDCl$_3$) δ 5.07 (d, J=8.1 Hz, 1H), 4.92-4.78 (m, 1H), 4.55 (td, J=5.6, 3.2 Hz, 1H), 4.47-4.37 (m, 1H), 4.15 (dt, J=10.7, 7.8 Hz, 1H), 3.43 (dd, J=8.4, 6.6 Hz, 1H), 3.24 (dd, J=8.4, 6.4 Hz, 1H), 3.09-2.96 (m, 1H), 2.22 (dt, J=13.4, 6.7 Hz, 1H), 2.10-1.95 (m, 1H), 1.83 (dp, J=13.2, 6.6 Hz, 1H), 1.67 (d, J=7.9 Hz, 3H), 1.64-1.53 (m, 2H), 1.44 (s, 9H), 1.40 (d, J=6.4 Hz, 3H), 1.17 (q, J=11.6 Hz, 1H), 1.08-0.97 (m, 1H), 0.94-0.88 (m, 6H); $^{13}$C NMR (101 MHz, CDCl$_3$) δ 173.30, 154.91, 83.83, 83.78, 82.14, 80.21, 79.82, 75.14, 52.97, 39.75, 34.06, 31.57, 31.37, 29.15, 28.69, 28.32, 19.44, 19.40, 19.07, 18.14; ESIMS m/z 412.3 ([M+Na]$^+$).

Example 7

Step 2f-1: Preparation of tert-butyl((3S,7R,8R,9S)-9-methyl-7-(2-((2-nitrophenyl)selanyl)ethyl)-2-oxo-8-phenoxyoxonan-3-yl)carbamate

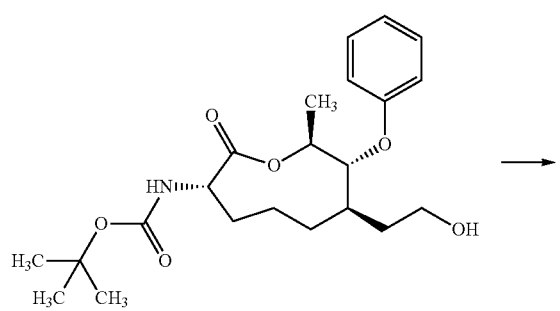

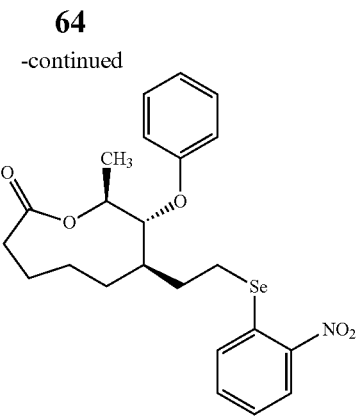

To a solution of tert-butyl((3S,7R,8R,9S)-7-(2-hydroxyethyl)-9-methyl-2-oxo-8-phenoxyoxonan-3-yl)carbamate (227 mg, 0.557 mmol) in anhydrous THF (5.6 mL) at 0° C. (ice water bath) were added 1-nitro-2-selenocyanatobenzene (177 mg, 0.780 mmol) and tributylphosphine (223 µl, 0.891 mmol). The resulting solution was stirred for 3 h and then treated with additional 1-nitro-2-selenocyanatobenzene and tributylphospine (53 mg and 67 µL, respectively). The reaction was stirred for an additional 1 h, then poured into 20 mL sat. NaCl solution and extracted with 3×20 mL EtOAc. The organic extracts were combined, dried over MgSO$_4$, filtered, and concentrated to provide a brown oil, which was purified by column chromatography on SiO$_2$ (2→20% acetone/hexanes) to provide the title compound as a bright yellow solid (294 mg, 89%): $^1$H NMR (400 MHz, CDCl$_3$) δ 8.24 (dt, J=8.2, 1.0 Hz, 1H), 7.36-7.19 (m, 5H), 7.00-6.92 (m, 1H), 6.92-6.84 (m, 2H), 5.16-4.98 (m, 2H), 4.21 (t, J=8.5 Hz, 2H), 3.05-2.76 (m, 2H), 2.30 (dt, J=13.2, 6.7 Hz, 1H), 1.94 (tdq, J=28.6, 14.1, 8.4, 6.4 Hz, 3H), 1.78-1.64 (m, 2H), 1.60 (d, J=4.5 Hz, 1H), 1.45 (s, 9H), 1.30 (d, J=6.5 Hz, 3H), 1.27-1.13 (m, 2H); $^{13}$C NMR (101 MHz, CDCl$_3$) δ 173.23, 159.12, 154.89, 146.86, 133.45, 133.21, 129.76, 128.95, 126.41, 125.29, 121.34, 115.33, 80.99, 79.97, 74.59, 52.99, 43.60, 34.00, 29.99, 28.58, 28.33, 24.24, 19.15, 18.29; ESIMS m/z 593.2 ([M+Na]$^+$).

Example 7

Step 2f-2: Preparation of tert-butyl((3S,7R,8R,9S)-9-methyl-2-oxo-8-phenoxy-7-vinyloxonan-3-yl)carbamate (F259)

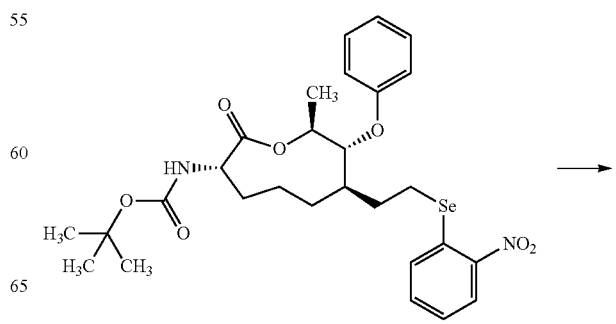

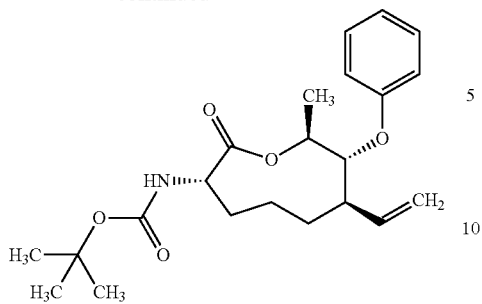

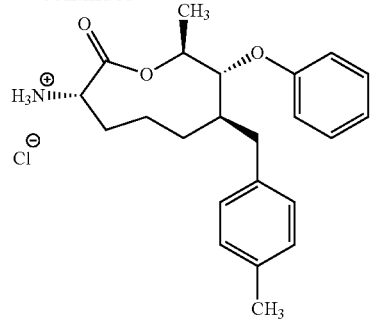

A 25 mL screw top vial was charged with tert-butyl((3S,7R,8R,9S)-9-methyl-7-(4-methylbenzyl)-2-oxo-8-phenoxyoxonan-3-yl)carbamate (300 mg, 0.642 mmol), anhydrous CH$_2$Cl$_2$ (4 mL), and 4.0 M HCl in dioxane (3.21 mL, 12.83 mmol). After stirring at room temperature for 80 min, the reaction mixture was concentrated under a stream of nitrogen and dried under high vacuum to provide the title compound as a beige solid (259 mg, 100%): mp 200-210° C. (dec.); $^1$H NMR (400 MHz, CDCl3) δ 7.46-6.81 (m, 9H), 5.14 (s, 1H), 3.78-3.52 (m, 3H), 2.86 (s, 1H), 2.60-1.12 (m, 12H), 0.96 (s, 1H); $^{13}$C NMR (101 MHz, CD$_3$OD) δ 171.05, 160.65, 137.89, 136.19, 130.75, 129.87, 129.75, 122.14, 117.03, 81.89, 76.55, 68.05, 46.67, 37.46, 32.38, 27.71, 21.05, 20.12, 18.85; ESIMS m/z 369 ([M+H]$^+$).

To a solution of tert-butyl((3S,7R,8R,9S)-9-methyl-7-(2-((2-nitrophenyl)-selanyl)ethyl)-2-oxo-8-phenoxyoxonan-3-yl)carbamate (284 mg, 0.480 mmol) in THF (4.8 mL) was added 30% aqueous hydrogen peroxide (H$_2$O$_2$ 392 μl, 3.84 mmol), and the resulting bright yellow solution was stirred at room temperature for 3 d. The reaction was cooled to 0° C. (icewater bath), quenched with sat. aqueous NaHSO$_3$ solution (4 mL), diluted with H$_2$O (20 mL), and extracted with EtOAc (3×20 mL). The organic extracts were combined, dried over MgSO$_4$, filtered, and concentrated to the title compound as an orange solid (134.9 mg, 72%): $^1$H NMR (400 MHz, CDCl$_3$) δ 7.34-7.19 (m, 2H), 7.02-6.86 (m, 3H), 5.76 (ddd, J=17.2, 10.3, 8.0 Hz, 1H), 5.17-5.06 (m, 2H), 5.03 (d, J=17.1 Hz, 1H), 4.94 (d, J=10.4 Hz, 1H), 4.28 (t, J=8.8 Hz, 1H), 4.25-4.17 (m, 1H), 2.56-2.41 (m, 1H), 2.27 (dt, J=13.5, 6.6 Hz, 1H), 1.85 (td, J=14.6, 7.1 Hz, 1H), 1.75 (dt, J=14.8, 7.3 Hz, 1H), 1.65 (s, 1H), 1.44 (s, 9H), 1.33 (d, J=6.4 Hz, 3H), 1.31-1.17 (m, 2H); $^{13}$C NMR (101 MHz, CDCl$_3$) δ 173.35, 159.33, 138.51, 129.49, 121.10, 116.18, 115.78, 99.98, 80.46, 74.39, 53.05, 47.47, 34.13, 31.07, 28.34, 19.66, 18.36; HRMS-ESI (m/z) ([M+Na]$^+$) calcd for C$_{22}$H$_{31}$NO$_5$Na, 412.2094, found 412.2106.

Example 8

Step 2: Preparation of 3-hydroxy-4-methoxy-N-((3S,7R,8R,9S)-9-methyl-7-(4-methylbenzyl)-2-oxo-8-phenoxyoxonan-3-yl)picolinamide (F49)

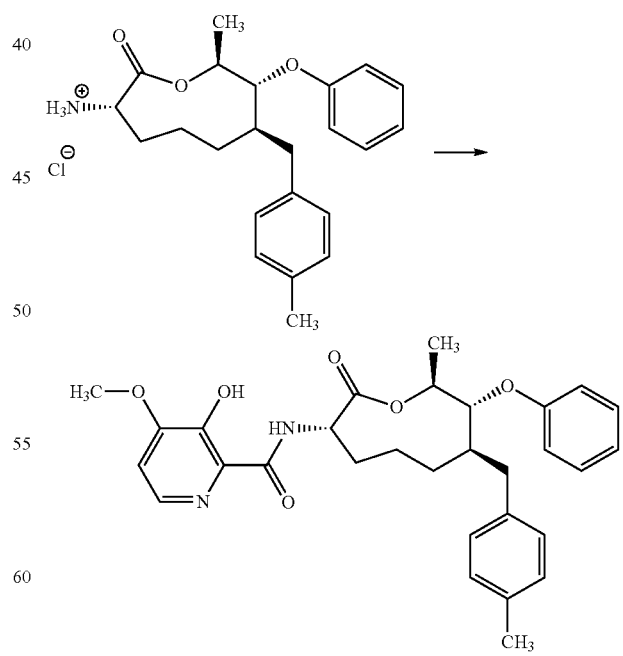

Example 8

Step 1: Preparation of (3S,7R,8R,9S)-9-methyl-7-(4-methylbenzyl)-2-oxo-8-phenoxyoxonan-3-aminium chloride (F244)

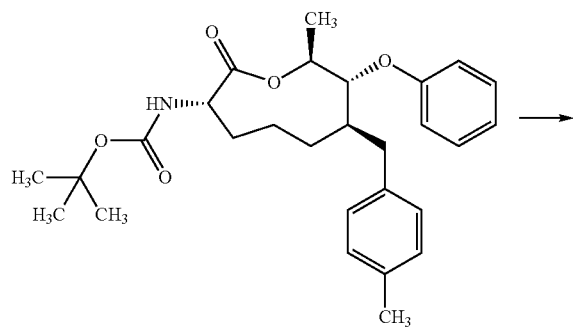

A 25 mL screw top vial was charged with (3S,7R,8R,9S)-9-methyl-7-(4-methylbenzyl)-2-oxo-8-phenoxyoxonan-3-aminium chloride (259 mg, 0.642 mmol), 3-hydroxy-4-methoxypicolinic acid (122 mg, 0.721 mmol), anhydrous $CH_2Cl_2$ (6.5 mL), and N,N-diisopropylethylamine (340 µL, 1.95 mmol). To the mixture was added PyBOP (376 mg, 0.723 mmol) and the reaction was stirred at room temperature for 1.5 h and then directly purified by column chromatography on $SiO_2$ (2→30% acetone/hexanes) to provide the title compound as a white solid (162 mg, 49%): mp 62-66° C.; $^1H$ NMR (400 MHz, CDCl3) δ 12.09 (s, 1H), 8.48 (d, J=8.2 Hz, 1H), 7.98 (d, J=5.1 Hz, 1H), 7.37-7.28 (m, 2H), 7.12-6.93 (m, 7H), 6.86 (d, J=5.2 Hz, 1H), 5.14 (dq, J=9.2, 6.4 Hz, 1H), 4.62 (dt, J=10.9, 7.4 Hz, 1H), 4.35 (t, J=8.9 Hz, 1H), 3.93 (s, 3H), 2.99 (dd, J=13.3, 3.2 Hz, 1H), 2.42-2.26 (m, 5H), 2.16-2.04 (m, 1H), 1.79-1.52 (m, 3H), 1.41-1.23 (m, 4H), 1.08-0.98 (m, 1H); $^{13}C$ NMR (101 MHz, CDCl3) δ 172.06, 168.59, 159.58, 155.27, 148.66, 140.47, 136.92, 135.38, 130.28, 129.63, 128.98, 128.59, 121.16, 115.48, 109.43, 81.02, 74.89, 55.99, 51.43, 45.59, 36.34, 33.47, 26.57, 20.95, 18.78, 18.33; ESIMS: m/z 519 ([M+H]$^+$).

Example 9

Preparation of ((2-(((3S,7R,8R,9S)-7-(2-fluoroethyl)-8-isobutoxy-9-methyl-2-oxooxonan-3-yl)carbamoyl)-4-methoxypyridin-3-yl)oxy)methyl acetate (F128)

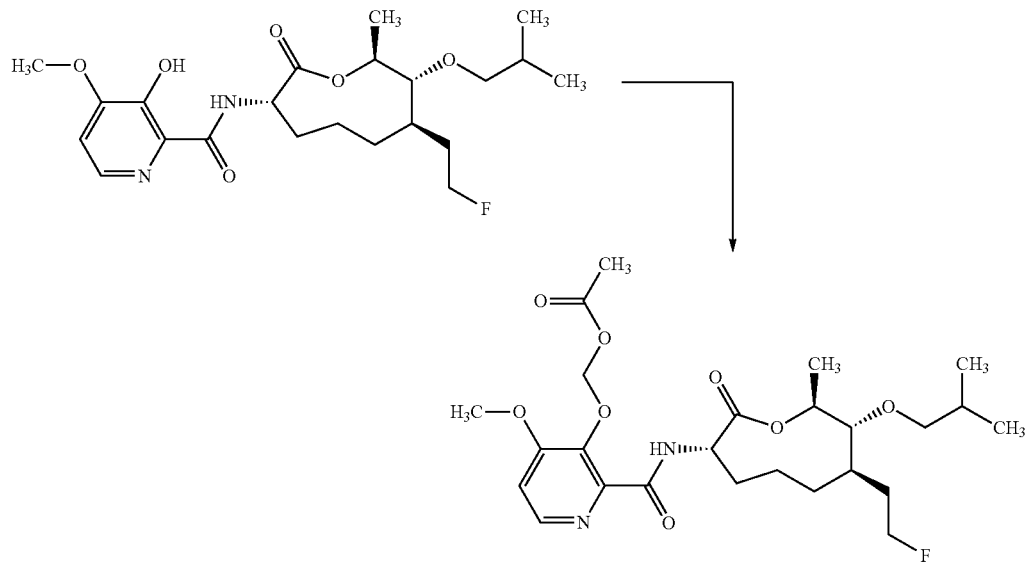

To a solution of N-((3S,7R,8R,9S)-7-(2-fluoroethyl)-8-isobutoxy-9-methyl-2-oxooxonan-3-yl)-3-hydroxy-4-methoxypicolinamide (97 mg, 0.220 mmol) in anhydrous acetone (2.2 mL) were added powdered $K_2CO_3$ (60.9 mg, 0.440 mmol) and bromomethyl acetate (32.4 µl, 0.330 mmol). The resulting mixture was heated to 50° C. and stirred vigorously for 16 h, then filtered through a plug of Celite®, concentrated, and purified by column chromatography on $SiO_2$ (5→50% acetone/hexanes) to provide the title compound as a sticky solid (87 mg, 77%): $^1H$ NMR (400 MHz, CDCl$_3$) δ 8.34 (d, J=8.1 Hz, 1H), 8.28 (d, J=5.4 Hz, 1H), 6.95 (d, J=5.4 Hz, 1H), 5.74 (s, 2H), 4.90 (dq, J=9.1, 6.4 Hz, 1H), 4.58 (ddt, J=9.4, 5.9, 4.6 Hz, 2H), 4.50-4.39 (m, 1H), 3.91 (s, 3H), 3.45 (dd, J=8.4, 6.6 Hz, 1H), 3.26 (dd, J=8.4, 6.4 Hz, 1H), 3.14-3.02 (m, 1H), 2.36 (dt, J=12.9, 6.7 Hz, 1H), 2.07 (s, 3H), 2.06-1.98 (m, 1H), 1.84 (dp, J=13.4, 6.7 Hz, 1H), 1.78-1.60 (m, 4H), 1.57 (s, 1H), 1.42 (d, J=6.4 Hz, 3H), 1.39-1.29 (m, 1H), 1.10 (dd, J=14.3, 5.7 Hz, 1H), 0.92 (d, J=6.8 Hz, 6H); $^{13}C$ NMR (101 MHz, CDCl$_3$) δ 170.35, 167.84, 160.52, 157.81, 143.31, 141.51, 140.02, 107.14, 87.11, 81.42, 81.36, 79.73, 77.78, 72.81, 53.74, 49.43, 37.34, 37.30, 31.13, 29.17, 28.98, 26.73, 26.26, 18.44, 17.02, 16.98, 16.74, 15.69; HRMS-ESI (m/z) ([M+Na]$^+$) calcd for $C_{25}H_{37}FN_2O_8Na$, 535.2426, found 535.2423.

Example 10

Preparation of 4-methoxy-2-(((3S,7R,8R,9S)-9-methyl-7-(4-methylbenzyl)-2-oxo-8-phenoxyoxonan-3-yl)carbamoyl)pyridin-3-yl acetate (F79)

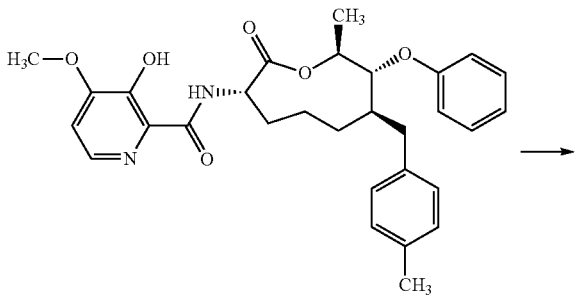

-continued

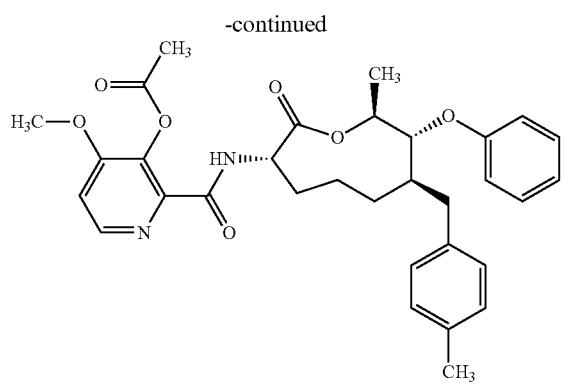

A 25 mL screw top vial was charged with 3-hydroxy-4-methoxy-N-((3S,7R,8R,9S)-9-methyl-7-(4-methylbenzyl)-2-oxo-8-phenoxyoxonan-3-yl)picolinamide (74.0 mg, 0.143 mmol), DMAP (19.4 mg, 0.159 mmol), 1,2-dichloroethane (DCE; 1 mL), acetyl chloride (20 μL, 0.281 mmol), and NEt₃ (70 μL, 0.502 mmol). The resulting mixture was heated to 50° C. for 7 h. After cooling to room temperature, the crude reaction mixture was directly purified by column chromatography on SiO₂ (2→40% acetone/hexanes) to provide the title compound as a white solid (56.0 mg, 70%): mp 96-100° C.; $^1$H NMR (400 MHz, CDCl3) δ 8.53 (d, J=8.4 Hz, 1H), 8.33 (d, J=5.5 Hz, 1H), 7.36-7.27 (m, 2H), 7.12-6.92 (m, 8H), 5.12 (dq, J=9.1, 6.4 Hz, 1H), 4.63 (dt, J=10.9, 7.5 Hz, 1H), 4.33 (t, J=8.9 Hz, 1H), 3.89 (s, 3H), 2.97 (dd, J=13.3, 3.2 Hz, 1H), 2.41 (s, 3H), 2.32 (d, J=9.3 Hz, 5H), 2.14-2.03 (m, 1H), 1.73-1.48 (m, 3H), 1.39-1.19 (m, 5H); $^{13}$C NMR (101 MHz, CDCl3) δ 172.55, 168.83, 162.34, 159.62, 159.36, 146.65, 141.31, 137.42, 137.01, 135.34, 129.62, 128.96, 128.61, 121.12, 115.50, 109.76, 81.10, 74.64, 56.22, 51.52, 45.62, 36.35, 33.75, 26.67, 20.95, 20.69, 18.83, 18.31; ESIMS: m/z 561 ([M+H]⁺).

Example 11

Preparation of 2-(((3S,7R,8R,9S)-8-(cyclopropylmethoxy)-7-(4-methoxybenzyl)-9-methyl-2-oxooxonan-3-yl)carbamoyl)-4-methoxypyridin-3-yl 3-methoxypropanoate (F195)

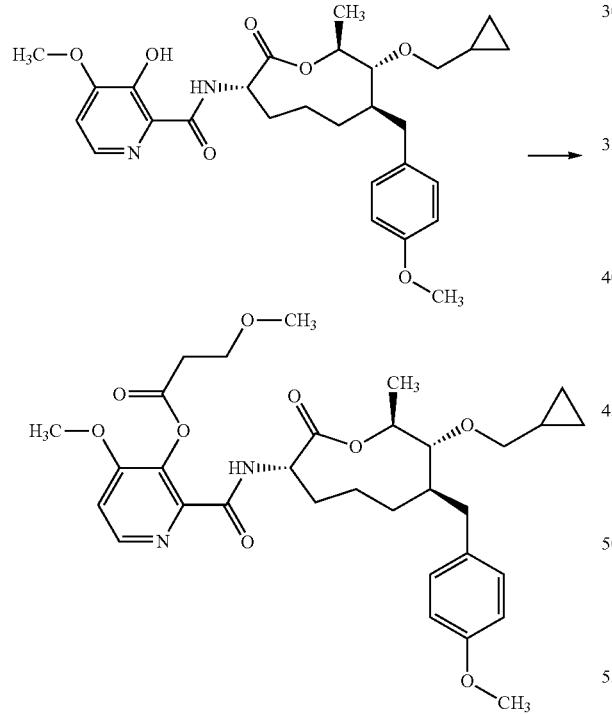

To a 4 mL vial were added N-((3S,7R,8R,9S)-8-(cyclopropylmethoxy)-7-(4-methoxybenzyl)-9-methyl-2-oxooxonan-3-yl)-3-hydroxy-4-methoxypicolinamide (85 mg, 0.166 mmol), CH₂Cl₂ (1 mL) and NEt₃ (0.069 mL, 0.497 mmol), 3-methoxypropanoyl chloride (30.5 mg, 0.249 mmol), and DMAP (3 mg, 0.02 mmol), and the resulting light yellow solution was stirred at room temperature overnight. The reaction mixture was concentrated and purified by column chromatography on SiO₂ (0→100% EtOAc/hexanes) to provide the title compound as a colorless semi-solid (77.8 mg, 78%): IR (neat) 3381, 2936, 1769, 1742, 1678, 1511, 1246, 1111 cm⁻¹; $^1$H NMR (400 MHz, CDCl₃) δ 8.47 (d, J=7.3 Hz, 1H), 8.31 (d, J=5.4 Hz, 1H), 7.09 (d, J=8.6 Hz, 2H), 6.98 (d, J=5.5 Hz, 1H), 6.83 (d, J=8.6 Hz, 2H), 4.91 (dq, J=9.1, 6.4 Hz, 1H), 4.55 (ddd, J=10.9, 8.4, 7.0 Hz, 1H), 3.88 (s, 3H), 3.81 (t, J=6.6 Hz, 2H), 3.78 (s, 3H), 3.57 (dd, J=9.7, 7.0 Hz, 1H), 3.44 (dd, J=9.7, 6.8 Hz, 1H), 3.41 (s, 3H), 3.15 (t, J=9.0 Hz, 1H), 3.07 (dd, J=13.4, 3.3 Hz, 1H), 2.98 (t, J=6.6 Hz, 2H), 2.35-2.20 (m, 2H), 1.87-1.77 (m, 1H), 1.61-1.47 (m, 2H), 1.48-1.37 (m, 1H), 1.45 (d, J=6.4 Hz, 3H), 1.22-1.05 (m, 2H), 0.90-0.79 (m, 1H), 0.63-0.49 (m, 2H), 0.29-0.14 (m, 2H); $^{13}$C NMR (101 MHz, CDCl₃) δ 172.61, 169.39, 162.32, 159.40, 157.82, 146.76, 141.45, 137.29, 132.66, 129.73, 113.77, 109.78, 83.79, 78.71, 75.22, 67.58, 58.78, 56.30, 55.22, 51.47, 46.17, 35.92, 34.62, 33.89, 26.55, 18.73, 18.08, 11.18, 3.16, 3.00; HRMS-ESI (m/z) ([M]⁺) calcd for C₃₂H₄₂N₂O₉, 598.2890; found, 598.2914.

Example 12

Preparation of ((2-(((3S,7R,8R,9S)-7-(cyclopentylmethyl)-8-(cyclopropylmethoxy)-9-methyl-2-oxooxonan-3-yl)carbamoyl)-4-methoxypyridin-3-yl)oxy) methyl isobutyrate (F154)

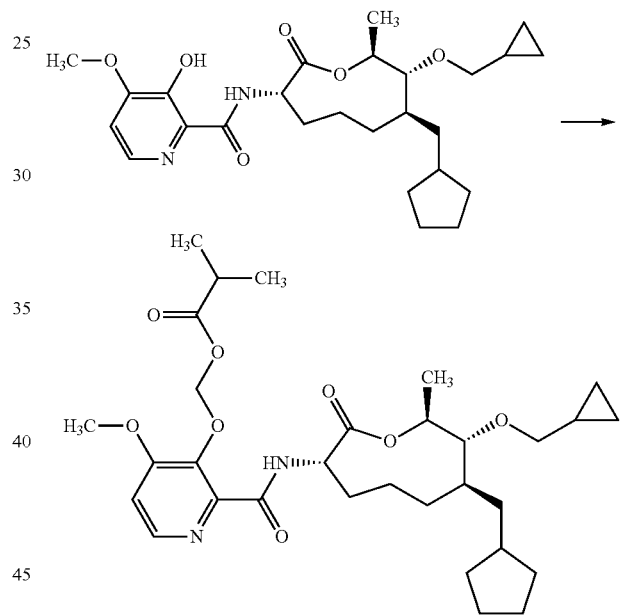

To a mixture of N-((3S,7R,8R,9S)-7-(cyclopentylmethyl)-8-(cyclopropylmethoxy)-9-methyl-2-oxooxonan-3-yl)-3-hydroxy-4-methoxypicolinamide (60 mg, 0.126 mmol) and K₂CO₃ (34.9 mg, 0.253 mmol) in acetone (1 mL) was added chloromethyl isobutyrate (34.5 mg, 0.253 mmol) and the reaction was heated to 60° C. After TLC analysis indicated full consumption of the picolinamide starting material, the mixture was concentrated under a stream of N₂ and the residue purified by column chromatography on SiO₂ (gradient, EtOAc/hexanes) to yield the title compound as a colorless semi-solid (60.4 mg, 83%): IR (thin film) 3381, 2942, 1745, 1678, 1506, 974 cm⁻¹; $^1$H NMR (400 MHz, CDCl₃) δ 8.38 (d, J=8.2 Hz, 1H), 8.27 (d, J=5.3 Hz, 1H), 6.93 (d, J=5.4 Hz, 1H), 5.81-5.61 (m, 2H), 4.89 (dd, J=9.2, 6.3 Hz, 1H), 4.57 (dt, J=11.0, 7.5 Hz, 1H), 3.89 (s, 3H), 3.50 (dd, J=9.6, 7.0 Hz, 1H), 3.36 (dd, J=9.6, 6.9 Hz, 1H), 3.01 (t, J=9.0 Hz, 1H), 2.54 (p, J=7.0 Hz, 1H), 2.36 (dd, J=13.1, 6.8 Hz, 1H), 1.92-1.43 (m, 15H), 1.42 (d, J=6.5 Hz, 2H), 1.35-1.19 (m, 2H), 1.14 (d, J=7.0 Hz, 3H), 1.17-0.92 (m, 5H), 0.62-0.48 (m, 2H), 0.29-0.17 (m, 2H); HRMS-ESI (m/z) ([M]⁺) calcd for C₃₁H₄₆N₂O₈, 574.3254; found, 574.3262.

Example 13

Preparation of (((4-methoxy-2-((((3S,7R,8R,9S)-9-methyl-7-(4-methylbenzyl)-2-oxo-8-(4,4,4-trifluorobutoxyl)oxonan-3-yl)carbamoyl)pyridin-3-yl)oxy) methyl 2-ethoxyacetate (F190)

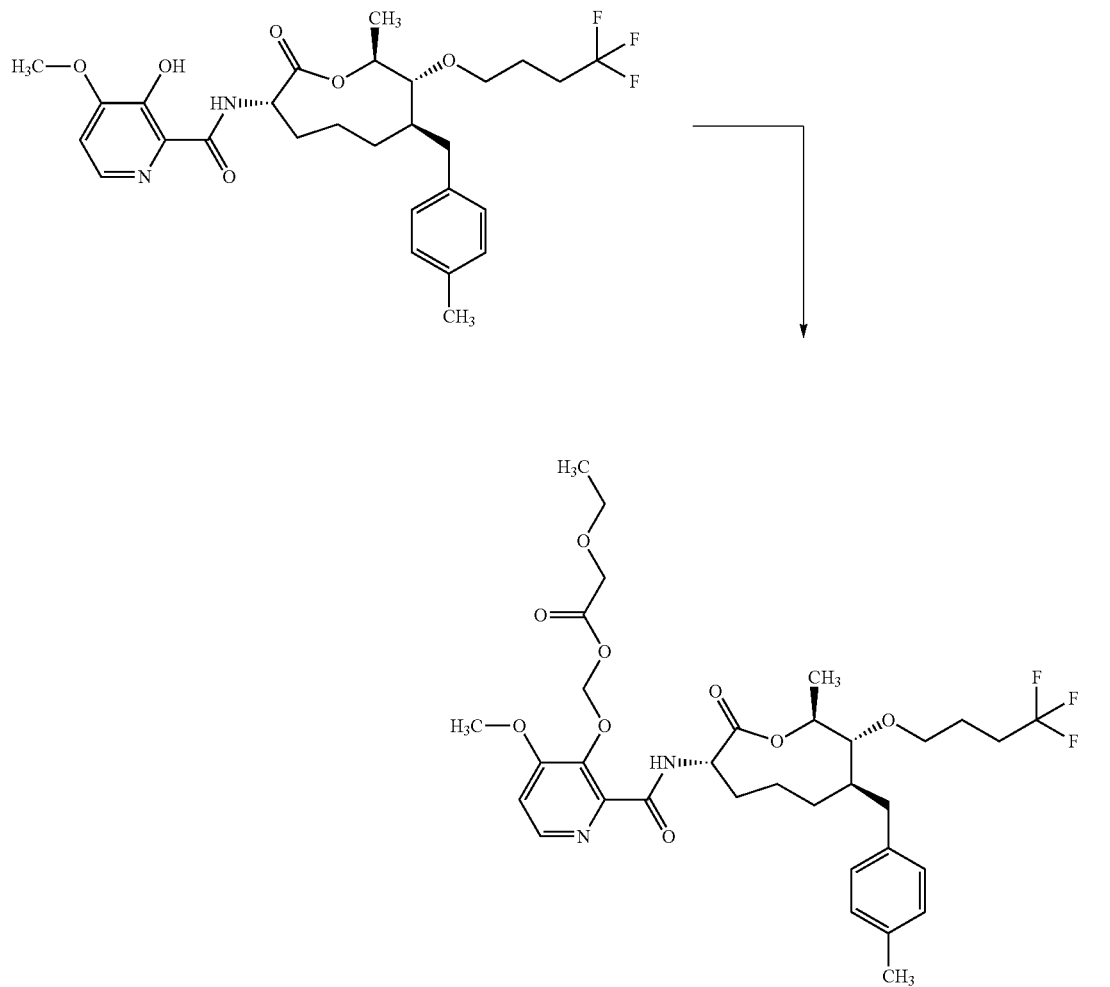

To a 25 mL screw top vial were added 3-hydroxy-4-methoxy-N-((3S,7R,8R,9S)-9-methyl-7-(4-methylbenzyl)-2-oxo-8-(4,4,4-trifluorobutoxyl)oxonan-3-yl)picolinamide (87.9 mg, 0.159 mmol), Na$_2$CO$_3$ (33.8 mg, 0.319 mmol), NaI (6.3 mg, 0.264 mmol), anhydrous acetone (2 mL), and chloromethyl 2-ethoxyacetate (40.8 mg, 1.68 mmol), and the resulting mixture was warmed to 40° C. and stirred for 17 h. The reaction was cooled to room temperature, concentrated under a stream of nitrogen, and purified by column chromatography on SiO$_2$ (2→40% acetone/hexanes) to provide the title compound as a colorless oil (58.8 mg, 52%): $^1$H NMR (400 MHz, CDCl3) δ 8.29 (d, J=8.1 Hz, 1H), 8.25 (d, J=5.4 Hz, 1H), 7.09 (d, J=7.9 Hz, 2H), 7.03 (d, J=8.0 Hz, 2H), 6.93 (d, J=5.4 Hz, 1H), 5.80 (s, 2H), 4.89 (dq, J=9.1, 6.4 Hz, 1H), 4.55 (dt, J=10.9, 7.4 Hz, 1H), 4.08 (s, 2H), 3.88 (s, 3H), 3.80 (dt, J=8.9, 6.1 Hz, 1H), 3.64-3.54 (m, 3H), 3.17 (t, J=9.0 Hz, 1H), 2.96 (dd, J=13.3, 3.4 Hz, 1H), 2.40-2.13 (m, 7H), 1.92-1.76 (m, 3H), 1.65-1.37 (m, 6H), 1.30-1.14 (m, 4H), 0.93-0.80 (m, 1H); $^{13}$C NMR (101 MHz, CDCl3) δ 172.62, 169.97, 162.83, 160.09, 145.73, 143.81, 142.18, 137.20, 135.41, 129.02, 128.58, 131.42-122.86 (m), 109.65, 89.44, 84.20, 74.83, 71.60, 67.71, 67.10, 56.15, 51.69, 45.80, 36.42, 33.56, 30.73 (q, J=29.0 Hz), 26.62, 23.01 (q, J=3.1 Hz), 20.93, 18.75, 18.05, 14.94; $^{19}$F NMR (376 MHz, CDCl3) δ −66.35, ESIMS: m/z 669 ([M+H]$^+$).

Example 14

Preparation of (S)-benzyl 5-((2R,3R)-2-((S)-1-(benzyloxy)ethyl)-tetrahydrofuran-3-yl)-2-((tert-butoxycarbonyl)amino)pentanoate

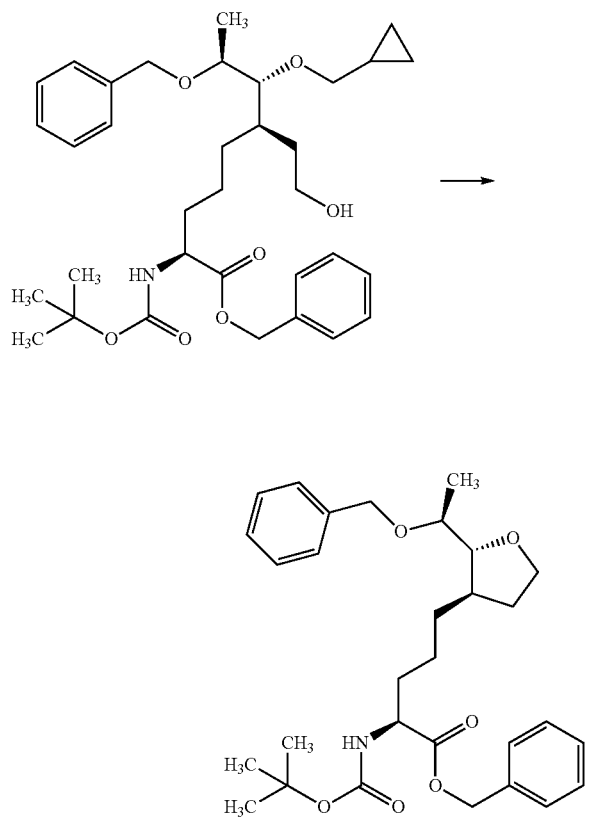

To a solution of (2S,6R,7R,8S)-benzyl 8-(benzyloxy)-2-((tert-butoxycarbonyl)amino)-7-(cyclopropylmethoxy)-6-(2-hydroxyethyl)nonanoate (570 mg, 0.976 mmol) in anhydrous CH$_2$Cl$_2$ (10 mL) at 0° C. were added CBr$_4$ (389 mg, 1.172 mmol) and triphenylphosphine (333 mg, 1.269 mmol). The resulting solution was stirred for 6 h, at which time UPLC-MS showed ~50% conversion to the desired product. The reaction was allowed to warm to room temperature and stirred for 3 d. The mixture was concentrated and purified by column chromatography on SiO$_2$ (2→25% acetone/hexanes) to provide the title compound as a clear, colorless oil (399.6 mg, 80%): $^1$H NMR (400 MHz, CDCl$_3$) δ 7.39-7.28 (m, 9H), 7.28-7.21 (m, 1H), 5.20 (d, J=12.3 Hz, 1H), 5.11 (d, J=12.3 Hz, 1H), 5.00 (d, J=8.1 Hz, 1H), 4.62 (d, J=11.9 Hz, 1H), 4.49 (d, J=11.9 Hz, 1H), 4.42-4.26 (m, 1H), 3.78 (dd, J=8.3, 4.8 Hz, 2H), 3.56-3.40 (m, 2H), 1.96 (ddd, J=14.2, 10.0, 7.2 Hz, 2H), 1.76 (dd, J=8.8, 4.7 Hz, 1H), 1.68-1.55 (m, 1H), 1.49 (dd, J=7.8, 3.6 Hz, 2H), 1.44 (s, 9H), 1.39-1.33 (m, 1H), 1.32-1.21 (m, 2H), 1.18 (d, J=6.1 Hz, 3H); $^{13}$C NMR (101 MHz, CDCl$_3$) δ 172.71, 155.37, 138.92, 135.43, 128.60, 128.43, 128.32, 128.29, 127.59, 127.41, 87.07, 79.88, 71.09, 67.77, 66.97, 53.39, 40.81, 33.92, 32.84, 32.66, 28.33, 24.04, 16.01; ESIMS m/z 412.3 ([M+H]$^+$) for M-BOC.

Example 15

Step 1: Preparation of (phenylthio)methyl 2-ethoxyacetate

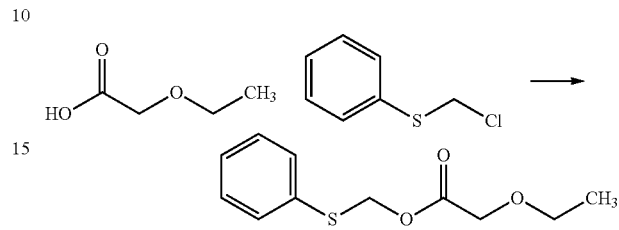

To a mixture of Cs$_2$CO$_3$ (29.5 g, 91 mmol) in DMF (150 mL) at 0° C. was added 2-ethoxyacetic acid (18.0 mL, 191 mmol), and the resulting mixture was heated at 70° C. for 30 min. The reaction was cooled to 0° C., chloromethyl phenylsulfide (10.56 mL, 79 mmol) was added, and the reaction was heated at 70° C. for 90 min. The mixture was cooled to room temperature, and then 0° C., before diluting with H$_2$O (200 mL; an exotherm was observed). The reaction mixture was divided into two equal portions and one portion was further diluted with water (400 mL) and extracted with Et$_2$O (200 mL×2, 100 mL×1). The combined organic extracts were diluted with hexane (100 mL) and washed successively with 1.0 M aqueous NaOH (100 mL) and brine (2×200 mL), dried over anhydrous MgSO$_4$, filtered, and concentrated. The second portion of the reaction mixture from above was processed in an identical fashion and the two lots were combined and concentrated in vacuo to afford the title compound as a yellow oil (12.28 g, 97%): $^1$H NMR (400 MHz, CDCl3) δ 7.48-7.41 (m, 2H), 7.31 (ddd, J=12.6, 7.9, 6.3 Hz, 3H), 5.51 (s, 2H), 4.11 (s, 2H), 3.59 (q, J=7.0 Hz, 2H), 1.24 (t, J=7.0 Hz, 3H); $^{13}$C NMR (101 MHz, CDCl3) δ 170.00, 134.35, 130.53, 129.16, 127.55, 68.46, 68.10, 67.32, 14.99; ESIMS: m/z 226 ([M]$^+$).

Example 15

Step 2: Preparation of chloromethyl 2-ethoxyacetate

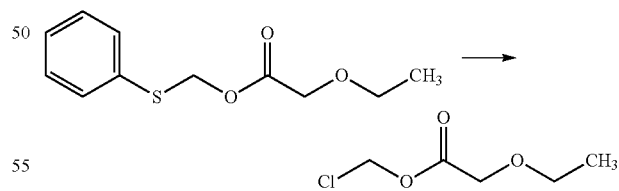

To a solution of (phenylthio)methyl 2-ethoxyacetate (17.28 g, 76 mmol) in CH$_2$Cl$_2$ (200 mL) at 0° C. was added a solution of sulfuryl chloride (7.36 mL, 92 mmol) in CH$_2$Cl$_2$ (50 mL) over a period of 15 min, and the reaction was stirred at room temperature for 90 min. The reaction was again cooled to 0° C. and treated with a second portion of sulfuryl chloride (7.36 mL, 92 mmol) in CH$_2$Cl$_2$ (50 mL) over a period of 15 min. The reaction was then warmed to 30° C., stirred for 1 hour, and then cooled back to 0° C. A solution of cyclohexene (24.5 mL, 242 mmol) in CH$_2$Cl$_2$ (50 mL) was added over a period of 10 min, during which gas evolution was observed. The reaction was stirred at room temperature for 90 min, stored at −20° C. overnight, and purified by vacuum distillation to give the target compound as a slightly yellow oil (11.33 g, 97%): by 58° C. at 6.8 mm Hg; $^1$H NMR (400 MHz, CDCl3) δ 5.77 (s, 2H), 4.16 (s, 2H), 3.62 (q, J=7.0 Hz, 2H), 1.27 (t, J=7.0 Hz, 3H); $^{13}$C NMR (101 MHz, CDCl3) δ 168.81, 68.59, 67.77, 67.48, 14.96.

Example 16

Preparation of N-((3S,7R,8R,9S)-7-(cyclohexylmethyl)-8-(cyclopropylmethoxy)-9-methyl-2-oxooxonan-3-yl)-3-hydroxy-4-methoxypicolinamide (F9)

A high pressure reactor equipped with a stir bar was charged with a solution of N-((3S,7R,8R,9S)-8-(cyclopropylmethoxy)-7-(4-fluorobenzyl)-9-methyl-2-oxooxonan-3-yl)-3-hydroxy-4-methoxypicolinamide (230 mg, 0.459 mmol) in THF (7 mL) and 5% rhodium on carbon (56.8 mg, 0.028 mmol). After the reactor was sealed and purged with H$_2$ (4×), the reaction was charged to ~600 psi of H$_2$ at room temperature. The reactor was warmed to 70° C. and stirred for 29 h, cooled to room temperature, and the reaction mixture was filtered through a Celite® pad. The filtrate was concentrated and purified by column chromatography on SiO$_2$ (gradient, hexanes/ethyl acetate) to furnish the title product as a white solid (60.8 mg, 27%): $^1$H NMR (400 MHz, CDCl$_3$) δ 12.11 (d, J=0.6 Hz, 1H), 8.49 (d, J=8.2 Hz, 1H), 7.99 (d, J=5.2 Hz, 1H), 6.87 (d, J=5.2 Hz, 1H), 4.95-4.84 (m, 1H), 4.55 (ddd, J=10.7, 8.2, 7.0 Hz, 1H), 3.94 (s, 3H), 3.49 (dd, J=9.6, 7.0 Hz, 1H), 3.37 (dd, J=9.6, 6.8 Hz, 1H), 3.01 (t, J=8.8 Hz, 1H), 2.39-2.28 (m, 1H), 1.78-1.46 (m, 10H), 1.45 (d, J=7.0 Hz, 3H), 1.41-0.71 (m, 10H), 0.59-0.52 (m, 2H), 0.26-0.18 (m, 2H); $^{13}$C NMR (101 MHz, CDCl$_3$) δ 172.21, 168.62, 155.31, 148.69, 140.51, 130.42, 109.44, 84.33, 78.51, 75.66, 56.05, 51.49, 40.09, 38.30, 35.05, 34.59, 33.63, 32.34, 27.44, 26.68, 26.48, 26.15, 18.77, 18.10, 11.14, 3.16, 2.94; ESIMS m/z 489.3 ([M+H]$^+$).

Example A

Evaluation of Fungicidal Activity: Leaf Blotch of Wheat (*Mycosphaerella graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia triticina*; Synonym: *Puccinia recondite* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example E

Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G

Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H

Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example I

Evaluation of Fungicidal Activity: Wheat Powdery Mildew (*Blumeria graminis* f. sp. *tritici*; Synonym: *Erysiphe graminis* f. sp. *tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J

Evaluation of Fungicidal Activity: Barley Powdery Mildew (*Blumeria graminis* f. sp. *hordei*; Synonym: *Erysiphe graminis* f. sp. *hordei*; Bayer Code ERYSGH)

Barley seedlings (variety *Harrington*) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Scald (*Rhyncosporium secalis*; Bayer Code RHYNSE)

Barley seedlings (variety *Harrington*) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop.

Fungicide formulation, application and disease assessment on the sprayed leaves followed the procedures as described in the Example A.

Example L

Evaluation of Fungicidal Activity: Rice Blast (*Magnaporthe grisea*; Anamorph: *Pyricularia oryzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M

Evaluation of Fungicidal Activity: Tomato Early Blight (*Alternaria solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N

Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

| Compound Number | Structure | Prepared According To Example | Appearance |
|---|---|---|---|
| F1 | 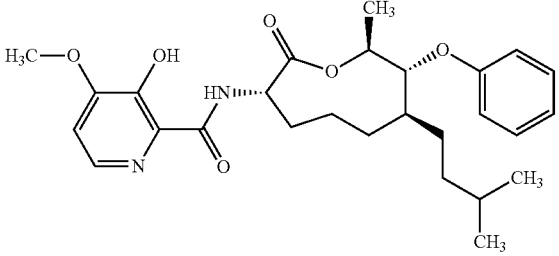 [SMILES: COc1ccnc(C(=O)N[C@H]2CCC[C@H](CCC(C)C)[C@@H](Oc3ccccc3)[C@H](C)OC2=O)c1O] | Example 1, Steps 1, 2c, 3, 4, 5c, 5b, 6; Example 2, Steps 1a-1, 1a-2; Example 7; Example 8, Steps 1, 2 | Colorless Solid |
| F2 | 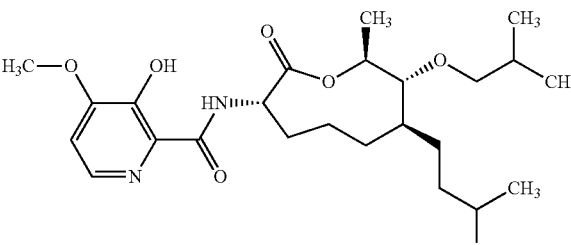 | Example 1, Steps 1, 2c, 3, 4, 5c, 5b, 6; Example 2, Steps 1a-1, 1a-2; Example 3, Steps 1, 2a; Example 8, Steps 1, 2 | White Solid |

TABLE 1-continued

Compound Structure and Appearance

| Compound Number | Structure | Prepared According To Example | Appearance |
|---|---|---|---|
| F3 | 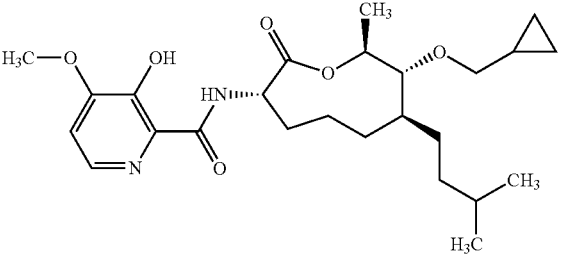 [SMILES: COc1ccnc(C(=O)N[C@H]2CCC[C@H](CCC(C)C)[C@@H](OCC3CC3)[C@H](C)OC2=O)c1O] | Example 1, Steps 1, 2b, 3, 5b, 5c, 6; Example 8, Steps 1, 2 | White Solid |
| F4 | 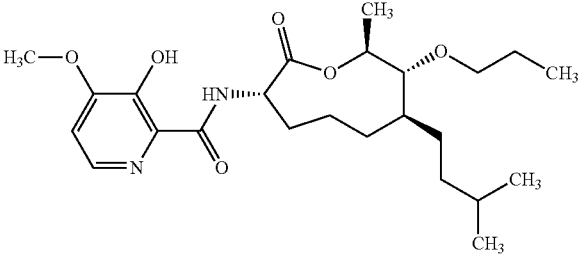 [SMILES: CCCO[C@@H]1[C@@H](CCC(C)C)CCC[C@H](NC(=O)c2nccc(OC)c2O)C(=O)O[C@H]1C] | Example 1, Steps 1, 2c, 3, 4, 5c, 5b, 6; Example 2, Steps 1a-Example 3, Steps 1, 2a; Example 8, Steps 1, 2? | White Solid |
| F5 | 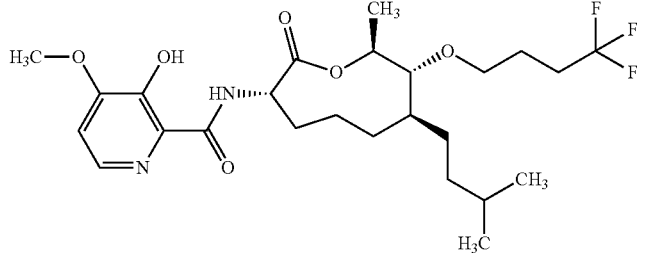 [SMILES: COc1ccnc(C(=O)N[C@H]2CCC[C@H](CCC(C)C)[C@@H](OCCCC(F)(F)F)[C@H](C)OC2=O)c1O] | Example 1, Steps 1, 2c, 3, 4, 5c, 5b, 6; Example 2, Steps 1a-1, 1 a-2; Example 3, Steps 1, 2a; Example 8, Steps 1, 2 | White Solid |
| F6 | 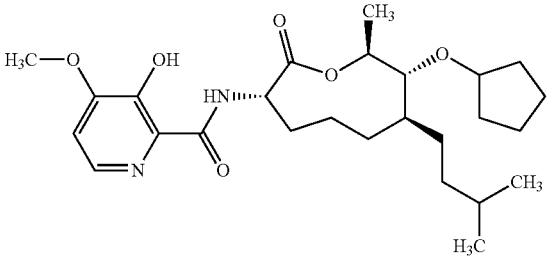 [SMILES: COc1ccnc(C(=O)N[C@H]2CCC[C@H](CCC(C)C)[C@@H](OC3CCCC3)[C@H](C)OC2=O)c1O] | Example 1, Steps 1, 2c, 3, 4, 5c, 5b, 6; Example 2, Steps 1a-1, 1a-2; Example 3, Steps 1, 2a; Example 8, Steps 1, 2 | Pale Yellow Sticky Solid |
| F7 | 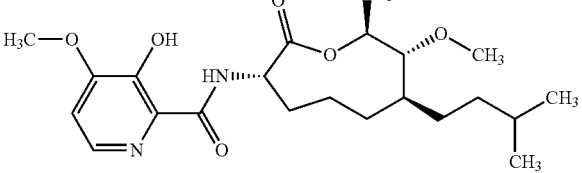 | Example 1, Steps 1, 2c 3, 4, 5c, 5b, 6; Example 2, Steps 1a-1, 1 a-2; Example 6; Example 8, Steps 1, 2 | Colorless Thick Oil |

TABLE 1-continued

Compound Structure and Appearance

| Compound Number | Structure | Prepared According To Example | Appearance |
| --- | --- | --- | --- |
| F8 | 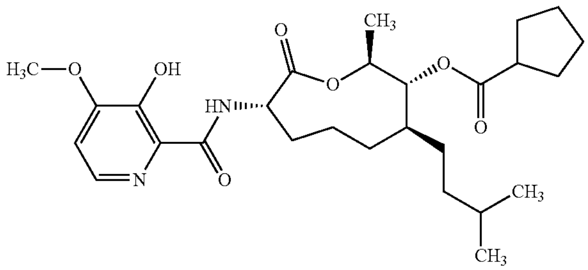 [SMILES: COc1ccnc(C(=O)N[C@H]2CCC[C@H](CCC(C)C)[C@@H](OC(=O)C3CCCC3)[C@H](C)OC2=O)c1O] | Example 1, Steps 1, 2c, 3, 4, 5c, 5b, 6; Example 2, Steps 1a-1, 1a-2; Example 5; Example 8, Steps 1, 2 | Sticky Colorless Solid |
| F9 | 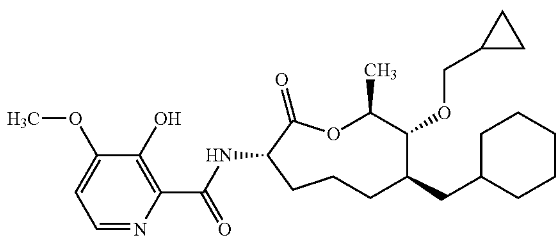 [SMILES: COc1ccnc(C(=O)N[C@H]2CCC[C@H](CC3CCCCC3)[C@@H](OCC3CC3)[C@H](C)OC2=O)c1O] | Example 1, Steps 1, 2b, 3, 4, 5a, 5b, 6; Example 8, Steps 1, 2 | White Solid |
| F10 | 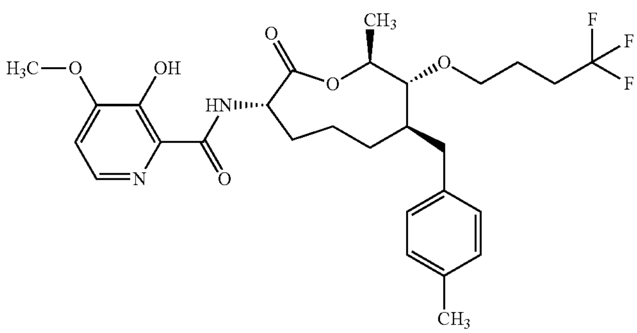 [SMILES: COc1ccnc(C(=O)N[C@H]2CCC[C@H](Cc3ccc(C)cc3)[C@@H](OCCCC(F)(F)F)[C@H](C)OC2=O)c1O] | Example 1, Steps 1, 2b, 3, 4, 5a, 5b, 6; Example 8, Steps 1, 2 | White Solid |
| F11 | 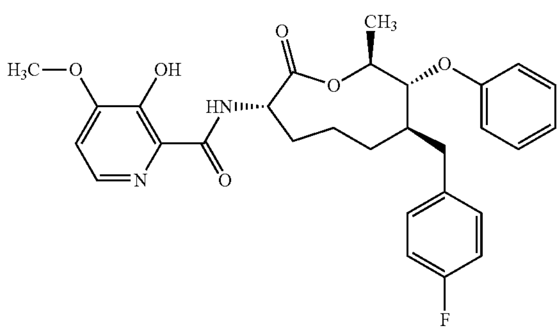 [SMILES: COc1ccnc(C(=O)N[C@H]2CCC[C@H](Cc3ccc(F)cc3)[C@@H](Oc3ccccc3)[C@H](C)OC2=O)c1O] | Example 1, Steps 1, 2a, 3, 4, 5a, 5b, 6; Example 8, Steps 1, 2 | Colorless Solid |
| F12 | 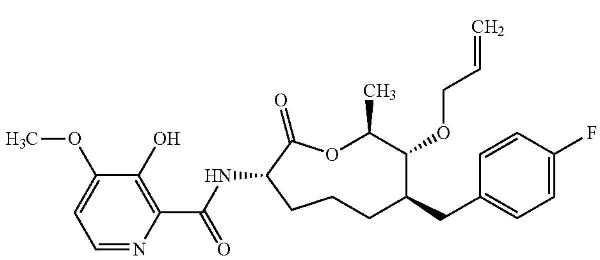 [SMILES: C=CCO[C@@H]1[C@@H](Cc2ccc(F)cc2)CCC[C@H](NC(=O)c2nccc(OC)c2O)C(=O)O[C@H]1C] | Example 1, Steps 1, 2c, 3, 4, 5a, 5b, 6; Example 2, Steps 1a-1, 1a-2; Example 3, Step 1; Example 8, Steps 1, 2 | White Solid |

TABLE 1-continued

Compound Structure and Appearance

| Compound Number | Structure | Prepared According To Example | Appearance |
|---|---|---|---|
| F13 | 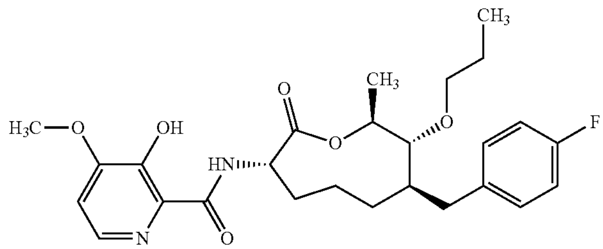 [SMILES: CCCO[C@@H]1[C@@H](Cc2ccc(F)cc2)CCC[C@H](NC(=O)c2nccc(OC)c2O)C(=O)O[C@H]1C] | Example 1, Steps 1, 2c, 3, 4, 5a, 5b, 6; Example 2, Steps 1a-1, 1a-2; Example 3, Steps 1, 2a; Example 8, Steps 1, 2 | White Solid |
| F14 | 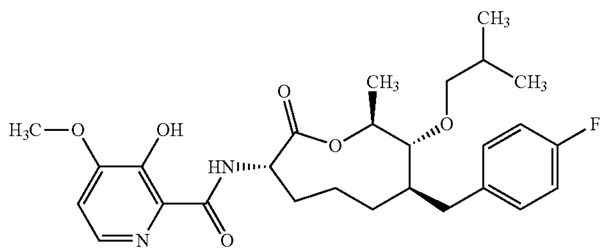 [SMILES: COc1ccnc(C(=O)N[C@H]2CCC[C@H](Cc3ccc(F)cc3)[C@@H](OCC(C)C)[C@H](C)OC2=O)c1O] | Example 1, Steps 1, 2c, 3, 4, 5a, 5b, 6; Example 2, Steps 1a-1, 1a-2; Example 3, Steps 1, 2a; Example 8, Steps 1, 2 | Colorless Solid |
| F15 | 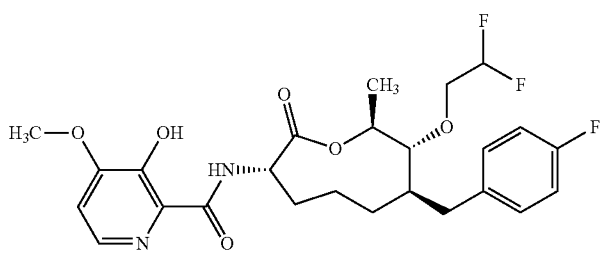 [SMILES: COc1ccnc(C(=O)N[C@H]2CCC[C@H](Cc3ccc(F)cc3)[C@@H](OCC(F)F)[C@H](C)OC2=O)c1O] | Example 1, Steps 1, 2c, 3, 4, 5a, 5b, 6; Example 2, Steps 1a-1, 1a-2; Example 3, Steps 1, 2b-1, 2b-2; Example 8, Steps 1, 2 | White Solid |
| F16 | 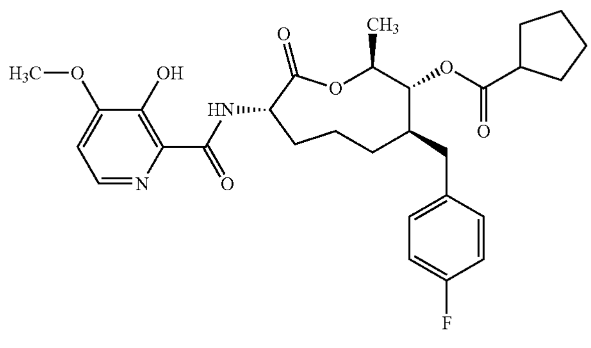 [SMILES: COc1ccnc(C(=O)N[C@H]2CCC[C@H](Cc3ccc(F)cc3)[C@@H](OC(=O)C3CCCC3)[C@H](C)OC2=O)c1O] | Example 1, Steps 1, 2c, 3, 4, 5a, 5b, 6; Example 2, Steps 1a-1a-2; Example 5; Example 8, Steps 1, 2 | White Solid |
| F17 | 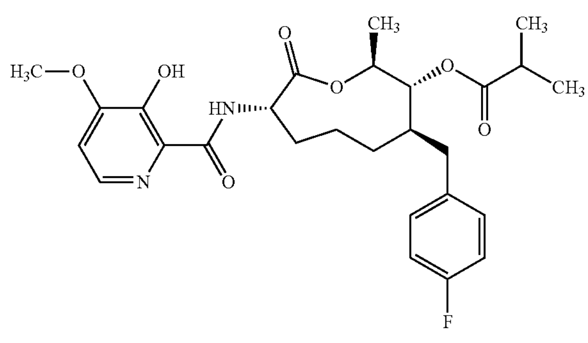 [SMILES: COc1ccnc(C(=O)N[C@H]2CCC[C@H](Cc3ccc(F)cc3)[C@@H](OC(=O)C(C)C)[C@H](C)OC2=O)c1O] | Example 1, Steps 1, 2c, 3, 4, 5a, 5b, 6; Example 2, Steps 1a-1a-2; Example 5; Example 8, Steps 1, 2 | White Solid |

TABLE 1-continued

Compound Structure and Appearance

| Compound Number | Structure | Prepared According To Example | Appearance |
| --- | --- | --- | --- |
| F18 | 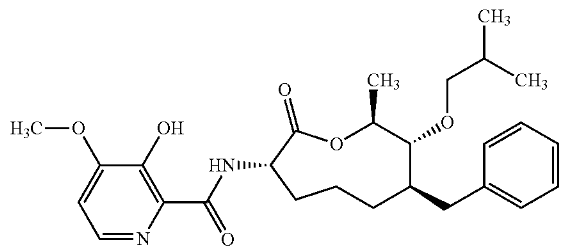 [SMILES: COc1ccnc(C(=O)N[C@H]2CCC[C@H](Cc3ccccc3)[C@@H](OCC(C)C)[C@H](C)OC2=O)c1O] | Example 1, Steps 1, 2b, 3, 4, 5b, 6, Example 8, Steps 1, 2 | White Solid |
| F19 | 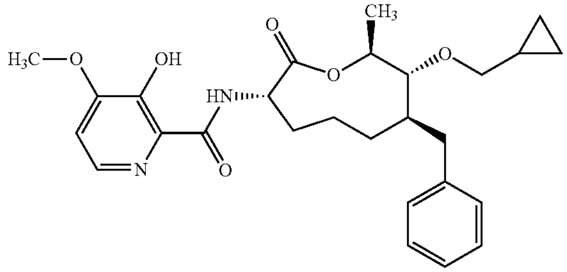 [SMILES: COc1ccnc(C(=O)N[C@H]2CCC[C@H](Cc3ccccc3)[C@@H](OCC3CC3)[C@H](C)OC2=O)c1O] | Example 1, Steps 1, 2b, 3, 4, 5a, 5c, 6, Example 8, Steps 1, 2 | Thick Oil |
| F20 | 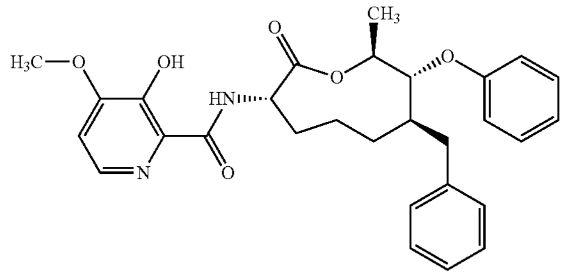 [SMILES: COc1ccnc(C(=O)N[C@H]2CCC[C@H](Cc3ccccc3)[C@@H](Oc3ccccc3)[C@H](C)OC2=O)c1O] | Example 1, Steps 1, 2a, 3, 4, 5b, 6, Example 8, Steps 1, 2 | White Solid |
| F21 | 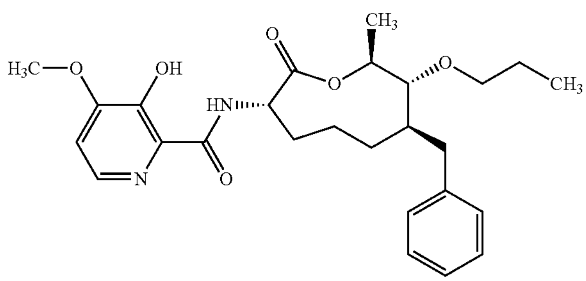 [SMILES: CCCO[C@@H]1[C@@H](Cc2ccccc2)CCC[C@H](NC(=O)c2nccc(OC)c2O)C(=O)O[C@H]1C] | Example 1, Steps 1, 2b, 3, 4, 5b, 6; Example 2, Step 1b; Example 8, Steps 1, 2 | White Solid |
| F22 | 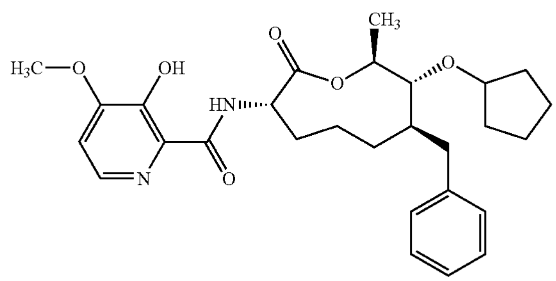 [SMILES: COc1ccnc(C(=O)N[C@H]2CCC[C@H](Cc3ccccc3)[C@@H](OC3CCCC3)[C@H](C)OC2=O)c1O] | Example 1, Steps 1, 2b, 3, 4, 5a, 5c, 6, 5b; Example 2, Step 1b; Example 3 Steps 1, 2a, Example 8, Steps 1, 2 | White Solid |

TABLE 1-continued

Compound Structure and Appearance

| Compound Number | Structure | Prepared According To Example | Appearance |
|---|---|---|---|
| F23 | 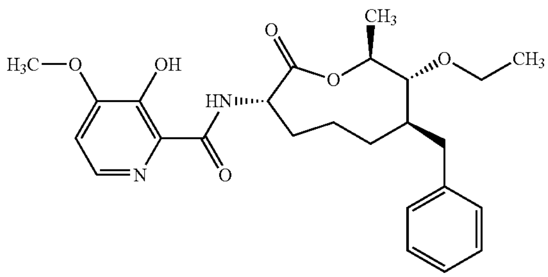 [SMILES: CCO[C@@H]1[C@@H](Cc2ccccc2)CCC[C@H](NC(=O)c2nccc(OC)c2O)C(=O)O[C@H]1C] | Example 1, Steps 1, 2b, 3, 4, 5b, 6, Example 8, Steps 1, 2 | White Solid |
| F24 | 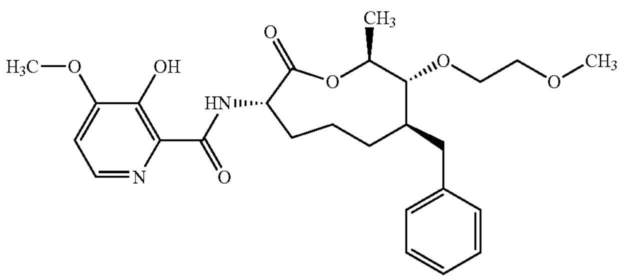 | Example 1, Steps 1, 2b, 3, 4, 5b, 6, Example 8, Steps 1, 2 | Foam |
| F25 | 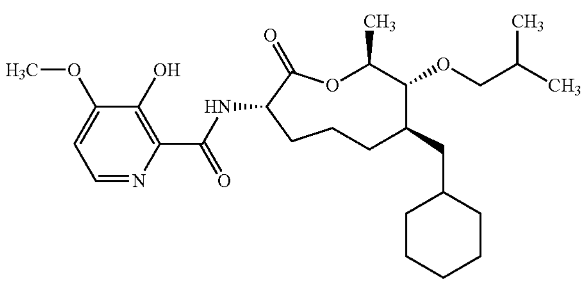 [SMILES: COc1ccnc(C(=O)N[C@H]2CCC[C@H](CC3CCCCC3)[C@@H](OCC(C)C)[C@H](C)OC2=O)c1O] | Example 1, Steps 1, 2b, 3, 4, 5b, 6, Example 8, Steps 1, 2; Example 16 | White Solid |
| F26 | 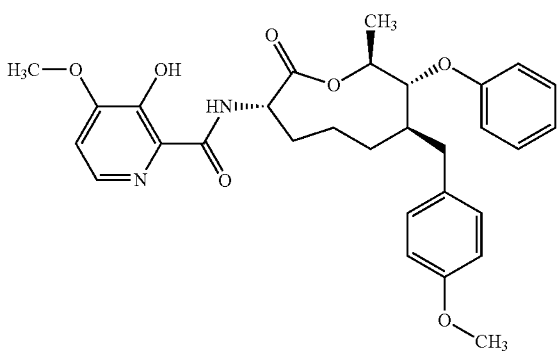 [SMILES: COc1ccc(C[C@H]2CCC[C@H](NC(=O)c3nccc(OC)c3O)C(=O)O[C@@H](C)[C@@H]2Oc2ccccc2)cc1] | Example 8, Steps 1, 2 | Colorless Semi-Solid |
| F27 | 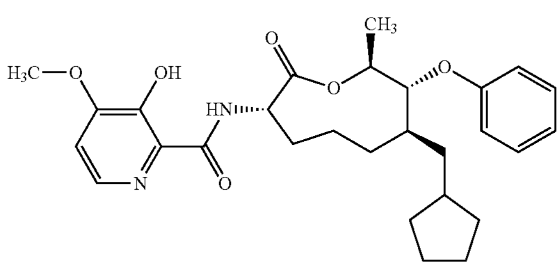 [SMILES: COc1ccnc(C(=O)N[C@H]2CCC[C@H](CC3CCCC3)[C@@H](Oc3ccccc3)[C@H](C)OC2=O)c1O] | Example 8 Steps 1, 2 | White Solid |

TABLE 1-continued

Compound Structure and Appearance

| Compound Number | Structure | Prepared According To Example | Appearance |
|---|---|---|---|
| F28 | 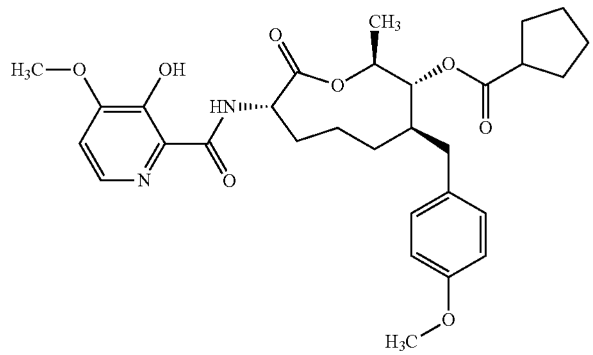 [SMILES: COc1ccc(C[C@H]2CCC[C@H](NC(=O)c3nccc(OC)c3O)C(=O)O[C@@H](C)[C@@H]2OC(=O)C2CCCC2)cc1] | Example 8, Steps 1, 2 | Colorless Oil |
| F29 | 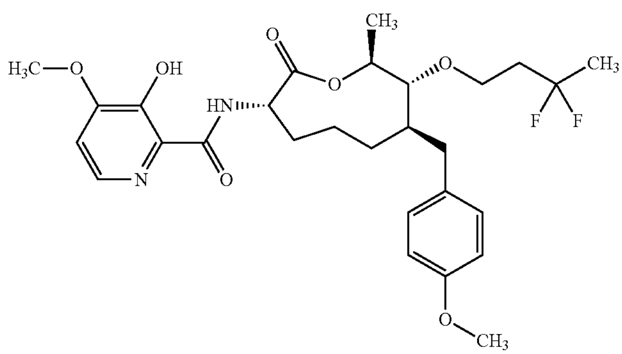 [SMILES: COc1ccc(C[C@H]2CCC[C@H](NC(=O)c3nccc(OC)c3O)C(=O)O[C@@H](C)[C@@H]2OCCC(C)(F)F)cc1] | Example 8, Steps 1, 2 | White Solid |
| F30 | 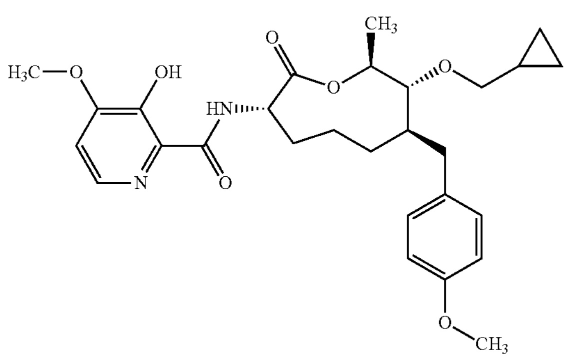 [SMILES: COc1ccc(C[C@H]2CCC[C@H](NC(=O)c3nccc(OC)c3O)C(=O)O[C@@H](C)[C@@H]2OCC2CC2)cc1] | Example 8, Steps 1, 2 | White Solid |
| F31 | 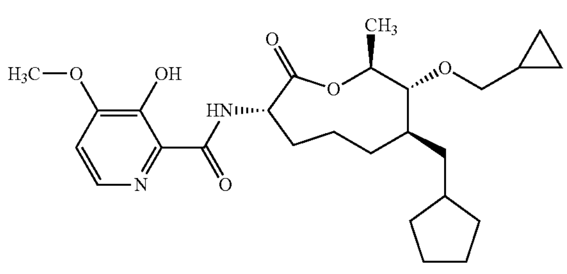 [SMILES: COc1ccnc(C(=O)N[C@H]2CCC[C@H](CC3CCCC3)[C@@H](OCC3CC3)[C@H](C)OC2=O)c1O] | Example 8, Steps 1, 2 | White Solid |

TABLE 1-continued

Compound Structure and Appearance

| Compound Number | Structure | Prepared According To Example | Appearance |
| --- | --- | --- | --- |
| F32 | 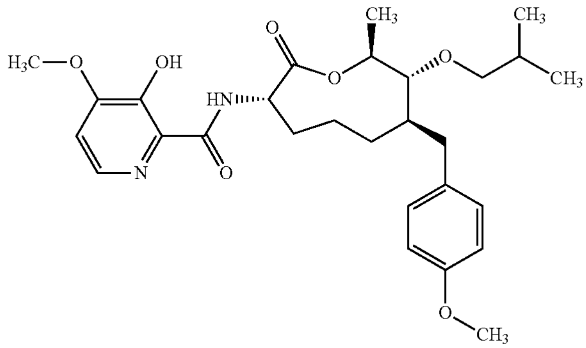 [SMILES: COc1ccc(C[C@H]2CCC[C@H](NC(=O)c3nccc(OC)c3O)C(=O)O[C@@H](C)[C@@H]2OCC(C)C)cc1] | Example 8, Steps 1, 2 | Colorless Semi Solid |
| F33 | 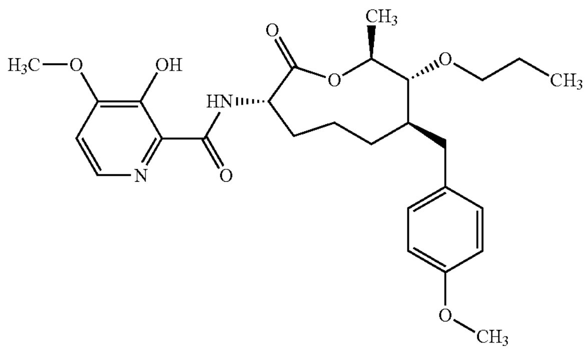 [SMILES: CCCO[C@@H]1[C@@H](Cc2ccc(OC)cc2)CCC[C@H](NC(=O)c2nccc(OC)c2O)C(=O)O[C@H]1C] | Example 8, Steps 1, 2 | Colorless Semi-Solid |
| F34 | 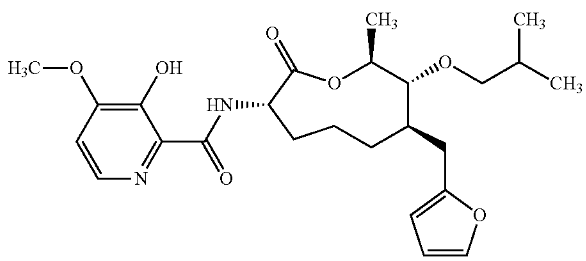 [SMILES: COc1ccnc(C(=O)N[C@H]2CCC[C@H](Cc3ccco3)[C@@H](OCC(C)C)[C@H](C)OC2=O)c1O] | Example 8, Steps 1, 2 | White Solid |
| F35 | 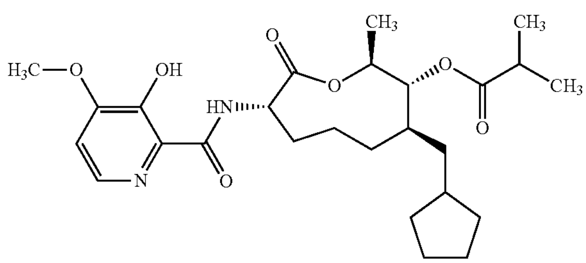 [SMILES: COc1ccnc(C(=O)N[C@H]2CCC[C@H](CC3CCCC3)[C@@H](OC(=O)C(C)C)[C@H](C)OC2=O)c1O] | Example 8, Steps 1, 2 | Light Yellow Solid |
| F36 | 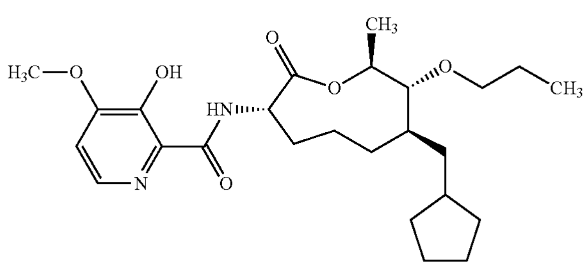 [SMILES: CCCO[C@@H]1[C@@H](CC2CCCC2)CCC[C@H](NC(=O)c2nccc(OC)c2O)C(=O)O[C@H]1C] | Example 8, Steps 1, 2 | White Solid |

TABLE 1-continued

Compound Structure and Appearance

| Compound Number | Structure | Prepared According To Example | Appearance |
|---|---|---|---|
| F37 | 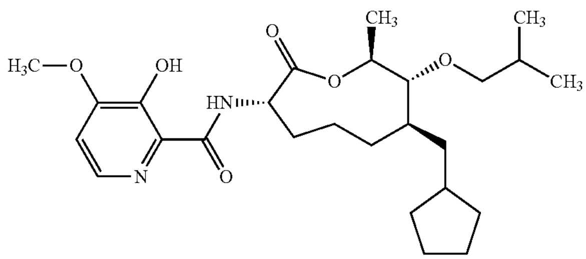 [SMILES: COc1ccnc(C(=O)N[C@H]2CCC[C@H](CC3CCCC3)[C@@H](OCC(C)C)[C@H](C)OC2=O)c1O] | Example 8, Steps 1, 2 | White Solid |
| F38 | 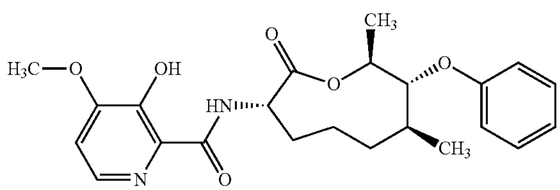 [SMILES: COc1ccnc(C(=O)N[C@H]2CCC[C@H](C)[C@@H](Oc3ccccc3)[C@H](C)OC2=O)c1O] | Example 8, Steps 1, Step 2 | White Solid |
| F39 | 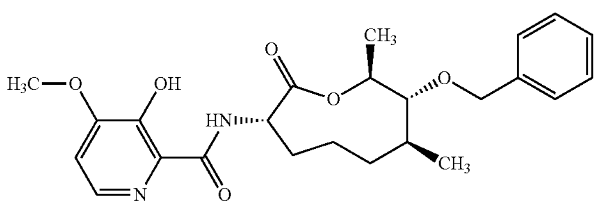 [SMILES: COc1ccnc(C(=O)N[C@H]2CCC[C@H](C)[C@@H](OCc3ccccc3)[C@H](C)OC2=O)c1O] | Example 8, Steps 1, 2 | White Solid |
| F40 | 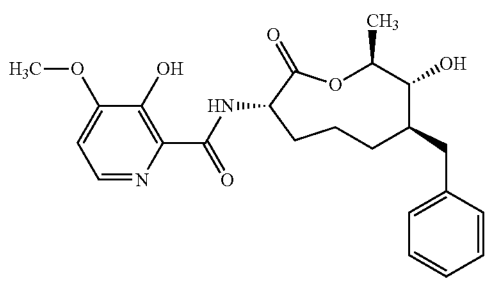 [SMILES: COc1ccnc(C(=O)N[C@H]2CCC[C@H](Cc3ccccc3)[C@@H](O)[C@H](C)OC2=O)c1O] | Example 1, Steps 1, 2b, 3, 4, 5a, 5c, 6, 5b; Example 2, Step 1b; Example 8, Steps 1, 2 | Colorless Thick Oil |
| F41 | 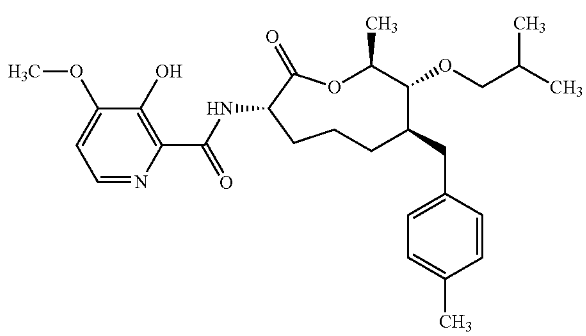 [SMILES: COc1ccnc(C(=O)N[C@H]2CCC[C@H](Cc3ccc(C)cc3)[C@@H](OCC(C)C)[C@H](C)OC2=O)c1O] | Example 8 | White Solid |

TABLE 1-continued

Compound Structure and Appearance

| Compound Number | Structure | Prepared According To Example | Appearance |
|---|---|---|---|
| F42 | 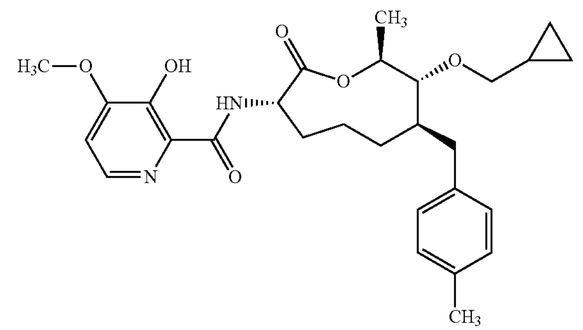 [SMILES: COc1ccnc(C(=O)N[C@H]2CCC[C@H](Cc3ccc(C)cc3)[C@@H](OCC3CC3)[C@H](C)OC2=O)c1O] | Example 8 | Colorless Oil |
| F43 | 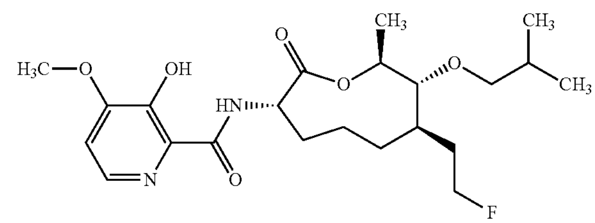 [SMILES: COc1ccnc(C(=O)N[C@H]2CCC[C@H](CCF)[C@@H](OCC(C)C)[C@H](C)OC2=O)c1O] | Example 8, Step 2 | White Solid |
| F44 | 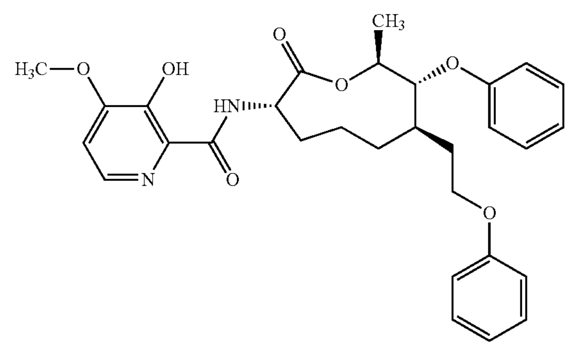 [SMILES: COc1ccnc(C(=O)N[C@H]2CCC[C@H](CCOc3ccccc3)[C@@H](Oc3ccccc3)[C@H](C)OC2=O)c1O] | Example 8, Step 2 | White Solid |
| F45 | 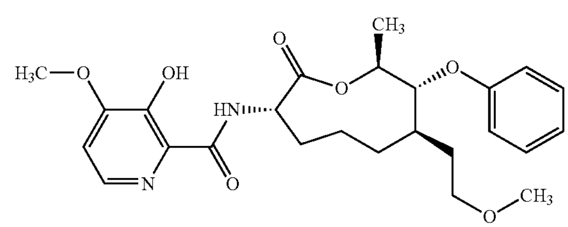 [SMILES: COCC[C@H]1CCC[C@H](NC(=O)c2nccc(OC)c2O)C(=O)O[C@@H](C)[C@@H]1Oc1ccccc1] | Example 8, Step 2 | White Solid |
| F46 | 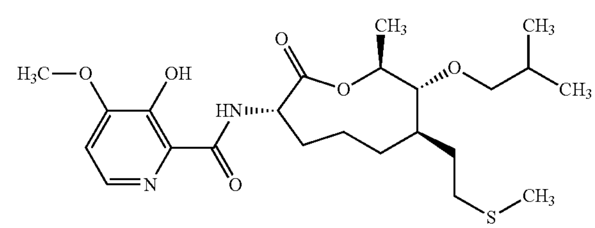 [SMILES: COc1ccnc(C(=O)N[C@H]2CCC[C@H](CCSC)[C@@H](OCC(C)C)[C@H](C)OC2=O)c1O] | Example 8, Step 2 | White Solid |

TABLE 1-continued

Compound Structure and Appearance

| Compound Number | Structure | Prepared According To Example | Appearance |
| --- | --- | --- | --- |
| F47 | 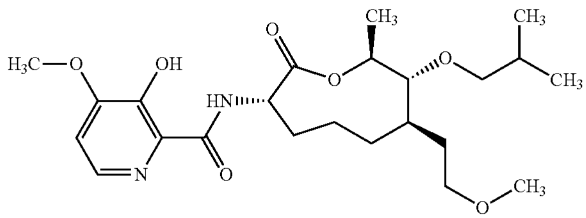 [SMILES: COCC[C@H]1CCC[C@H](NC(=O)c2nccc(OC)c2O)C(=O)O[C@@H](C)[C@@H]1OCC(C)C] | Example 8, Step 2 | White Solid |
| F48 | 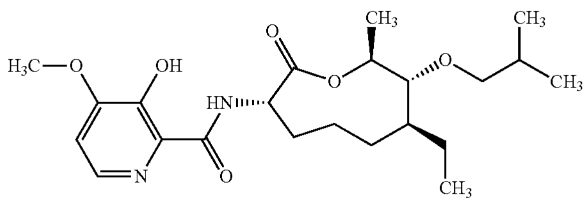 [SMILES: CC[C@H]1CCC[C@H](NC(=O)c2nccc(OC)c2O)C(=O)O[C@@H](C)[C@@H]1OCC(C)C] | Example 8, Step 2 | White Solid |
| F49 | 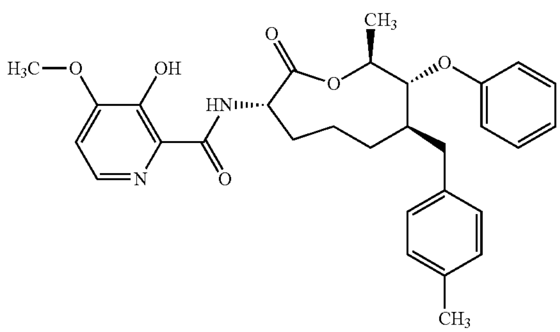 [SMILES: COc1ccnc(C(=O)N[C@H]2CCC[C@H](Cc3ccc(C)cc3)[C@@H](Oc3ccccc3)[C@H](C)OC2=O)c1O] | Example 8 | White Solid |
| F50 | 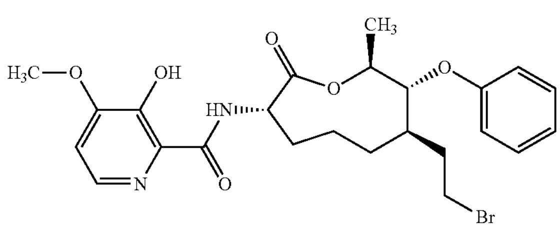 [SMILES: COc1ccnc(C(=O)N[C@H]2CCC[C@H](CCBr)[C@@H](Oc3ccccc3)[C@H](C)OC2=O)c1O] | Example 8 Step 2 | White Solid |
| F51 | 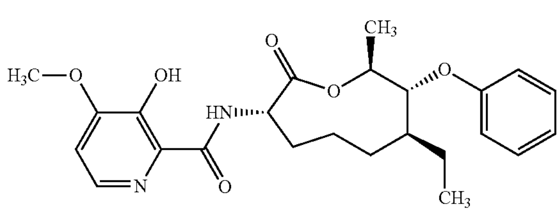 [SMILES: CC[C@H]1CCC[C@H](NC(=O)c2nccc(OC)c2O)C(=O)O[C@@H](C)[C@@H]1Oc1ccccc1] | Example 8 Step 2 | Hard White Foam |

TABLE 1-continued

Compound Structure and Appearance

| Compound Number | Structure | Prepared According To Example | Appearance |
|---|---|---|---|
| F52 | 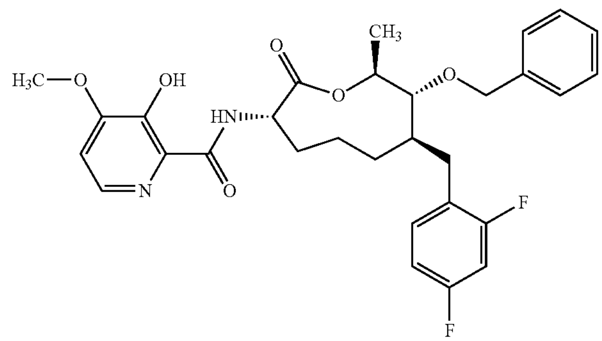 [SMILES: COc1ccnc(C(=O)N[C@H]2CCC[C@H](Cc3ccc(F)cc3F)[C@@H](OCc3ccccc3)[C@H](C)OC2=O)c1O] | Example 8 | White Solid |
| F53 | 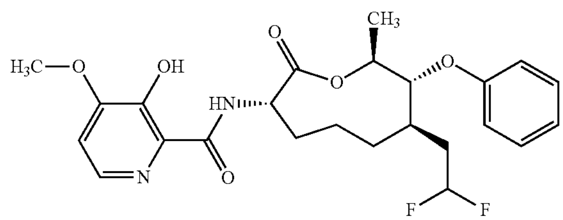 [SMILES: COc1ccnc(C(=O)N[C@H]2CCC[C@H](CC(F)F)[C@@H](Oc3ccccc3)[C@H](C)OC2=O)c1O] | Example 8, Step 2 | White Solid |
| F54 | 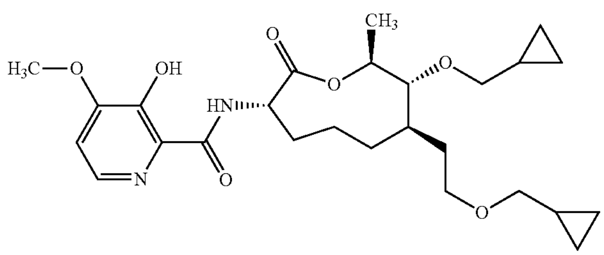 [SMILES: COc1ccnc(C(=O)N[C@H]2CCC[C@H](CCOCC3CC3)[C@@H](OCC3CC3)[C@H](C)OC2=O)c1O] | Example 8, Step 2 | Sticky Glassy Solid |
| F55 | 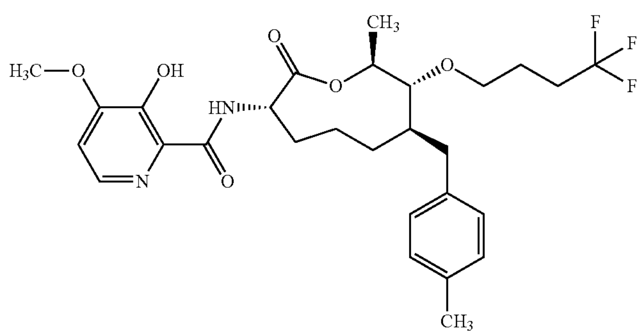 [SMILES: COc1ccnc(C(=O)N[C@H]2CCC[C@H](Cc3ccc(C)cc3)[C@@H](OCCCC(F)(F)F)[C@H](C)OC2=O)c1O] | Example 8 | White Solid |
| F56 | 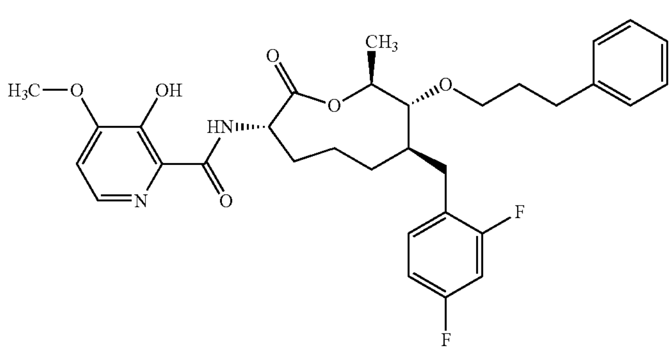 [SMILES: COc1ccnc(C(=O)N[C@H]2CCC[C@H](Cc3ccc(F)cc3F)[C@@H](OCCCc3ccccc3)[C@H](C)OC2=O)c1O] | Example 8 | Colorless Oil |

TABLE 1-continued

Compound Structure and Appearance

| Compound Number | Structure | Prepared According To Example | Appearance |
|---|---|---|---|
| F57 | 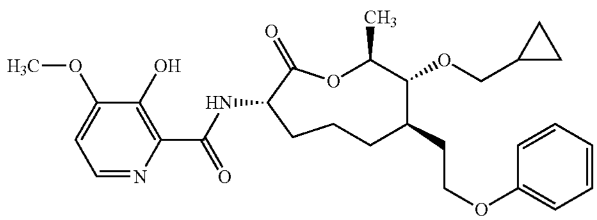 [SMILES: COc1ccnc(C(=O)N[C@H]2CCC[C@H](CCOc3ccccc3)[C@@H](OCC3CC3)[C@H](C)OC2=O)c1O] | Example 8, Step 2 | White Solid |
| F58 | 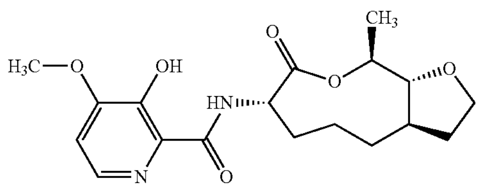 [SMILES: COc1ccnc(C(=O)N[C@H]2CCC[C@@H]3CCO[C@H]3[C@H](C)OC2=O)c1O] | Example 8, Step 2 | White Solid |
| F59 | 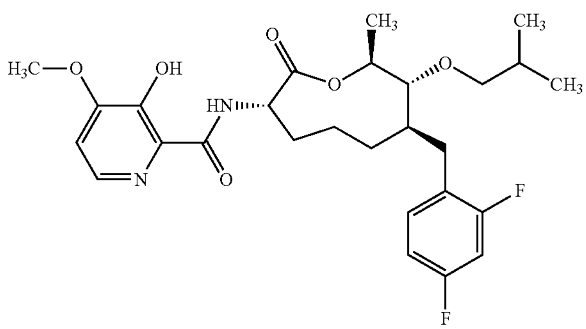 [SMILES: COc1ccnc(C(=O)N[C@H]2CCC[C@H](Cc3ccc(F)cc3F)[C@@H](OCC(C)C)[C@H](C)OC2=O)c1O] | Example 8 | White Solid |
| F60 | 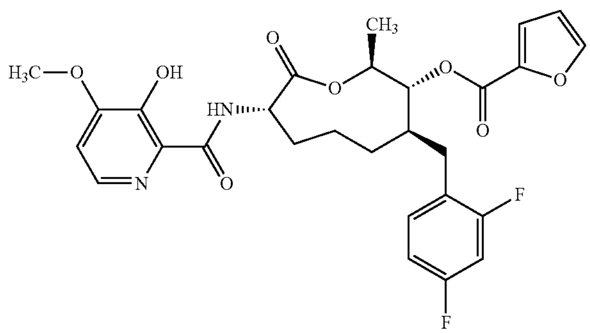 [SMILES: COc1ccnc(C(=O)N[C@H]2CCC[C@H](Cc3ccc(F)cc3F)[C@@H](OC(=O)c3ccco3)[C@H](C)OC2=O)c1O] | Example 8 | White Solid |
| F61 | 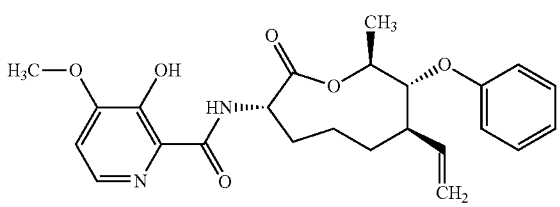 [SMILES: C=C[C@H]1CCC[C@H](NC(=O)c2nccc(OC)c2O)C(=O)O[C@@H](C)[C@@H]1Oc1ccccc1] | Example 8, Step 2 | Yellow Solid |

TABLE 1-continued

Compound Structure and Appearance

| Compound Number | Structure | Prepared According To Example | Appearance |
|---|---|---|---|
| F62 | 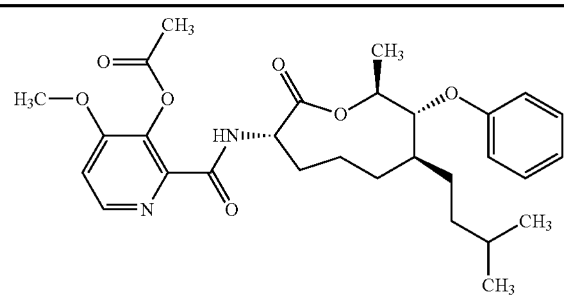 | Example 1, Steps 1, 2c, 3, 4, 5c, 5b, 6; Example 2, Steps 1a-1, 1a-2; Example 7, Step 2a; Example 8, Steps 1, 2; Example 10 | Yellow Solid |
| F63 | 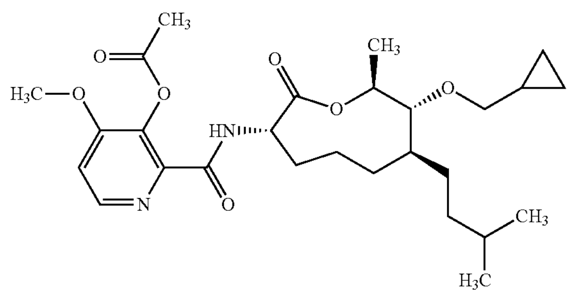 [SMILES: COc1ccnc(C(=O)N[C@H]2CCC[C@H](CCC(C)C)[C@@H](OCC3CC3)[C@H](C)OC2=O)c1OC(C)=O] | Example 1, Steps 1, 2b, 3, 5b, 5c, 6; Example 8, Steps 1, 2; Example 10 | Yellow Oil |
| F64 | 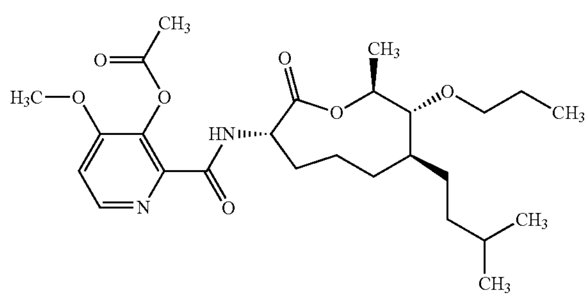 [SMILES: CCCO[C@@H]1[C@@H](CCC(C)C)CCC[C@H](NC(=O)c2nccc(OC)c2OC(C)=O)C(=O)O[C@H]1C] | Example 1, Steps 1, 2c, 3, 4, 5c, 5b, 6; Example 2, Steps 1a-2; Example 3, Steps 1, 2a; Example 8, Steps 1, 2; Example 10 | Yellow Solid |
| F65 | 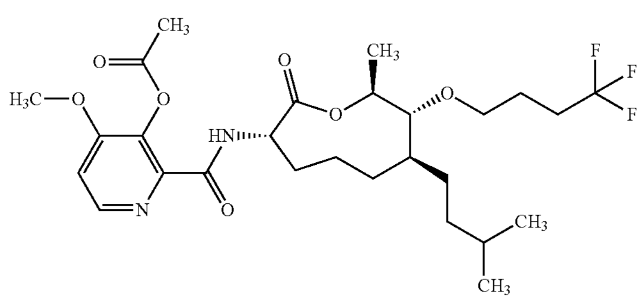 [SMILES: COc1ccnc(C(=O)N[C@H]2CCC[C@H](CCC(C)C)[C@@H](OCCCC(F)(F)F)[C@H](C)OC2=O)c1OC(C)=O] | Example 1, Steps 1, 2c, 3, 4, 5c, 5b, 6; Example 2, Steps 1a-1, 1a-2; Example 3, Steps 1, 2a; Example 8, Steps 1, 2; Example 10 | Crystalline Yellow Solid |
| F66 | 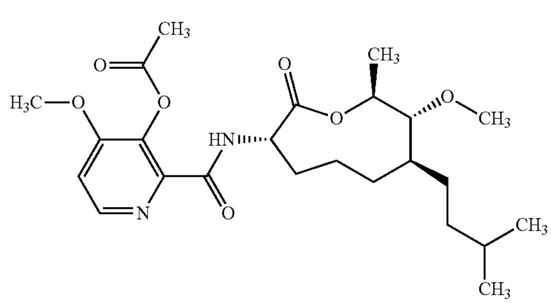 [SMILES: COc1ccnc(C(=O)N[C@H]2CCC[C@H](CCC(C)C)[C@@H](OC)[C@H](C)OC2=O)c1OC(C)=O] | Example 1, Steps 1, 2c, 3, 4, 5c, 5b, 6; Example 2, Steps 1a-1, 1a-2; Example 6; Example 8, Steps 1, 2; Example 10 | Yellow Solid |

TABLE 1-continued

Compound Structure and Appearance

| Compound Number | Structure | Prepared According To Example | Appearance |
|---|---|---|---|
| F67 | 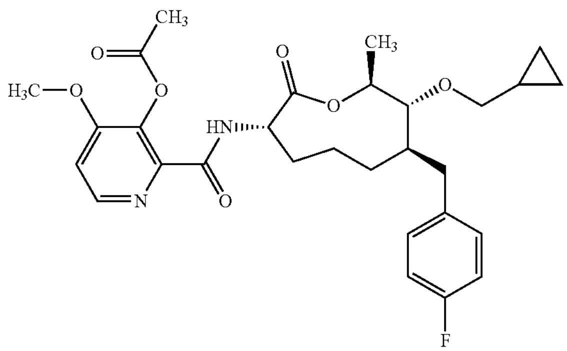 [SMILES: COc1ccnc(C(=O)N[C@H]2CCC[C@H](Cc3ccc(F)cc3)[C@@H](OCC3CC3)[C@H](C)OC2=O)c1OC(C)=O] | Example 1, Steps 1, 2b, 3, 4, 5a, 5b, 6; Example 8, Steps 1, 2; Example 10 | Yellow Oil |
| F68 | 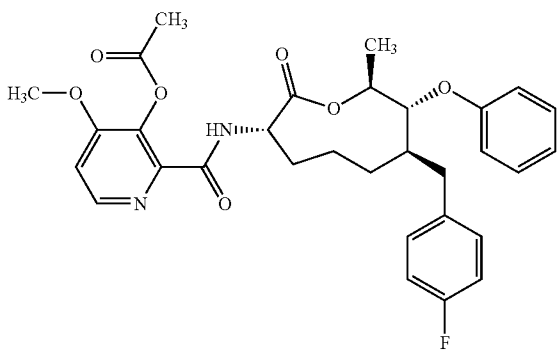 [SMILES: COc1ccnc(C(=O)N[C@H]2CCC[C@H](Cc3ccc(F)cc3)[C@@H](Oc3ccccc3)[C@H](C)OC2=O)c1OC(C)=O] | Example 1, Steps 1, 2a, 3, 4, 5a, 5b, 6; Example 8, Steps 1, 2; Example 10 | Yellow Oil |
| F69 | 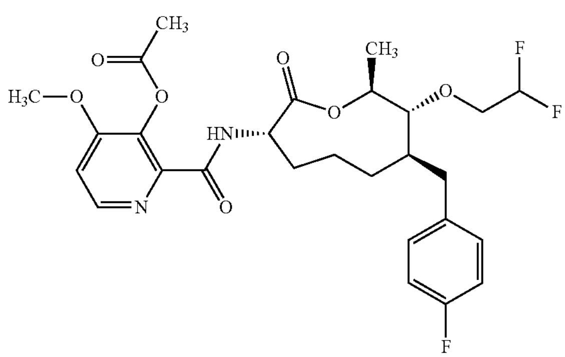 [SMILES: COc1ccnc(C(=O)N[C@H]2CCC[C@H](Cc3ccc(F)cc3)[C@@H](OCC(F)F)[C@H](C)OC2=O)c1OC(C)=O] | Example 1, Steps 1, 2c, 3, 4, 5a, 5b, 6; Example 2, Steps 1a-1, 1a-2; Example 3, Steps 1, 2b-1, 2b-2; Example 8, Steps 1, 2; Example 10 | Pale Yellow Solid |
| F70 | 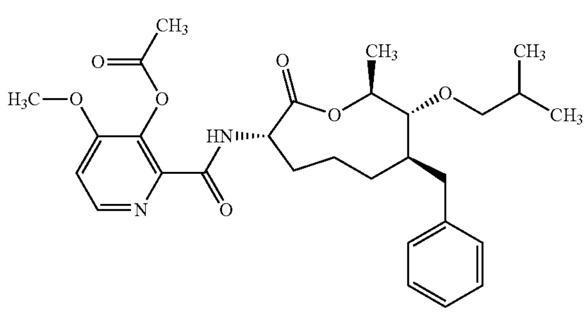 [SMILES: COc1ccnc(C(=O)N[C@H]2CCC[C@H](Cc3ccccc3)[C@@H](OCC(C)C)[C@H](C)OC2=O)c1OC(C)=O] | Example 10 | Colorless Thick Oil |

TABLE 1-continued

Compound Structure and Appearance

| Compound Number | Structure | Prepared According To Example | Appearance |
|---|---|---|---|
| F71 | 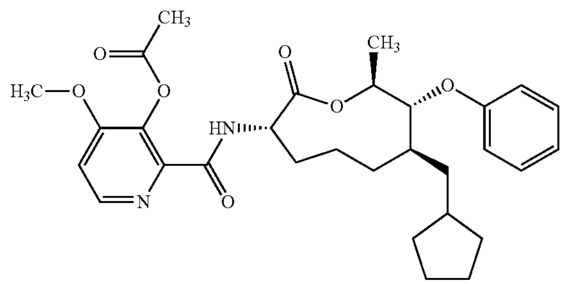 [SMILES: COc1ccnc(C(=O)N[C@H]2CCC[C@H](CC3CCCC3)[C@@H](Oc3ccccc3)[C@H](C)OC2=O)c1OC(C)=O] | Example 10 | Colorless Oil |
| F72 | 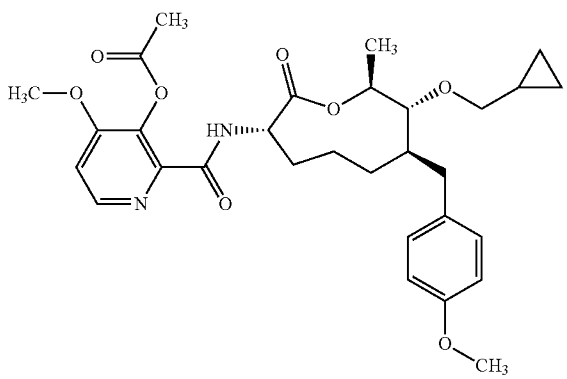 [SMILES: COc1ccc(C[C@H]2CCC[C@H](NC(=O)c3nccc(OC)c3OC(C)=O)C(=O)O[C@@H](C)[C@@H]2OCC2CC2)cc1] | Example 10 | White Solid |
| F73 | 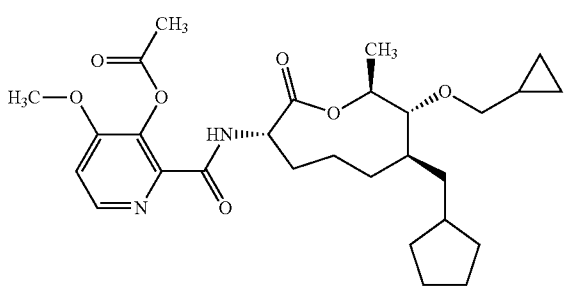 [SMILES: COc1ccnc(C(=O)N[C@H]2CCC[C@H](CC3CCCC3)[C@@H](OCC3CC3)[C@H](C)OC2=O)c1OC(C)=O] | Example 10 | Sticky Yellow Semi Solid |
| F74 | 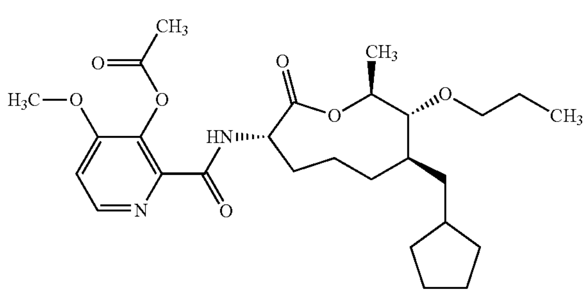 [SMILES: CCCO[C@@H]1[C@@H](CC2CCCC2)CCC[C@H](NC(=O)c2nccc(OC)c2OC(C)=O)C(=O)O[C@H]1C] | Example 10 | Sticky White Solid |

TABLE 1-continued

Compound Structure and Appearance

| Compound Number | Structure | Prepared According To Example | Appearance |
|---|---|---|---|
| F75 | 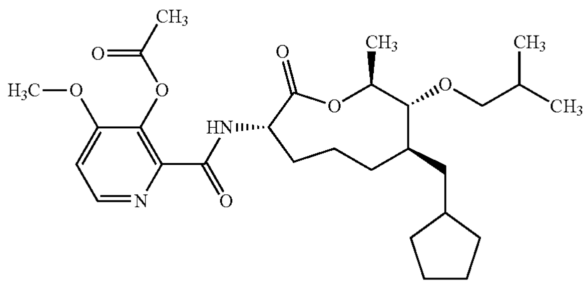 [SMILES: COc1ccnc(C(=O)N[C@H]2CCC[C@H](CC3CCCC3)[C@@H](OCC(C)C)[C@H](C)OC2=O)c1OC(C)=O] | Example 10 | White Solid |
| F76 | 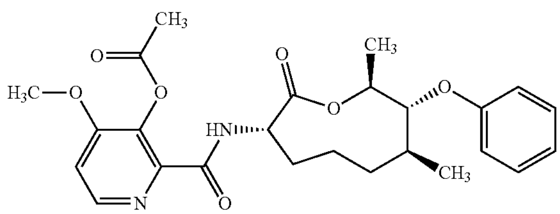 [SMILES: COc1ccnc(C(=O)N[C@H]2CCC[C@H](C)[C@@H](Oc3ccccc3)[C@H](C)OC2=O)c1OC(C)=O] | Example 10 | White Glassy Solid |
| F77 | 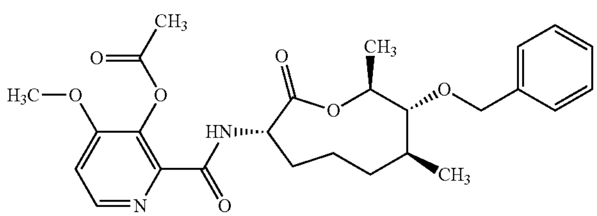 [SMILES: COc1ccnc(C(=O)N[C@H]2CCC[C@H](C)[C@@H](OCc3ccccc3)[C@H](C)OC2=O)c1OC(C)=O] | Example 10 | White Solid |
| F78 | 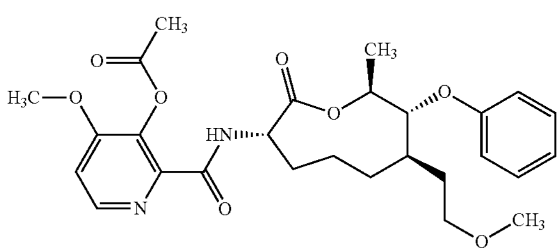 [SMILES: COCC[C@H]1CCC[C@H](NC(=O)c2nccc(OC)c2OC(C)=O)C(=O)O[C@@H](C)[C@@H]1Oc1ccccc1] | Example 10 | White Solid |
| F79 | 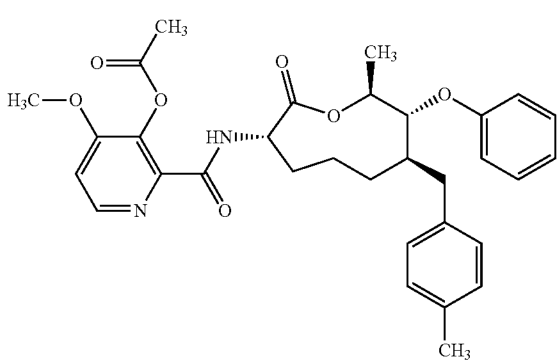 [SMILES: COc1ccnc(C(=O)N[C@H]2CCC[C@H](Cc3ccc(C)cc3)[C@@H](Oc3ccccc3)[C@H](C)OC2=O)c1OC(C)=O] | Example 10 | White Solid |

TABLE 1-continued

Compound Structure and Appearance

| Compound Number | Structure | Prepared According To Example | Appearance |
|---|---|---|---|
| F80 | 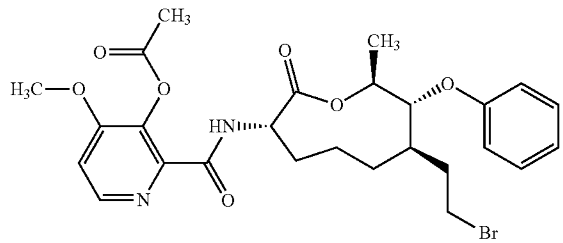 [SMILES: COc1ccnc(C(=O)N[C@H]2CCC[C@H](CCBr)[C@@H](Oc3ccccc3)[C@H](C)OC2=O)c1OC(C)=O] | Example 10 | Hard White Foam |
| F81 | 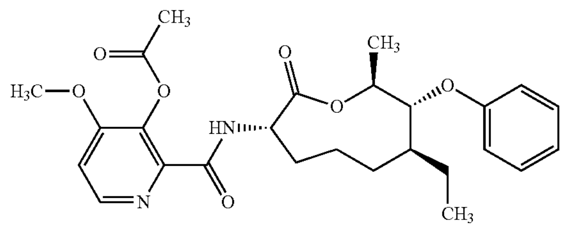 [SMILES: CC[C@H]1CCC[C@H](NC(=O)c2nccc(OC)c2OC(C)=O)C(=O)O[C@@H](C)[C@@H]1Oc1ccccc1] | Example 10 | White Solid |
| F82 | 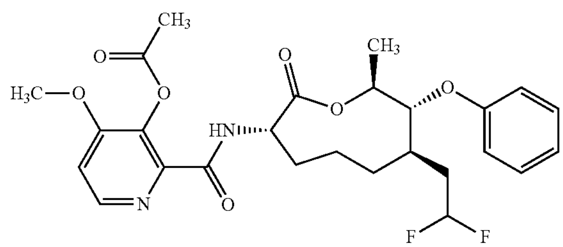 [SMILES: COc1ccnc(C(=O)N[C@H]2CCC[C@H](CC(F)F)[C@@H](Oc3ccccc3)[C@H](C)OC2=O)c1OC(C)=O] | Example 10 | White Solid |
| F83 | 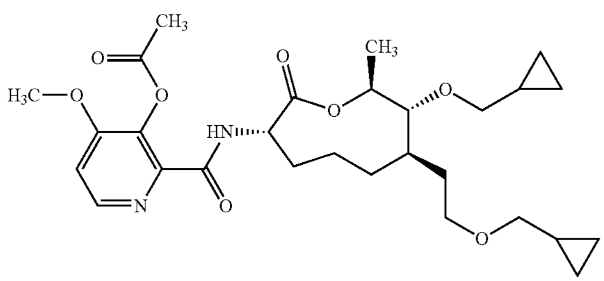 [SMILES: COc1ccnc(C(=O)N[C@H]2CCC[C@H](CCOCC3CC3)[C@@H](OCC3CC3)[C@H](C)OC2=O)c1OC(C)=O] | Example 10 | White Solid |
| F84 | 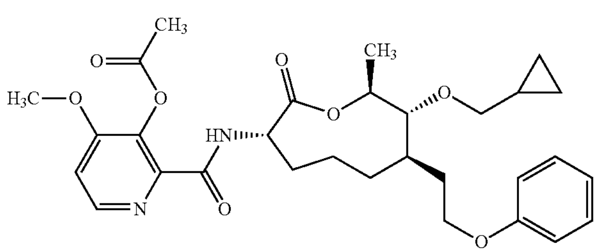 [SMILES: COc1ccnc(C(=O)N[C@H]2CCC[C@H](CCOc3ccccc3)[C@@H](OCC3CC3)[C@H](C)OC2=O)c1OC(C)=O] | Example 10 | White Solid |
| F85 | 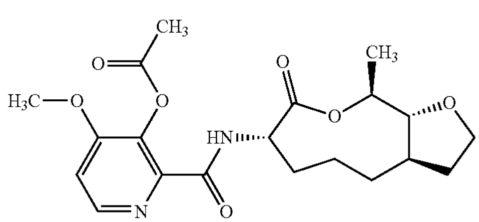 [SMILES: COc1ccnc(C(=O)N[C@H]2CCC[C@@H]3CCO[C@H]3[C@H](C)OC2=O)c1OC(C)=O] | Example 10 | White Solid |

TABLE 1-continued

Compound Structure and Appearance

| Compound Number | Structure | Prepared According To Example | Appearance |
|---|---|---|---|
| F86 | 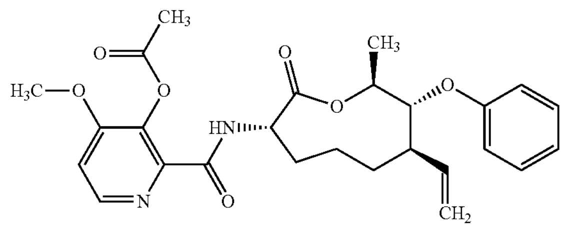 [SMILES: C=C[C@H]1CCC[C@H](NC(=O)c2nccc(OC)c2OC(C)=O)C(=O)O[C@@H](C)[C@@H]1Oc1ccccc1] | Example 10 | White Solid |
| F87 | 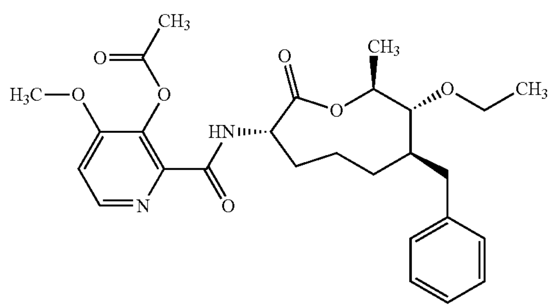 [SMILES: CCO[C@@H]1[C@@H](Cc2ccccc2)CCC[C@H](NC(=O)c2nccc(OC)c2OC(C)=O)C(=O)O[C@H]1C] | Example 10 | White Foam |
| F88 | 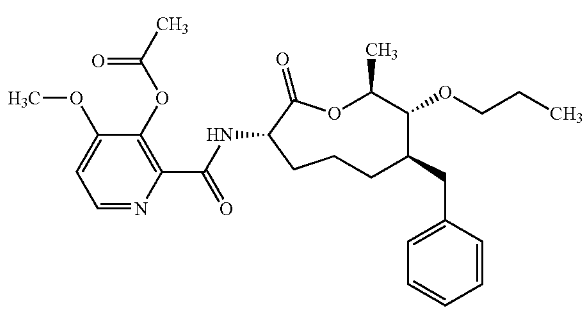 [SMILES: CCCO[C@@H]1[C@@H](Cc2ccccc2)CCC[C@H](NC(=O)c2nccc(OC)c2OC(C)=O)C(=O)O[C@H]1C] | Example 10 | White Foam |
| F89 | 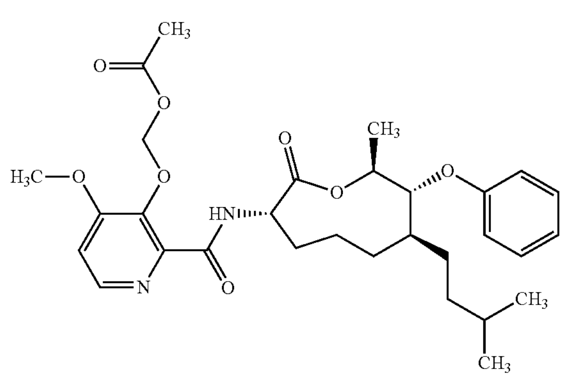 [SMILES: COc1ccnc(C(=O)N[C@H]2CCC[C@H](CCC(C)C)[C@@H](Oc3ccccc3)[C@H](C)OC2=O)c1OCOC(C)=O] | Example 1, Steps 1, 2c, 3, 4, 5c, 5b, 6; Example 2, Steps 1a-1, 1a-2; Example 7; Step 2a; Example 8, Steps 1, 2; Example 9 | Colorless Solid |

TABLE 1-continued

Compound Structure and Appearance

| Compound Number | Structure | Prepared According To Example | Appearance |
|---|---|---|---|
| F90 | 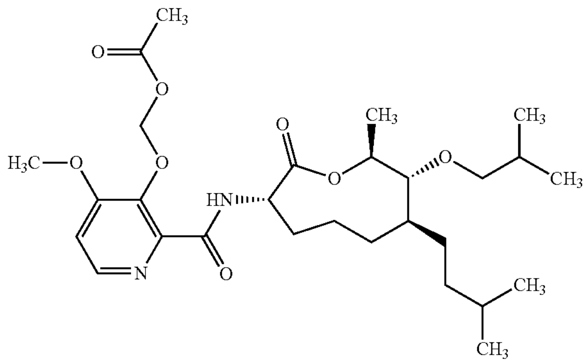 [SMILES: COc1ccnc(C(=O)N[C@H]2CCC[C@H](CCC(C)C)[C@@H](OCC(C)C)[C@H](C)OC2=O)c1OCOC(C)=O] | Example 1, Steps 1, 2c, 3, 4, 5c, 5b, 6; Example 2, Steps 1a-1, 1a-2; Example 3; Example 8, Steps 1, 2; Example 9 | Colorless Oil |
| F91 | 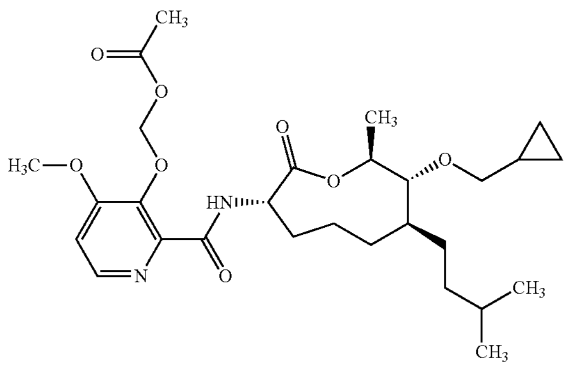 [SMILES: COc1ccnc(C(=O)N[C@H]2CCC[C@H](CCC(C)C)[C@@H](OCC3CC3)[C@H](C)OC2=O)c1OCOC(C)=O] | Example 1, Steps 1, 2b, 3, 5b, 5c, 6; Example 8, Steps 1, 2; Example 9 | Colorless Oil |
| F92 | 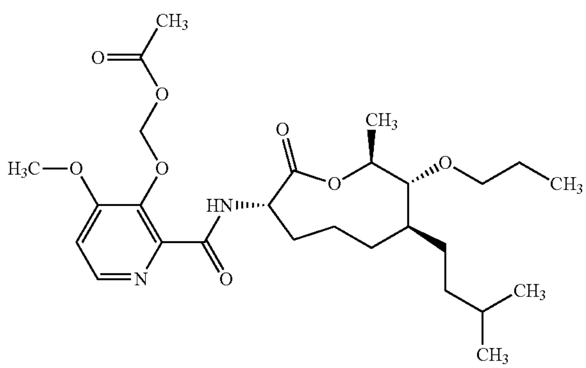 [SMILES: CCCO[C@@H]1[C@@H](CCC(C)C)CCC[C@H](NC(=O)c2nccc(OC)c2OCOC(C)=O)C(=O)O[C@H]1C] | Example 1, Steps 1, 2c, 3, 4, 5c, 5b, 6; Example 2, Steps 1a-1, 1a-2; Example 3, Steps 1, 2a; Example 8, Steps 1, 2; Example 9 | Thick Colorless Oil |
| F93 | 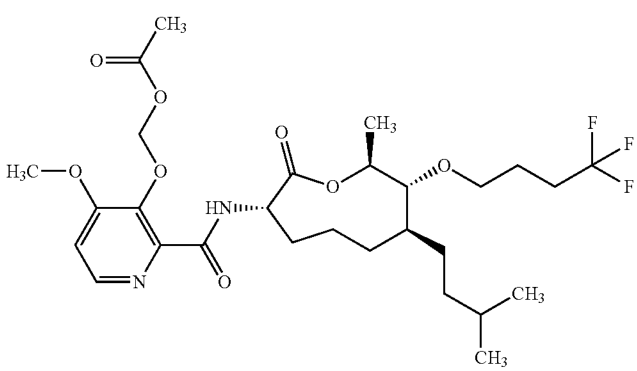 [SMILES: COc1ccnc(C(=O)N[C@H]2CCC[C@H](CCC(C)C)[C@@H](OCCCC(F)(F)F)[C@H](C)OC2=O)c1OCOC(C)=O] | Example 1, Steps 1, 2c, 3, 4, 5c, 5b, 6; Example 2, Steps 1a-1, 1a-2; Example 3, Steps 1, 2a; Example 8, Steps 1, 2; Example 9 | Pale Yellow Oil |

TABLE 1-continued

Compound Structure and Appearance

| Compound Number | Structure | Prepared According To Example | Appearance |
|---|---|---|---|
| F94 | 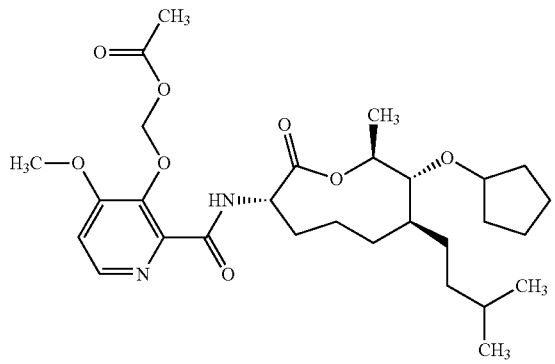 [SMILES: COc1ccnc(C(=O)N[C@H]2CCC[C@H](CCC(C)C)[C@@H](OC3CCCC3)[C@H](C)OC2=O)c1OCOC(C)=O] | Example 1, Steps 1, 2c, 3, 4, 5c, 5b, 6; Example 2, Steps 1a-1, 1a-2; Example 3, Steps 1, 2a; Example 8, Steps 1, 2; Example 9 | Pale Yellow Sticky Solid |
| F95 | 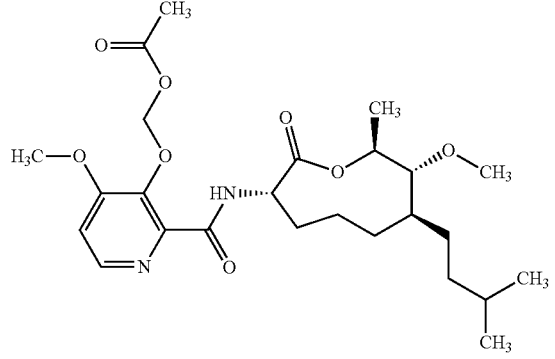 [SMILES: COc1ccnc(C(=O)N[C@H]2CCC[C@H](CCC(C)C)[C@@H](OC)[C@H](C)OC2=O)c1OCOC(C)=O] | Example 1, Steps 1, 2c, 3, 4, 5c, 5b, 6; Example 2, Steps 1a-1, 1a-2; Example 6; Example 8, Steps 1, 2; Example 9 | Pale Yellow Oil |
| F96 | 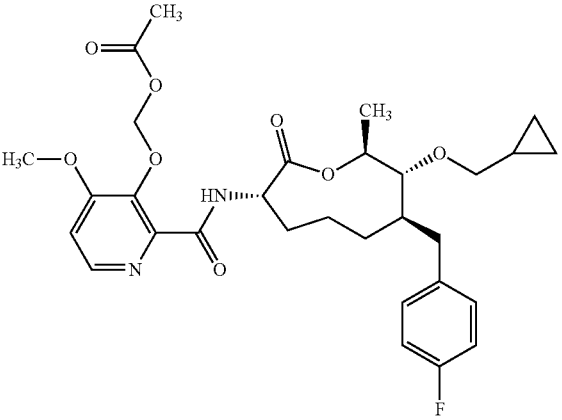 [SMILES: COc1ccnc(C(=O)N[C@H]2CCC[C@H](Cc3ccc(F)cc3)[C@@H](OCC3CC3)[C@H](C)OC2=O)c1OCOC(C)=O] | Example 1, Steps 1, 2c, 3, 4, 5c, 5b, 6; Example 2, Steps 1a-1, 1a-2; Example 5; Example 8, Steps 1, 2; Example 9 | Colorless Oil |

TABLE 1-continued
Compound Structure and Appearance
| Compound Number | Structure | Prepared According To Example | Appearance |
|---|---|---|---|
| F97 | 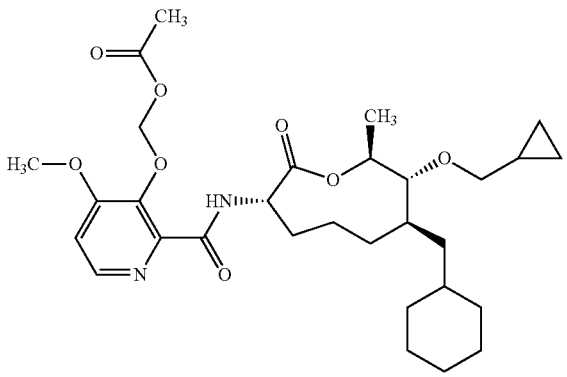 [SMILES: COc1ccnc(C(=O)N[C@H]2CCC[C@H](CC3CCCCC3)[C@@H](OCC3CC3)[C@H](C)OC2=O)c1OCOC(C)=O] | Example 1, Steps 1, 2b, 3, 4, 5a, 5b, 6; Example 8, Steps 1, 2; Example 16; Example 9 | Pale Yellow Oil |
| F98 | 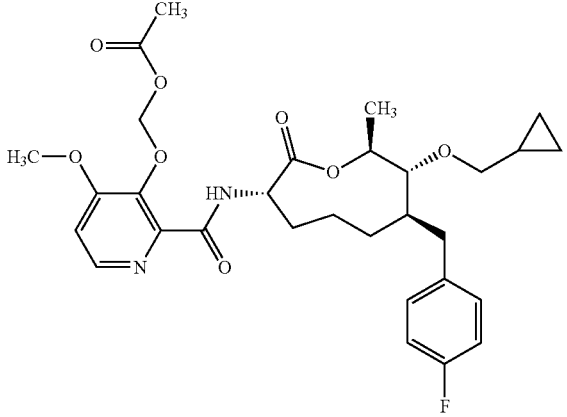 [SMILES: COc1ccnc(C(=O)N[C@H]2CCC[C@H](Cc3ccc(F)cc3)[C@@H](OCC3CC3)[C@H](C)OC2=O)c1OCOC(C)=O] | Example 1, Steps 1, 2b, 3, 4, 5a, 5b, 6; Example 8, Steps 1, 2; Example 9 | Pale Yellow Oil |
| F99 | 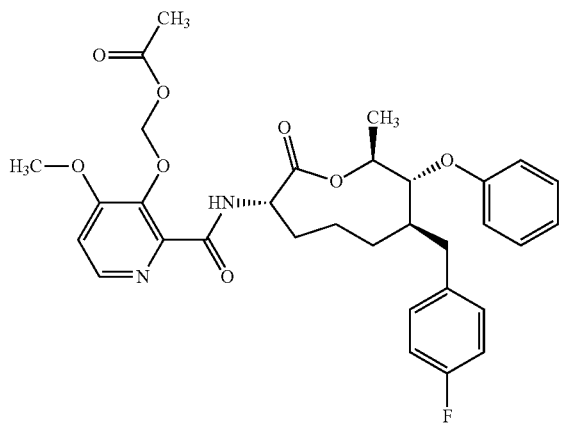 [SMILES: COc1ccnc(C(=O)N[C@H]2CCC[C@H](Cc3ccc(F)cc3)[C@@H](Oc3ccccc3)[C@H](C)OC2=O)c1OCOC(C)=O] | Example 1, Steps 1, 2a, 3, 4, 5a, 5b, 6; Example 8, Steps 1, 2; Example 9 | Pale Yellow Oil |

TABLE 1-continued

Compound Structure and Appearance

| Compound Number | Structure | Prepared According To Example | Appearance |
|---|---|---|---|
| F100 | 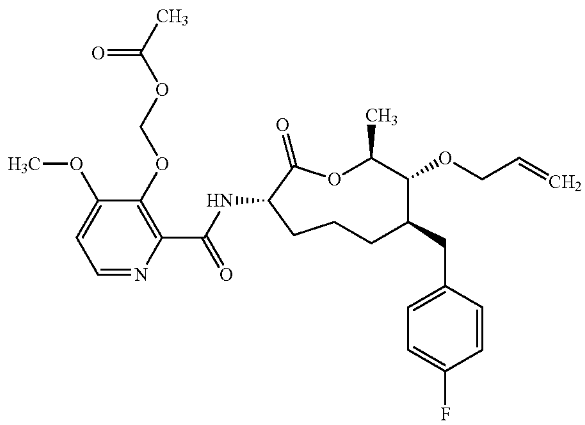 [SMILES: C=CCO[C@@H]1[C@@H](Cc2ccc(F)cc2)CCC[C@H](NC(=O)c2nccc(OC)c2OCOC(C)=O)C(=O)O[C@H]1C] | Example 1, Steps 1, 2c, 3, 4, 5a, 5b, 6; Example 2, Steps 1a-1, 1a-2; Example 3, Step 1; Example 8, Steps 1, 2; Example 9 | Pale Yellow Oil |
| F101 | 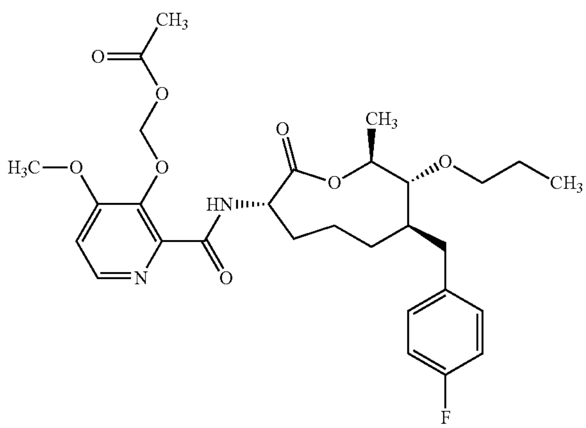 [SMILES: CCCO[C@@H]1[C@@H](Cc2ccc(F)cc2)CCC[C@H](NC(=O)c2nccc(OC)c2OCOC(C)=O)C(=O)O[C@H]1C] | Example 1, Steps 1, 2c, 3, 4, 5a, 5b, 6; Example 2, Steps 1a-1, 1a-2; Example 3, Steps 1, 2a; Example 8, Steps 1, 2; Example 9 | Pale Yellow Oil |
| F102 | 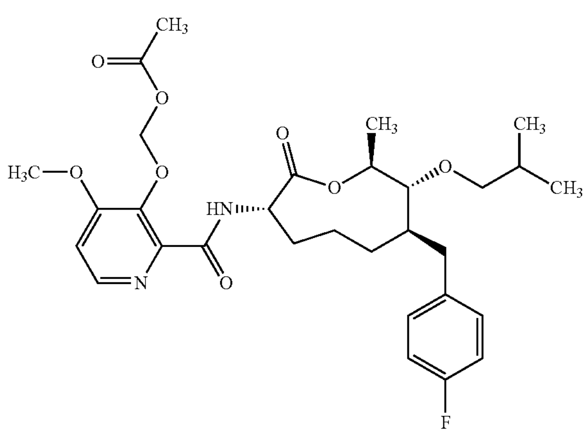 [SMILES: COc1ccnc(C(=O)N[C@H]2CCC[C@H](Cc3ccc(F)cc3)[C@@H](OCC(C)C)[C@H](C)OC2=O)c1OCOC(C)=O] | Example 1, Steps 1, 2c, 3, 4, 5a, 5b, 6; Example 2, Steps 1a-1, 1a-2; Example 3, Steps 1, 2a; Example 8, Steps 1, 2; Example 9 | Pale Yellow Oil |

TABLE 1-continued

Compound Structure and Appearance

| Compound Number | Structure | Prepared According To Example | Appearance |
|---|---|---|---|
| F103 | 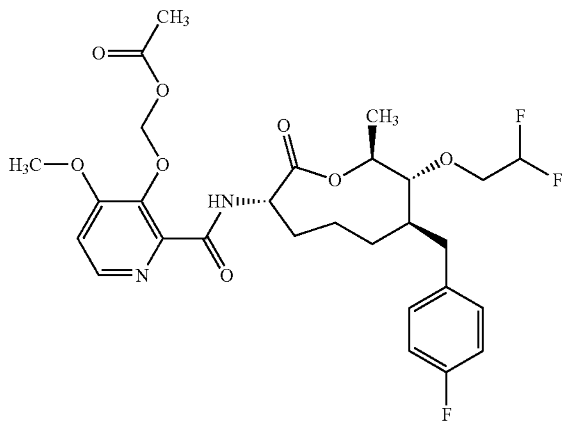 [SMILES: COc1ccnc(C(=O)N[C@H]2CCC[C@H](Cc3ccc(F)cc3)[C@@H](OCC(F)F)[C@H](C)OC2=O)c1OCOC(C)=O] | Example 1, Steps 1, 2c, 3, 4, 5a, 5b, 6; Example 2, Steps 1a-1, 1a-2; Example 3, Steps 1, 2b-1, 2b-2; Example 8, Steps 1, 2; Example 9 | Pale Yellow Oil |
| F104 | 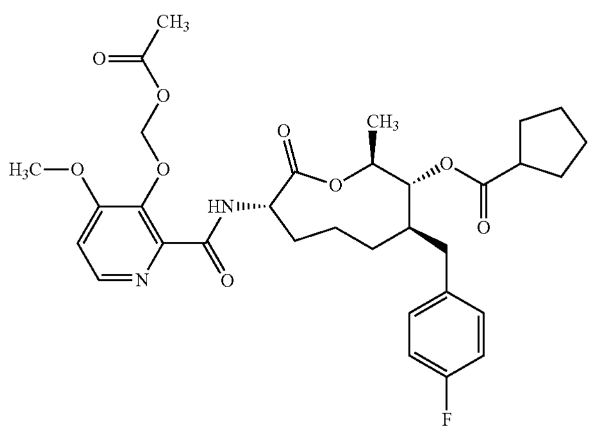 [SMILES: COc1ccnc(C(=O)N[C@H]2CCC[C@H](Cc3ccc(F)cc3)[C@@H](OC(=O)C3CCCC3)[C@H](C)OC2=O)c1OCOC(C)=O] | Example 1, Steps 1, 2c, 3, 4, 5a, 5b, 6; Example 2, Steps 1a-1, 1a-2; Example 5; Example 8, Steps 1, 2; Example 9 | Colorless Oil |
| F105 | 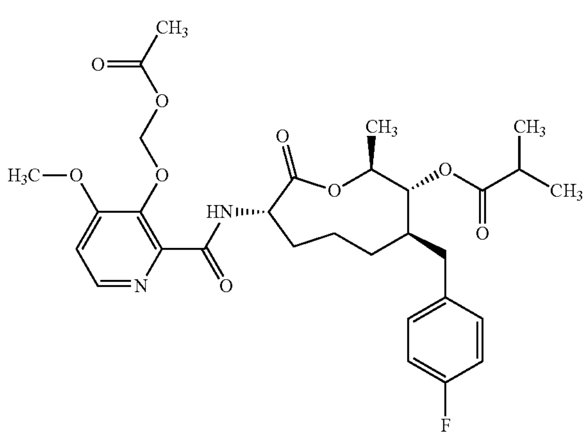 [SMILES: COc1ccnc(C(=O)N[C@H]2CCC[C@H](Cc3ccc(F)cc3)[C@@H](OC(=O)C(C)C)[C@H](C)OC2=O)c1OCOC(C)=O] | Example 1, Steps 1, 2c, 3, 4, 5a, 5b, 6; Example 2, Steps 1a-1, 1a-2; Example 5; Example 8, Steps 1, 2; Example 9 | Pale Yellow Oil |

TABLE 1-continued

Compound Structure and Appearance

| Compound Number | Structure | Prepared According To Example | Appearance |
|---|---|---|---|
| F106 | 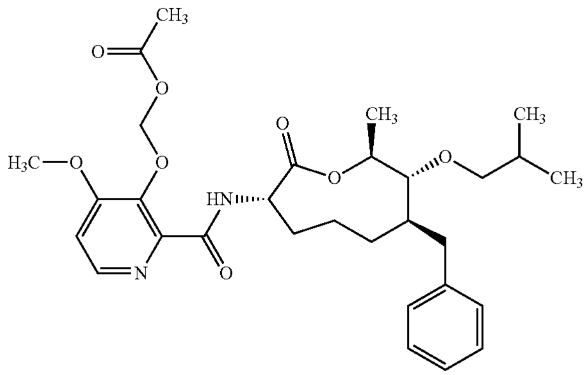 [SMILES: COc1ccnc(C(=O)N[C@H]2CCC[C@H](Cc3ccccc3)[C@@H](OCC(C)C)[C@H](C)OC2=O)c1OCOC(C)=O] | Example 9 | Thick Oil |
| F107 | 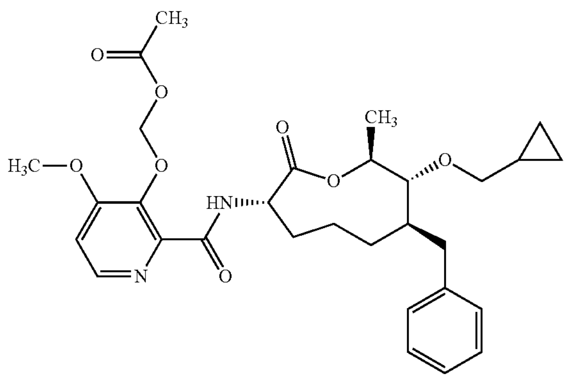 [SMILES: COc1ccnc(C(=O)N[C@H]2CCC[C@H](Cc3ccccc3)[C@@H](OCC3CC3)[C@H](C)OC2=O)c1OCOC(C)=O] | Example 9 | Sticky Oil |
| F108 | 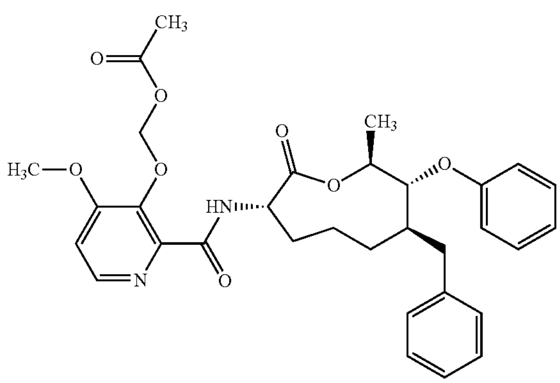 [SMILES: COc1ccnc(C(=O)N[C@H]2CCC[C@H](Cc3ccccc3)[C@@H](Oc3ccccc3)[C@H](C)OC2=O)c1OCOC(C)=O] | Example 9 | White Solid |
| F109 | 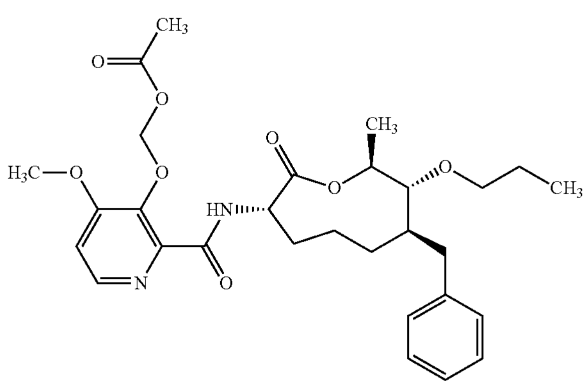 [SMILES: CCCO[C@@H]1[C@@H](Cc2ccccc2)CCC[C@H](NC(=O)c2nccc(OC)c2OCOC(C)=O)C(=O)O[C@H]1C] | Example 9 | Sticky White Foam |

TABLE 1-continued
Compound Structure and Appearance
| Compound Number | Structure | Prepared According To Example | Appearance |
|---|---|---|---|
| F110 | 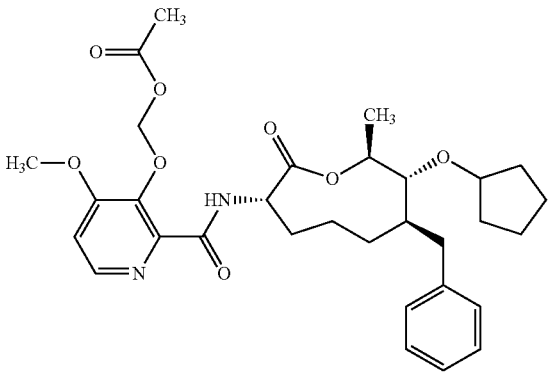 [SMILES: COc1ccnc(C(=O)N[C@H]2CCC[C@H](Cc3ccccc3)[C@@H](OC3CCCC3)[C@H](C)OC2=O)c1OCOC(C)=O] | Example 9 | White Foam |
| F111 | 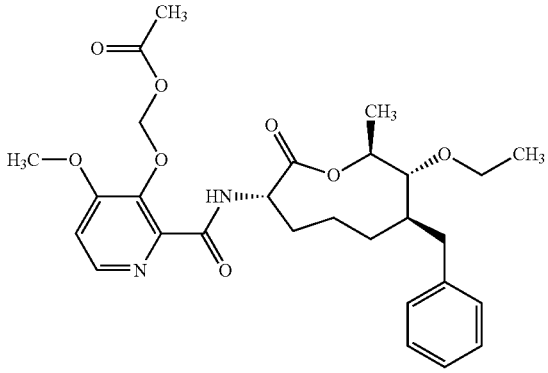 [SMILES: CCO[C@@H]1[C@@H](Cc2ccccc2)CCC[C@H](NC(=O)c2nccc(OC)c2OCOC(C)=O)C(=O)O[C@H]1C] | Example 9 | White Foam |
| F112 | 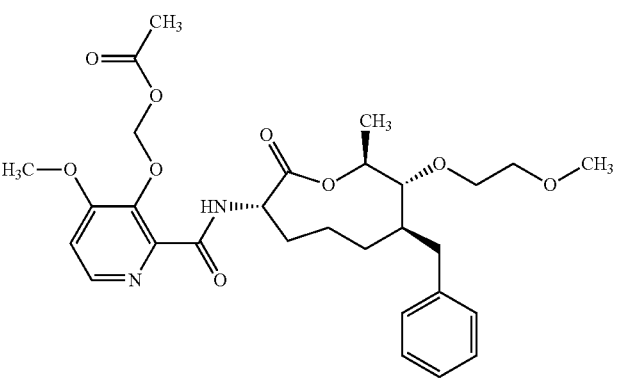 | Example 9 | White Foam |

TABLE 1-continued
Compound Structure and Appearance
| Compound Number | Structure | Prepared According To Example | Appearance |
|---|---|---|---|
| F113 | 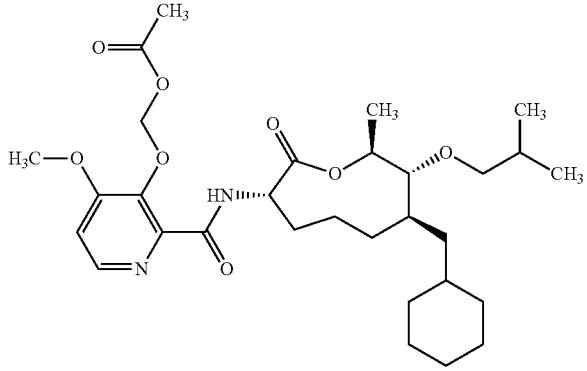 [SMILES: COc1ccnc(C(=O)N[C@H]2CCC[C@H](CC3CCCCC3)[C@@H](OCC(C)C)[C@H](C)OC2=O)c1OCOC(C)=O] | Example 9 | Colorless Thick Oil |
| F114 | 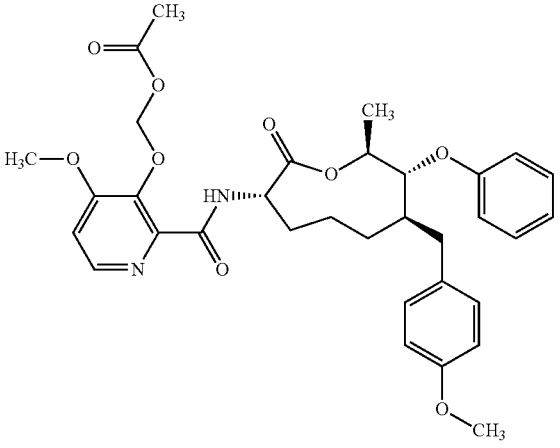 [SMILES: COc1ccc(C[C@H]2CCC[C@H](NC(=O)c3nccc(OC)c3OCOC(C)=O)C(=O)O[C@@H](C)[C@@H]2Oc2ccccc2)cc1] | Example 9 | Colorless Semi-Solid |
| F115 | 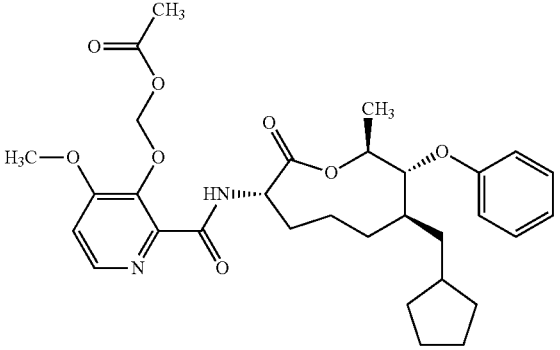 [SMILES: COc1ccnc(C(=O)N[C@H]2CCC[C@H](CC3CCCC3)[C@@H](Oc3ccccc3)[C@H](C)OC2=O)c1OCOC(C)=O] | Example 9 | Yellow Oil |

TABLE 1-continued
Compound Structure and Appearance
| Compound Number | Structure | Prepared According To Example | Appearance |
|---|---|---|---|
| F116 | 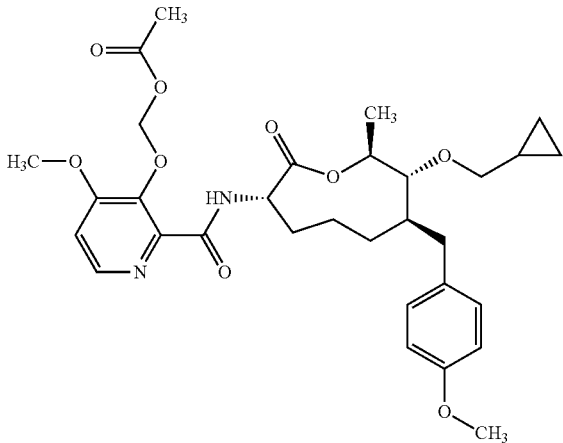 [SMILES: COc1ccc(C[C@H]2CCC[C@H](NC(=O)c3nccc(OC)c3OCOC(C)=O)C(=O)O[C@@H](C)[C@@H]2OCC2CC2)cc1] | Example 9 | Sticky White Solid |
| F117 | 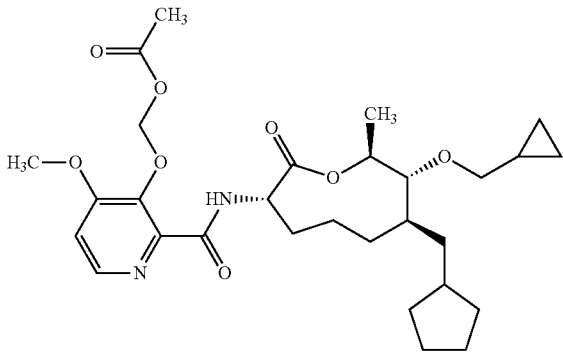 [SMILES: COc1ccnc(C(=O)N[C@H]2CCC[C@H](CC3CCCC3)[C@@H](OCC3CC3)[C@H](C)OC2=O)c1OCOC(C)=O] | Example 9 | Colorless Semi Solid |
| F118 | 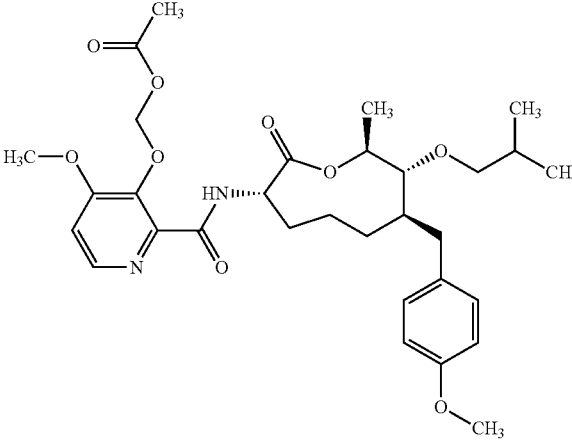 | Example 9 | Colorless Semi Solid |

TABLE 1-continued

Compound Structure and Appearance

| Compound Number | Structure | Prepared According To Example | Appearance |
|---|---|---|---|
| F119 | 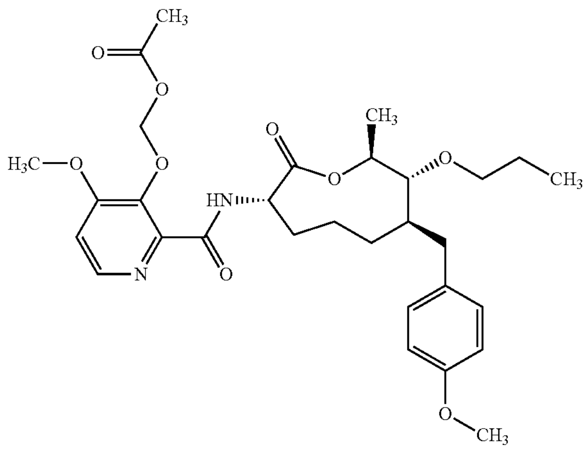 [SMILES: CCCO[C@@H]1[C@@H](Cc2ccc(OC)cc2)CCC[C@H](NC(=O)c2nccc(OC)c2OCOC(C)=O)C(=O)O[C@H]1C] | Example 9 | Light Yellow Oil |
| F120 | 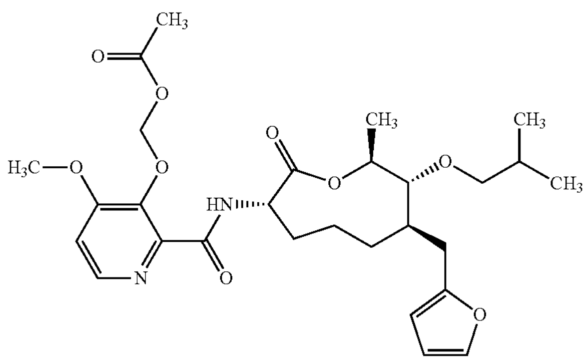 [SMILES: COc1ccnc(C(=O)N[C@H]2CCC[C@H](Cc3ccco3)[C@@H](OCC(C)C)[C@H](C)OC2=O)c1OCOC(C)=O] | Example 9 | Colorless Solid |
| F121 | 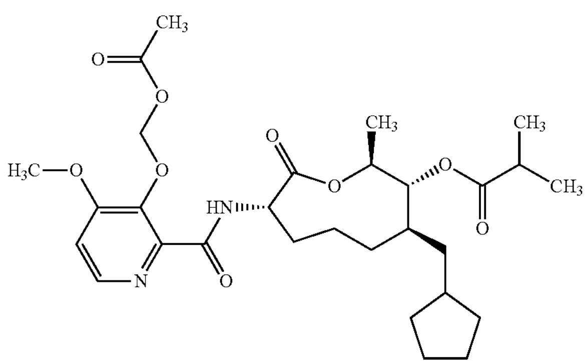 [SMILES: COc1ccnc(C(=O)N[C@H]2CCC[C@H](CC3CCCC3)[C@@H](OC(=O)C(C)C)[C@H](C)OC2=O)c1OCOC(C)=O] | Example 9 | Colorless Oil |
| F122 | 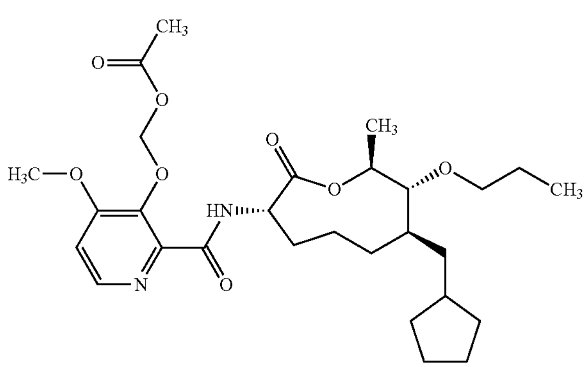 [SMILES: CCCO[C@@H]1[C@@H](CC2CCCC2)CCC[C@H](NC(=O)c2nccc(OC)c2OCOC(C)=O)C(=O)O[C@H]1C] | Example 9 | Colorless Oil |

TABLE 1-continued

Compound Structure and Appearance

| Compound Number | Structure | Prepared According To Example | Appearance |
|---|---|---|---|
| F123 | 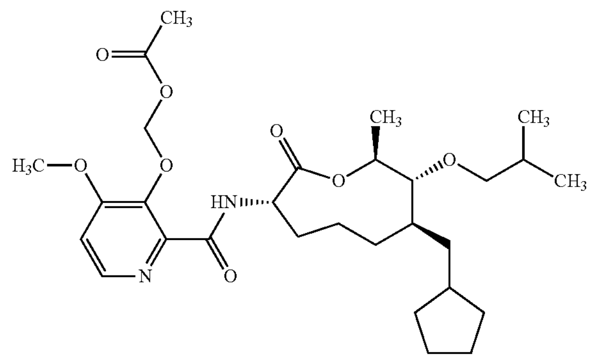 [SMILES: COc1ccnc(C(=O)N[C@H]2CCC[C@H](CC3CCCC3)[C@@H](OCC(C)C)[C@H](C)OC2=O)c1OCOC(C)=O] | Example 9 | Colorless Oil |
| F124 | 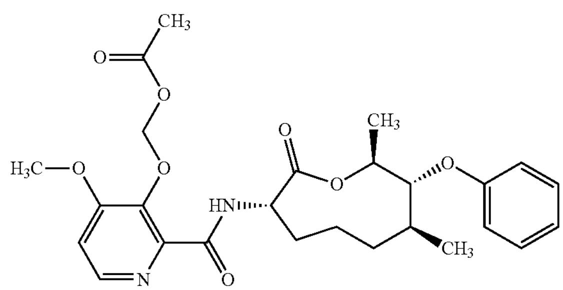 [SMILES: COc1ccnc(C(=O)N[C@H]2CCC[C@H](C)[C@@H](Oc3ccccc3)[C@H](C)OC2=O)c1OCOC(C)=O] | Example 9 | White Glassy Solid |
| F125 | 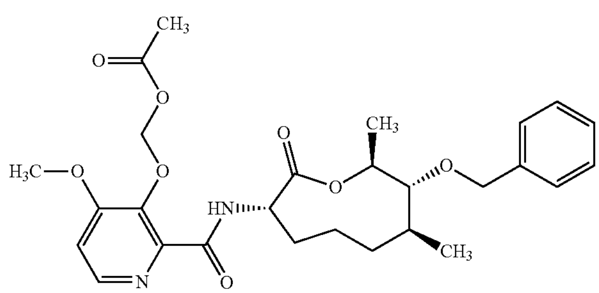 [SMILES: COc1ccnc(C(=O)N[C@H]2CCC[C@H](C)[C@@H](OCc3ccccc3)[C@H](C)OC2=O)c1OCOC(C)=O] | Example 9 | Solid |
| F126 | 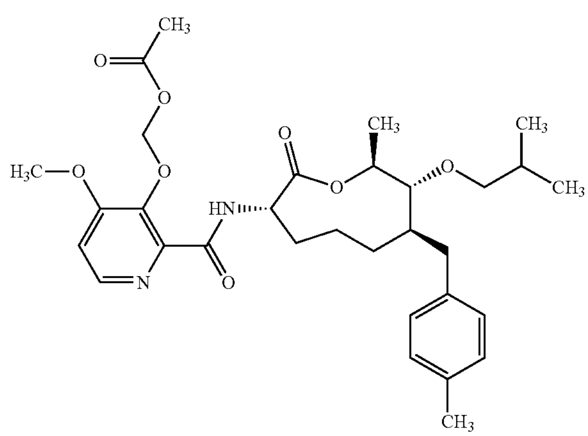 [SMILES: COc1ccnc(C(=O)N[C@H]2CCC[C@H](Cc3ccc(C)cc3)[C@@H](OCC(C)C)[C@H](C)OC2=O)c1OCOC(C)=O] | Example 9 | White Oil |

TABLE 1-continued

Compound Structure and Appearance

| Compound Number | Structure | Prepared According To Example | Appearance |
|---|---|---|---|
| F127 | 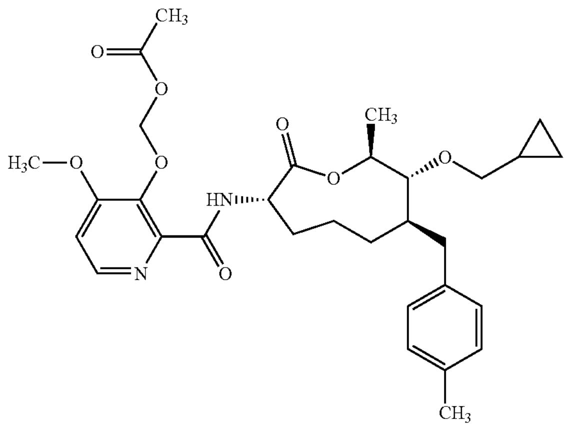 [SMILES: COc1ccnc(C(=O)N[C@H]2CCC[C@H](Cc3ccc(C)cc3)[C@@H](OCC3CC3)[C@H](C)OC2=O)c1OCOC(C)=O] | Example 9 | White Solid |
| F128 | 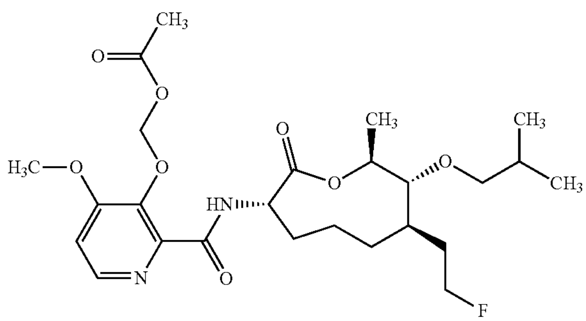 [SMILES: COc1ccnc(C(=O)N[C@H]2CCC[C@H](CCF)[C@@H](OCC(C)C)[C@H](C)OC2=O)c1OCOC(C)=O] | Example 9 | White Solid |
| F129 | 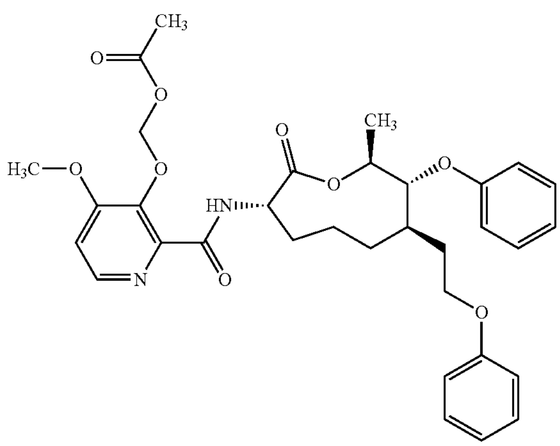 [SMILES: COc1ccnc(C(=O)N[C@H]2CCC[C@H](CCOc3ccccc3)[C@@H](Oc3ccccc3)[C@H](C)OC2=O)c1OCOC(C)=O] | Example 9 | White Solid |
| F130 | 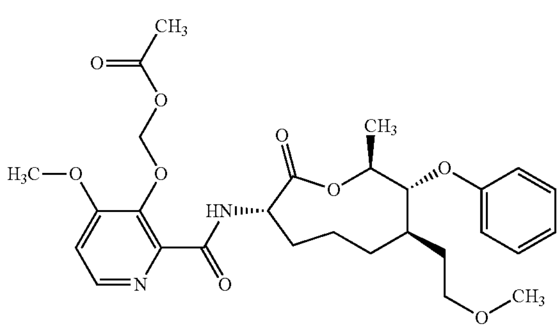 [SMILES: COCC[C@H]1CCC[C@H](NC(=O)c2nccc(OC)c2OCOC(C)=O)C(=O)O[C@@H](C)[C@@H]1Oc1ccccc1] | Example 9 | White Solid |

TABLE 1-continued

Compound Structure and Appearance

| Compound Number | Structure | Prepared According To Example | Appearance |
|---|---|---|---|
| F131 | 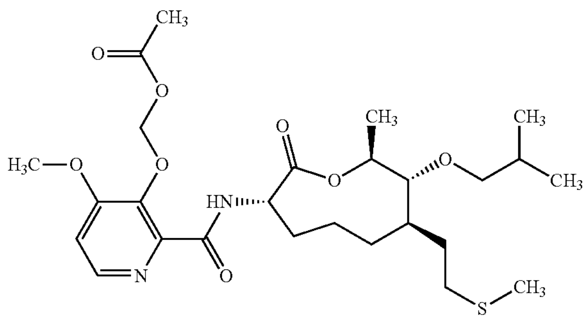 [SMILES: COc1ccnc(C(=O)N[C@H]2CCC[C@H](CCSC)[C@@H](OCC(C)C)[C@H](C)OC2=O)c1OCOC(C)=O] | Example 9 | Sticky Yellow Solid |
| F132 | 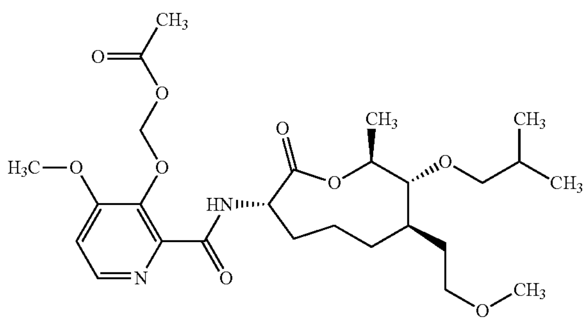 [SMILES: COCC[C@H]1CCC[C@H](NC(=O)c2nccc(OC)c2OCOC(C)=O)C(=O)O[C@@H](C)[C@@H]1OCC(C)C] | Example 9 | Sticky Oil |
| F133 | 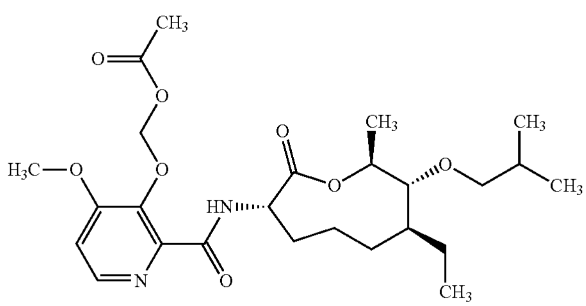 [SMILES: CC[C@H]1CCC[C@H](NC(=O)c2nccc(OC)c2OCOC(C)=O)C(=O)O[C@@H](C)[C@@H]1OCC(C)C] | Example 9 | Sticky Solid |
| F134 | 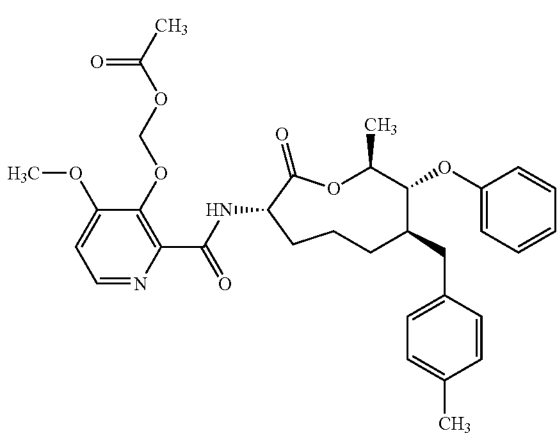 [SMILES: COc1ccnc(C(=O)N[C@H]2CCC[C@H](Cc3ccc(C)cc3)[C@@H](Oc3ccccc3)[C@H](C)OC2=O)c1OCOC(C)=O] | Example 9 | White Solid |

TABLE 1-continued

Compound Structure and Appearance

| Compound Number | Structure | Prepared According To Example | Appearance |
|---|---|---|---|
| F135 | 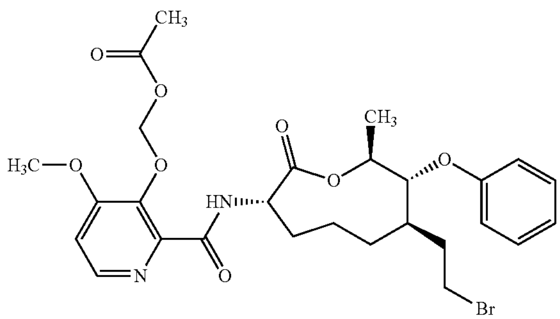 [SMILES: COc1ccnc(C(=O)N[C@H]2CCC[C@H](CCBr)[C@@H](Oc3ccccc3)[C@H](C)OC2=O)c1OCOC(C)=O] | Example 9 | White Solid |
| F136 | 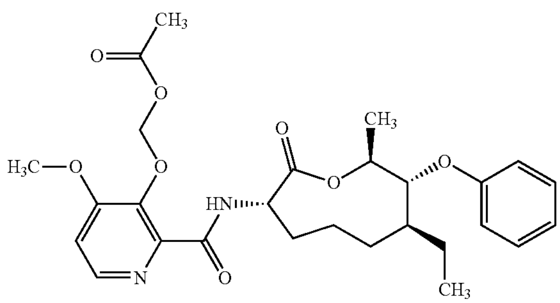 [SMILES: CC[C@H]1CCC[C@H](NC(=O)c2nccc(OC)c2OCOC(C)=O)C(=O)O[C@@H](C)[C@@H]1Oc1ccccc1] | Example 9 | Yellow Solid |
| F137 | 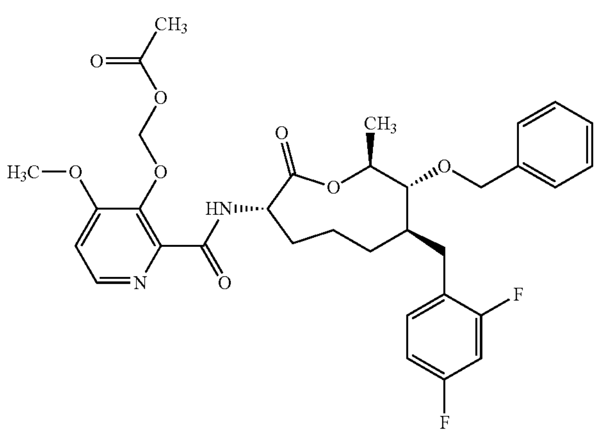 [SMILES: COc1ccnc(C(=O)N[C@H]2CCC[C@H](Cc3ccc(F)cc3F)[C@@H](OCc3ccccc3)[C@H](C)OC2=O)c1OCOC(C)=O] | Example 9 | Colorless Oil |
| F138 | 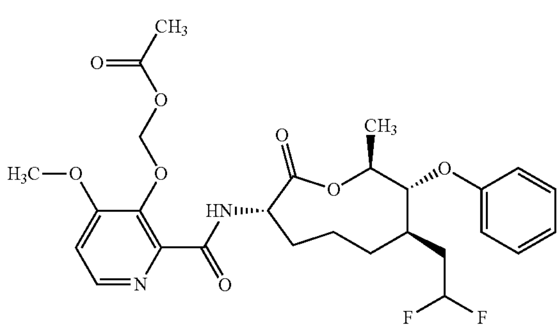 [SMILES: COc1ccnc(C(=O)N[C@H]2CCC[C@H](CC(F)F)[C@@H](Oc3ccccc3)[C@H](C)OC2=O)c1OCOC(C)=O] | Example 9 | White Solid |

TABLE 1-continued

| Compound Number | Structure | Prepared According To Example | Appearance |
|---|---|---|---|
| F139 | 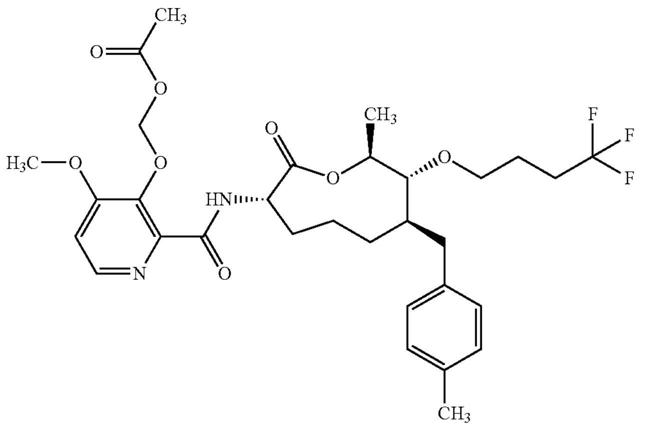 [SMILES: COc1ccnc(C(=O)N[C@H]2CCC[C@H](Cc3ccc(C)cc3)[C@@H](OCCCC(F)(F)F)[C@H](C)OC2=O)c1OCOC(C)=O] | Example 9 | Colorless Oil |
| F140 | 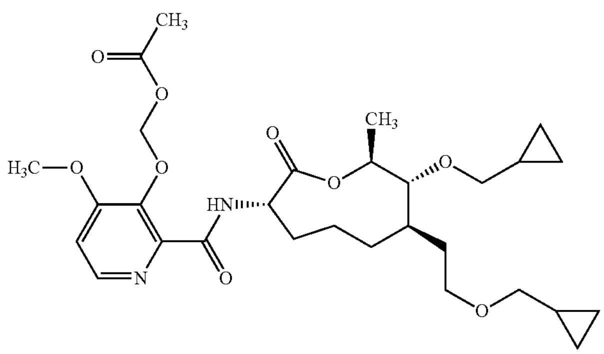 [SMILES: COc1ccnc(C(=O)N[C@H]2CCC[C@H](CCOCC3CC3)[C@@H](OCC3CC3)[C@H](C)OC2=O)c1OCOC(C)=O] | Example 9 | Colorless Oil |
| F141 | 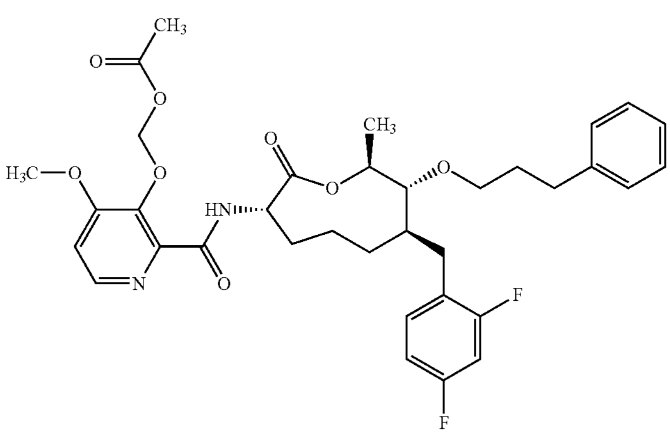 [SMILES: COc1ccnc(C(=O)N[C@H]2CCC[C@H](Cc3ccc(F)cc3F)[C@@H](OCCCc3ccccc3)[C@H](C)OC2=O)c1OCOC(C)=O] | Example 9 | White Solid |

TABLE 1-continued

Compound Structure and Appearance

| Compound Number | Structure | Prepared According To Example | Appearance |
|---|---|---|---|
| F142 | 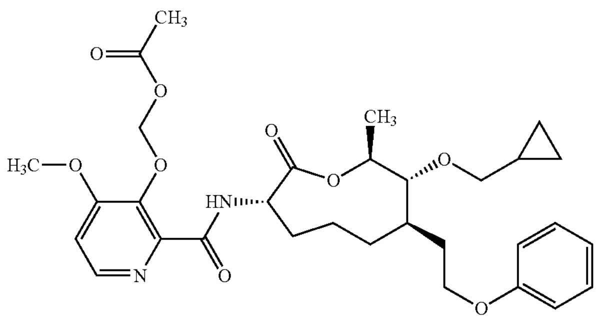 [SMILES: COc1ccnc(C(=O)N[C@H]2CCC[C@H](CCOc3ccccc3)[C@@H](OCC3CC3)[C@H](C)OC2=O)c1OCOC(C)=O] | Example 9 | White Solid |
| F143 | 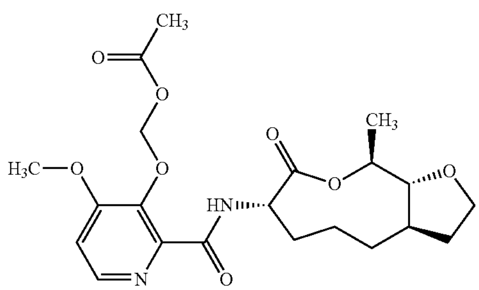 [SMILES: COc1ccnc(C(=O)N[C@H]2CCC[C@@H]3CCO[C@H]3[C@H](C)OC2=O)c1OCOC(C)=O] | Example 9 | White Solid |
| F144 | 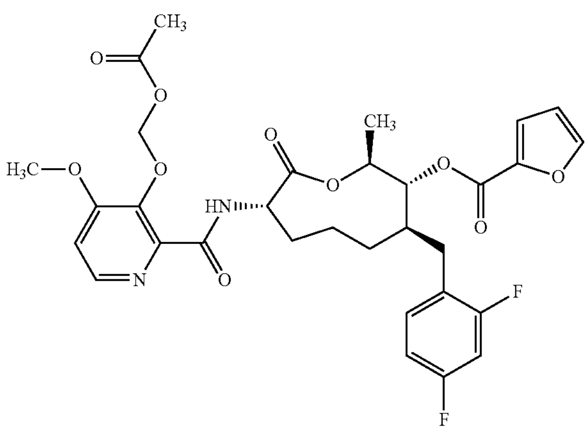 [SMILES: COc1ccnc(C(=O)N[C@H]2CCC[C@H](Cc3ccc(F)cc3F)[C@@H](OC(=O)c3ccco3)[C@H](C)OC2=O)c1OCOC(C)=O] | Example 9 | Off White Solid |
| F145 | 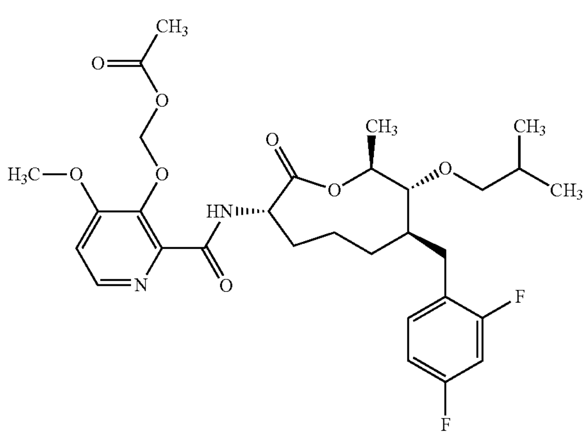 [SMILES: COc1ccnc(C(=O)N[C@H]2CCC[C@H](Cc3ccc(F)cc3F)[C@@H](OCC(C)C)[C@H](C)OC2=O)c1OCOC(C)=O] | Example 9 | Off White Solid |

TABLE 1-continued

Compound Structure and Appearance

| Compound Number | Structure | Prepared According To Example | Appearance |
|---|---|---|---|
| F146 | 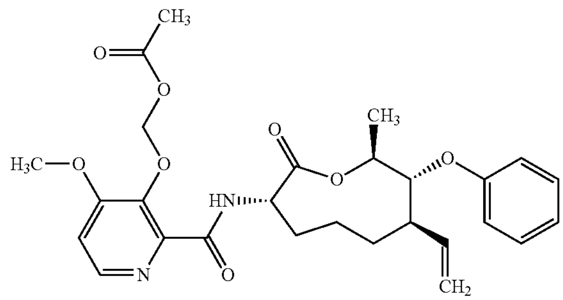 [SMILES: C=C[C@H]1CCC[C@H](NC(=O)c2nccc(OC)c2OCOC(C)=O)C(=O)O[C@@H](C)[C@@H]1Oc1ccccc1] | Example 9 | White Solid |
| F147 | 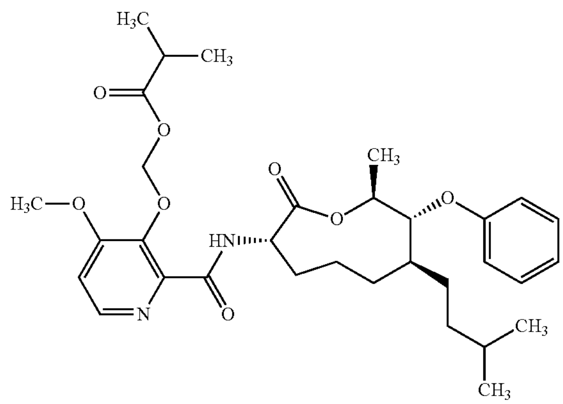 [SMILES: COc1ccnc(C(=O)N[C@H]2CCC[C@H](CCC(C)C)[C@@H](Oc3ccccc3)[C@H](C)OC2=O)c1OCOC(=O)C(C)C] | Example 1, Steps 1, 2c, 3, 4, 5c, 5b, 6; Example 2, Steps 1a-1, 1a-2; Example 7; Step 2a, Example 8, Steps 1, 2; Example 12 | Colorless Oil |
| F148 | 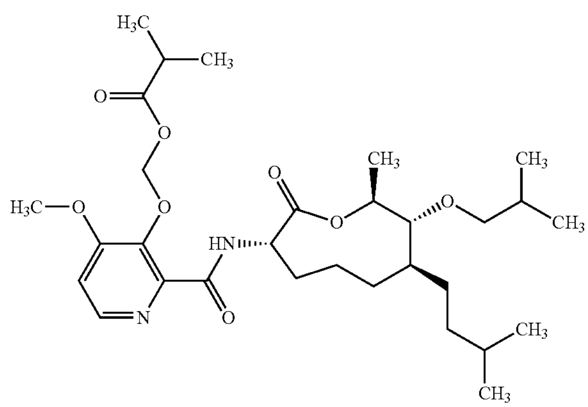 [SMILES: COc1ccnc(C(=O)N[C@H]2CCC[C@H](CCC(C)C)[C@@H](OCC(C)C)[C@H](C)OC2=O)c1OCOC(=O)C(C)C] | Example 1, Steps 1, 2c, 3, 4, 5c, 5b, 6; Example 2, Steps 1a-1, 1a-2 Example 3; Steps 1, 2a; Example 8, Steps 1, 2; Example 12 | Pale Yellow Oil |
| F149 | 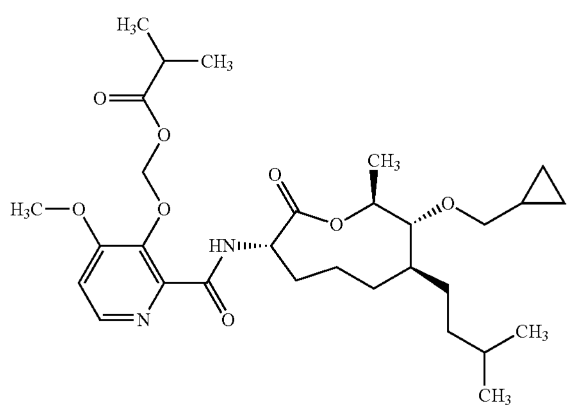 [SMILES: COc1ccnc(C(=O)N[C@H]2CCC[C@H](CCC(C)C)[C@@H](OCC3CC3)[C@H](C)OC2=O)c1OCOC(=O)C(C)C] | Example 1, Steps 1, 2b, 3, 5b, 5c, 6; Example 8, Steps 1, 2; Example 12 | Yellow Oil |

TABLE 1-continued

Compound Structure and Appearance

| Compound Number | Structure | Prepared According To Example | Appearance |
|---|---|---|---|
| F150 | 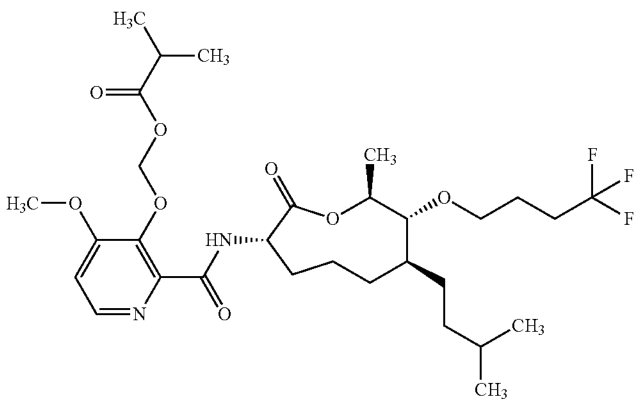 [SMILES: COc1ccnc(C(=O)N[C@H]2CCC[C@H](CCC(C)C)[C@@H](OCCCC(F)(F)F)[C@H](C)OC2=O)c1OCOC(=O)C(C)C] | Example 1, Steps 1, 2c, 3, 4, 5c, 5b, 6; Example 2, Steps 1a-1, 1a-2; Example 3, Steps 1, 2a; Example 8, Steps 1, 2; Example 12 | Sticky Yellow Solid |
| F151 | 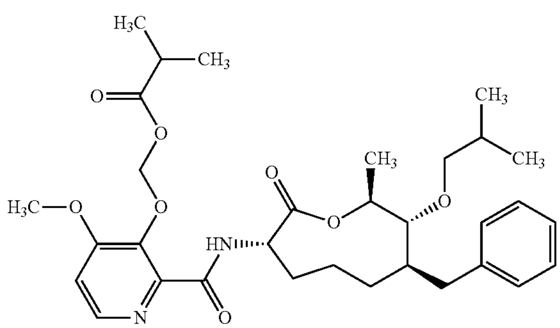 [SMILES: COc1ccnc(C(=O)N[C@H]2CCC[C@H](Cc3ccccc3)[C@@H](OCC(C)C)[C@H](C)OC2=O)c1OCOC(=O)C(C)C] | Example 12 | White Solid |
| F152 | 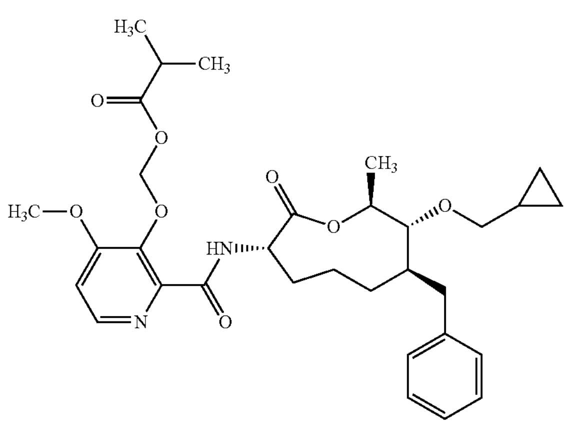 [SMILES: COc1ccnc(C(=O)N[C@H]2CCC[C@H](Cc3ccccc3)[C@@H](OCC3CC3)[C@H](C)OC2=O)c1OCOC(=O)C(C)C] | Example 12 | Thick Oil |

TABLE 1-continued

Compound Structure and Appearance

| Compound Number | Structure | Prepared According To Example | Appearance |
|---|---|---|---|
| F153 | 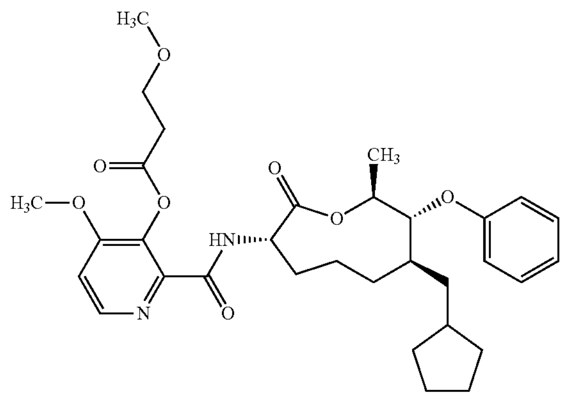 [SMILES: COCCC(=O)Oc1c(OC)ccnc1C(=O)N[C@H]1CCC[C@H](CC2CCCC2)[C@@H](Oc2ccccc2)[C@H](C)OC1=O] | Example 11 | Colorless Oil |
| F154 | 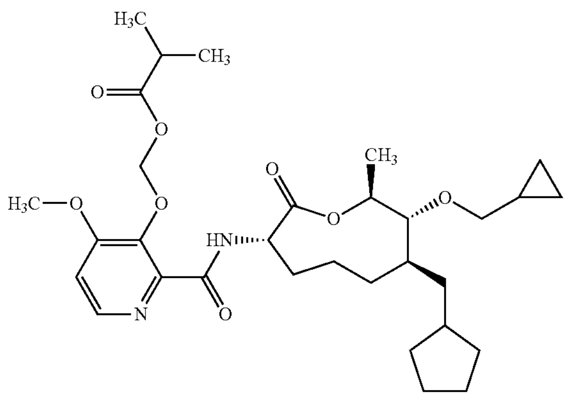 [SMILES: COc1ccnc(C(=O)N[C@H]2CCC[C@H](CC3CCCC3)[C@@H](OCC3CC3)[C@H](C)OC2=O)c1OCOC(=O)C(C)C] | Example 12 | Colorless Semi Solid |
| F155 | 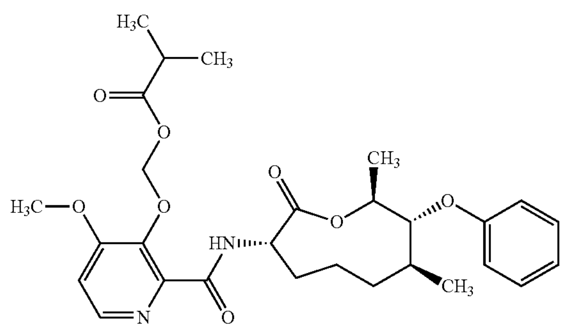 [SMILES: COc1ccnc(C(=O)N[C@H]2CCC[C@H](C)[C@@H](Oc3ccccc3)[C@H](C)OC2=O)c1OCOC(=O)C(C)C] | Example 12 | White Glassy Solid |
| F156 | 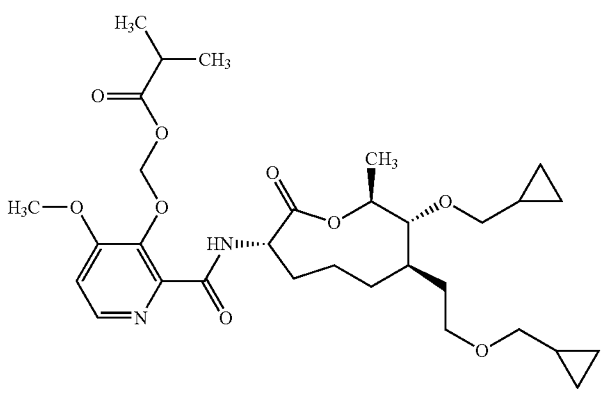 [SMILES: COc1ccnc(C(=O)N[C@H]2CCC[C@H](CCOCC3CC3)[C@@H](OCC3CC3)[C@H](C)OC2=O)c1OCOC(=O)C(C)C] | Example 12 | Colorless Oil |

TABLE 1-continued
Compound Structure and Appearance
| Compound Number | Structure | Prepared According To Example | Appearance |
|---|---|---|---|
| F157 | 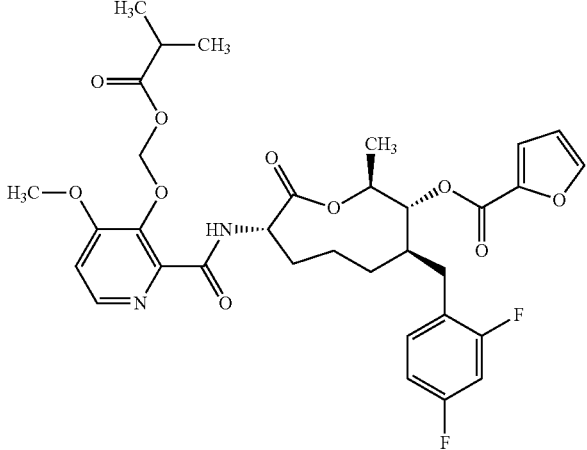 [SMILES: COc1ccnc(C(=O)N[C@H]2CCC[C@H](Cc3ccc(F)cc3F)[C@@H](OC(=O)c3ccco3)[C@H](C)OC2=O)c1OCOC(=O)C(C)C] | Example 12 | White Solid |
| F158 | 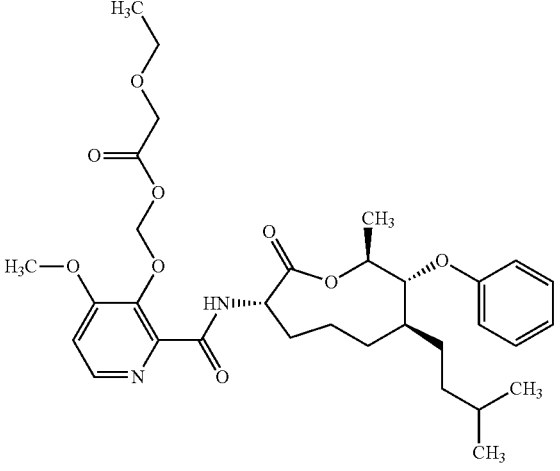 [SMILES: CCOCC(=O)OCOc1c(OC)ccnc1C(=O)N[C@H]1CCC[C@H](CCC(C)C)[C@@H](Oc2ccccc2)[C@H](C)OC1=O] | Example 1, Steps 1, 2c, 3, 4, 5c, 5b, 6; Example 2, Steps 1a-1, 1a-2; Example 7; Step 2a; Example 8, Steps 1, 2; Example 13 | Colorless Oil |
| F159 | 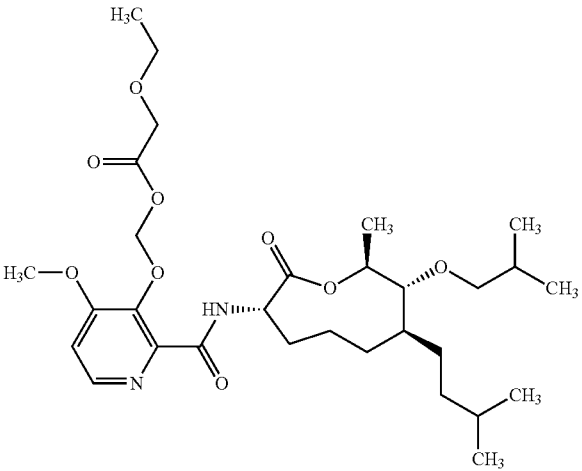 [SMILES: CCOCC(=O)OCOc1c(OC)ccnc1C(=O)N[C@H]1CCC[C@H](CCC(C)C)[C@@H](OCC(C)C)[C@H](C)OC1=O] | Example 1, Steps 1, 2c, 3, 4, 5c, 5b, 6; Example 2, Steps 1a-1, 1a-2; Example 3; Steps 1, 2a; Example 8, Steps 1, 2; Example 13 | White Sticky Solid |

TABLE 1-continued

Compound Structure and Appearance

| Compound Number | Structure | Prepared According To Example | Appearance |
|---|---|---|---|
| F160 | 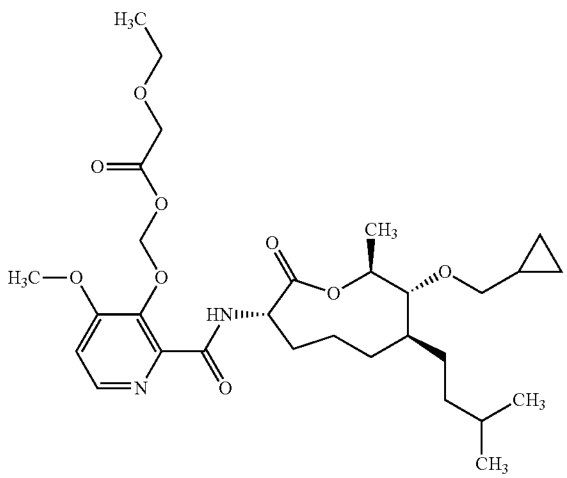 [SMILES: CCOCC(=O)OCOc1c(OC)ccnc1C(=O)N[C@H]1CCC[C@H](CCC(C)C)[C@@H](OCC2CC2)[C@H](C)OC1=O] | Example 1, Steps 1, 2b, 3, 5b, 5c, 6; Example 8, Steps 1, 2; Example 13 | Colorless Sticky Solid |
| F161 | 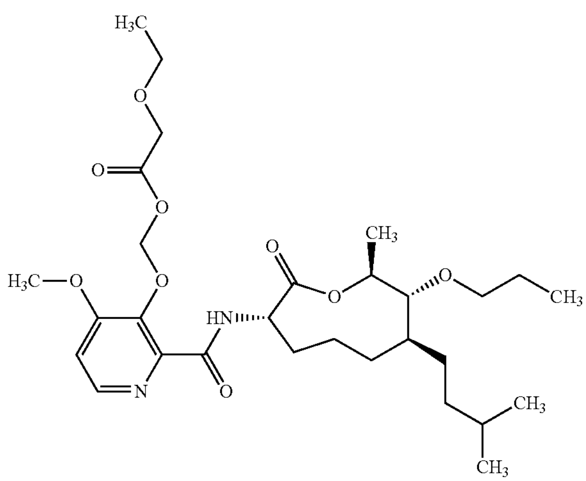 [SMILES: CCCO[C@@H]1[C@@H](CCC(C)C)CCC[C@H](NC(=O)c2nccc(OC)c2OCOC(=O)COCC)C(=O)O[C@H]1C] | Example 1, Steps 1, 2c, 3, 4, 5c, 5b, 6; Example 2, Steps 1a-1, 1a-2; Example 3; Steps 1, 2a; Example 8, Steps 1, 2; Example 13 | Colorless Oil |
| F162 | 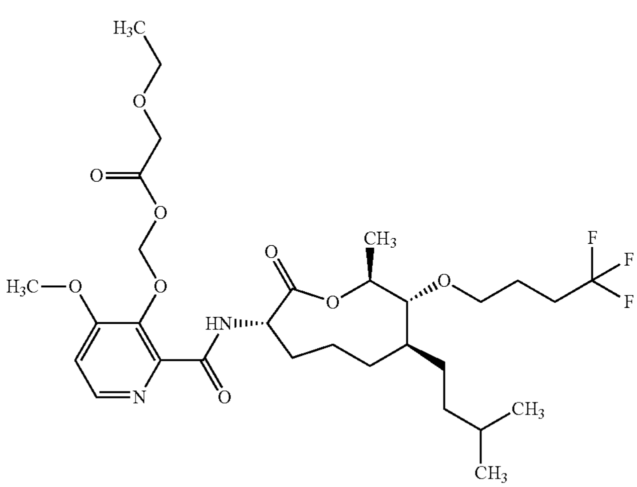 [SMILES: CCOCC(=O)OCOc1c(OC)ccnc1C(=O)N[C@H]1CCC[C@H](CCC(C)C)[C@@H](OCCCC(F)(F)F)[C@H](C)OC1=O] | Example 1, Steps 1,2c, 3, 4, 5c, 5b, 6; Example 2, Steps 1a-1, 1a-2; Example 3; Steps 1, 2a; Example 8, Steps 1,2; Example 13 | Yellow Oil |

TABLE 1-continued
Compound Structure and Appearance
| Compound Number | Structure | Prepared According To Example | Appearance |
|---|---|---|---|
| F163 | 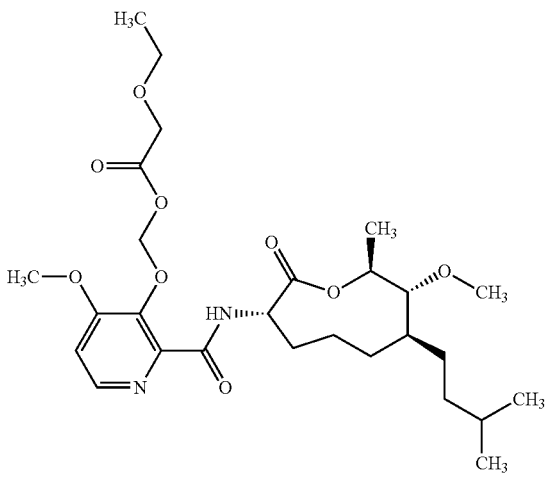 [SMILES: CCOCC(=O)OCOc1c(OC)ccnc1C(=O)N[C@H]1CCC[C@H](CCC(C)C)[C@@H](OC)[C@H](C)OC1=O] | Example 1, Steps 1,2c, 3, 4, 5c, 5b, 6; Example 2, Steps 1a-1, 1a-2; Example 6; Example 8, Steps 1, 2; Example 13 | Colorless Oil |
| F164 | 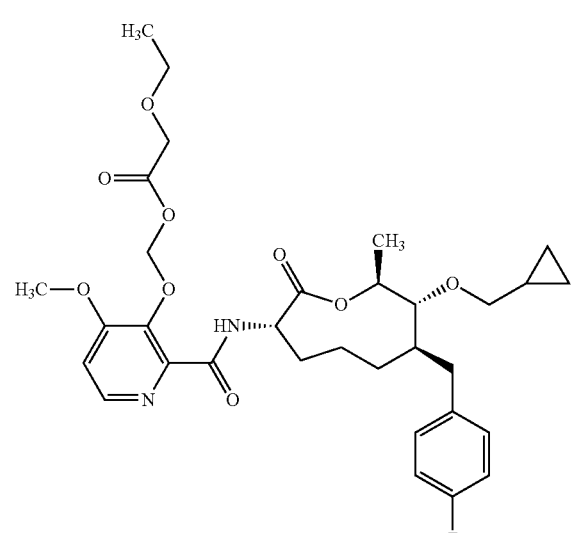 | Example 1, Steps 1, 2b, 3, 4, 5a, 5b, 6; Example 8, Steps 1, 2; Example 13 | Colorless Oil |

TABLE 1-continued
Compound Structure and Appearance
| Compound Number | Structure | Prepared According To Example | Appearance |
|---|---|---|---|
| F165 | 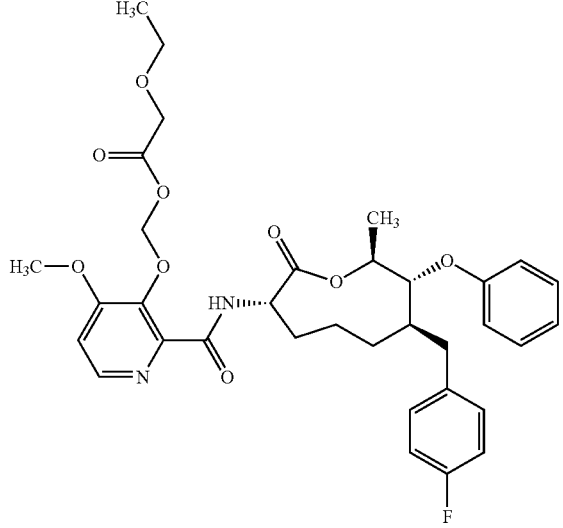 [SMILES: CCOCC(=O)OCOc1c(OC)ccnc1C(=O)N[C@H]1CCC[C@H](Cc2ccc(F)cc2)[C@@H](Oc2ccccc2)[C@H](C)OC1=O] | Example 1, Steps 1, 2a, 3, 4, 5a, 5b. 6; Example 8. Steps 1, 2; Example 13 | Colorless Solid |
| F166 | 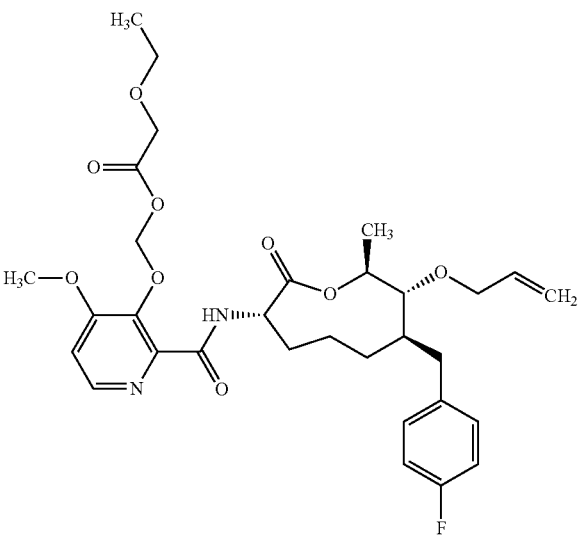 [SMILES: C=CCO[C@@H]1[C@@H](Cc2ccc(F)cc2)CCC[C@H](NC(=O)c2nccc(OC)c2OCOC(=O)COCC)C(=O)O[C@H]1C] | Example 1, Steps 1, 2c, 3, 4, 5a, 5b, 6; Example 2, Steps 1a-1, 1a-2; Example 3, Step 1; Example 8, Steps 1, 2; Example 13 | Colorless Oil |

TABLE 1-continued

Compound Structure and Appearance

| Compound Number | Structure | Prepared According To Example | Appearance |
|---|---|---|---|
| F167 | 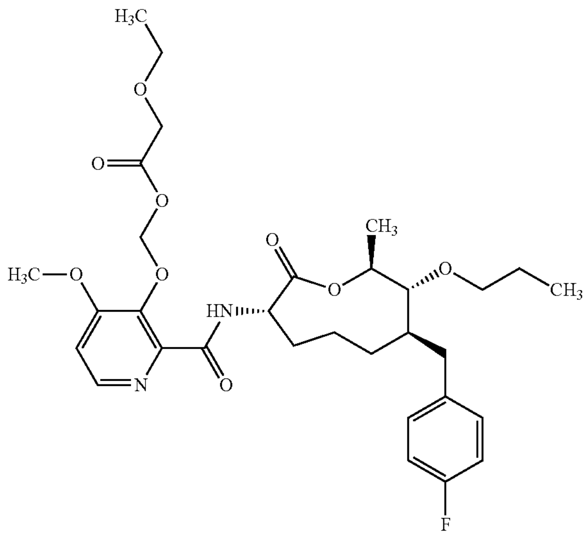 [SMILES: CCCO[C@@H]1[C@@H](Cc2ccc(F)cc2)CCC[C@H](NC(=O)c2nccc(OC)c2OCOC(=O)COCC)C(=O)O[C@H]1C] | Example 1, Steps 1, 2c, 3, 4, 5a, 5b, 6; Example 2, Steps 1a-1, 1a-2; Example 3, Steps 1, 2a; Example 8, Steps 1, 2; Example 13 | Colorless Oil |
| F168 | 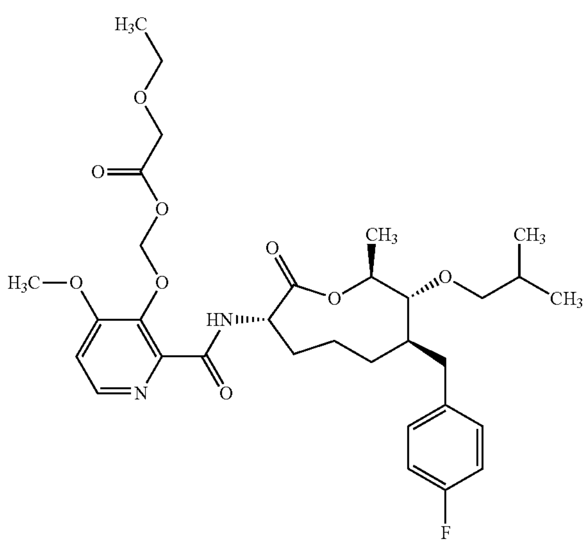 [SMILES: CCOCC(=O)OCOc1c(OC)ccnc1C(=O)N[C@H]1CCC[C@H](Cc2ccc(F)cc2)[C@@H](OCC(C)C)[C@H](C)OC1=O] | Example 1, Steps 1, 2c, 3, 4, 5a, 5b, 6; Example 2, Steps 1a-1, 1a-2; Example 3, Steps 1, 2a; Example 8, Steps 1, 2; Example 13 | Colorless Oil |

TABLE 1-continued
Compound Structure and Appearance
| Compound Number | Structure | Prepared According To Example | Appearance |
|---|---|---|---|
| F169 | 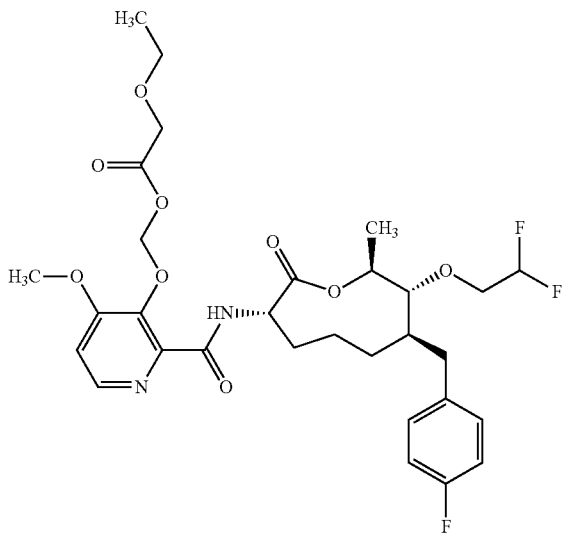 [SMILES: CCOCC(=O)OCOc1c(OC)ccnc1C(=O)N[C@H]1CCC[C@H](Cc2ccc(F)cc2)[C@@H](OCC(F)F)[C@H](C)OC1=O] | Example 1, Steps 1, 2c, 3, 4, 5a, 5b, 6; Example 2, Steps 1a-1, 1a-2; Example 3, Steps 1, 2b-1, 2b-2; Example 8, Steps 1, 2; Example 13 | Colorless Oil |
| F170 | 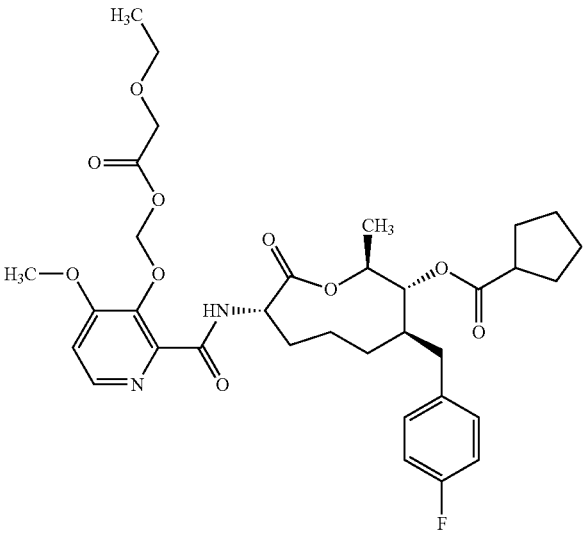 [SMILES: CCOCC(=O)OCOc1c(OC)ccnc1C(=O)N[C@H]1CCC[C@H](Cc2ccc(F)cc2)[C@@H](OC(=O)C2CCCC2)[C@H](C)OC1=O] | Example 1, Steps 1, 2c, 3, 4, 5a, 5b, 6; Example 2, Steps 1a-1, 1a-2; Example 5; Example 8, Steps 1, 2; Example 13 | Pale Yellow Oil |

TABLE 1-continued

Compound Structure and Appearance

| Compound Number | Structure | Prepared According To Example | Appearance |
|---|---|---|---|
| F171 | 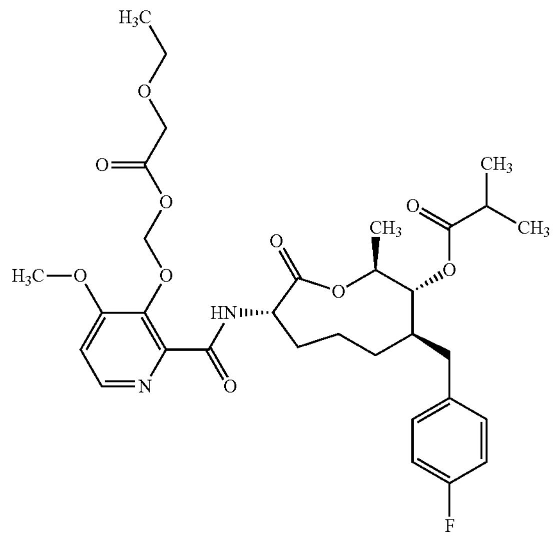 [SMILES: CCOCC(=O)OCOc1c(OC)ccnc1C(=O)N[C@H]1CCC[C@H](Cc2ccc(F)cc2)[C@@H](OC(=O)C(C)C)[C@H](C)OC1=O] | Example 1, Steps 1, 2c, 3, 4, 5a, 5b, 6; Example 2, Steps 1a-1, 1a-2; Example 5; Example 8, Steps 1, 2; Example 13 | White Solid |
| F172 | 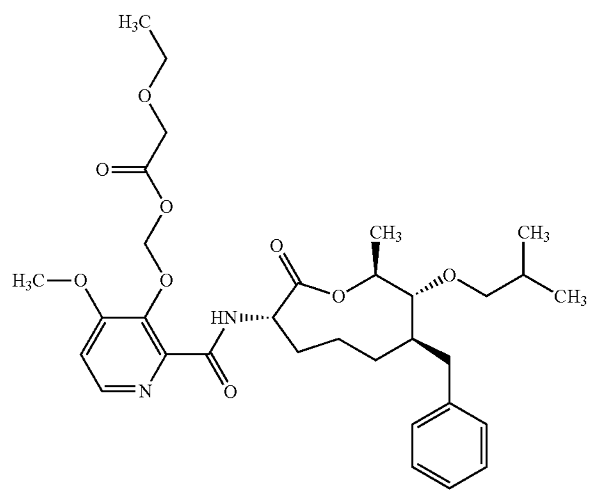 [SMILES: CCOCC(=O)OCOc1c(OC)ccnc1C(=O)N[C@H]1CCC[C@H](Cc2ccccc2)[C@@H](OCC(C)C)[C@H](C)OC1=O] | Example 13 | Colorless Thick Oil |
| F173 | 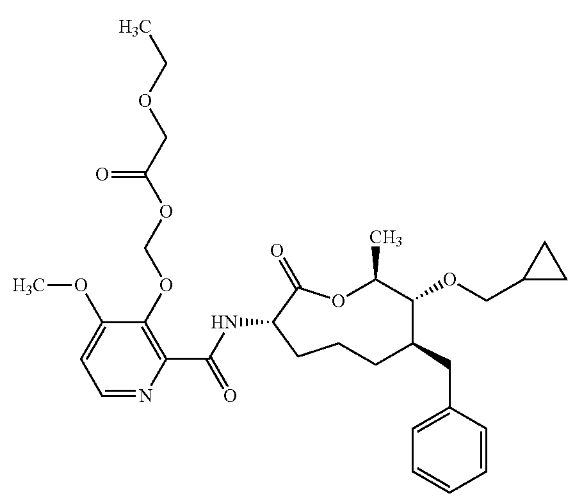 [SMILES: CCOCC(=O)OCOc1c(OC)ccnc1C(=O)N[C@H]1CCC[C@H](Cc2ccccc2)[C@@H](OCC2CC2)[C@H](C)OC1=O] | Example 13 | Colorless Thick Oil |

TABLE 1-continued

Compound Structure and Appearance

| Compound Number | Structure | Prepared According To Example | Appearance |
|---|---|---|---|
| F174 | 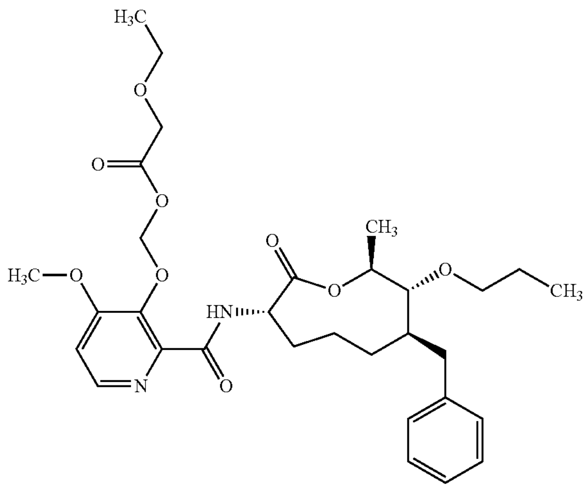 [SMILES: CCCO[C@@H]1[C@@H](Cc2ccccc2)CCC[C@H](NC(=O)c2nccc(OC)c2OCOC(=O)COCC)C(=O)O[C@H]1C] | Example 13 | White Foam |
| F175 | 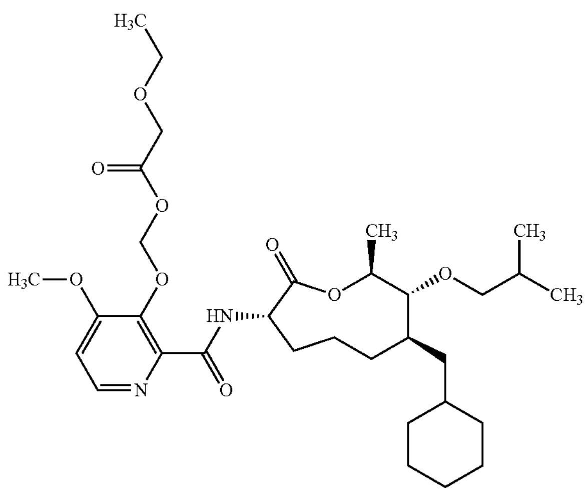 [SMILES: CCOCC(=O)OCOc1c(OC)ccnc1C(=O)N[C@H]1CCC[C@H](CC2CCCCC2)[C@@H](OCC(C)C)[C@H](C)OC1=O] | Example 13 | Colorless Thick Oil |
| F176 | 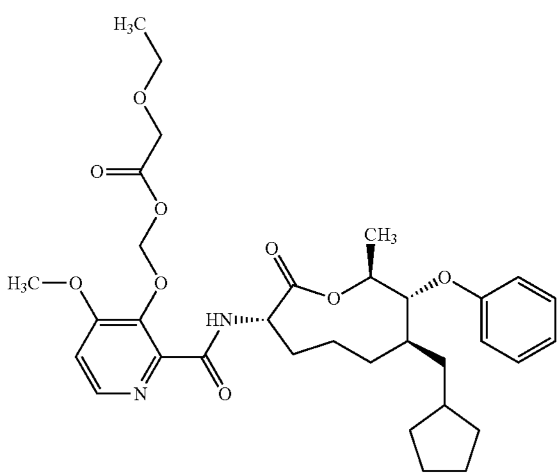 [SMILES: CCOCC(=O)OCOc1c(OC)ccnc1C(=O)N[C@H]1CCC[C@H](CC2CCCC2)[C@@H](Oc2ccccc2)[C@H](C)OC1=O] | Example 13 | Colorless Oil |

TABLE 1-continued
Compound Structure and Appearance
| Compound Number | Structure | Prepared According To Example | Appearance |
|---|---|---|---|
| F177 | 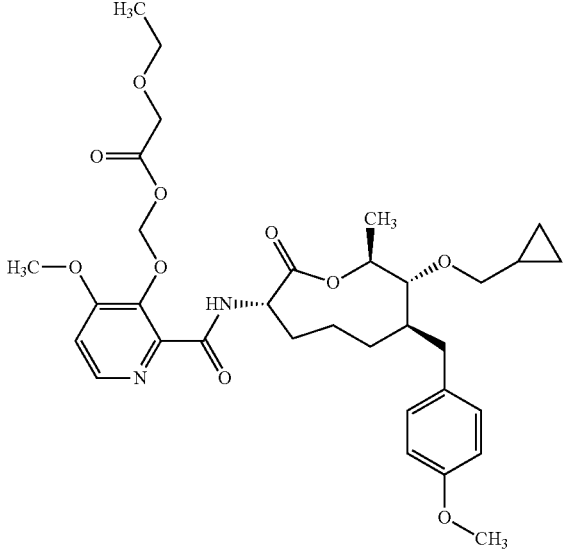 [SMILES: CCOCC(=O)OCOc1c(OC)ccnc1C(=O)N[C@H]1CCC[C@H](Cc2ccc(OC)cc2)[C@@H](OCC2CC2)[C@H](C)OC1=O] | Example 13 | Sticky White Solid |
| F178 | 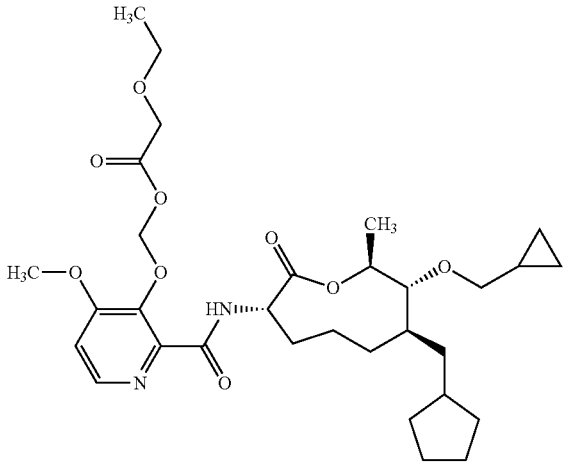 [SMILES: CCOCC(=O)OCOc1c(OC)ccnc1C(=O)N[C@H]1CCC[C@H](CC2CCCC2)[C@@H](OCC2CC2)[C@H](C)OC1=O] | Example 13 | Colorless Semit-Solid |

TABLE 1-continued

Compound Structure and Appearance

| Compound Number | Structure | Prepared According To Example | Appearance |
|---|---|---|---|
| F179 | 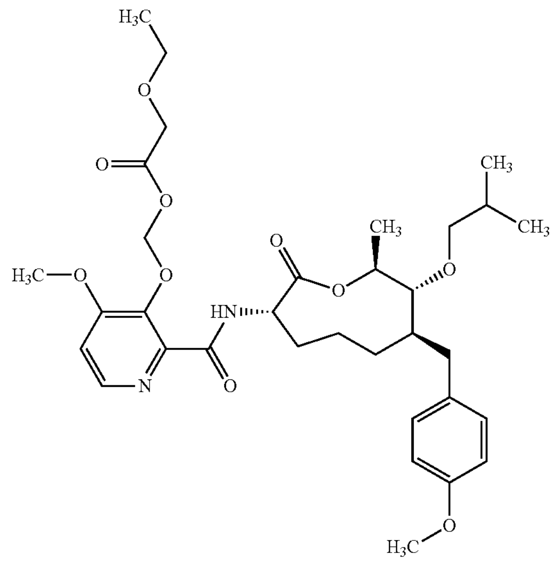 [SMILES: CCOCC(=O)OCOc1c(OC)ccnc1C(=O)N[C@H]1CCC[C@H](Cc2ccc(OC)cc2)[C@@H](OCC(C)C)[C@H](C)OC1=O] | Example 13 | Colorless Oil |
| F180 | 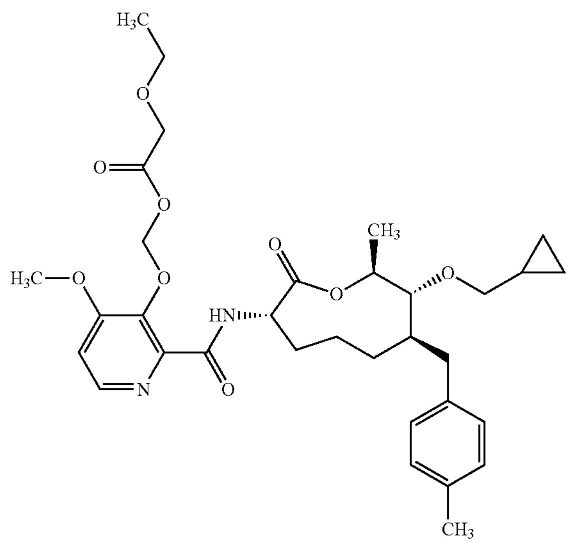 [SMILES: CCOCC(=O)OCOc1c(OC)ccnc1C(=O)N[C@H]1CCC[C@H](Cc2ccc(C)cc2)[C@@H](OCC2CC2)[C@H](C)OC1=O] | Example 13 | White Solid |
| F181 | 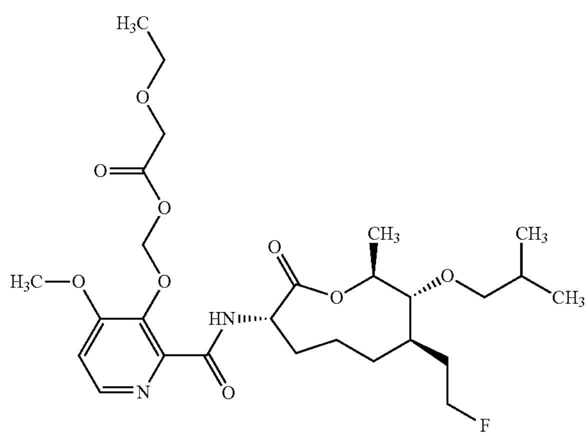 [SMILES: CCOCC(=O)OCOc1c(OC)ccnc1C(=O)N[C@H]1CCC[C@H](CCF)[C@@H](OCC(C)C)[C@H](C)OC1=O] | Example 13 | Sticky Solid |

TABLE 1-continued

Compound Structure and Appearance

| Compound Number | Structure | Prepared According To Example | Appearance |
|---|---|---|---|
| F182 | 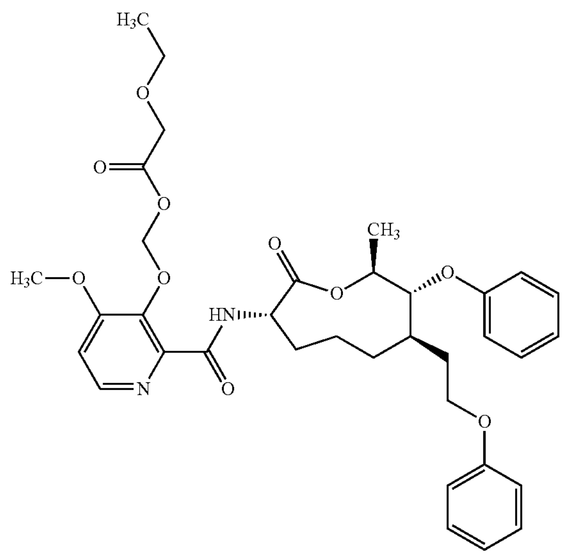 [SMILES: CCOCC(=O)OCOc1c(OC)ccnc1C(=O)N[C@H]1CCC[C@H](CCOc2ccccc2)[C@@H](Oc2ccccc2)[C@H](C)OC1=O] | Example 13 | White Solid |
| F183 | 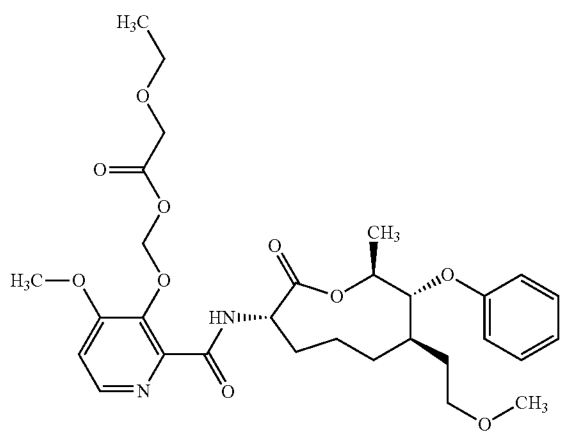 [SMILES: CCOCC(=O)OCOc1c(OC)ccnc1C(=O)N[C@H]1CCC[C@H](CCOC)[C@@H](Oc2ccccc2)[C@H](C)OC1=O] | Example 13 | White Solid |
| F184 | 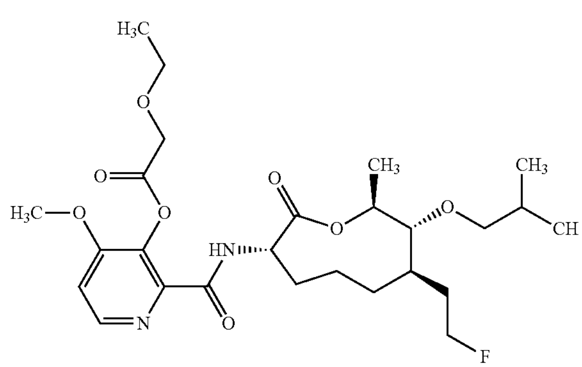 [SMILES: CCOCC(=O)Oc1c(OC)ccnc1C(=O)N[C@H]1CCC[C@H](CCF)[C@@H](OCC(C)C)[C@H](C)OC1=O] | Example 13 | Colorless Film |

TABLE 1-continued

| Compound Number | Structure | Prepared According To Example | Appearance |
|---|---|---|---|
| F185 | 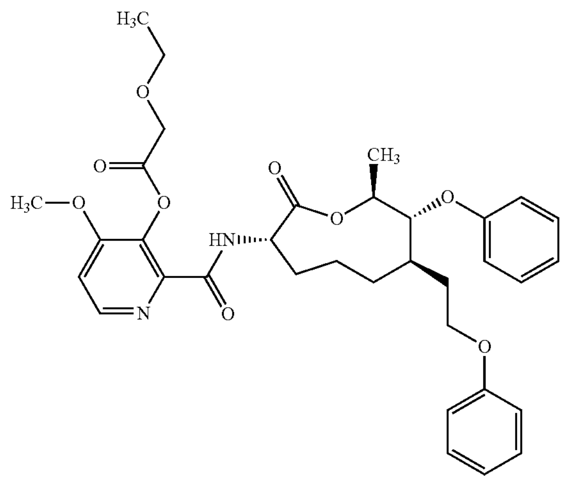 [SMILES: CCOCC(=O)Oc1c(OC)ccnc1C(=O)N[C@H]1CCC[C@H](CCOc2ccccc2)[C@@H](Oc2ccccc2)[C@H](C)OC1=O] | Example 13 | Colorless Film |
| F186 | 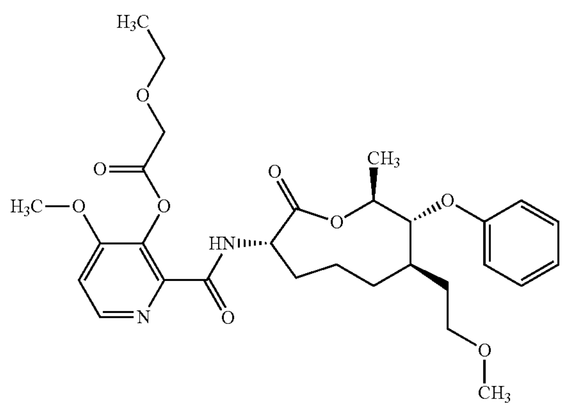 [SMILES: CCOCC(=O)Oc1c(OC)ccnc1C(=O)N[C@H]1CCC[C@H](CCOC)[C@@H](Oc2ccccc2)[C@H](C)OC1=O] | Example 13 | Colorless Film |
| F187 | 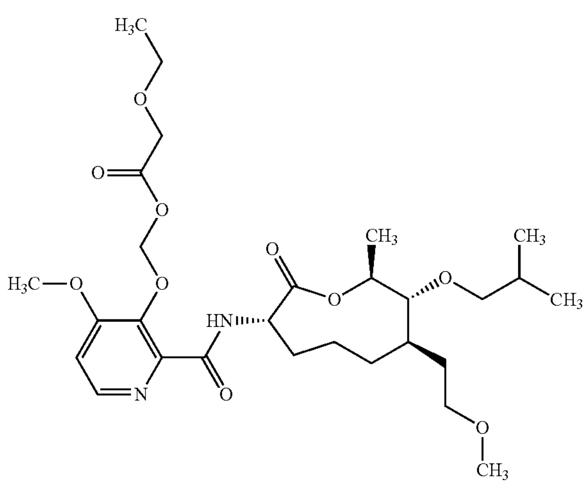 [SMILES: CCOCC(=O)OCOc1c(OC)ccnc1C(=O)N[C@H]1CCC[C@H](CCOC)[C@@H](OCC(C)C)[C@H](C)OC1=O] | Example 13 | Colorless Oil |

TABLE 1-continued

Compound Structure and Appearance

| Compound Number | Structure | Prepared According To Example | Appearance |
|---|---|---|---|
| F188 | 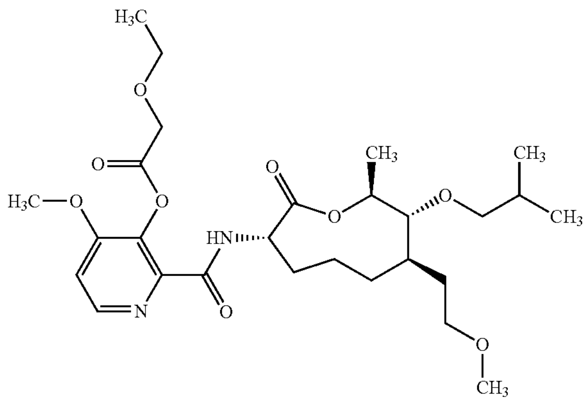 [SMILES: CCOCC(=O)Oc1c(OC)ccnc1C(=O)N[C@H]1CCC[C@H](CCOC)[C@@H](OCC(C)C)[C@H](C)OC1=O] | Example 13 | Colorless Film |
| F189 | 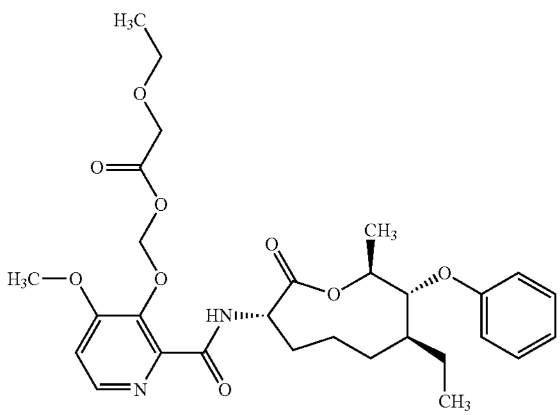 [SMILES: CCOCC(=O)OCOc1c(OC)ccnc1C(=O)N[C@H]1CCC[C@H](CC)[C@@H](Oc2ccccc2)[C@H](C)OC1=O] | Example 13 | White Solid |
| F190 | 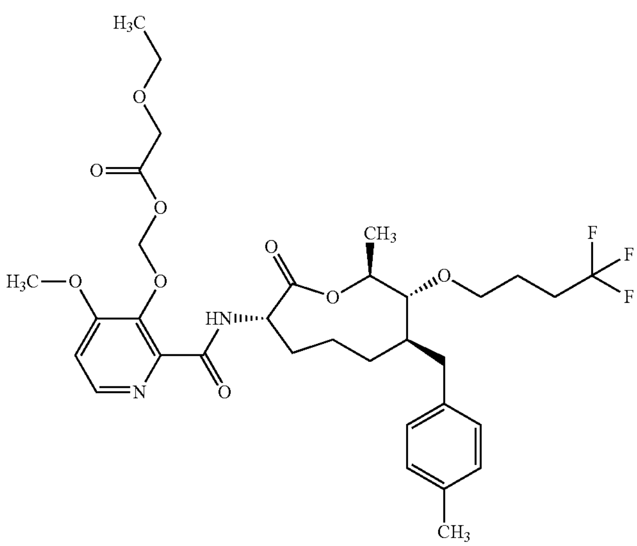 [SMILES: CCOCC(=O)OCOc1c(OC)ccnc1C(=O)N[C@H]1CCC[C@H](Cc2ccc(C)cc2)[C@@H](OCCCC(F)(F)F)[C@H](C)OC1=O] | Example 13 | Colorless Oil |

TABLE 1-continued
Compound Structure and Appearance
| Compound Number | Structure | Prepared According To Example | Appearance |
|---|---|---|---|
| F191 | 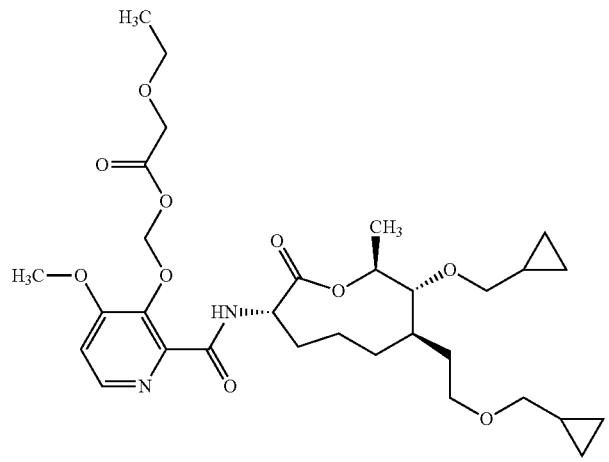 [SMILES: CCOCC(=O)OCOc1c(OC)ccnc1C(=O)N[C@H]1CCC[C@H](CCOCC2CC2)[C@@H](OCC2CC2)[C@H](C)OC1=O] | Example 13 | Colorless Oil |
| F192 | 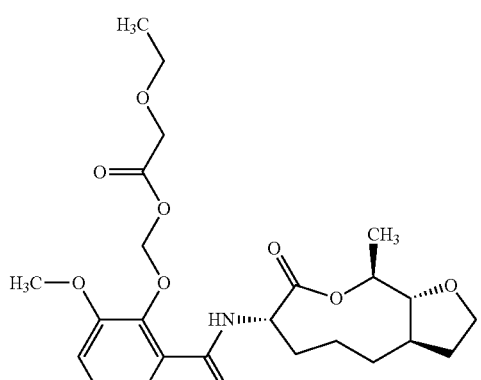 | Example 13 | White Solid |
| F193 | 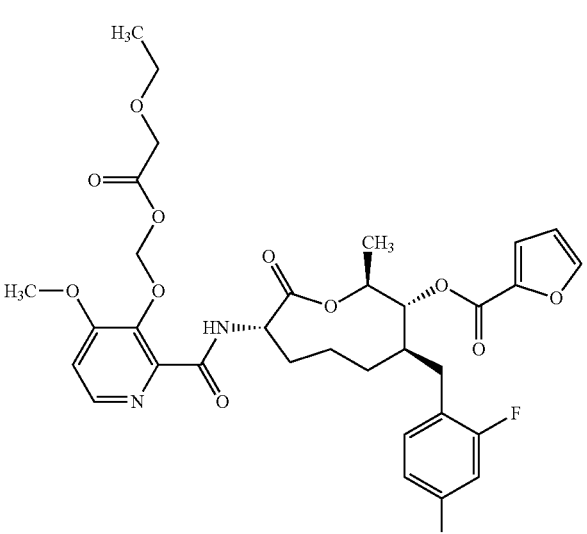 | Example 13 | White Solid |

TABLE 1-continued

Compound Structure and Appearance

| Compound Number | Structure | Prepared According To Example | Appearance |
|---|---|---|---|
| F194 | 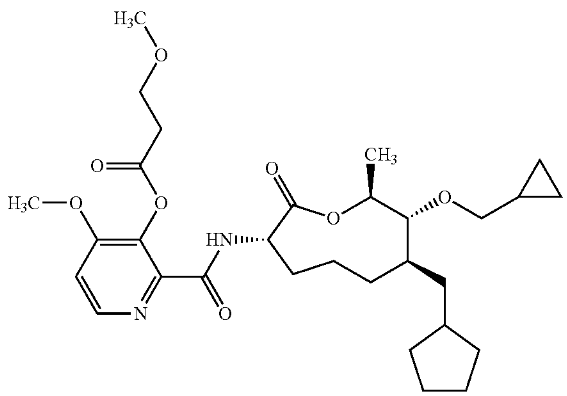 [SMILES: COCCC(=O)Oc1c(OC)ccnc1C(=O)N[C@H]1CCC[C@H](CC2CCCC2)[C@@H](OCC2CC2)[C@H](C)OC1=O] | Example 11 | Colorless Semi Solid |
| F195 | 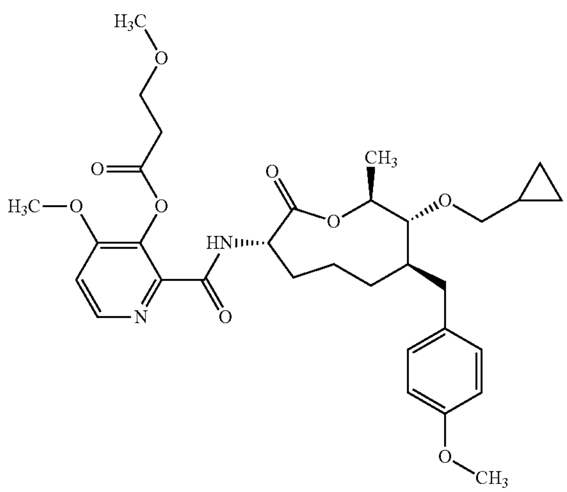 [SMILES: COCCC(=O)Oc1c(OC)ccnc1C(=O)N[C@H]1CCC[C@H](Cc2ccc(OC)cc2)[C@@H](OCC2CC2)[C@H](C)OC1=O] | Example 11 | Colorless Semi-Solid |
| F196 | 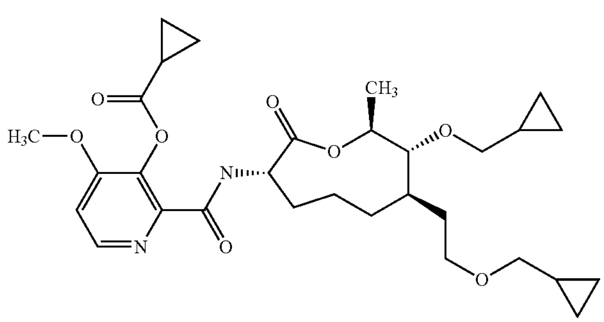 [SMILES: COc1ccnc(C(=O)N[C@H]2CCC[C@H](CCOCC3CC3)[C@@H](OCC3CC3)[C@H](C)OC2=O)c1OC(=O)C1CC1] | Example 10 | White Solid |

TABLE 1-continued

Compound Structure and Appearance

| Compound Number | Structure | Prepared According To Example | Appearance |
|---|---|---|---|
| F197 | 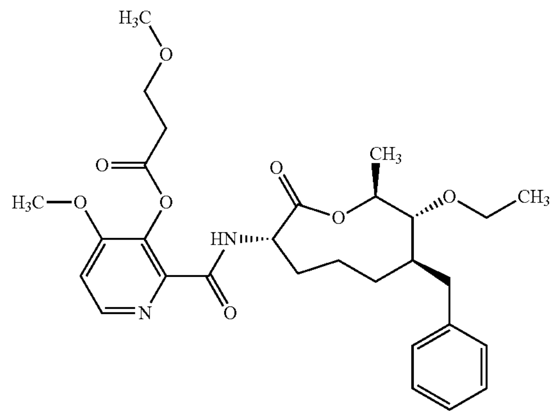 [SMILES: CCO[C@@H]1[C@@H](Cc2ccccc2)CCC[C@H](NC(=O)c2nccc(OC)c2OC(=O)CCOC)C(=O)O[C@H]1C] | Example 11 | White Foam |
| F198 | 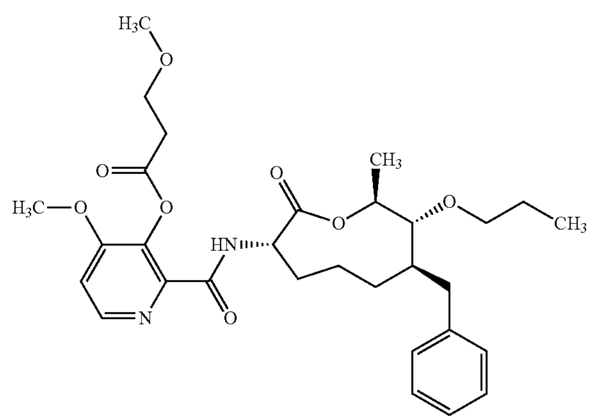 [SMILES: CCCO[C@@H]1[C@@H](Cc2ccccc2)CCC[C@H](NC(=O)c2nccc(OC)c2OC(=O)CCOC)C(=O)O[C@H]1C] | Example 11 | White Foam |
| F199 | 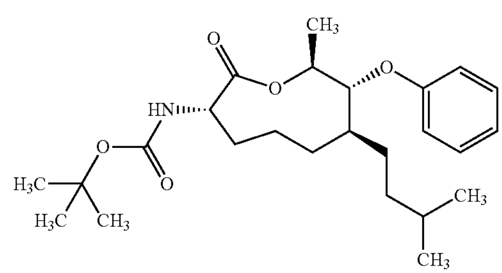 [SMILES: CC(C)CC[C@H]1CCC[C@H](NC(=O)OC(C)(C)C)C(=O)O[C@@H](C)[C@@H]1Oc1ccccc1] | Example 1, Steps 1, 2a, 3, 5b, 5c, 6 | White Solid |
| F200 | 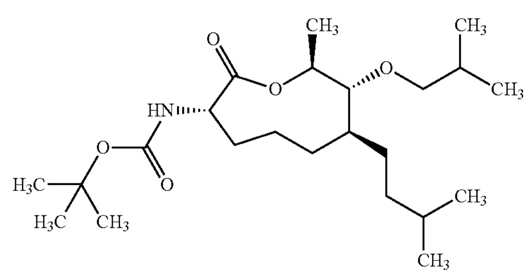 [SMILES: CC(C)CC[C@H]1CCC[C@H](NC(=O)OC(C)(C)C)C(=O)O[C@@H](C)[C@@H]1OCC(C)C] | Example 1, Steps 1, 2a, 3, 5b, 5c, 6 | Colorless Oil |

TABLE 1-continued

Compound Structure and Appearance

| Compound Number | Structure | Prepared According To Example | Appearance |
|---|---|---|---|
| F201 | 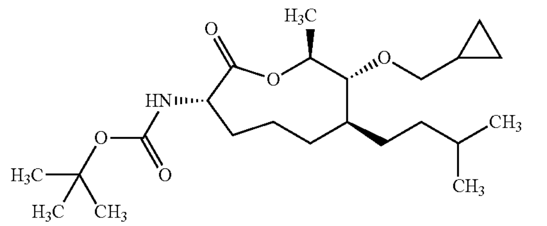 [SMILES: CC(C)CC[C@H]1CCC[C@H](NC(=O)OC(C)(C)C)C(=O)O[C@@H](C)[C@@H]1OCC1CC1] | Example 1, Steps 1, 2b, 3, 5b, 5c, 6 | Colorless Solid |
| F102 | 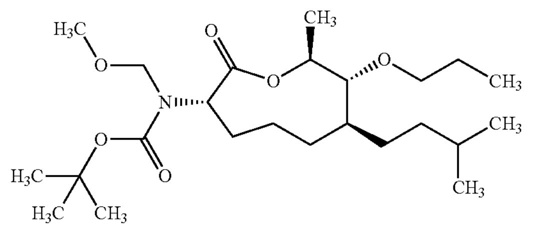 [SMILES: CCCO[C@@H]1[C@@H](CCC(C)C)CCC[C@H](N(COC)C(=O)OC(C)(C)C)C(=O)O[C@H]1C] | Example 1, Steps 1, 2c, 3, 4, 5c, 5b, 6; Example 2, Steps 1a-1, 1a-2; Example 3; Steps 1, 2a | Colorless Oil |
| F203 | 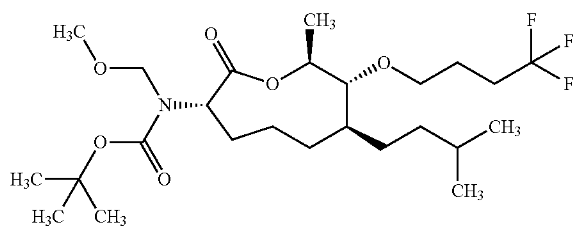 [SMILES: COCN(C(=O)OC(C)(C)C)[C@H]1CCC[C@H](CCC(C)C)[C@@H](OCCCC(F)(F)F)[C@H](C)OC1=O] | Example 1, Steps 1, 2c, 3, 4, 5c, 5b, 6; Example 2, Steps 1a-1, 1a-2; Example 3; Steps 1, 2a | White Solid |
| F204 | 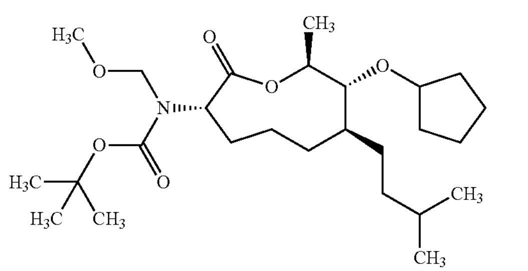 [SMILES: COCN(C(=O)OC(C)(C)C)[C@H]1CCC[C@H](CCC(C)C)[C@@H](OC2CCCC2)[C@H](C)OC1=O] | Example 1, Steps 1, 2c, 3, 4, 5c, 5b, 6; Example 2, Steps 1a-1, 1a-2; Example 3; Steps 1, 2a | Colorless Oil |
| F205 | 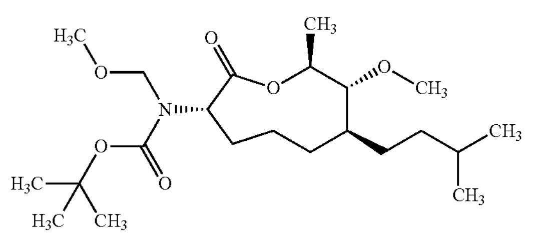 [SMILES: COCN(C(=O)OC(C)(C)C)[C@H]1CCC[C@H](CCC(C)C)[C@@H](OC)[C@H](C)OC1=O] | Example 1, Steps 1, 2c, 3, 4, 5c, 5b, 6; Example 2, Steps 1a-1, 1a-2; Example 6 | White Solid |
| F206 | 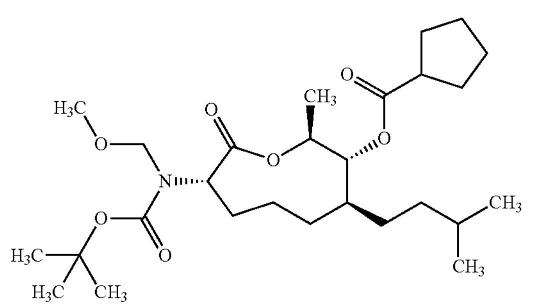 [SMILES: COCN(C(=O)OC(C)(C)C)[C@H]1CCC[C@H](CCC(C)C)[C@@H](OC(=O)C2CCCC2)[C@H](C)OC1=O] | Example 1, Steps 1, 2e, 3, 4, 5c, 5b, 6; Example 2, Steps 1a-1, 1a-2; Example 5 | Colorless Thick Oil |

TABLE 1-continued

Compound Structure and Appearance

| Compound Number | Structure | Prepared According To Example | Appearance |
|---|---|---|---|
| F207 | 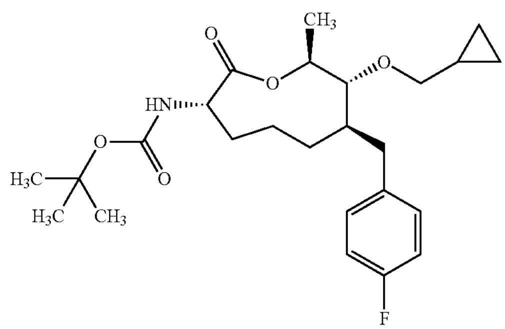 [SMILES: C[C@@H]1OC(=O)[C@@H](NC(=O)OC(C)(C)C)CCC[C@H](Cc2ccc(F)cc2)[C@H]1OCC1CC1] | Example 1, Steps 1, 2b, 3, 4, 5a, 5b, 6 | Colorless Foam |
| F208 | 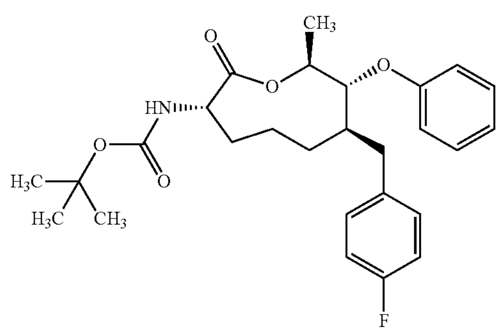 [SMILES: C[C@@H]1OC(=O)[C@@H](NC(=O)OC(C)(C)C)CCC[C@H](Cc2ccc(F)cc2)[C@H]1Oc1ccccc1] | Example 1, Steps 1, 2a, 3, 4, 5a, 5b, 6 | Colorless Solid |
| F209 | 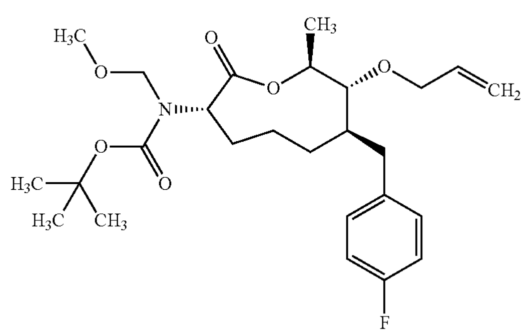 [SMILES: C=CCO[C@@H]1[C@@H](Cc2ccc(F)cc2)CCC[C@H](N(COC)C(=O)OC(C)(C)C)C(=O)O[C@H]1C] | Example 1, Steps 1, 2c, 3, 4, 5a, 5b, 6; Example 2, Steps 1a-1, 1a-2; Example 3, Step 1 | Pale Yellow Oil |
| F210 | 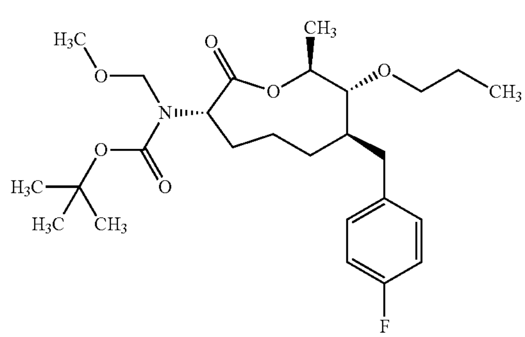 [SMILES: CCCO[C@@H]1[C@@H](Cc2ccc(F)cc2)CCC[C@H](N(COC)C(=O)OC(C)(C)C)C(=O)O[C@H]1C] | Example 1, Steps 1, 2c, 3, 4, 5a, 5b, 6; Example 2, Steps 1a-1, 1a-2; Example 3, Steps 1, 2a | Colorless Oil |

TABLE 1-continued

Compound Structure and Appearance

| Compound Number | Structure | Prepared According To Example | Appearance |
|---|---|---|---|
| F211 | 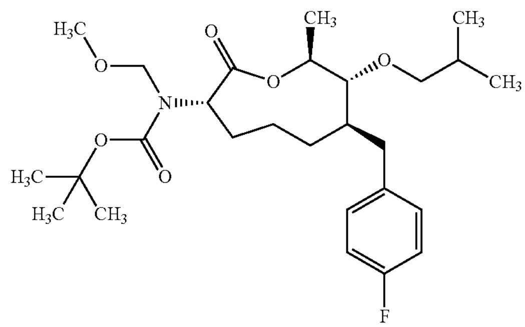 [SMILES: COCN(C(=O)OC(C)(C)C)[C@H]1CCC[C@H](Cc2ccc(F)cc2)[C@@H](OCC(C)C)[C@H](C)OC1=O] | Example 1, Steps 1, 2c, 3, 4, 5a, 5b, 6; Example 2, Steps 1a-1, 1a-2; Example 3, Steps 1, 2a | Colorless Oil |
| F212 | 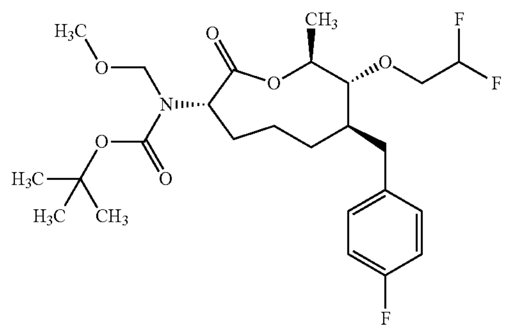 [SMILES: COCN(C(=O)OC(C)(C)C)[C@H]1CCC[C@H](Cc2ccc(F)cc2)[C@@H](OCC(F)F)[C@H](C)OC1=O] | Example 1, Steps 1,2c, 3, 4, 5a, 5b, 6; Example 2, Steps 1a-1. 1a-2; Example 3, Steps 1, 2b-1, 2b-2 | White Solid |
| F213 | 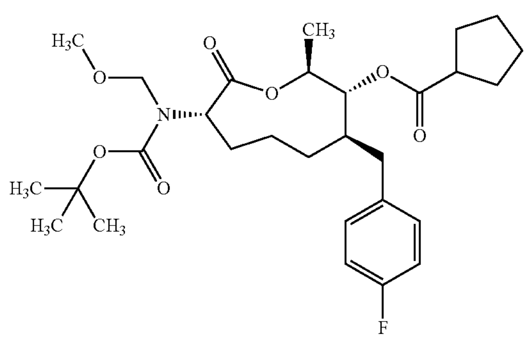 [SMILES: COCN(C(=O)OC(C)(C)C)[C@H]1CCC[C@H](Cc2ccc(F)cc2)[C@@H](OC(=O)C2CCCC2)[C@H](C)OC1=O] | Example 1, Steps 1, 2c, 3, 4, 5a, 5b, 6; Example 2, Steps 1a-1, 1a-2; Example 5 | Colorless Oil |
| F214 | 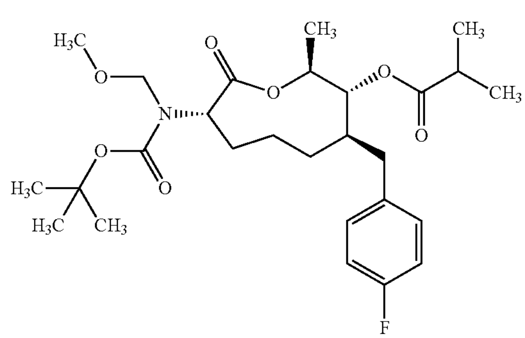 [SMILES: COCN(C(=O)OC(C)(C)C)[C@H]1CCC[C@H](Cc2ccc(F)cc2)[C@@H](OC(=O)C(C)C)[C@H](C)OC1=O] | Example 1, Steps 1, 2c, 3, 4, 5a, 5b, 6; Example 2, Steps 1a-1, 1a-2; Example 5 | Colorless Oil |

TABLE 1-continued

Compound Structure and Appearance

| Compound Number | Structure | Prepared According To Example | Appearance |
|---|---|---|---|
| F215 | 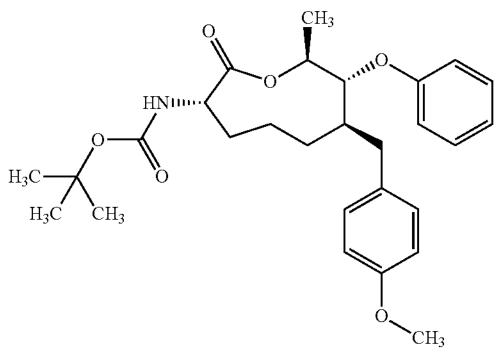 [SMILES: COc1ccc(C[C@H]2CCC[C@H](NC(=O)OC(C)(C)C)C(=O)O[C@@H](C)[C@@H]2Oc2ccccc2)cc1] | Example 1, Steps 1, 2a, 3, 4, 5a, 5c, 6 | Colorless Semi Solid |
| F216 | 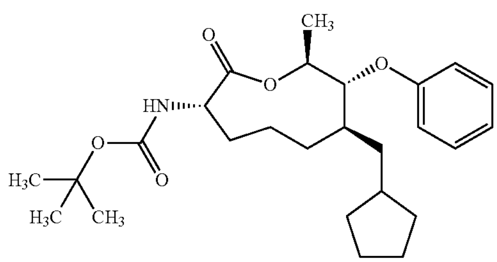 [SMILES: C[C@@H]1OC(=O)[C@@H](NC(=O)OC(C)(C)C)CCC[C@H](CC2CCCC2)[C@H]1Oc1ccccc1] | Example 1, Steps 1, 2a, 3, 4, 5a, 5c, 6 | White Foam |
| F217 | 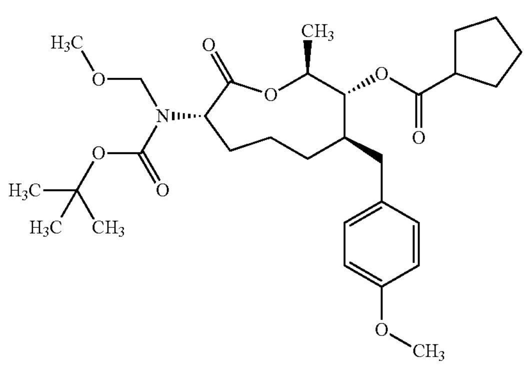 [SMILES: COCN(C(=O)OC(C)(C)C)[C@H]1CCC[C@H](Cc2ccc(OC)cc2)[C@@H](OC(=O)C2CCCC2)[C@H](C)OC1=O] | Example 1, Step 1, 2c, 3, 4, 5a, 5e, 6; Example 2, Step 1a-1, 1a-2; Example 5 | Yellow Solid |
| F218 | 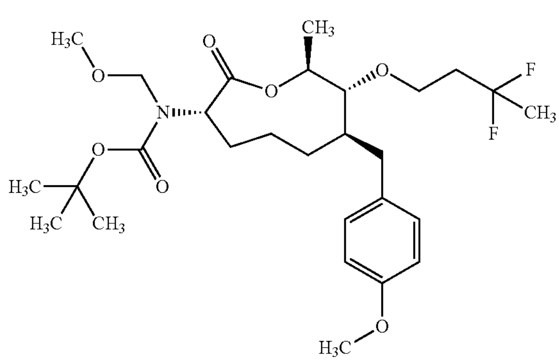 [SMILES: COCN(C(=O)OC(C)(C)C)[C@H]1CCC[C@H](Cc2ccc(OC)cc2)[C@@H](OCCC(C)(F)F)[C@H](C)OC1=O] | Example 1, Steps 1, 2c, 3, 4, 5a, 5c, 6; Example 2, Steps 1a-1, 1a-2; Example 4 | Colorless Oil |

TABLE 1-continued

Compound Structure and Appearance

| Compound Number | Structure | Prepared According To Example | Appearance |
|---|---|---|---|
| F219 | 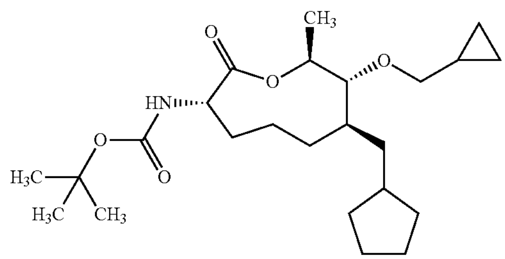 [SMILES: C[C@@H]1OC(=O)[C@@H](NC(=O)OC(C)(C)C)CCC[C@H](CC2CCCC2)[C@H]1OCC1CC1] | Example 1, Steps 1, 2b, 3, 4, 5a, 5c, 6 | Thick Colorless Oil |
| F220 | 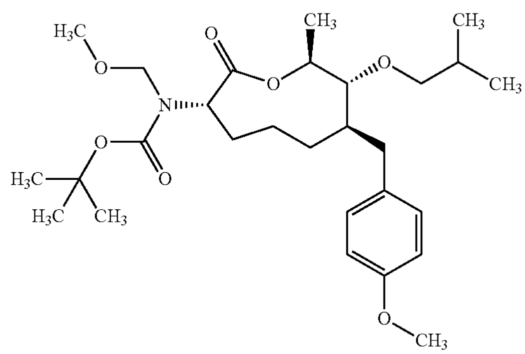 [SMILES: COCN(C(=O)OC(C)(C)C)[C@H]1CCC[C@H](Cc2ccc(OC)cc2)[C@@H](OCC(C)C)[C@H](C)OC1=O] | Example 1, Steps 1, 2c, 3, 4, 5a, 5c, 6; Example 2, Steps 1, 2; Example 3 | Colorless Oil |
| F221 | 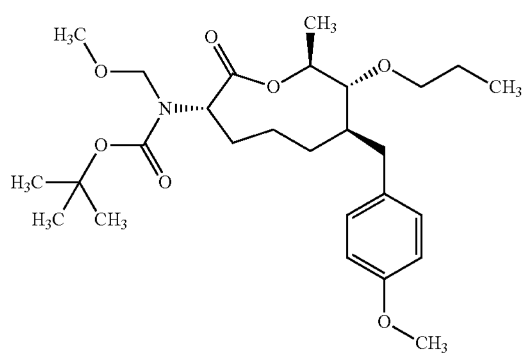 [SMILES: CCCO[C@@H]1[C@@H](Cc2ccc(OC)cc2)CCC[C@H](N(COC)C(=O)OC(C)(C)C)C(=O)O[C@H]1C] | Example 1, Steps 1, 2c, 3, 4, 5a, 5c, 6; Example 2, Steps 1, 2; Example 3 | Colorless Oil |
| F222 | 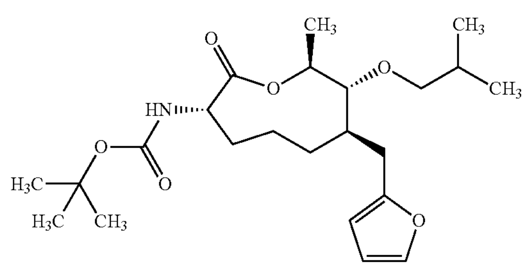 [SMILES: CC(C)CO[C@@H]1[C@@H](Cc2ccco2)CCC[C@H](NC(=O)OC(C)(C)C)C(=O)O[C@H]1C] | Example 1, Steps 1, 2b, 3, 4, 5a, 5c, 6 | Colorless Oil |
| F223 | 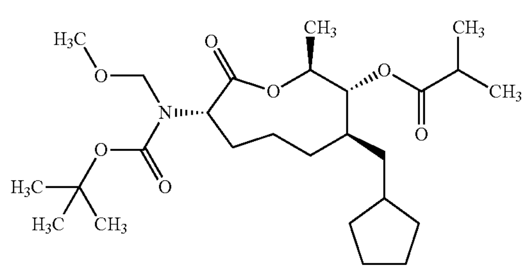 [SMILES: COCN(C(=O)OC(C)(C)C)[C@H]1CCC[C@H](CC2CCCC2)[C@@H](OC(=O)C(C)C)[C@H](C)OC1=O] | Example 1, Step 1, 2c, 3, 4, 5a, 5b, 6; Example 2, Step 1, 2; Example 5 | Yellow Solid |

TABLE 1-continued

Compound Structure and Appearance

| Compound Number | Structure | Prepared According To Example | Appearance |
|---|---|---|---|
| F224 | 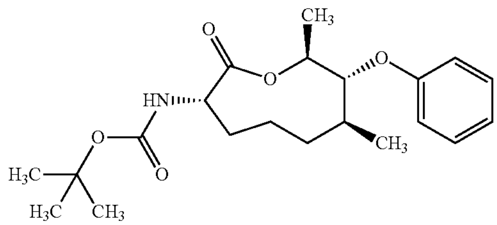 [SMILES: C[C@@H]1OC(=O)[C@@H](NC(=O)OC(C)(C)C)CCC[C@H](C)[C@H]1Oc1ccccc1] | Example 1, Step 1 2a, 3, 4, 5a, 5b, 6 | White Solid |
| F225 | 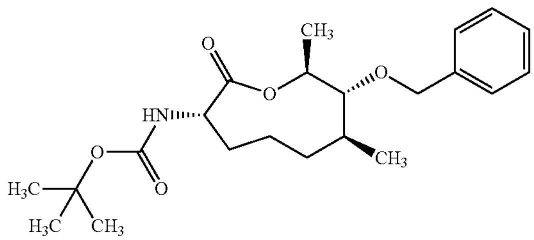 [SMILES: C[C@@H]1OC(=O)[C@@H](NC(=O)OC(C)(C)C)CCC[C@H](C)[C@H]1OCc1ccccc1] | Example 1, Step 1 2a, 3, 4, 5a, 5b, 6 | Thick Oil |
| F226 | 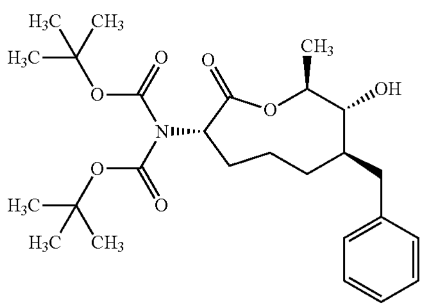 [SMILES: C[C@@H]1OC(=O)[C@@H](N(C(=O)OC(C)(C)C)C(=O)OC(C)(C)C)CCC[C@H](Cc2ccccc2)[C@H]1O] | Example 1, Steps 1, 2b, 3, 4, 5a, 5c, 6, 5b; Example 2, Step 1b | White Solid |
| F227 | 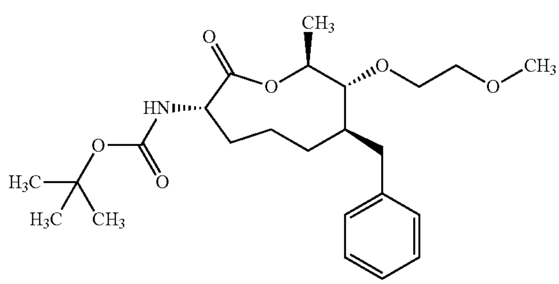 [SMILES: COCCO[C@@H]1[C@@H](Cc2ccccc2)CCC[C@H](NC(=O)OC(C)(C)C)C(=O)O[C@H]1C] | Example 1, Steps 1, 2b, 3, 4, 5b, 6 | Colorless Oil |
| F229 | 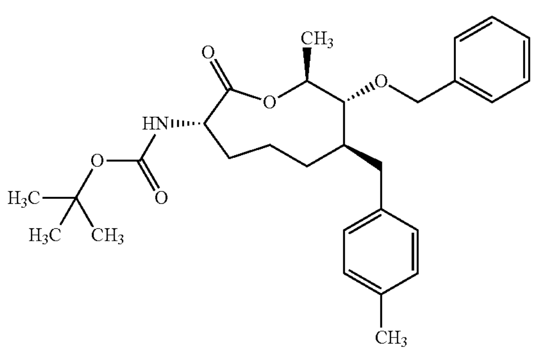 [SMILES: Cc1ccc(C[C@H]2CCC[C@H](NC(=O)OC(C)(C)C)C(=O)O[C@@H](C)[C@@H]2OCc2ccccc2)cc1] | Example 1 | White Solid |

TABLE 1-continued

Compound Structure and Appearance

| Compound Number | Structure | Prepared According To Example | Appearance |
|---|---|---|---|
| F230 | 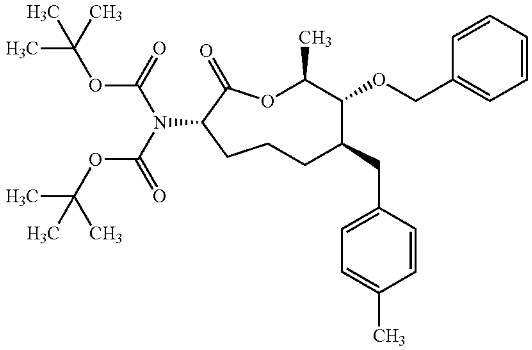 [SMILES: Cc1ccc(C[C@H]2CCC[C@H](N(C(=O)OC(C)(C)C)C(=O)OC(C)(C)C)C(=O)O[C@@H](C)[C@@H]2OCc2ccccc2)cc1] | Example 2, Step 1b | White Solid |
| F231 | 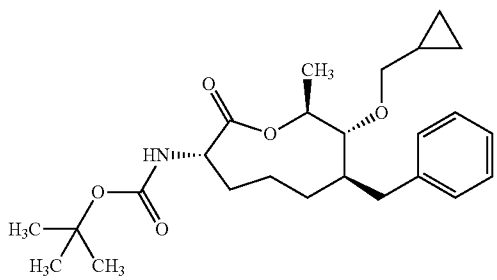 [SMILES: C[C@@H]1OC(=O)[C@@H](NC(=O)OC(C)(C)C)CCC[C@H](Cc2ccccc2)[C@H]1OCC1CC1] | Example 1, Steps 1, 2b, 3, 4, 5a, 5c, 6 | White Solid |
| F232 | 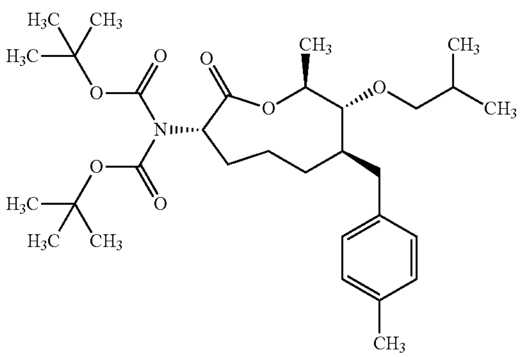 [SMILES: Cc1ccc(C[C@H]2CCC[C@H](N(C(=O)OC(C)(C)C)C(=O)OC(C)(C)C)C(=O)O[C@@H](C)[C@@H]2OCC(C)C)cc1] | Example 1, Steps 1, 2b, 3, 4, 5b, 6; Example 2, Step 1b | White Solid |
| F233 | 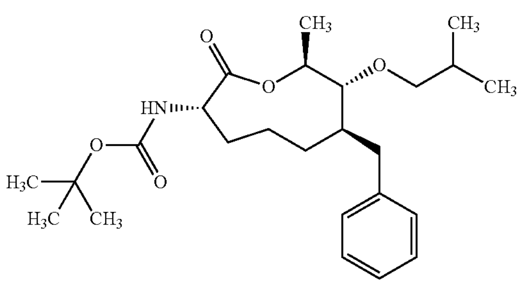 [SMILES: CC(C)CO[C@@H]1[C@@H](Cc2ccccc2)CCC[C@H](NC(=O)OC(C)(C)C)C(=O)O[C@H]1C] | Example 1, Steps 1, 2b, 3, 4, 5b, 6 | White Solid |
| F234 | 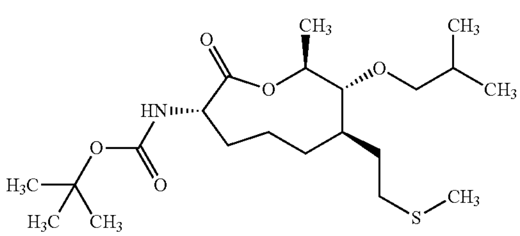 [SMILES: CSCC[C@H]1CCC[C@H](NC(=O)OC(C)(C)C)C(=O)O[C@@H](C)[C@@H]1OCC(C)C] | Example 1, Steps 1, 2b, 3, 4, 5b, 6 | Oily White Solid |

TABLE 1-continued

Compound Structure and Appearance

| Compound Number | Structure | Prepared According To Example | Appearance |
|---|---|---|---|
| F235 | 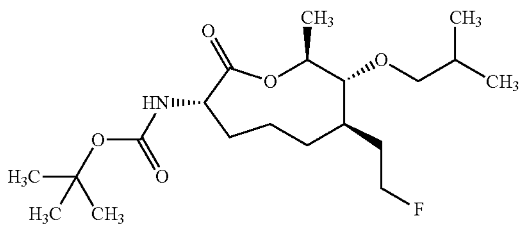 [SMILES: CC(C)CO[C@@H]1[C@@H](CCF)CCC[C@H](NC(=O)OC(C)(C)C)C(=O)O[C@H]1C] | Example 7, Step 2e | — |
| F236 | 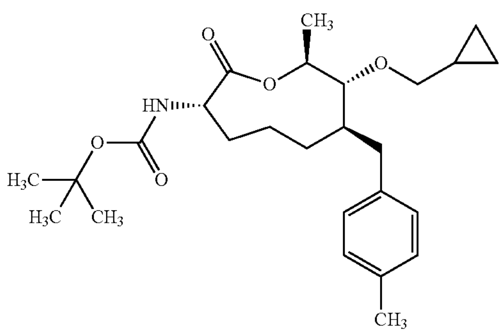 [SMILES: Cc1ccc(C[C@H]2CCC[C@H](NC(=O)OC(C)(C)C)C(=O)O[C@@H](C)[C@@H]2OCC2CC2)cc1] | Example 1 | White Solid |
| F237 | 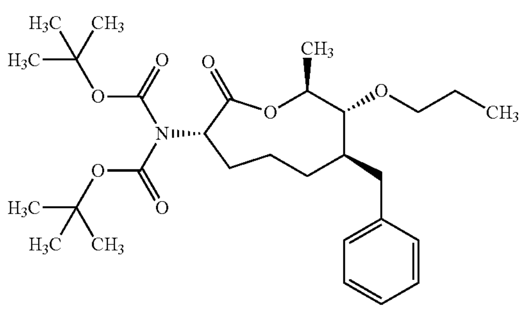 [SMILES: CCCO[C@@H]1[C@@H](Cc2ccccc2)CCC[C@H](N(C(=O)OC(C)(C)C)C(=O)OC(C)(C)C)C(=O)O[C@H]1C] | Example 1, Steps 1, 2b, 3, 4, 5b, 6 | White Solid |
| F238 | 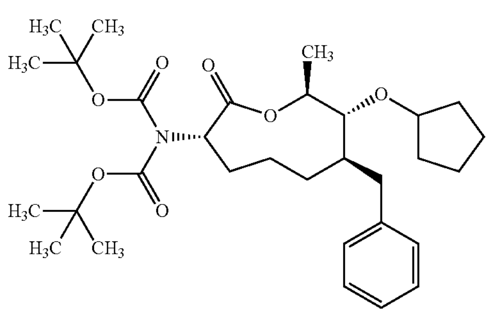 [SMILES: C[C@@H]1OC(=O)[C@@H](N(C(=O)OC(C)(C)C)C(=O)OC(C)(C)C)CCC[C@H](Cc2ccccc2)[C@H]1OC1CCCC1] | Example 1, Steps 1, 2b, 3, 4, 5a, 5c, 6, 5b; Example 2, Step 1b; Example 3 Steps 1, 2a, | Colorless Oil |

TABLE 1-continued

Compound Structure and Appearance

| Compound Number | Structure | Prepared According To Example | Appearance |
|---|---|---|---|
| F239 | 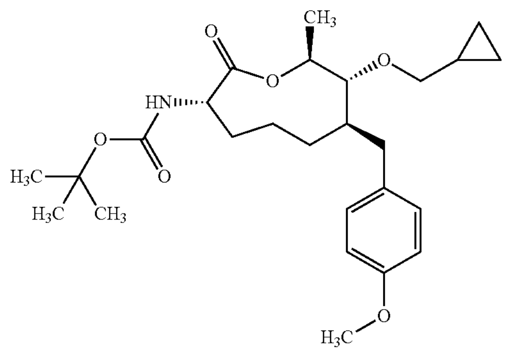 [SMILES: COc1ccc(C[C@H]2CCC[C@H](NC(=O)OC(C)(C)C)C(=O)O[C@@H](C)[C@@H]2OCC2CC2)cc1] | Example 1, Steps 1, 2b, 3, 4, 5a, 5c, 6 | Colorless Semi Solid |
| F240 | 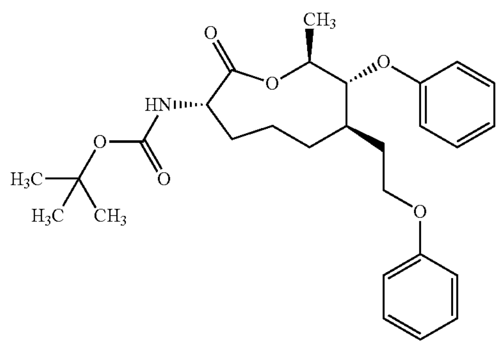 [SMILES: C[C@@H]1OC(=O)[C@@H](NC(=O)OC(C)(C)C)CCC[C@H](CCOc2ccccc2)[C@H]1Oc1ccccc1] | Example 7, Step 2a | — |
| F241 | 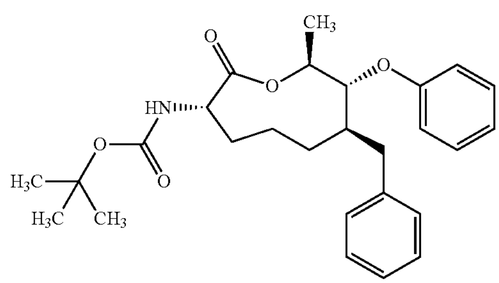 [SMILES: C[C@@H]1OC(=O)[C@@H](NC(=O)OC(C)(C)C)CCC[C@H](Cc2ccccc2)[C@H]1Oc1ccccc1] | Example 1, Steps 1, 2a, 3, 4, 5b, 6 | White Foam |
| F242 | 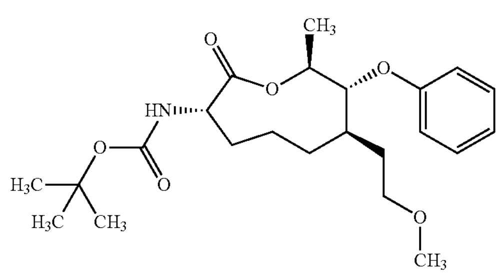 [SMILES: COCC[C@H]1CCC[C@H](NC(=O)OC(C)(C)C)C(=O)O[C@@H](C)[C@@H]1Oc1ccccc1] | Example 7, Step 2b | — |
| F243 | 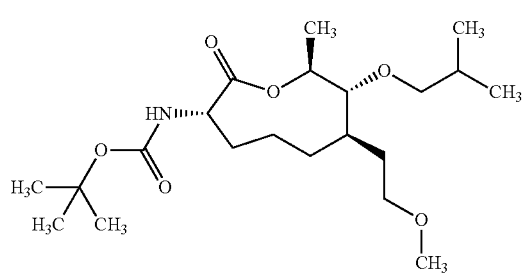 [SMILES: COCC[C@H]1CCC[C@H](NC(=O)OC(C)(C)C)C(=O)O[C@@H](C)[C@@H]1OCC(C)C] | Example 7, Step 2b | White Solid |

TABLE 1-continued

Compound Structure and Appearance

| Compound Number | Structure | Prepared According To Example | Appearance |
|---|---|---|---|
| F244 | 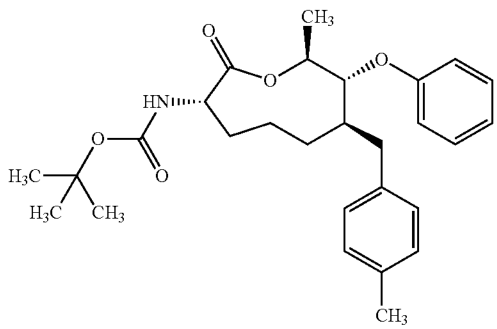 [SMILES: Cc1ccc(C[C@H]2CCC[C@H](NC(=O)OC(C)(C)C)C(=O)O[C@@H](C)[C@@H]2Oc2ccccc2)cc1] | Example 1 | White Solid |
| F245 | 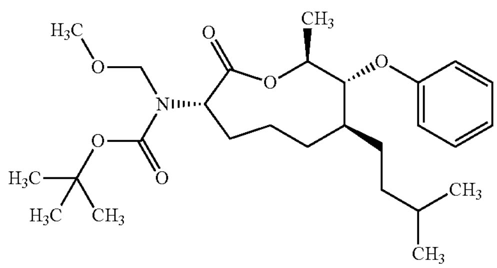 [SMILES: COCN(C(=O)OC(C)(C)C)[C@H]1CCC[C@H](CCC(C)C)[C@@H](Oc2ccccc2)[C@H](C)OC1=O] | Example 1, Steps 1, 2c, 3, 4, 5c, 5b, 6; Example 2, Steps 1a-1, 1a-2; Example 7, Step 2a | Colorless Sticky Oil |
| F246 | 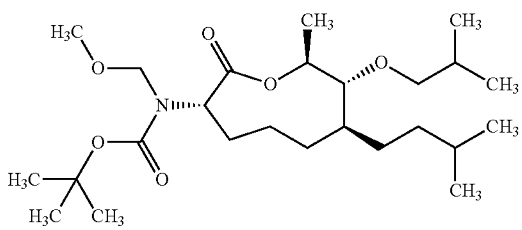 [SMILES: COCN(C(=O)OC(C)(C)C)[C@H]1CCC[C@H](CCC(C)C)[C@@H](OCC(C)C)[C@H](C)OC1=O] | Example 1, Steps 1, 2c, 3, 4, 5c, 5b, 6; Example 2, Steps 1a-1, 1a-2; Example 3; Steps 1, 2a | Colorless Oil |
| F247 | 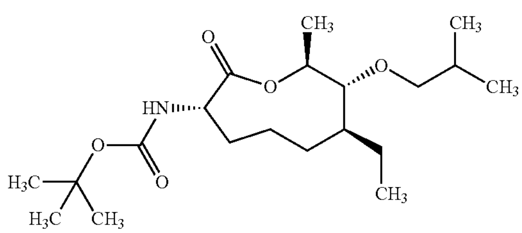 [SMILES: CC[C@H]1CCC[C@H](NC(=O)OC(C)(C)C)C(=O)O[C@@H](C)[C@@H]1OCC(C)C] | Example 7, Step 2d-2 | — |
| F248 | 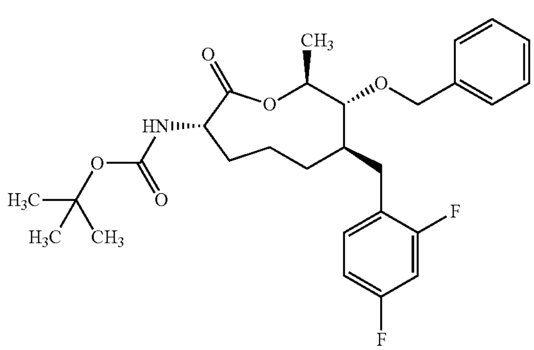 [SMILES: C[C@@H]1OC(=O)[C@@H](NC(=O)OC(C)(C)C)CCC[C@H](Cc2ccc(F)cc2F)[C@H]1OCc1ccccc1] | Example 1 | Colorless Oil |

TABLE 1-continued

Compound Structure and Appearance

| Compound Number | Structure | Prepared According To Example | Appearance |
|---|---|---|---|
| F249 | 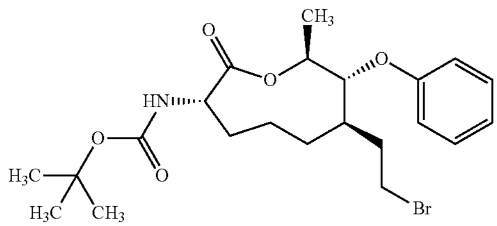 [SMILES: C[C@@H]1OC(=O)[C@@H](NC(=O)OC(C)(C)C)CCC[C@H](CCBr)[C@H]1Oc1ccccc1] | Example 7, Step 2d-1 | White Foam |
| F250 | 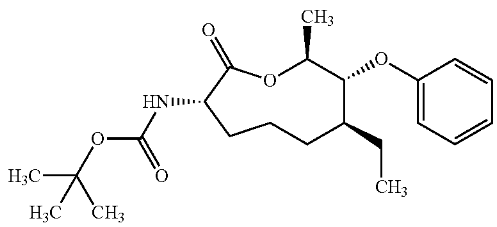 | Example 7, Step 2d-1 | White Foam |
| F251 | 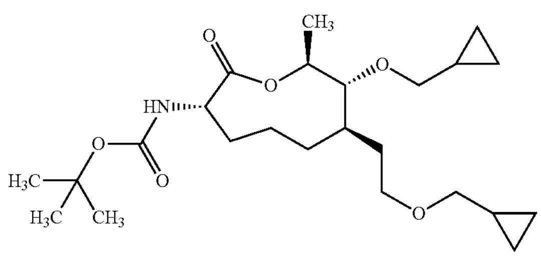 [SMILES: C[C@@H]1OC(=O)[C@@H](NC(=O)OC(C)(C)C)CCC[C@H](CCOCC2CC2)[C@H]1OCC1CC1] | Example 1, Step 6 | Oil |
| F253 | 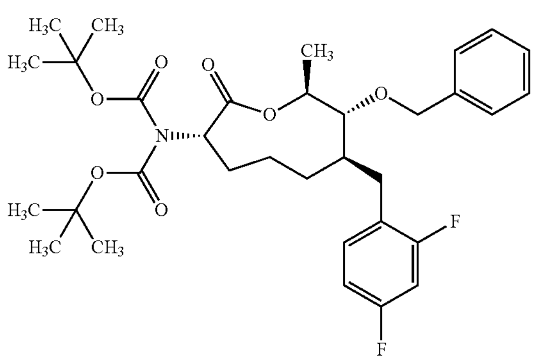 [SMILES: C[C@@H]1OC(=O)[C@@H](N(C(=O)OC(C)(C)C)C(=O)OC(C)(C)C)CCC[C@H](Cc2ccc(F)cc2F)[C@H]1OCc1ccccc1] | Example 2, Step 1b | Colorless Oil |
| F254 | 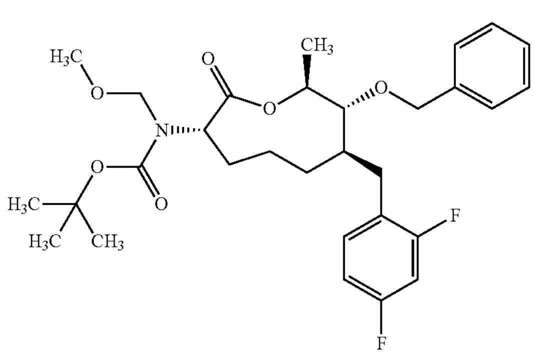 [SMILES: COCN(C(=O)OC(C)(C)C)[C@H]1CCC[C@H](Cc2ccc(F)cc2F)[C@@H](OCc2ccccc2)[C@H](C)OC1=O] | Example 2, Step 1a-1, 1a-2 | Yellow Solid |

TABLE 1-continued

| Compound Number | Structure | Prepared According To Example | Appearance |
|---|---|---|---|
| F255 | 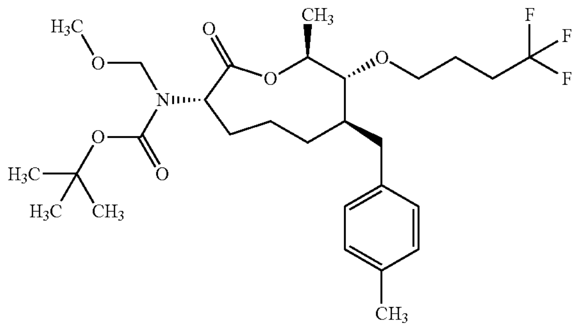 [SMILES: COCN(C(=O)OC(C)(C)C)[C@H]1CCC[C@H](Cc2ccc(C)cc2)[C@@H](OCCCC(F)(F)F)[C@H](C)OC1=O] | Example 3 | |
| F256 | 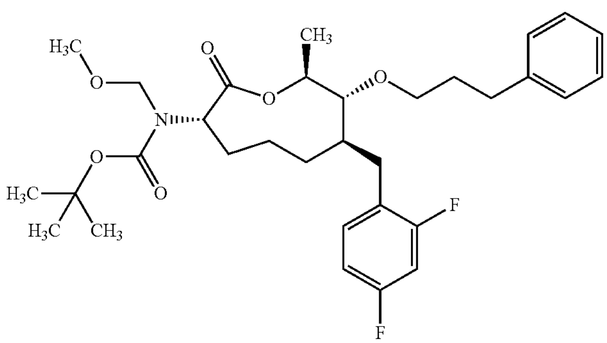 [SMILES: COCN(C(=O)OC(C)(C)C)[C@H]1CCC[C@H](Cc2ccc(F)cc2F)[C@@H](OCCCc2ccccc2)[C@H](C)OC1=O] | Example 3 | Colorless Oil |
| F257 | 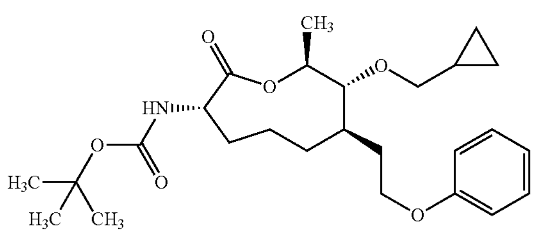 [SMILES: C[C@@H]1OC(=O)[C@@H](NC(=O)OC(C)(C)C)CCC[C@H](CCOc2ccccc2)[C@H]1OCC1CC1] | Example 1, Step 6 | Sticky Oil |
| F258 | 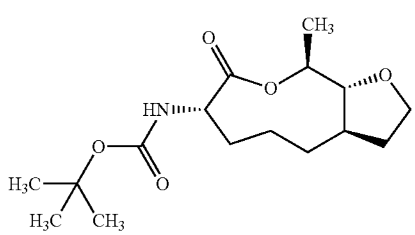 [SMILES: C[C@@H]1OC(=O)[C@@H](NC(=O)OC(C)(C)C)CCC[C@@H]2CCO[C@H]21] | Example 1, Step 6 | White Solid |
| F259 | 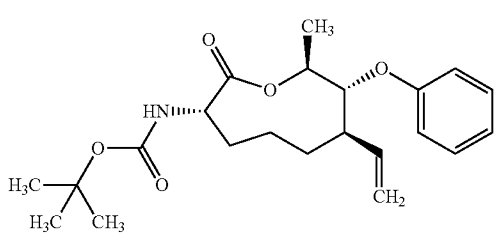 [SMILES: C=C[C@H]1CCC[C@H](NC(=O)OC(C)(C)C)C(=O)O[C@@H](C)[C@@H]1Oc1ccccc1] | Example 7, Step 2f-2 | Orange Solid |

TABLE 1-continued

Compound Structure and Appearance

| Compound Number | Structure | Prepared According To Example | Appearance |
|---|---|---|---|
| F260 | 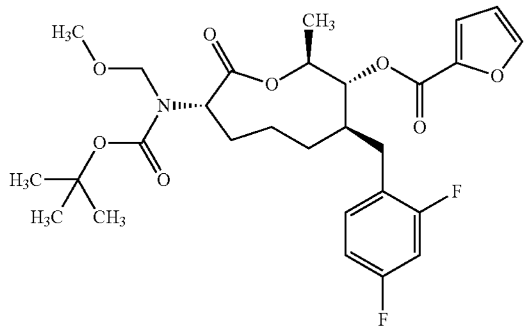 [SMILES: COCN(C(=O)OC(C)(C)C)[C@H]1CCC[C@H](Cc2ccc(F)cc2F)[C@@H](OC(=O)c2ccco2)[C@H](C)OC1=O] | Example 5 | White Solid |
| F261 | 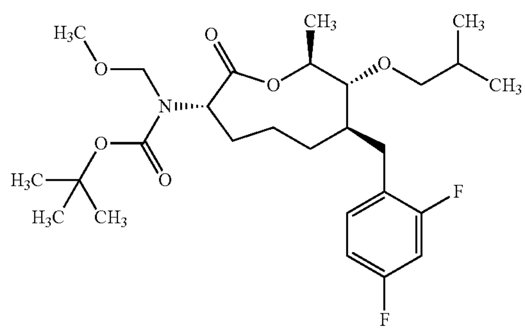 [SMILES: COCN(C(=O)OC(C)(C)C)[C@H]1CCC[C@H](Cc2ccc(F)cc2F)[C@@H](OCC(C)C)[C@H](C)OC1=O] | Example 3 | Colorless Oil |
| F262 | 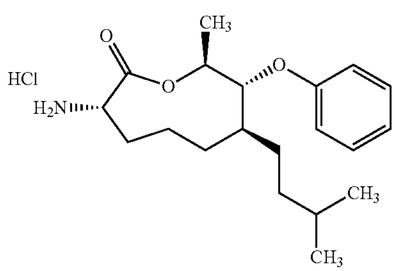 [SMILES: Cl ; CC(C)CC[C@H]1CCC[C@H](N)C(=O)O[C@@H](C)[C@@H]1Oc1ccccc1] | Example 1, Steps 1, 2c, 3, 4, 5c, 5b, 6; Example 2, Steps 1a-1, 1a-2; Example 7; Step 2a; Example 8, Step 1 | White Solid |
| F263 | 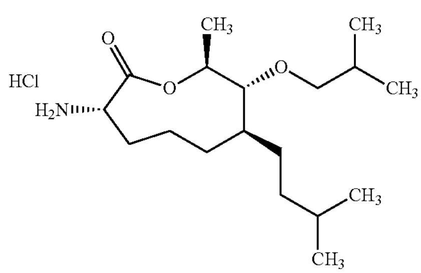 [SMILES: Cl ; CC(C)CC[C@H]1CCC[C@H](N)C(=O)O[C@@H](C)[C@@H]1OCC(C)C] | Example 1, Steps 1, 2c, 3,4, 5c, 5b, 6; Example 2, Steps 1a-1, 1a-2; Example 3; Steps 1, 2a; Example 8, Step 1 | White Solid |
| F264 | 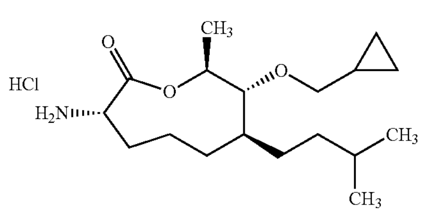 [SMILES: Cl ; CC(C)CC[C@H]1CCC[C@H](N)C(=O)O[C@@H](C)[C@@H]1OCC1CC1] | Example 1, Steps 1, 2b, 3, 5b, 5c, 6; Example 8, Step 1 | White Solid |

TABLE 1-continued

Compound Structure and Appearance

| Compound Number | Structure | Prepared According To Example | Appearance |
|---|---|---|---|
| F265 | 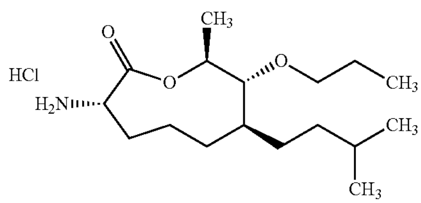 [SMILES: Cl ; CCCO[C@@H]1[C@@H](CCC(C)C)CCC[C@H](N)C(=O)O[C@H]1C] | Example 1, Steps 1, 2c, 3, 4, 5c, 5b, 6; Example 2, Steps 1a-1, 1a-2; Example 3; Steps 1, 2a; Example 8, Step 1 | White Solid |
| F266 | 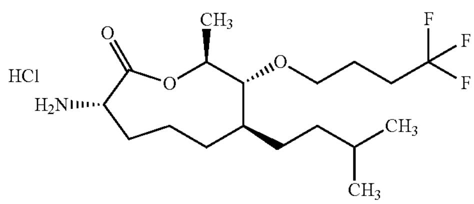 [SMILES: Cl ; CC(C)CC[C@H]1CCC[C@H](N)C(=O)O[C@@H](C)[C@@H]1OCCCC(F)(F)F] | Example 1, Steps 1, 2c, 3, 4, 5c, 5b, 6; Example 2, Steps 1a-1, 1a-2; Example 3; Steps 1, 2a; Example 8, Step 1 | White Solid |
| F267 | 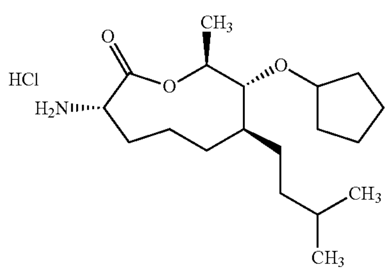 [SMILES: Cl ; CC(C)CC[C@H]1CCC[C@H](N)C(=O)O[C@@H](C)[C@@H]1OC1CCCC1] | Example 1, Steps 1, 2c, 3, 4, 5c, 5b, 6; Example 2, Steps 1a-1, 1a-2; Example 3; Steps 1, 2a; Example 8, Step 1 | Pale Yellow Thick Oil |
| F268 | 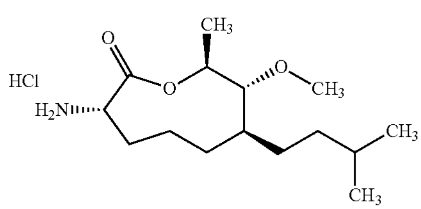 [SMILES: Cl ; CO[C@@H]1[C@@H](CCC(C)C)CCC[C@H](N)C(=O)O[C@H]1C] | Example 1, Steps 1, 2c, 3, 4, 5c, 5b, 6; Example 2, Steps 1a-1, 1a-2; Example 6; Example 8, Step 1 | White Solid |
| F269 | 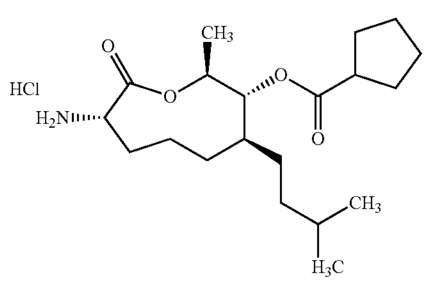 [SMILES: Cl ; CC(C)CC[C@H]1CCC[C@H](N)C(=O)O[C@@H](C)[C@@H]1OC(=O)C1CCCC1] | Example 1, Steps 1, 2c, 3, 4, 5c, 5b, 6; Example 2, Steps 1a-1, 1a-2; Example 5; Example 8, Step 1 | White Sticky Solid |

TABLE 1-continued

Compound Structure and Appearance

| Compound Number | Structure | Prepared According To Example | Appearance |
|---|---|---|---|
| F271 | 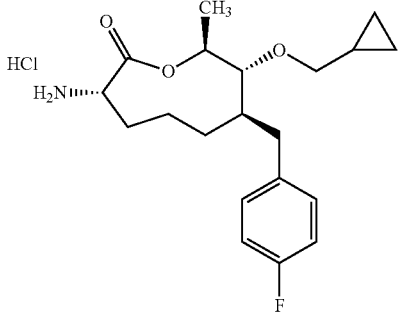 [SMILES: Cl ; C[C@@H]1OC(=O)[C@@H](N)CCC[C@H](Cc2ccc(F)cc2)[C@H]1OCC1CC1] | Example 1, Steps 1, 2b, 3, 4, 5a, 5b, 6; Example 8, Step 1 | White Solid |
| F272 | 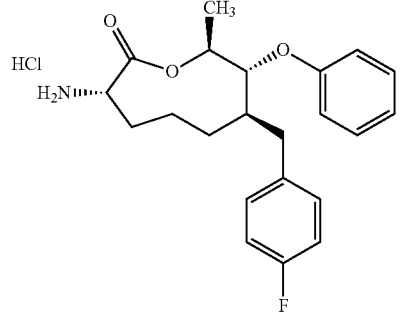 [SMILES: Cl ; C[C@@H]1OC(=O)[C@@H](N)CCC[C@H](Cc2ccc(F)cc2)[C@H]1Oc1ccccc1] | Example 1, Steps 1, 2a, 3, 4, 5a, 5b, 6; Example 8, Step 1 | Colorless Solid |
| F273 | 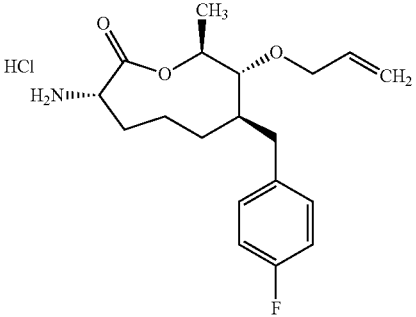 [SMILES: Cl ; C=CCO[C@@H]1[C@@H](Cc2ccc(F)cc2)CCC[C@H](N)C(=O)O[C@H]1C] | Example 1, Steps 1, 2c, 3, 4, 5a, 5b, 6; Example 2, Steps 1a-1, 1a-2; Example 3, Step 1; Example 8, Step 1 | Off-White Solid |
| F274 | 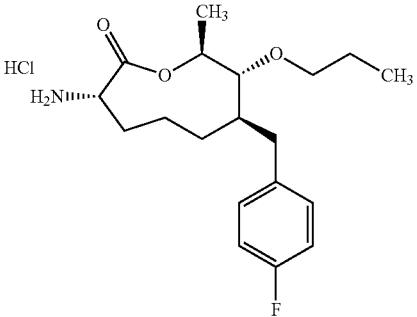 [SMILES: Cl ; CCCO[C@@H]1[C@@H](Cc2ccc(F)cc2)CCC[C@H](N)C(=O)O[C@H]1C] | Example 1, Steps 1, 2c, 3, 4, 5a, 5b, 6; Example 2, Steps 1a-1, 1a-2; Example 3, Steps 1, 2a; Example 8, Step 1 | White Solid |

TABLE 1-continued

Compound Structure and Appearance

| Compound Number | Structure | Prepared According To Example | Appearance |
|---|---|---|---|
| F275 | 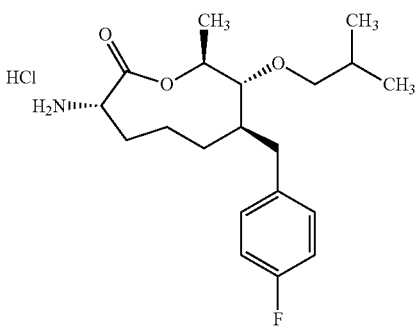 [SMILES: Cl ; CC(C)CO[C@@H]1[C@@H](Cc2ccc(F)cc2)CCC[C@H](N)C(=O)O[C@H]1C] | Example 1, Steps 1, 2c, 3, 4, 5a, 5b, 6; Example 2, Steps 1a-1, 1a-2; Example 3, Steps 1, 2a; Example 8, Step 1 | White Solid |
| F276 | 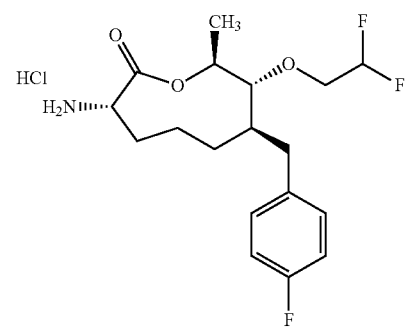 [SMILES: Cl ; C[C@@H]1OC(=O)[C@@H](N)CCC[C@H](Cc2ccc(F)cc2)[C@H]1OCC(F)F] | Example 1, Steps 1, 2c, 3, 4, 5a, 5b, 6; Example 2, Steps 1a-1, 1a-2; Example 3, Steps 1, 2b-1, 2b-2; Example 8, Step 1 | White Solid |
| F277 | 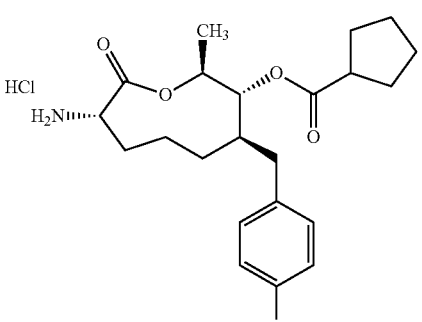 | Example 1, Steps 1, 2c, 3, 4, 5a, 5b, 6; Example 2, Steps 1a-1, 1a-2; Example 5; Example 8, Step 1 | White Solid |
| F278 | 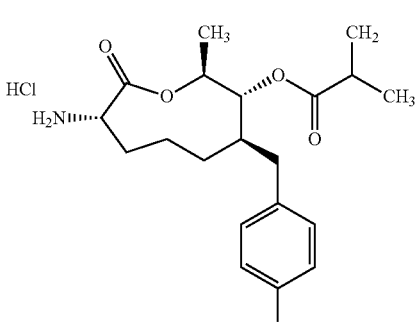 | Example 1, Steps 1, 2c, 3, 4, 5a, 5b, 6; Example 2, Steps 1a-1, 1a-2; Example 5; Example 8, Step 1 | White Solid |

TABLE 1-continued

Compound Structure and Appearance

| Compound Number | Structure | Prepared According To Example | Appearance |
|---|---|---|---|
| F279 | 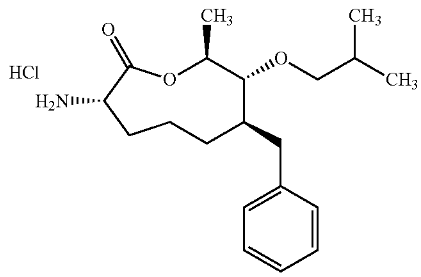 [SMILES: Cl ; CC(C)CO[C@@H]1[C@@H](Cc2ccccc2)CCC[C@H](N)C(=O)O[C@H]1C] | Example 8 Step 1 | White Solid |
| F280 | 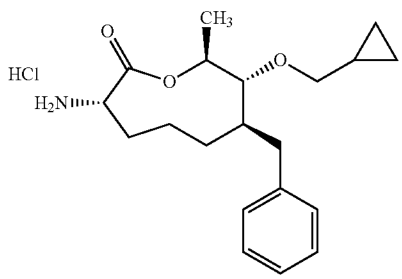 [SMILES: Cl ; C[C@@H]1OC(=O)[C@@H](N)CCC[C@H](Cc2ccccc2)[C@H]1OCC1CC1] | Example 8 Step 1 | White Solid |
| F281 | 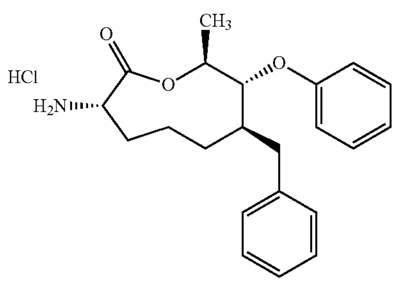 [SMILES: Cl ; C[C@@H]1OC(=O)[C@@H](N)CCC[C@H](Cc2ccccc2)[C@H]1Oc1ccccc1] | Example 8 Step 1 | White Solid |
| F282 | 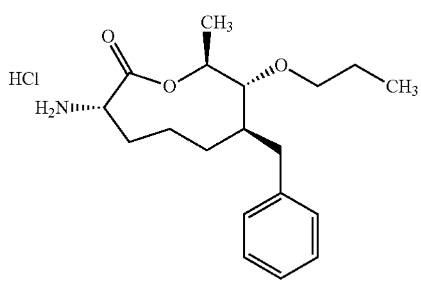 [SMILES: Cl ; CCCO[C@@H]1[C@@H](Cc2ccccc2)CCC[C@H](N)C(=O)O[C@H]1C] | Example 8 Step 1 | White Solid |
| F283 | 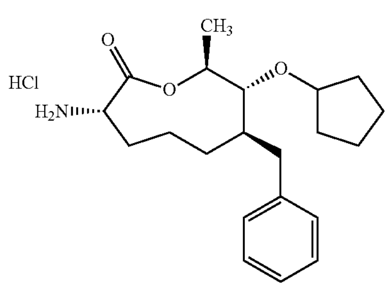 [SMILES: Cl ; C[C@@H]1OC(=O)[C@@H](N)CCC[C@H](Cc2ccccc2)[C@H]1OC1CCCC1] | Example 8 Step 1 | White Solid |

TABLE 1-continued
Compound Structure and Appearance
| Compound Number | Structure | Prepared According To Example | Appearance |
|---|---|---|---|
| F284 | 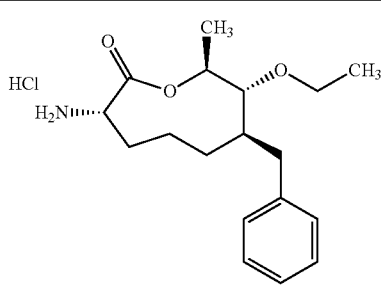 | Example 8 Step 1 | White Solid |
| F285 | 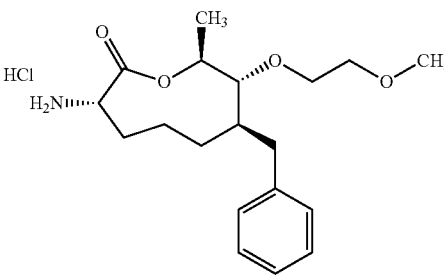 | Example 8 Step 1 | White Solid |
| F287 | 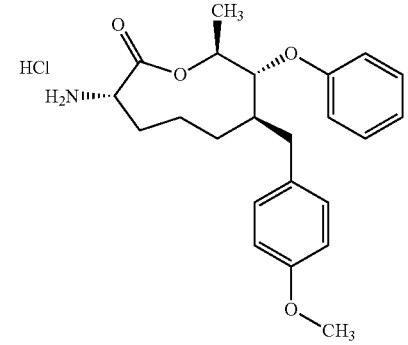 [SMILES: Cl ; COc1ccc(C[C@H]2CCC[C@H](N)C(=O)O[C@@H](C)[C@@H]2Oc2ccccc2)cc1] | Example 8, Step 1 | White Solid |
| F288 | 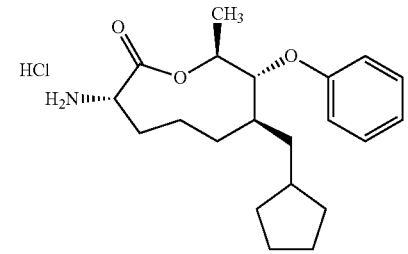 [SMILES: Cl ; C[C@@H]1OC(=O)[C@@H](N)CCC[C@H](CC2CCCC2)[C@H]1Oc1ccccc1] | Example 8, Step 1 | White Solid |

TABLE 1-continued

Compound Structure and Appearance

| Compound Number | Structure | Prepared According To Example | Appearance |
|---|---|---|---|
| F289 | 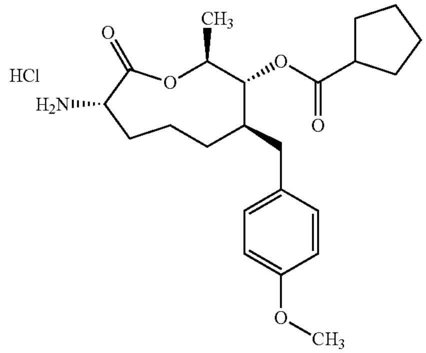 [SMILES: Cl ; COc1ccc(C[C@H]2CCC[C@H](N)C(=O)O[C@@H](C)[C@@H]2OC(=O)C2CCCC2)cc1] | Example 8, Step 1 | White Solid |
| F290 | 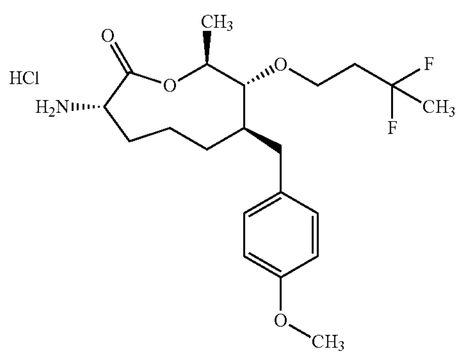 [SMILES: Cl ; COc1ccc(C[C@H]2CCC[C@H](N)C(=O)O[C@@H](C)[C@@H]2OCCC(C)(F)F)cc1] | Example 8, Step 1 | White Solid |
| F291 | 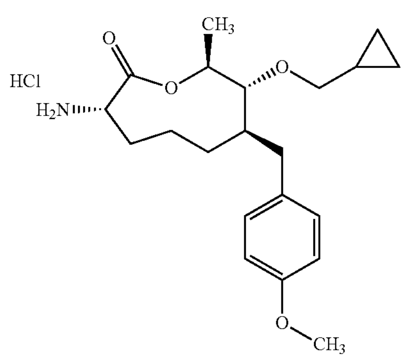 [SMILES: Cl ; COc1ccc(C[C@H]2CCC[C@H](N)C(=O)O[C@@H](C)[C@@H]2OCC2CC2)cc1] | Example 8, Step 1 | White Solid |
| F292 | 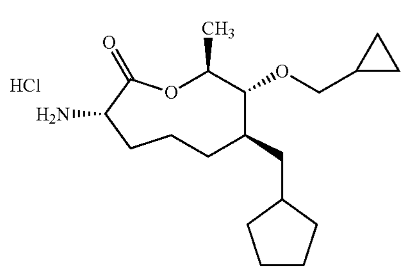 [SMILES: Cl ; C[C@@H]1OC(=O)[C@@H](N)CCC[C@H](CC2CCCC2)[C@H]1OCC1CC1] | Example 8, Step 1 | White Solid |

TABLE 1-continued

Compound Structure and Appearance

| Compound Number | Structure | Prepared According To Example | Appearance |
|---|---|---|---|
| F293 | 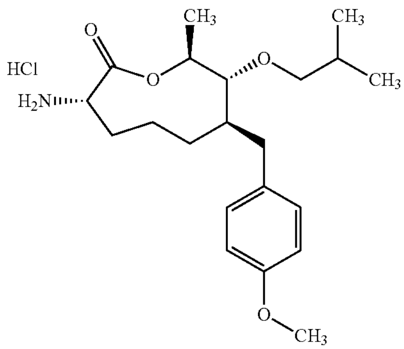 [SMILES: Cl ; COc1ccc(C[C@H]2CCC[C@H](N)C(=O)O[C@@H](C)[C@@H]2OCC(C)C)cc1] | Example 8, Step 1 | Colorless Semi-Solid |
| F294 | 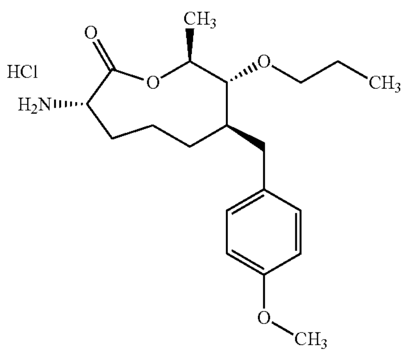 [SMILES: Cl ; CCCO[C@@H]1[C@@H](Cc2ccc(OC)cc2)CCC[C@H](N)C(=O)O[C@H]1C] | Example 8, Step 1 | Colorless Semi-Solid |
| F295 | 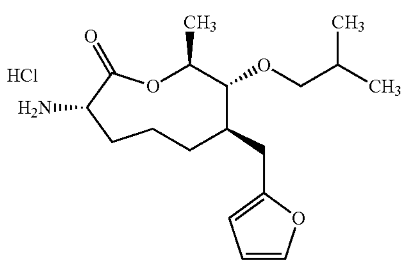 [SMILES: Cl ; CC(C)CO[C@@H]1[C@@H](Cc2ccco2)CCC[C@H](N)C(=O)O[C@H]1C] | Example 8, Step 1 | White Solid |
| F296 | 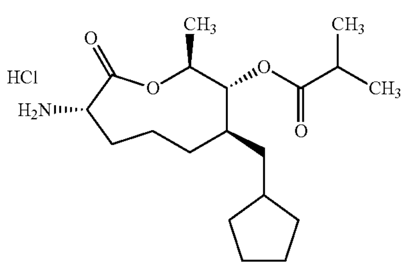 [SMILES: Cl ; CC(C)C(=O)O[C@@H]1[C@@H](CC2CCCC2)CCC[C@H](N)C(=O)O[C@H]1C] | Example 8, Step 1 | Orange Solid |
| F297 | 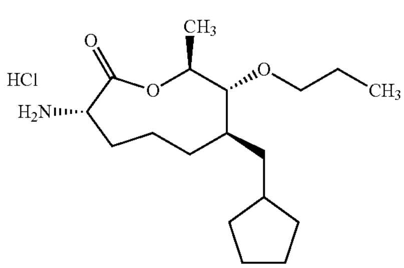 [SMILES: Cl ; CCCO[C@@H]1[C@@H](CC2CCCC2)CCC[C@H](N)C(=O)O[C@H]1C] | Example 8, Step 1 | White Solid |

TABLE 1-continued

Compound Structure and Appearance

| Compound Number | Structure | Prepared According To Example | Appearance |
|---|---|---|---|
| F298 | 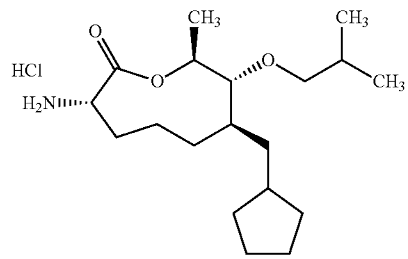 [SMILES: Cl ; CC(C)CO[C@@H]1[C@@H](CC2CCCC2)CCC[C@H](N)C(=O)O[C@H]1C] | Example 8, Step 1 | White Solid |
| F299 | 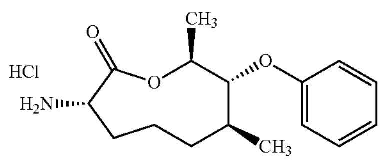 | Example 8, Step 1 | White Solid |
| F300 | 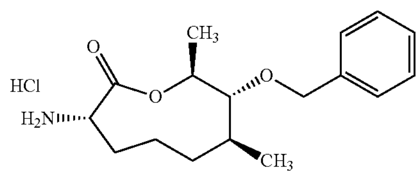 [SMILES: Cl ; C[C@@H]1OC(=O)[C@@H](N)CCC[C@H](C)[C@H]1OCc1ccccc1] | Example 8, Step 1 | White Solid |
| F301 | 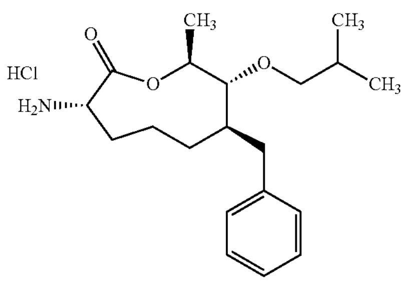 [SMILES: Cl ; CC(C)CO[C@@H]1[C@@H](Cc2ccccc2)CCC[C@H](N)C(=O)O[C@H]1C] | Example 8, Step 1 | White Solid |
| F302 | 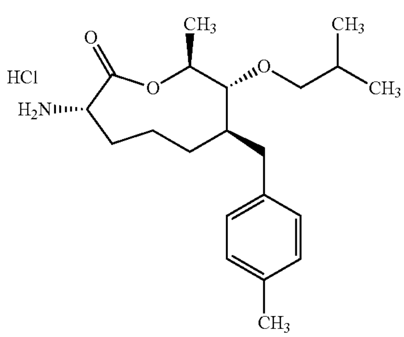 [SMILES: Cl ; Cc1ccc(C[C@H]2CCC[C@H](N)C(=O)O[C@@H](C)[C@@H]2OCC(C)C)cc1] | Example 8 | White Solid |
| F303 | 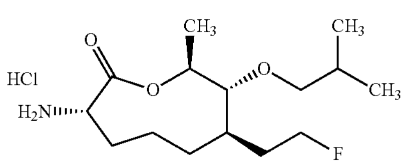 [SMILES: Cl ; CC(C)CO[C@@H]1[C@@H](CCF)CCC[C@H](N)C(=O)O[C@H]1C] | Example 8, Step 1 | White Solid |

| Compound Number | Structure | Prepared According To Example | Appearance |
|---|---|---|---|
| F304 | 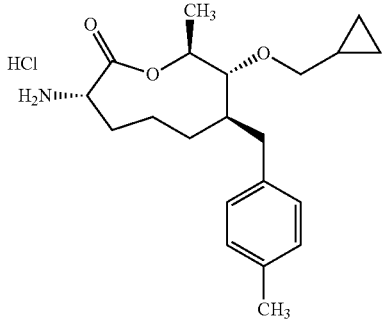 [SMILES: Cl ; Cc1ccc(C[C@H]2CCC[C@H](N)C(=O)O[C@@H](C)[C@@H]2OCC2CC2)cc1] | Example 8, Step 1 | White Solid |
| F305 | 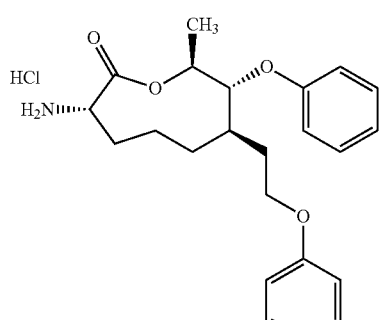 | Example 8, Step 1 | White Solid |
| F306 | 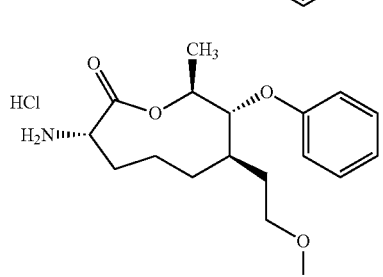 | Example 8, Step 1 | — |
| F307 | 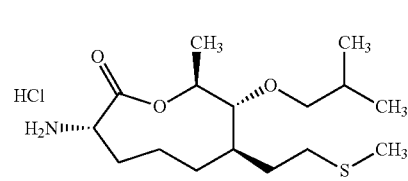 [SMILES: Cl ; CSCC[C@H]1CCC[C@H](N)C(=O)O[C@@H](C)[C@@H]1OCC(C)C] | Example 8, Step 1 | Yellow Solid |
| F308 | 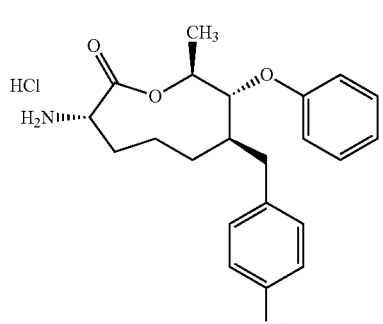 | Example 8 | Beige Solid |

TABLE 1-continued
| Compound Number | Structure | Prepared According To Example | Appearance |
|---|---|---|---|
| F309 | 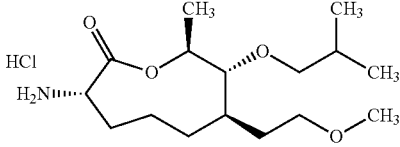 | Example 8, Step 1 | White Solid |
| F310 | 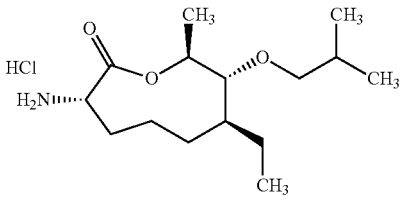 [SMILES: Cl ; CC[C@H]1CCC[C@H](N)C(=O)O[C@@H](C)[C@@H]1OCC(C)C] | Example 8, Step 1 | White Solid |
| F311 | 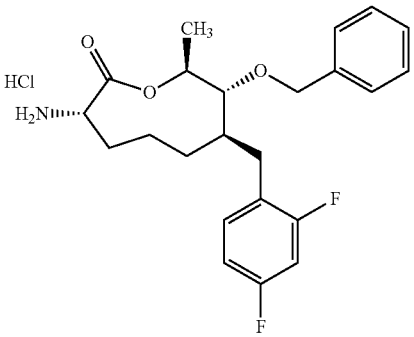 [SMILES: Cl ; C[C@@H]1OC(=O)[C@@H](N)CCC[C@H](Cc2ccc(F)cc2F)[C@H]1OCc1ccccc1] | Example 8 | White Solid |
| F312 | 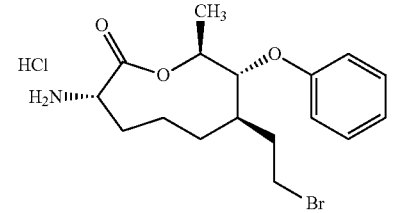 [SMILES: Cl ; C[C@@H]1OC(=O)[C@@H](N)CCC[C@H](CCBr)[C@H]1Oc1ccccc1] | Example 8, Step 1 | White Solid |
| F313 | 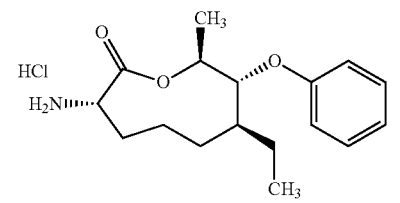 | Example 8, Step 1 | — |
| F314 | 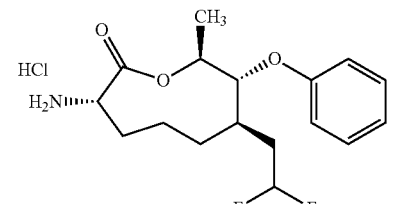 | Example 8, Step 1 | White Solid |

TABLE 1-continued
Compound Structure and Appearance
| Compound Number | Structure | Prepared According To Example | Appearance |
|---|---|---|---|
| F315 | 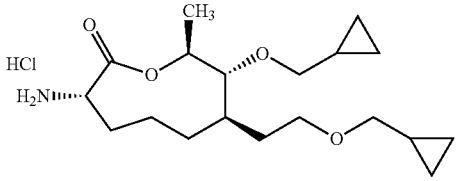 [SMILES: Cl ; C[C@@H]1OC(=O)[C@@H](N)CCC[C@H](CCOCC2CC2)[C@H]1OCC1CC1] | Example 8, Step 1 | — |
| F316 | 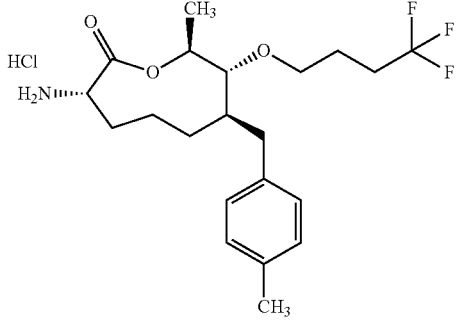 [SMILES: Cl ; Cc1ccc(C[C@H]2CCC[C@H](N)C(=O)O[C@@H](C)[C@@H]2OCCCC(F)(F)F)cc1] | Example 8 | Tacky White Solid |
| F317 | 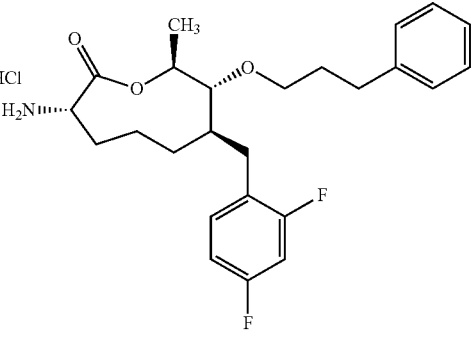 | Example 8 | White Solid |
| F318 | 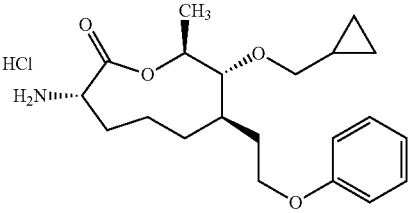 [SMILES: Cl ; C[C@@H]1OC(=O)[C@@H](N)CCC[C@H](CCOc2ccccc2)[C@H]1OCC1CC1] | Example 8, Step 1 | White Solid |
| F319 | 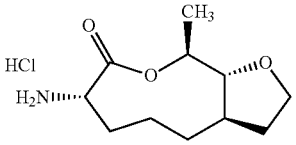 | Example 8, Step 1 | White Solid |
| F320 | 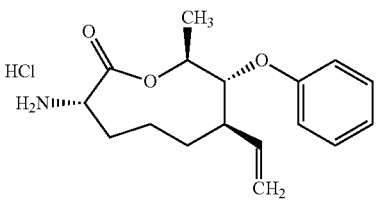 [SMILES: Cl ; C=C[C@H]1CCC[C@H](N)C(=O)O[C@@H](C)[C@@H]1Oc1ccccc1] | Example 8, Step 1 | — |

TABLE 1-continued

Compound Structure and Appearance

| Compound Number | Structure | Prepared According To Example | Appearance |
|---|---|---|---|
| F321 | [Structure: macrolactone with HCl·H₂N substituent, CH₃ groups, isobutoxy ether, and 2,4-difluorobenzyl group] | Example 8 | White Solid |
| F322 | [Structure: macrolactone with HCl·H₂N substituent, CH₃ group, 2-furoate ester, and 2,4-difluorobenzyl group] | Example 8 | White Solid |

TABLE 2

Analytical Data

| Cmpd. No. | MP (° C.) | IR (cm⁻¹) | MASS | ¹H NMR | ¹³C or ¹⁹F NMR |
|---|---|---|---|---|---|
| F1 | 57-59 | (Neat) 3366, 2949, 1743, 1649, 1529, 1482, 1209 | HRMS-ESI (m/z) ([M]⁺) calcd for $C_{27}H_{36}N_2O_6$, 484.2573; found, 484.2576 | ¹H NMR (CDCl₃) δ 12.09 (s, 1H), 8.53 (d, J = 8.2 Hz, 1H), 7.99 (d, J = 5.2 Hz, 1H), 7.33-7.24 (m, 2H), 7.00-6.91 (m, 3H), 6.87 (d, J = 5.2 Hz, 1H), 5.15-5.04 (m, 1H), 4.61 (ddd, J = 10.8, 8.1, 6.9 Hz, 1H), 4.27-4.18 (m, 1H), 3.93 (s, 3H), 2.46-2.33 (m, 1H), 1.93-1.35 (m, 7H), 1.32 (d, J = 6.5 Hz, 3H), 1.29-1.05 (m, 4H), 0.81 (d, J = 6.6 Hz, 3H), 0.80 (d, J = 6.5 Hz, 3H) | ¹³C NMR (CDCl₃) δ 172.22, 168.65, 159.68, 155.33, 148.71, 140.54, 130.38, 129.59, 121.01, 115.48, 109.49, 81.55, 75.13, 56.06, 51.56, 43.20, 36.39, 33.54, 28.26, 27.87, 27.51, 23.04, 22.05, 18.88, 18.41 |
| F2 | 131-133 | (Neat) 3368, 2954, 1742, 1650, 1530, 1450, 1265 | HRMS-ESI (m/z) ([M]⁺) calcd for $C_{25}H_{40}N_2O_6$, 464.2886; found, 464.2891 | ¹H NMR (CDCl₃) δ 12.12 (s, 1H), 8.52 (d, J = 8.2 Hz, 1H), 7.98 (d, J = 5.2 Hz, 1H), 6.86 (d, J = 5.2 Hz, 1H), 4.96-4.82 (m, 1H), 4.56 (dt, J = 10.5, 7.4 Hz, 1H), 3.93 (s, 3H), 3.46 (dd, J = 8.4, 6.3 Hz, 1H), 3.27 (dd, J = 8.4, 6.5 Hz, 1H), 3.07-2.96 (m, 1H), 2.41-2.25 (m, 1H), 1.96-1.31 (m, 7H), 1.43 (d, J = 6.4 Hz, 3H), 1.31-0.95 (m, 5H), 0.95-0.78 (m, 12H) | ¹³C NMR (CDCl₃) δ 172.25, 168.60, 155.27, 148.65, 140.48, 130.38, 109.43, 84.23, 80.42, 75.68, 56.02, 51.51, 43.50, 36.53, 33.54, 29.17, 28.08, 28.01, 27.52, 22.96, 22.26, 19.50, 19.45, 18.80, 18.16 |
| F3 | 118-120 | (Neat) 3366, 2949, 1743, 1649, | HRMS-ESI (m/z) ([M]⁺) calcd for $C_{25}H_{38}N_2O_6$, | ¹H NMR (CDCl₃) δ 12.11 (s, 1H), 8.50 (d, J = 8.1 Hz, 1H), 7.98 (d, J = 5.2 Hz, 1H), 6.87 (d, J = 5.2 Hz, 1H), 4.96-4.84 (m, 1H), 4.55 (ddd, J = | ¹³C NMR (CDCl₃) δ 172.22, 168.61, 155.30, 148.67, 140.51, 130.40, 109.44, 84.29, 78.63, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | 1583, 1482, 1209 | 462.2730; found, 462.2742 | 10.6, 8.1, 7.0 Hz, 1H), 3.94 (s, 3H), 3.56-3.33 (m, 2H), 3.10-2.99 (m, 1H), 2.41-2.26 (m, 1H), 1.82-1.31 (m, 7H), 1.44 (d, J = 6.4 Hz, 3H), 1.31-0.93 (m, 5H), 0.90 (d, J = 6.6 Hz, 3H), 0.89 (d, J = 6.6 Hz, 3H), 0.62-0.51 (m, 2H), 0.27-0.17 (m, 2H) | 75.66, 56.05, 51.49, 43.55, 36.42, 33.59, 28.06, 27.32, 23.02, 22.21, 18.70, 18.11, 11.12, 3.08, 3.02 |
| F4 | 101-103 | (Neat) 3368, 2937, 1740, 1649, 1527, 1449, 1263 | HRMS-ESI (m/z) ([M]$^+$) calcd for C$_{24}$H$_{38}$N$_2$O$_6$, 450.2730; found, 450.2745 | $^1$H NMR (CDCl$_3$) δ 12.11 (d, J = 0.6 Hz, 1H), 8.50 (d, J = 8.2 Hz, 1H), 7.99 (d, J = 5.2 Hz, 1H), 6.86 (d, J = 5.2 Hz, 1H), 4.97-4.82 (m, 1H), 4.55 (ddd, J = 10.7, 8.2, 7.0 Hz, 1H), 3.94 (s, 3H), 3.69-3.59 (m, 1H), 3.52-3.41 (m, 1H), 3.09-2.97 (m, 1H), 2.40-2.27 (m, 1H), 1.83-1.30 (m, 9H), 1.43 (d, J = 6.4 Hz, 3H), 1.30-0.95 (m, 4H), 0.94 (t, J = 7.5 Hz, 3H), 0.89 (d, J = 6.7 Hz, 3H), 0.88 (d, J = 6.6 Hz, 3H) | $^{13}$C NMR (CDCl$_3$) δ 172.26, 168.62, 155.32, 148.70, 140.51, 130.44, 109.44, 84.52, 75.68, 75.44, 56.06, 51.52, 43.49, 36.50, 33.62, 28.10, 27.46, 23.54, 23.03, 22.22, 18.77, 18.12, 10.71 |
| F5 | 49-51 | (Neat) 3368, 2950, 1741, 1650, 1528, 1450, 1279 | HRMS-ESI (m/z) ([M]$^+$) calcd for C$_{25}$H$_{37}$F$_3$N$_2$O$_6$, 518.2604; found, 518.2602 | $^1$H NMR (CDCl$_3$) δ 12.10 (s, 1H), 8.51 (d, J = 8.2 Hz, 1H), 7.98 (d, J = 5.2 Hz, 1H), 6.87 (d, J = 5.2 Hz, 1H), 4.95-4.82 (m, 1H), 4.56 (ddd, J = 10.6, 8.2, 7.0 Hz, 1H), 3.94 (s, 3H), 3.81-3.68 (m, 1H), 3.62-3.48 (m, 1H), 3.11-2.97 (m, 1H), 2.40-2.28 (m, 1H), 2.28-2.12 (m, 2H), 1.95-1.32 (m, 9H), 1.41 (d, J = 6.5 Hz, 3H), 1.31-0.94 (m, 4H), 0.95-0.82 (m, 6H) | $^{13}$C NMR (CDCl$_3$) δ 172.20, 168.63, 155.30, 148.67, 140.52, 130.35, 127.16 (q, J = 276.0 Hz), 109.46, 84.75, 75.28, 71.54, 56.02, 51.49, 43.43, 36.44, 33.49, 30.77 (q, J = 29.0 Hz), 28.15, 28.05, 27.40, 23.04 (q, J = 3.0 Hz), 22.93, 22.14, 18.75, 18.11 $^{19}$F NMR (CDCl$_3$) δ −66.41 |
| F6 | — | — | ESIMS m/z 477.4 ([M + H]$^+$) | $^1$H NMR (CDCl$_3$) δ 12.11 (d, J = 0.6 Hz, 1H), 8.52 (d, J = 8.2 Hz, 1H), 7.99 (d, J = 5.2 Hz, 1H), 6.86 (d, J = 5.2 Hz, 1H), 4.94-4.80 (m, 1H), 4.55 (ddd, J = 10.9, 8.1, 6.6 Hz, 1H), 4.08-3.98 (m, 1H), 3.94 (s, 3H), 3.81-3.58 (m, 1H), 3.14 (dd, J = 9.1, 7.8 Hz, 1H), 2.41-2.27 (m, 1H), 1.87-0.99 (m, 18H), 1.44 (d, J = 6.5 Hz, 3H), 0.89 (d, J = 6.6 Hz, 3H), 0.88 (d, J = 6.6 Hz, 3H) | $^{13}$C NMR (CDCl$_3$) δ 172.42, 168.60, 155.33, 148.70, 140.52, 130.47, 109.44, 83.57, 82.83, 76.11, 56.07, 51.77, 42.85, 36.86, 33.51, 32.75, 32.50, 28.27, 23.04, 22.97, 22.96, 22.37, 19.15, 18.37 |
| F7 | — | (Neat) 3369, 2942, 1742, 1650, 1530, 1482, 1265 | HRMS-ESI (m/z) ([M]$^+$) calcd for C$_{22}$H$_{34}$N$_2$O$_6$, 422.2417; found, 422.2427 | $^1$H NMR (CDCl$_3$) δ 12.11 (d, J = 0.6 Hz, 1H), 8.49 (d, J = 8.2 Hz, 1H), 7.99 (d, J = 5.2 Hz, 1H), 6.87 (d, J = 5.2 Hz, 1H), 4.95-4.80 (m, 1H), 4.56 (ddd, J = 10.7, 8.2, 7.1 Hz, 1H), 3.94 (s, 3H), 3.51 (s, 3H), 3.03-2.88 (m, 1H), 2.41-2.26 (m, 1H), 1.85-1.31 (m, 7H), 1.44 (d, J = 6.4 Hz, 3H), 1.31-0.93 (m, 4H), 0.90 (d, J = 6.6 Hz, 3H), 0.89 (d, J = 6.6 Hz, 3H) | $^{13}$C NMR (CDCl$_3$) δ 172.20, 168.62, 155.33, 148.70, 140.51, 130.43, 109.45, 86.37, 75.42, 61.23, 56.07, 51.49, 43.53, 36.48, 33.62, 28.24, 28.17, 27.21, 23.09, 22.17, 18.71, 18.07 |
| F8 | — | (Neat) 3369, 2952, 1734, 1651, 1529, 1482, 1265, 1176 | HRMS-ESI (m/z) ([M]$^+$) calcd for C$_{27}$H$_{40}$N$_2$O$_7$, 504.2836; found, 504.2861 | $^1$H NMR (CDCl$_3$) δ 12.08 (d, J = 0.6 Hz, 1H), 8.47 (d, J = 8.1 Hz, 1H), 7.99 (d, J = 5.2 Hz, 1H), 6.87 (d, J = 5.2 Hz, 1H), 5.08-4.96 (m, 1H), 4.94-4.83 (m, 1H), 4.59 (ddd, J = 10.8, 8.1, 7.1 Hz, 1H), 3.94 (s, 3H), 2.81-2.67 (m, 1H), 2.44-2.31 (m, 1H), 2.01-1.33 (m, 14H), 1.33-1.14 (m, 3H), 1.27 (d, J = 6.3 Hz, 3H), 1.14- | $^{13}$C NMR (CDCl$_3$) δ 176.20, 172.28, 168.63, 155.36, 148.75, 140.50, 130.41, 109.47, 76.04, 73.69, 56.08, 51.49, 44.10, 41.92, 36.35, 33.46, 30.08, 30.00, 28.00, 27.90, 27.40, 25.71, 25.70, 22.90, 22.20, 18.68, 17.56 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 0.96 (m, 2H), 0.86 (d, J = 6.6 Hz, 3H), 0.85 (d, J = 6.6 Hz, 3H) | |
| F9 | — | — | ESIMS m/z 489.3 ([M + H]$^+$) | $^1$H NMR (CDCl$_3$) δ 12.11 (d, J = 0.6 Hz, 1H), 8.49 (d, J = 8.2 Hz, 1H), 7.99 (d, J = 5.2 Hz, 1H), 6.87 (d, J = 5.2 Hz, 1H), 4.97-4.84 (m, 1H), 4.55 (ddd, J = 10.7, 8.2, 7.0 Hz, 1H), 3.94 (s, 3H), 3.49 (dd, J = 9.6, 7.0 Hz, 1H), 3.37 (dd, J = 9.6, 6.8 Hz, 1H), 3.07-2.95 (m, 1H), 2.40-2.28 (m, 1H), 1.80-1.44 (m, 11H), 1.43 (d, J = 6.4 Hz, 3H), 1.42-0.68 (m, 9H), 0.61-0.50 (m, 2H), 0.28-0.17 (m, 2H) | $^{13}$C NMR (CDCl$_3$) δ 172.21, 168.62, 155.31, 148.69, 140.51, 130.42, 109.44, 84.33, 78.51, 75.66, 56.05, 51.49, 40.09, 38.30, 35.05, 34.59, 33.63, 32.34, 27.44, 26.68, 26.48, 26.15, 18.77, 18.10, 11.14, 3.16, 2.94 |
| F10 | 69-71 | (Neat) 3367, 2939, 1740, 1648, 1528, 1447, 1214, 1056 | HRMS-ESI (m/z) ([M]$^+$) calcd for C$_{27}$H$_{33}$FN$_2$O$_6$, 500.2323; found, 500.2329 | $^1$H NMR (CDCl$_3$) δ 12.08 (d, J = 0.6 Hz, 1H), 8.45 (d, J = 8.2 Hz, 1H), 7.98 (d, J = 5.2 Hz, 1H), 7.17-7.08 (m, 2H), 7.02-6.93 (m, 2H), 6.86 (d, J = 5.2 Hz, 1H), 5.00-4.86 (m, 1H), 4.56 (ddd, J = 10.9, 8.2, 7.0 Hz, 1H), 3.93 (s, 3H), 3.58 (dd, J = 9.7, 7.0 Hz, 1H), 3.45 (dd, J = 9.7, 6.8 Hz, 1H), 3.21-3.14 (m, 1H), 3.14-3.07 (m, 1H), 2.38-2.23 (m, 2H), 1.91-1.77 (m, 1H), 1.64-1.51 (m, 2H), 1.48-1.37 (m, 1H), 1.47 (d, J = 6.4 Hz, 3H), 1.32-1.20 (m, 1H), 1.18-1.06 (m, 1H), 0.96-0.82 (m, 1H), 0.65-0.53 (m, 2H), 0.31-0.19 (m, 2H) | $^{13}$C NMR (CDCl$_3$) δ 172.09, 168.64, 161.31 (d, J = 243.7 Hz), 155.33, 148.70, 140.53, 136.24 (d, J = 3.2 Hz), 130.37, 130.14 (d, J = 7.7 Hz), 115.16 (d, J = 21.1 Hz), 109.47, 83.69, 78.79, 75.46, 56.06, 51.41, 46.09, 36.06, 33.55, 26.61, 18.73, 18.10, 11.17, 3.16, 3.02 $^{19}$F NMR (CDCl$_3$) δ −117.38 |
| F11 | 88-90 | (Neat) 3370, 2939, 1745, 1650, 1509, 1327, 1210 | HRMS-ESI (m/z) ([M]$^+$) calcd for C$_{29}$H$_{31}$FN$_2$O$_6$, 522.2166; found, 522.2182 | $^1$H NMR (CDCl$_3$) δ 12.07 (d, J = 0.6 Hz, 1H), 8.48 (d, J = 8.2 Hz, 1H), 7.98 (d, J = 5.2 Hz 1H), 7.37-7.27 (m, 2H), 7.12-6.90 (m, 7H), 6.86 (d, J = 5.2 Hz, 1H), 5.21-5.07 (m, 1H), 4.62 (ddd, J = 11.0, 8.2, 6.9 Hz, 1H), 3.93 (s, 3H), 2.98 (dd, J = 13.5, 3.4 Hz, 1H), 2.44-2.27 (m, 2H), 2.14-1.99 (m, 1H), 1.76-1.48 (m, 3H), 1.38-1.21 (m, 2H), 1.36 (d, J = 6.5 Hz, 3H), 1.11-0.97 (m, 1H) | $^{13}$C NMR (CDCl$_3$) δ 172.11, 168.68, 161.33 (d, J = 243.7 Hz), 159.53, 155.36, 148.74, 140.56, 135.77, (d, J = 3.2 Hz), 130.34 130.11 (d, J = 7.8 Hz), 129.75, 121.32, 115.47, 115.16 (d, J = 21.1 Hz), 109.52, 80.93, 74.89, 56.08, 51.50, 45.70, 36.12, 33.50, 26.77, 18.89, 18.38 $^{19}$F NMR (CDCl$_3$) δ −117.22 |
| F12 | 65-67 | (Neat) 3366, 2938, 1742, 1649, 1529, 1218 | HRMS-ESI (m/z) ([M]$^+$) calcd for C$_{26}$H$_{31}$FN$_2$O$_6$, 486.2166; found, 486.2172 | $^1$H NMR (CDCl$_3$) δ 12.09 (s, 1H), 8.46 (d, J = 8.2 Hz, 1H), 7.97 (d, J = 5.2 Hz, 1H), 7.17-7.06 (m, 2H), 7.02-6.92 (m, 2H), 6.86 (d, J = 5.2 Hz, 1H), 6.03-5.87 (m, 1H), 5.34 (dq, J = 17.2, 1.6 Hz, 1H), 5.21 (dq, J = 10.4, 1.3 Hz, 1H), 5.00-4.88 (m, 1H), 4.57 (ddd, J = 10.9, 8.2, 7.0 Hz, 1H), 4.29 (ddt, J = 12.2, 5.5, 1.5 Hz, 1H), 4.11 (ddt, J = 12.3, 5.6, 1.4 Hz, 1H), 3.93 (s, 3H), 3.30-3.18 (m, 1H), 3.13-3.01 (m, 1H), 2.41-2.23 (m, 2H), 1.91-1.75 (m, 1H), 1.68-1.53 (m, 2H), 1.50-1.37(m, 1H), 1.48 (d, J = 6.4 Hz, 3H), 1.37-1.17 (m, 1H), 0.98-0.81 (m, 1H) | $^{13}$C NMR (CDCl$_3$) δ 172.10, 168.65, 161.29 (d, J = 243.7 Hz), 155.32, 148.70, 140.54, 136.20 (d, J = 3.2 Hz), 134.28, 130.34, 130.13 (d, J = 7.7 Hz), 117.12, 115.14 (d, J = 21.1 Hz), 109.50, 84.06, 75.29, 74.68, 56.05, 51.42, 45.92, 36.08, 33.49, 26.58, 18.75, 18.14 $^{19}$F NMR (CDCl$_3$) δ −117.33 |
| F13 | 127-129 | (Neat) 3367, 2937, | HRMS-ESI (m/z) ([M]$^+$) | $^1$H NMR (CDCl$_3$) δ 12.08 (d, J = 0.6 Hz, 1H), 8.45 (d, J = 8.2 Hz, 1H), 7.98 (d, J = 5.2 Hz | $^{13}$C NMR (CDCl$_3$) δ 172.12, 168.64, 161.30 (d, J = 243.7 Hz), |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | 1741, 1649, 1528, 1508, 1217 | calcd for C$_{26}$H$_{33}$FN$_2$O$_6$, 488.2323; found, 488.2322 | 1H), 7.17-7.05 (m, 2H), 7.02-6.92 (m, 2H), 6.86 (d, J = 5.2 Hz, 1H), 4.99-4.86 (m, 1H), 4.56 (ddd, J = 10.9, 8.2, 7.0 Hz, 1H), 3.94 (s, 3H), 3.81-3.66 (m, 1H), 3.52 (dt, J = 8.7, 6.7 Hz, 1H), 3.21-3.12 (m, 1H), 3.11-3.01 (m, 1H), 2.39-2.23 (m, 2H), 1.87-1.73 (m, 1H), 1.71-1.52 (m, 4H), 1.47 (d, J = 6.5 Hz, 3H), 1.46-1.36 (m, 1H), 1.33-1.18 (m, 1H), 0.98 (t, J = 7.4 Hz, 3H), 0.95-0.83 (m, 1H) | 155.34, 148.71, 140.53, 136.31 (d, J = 3.3 Hz), 130.39, 130.13 (d, J = 7.7 Hz), 115.15 (d, J = 21.1 Hz), 109.47, 83.89, 75.66, 75.48, 56.07, 51.43, 46.10, 36.01, 33.56, 26.61, 23.59, 18.77, 18.10, 10.74 ¹⁹F NMR (CDCl$_3$) δ −117.43 |
| F14 | 71-73 | (Neat) 3368, 2939, 1741, 1650, 1529, 1508, 1219 | HRMS-ESI (m/z) ([M]⁺) calcd for C$_{27}$H$_{35}$FN$_2$O$_6$, 502.2479; found, 502.2485 | ¹H NMR (CDCl$_3$) δ 12.08 (s, 1H), 8.45 (d, J = 8.2 Hz, 1H), 7.98 (d, J = 5.2 Hz, 1H), 7.17-7.04 (m, 2H), 7.02-6.91 (m, 2H), 6.86 (d, J = 5.2 Hz, 1H), 5.00-4.84 (m, 1H), 4.56 (ddd, J = 11.0, 8.2, 7.0 Hz, 1H), 3.94 (s, 3H), 3.56 (dd, J = 8.4, 6.3 Hz, 1H), 3.34 (dd, J = 8.4, 6.5 Hz, 1H), 3.18-3.11 (m, 1H), 3.11-3.01 (m, 1H), 2.40-2.24 (m, 2H), 1.97-1.73 (m, 2H), 1.68-1.52 (m, 2H), 1.49-1.36 (m, 1H), 1.47 (d, J = 6.5 Hz, 3H), 1.33-1.19 (m, 1H), 0.97 (d, J = 6.7 Hz, 3H), 0.96 (d, J = 6.7 Hz, 3H), 0.93-0.83 (m, 1H) | ¹³C NMR (CDCl$_3$) δ 172.12, 168.63, 161.30 (d, J = 243.6 Hz), 155.34, 148.71, 140.52, 136.35 (d, J = 3.2 Hz), 130.39, 130.12 (d, J = 7.6 Hz), 115.15 (d, J = 21.1 Hz), 109.47, 83.62, 80.71, 75.51, 56.07, 51.44, 46.22, 35.92, 33.57, 29.27, 26.58, 19.52, 19.49, 18.80, 18.17 ¹⁹F NMR (CDCl$_3$) δ −117.44 |
| F15 | 164-166 | (Neat) 3369, 2941, 1743, 1649, 1529, 1509, 1217 | HRMS-ESI (m/z) ([M]⁺) calcd for C$_{25}$H$_{29}$F$_3$N$_2$O$_6$, 510.1978; found, 510.1977 | ¹H NMR (CDCl$_3$) δ 12.12 (s, 1H), 8.47 (d, J = 8.2 Hz, 1H), 7.96 (d, J = 5.2 Hz, 1H), 7.19-7.05 (m, 2H), 7.03-6.91 (m, 2H), 6.86 (d, J = 5.2 Hz, 1H), 5.88 (tt, J = 55.1, 3.9 Hz, 1H), 4.93 (dq, J = 9.4, 6.2 Hz, 1H), 4.65-4.53 (m, 1H), 4.07-3.91 (m, 1H), 3.91 (s, 3H), 3.86-3.71 (m, 1H), 3.31-3.19 (m, 1H), 3.09-2.98 (m, 1H), 2.42-2.22 (m, 2H), 1.90-1.76 (m, 1H), 1.71-1.48 (m, 2H), 1.47 (d, J = 6.5 Hz, 3H), 1.47-1.36 (m, 1H), 1.35-1.20 (m, 1H), 0.95-0.80 (m, 1H) | ¹³C NMR (CDCl$_3$) δ 171.96, 168.62, 161.25 (d, J = 243.8 Hz), 155.26, 148.63, 140.53, 135.81 (d, J = 3.2 Hz), 130.19, 130.09 (d, J = 7.7 Hz), 115.10 (d, J = 21.0 Hz), 113.87 (t, J = 241.0 Hz), 109.51, 85.27, 74.63, 72.49 (t, J = 27.5 Hz), 55.95, 51.29, 45.75, 35.77, 33.32, 26.38, 18.65, 18.00 ¹⁹F NMR (CDCl$_3$) δ −117.13, −125.48 (d, J = 9.4 Hz, 2F) |
| F16 | 70-72 | (Neat) 3368, 2946, 1732, 1649, 1529, 1509, 1448, 1263 | HRMS-ESI (m/z) ([M]⁺) calcd for C$_{29}$H$_{35}$FN$_2$O$_7$, 542.2428; found, 542.2417 | ¹H NMR (CDCl$_3$) δ 12.05 (s, 1H), 8.43 (d, J = 8.1 Hz, 1H), 7.98 (d, J = 5.2 Hz, 1H), 7.11-7.02 (m, 2H), 7.01-6.92 (m, 2H), 6.86 (d, J = 5.2 Hz 1H), 5.13-4.92 (m, 2H), 4.60 (ddd, J = 11.0, 8.1, 7.0 Hz, 1H), 3.94 (s, 3H), 2.82-2.57 (m, 2H), 2.44-2.25 (m, 2H), 2.04-1.43 (m, 11H), 1.38-1.18 (m, 2H), 1.30 (d, J = 5.8 Hz, 3H), 1.05-0.93 (m, 1H) | ¹³C NMR (CDCl$_3$) δ 176.13, 172.14, 168.65, 161.39 (d, J = 244.1 Hz) 155.36, 148.75, 140.52, 135.50 7.98 (d, J = 5.2 Hz, 1H), 7.11 (d, J = 3.2 Hz), 130.34, 130.06 (d, J = 7.8 Hz), 115.26 (d, J = 21.1 Hz), 109.49, 75.44, 73.45, 56.08, 51.40, 44.11, 44.01, 35.92, 33.37, 30.07, 30.05, 26.79, 25.73, 25.71, 18.66, 17.55 ¹⁹F NMR (CDCl$_3$) δ −117.01 |
| F17 | 177-179 | (Neat) 3370, 2939, 1735, 1650, 1529, 1509, 1264 | HRMS-ESI (m/z) ([M]⁺) calcd for C$_{27}$H$_{33}$FN$_2$O$_7$, 516.2272; found, 516.2257 | ¹H NMR (CDCl$_3$) δ 12.05 (s, 1H), 8.44 (d, J = 8.1 Hz, 1H), 7.98 (d, J = 5.2 Hz, 1H), 7.12-7.02 (m, 2H), 7.02-6.91 (m, 2H), 6.86 (d, J = 5.2 Hz, 1H), 5.13-4.96 (m, 2H), 4.61 (ddd, J = 11.0, 8.1, 7.0 Hz, 1H), 3.94 (s, 3H), 2.70-2.62 (m, 1H), | ¹³C NMR (CDCl$_3$) δ 176.46, 172.13, 168.65, 161.39 (d, J = 244.2 Hz), 155.36, 148.74, 140.52, 135.46 (d, J = 3.2 Hz), 130.33, 130.05 (d, J = 7.8 Hz), 115.27 (d, J = |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 2.59 (hept, J = 7.0 Hz, 1H), 2.43-2.28 (m, 2H), 2.01-1.86 (m, 1H), 1.77-1.46 (m, 3H), 1.35-1.20 (m, 1H), 1.30 (d, J = 5.9 Hz, 3H), 1.22 (d, J = 7.0 Hz, 3H), 1.22 (d, J = 7.0 Hz, 3H), 1.06-0.93 (m, 1H) | 21.1 Hz), 109.50, 75.38, 73.38, 56.07, 51.39, 44.09, 35.84, 34.22, 33.36, 26.71, 19.09, 19.00, 18.65, 17.51 ¹⁹F NMR (CDCl₃) δ -116.98 |
| F18 | — | — | ESIMS m/z 485.4 ([M + H]⁺) | ¹H NMR (CDCl₃) δ 12.11 (s, 1H), 8.46 (d, J = 8.2 Hz, 1H), 7.96 (d, J = 5.2 Hz, 1H), 7.28 (dd, J = 10.2, 4.4 Hz, 2H), 7.23-7.12 (m, 3H), 6.85 (d, J = 5.2 Hz, 1H), 4.99-4.86 (m, 1H), 4.55 (tt, J = 25.8, 12.9 Hz, 1H), 3.92 (s, 3H), 3.56 (dd, J = 8.3, 6.3 Hz, 1H), 3.34 (dd, J = 8.3, 6.6 Hz, 1H), 3.19-3.08 (m, 2H), 2.42-2.22 (m, 2H), 1.97-1.78 (m, 2H), 1.69-1.52 (m, 2H), 1.51-1.41 (m, 5H), 0.96 (dt, J = 13.2, 6.6 Hz, 6H), 0.82-09.82 (m, 1H) | ¹³C NMR (CDCl₃) δ 172.16, 168.65, 155.33, 148.71, 140.78, 140.54, 130.39, 128.86, 128.38, 125.93, 109.48, 83.66, 80.66, 75.54, 56.06, 51.45, 46.14, 36.73, 33.58, 29.27, 26.55, 19.55, 19.50, 18.79, 18.19 |
| F19 | — | — | ESIMS m/z 483.5 ([M + H]⁺) | ¹H NMR (CDCl₃) δ 12.12 (s, 1H), 8.47 (d, J = 8.2 Hz, 1H), 7.94 (d, J = 5.2 Hz, 1H), 7.35-7.23 (m, 2H), 7.18 (td, J = 6.4, 1.5 Hz, 3H), 6.84 (d, J = 5.3 Hz, 1H), 4.94 (dq, J = 9.1, 6.4 Hz, 1H), 4.57 (ddd, J = 10.9, 8.2, 7.0 Hz, 1H), 3.90 (s, 3H), 3.58 (dd, J = 9.7, 7.0 Hz, 1H), 3.44 (dd, J = 9.7, 6.8 Hz, 1H), 3.31 - 3.03 (m, 2H), 2.41-2.19 (m, 2H), 1.88 (tt, J = 8.3, 4.0 Hz, 1H), 1.58 (ddt, J = 12.9, 6.9, 2.6 Hz, 2H), 1.47 (d, J = 6.4 Hz, 3H), 1.53-1.38 (m, overlapping, 1H), 1.30-1.20 (m, 1H), 1.17-1.02 (m, 1H), 0.99-0.78 (m, 1H), 0.69-0.48 (m, 2H), 0.25 (qd, J = 4.2, 1.7 Hz, 2H) | ¹³C NMR (75 MHz, CDCl₃) δ 172.01, 168.54, 155.18, 148.58, 140.54, 140.42, 130.22, 128.75, 128.26, 125.83, 109.42, 83.61, 78.59, 75.37, 55.93, 51.34, 45.94, 36.79, 33.42, 26.52, 18.65, 18.02, 11.11, 3.08, 2.94 |
| F20 | — | — | ESIMS m/z 505.4 ([M + H]⁺) | ¹H NMR (CDCl₃) δ 12.08 (d, J = 0.6 Hz, 1H), 8.47 (d, J = 8.1 Hz, 1H), 7.98 (d, J = 5.2 Hz, 1H), 7.40-7.21 (m, 3H), 7.21-7.08 (m, 3H), 7.08-6.93 (m, 3H), 6.89-6.82 (m, 1H), 5.20-5.07 (m, 1H), 4.62 (ddd, J = 11.0, 8.2, 7.0 Hz, 1H), 4.36 (t, J = 8.9 Hz, 1H), 3.93 (s, 3H), 3.78-3.62 (m, 1H), 3.03 (dd, J = 13.3, 3.3 Hz, 1H), 2.35 (ddd, J = 11.3, 9.4, 6.5 Hz, 2H), 2.20-2.07 (m, 1H), 1.78-1.64 (m, 2H), 1.64-1.50 (m, 1H), 1.36 (d, J = 6.5 Hz, 3H), 1.34-1.27 (m, 1H), 1.08-0.97 (m, 1H) | ¹³C NMR (CDCl₃) δ 172.24, 168.77, 159.73, 155.46, 148.84, 140.65, 140.27, 130.46, 129.83, 128.91, 128.47, 126.13, 121.38, 115.65, 109.61, 81.17, 75.05, 56.18, 51.61, 45.75, 37.00, 33.64, 26.80, 18.98, 18.51 |
| F21 | — | — | ESIMS m/z 471.4 ([M + H]⁺) | ¹H NMR (CDCl₃) δ 12.10 (s, 1H), 8.45 (d, J = 8.2 Hz, 1H), 7.97 (d, J = 5.2 Hz, 1H), 7.33-7.24 (m, 2H), 7.23-7.13 (m, 3H), 6.85 (d, J = 5.2 Hz, 1H), 4.93 (dq, J = 9.2, 6.4 Hz, 1H), 4.56 (ddd, J = 11.0, 8.2, 7.0 Hz, 1H), 3.93 (s, 3H), 3.79-3.67 (m, 1H), 3.53 (dt, J = 8.7, 6.7 Hz, 1H), 3.18 (t, J = 9.0 Hz, 1H), 3.15-3.06 (m, 1H), 2.41-2.23 (m, 2H), 1.86 (ddd, J = 12.1, 8.4, 3.9 Hz, 1H), 1.72-1.55 (m, 4H), 1.48 (d, J = 6.4 Hz, 3H), 1.45-.38 (m, 1H), | ¹³C NMR (CDCl₃) δ 172.26, 168.73, 155.43, 148.81, 140.83, 140.63, 130.50, 128.96, 128.47, 126.03, 109.57, 84.05, 75.72, 75.62, 56.17, 51.55, 46.11, 36.93, 33.70, 26.69, 23.70, 18.87, 18.23, 10.86 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| F22 | — | — | ESIMS m/z 497.4 ([M + H]⁺) | 1.33-1.19 (m, 1H), 0.98 (t, J = 7.4 Hz, 3H), 0.94-0.82 (m, 1H) ¹H NMR (CDCl₃) δ 12.10 (s, 1H), 8.45 (d, J = 8.2 Hz, 1H), 7.97 (d, J = 5.2 Hz, 1H), 7.38-7.23 (m, 2H), 7.22-7.13 (m, 3H), 6.85 (d, J = 5.2 Hz, 1H), 4.91 (dq, J = 9.1, 6.5 Hz, 1H), 4.54 (ddd, J = 11.1, 8.2, 6.6 Hz, 1H), 4.18-4.06 (m, 1H), 3.93 (s, 3H), 3.30 (t, J = 8.6 Hz, 1H), 3.20 (dd, J = 13.3, 3.3 Hz, 1H), 2.40-2.16 (m, 2H), 1.87-1.67 (m, 7H), 1.66-1.52 (m, 4H), 1.49 (d, J = 6.5 Hz, 3H), 1.46-1.36 (m, 1H), 1.32-1.14 (m, 1H), 1.04-0.84 (m, 1H) | ¹³C NMR (CDCl₃) δ 172.34, 168.60, 155.32, 148.70, 141.05, 140.51, 130.40, 128.87, 128.37, 125.87, 109.45, 83.87, 82.31, 75.95, 56.06, 51.68, 45.22, 36.93, 33.42, 32.84, 32.57, 27.89, 23.05, 22.99, 19.10, 18.39 |
| F23 | — | — | ESIMS m/z 457.2 ([M + H]⁺) | ¹H NMR (CDCl₃) δ 12.09 (d, J = 0.6 Hz, 1H), 8.45 (d, J = 8.2 Hz, 1H), 7.98 (d, J = 5.2 Hz, 1H), 7.33-7.24 (m, 2H), 7.23-7.15 (m, 3H), 6.85 (d, J = 5.1 Hz, 1H), 4.93 (dq, J = 9.2, 6.4 Hz, 1H), 4.56 (ddd, J = 10.9, 8.2, 7.0 Hz, 1H), 3.93 (s, 3H), 3.83 (dq, J = 8.8, 6.9 Hz, 1H), 3.64 (dq, J = 8.9, 7.0 Hz, 1H), 3.24-3.15 (m, 1H), 3.11 (dd, J = 13.3, 3.4 Hz, 1H), 2.44-2.20 (m, 2H), 1.85 1.90-1.79 (m, 1H), 1.68-1.53 (m, 2H), 1.52-1.41 (m, 1H), 1.48 (d, J = 6.5 Hz, 3H), 1.31-1.21 (m, 1H), 1.25 (t, J = 6.9 Hz, 3H), 0.95-0.83 (m, 1H) | ¹³C NMR (CDCl₃) δ 172.15, 168.63, 155.33, 148.71, 140.68, 140.52, 130.40, 128.86, 128.37, 125.94, 109.46, 84.17, 75.48, 69.26, 56.07, 51.45, 45.88, 36.92, 33.61, 26.62, 18.74, 18.05, 15.73 |
| F24 | — | — | ESIMS m/z 487.4 ([M + H]⁺) | ¹H NMR (CDCl₃) δ 12.09 (d, J = 0.6 Hz, 1H), 8.45 (d, J = 8.2 Hz, 1H), 7.97 (d, J = 5.2 Hz, 1H), 7.33-7.23 (m, 2H), 7.23-7.15 (m, 3H), 6.85 (dd, J = 5.3, 0.6 Hz, 1H), 4.96 (dq, J = 9.2, 6.4 Hz, 1H), 4.56 (ddd, J = 10.9, 8.2, 7.0 Hz, 1H), 3.98-3.94 (m, 1H), 3.93 (s, 3H), 3.73 (ddd, J = 10.4, 5.7, 3.5 Hz, 1H), 3.62-3.53 (m, 2H), 3.40 (s, 3H), 3.24 (t, J = 9.1 Hz, 1H), 3.17 (dd, J = 13.2, 3.4 Hz, 1H), 2.43-2.24 (m, 2H), 1.98-1.85 (m, 1H), 1.60 (dtt, J = 9.1, 6.6, 3.2 Hz, 2H), 1.54-1.42 (m, 4H), 1.33-1.20 (m, 1H), 0.95-0.81 (m, 1H) | ¹³C NMR (75 MHz, CDCl₃) δ 172.28, 168.83, 155.52, 148.91, 140.89, 140.72, 130.59, 129.09, 128.99, 128.55, 126.12, 109.68, 84.89, 75.53, 73.05, 72.36, 59.29, 56.27, 51.64, 45.98, 37.00, 33.80, 26.79, 18.99, 18.38 |
| F25 | — | — | ESIMS m/z 491.3 ([M + H]⁺) | ¹H NMR (CDCl₃) δ 12.11 (d, J = 0.6 Hz, 1H), 8.49 (d, J = 8.2 Hz, 1H), 7.99 (d, J = 5.2 Hz, 1H), 6.86 (d, J = 5.2 Hz, 1H), 4.89 (dq, J = 9.2, 6.4 Hz, 1H), 4.55 (ddd, J = 10.8, 8.2, 7.0 Hz, 1H), 3.94 (s, 3H), 3.46 (dd, J = 8.4, 6.1 Hz, 1H), 3.24 (dd, J = 8.4, 6.6 Hz, 1H), 2.98 (t, J = 8.8 Hz, 1H), 2.34 (dt, J = 13.2, 6.7 Hz, 1H), 1.83 (hept, J = 6.5 Hz, 1H), 1.77-1.61 (m, 8H), 1.42 (d, J = 6.4 Hz, 3H), 1.40-1.08 (m, 8H), 1.02-0.93 (m, 8H), 0.76 (qd, J = 13.6, 12.2, 4.1 Hz, 1H) | ¹³C NMR (CDCl₃) δ 172.25, 168.61, 155.33, 148.70, 140.50, 130.45, 109.44, 84.26, 80.38, 75.75, 56.06, 51.53, 40.00, 38.14, 35.09, 34.60, 33.65, 32.27, 29.21, 27.42, 26.69, 26.52, 26.20, 19.58, 19.47, 18.81, 18.17 |
| F26 | — | (Thin Film) 3366, | HRMS-ESI (m/z) ([M]+) | ¹H NMR (CDCl₃) δ 12.07 (s, 1H), 8.47 (d, J = 8.1 Hz, 1H), 7.99 (d, J = 5.1 Hz, 1H), 7.31 | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | 2938, 1743, 1649, 1530, 1512, 1243 | calcd for C$_{30}$H$_{34}$N$_2$O$_7$, 534.2366; found, 534.2373 | (dd, J = 8.7, 7.3 Hz, 2H), 7.09-6.94 (m, 5H), 6.87 (d, J = 5.3 Hz, 1H), 6.80 (d, J = 8.7 Hz, 2H), 5.14 (dq, J = 9.3, 6.4 Hz, 1H), 4.70-4.53 (m, 1H), 4.34 (t, J = 8.9 Hz, 1H), 3.94 (s, 3H), 3.78 (s, 3H), 2.96 (dd, J = 13.8, 3.2 Hz, 1H), 2.33 (ddd, J = 17.7, 12.3, 9.0 Hz, 2H), 2.05 (s, 2H), 1.69 (dt, J = 10.7, 5.0 Hz, 2H), 1.38-1.25 (m, 1H), 1.36 (d, J = 6.5 Hz, 3H), 1.14-0.88 (m, 1H) | |
| F27 | — | — | HRMS-ESI (m/z) ([M]$^+$) calcd for C$_{28}$H$_{36}$N$_2$O$_6$, 496.2573; found, 496.2600 | $^1$H NMR (CDCl$_3$) δ 12.11 (s, 1H), 8.55 (d, J = 8.2 Hz, 1H), 7.98 (d, J = 5.2 Hz, 1H), 7.35-7.23 (m, 2H), 6.95 (d, J = 7.5 Hz, 3H), 6.86 (d, J = 5.2 Hz, 1H), 5.10 (dq, J = 9.1, 6.5 Hz, 1H), 4.61 (ddd, J = 10.8, 8.1, 7.0 Hz, 1H), 4.20 (t, J = 8.7 Hz, 1H), 3.92 (s, 3H), 2.45-2.31 (m, 1H), 1.97-1.35 (m, 14H), 1.31 (d, J = 6.5 Hz, 3H), 1.22-1.06 (m, 1H), 1.10-0.89 (m, 2H) | $^{13}$C NMR (CDCl$_3$) δ 172.21, 168.64, 159.73, 155.35, 148.72, 140.53, 130.40, 129.59, 120.98, 115.55, 109.47, 81.58, 75.16, 56.08, 51.58, 42.02, 37.25, 36.82, 33.66, 33.63, 31.76, 25.04, 19.03, 18.40 |
| F28 | — | (Thin Film) 2941, 1731, 1512 | HRMS-ESI (m/z) ([M]+) calcd for C$_{30}$H$_{38}$N$_2$O$_8$, 554.2628; found, 554.2634 | $^1$H NMR (CDCl$_3$) δ 12.06 (d, J = 0.6 Hz, 1H), 8.43 (d, J = 8.1 Hz, 1H), 7.98 (d, J = 5.2 Hz, 1H), 7.07-6.99 (m, 2H), 6.89-6.77 (m, 3H), 5.12-4.97 (m, 2H), 4.60 (ddd, J = 11.0, 8.1, 7.0 Hz, 1H), 3.94 (s, 3H), 3.79 (s, 3H), 2.82-2.71 (m, 1H), 2.64 (dd, J = 13.6, 3.8 Hz, 1H), 2.38-2.27 (m, 2H), 2.02-1.56 (m, 13H), 1.30 (d, J = 5.8 Hz, 3H), 1.02-0.92 (m, 1H) | $^{13}$C NMR (CDCl$_3$) δ 176.16, 172.19, 168.64, 157.98, 155.37, 148.76, 140.50, 131.86, 130.38, 129.64, 113.87, 109.48, 75.53, 73.53, 56.08, 55.24, 51.43, 44.17, 44.04, 35.75, 33.45, 30.10, 30.03, 26.72, 25.73, 18.66, 17.57 |
| F29 | — | (Thin Film) 2938, 1741, 1649, 1528, 1448, 1264 | HRMS-ESI (m/z) ([M]$^+$) calcd for C$_{28}$H$_{36}$F$_2$N$_2$O$_7$, 550.2491; found, 550.2503 | $^1$H NMR (CDCl$_3$) δ 12.08 (d, J = 0.6 Hz, 1H), 8.45 (d, J = 8.2 Hz, 1H), 7.97 (d, J = 5.2 Hz, 1H), 7.12-7.03 (m, 4H), 6.86 (d, J = 5.1 Hz, 1H), 6.83 (d, J = 2.0 Hz, 3H), 4.92 (dq, J = 9.2, 6.4 Hz, 1H), 4.56 (ddd, J = 10.9, 8.2, 7.0 Hz, 1H), 3.93 (s, 3H), 3.79 (s, 3H), 3.18 (t, J = 9.0 Hz, 1H), 3.00 (dd, J = 13.4, 3.5 Hz, 1H), 2.39-2.11 (m, 4H), 1.87-1.74 (m, 1H), 1.67 (t, J = 18.7 Hz, 3H), 1.62-1.49 (m, 1H), 1.45 (s, 3H), 1.38-1.17 (m, 2H), 0.96-0.82 (m, 1H) | $^{19}$F NMR (CDCl$_3$) δ-89.56 |
| F30 | — | (Thin Film) 3366, 2938, 1741, 1649, 1528, 1511, 1243 | HRMS-ESI (m/z) ([M]$^+$) calcd for C$_{28}$H$_{36}$N$_2$O$_7$, 512.2523; found, 512.2536 | $^1$H NMR (CDCl$_3$) δ 12.09 (d, J = 0.9 Hz, 1H), 8.44 (d, J = 8.2 Hz, 1H), 7.98 (dd, J = 5.2, 1.1 Hz, 1H), 7.09 (d, J = 8.4 Hz, 1H), 6.92-6.74 (m, 2H), 5.03-4.85 (m, 1H), 4.56 (dt, J = 10.7, 7.6 Hz, 1H), 3.94 (s, 3H), 3.79 (s, 3H), 3.58 (dd, J = 9.7, 7.0 Hz, 1H), 3.45 (dd, J = 9.7, 6.8 Hz, 1H), 3.17 (t, J = 9.0 Hz, 1H), 3.09 (d, J = 13.6 Hz, 1H), 2.34-2.20 (m, 2H), 1.90-1.78 (m, 1H), 1.60-1.51 (m, 5H), 1.47 (d, J = 6.4 Hz, 3H), 1.35-1.18 (m, 1H), 1.18-1.07 (m, 1H), 0.93-0.82 (m, 1H), 0.70-0.40 (m, 2H), 0.34-0.22 (m, 2H) | $^{13}$C NMR (CDCl$_3$) δ 172.13, 168.62, 157.86, 155.33, 148.71, 140.51, 132.60, 129.73, 113.80, 109.45, 99.99, 83.78, 78.76, 75.52, 56.07, 55.24, 51.44, 46.11, 35.94, 33.63, 26.56, 18.73, 18.12, 11.18, 3.16, 3.02 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F31 | — | (Thin Film) 3367, 2942, 2868, 1740, 1649, 1528, 1057 | HRMS-ESI (m/z) ([M]$^+$) calcd for C$_{26}$H$_{38}$N$_2$O$_6$ 474.2730; found, 474.2743 | $^1$H NMR (CDCl$_3$) δ 12.10 (s, 1H), 8.49 (d, J = 8.2 Hz, 1H), 7.99 (d, J = 5.2 Hz, 1H), 6.86 (d, J = 5.2 Hz, 1H), 4.91 (dq, J = 9.3, 6.4 Hz, 1H), 4.55 (ddd, J = 10.7, 8.2, 6.9 Hz, 1H), 3.94 (s, 3H), 3.50 (dd J = 9.6, 7.0 Hz, 1H), 3.36 (dd, J = 9.6, 6.8 Hz, 1H), 3.01 (t, J = 8.9 Hz, 1H), 2.34 (dt, J = 13.3, 6.8 Hz, 1H), 1.92-1.45 (m, 13H), 1.43 (d, J = 6.4 Hz, 3H), 1.40-1.29 (m, 1H), 1.16-0.94 (m, 4H), 0.59-0.49 (m, 2H), 0.21 (dt, J = 6.0, 4.5 Hz, 2H) | $^{13}$C NMR (CDCl$_3$) δ 172.23, 168.62, 155.34, 148.71, 140.52, 130.46, 109.45, 84.31, 78.54, 75.64, 56.07, 51.54, 42.29, 37.27, 36.90, 33.97, 33.67, 31.85, 27.52, 25.11, 25.08, 18.93, 18.11, 11.14, 3.14, 2.95 |
| F32 | — | (Thin Film) 3368, 2939, 1742, 1650, 1529, 1511, 1244 | HRMS-ESI (m/z) ([M]$^+$) calcd for C$_{28}$H$_{38}$N$_2$O$_7$ 514.2679; found, 514.2659 | $^1$H NMR (CDCl$_3$) δ 12.10 (s, 1H), 8.45 (d, J = 8.2 Hz, 1H), 7.98 (d, J = 5.2 Hz, 1H), 7.08 (d, J = 8.6 Hz, 2H), 6.86 (d, J = 5.3 Hz, 1H), 6.83 (d, J = 8.6 Hz, 2H), 4.93 (dq, J = 9.3, 6.4 Hz, 1H), 4.56 (ddd, J = 10.9, 8.2, 7.0 Hz, 1H), 3.93 (s, 3H), 3.79 (s, 3H), 3.56 (dd, J = 8.4, 6.2 Hz, 1H), 3.34 (dd, J = 8.4, 6.5 Hz, 1H), 3.15 (t, J = 9.0 Hz, 1H), 3.05 (dd, J = 13.3, 3.2 Hz, 1H), 2.37-2.22 (m, 2H), 1.91 (dq, J = 13.2, 6.6 Hz, 1H), 1.80 (ddq, J = 12.0, 7.5, 4.3, 3.6 Hz, 1H), 1.66-1.54 (m, 3H), 1.53-1.38 (m, 1H), 1.46 (d, J = 6.4 Hz, 3H), 0.97 (dd, J = 6.7, 4.8 Hz, 6H), 0.94-0.81 (m, 1H) | $^{13}$C NMR (CDCl$_3$) δ 172.15, 168.61, 157.83, 155.32, 148.69, 140.51, 132.72, 130.39, 129.70, 113.77, 109.44, 83.66, 80.65, 75.56, 56.06, 55.23, 51.44, 46.25, 35.76, 33.62, 29.26, 26.50, 19.54, 19.49, 18.77, 18.18 |
| F33 | — | (Thin Film) 3369, 2938, 2877, 1742, 1650, 1529, 1512, 1244 | HRMS-ESI (m/z) ([M]$^+$) calcd for C$_{27}$H$_{36}$N$_2$O$_7$ 500.2523; found, 500.2522 | $^1$H NMR (CDCl$_3$) δ 12.09 (s, 1H), 8.45 (d, J = 8.2 Hz, 1H), 7.98 (d, J = 5.1 Hz, 1H), 7.08 (d, J = 8.6 Hz, 2H), 6.86 (d, J = 5.3 Hz, 1H), 6.83 (d, J = 8.6 Hz, 2H), 4.93 (dq, J = 9.2, 6.4 Hz, 1H), 4.56 (ddd, J = 11.0, 8.3, 7.0 Hz, 1H), 3.94 (s, 3H), 3.79 (s, 3H), 3.73 (dt, J = 8.6, 6.5 Hz, 1H), 3.52 (dt, J = 8.7, 6.7 Hz, 1H), 3.16 (t, J = 9.0 Hz, 1H), 3.05 (dd, J = 13.3, 3.3 Hz, 1H), 2.37-2.24 (m, 2H), 1.80 (ddt, J = 12.1, 8.3, 3.9 Hz, 1H), 1.64 (dt, J = 14.0, 7.0 Hz, 3H), 1.64-1.54 (m, 1H), 1.54-1.41 (m, 1H), 1.47 (d, J = 6.4 Hz, 3H), 1.32-1.19 (m, 1H), 0.99 (d, J = 7.3 Hz, 3H), 0.94-0.79 (m, 1H) | $^{13}$C NMR (CDCl$_3$) δ 172.15, 168.61, 157.83, 155.32, 148.70, 140.51, 132.67, 130.40, 129.71, 113.77, 109.44, 83.95, 75.62, 75.53, 56.07, 55.23, 51.45, 46.12, 35.86, 33.63, 26.53, 23.59, 18.75, 18.12, 10.75 |
| F34 | — | (Thin Film) 3367, 2941, 2874, 1741, 1649, 1528, 1056 | HRMS-ESI (m/z) ([M]$^+$) calcd for C$_{25}$H$_{34}$N$_2$O$_7$ 474.2366; found, 474.2394 | $^1$H NMR (CDCl$_3$) δ 12.09 (d, J = 0.7 Hz, 1H), 8.47 (d, J = 8.2 Hz, 1H), 7.98 (d, J = 5.2 Hz, 1H), 7.31 (dd, J = 2.0, 0.8 Hz, 1H), 6.89-6.83 (m, 1H), 6.28 (dd, J = 3.1, 1.9 Hz, 1H), 6.02 (d, J = 3.1 Hz, 1H), 4.94 (dq, J = 9.2, 6.4 Hz, 1H), 4.56 (ddd, J = 10.9, 8.2, 6.9 Hz, 1H), 3.94 (s, 3H), 3.50 (dd, J = 8.4, 6.5 Hz, 1H), 3.31 (dd, J = 8.4, 6.3 Hz, 1H), 3.15 (t, J = 9.0 Hz, 1H), 3.01 (dd, J = 14.6, 3.5 Hz, 1H), 2.52 (dd, J = 14.6, 11.2 Hz, 1H), 2.35-2.22 (m, 1H), 1.96 (ddt, J = 14.8, 6.8, | $^{13}$C NMR (CDCl$_3$) δ 172.16, 168.62, 155.32, 154.60, 148.70, 141.04, 140.52, 130.40, 110.11, 109.45, 106.08, 83.43, 80.26, 75.45, 56.06, 51.48, 43.15, 33.52, 29.35, 29.21, 27.93, 19.48, 19.46, 18.84, 18.18 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 3.5 Hz, 1H), 1.86 (dq, J = 13.2, 6.6 Hz, 1H), 1.71-1.49 (m, 3H), 1.45 (d, J = 6.4 Hz, 3H), 1.39-1.28 (m, 1H), 1.07-0.95 (m, 1H), 0.94 (d, J = 6.7 Hz, 6H) | |
| F35 | — | (Thin Film) 3388, 2957, 1730, 1649, 1525, 1146 | HRMS-ESI (m/z) ([M]⁺) calcd for $C_{26}H_{38}N_2O_7$, 490.2679; found, 490.2689 | ¹H NMR (CDCl₃) δ 12.08 (s, 1H), 8.48 (d, J = 8.1 Hz, 1H), 7.99 (d, J = 5.2 Hz, 1H), 6.87 (d, J = 5.2 Hz, 1H), 5.03 (dq, J = 9.5, 6.4 Hz, 1H), 4.86 (t, J = 9.1 Hz, 1H), 4.59 (ddd, J = 10.9, 8.1, 7.0 Hz, 1H), 3.94 (s, 3H), 2.58 (hept, J = 7.0 Hz, 1H), 2.44-2.32 (m, 1H), 1.93-0.87 (m, 26H) | ¹³C NMR (CDCl₃) δ 176.47, 172.25, 168.63, 155.35, 148.74 140.50, 130.39, 109.47, 73.59, 56.01, 51.49, 40.61, 36.99, 36.50, 34.29, 33.68, 33.47, 31.85, 27.24 25.03, 25.01 19.11, 18.95, 18.78, 17.50 |
| F36 | — | (Thin Film) 3323, 2941, 2869, 1736, 1650, 1532, 1190 | HRMS-ESI (m/z) ([M]⁺) calcd for $C_{25}H_{38}N_2O_6$, 462.2730; found, 462.2738 | ¹H NMR (CDCl₃) δ 12.11 (s, 1H), 8.51 (d, J = 8.1 Hz, 1H), 7.98 (d, J = 5.2 Hz, 1H), 6.86 (d, J = 5.2 Hz, 1H), 4.89 (dq, J = 9.3, 6.4 Hz, 1H), 4.55 (ddd, J = 10.8, 8.3, 7.0 Hz, 1H), 3.94 (s, 3H), 3.64 (dt, J = 8.6, 6.5 Hz, 1H), 3.44 (dt, J = 8.7, 6.8 Hz, 1H), 3.01 (t, J = 8.9 Hz, 1H), 2.34 (dt, J = 13.4, 6.9 Hz, 1H), 1.91-1.22 (m, 18H), 1.18-0.98 (m, 4H), 0.94 (t, J = 7.4 Hz, 3H) | ¹³C NMR (CDCl₃) δ 172.25, 168.61, 155.29, 148.67, 140.50, 130.40, 109.44, 84.49, 75.64, 75.34, 56.04, 51.53, 42.19, 37.25, 36.80, 33.93, 33.60, 31.77, 27.51, 25.09, 25.07, 23.53, 18.94, 18.10, 10.73 |
| F37 | — | (Thin Film) 3342, 2946, 2869, 1738, 1648, 1189, 1054 | HRMS-ESI (m/z) ([M]⁺) calcd for $C_{26}H_{40}N_2O_6$, 476.2886; found, 476.2890 | ¹H NMR (CDCl₃) δ 12.11 (d, J = 0.6 Hz, 1H), 8.51 (d, J = 8.2 Hz, 1H), 7.98 (d, J = 5.2 Hz, 1H), 6.86 (d, J = 5.2 Hz, 1H), 4.89 (dq, J = 9.4, 6.5 Hz, 1H), 4.55 (ddd, J = 10.8, 8.2, 7.0 Hz, 1H), 3.94 (s, 3H), 3.81-3.60 (m, 1H), 3.47 (dd, J = 8.4, 6.0 Hz, 1H), 3.25 (dd, J = 8.4, 6.7 Hz, 1H), 2.99 (t, J = 8.8 Hz, 1H), 2.34 (dt, J = 13.0, 6.6 Hz, 1H), 1.93-1.21 (m, 16H), 1.20-0.84 (m, 10H) | ¹³C NMR (CDCl₃) δ 172.25, 168.61, 155.29, 148.67, 140.50, 130.41, 109.44, 84.21, 80.40, 75.70, 56.04, 51.54, 42.21, 37.21, 36.70, 33.96, 33.60, 31.72, 29.19, 27.50, 25.08, 25.07, 19.54, 19.43, 18.96, 18.15 |
| F38 | 160-163 | — | HRMS-ESI (m/z) [M + H]⁺ calcd for $C_{23}H_{29}N_2O_6$, 429.2020; found, 429.2028 | ¹H NMR (CDCl₃) δ 12.08 (s, 1H), 8.52 (d, J = 8.1 Hz, 1H), 8.00 (d, J = 5.2 Hz, 1H), 7.34-7.23 (m, 2H), 6.96 (dq, J = 7.9, 3.7 Hz, 3H), 6.87 (d, J = 5.2 Hz, 1H), 5.12 (dq, J = 9.1, 6.4 Hz, 1H), 4.61 (dt, J = 11.0, 7.1 Hz, 1H), 4.18 (t, J = 8.8 Hz, 1H), 3.94 (s, 3H), 2.40 (dt, J = 13.3, 6.7 Hz, 1H), 1.99-1.87 (m, 1H), 1.73 (ddt, J = 19.3, 12.4, 6.2 Hz, 3H), 1.52-1.39 (m, 1H), 1.33 (d, J = 6.5 Hz, 3H), 1.28 (dt, J = 10.5, 5.2 Hz, 1H), 1.02 (d, J = 6.9 Hz, 3H) | ¹³C NMR (CDCl₃) δ 172.23, 168.64, 159.64, 155.34, 148.71, 140.54, 130.39, 129.61, 121.04, 115.48, 109.47, 82.22, 74.96, 56.08, 51.60, 37.65, 33.55, 32.29, 19.19, 18.31, 17.75 |
| F39 | 129-130 | — | HRMS-ESI (m/z) [M + H]⁺ calcd for $C_{24}H_{31}N_2O_6$, 443.2177; found, 443.2171 | ¹H NMR (CDCl₃) δ 12.10 (s, 1H), 8.50 (d, J = 8.1 Hz, 1H), 7.99 (d, J = 5.2 Hz, 1H), 7.35 (d, J = 3.8 Hz, 5H), 6.86 (d, J = 5.2 Hz, 1H), 4.97 (dq, J = 9.1, 6.4 Hz, 1H), 4.72 (d, J = 10.8 Hz, 1H), 4.64-4.54 (m, 2H), 3.94 (s, 3H), 3.24 (t, J = 8.9 Hz, 1H), 2.36 (dt, J = 13.3, 6.7 Hz, 1H), 1.84-1.55 (m, 4H), 1.49 (d, J = 6.4 Hz, 3H), 1.41 (dt, J = 13.3, 10.8 Hz, 1H), 1.22-1.16 (m, 1H), 1.08 (d, J = 6.8 Hz, 3H) | ¹³C NMR (CDCl₃) δ 172.27, 168.64, 155.33, 148.71, 140.53, 138.00, 130.43, 128.48, 127.84, 127.73, 109.46, 85.25, 75.60, 75.45, 56.07, 51.56, 37.94, 33.61, 32.24, 19.07, 18.23, 17.79 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| F40 | — | — | ESIMS m/z 429.3 ([M + H]⁺) | ¹H NMR (CDCl₃) δ 12.09 (s, 1H), 8.46 (d, J = 8.2 Hz, 1H), 7.98 (d, J = 5.2 Hz, 1H), 7.30 (dd, J = 8.4, 6.3 Hz, 2H), 7.21 (td, J = 7.2, 6.7, 1.5 Hz, 3H), 6.86 (d, J = 5.3 Hz, 1H), 4.90 (dq, J = 9.3, 6.3 Hz, 1H), 4.58 (ddd, J = 10.9, 8.2, 7.1 Hz, 1H), 3.94 (s, 3H), 3.56 (td, J = 9.0, 8.5, 2.7 Hz, 1H), 3.13 (dd, J = 13.5, 4.5 Hz, 1H), 2.48 (dd, J = 13.5, 10.5 Hz, 1H), 2.33 (dt, J = 14.0, 7.2 Hz, 1H), 1.85-1.73 (m, 2H), 1.72-1.51 (m, 3H), 1.44 (d, J = 6.3 Hz, 3H), 1.36-1.24 (m, 1H), 1.04-0.91 (m, 1H) | ¹³C NMR (CDCl₃) δ 172.06, 168.65, 155.36, 148.72, 140.53, 140.45, 130.37, 128.86, 128.55, 126.17, 109.48, 76.11, 74.90, 56.08, 51.35, 47.48, 37.78, 33.51, 26.97, 18.89, 18.14 |
| F41 | 129-131 | — | ESIMS m/z 499 ([M + H]⁺) | ¹H NMR (CDCl₃) δ 12.10 (s, 1H), 8.45 (d, J = 8.2 Hz, 1H), 8.03-7.89 (m, 1H), 7.12-7.02 (m, 4H), 6.85 (d, J = 5.2 Hz, 1H), 4.93 (dq, J = 9.2, 6.4 Hz, 1H), 4.62-4.50 (m, 1H), 3.92 (s, 3H), 3.56 (dd, J = 8.4, 6.2 Hz, 1H), 3.34 (dd, J = 8.4, 6.5 Hz, 1H), 3.15 (t, J = 9.0 Hz, 1H), 3.07 (dd, J = 13.3, 3.2 Hz, 1H), 2.38-2.24 (m, 5H), 1.97-1.78 (m, 2H), 1.68-1.54 (m, 2H), 1.54-1.40 (m, 4H), 1.25 (dtd, J = 13.2, 10.6, 2.2 Hz, 1H), 0.97 (d, J = 6.7 Hz, 3H), 0.96 (d, J = 6.7 Hz, 3H), 0.92-0.81 (m, 1H) | ¹³C NMR (CDCl₃) δ 172.16, 168.63, 155.32, 148.70, 140.52, 137.60, 135.37, 130.40, 129.06, 128.72, 109.46, 83.67, 80.66, 75.57, 56.06, 51.46, 46.15, 36.24, 33.61, 29.28, 26.50, 21.04, 19.56, 19.50, 18.77, 18.19 |
| F42 | — | — | ESIMS m/z 497 ([M + H]⁺) | ¹H NMR (CDCl₃) δ 12.09 (s, 1H), 8.45 (d, J = 8.2 Hz, 1H), 7.97 (d, J = 5.2 Hz, 1H), 7.14-7.03 (m, 4H), 6.85 (d, J = 5.2 Hz, 1H), 4.94 (dq, J = 9.2, 6.4 Hz, 1H), 4.56 (ddd, J = 10.9, 8.3, 7.0 Hz, 1H), 3.93 (s, 3H), 3.58 (dd, J = 9.7, 7.0 Hz, 1H), 3.45 (dd, J = 9.7, 6.8 Hz, 1H), 3.18 (t, J = 9.0 Hz, 1H), 3.11 (dd, J = 13.2, 3.3 Hz, 1H), 2.37-2.23 (m, 5H), 1.93-1.82 (m, 1H), 1.66-1.53 (m, 2H), 1.53-1.41 (m, 4H), 1.31-1.20 (m, 1H), 1.18-1.08 (m, 1H), 0.93-0.83 (m, 1H), 0.62-0.55 (m, 2H), 0.29-0.22 (m, 2H) | ¹³C NMR (CDCl₃) δ 172.13, 168.62, 155.32, 148.70, 140.52, 137.47, 135.39, 130.38, 129.07, 128.73, 109.46, 83.75, 78.75, 75.51, 56.06, 51.43, 46.01, 36.39, 33.60, 26.54, 21.03, 18.71, 18.11, 11.18, 3.16, 3.02 |
| F43 | — | — | HRMS-ESI (m/z) [M + H]⁺ calcd for C₂₂H₃₄N₂O₆, 441.2395; found, 441.2411 | ¹H NMR (CDCl₃) δ 12.19-11.98 (m, 1H), 8.50 (d, J = 8.2 Hz, 1H), 7.99 (d, J = 5.2 Hz, 1H), 6.87 (d, J = 5.2 Hz, 1H), 4.91 (dt, J = 9.1, 6.4 Hz, 1H), 4.63-4.52 (m, 2H), 4.52-4.39 (m, 1H), 3.94 (s, 3H), 3.45 (dd, J = 8.3, 6.6 Hz, 1H), 3.26 (dd, J = 8.4, 6.4 Hz, 1H), 3.08 (t, J = 8.6 Hz, 1H), 2.35 (dt, J = 13.3, 6.6 Hz, 1H), 2.16-1.95 (m, 1H), 1.92-1.79 (m, 1H), 1.79-1.60 (m, 4H), 1.60-1.52 (m, 1H), 1.43 (d, J = 6.4 Hz, 3H), 1.42-1.34 (m, 1H), 1.11 (dd, J = 14.9, 5.2 Hz, 1H), 0.92 (dd, J = 6.7, 0.7 Hz, 6H) | ¹³C NMR (CDCl₃) δ 172.18, 168.63, 155.34, 148.71, 140.54, 130.40, 109.46, 83.79, 82.16, 80.24, 75.52, 56.08, 51.52, 39.76, 33.48, 31.59, 31.39, 29.17, 28.64, 19.45, 19.41, 19.12, 18.14 |
| F44 | — | — | HRMS-ESI (m/z) [M + H]⁺ calcd for C₃₀H₃₅N₂O₇, | ¹H NMR (CDCl₃) δ 12.17-11.97 (m, 1H), 8.52 (d, J = 8.1 Hz, 1H), 8.00 (d, J = 5.2 Hz, 1H), 7.37-7.27 (m, 2H), 7.25-7.20 (m, 2H), 7.03-6.78 (m, | ¹³C NMR (CDCl₃) δ 172.16, 168.66, 159.31, 158.75, 155.35, 148.72, 140.56, 130.37, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | 535.2439; found, 535.2459 | 7H), 5.13 (dt, J = 9.1, 6.5 Hz 1H), 4.69-4.56 (m, 1H), 4.30 (t, J = 8.7 Hz, 1H), 3.95 (d, J = 7.6 Hz, 5H), 2.41 (dt, J = 12.7, 6.5 Hz, 1H), 2.17-2.02 (m, 2H), 2.02-1.86 (m, 1H), 1.86-1.64 (m, 3H), 1.45 (q, J = 11.1 Hz, 1H), 1.34 (d, J = 6.5 Hz, 3H), 1.31-1.20 (m, 1H) | 129.71, 129.40, 121.23, 120.64, 115.40, 114.44, 109.49, 81.08, 75.04, 66.00, 56.08, 51.56, 40.19, 37.62, 33.51, 30.50, 28.39, 19.25, 18.35 |
| F45 | — | — | HRMS-ESI (m/z) [M + H]⁺ calcd for $C_{25}H_{33}N_2O_7$, 473.2282; found, 473.2297 | ¹H NMR (CDCl₃) δ 12.08 (s, 1H), 8.52 (d, J = 8.1 Hz, 1H), 8.00 (d, J = 5.2 Hz, 1H), 7.33-7.27 (m, 2H), 6.94 (dd, J = 7.9, 5.5 Hz, 3H), 6.87 (d, J = 5.2 Hz, 1H), 5.19-5.01 (m, 1H), 4.61 (dt, J = 10.9, 7.1 Hz, 1H), 4.25 (t, J = 8.8 Hz, 1H), 3.95 (s, 3H), 3.38 (t, J = 6.4 Hz, 2H), 3.27 (s, 3H), 2.40 (dt, J = 12.8, 6.5 Hz, 1H), 2.02-1.80 (m, 3H), 1.80-1.60 (m, 2H), 1.56-1.37 (m, 2H), 1.31 (d, J = 6.5 Hz, 3H), 1.19 (dd, J = 14.7, 7.8 Hz, 1H) | ¹³C NMR (CDCl₃) δ 171.49, 167.99, 158.77, 154.70, 148.07, 139.89, 129.73, 128.98, 120.45, 114.72, 108.83, 80.40, 74.44, 70.13, 57.80, 55.42, 50.89, 39.47, 32.90, 29.89, 27.44, 18.46, 17.70 |
| F46 | — | — | HRMS-ESI (m/z) ([M + Na]⁺) calcd for $C_{23}H_{36}N_2O_6SNa$, 491.2186; found, 491.2199 | ¹H NMR (CDCl₃) δ 12.09 (d, J = 0.5 Hz, 1H), 8.52 (d, J = 8.1 Hz, 1H), 7.98 (d, J = 5.2 Hz, 1H), 6.87 (d, J = 5.2 Hz, 1H), 4.91 (dq, J = 9.1, 6.4 Hz, 1H), 4.64-4.50 (m, 1H), 3.94 (s, 3H), 3.46 (dd, J = 8.4, 6.5 Hz, 1H), 3.28 (dd, J = 8.4, 6.4 Hz, 1H), 3.05 (t, J = 8.8 Hz, 1H), 2.59 (ddd, J = 12.9, 9.6, 4.6 Hz, 1H), 2.44 (ddd, J = 12.7, 9.0, 7.3 Hz, 1H), 2.35 (dt, J = 12.9, 6.7 Hz, 1H), 2.10 (s, 3H), 1.95 (dddd, J = 12.5, 9.8, 6.0, 3.0 Hz, 1H), 1.85 (dt, J = 13.2, 6.6 Hz, 1H), 1.80-1.58(m, 4H), 1.58-1.46 (m, 2H), 1.43 (d, J = 6.4 Hz, 3H), 1.06 (ddd, J = 11.4, 6.3, 3.2 Hz, 1H), 0.93 (dd, J = 6.7, 0.9 Hz, 6H) | ¹³C NMR (CDCl₃) δ 172.14, 168.61, 155.28, 148.65, 140.50, 130.35, 109.45, 83.85, 80.36, 75.55, 56.03, 51.48, 42.19, 33.42, 32.10, 29.90, 29.17, 29.02, 27.74, 25.25, 19.45, 18.91, 18.12, 15.33 |
| F47 | — | — | HRMS-ESI (m/z) [M + H]⁺ calcd for $C_{23}H_{36}O_7Na$, 475.2415; found, 475.2836 | ¹H NMR (CDCl₃) δ 12.10 (d, J = 0.5 Hz, 1H), 8.50 (d, J = 8.1 Hz, 1H), 7.99 (d, J = 5.2 Hz, 1H), 6.86 (d, J = 5.2 Hz, 1H), 4.90 (dq, J = 9.1, 6.4 Hz, 1H), 4.56 (ddd, J = 10.8, 8.1, 7.0 Hz, 1H), 3.94 (s, 3H), 3.42 (q, J = 6.7, 6.3 Hz, 3H), 3.33 (s, 3H), 3.32-3.26 (m, 1H), 3.05 (t, J = 8.8 Hz, 1H), 2.35 (dt, J = 13.2, 6.5 Hz, 1H), 2.05-1.91 (m, 1H), 1.91-1.78 (m, 1H), 1.78-1.62 (m, 3H), 1.59-1.45 (m, 2H), 1.43 (d, J = 6.4 Hz, 3H), 1.40-1.32 (m, 1H), 1.11-1.02 (m, 1H), 0.92 (dd, J = 6.7, 2.7 Hz, 6H) | ¹³C NMR (CDCl₃) δ 172.22, 168.61, 155.33, 148.70, 140.52, 130.42, 109.44, 83.97, 80.37, 75.65, 71.25, 58.52, 56.07, 51.53, 40.24, 33.56, 30.39, 29.17, 28.30, 19.51, 19.42, 19.04, 18.16 |
| F48 | — | — | HRMS-ESI (m/z) [M + H]⁺ calcd for $C_{22}H_{35}O_6N_2$, 423.2490; found, 423.2500 | ¹H NMR (CDCl₃) δ 12.11 (d, J = 0.5 Hz, 1H), 8.50 (d, J = 8.1 Hz, 1H), 7.99 (d, J = 5.2 Hz, 1H), 6.86 (d, J = 5.2 Hz, 1H), 4.90 (dq, J = 9.2, 6.4 Hz, 1H), 4.62-4.48 (m, 1H), 3.94 (s, 3H), 3.43 (dd, J = 8.4, 6.6 Hz, 1H), 3.27 (dd, J = 8.4, 6.4 Hz, 1H), 3.02 (t, J = 8.9 Hz, 1H), 2.34 (dt, J = 13.1, 6.9 Hz, 1H), 1.92-1.80 (m, 1H), 1.73 (dtt, J = 15.4, 7.5, 3.5 Hz, 2H), 1.61 (dd, J = 14.8, 7.1 Hz, 1H), 1.55-1.45 (m, 1H), 1.42 (d, J = | ¹³C NMR (CDCl₃) δ 172.26, 168.61, 155.32, 148.69, 140.52, 130.44, 109.43, 84.18, 80.43, 75.72, 56.07, 51.53, 45.18, 33.64, 29.18, 27.05, 23.25, 19.50, 19.45, 18.74, 18.19, 11.96 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 6.4 Hz, 4H), 1.40-1.32 (m, 1H), 1.28-1.17 (m, 1H), 1.06-0.96 (m, 1H), 0.94-0.88 (m, 9H) | |
| F49 | 62-66 | — | ESIMS m/z 519 ([M + H]$^+$) | $^1$H NMR (CDCl$_3$) δ 12.09 (s, 1H), 8.48 (d, J = 8.2 Hz, 1H), 7.98 (d, J = 5.1 Hz, 1H), 7.37-7.28 (m, 2H), 7.12-6.93 (m, 7H), 6.86 (d, J = 5.2 Hz, 1H), 5.14 (dq, J = 9.2, 6.4 Hz, 1H), 4.62 (dt, J = 10.9, 7.4 Hz, 1H), 4.35 (t, J = 8.9 Hz, 1H), 3.93 (s, 3H), 2.99 (dd, J = 13.3, 3.2 Hz, 1H), 2.42-2.26 (m, 5H), 2.16-2.04 (m, 1H), 1.79-1.52 (m, 3H), 1.41-1.23 (m, 4H), 1.08-0.98 (m, 1H) | $^{13}$C NMR (CDCl$_3$) δ 172.06, 168.59, 159.58, 155.27, 148.66, 140.47, 136.92, 135.38, 130.28, 129.63, 128.98, 128.59, 121.16, 115.48, 109.43, 81.02, 74.89, 55.99, 51.43, 45.59, 36.34, 33.47, 26.57, 20.95, 18.78, 18.33 |
| F50 | — | — | HRMS-ESI (m/z) [M + H]$^+$ calcd for C$_{24}$H$_{30}$O$_6$BrN$_2$, 521.1282; found, 521.1283 | $^1$H NMR (CDCl$_3$) δ 12.27-11.86 (m, 1H), 8.53 (d, J = 8.1 Hz, 1H), 8.00 (d, J = 5.2 Hz, 1H), 7.37-7.27 (m, 2H), 7.04-6.92 (m, 3H), 6.88 (d, J = 5.2 Hz, 1H), 5.13 (dq, J = 9.1, 6.5 Hz, 1H), 4.62 (ddd, J = 10.9, 8.0, 6.8 Hz, 1H), 4.25 (t, J = 8.7 Hz, 1H), 3.95 (s, 3H), 3.46 (ddd, J = 10.0, 7.3, 5.0 Hz, 1H), 3.35 (ddd, J = 10.0, 8.3, 6.9 Hz, 1H), 2.50-2.33 (m, 1H), 2.10 (m, 2H), 1.94-1.78 (m, 2H), 1.73 (dt, J = 15.8, 8.0 Hz, 2H), 1.54-1.40 (m, 1H), 1.33 (d, J = 6.5 Hz, 3H), 1.30-1.18 (m, 1H) | $^{13}$C NMR (CDCl$_3$) δ 172.08, 168.68, 159.15, 155.37, 148.74, 140.58, 130.35, 129.77, 121.39, 115.38, 109.52, 80.87, 74.94, 56.09, 51.57, 41.28, 34.14, 33.37, 31.47, 28.22, 19.16, 18.29 |
| 51 | — | — | HRMS-ESI (m/z) [M + H]$^+$ calcd for C$_{24}$H$_{31}$O$_6$N$_2$, 443.2177; found, 443.2186 | $^1$H NMR (CDCl$_3$) δ 12.08 (d, J = 0.5 Hz, 1H), 8.52 (d, J = 8.1 Hz, 1H), 8.00 (d, J = 5.2 Hz, 1H), 7.34-7.27 (m, 2H), 7.01-6.91 (m, 3H), 6.87 (d, J = 5.2 Hz, 1H), 5.10 (dq, J = 9.1, 6.5 Hz, 1H), 4.61 (ddd, J = 10.8, 8.0, 7.1 Hz, 1H), 4.23 (t, J = 8.8 Hz, 1H), 3.94 (s, 3H), 2.47-2.33 (m, 1H), 1.95-1.83 (m, 1H), 1.78-1.59 (m, 4H), 1.50-1.38 (m, 1H), 1.31 (d, J = 6.5 Hz, 3H), 1.28-1.21 (m, 1H), 1.21-1.10 (m, 1H), 0.88 (t, J = 7.3 Hz, 3H) | $^{13}$C NMR (CDCl$_3$) δ 172.20, 168.65, 159.64, 155.35, 148.73, 140.54, 130.41, 129.61, 121.00, 115.40, 109.48, 81.38, 75.11, 56.08, 51.56, 44.97, 33.61, 26.99, 23.52, 18.80, 18.39, 11.87 |
| F52 | 68-72 | — | ESIMS m/z 555 ([M + H]$^+$) | $^1$H NMR (CDCl$_3$) δ 12.09 (s, 1H), 8.46 (d, J = 8.2 Hz, 1H), 7.98 (d, J = 5.2 Hz, 1H), 7.42-7.28 (m, 5H), 7.09 (td, J = 8.7, 6.6 Hz, 1H), 6.86 (d, J = 5.3 Hz, 1H), 6.83-6.72 (m, 2H), 5.01 (dq, J = 9.2, 6.4 Hz, 1H), 4.82 (d, J = 10.9 Hz, 1H), 4.64 (d, J = 10.9 Hz, 1H), 4.59 (dt, J = 10.9, 7.4 Hz, 1H), 3.93 (s, 3H), 3.42 (t, J = 9.0 Hz, 1H), 3.10-2.99 (m, 1H), 2.51 (dd, J = 13.5, 11.5 Hz, 1H), 2.32 (dtd, J = 13.2, 6.6, 2.0 Hz, 1H), 1.95 (ddq, J = 12.0, 7.8, 3.8 Hz, 1H), 1.74-1.40 (m, 6H), 1.34-1.22 (m, 1H), 1.02-0.90 (m, 1H) | $^{13}$C NMR (CDCl$_3$) δ 172.03, 168.60, 161.32 (dd, J = 247.2, 12.6 Hz), 161.06 (dd, J = 247.1, 11.6 Hz), 155.28, 148.66, 140.48, 137.70, 131.77-131.21 (m), 130.30, 128.48, 127.88, 127.60, 123.02 (dd, J = 16.0, 3.9 Hz), 111.04 (dd, J = 20.9, 3.6 Hz), 109.43, 104.17-103.09 (m), 83.83, 75.34, 75.17, 56.00, 51.38, 44.42, 33.44, 29.25, 27.07, 18.77, 18.20 $^{19}$F NMR (CDCl$_3$) δ −113.21 (d, J = 6.7 Hz), −113.59 (d, J = 6.8 Hz) |
| F53 | — | — | HRMS-ESI (m/z) [M + H]$^+$ calcd for C$_{24}$H$_{29}$O$_6$N$_2$F$_2$, | $^1$H NMR (CDCl$_3$) δ 12.06 (d, J = 0.5 Hz, 1H), 8.54 (d, J = 8.1 Hz, 1H), 8.03 (d, J = 5.2 Hz, 1H), 7.42-7.30 (m, 2H), 7.05-6.99 (m, 1H), 6.99-6.94 (m, | $^{13}$C NMR (CDCl$_3$) δ 172.08, 168.69, 158.89, 155.37, 148.74, 140.59, 130.32, 129.86, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | 479.1988; found, 479.1989 | 2H), 6.90 (d, J = 5.1 Hz, 1H), 6.09-5.68 (m, 1H), 5.15 (dq, J = 9.2, 6.5 Hz, 1H), 4.65 (ddd, J = 11.0, 8.1, 6.9 Hz, 1H), 4.27 (t, J = 8.7 Hz, 1H), 3.97 (s, 3H), 2.45 (dt, J = 13.2, 6.7 Hz, 1H), 2.12 (dt, J = 8.7, 3.7 Hz, 1H), 2.04 (ddt, J = 14.5, 9.1, 4.6 Hz, 1H), 1.88 (dddd, J = 22.5, 14.7, 11.4, 7.1 Hz, 3H), 1.77-1.65 (m, 1H), 1.48 (q, J = 11.1 Hz, 1H), 1.35 (d, J = 6.5 Hz, 3H), 1.33-1.25 (m, 1H) | 121.62, 116.72 (t, J = 239 hz), 115.25, 109.53, 80.51, 74.76, 56.09, 51.54, 35.73 (t, J = 21 Hz), 33.31, 29.34, 19.25, 18.27 |
| F54 | — | — | HRMS-ESI (m/z) [M + H]$^+$ calcd for C$_{26}$H$_{39}$O$_7$N$_2$, 491.2752; found, 491.2758 | $^1$H NMR (CDCl$_3$) δ 12.09 (d, J = 0.5 Hz, 1H), 8.49 (d, J = 8.1 Hz, 1H), 7.99 (d, J = 5.2 Hz, 1H), 6.86 (d, J = 5.1 Hz, 1H), 4.91 (dq, J = 9.1, 6.4 Hz, 1H), 4.66-4.47 (m, 1H), 3.94 (s, 3H), 3.55-3.37 (m, 4H), 3.36-3.17 (m, 2H), 3.09 (t, J = 8.9 Hz, 1H), 2.35 (dt, J = 13.3, 6.6 Hz, 1H), 2.08-1.93 (m, 1H), 1.70 (tq, J = 13.2, 7.3, 5.3 Hz, 3H), 1.60-1.47 (m, 2H), 1.44 (d, J = 6.5 Hz, 3H), 1.42-1.31 (m, 1H), 1.17-0.94 (m, 3H), 0.54 (dddd, J = 10.0, 8.0, 4.1, 2.8 Hz, 4H), 0.32-0.13 (m, 4H) | $^{13}$C NMR (CDCl$_3$) δ 172.18, 168.62, 155.32, 148.70, 140.52, 130.41, 109.44, 83.96, 78.39, 75.59, 75.48, 69.09, 56.07, 51.48, 40.49, 33.58, 30.66, 28.15, 18.97, 18.10, 11.09, 10.66, 3.18, 3.02, 2.95, 2.90 |
| 55 | 66-70 | — | ESIMS m/z 553 ([M + H]$^+$) | $^1$H NMR (CDCl$_3$) δ 12.09 (s, 1H), 8.45 (d, J = 8.2 Hz, 1H), 8.00-7.93 (m, 1H), 7.10 (d, J = 7.8 Hz, 2H), 7.04 (d, J = 8.0 Hz, 2H), 6.85 (d, J = 5.2 Hz, 1H), 4.92 (dq, J = 9.2, 6.4 Hz, 1H), 4.61-4.50 (m, 1H), 3.92 (s, 3H), 3.80 (dt, J = 8.9, 6.1 Hz, 1H), 3.61 (dt, J = 8.8, 6.2 Hz, 1H), 3.18 (t, J = 9.0 Hz, 1H), 2.97 (dd, J = 13.3, 3.5 Hz, 1H), 2.41-2.13 (m, 7H), 1.91-1.76 (m, 3H), 1.69-1.40 (m, 6H), 1.33-1.20 (m, 1H), 0.93-0.82 (m, 1H) | $^{13}$C NMR (CDCl$_3$) δ 172.04 168.57, 155.26, 148.64, 140.46, 137.13, 135.46, 130.28, 129.05, 128.57, 131.35-122.86 (m), 109.41, 84.15, 75.08, 71.62, 55.98, 51.37, 45.75, J = 29.1 Hz) 26.60, 23.01 (q, J = 3.1 Hz), 20.93, 18.69, 18.04 $^{19}$F NMR R (CDCl$_3$) δ −66.33 |
| F56 | — | — | ESIMS m/z 583 ([M + H]$^+$) | $^1$H NMR (CDCl$_3$) δ 12.09 (s, 1H), 8.46 (d, J = 8.2 Hz, 1H), 7.97 (d, J = 5.2 Hz, 1H), 7.32-7.07 (m, 6H), 6.88-6.74 (m, 3H), 4.94 (dq, J = 9.2, 6.4 Hz, 1H), 4.56 (dt, J = 10.9, 7.5 Hz, 1H), 3.92 (s, 3H), 3.79 (dt, J = 8.8, 6.3 Hz, 1H), 3.58 (dt, J = 8.9, 6.5 Hz, 1H), 3.19 (t, J = 9.0 Hz, 1H), 2.99 (d, J = 13.2 Hz, 1H), 2.74 (td, J = 7.5, 3.7 Hz, 2H), 2.48 (dd, J = 13.6, 11.5 Hz, 1H), 2.31 (dt, J = 12.7, 6.7 Hz, 1H), 2.03-1.80 (m, 3H), 1.72-1.37 (m, 6H), 1.34-1.20 (m, 1H), 0.99-0.86 (m, 1H) | $^{13}$C NMR (CDCl$_3$) δ 172.04, 168.58, 162.89-159.93 (m) 161.08 (dd, J = 247.0, 11.6 Hz), 155.27, 7 148.65, 141.66, 140.46, 131.49 (dd, J = 9.4, 6.5 Hz), 130.31, 128.32 128.27, 125.83, 123.13 (dd, J = 15.9, 3.7 Hz), 111.02 (dd, J = 20.9, 3.7 Hz), 109.42, 104.28-102.96 (m), 83.96, 75.25, 72.90, 56.00, 51.36, 44.44, 33.45, 32.35, 31.88, 29.29, 27.04, 18.72, 18.07 $^{19}$F NMR (CDCl$_3$) δ −113.26 (d, J = 7.1 Hz), −113.60 (d, J = 6.9 Hz) |
| F57 | — | — | HRMS-ESI (m/z) [M + H]$^+$ calcd for C$_{28}$H$_{37}$O$_7$N$_2$, 513.2595; found, 513.2605 | $^1$H NMR (CDCl$_3$) δ 12.08 (s, 1H), 8.49 (d, J = 8.0 Hz, 1H), 7.99 (d, J = 5.2 Hz, 1H), 7.37-7.27 (m, 2H), 6.99-6.80 (m, 4H), 5.06-4.87 (m, 1H), 4.57 (dt, J = 10.8, 7.2 Hz, 1H), 4.09-3.98 (m, 2H), 3.94 (s, 3H), 3.57-3.35 (m, 2H), 3.15 (t, J = | $^{13}$C NMR (CDCl$_3$) δ 172.15, 168.63, 158.82, 155.32, 148.70, 140.53, 130.39, 129.43, 120.62, 114.46, 109.45, 83.88, 78.27, 75.52, 66.14, 56.07, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 8.9 Hz, 1H), 2.35 (dt, J = 13.1, 6.6 Hz, 1H), 2.21 (dq, J = 10.4, 3.8 Hz, 1H), 1.81 (dd, J = 11.2, 5.8 Hz, 2H), 1.79-1.66 (m, 2H), 1.61 (d, J = 10.7 Hz, 1H), 1.45 (d, J = 6.4 Hz, 3H), 1.44-1.33 (m, 1H), 1.08 (dq, J = 12.4, 6.3, 5.4 Hz, 2H), 0.55 (dt, J = 8.0, 4.6 Hz, 2H), 0.21 (q, J = 5.1 Hz, 2H) | 51.47, 40.30, 33.54, 30.31, 28.11, 19.03, 18.11, 11.08, 3.16, 2.94 |
| F58 | — | — | HRMS-ESI (m/z) [M + H]⁺ calcd for $C_{18}H_{25}O_6N_2$, 365.1707; found, 365.17012 | ¹H NMR (CDCl₃) δ 12.09 (d, J = 0.6 Hz, 1H), 8.58 (d, J = 7.7 Hz, 1H), 7.99 (d, J = 5.2 Hz, 1H), 6.87 (d, J = 5.1 Hz, 1H), 5.02 (dq, J = 9.5, 6.3 Hz, 1H), 4.52 (ddd, J = 12.0, 7.9, 5.2 Hz, 1H), 3.94 (s, 3H), 3.82 (ddd, J = 8.6, 7.1, 3.4 Hz, 1H) 3.71 (td, J = 8.9, 5.3 Hz, 1H), 3.44 (dd, J = 9.5, 6.3 Hz, 1H), 2.38 (dddd, J = 14.0, 11.4, 5.2, 1.9 Hz, 1H), 2.13-2.03 (m, 1H), 1.98 (ddt, J = 14.7, 8.1, 3.3 Hz, 1H), 1.94-1.86(m, 1H), 1.84-1.72 (m, 1H), 1.71-1.60 (m, 1H), 1.56-1.48 (m, 2H), 1.47 (dd, J = 5.8, 2.1 Hz, 1H), 1.44 (d, J = 6.3 Hz, 3H) | 13C NMR (151 MHz, CDCl₃) 173.09, 168.55, 155.35, 148.74, 140.54, 130.44, 109.46, 86.83, 73.59, 67.75, 56.08, 52.94, 39.75, 36.06, 35.77, 32.40, 21.75, 18.39 |
| F59 | 69-72 | — | ESIMS m/z 521 ([M + H]⁺) | ¹H NMR (CDCl₃) δ 12.08 (s, 1H), 8.44 (d, J = 8.2 Hz, 1H), 7.95 (d, J = 5.1 Hz, 1H), 7.11 (td, J = 8.5, 6.4 Hz, 1H), 6.84 (d, J = 5.2 Hz, 1H), 6.82-6.71 (m, 2H), 4.91 (dq, J = 9.2, 6.4 Hz, 1H), 4.55 (dt, J = 10.9, 7.5 Hz, 1H), 3.91 (s, 3H) 3.54 (dd, J = 8.4, 6.3 Hz, 1H), 3.31 (dd, J = 8.4, 6.5 Hz, 1H), 3.15 (t, J = 9.0 Hz, 1H), 3.04-2.93 (m, 1H), 2.46 (dd, J = 13.5, 11.6 Hz, 1H), 2.36-2.24 (m, 1H), 1.94-1.77 (m, 2H), 1.70-1.51 (m, 2H), 1.45 (d, J = 6.4 Hz, 4H), 1.33-1.19 (m, 1H), 0.95 (dd, J = 6.7, 4.7 Hz, 7H) | ¹³C NMR (CDCl₃) δ 172.03, 168.56, 161.27 (dd, J = 246.8, 12.2 Hz), 162.42-159.71 (m), 155.25, 148.62, 140.45, 131.50 (dd, J = 9.2, 6.6 Hz), 130.29, 123.20 (dd, J = 16.2, 3.7 Hz), 111.00 (dd, J = 20.9, 3.7 Hz), 109.40, 103.99-103.17 (m), 83.45, 80.36, 75.37, 55.98, 51.34, 44.65, 33.44, 29.16, 29.10, 26.96, 19.40, 19.38, 18.70, 18.06 ¹⁹F NMR (CDCl₃) δ −113.36 (d, J = 6.4 Hz), −113.63 (d, J = 6.4 Hz) |
| F60 | 93-97 | — | ESIMS m/z 559 [M + H]⁺ | ¹H NMR (CDCl₃) δ 12.03 (d, J = 0.5 Hz, 1H), 8.43 (d, J = 8.1 Hz, 1H), 7.95 (d, J = 5.2 Hz, 1H), 7.60 (dd, J = 1.8, 0.9 Hz, 1H), 7.17 (dd, J = 3.5, 0.9 Hz, 1H), 7.04 (td, J = 8.4, 6.4 Hz, 1H), 6.84 (d, J = 5.2 Hz, 1H), 6.75-6.65 (m, 2H), 6.51 (dd, J = 3.5, 1.7 Hz, 1H), 5.21 (t, J = 9.2 Hz, 1H), 5.12 (dq, J = 9.5, 6.2 Hz, 1H), 4.60 (dt, J = 10.9, 7.5 Hz, 1H), 3.91 (s, 3H), 2.72 (dd, J = 13.9, 4.5 Hz, 1H), 2.51 (dd, J = 13.9, 10.3 Hz, 1H), 2.36 (dtd, J = 13.3, 7.7, 6.7, 3.4 Hz, 1H), 2.20-2.08 (m, 1H), 1.77-1.54 (m, 3H), 1.40-1.25 (m, 4H), 1.13-1.01 (m, 1H) | ¹³C NMR (CDCl₃) δ 171.98, 168.58, 161.44 (dd, J = 246.7, 11.8 Hz) 160.93 (dd, J =, 247.6, 11.8 Hz), 158.10, 155.25, 148.63, 146.90, 143.79, 140.44, 131.51 (dd, J = 9.4, 6.5 Hz), 130.20, 122.32 (dd, J = 15.9, 3.7 Hz), 118.60, 111.94, 110.89 (dd, J = 21.0, 3.6 Hz), 109.43, 103.64 (t, J = 25.6 Hz), 76.26, 73.31, 55.97, 51.28, 42.53, 33.25, 29.99, 27.24, 18.61, 17.44 ¹⁹F NMR (CDCl₃) δ −112.90 (d, J = 6.8 Hz), −113.48 (d, J = 6.7 Hz) |
| F61 | — | — | HRMS-ESI (m/z) [2M + Na]⁺ calcd for $C_{48}H_{56}N_4NaO_{12}$, 903.3787; | ¹H NMR (CDCl₃) δ 12.07 (s, 1H), 8.53 (d, J = 8.1 Hz, 1H), 7.35-7.22 (m, 3H), 6.93 (dd, J = 7.4, 4.7 Hz, 3H), 6.87 (d, J = 5.2 Hz, 1H), 5.79 (ddd, J = 17.2, 10.3, 8.0 Hz, 1H), 5.17 | ¹³C NMR (CDCl₃) δ 172.22, 168.65, 159.29, 155.35, 148.73, 140.56, 138.40, 130.37, 129.51, 121.15, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | found, 903.3801 | (dq, J = 9.0, 6.4 Hz, 1H), 5.05 (d, J = 17.1 Hz, 1H), 4.97 (d, J = 10.4 Hz, 1H), 4.71-4.55 (m, 1H), 4.33 (t, J = 8.8 Hz, 1H), 3.95 (s, 3H), 2.59-2.48 (m, 1H), 2.40 (dt, J = 12.2, 6.8 Hz, 1H), 1.92 (dt, J = 16.2, 8.3 Hz, 1H), 1.86-1.68 (m, 2H), 1.53-1.41 (m, 1H), 1.36 (d, J = 6.4 Hz, 4H) | 116.30, 115.78, 109.49, 80.41, 74.75, 56.08, 51.59, 47.47, 33.55, 31.01, 19.70, 18.34 |
| F62 | 67-69 | (Neat) 3383, 2950, 1772, 1744, 1679, 1509, 1197 | HRMS-ESI (m/z) ([M]$^+$) calcd for C$_{29}$H$_{38}$N$_2$O$_7$, 526.2679; found, 526.2687 | $^1$H NMR (CDCl$_3$) δ 8.56 (d, J = 8.0 Hz, 1H), 8.34 (d, J = 5.5 Hz, 1H), 7.33-7.24 (m, 2H), 7.00 (d, J = 5.5 Hz, 1H), 6.99-6.89 (m, 3H), 5.13-5.01 (m, 1H), 4.61 (ddd, J = 10.8, 8.3, 6.9 Hz, 1H), 4.23-4.15 (m, 1H), 3.90 (s, 3H), 2.45-2.32 (m, 1H), 2.40 (s, 3H), 1.91-1.30 (m, 7H), 1.29 (d, J = 6.5 Hz, 3H), 1.28-1.04 (m, 4H), 0.80 (d, J = 6.6 Hz, 3H), 0.79 (d, J = 6.6 Hz, 3H) | $^{13}$C NMR (CDCl$_3$) δ 172.71, 168.89, 162.40, 159.71, 159.43, 146.72, 141.42, 137.48, 129.57, 120.96, 115.49, 109.82, 81.64, 74.87, 56.29, 51.66, 43.19, 36.41, 33.81, 28.28, 27.88, 27.64, 23.03, 22.06, 20.75, 18.92, 18.37 |
| F63 | — | (Neat) 3380, 2949, 1772, 1741, 1677, 1508, 1368, 1196 | HRMS-ESI (m/z) ([M]$^+$) calcd for C$_{27}$H$_{40}$N$_2$O$_7$, 504.2836; found, 504.2842 | $^1$H NMR (CDCl$_3$) δ 8.54 (d, J = 8.2 Hz, 1H), 8.33 (d, J = 5.4 Hz, 1H), 7.00 (d, J = 5.5 Hz, 1H), 4.95-4.82 (m, 1H), 4.55 (ddd, J = 10.7, 8.4, 7.0 Hz, 1H), 3.90 (s, 3H), 3.56-3.32 (m, 2H), 3.09-2.95 (m, 1H), 2.39 (s, 3H), 2.38-2.24 (m, 1H), 1.81-1.43 (m, 6H), 1.41 (d, J = 6.4 Hz, 3H), 1.36-0.92 (m, 6H), 0.89 (d, J = 6.6 Hz, 3H), 0.88 (d, J = 6.6 Hz, 3H), 0.62-0.49 (m, 2H), 0.27-0.15 (m, 2H) | $^{13}$C NMR (CDCl$_3$) δ 172.71, 168.87, 162.36, 159.40, 146.70, 141.44, 137.44, 109.78, 84.35, 78.61, 75.40, 56.27, 51.57, 43.56, 36.44, 33.88, 28.07, 27.40, 23.02, 22.22, 20.74, 18.71, 18.08, 11.12, 3.08, 3.00 |
| F64 | 121-123 | (Neat) 3379, 2936, 1772, 1742, 1678, 1507, 1368, 1195 | HRMS-ESI (m/z) ([M]$^+$) calcd for C$_{26}$H$_{40}$N$_2$O$_7$, 492.2836; found, 492.2862 | $^1$H NMR (CDCl$_3$) δ 8.54 (d, J = 8.7 Hz, 1H), 8.33 (d, J = 5.4 Hz, 1H), 7.00 (d, J = 5.5 Hz, 1H), 4.93-4.78 (m, 1H), 4.56 (ddd, J = 10.7, 8.4, 7.0 Hz, 1H), 3.90 (s, 3H), 3.69-3.56 (m, 1H), 3.51-3.39 (m, 1H), 3.07-2.94 (m, 1H), 2.40 (s, 3H), 2.38-2.25 (m, 1H), 1.84-1.25 (m, 9H), 1.41 (d, J = 6.5 Hz, 3H), 1.25-0.95 (m, 4H), 0.93 (t, J = 7.4 Hz, 3H), 0.89 (d, J = 6.6 Hz, 3H), 0.88 (d, J = 6.6 Hz, 3H) | $^{13}$C NMR (CDCl$_3$) δ 172.75, 168.88, 162.35, 159.40, 146.70, 141.48, 137.45, 109.76, 84.57, 75.41, 56.27, 51.59, 43.50, 36.52, 33.89, 28.10, 27.54, 23.53, 23.02, 22.22, 20.74, 18.78, 18.09, 10.70 |
| F65 | 60-62 | (Neat) 3375, 2951, 1772, 1742, 1677, 1508, 1369, 1196 | HRMS-ESI (m/z) ([M]$^+$) calcd for C$_{27}$H$_{39}$F$_3$N$_2$O$_7$, 560.2709; found, 560.2733 | $^1$H NMR (CDCl$_3$) δ 8.54 (d, J = 8.9 Hz, 1H), 8.33 (d, J = 5.4 Hz, 1H), 7.00 (d, J = 5.5 Hz, 1H), 4.92-4.80 (m, 1H), 4.56 (ddd, J = 10.7, 8.4, 7.0 Hz, 1H), 3.90 (s, 3H), 3.78-3.68 (m, 1H), 3.61-3.49 (m, 1H), 3.08-2.97 (m, 1H), 2.39 (s, 3H), 2.38-2.27 (m, 1H), 2.27-2.11 (m, 2H), 1.88-1.27 (m, 9H), 1.39 (d, J = 6.4 Hz, 3H), 1.27-0.93 (m, 4H), 0.93-0.83 (m, 6H) | $^{13}$C NMR (CDCl$_3$) δ 172.70, 168.87, 162.37, 159.41, 146.70, 141.42, 137.46, 127.16 (q, J = 276.2 Hz), 109.79, 84.83, 75.03, 71.53, 56.27, 51.58, 43.44, 36.48, 33.83, 30.81 (q, J = 29.0 Hz), 28.19, 28.07, 27.52, 23.06 (d J = 3.0 Hz), 22.95, 22.17, 20.74, 18.79, 18.11 $^{19}$F NMR (CDCl$_3$) δ −66.44 |
| F66 | 58-60 | (Neat) 3380, 2942, 1772, 1741, 1678, 1507, 1368, | HRMS-ESI (m/z) ([M]$^+$) calcd for C$_{24}$H$_{36}$N$_2$O$_7$, 464.2523; found, 464.2545 | $^1$H NMR (CDCl$_3$) δ 8.54 (d, J = 8.3 Hz, 1H), 8.33 (d, J = 5.4 Hz, 1H), 7.00 (d, J = 5.5 Hz, 1H), 4.92-4.79 (m, 1H), 4.56 (ddd, J = 10.7, 8.5, 7.1 Hz, 1H), 3.90 (s, 3H), 3.50 (s, 3H), 2.99-2.87 (m, 1H), 2.40 (s, 3H), 2.38-2.25 (m, 1H), 1.83- | $^{13}$C NMR (CDCl$_3$) δ 172.69, 168.87, 162.36, 159.41, 146.70, 141.44, 137.45, 109.78, 86.40, 75.14, 61.18, 56.27, 51.55, 43.52, 36.48, 33.88, 28.24, 28.15, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | 1196 | | 1.27 (m, 7H), 1.41 (d, J = 6.4 Hz, 3H), 1.27-0.91 (m, 4H), 0.89 (d, J = 6.6 Hz, 3H), 0.88 (d, J = 6.6 Hz, 3H) | 27.29, 23.08, 22.17, 20.74, 18.72, 18.03 |
| F67 | — | (Neat) 3378, 2939, 1772, 1742, 1678, 1508, 1314, 1199 | HRMS-ESI (m/z) ([M]$^+$) calcd for C$_{29}$H$_{35}$FN$_2$O$_7$, 542.2428; found, 542.2436 | $^1$H NMR (CDCl$_3$) δ 8.50 (d, J = 8.4 Hz, 1H), 8.32 (d, J = 5.4 Hz, 1H), 7.18-7.07 (m, 2H), 7.04-6.90 (m, 3H), 5.00-4.85 (m, 1H), 4.64-4.50 (m, 1H), 3.89 (s, 3H), 3.63-3.51 (m, 1H), 3.50-3.37 (m, 1H), 3.20-3.10 (m, 1H), 3.14-3.04 (m, 1H), 2.39 (s, 3H), 2.39-2.20 (m, 2H), 1.90-1.75 (m, 1H), 1.65-1.49 (m, 2H), 1.47-1.33 (m, 1H), 1.45 (d, J = 6.4 Hz, 3H), 1.25-1.05 (m, 2H), 0.96-0.80 (m, 1H), 0.65-0.51 (m, 2H), 0.32-0.17 (m, 2H) | $^{13}$C NMR (CDC;3) δ 172.57, 168.85, 162.38, 161.28 (d, J = 243.6 Hz), 159.40, 146.70, 141.38, 137.45, 136.31 (d, J = 3.2 Hz), 130.14 (d, J = 7.7 Hz) 115.12 (d J = 21.1 Hz), 109.80, 83.72, 78.75, 75.18, 56.27, 51.47, 46.14, 36.04, 33.82, 26.63, 20.73, 18.73, 18.06, 11.16, 3.14, 2.99 $^{19}$F NMR (CDCl$_3$) δ −117.47 |
| F68 | — | (Neat) 3375, 2939, 1742 1676, 1508, 1197 | HRMS-ESI (m/z) ([M]$^+$) calcd for C$_{31}$H$_{33}$FN$_2$O$_7$, 564.2272; found, 564.2280 | $^1$H NMR (CDCl$_3$) δ 8.53 (d, J = 8.4 Hz, 1H), 8.33 (d, J = 5.4 Hz, 1H), 7.35-7.27 (m, 2H), 7.12-6.89 (m, 8H), 5.17-5.05 (m, 1H), 4.62 (ddd, J = 11.0, 8.4, 6.9 Hz, 1H), 4.36-4.26 (m, 1H), 3.90 (s, 3H), 3.02-2.91 (m, 1H), 2.40 (s, 3H), 2.39-2.28 (m, 2H), 2.12-1.99 (m, 1H), 1.74-1.60 (m, 2H), 1.60-1.46 (m, 1H), 1.33 (d, J = 6.5 Hz, 3H), 1.30-1.23 (m, 1H), 1.09-0.96 (m, 1H) | $^{13}$C NMR (CDCl$_3$) δ 172.59, 168.88, 162.41, 161.31 (d, J = 243.6 Hz), 159.55, 159.44, 146.71, 141.37, 137.50, 135.84 (d, J = 3.2 Hz), 130.11 (d, J = 7.8 Hz), 129.72, 121.26, 115.47, 115.12 (d, J = 21.1 Hz), 109.83, 81.01, 74.62, 56.29, 51.57, 45.70, 36.12, 33.77, 26.87, 20.75, 18.93, 18.34 $^{19}$F NMR (CDCl$_3$) δ −117.35 |
| F69 | 74-76 | (Neat) 3376, 2940, 1770, 1743, 1676, 1508, 1199 | HRMS-ESI (m/z) ([M]$^+$) calcd for C$_{27}$H$_{31}$F$_3$N$_2$O$_7$, 552.2083; found, 552.2081 | $^1$H NMR (CDCl$_3$) δ 8.50 (d, J = 8.3 Hz, 1H), 8.32 (d, J = 5.4 Hz, 1H), 7.17-7.06 (m, 2H), 7.04-6.91 (m, 3H), 5.86 (tt, J = 55.1, 3.9 Hz, 1H), 5.00-4.86 (m, 1H), 4.63-4.51 (m, 1H), 4.05-3.90 (m, 1H), 3.89 (s, 3H), 3.85-3.67 (m, 1H), 3.30-3.20 (m, 1H), 3.10-2.98 (m, 1H), 2.39 (s, 3H), 2.39-2.20 (m, 2H), 1.89-1.76 (m, 1H), 1.68-1.36 (m, 3H), 1.45 (d, J = 6.4 Hz, 3H), 1.30-1.11 (m, 1H), 0.96-0.81 (m, 1H) | $^{13}$C NMR (CDCl$_3$) δ 172.47, 168.87, 162.41, 161.36 (d, J = 243.8 Hz), 159.44, 146.72, 141.32, 137.49, 135.85 (d, J = 3.1 Hz), 130.14 (d, J = 7.8 Hz), 115.20 (d, J = 21.1 Hz), 113.88 (t, J = 241.2 Hz), 109.85, 85.51, 74.42, 72.59 (t, J = 27.7 Hz), 56.29, 51.46, 45.79, 35.92, 33.72, 26.60, 20.74, 18.82, 18.12 $^{19}$F NMR (CDCl$_3$) δ −117.20, −25.46 (d, J = 9.5 Hz, 2F) |
| F70 | — | — | ESIMS m/z 527.5 ([M + H]$^+$) | $^1$H NMR (CDCl$_3$) δ 8.63-8.40 (m, 1H), 8.32 (d, J = 5.5 Hz, 1H), 7.32-7.25 (m, 2H), 7.22-7.13 (m, 3H), 6.99 (d, J = 5.5 Hz, 1H), 4.91 (dq, J = 9.2, 6.4 Hz, 1H), 4.57 (ddd, J = 10.9, 8.5, 7.0 Hz, 1H), 3.90 (s, 3H), 3.56 (dd, J = 8.4, 6.3 Hz, 1H), 3.34 (dd, J = 8.4, 6.5 Hz, 1H), 3.21-3.04 (m, 2H), 2.40 (s, 3H), 2.38-2.21 (m 2H), 1.96-1.78 (m, 2H), 1.61-1.51 (m, 2H), 1.50-1.38 (m, overlapping, 1H), 1.44 (d, J = 6.4 Hz, 3H), 1.29-1.12 (m, 1H), 0.97 (dd, J = 6.7, 5.3 Hz, 6H), 0.92-0.80 (m, 1H) | $^{13}$C NMR (CDCl$_3$) δ 172.64, 168.91, 162.38, 159.41, 146.70, 141.44, 140.86, 137.46, 128.87, 128.34, 125.88, 109.77, 83.70, 80.65, 75.29, 56.28, 51.51, 46.19, 36.73, 33.91 29.28, 26.57, 20.76, 19.56, 19.50, 18.80, 18.16 |
| F71 | — | (Thin Film) 3379, | HRMS-ESI (m/z) ([M]$^+$) | $^1$H NMR (CDCl$_3$) δ 8.56 (d, J = 8.6 Hz, 1H), 8.34 (d, J = 5.5 Hz, 1H), 7.35-7.22 (m, 2H), | $^{13}$C NMR (CDCl$_3$) δ 172.71, 168.90, 162.40, 159.77, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | 2943, 2868, 1771, 1737, 1676, 1506, 1493, 1172 | calcd for $C_{30}H_{38}N_2O_7$, 538.2679; found, 538.2684 | 7.00 (d, J = 5.5 Hz, 1H), 6.99-6.89 (m, 3H), 5.07 (dq, J = 9.4, 6.5 Hz, 1H), 4.61 (ddd, J = 10.9, 8.3, 6.9 Hz, 1H), 4.16 (t, J = 8.7 Hz, 1H), 3.91 (s, 3H), 2.40 (s, 3H), 1.92-1.32 (m, 15H), 1.28 (d, J = 6.3 Hz, 3H), 1.20-1.06 (m, 1H), 1.07-0.88 (m, 2H) | 159.43, 146.72, 141.42, 137.48, 129.58, 120.93, 115.56, 109.82, 101.26, 101.07, 81.67, 74.88, 56.30, 51.67, 42.01, 37.26, 36.85, 33.66, 31.77, 27.65, 25.04, 20.76, 19.07, 18.38 |
| F72 | — | (Thin Film) 3378, 2938, 1771, 1742, 1678, 1510, 1200 | HRMS-ESI (m/z) ([M]⁺) calcd for $C_{30}H_{38}N_2O_8$, 554.2628; found, 554.2644 | ¹H NMR (CDCl₃) δ 8.53-8.43 (m, 1H), 8.32 (d, J = 5.5 Hz, 1H), 7.15-7.03 (m, 2H), 6.99 (d, J = 5.5 Hz, 1H), 6.88-6.72 (m, 2H), 4.91 (dq, J = 9.3, 6.4 Hz, 1H), 4.56 (dt, J = 10.9, 7.7 Hz, 1H), 3.90 (s, 3H), 3.79 (s, 3H), 3.57 (dd, J = 9.7, 7.0 Hz, 1H), 3.44 (dd, J = 9.7, 6.9 Hz, 1H), 3.15 (t, J = 9.1 Hz, 1H), 3.07 (d, J = 13.1 Hz, 1H), 2.39 (s, 3H), 2.33-2.22 (m, 2H), 1.87-1.76 (m, 1H), 1.55-1.47 (m, 2H), 1.49-1.38 (m, 1H), 1.45 (d, J = 6.5 Hz, 3H), 1.19-1.05 (m, 2H), 0.91-0.80 (m, 1H), 0.64-0.47 (m, 2H), 0.32-0.20 (m, 2H) | — |
| F73 | — | — | ESIMS m/z 517 ([M + H]⁺) | ¹H NMR (CDCl₃) δ 8.54 (s, 1H), 8.34 (d, J = 5.4 Hz, 1H), 7.00 (d, J = 5.5 Hz, 1H), 4.94-4.82 (m, 1H), 4.55 (dt, J = 10.8, 7.5 Hz, 1H), 3.90 (s, 3H), 3.49 (dd, J = 9.7, 7.0 Hz, 1H), 3.36 (dd, J = 9.7, 6.9 Hz, 1H), 2.99 (t, J = 8.9 Hz, 1H), 2.39 (s, 3H), 2.38-2.26 (m, 1H), 1.92-1.66 (m, 4H), 1.64-1.44 (m, 10H), 1.40 (d, J = 6.5 Hz, 3H), 1.35-1.22 (m, 1H), 1.15 - 0.91 (m, 3H), 0.60-0.50 (m, 2H), 0.21 (dt, J = 6.0, 4.5 Hz, 2H) | ¹³C NMR (CDCl₃) δ 172.71, 168.87, 162.36, 159.40, 146.71, 141.44, 137.44, 109.78, 101.25, 101.05, 84.33, 78.50, 75.35, 56.28, 51.59, 42.29, 37.25, 36.88, 33.94, 31.83, 25.09, 25.06, 20.73, 18.92, 18.06, 11.13, 3.12, 2.93 |
| F74 | — | — | HRMS-ESI (m/z) ([M]⁺) calcd for $C_{27}H_{40}N_2O_7$, 504.2836; found, 504.2858 | ¹H NMR (CDCl₃) δ 8.55 (d, J = 6.9 Hz, 1H), 8.33 (d, J = 5.4 Hz, 1H), 7.00 (d, J = 5.5 Hz, 1H), 4.87 (dq, J = 9.3, 6.4 Hz, 1H), 4.55 (ddd, J = 10.8, 8.4, 7.0 Hz, 1H), 3.90 (s, 3H), 3.63 (dt, J = 8.7, 6.4 Hz, 1H), 3.43 (dt, J = 8.8, 6.8 Hz, 1H), 2.98 (t, J = 8.9 Hz, 1H), 2.40 (s, 3H), 2.33 (dt, J = 13.5, 7.1 Hz, 1H), 1.90-1.42 (m, 17H), 1.40 (d, J = 6.4 Hz, 3H), 1.35-1.22 (m, 1H), 1.17-0.97 (m, 1H), 0.93 (t, J = 7.4 Hz, 3H) | ¹³C NMR (CDCl₃) δ 172.75, 168.89, 162.36, 159.41, 146.70, 141.49, 137.46, 109.75, 84.56, 75.40, 75.35, 55.33, 56.28, 51.62, 42.21, 37.27, 36.83, 33.94, 31.79, 27.59, 25.10, 25.08, 23.54, 20.75, 18.96, 18.08, 10.73 |
| F75 | — | — | HRMS-ESI (m/z) ([M]⁺) calcd for $C_{28}H_{42}N_2O_7$, 518.2992; found, 518.2998 | ¹H NMR (CDCl₃) δ 8.55 (d, J = 8.1 Hz, 1H), 8.33 (d, J = 5.4 Hz, 1H), 7.00 (d, J = 5.4 Hz, 1H), 4.87 (dq, J = 9.3, 6.4 Hz, 1H), 4.55 (ddd, J = 10.8, 8.4, 6.9 Hz, 1H), 3.90 (s, 3H), 3.46 (dd, J = 8.4, 6.1 Hz, 1H), 3.24 (dd, J = 8.4, 6.7 Hz, 1H), 2.96 (t, J = 8.9 Hz, 1H), 2.40 (s, 3H), 2.36-2.26 (m, 1H), 1.92-1.42 (m, 13H), 1.40 (d, J = 6.4 Hz, 3H), 1.36-1.21 (m, 2H), 1.16-0.96 (m, 3H), 0.99-0.83 (m, 6H) | ¹³C NMR (CDCl₃) δ 172.76, 168.89, 162.36, 159.41, 146.70, 141.49, 137.45, 109.75, 84.28, 80.39, 75.46, 56.28, 51.63, 42.23, 37.23, 36.73, 33.97, 31.73, 29.21, 27.58, 25.09, 20.75, 19.56, 19.44, 18.98, 18.14 |
| F76 | — | — | HRMS-ESI (m/z) ([M]⁺) calcd for | ¹H NMR (CDCl₃) δ 8.57 (d, J = 7.3 Hz, 1H), 8.34 (d, J = 5.4 Hz, 1H), 7.34-7.23 (m, 2H), 7.00 (d, J = 5.5 Hz, 1H), 6.95 | ¹³C NMR (CDCl₃) δ 172.74, 168.92, 162.39, 159.67, 159.42 146.71, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | $C_{25}H_{30}N_2O_7$, 470.2053; found, 470.2059 | (dd, J = 7.6, 5.2 Hz, 3H), 5.09 (dq, J = 9.1, 6.4 Hz, 1H), 4.61 (ddd, J = 10.9, 8.2, 7.0 Hz, 1H), 4.15 (t, J = 8.8 Hz, 1H), 3.91 (s, 3H), 2.40 (s, 3H), 2.36 (m, 1H), 1.99-1.86 (m, 1H), 1.68 (ddt, J = 17.7, 14.9, 8.9 Hz, 3H), 1.38 (m, 1H), 1.30 (d, J = 6.5 Hz, 3H), 1.27 (m, 1H), 1.00 (d, J = 6.9 Hz, 3H) | 141.42, 137.48, 129.58, 120.98, 115.48, 109.80, 82.30, 74.69, 56.29, 51.70, 37.61, 33.80, 32.47, 20.76, 19.24, 18.27, 17.76 |
| F77 | 68-70 | — | HRMS-ESI (m/z) [M + H]⁺ calcd for $C_{26}H_{33}N_2O_7$, 485.2282; found, 485.2286 | ¹H NMR (CDCl₃) δ 8.55 (s, 1H), 8.33 (d, J = 5.4 Hz, 1H), 7.42-7.24 (m, 5H), 7.00 (d, J = 5.5 Hz, 1H), 4.94 (dq, J = 9.2, 6.4 Hz, 1H), 4.71 (d, J = 10.8 Hz, 1H), 4.63-4.54 (m 2H), 3.90 (s, 3H), 3.22 (t, J = 8.9 Hz, 1H), 2.40 (s, 3H), 2.39-2.29 (m, 1H), 1.82-1.72 (m, 1H), 1.61 (ddt, J = 19.1, 9.4, 5.7 Hz, 3H), 1.46 (d, J = 6.4 Hz, 3H), 1.33 (q, J = 10.8 Hz, 1H), 1.16 (dd, J = 7.3, 3.7 Hz, 1H), 1.07 (d, J = 6.8 Hz, 3H) | ¹³C NMR (CDCl₃) δ 172.77, 168.94, 162.39, 159.41, 146.72 141.44, , 138.05, 137.46, 128.47, 127.82, 127.74, 109.78, 99.99, 85.30, 75.59, 75.19, 56.30, 51.63, 37.95, 33.89, 32.32, 20.78, 19.07, 18.20, 17.79 |
| F78 | — | — | HRMS-ESI (m/z) [M + H]⁺ calcd for $C_{27}H_{35}N_2O_8$ 515.2388, found 515.2409 | ¹H NMR (CDCl₃) δ 8.57 (d, J = 7.3 Hz, 1H), 8.34 (d, J = 5.4 Hz, 1H), 7.29 (d, J = 7.6 Hz, 2H), 7.01 (d, J = 5.5 Hz, 1H), 6.98-6.90 (m, 3H), 5.07 (dq, J = 9.1, 6.5 Hz, 1H), 4.68-4.55 (m, 1H), 4.23 (t, J = 8.8 Hz, 1H), 3.91 (s, 3H), 3.37 (t, J = 6.8 Hz, 2H), 3.26 (s, 3H), 2.44-2.34 (m, 4H), 1.86 (dddd, J = 23.6, 19.2, 11.4, 6.0 Hz, 3H), 1.77-1.59 (m, 2H), 1.55-1.43 (m, 1H), 1.37 (d, J = 11.6 Hz, 1H), 1.28 (t, J = 6.0 Hz, 3H), 1.23-1.13 (m, 1H) | ¹³C NMR (CDCl₃) δ 172.65, 168.92, 162.39, 159.45, 146.72, 141.41, 129.62, 121.05, 115.38, 109.80, 81.12, 74.82, 70.80, 58.45, 56.29, 51.63, 40.10, 33.81, 30.56, 28.18, 20.76, 19.14, 18.33 |
| F79 | 96-100 | — | ESIMS m/z 561 ([M + H]⁺) | ¹H NMR (CDCl₃) δ 8.53 (d, J = 8.4 Hz, 1H), 8.33 (d, J = 5.5 Hz, 1H), 7.35-7.27 (m, 2H), 7.10-6.94 (m, 8H), 5.12 (dq, J = 9.1, 6.4 Hz, 1H), 4.63 (dt, J = 10.9, 7.5 Hz, 1H), 4.33 (t, J = 8.9 Hz, 1H), 3.89 (s, 3H), 2.97 (dd, J = 13.3, 3.2 Hz, 1H), 2.41 (s, 3H), 2.39-2.27 (m, 5H), 2.16-2.02 (m, 1H), 1.72-1.50 (m, 3H), 1.34 (d, J = 6.5 Hz, 3H), 1.33-1.19 (m, 2H) | ¹³C NMR (CDCl₃) δ 172.55, 168.83, 162.34, 159.62, 159.36, 146.65, 141.31, 137.42, 137.01, 135.34, 129.62, 128.96, 128.61, 121.12, 115.50, 109.76, 81.10, 74.64, 56.22, 51.52, 45.62, 36.35, 33.75, 26.67, 20.95, 20.69, 18.83, 18.31 |
| F80 | — | — | HRMS-ESI (m/z) [M + H]⁺ calcd for $C_{26}H_{32}O_7BrN_2$, 563.1387; found, 563.1387 | ¹H NMR (CDCl₃) δ 8.58 (d, J = 7.5 Hz, 1H), 8.33 (d, J = 5.4 Hz, 1H), 7.39-7.22 (m, 2H), 7.10-6.82 (m, 4H), 5.10 (dq, J = 9.1, 6.4 Hz, 1H), 4.61 (ddd, J = 10.9, 8.1, 6.9 Hz, 1H), 4.22 (t, J = 8.7 Hz, 1H), 3.89 (s, 3H), 3.45 (ddd, J = 10.0, 7.4, 5.0 Hz, 1H), 3.39-3.26 (m, 1H), 2.40 (s, 3H), 2.43-2.33 (m, 1H), 2.19-1.98 (m, 2H), 1.88-1.75 (m, 2H), 1.75-1.57 (m, 2H), 1.46-1.34 (m, 1H), 1.30 (d, J = 6.5 Hz, 3H), 1.26-1.15 (m, 1H) | ¹³C NMR (CDCl₃) δ 172.57, 168.89, 162.44, 159.44, 159.18, 146.77, 141.32, 137.49, 129.75, 121.34, 115.39, 109.91, 80.93, 74.67, 56.32, 51.66, 41.28, 34.17, 33.58, 31.56, 28.28, 20.77, 19.18, 18.27 |
| F81 | — | — | HRMS-ESI (m/z) [M + H]⁺ calcd for $C_{26}H_{33}O_7N_2$, 485.2282; found, 485.2288 | ¹H NMR (CDCl₃) δ 8.58 (s, 1H), 8.34 (d, J = 5.4 Hz, 1H), 7.29 (d, J = 7.9 Hz, 2H), 7.00 (d, J = 5.5 Hz, 1H), 6.99-6.90 (m, 3H), 5.18-5.00 (m, 1H), 4.61 (dt, J = 10.6, 7.7 Hz, 1H), 4.20 (t, J = 8.8 Hz, 1H), 3.91 (s, 3H), 2.40 (s, 3H), 2.39- | ¹³C NMR (CDCl₃) δ 172.70, 168.92, 162.39, 159.67, 159.43, 146.71, 141.44, 129.59, 120.94, 115.40, 109.79, 81.46, 74.84, 56.29, 51.65, 44.96, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | — | — | | 2.30 (m, 1H), 1.85 (dt, J = 14.6, 6.9 Hz, 1H), 1.74-1.58 (m, 4H), 1.37 (q, J = 11.5 Hz, 1H), 1.28 (d, J = 6.4 Hz, 3H), 1.26 - 1.19 (m, 1H), 1.15 (d, J = 15.0 Hz, 1H), 0.87 (t, J = 7.2 Hz, 3H) | 33.86, 27.10, 23.53, 20.76, 18.82, 18.36, 11.89 |
| F82 | — | — | HRMS-ESI (m/z) [M + H]$^+$ calcd for C$_{26}$H$_{31}$O$_7$N$_2$F$_2$, 521.2094; found, 521.2107 | $^1$H NMR (CDCl$_3$) δ 8.57 (d, J = 7.4 Hz, 1H), 8.34 (d, J = 5.4 Hz, 1H), 7.40-7.27 (m, 2H), 7.10-6.86 (m, 4H), 6.06-5.65 (m, 1H), 5.10 (dq, J = 9.1, 6.5 Hz, 1H), 4.62 (ddd, J = 11.0, 8.3, 6.9 Hz, 1H), 4.22 (t, J = 8.7 Hz, 1H), 3.91 (s, 3H), 2.48-2.33 (m, 4H), 2.14-1.94 (m, 2H), 1.94-1.71 (m, 3H), 1.71-1.59 (m, 1H), 1.47-1.34 (m, 1H), 1.30 (d, J = 6.5 Hz, 3H), 1.29-1.22 (m, 1H) | $^{13}$C NMR (CDCl$_3$) δ 172.57, 168.90, 162.43, 159.45, 158.92, 146.73, 141.33, 137.51, 129.84, 121.56, 116.74 (t, J = 239.3 Hz), 115.26, 109.85, 80.59, 74.49, 56.30, 51.64, 37.56, 35.79 (t, j= 20.9 Hz), 33.55, 29.50, 20.75, 19.30, 18.24 |
| F83 | — | — | HRMS-ESI (m/z) [M + H]$^+$ calcd for C$_{28}$H$_{41}$O$_8$N$_2$, 533.2857; found, 533.2857 | $^1$H NMR (CDCl$_3$) δ 8.55 (s, 1H), 8.33 (d, J = 5.4 Hz, 1H), 7.00 (d, J = 5.4 Hz, 1H), 4.99-4.79 (m, 1H), 4.56 (dt, J = 10.7, 7.7 Hz, 1H), 3.91 (s, 3H), 3.55-3.38 (m, 4H), 3.25 (dq, J = 6.6, 3.3 Hz, 2H), 3.06 (t, J = 8.8 Hz, 1H), 2.40 (s, 3H), 2.33 (dt, J = 13.3, 6.3 Hz, 1H), 1.99 (d, J = 9.7 Hz, 1H), 1.78-1.60 (m, 3H), 1.57-1.45 (m, 2H), 1.41 (d, J = 6.4 Hz, 3H), 1.30 (q, J = 11.8, 11.4 Hz, 1H), 1.06 (ddd, J = 12.9, 11.1, 6.7 Hz, 3H), 0.60-0.48 (m, 4H), 0.29-0.15 (m, 4H) | $^{13}$C NMR (CDCl$_3$) δ 172.67, 168.92, 162.36, 159.40, 146.70, 141.43, 137.45, 109.76, 83.99, 78.39, 75.47, 75.33, 69.12, 56.28, 51.55, 40.50, 33.86, 30.65, 28.19, 20.76, 18.96, 18.06, 11.09, 10.66, 3.18, 3.02, 2.95, 2.88 |
| F84 | — | — | HRMS-ESI (m/z) [M + H]$^+$ calcd for C$_{30}$H$_{38}$O$_8$N$_2$, 555.2701; found, 555.2713 | $^1$H NMR (CDCl$_3$) δ 8.34 (d, J = 7.0 Hz, 1H), 8.20-7.97 (m, 1H), 7.06 (t, J = 7.9 Hz, 2H), 6.78 (d, J = 5.4 Hz, 1H), 6.76-6.64 (m, 3H), 4.71 (dq, J = 8.9, 6.4 Hz, 1H), 4.36 (dt, J = 10.7, 7.2 Hz, 1H), 3.80 (td, J = 7.1, 6.3, 2.7 Hz, 2H), 3.68 (s, 3H), 3.27 (dd, J = 9.6, 7.2 Hz, 1H), 3.21 (dd, J = 9.6, 6.8 Hz, 1H), 2.91 (t, J = 8.9 Hz, 1H) 2.18 (s, 3H), 2.13 (dt, J = 13.2, 6.8 Hz, 1H), 2.06-1.90 (m, 1H), 1.71-1.55 (m, 2H), 1.48 (dddd, J = 25.6, 20.4, 14.3, 7.2 Hz, 2H), 1.34 (dt, J = 22.3, 9.7 Hz, 1H), 1.22 (d, J = 6.4 Hz, 3H), 1.18-1.02 (m, 1H), 0.86 (ddt, J = 12.2, 7.3, 4.1 Hz, 2H), 0.39-0.29 (m, 2H), −0.01 (q, J = 4.8 Hz, 2H) | $^{13}$C NMR (CDCl$_3$) δ 172.64, 168.87, 162.39, 159.42, 158.86, 146.73, 141.40, 137.46, 129.42, 120.60, 114.49, 109.82, 83.94, 78.22, 75.25, 66.18, 56.29, 51.56, 40.29, 34.67, 33.81, 30.35, 28.23, 20.75, 19.07, 18.08, 11.09, 3.16, 2.93 |
| F85 | — | — | HRMS-ESI (m/z) [M + H]$^+$ calcd for C$_{20}$H$_{27}$O$_7$N$_2$, 407.1813; found, 407.1829 | $^1$H NMR (CDCl$_3$) δ 8.63 (d, J = 6.9 Hz, 1H), 8.32 (dd, J = 5.4, 1.5 Hz, 1H), 7.00 (d, J = 5.5 Hz, 1H), 5.10-4.92 (m, 1H), 4.67-4.38 (m, 1H), 3.89 (d, J = 1.5 Hz, 3H), 3.85-3.75 (m, 1H), 3.75-3.62 (m, 1H), 3.42 (dd, J = 9.5, 6.3 Hz, 1H), 2.40 (d, J = 1.2 Hz, 3H), 2.39-2.29 (m, 1H), 2.13-1.93 (m, 2H), 1.89 (dd, J = 17.2, 7.8 Hz, 1H), 1.74 (td, J = 14.9, 14.0, 5.0 Hz, 1H), 1.63 (t, J = 13.5 Hz, 1H), 1.57-1.44 (m, 1H), 1.41 (d, J = 6.3 Hz, 3H), 1.36 (dd, J = 12.8, 6.0 Hz, 1H), 1.26 (s, 1H) | $^{13}$C NMR (CDCl$_3$) δ 173.54, 168.83, 162.26, 159.39, 146.70, 141.43, 137.42, 109.81, 86.83, 73.26, 67.69, 56.27, 53.00, 39.69, 36.09, 35.75, 32.56, 21.77, 20.73, 18.35 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F86 | — | — | HRMS-ESI (m/z) [M + H]$^+$ calcd for C$_{26}$H$_{31}$N$_2$O$_7$, 483.2126; found, 483.2144 | $^1$H NMR (CDCl$_3$) δ 8.59 (s, 1H), 8.35 (d, J = 5.4 Hz, 1H), 7.27 (d, J = 2.9 Hz, 2H), 7.01 (d, J = 5.5 Hz, 1H), 6.93 (dd, J = 13.2, 7.6 Hz, 3H), 5.77 (ddd, J = 18.2, 10.3, 8.1 Hz, 1H), 5.16 (dt, J = 9.1, 6.4 Hz, 1H) 5.04 (d, J = 17.1 Hz, 1H), 4.95 (d, J = 10.3 Hz, 1H), 4.69-4.57 (m, 1H), 4.30 (t, J = 8.8 Hz, 1H), 3.91 (s, 3H), 2.58-2.46 (m, 1H), 2.40 (s, 3H), 2.40-2.33 (m, 1H), 1.89 (dq, J = 14.3, 7.4 Hz, 1H), 1.77 (td, J = 16.3, 15.5, 8.5 Hz, 2H), 1.46 -1.24 (m, 5H) | $^{13}$C NMR (CDCl$_3$) δ 172.71, 168.92, 162.40, 159.43, 159.32, 146.72, 141.38, 138.52, 129.49, 121.09, 116.17, 115.78, 109.81, 80.51, 74.46, 56.29, 51.68, 47.45, 33.80, 31.19, 20.76, 19.75, 18.30 |
| F87 | — | — | HRMS-ESI (m/z) [M + H]$^+$ calcd for C$_{27}$H$_{35}$N$_2$O$_7$, 499.2439; found, 499.2449 | $^1$H NMR (CDCl$_3$) δ 8.49 (d, J = 8.0 Hz, 1H), 8.32 (dd, J = 5.4, 0.6 Hz, 1H), 7.33-7.26 (m, 2H), 7.22-7.13 (m, 3H), 6.99 (d, J = 5.5 Hz, 1H), 4.90 (dq, J = 9.2, 6.4 Hz, 1H), 4.57 (ddd, J = 10.9, 8.4, 7.0 Hz, 1H), 3.89 (d, J = 0.9 Hz, 3H), 3.82 (dq, J = 8.8, 6.9 Hz, 1H), 3.63 (dq, J = 8.9, 7.0 Hz, 1H), 3.17 (t, J = 9.1 Hz, 1H), 3.09 (dd, J = 13.2, 3.4 Hz, 1H), 2.39 (s, 3H), 2.35 (dd, J = 13.4, 11.8 Hz, 1H), 2.32-2.20 (m, 1H), 1.83 (ddq, J = 12.2, 7.7, 3.7 Hz, 1H), 1.70-1.52 (m, 2H), 1.50-1.38 (m, 1H), 1.45 (d, J = 6.4 Hz, 3H), 1.25 (t, J = 7.0 Hz, 3H), 1.21-1.12 (m, 1H), 0.87 (ddt, J = 18.0, 6.4, 3.2 Hz, 1H) | $^{13}$C NMR (CDCl$_3$) δ 172.64, 168.90, 162.38, 159.41, 146.70, 141.43, 140.75, 137.46, 128.87, 128.34, 125.90, 109.78, 84.20, 75.21, 69.22, 56.28, 51.51, 45.94, 36.91, 33.90, 26.64, 20.76, 18.75, 18.02, 15.73 |
| F88 | — | — | HRMS-ESI (m/z) [M + H]$^+$ calcd for C$_{28}$H$_{37}$N$_2$O$_7$, 513.2595; found, 513.2606 | $^1$H NMR (CDCl$_3$) δ 8.49 (d, J = 8.4 Hz, 1H), 8.32 (d, J = 5.4 Hz, 1H), 7.31-7.26 (m, 1H), 7.22-7.14 (m, 3H), 6.99 (d, J = 5.4 Hz, 1H), 4.90 (dq, J = 9.2, 6.4 Hz, 1H), 4.57 (ddd, J = 10.9, 8.4, 7.0 Hz, 1H), 3.89 (s, 3H), 3.73 (dt, J = 8.7, 6.5 Hz, 1H), 3.59-3.41 (m, 1H), 3.16 (t, J = 9.1 Hz, 1H), 3.10 (dd, J = 13.3, 3.3 Hz, 1H), 2.39 (s, 3H), 2.35 (dd, J = 13.3, 11.8 Hz, 1H), 2.31-2.20 (m, 1H), 1.84 (ddt, J = 12.1, 8.2, 3.9 Hz, 1H), 1.72-1.51 (m, 5H), 1.49-1.40 (m, 1H), 1.45 (d, J = 6.4 Hz, 3H), 1.21-1.11 (m, 1H), 0.98 (t, J = 7.4 Hz, 3H), 0.91-0.79 (m, 1H) | $^{13}$C NMR (CDCl$_3$) δ 172.63, 168.90, 162.38, 159.41, 146.70, 141.43, 140.81, 137.46, 128.87, 128.34, 125.88, 109.77, 83.99, 75.59, 75.25, 56.28, 51.51, 46.06, 36.82, 33.90, 26.61, 23.60, 20.76, 18.77, 18.09, 10.75 |
| F89 | 48-50 | (Neat) 3375, 2951, 1746, 1675, 1492, 1202 | HRMS-ESI (m/z) ([M]$^+$) calcd for C$_{30}$H$_{40}$N$_2$O$_8$, 556.2785; found, 556.2794 | $^1$H NMR (CDCl$_3$) δ 8.36 (d, J = 8.0 Hz, 1H), 8.29 (d, J = 5.4 Hz, 1H), 7.34-7.22 (m, 2H), 7.01-6.88 (m, 4H), 5.75 (s, 2H), 5.14-5.02 (m, 1H), 4.62 (ddd, J = 10.8, 8.1, 7.0 Hz, 1H), 4.26-4.17 (m, 1H), 3.91 (s, 3H), 2.46-2.33 (m, 1H), 2.07 (s, 3H), 1.93-1.31 (m, 7H), 1.30 (d, J = 6.4 Hz, 3H), 1.28-1.04 (m, 4H), 0.80 (d, J = 6.6 Hz, 3H), 0.79 (d, J = 6.6 Hz, 3H) | $^{13}$C NMR (CDCl$_3$) δ 172.82, 170.26, 162.97, 160.25, 159.71, 145.76, 143.94, 142.42, 129.57, 120.96, 115.49, 109.63, 89.49, 81.63, 74.87, 56.19, 51.93, 43.23, 36.40, 33.62, 28.27, 27.88, 27.57, 23.04, 22.06, 20.88, 18.94, 18.39 |
| F90 | — | (Neat) 3378, 2953, 1745, 1678, 1506, | HRMS-ESI (m/z) ([M]$^+$) calcd for C$_{28}$H$_{44}$N$_2$O$_8$, 536.3098; | $^1$H NMR (CDCl$_3$) δ 8.34 (d, J = 8.1 Hz, 1H), 8.27 (d, J = 5.3 Hz, 1H), 6.95 (d, J = 5.4 Hz, 1H), 5.74 (s, 2H), 4.94-4.80 (m, 1H), 4.57 (ddd, J = 10.7, 8.1, 7.0 Hz, 1H), 3.91 (s, 3H), | $^{13}$C NMR (CDCl$_3$) δ 172.86, 170.24, 162.92, 160.22, 145.74, 143.88, 142.48, 109.57, 89.49, 84.30, 80.42, 75.43, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | 1203 | found, 536.3107 | 3.46 (dd, J = 8.4, 6.3 Hz, 1H), 3.27 (dd, J = 8.4, 6.5 Hz, 1H), 3.07-2.95 (m, 1H), 2.41-2.28 (m, 1H), 2.07 (s, 3H), 1.91-1.39 (m, 7H), 1.41 (d, J = 6.4 Hz, 3H), 1.38-0.95 (m, 5H), 0.95-0.81 (m, 12H) | 56.17, 51.86, 43.53, 36.54, 33.67, 29.17, 28.09, 28.02, 27.55, 22.96, 22.27, 20.85, 19.50, 19.45, 18.84, 18.16 |
| F91 | — | (Neat) 3378, 2949, 1742, 1676, 1504, 1368, 1201 | HRMS-ESI (m/z) ([M]$^+$) calcd for C$_{28}$H$_{42}$N$_2$O$_8$, 534.2941; found, 534.2945 | $^1$H NMR (CDCl$_3$) δ 8.32 (d, J = 8.1 Hz, 1H), 8.28 (d, J = 5.3 Hz, 1H), 6.95 (d, J = 5.4 Hz, 1H), 5.74 (s, 2H), 4.96-4.81 (m, 1H), 4.63-4.50 (m, 1H), 3.91 (s, 3H), 3.57-3.31 (m 2H), 3.09-2.97 (m, 1H), 2.43-2.25 (m, 1H), 2.07 (s, 3H), 1.85-1.45 (m, 6H), 1.42 (d, J = 6.4 Hz, 3H), 1.38-0.92 (m, 6H), 0.89 (d, J = 6.6 Hz, 3H), 0.88 (d, J = 6.6 Hz, 3H), 0.62-0.51 (m, 2H), 0.27-0.17 (m, 2H) | $^{13}$C NMR (CDCl$_3$) δ 172.84, 170.27, 162.95, 160.23, 145.76, 143.90, 142.50, 109.57, 89.52, 84.36, 78.65, 75.41, 56.18, 51.85, 43.61, 36.44 33.71 28.08, 27.34, 23.03, 22.22, 20.88, 18.74, 18.11, 11.13, 3.09, 3.02 |
| F92 | — | (Neat) 3378, 2937, 1744, 1678, 1504, 1369, 1202; | HRMS-ESI (m/z) ([M]$^+$) calcd for C$_{27}$H$_{42}$N$_2$O$_8$, 522.2941; found, 522.2965 | $^1$H NMR (CDCl$_3$) δ 8.33 (d, J = 8.1 Hz, 1H), 8.28 (d, J = 5.4 Hz, 1H), 6.95 (d, J = 5.4 Hz, 1H), 5.74 (s, 2H), 4.93-4.81 (m, 1H), 4.57 (ddd, J = 10.8, 8.1, 7.0 Hz, 1H), 3.91 (s, 3H), 3.69-3.58 (m, 1H), 3.52-3.41 (m, 1H), 3.08-2.98 (m, 1H), 2.41-2.28 (m, 1H), 2.07 (s, 3H), 1.83-1.26 (m, 9H), 1.42 (d, J = 6.5 Hz, 3H), 1.26-0.95 (m, 4H), 0.94 (t, J = 7.4 Hz, 3H), 0.89 (d, J = 6.6 Hz, 3H), 0.88 (d, J = 6.6 Hz, 3H) | $^{13}$C NMR (CDCl$_3$) δ 172.87, 170.27, 162.93, 160.24, 145.74 143.92, 142.51, 109.56, 89.54, 84.58, 75.42, 56.17, 51.86, 43.54, 36.51, 33.71, 28.10, 27.48, 23.54, 23.03, 22.22, 20.88, 18.81, 18.11, 10.71 |
| F93 | — | (Neat) 3384, 2951, 1747, 1678, 1506, 1371, 1252 | HRMS-ESI (m/z) ([M]$^+$) calcd for C$_{28}$H$_{41}$F$_3$N$_2$O$_8$, 590.2815; found, 590.2828 | $^1$H NMR (CDCl$_3$) δ 8.33 (d, J = 8.1 Hz, 1H), 8.28 (d, J = 5.3 Hz, 1H), 6.95 (d, J = 5.4 Hz, 1H), 5.74 (s, 2H), 4.93-4.80 (m, 1H), 4.57 (ddd, J = 10.8, 8.1, 7.0 Hz, 1H), 3.91 (s, 3H), 3.79-3.68 (m, 1H), 3.61-3.50 (m, 1H), 3.09-2.98 (m, 1H), 2.41-2.28 (m, 1H), 2.28-2.12 (m, 2H), 2.07 (s, 3H), 1.91-1.29 (m, 9H), 1.40 (d, J = 6.4 Hz, 3H), 1.29-0.92 (m, 4H), 0.92-0.83 (m, 6H) | $^{13}$C NMR (CDCl$_3$) δ 172.82, 170.26, 162.95, 160.24, 145.74, 143.92, 142.45, 127.16 (q, J = 276.1 Hz), 109.59, 89.51, 84.84, 75.03, 71.54, 56.17, 51.85, 43.47, 36.47, 33.63, 30.81 (q, J = 28.9 Hz), 28.19, 28.07, 27.46, 23.05 (q, J = 3.2 Hz), 22.95, 22.16, 20.86, 18.83, 18.13 $^{19}$F NMR (CDCl$_3$) δ −66.44 |
| F94 | — | (Neat) 3379, 2952, 1743, 1678, 1505, 1369, 1202 | HRMS-ESI (m/z) ([M]$^+$) calcd for C$_{29}$H$_{44}$N$_2$O$_8$, 548.3098; found, 548.3112 | $^1$H NMR (CDCl$_3$) δ 8.35 (d, J = 8.0 Hz, 1H), 8.28 (d, J = 5.4 Hz, 1H), 6.94 (d, J = 5.4 Hz, 1H), 5.74 (s, 2H), 4.90-4.78 (m, 1H), 4.57 (ddd, J = 10.9, 8.0, 6.6 Hz, 1H), 4.08-3.99 (m, 1H), 3.91 (s, 3H), 3.14 (dd, J = 9.1, 7.9 Hz, 1H), 2.42-2.28 (m, 1H), 2.07 (s, 3H), 1.86-0.98 (m, 19H), 1.43 (d, J = 6.5 Hz, 3H), 0.89 (d, J = 6.6 Hz, 3H), 0.88 (d, J = 6.6 Hz, 3H) | $^{13}$C NMR (CDCl$_3$) δ 173.03, 170.28, 162.92, 160.25, 145.75, 143.93, 142.54, 109.55, 89.57, 83.55, 82.90, 75.85, 56.18, 52.12, 42.89, 36.86, 33.60, 32.75, 32.50, 28.27, 23.04, 22.97, 22.96, 22.37, 20.89, 19.19, 18.36 |
| F95 | — | (Neat) 3380, 2942, 1744, 1678, 1504, 1369, 1202 | HRMS-ESI (m/z) ([M]$^+$) calcd for C$_{25}$H$_{38}$N$_2$O$_8$, 494.2628; found, 494.2648 | $^1$H NMR (CDCl$_3$) δ 8.33 (d, J = 8.1 Hz, 1H), 8.28 (d, J = 5.4 Hz, 1H), 6.95 (d, J = 5.4 Hz, 1H), 5.74 (s, 2H), 4.92-4.78 (m, 1H), 4.58 (ddd, J = 10.7, 8.1, 7.1 Hz, 1H), 3.91 (s, 3H), 3.50 (s, 3H), 3.00-2.89 (m, 1H), 2.42-2.28 (m, 1H), 2.07 (s, 3H), 1.83-1.27 (m, 7H), 1.43 (d, J = 6.4 Hz, 3H), 1.27-0.91 (m, 4H), 0.90 (d, J = 6.6 | $^{13}$C NMR (CDCl$_3$) δ 172.82, 170.26, 162.94, 160.24, 145.75, 143.92, 142.50, 109.57, 89.53, 86.42, 75.14, 61.21, 56.18, 51.82, 43.57, 36.48, 33.70, 28.25, 28.16, 27.25, 23.09, 22.18, 20.88, 18.75, 18.06 |

TABLE 2-continued

Analytical Data

| Cmpd. No. | MP (°C.) | IR (cm$^{-1}$) | MASS | $^1$H NMR | $^{13}$C or $^{19}$F NMR |
|---|---|---|---|---|---|
| | | | | Hz, 3H), 0.88 (d, J = 6.6 Hz, 3H) | |
| F96 | — | (Neat) 3379, 2953, 1735, 1679, 1505, 1368, 1202 | HRMS-ESI (m/z) ([M]$^+$) calcd for C$_{30}$H$_{44}$N$_2$O$_9$, 576.3047; found, 576.3060 | $^1$H NMR (CDCl$_3$) δ 8.32 (d, J = 7.9 Hz, 1H), 8.28 (d, J = 5.4 Hz, 1H), 6.95 (d, J = 5.4 Hz, 1H), 5.74 (s, 2H), 5.09-4.94 (m, 1H), 4.93-4.82 (m, 1H), 4.68-4.54 (m, 1H), 3.91 (s, 3H), 2.82-2.67 (m, 1H), 2.45-2.31 (m, 1H), 2.07 (s, 3H), 1.99-1.39 (m, 13H), 1.39-1.14 (m, 4H), 1.26 (d, J = 6.3 Hz, 3H), 1.14-0.96 (m, 2H), 0.92-0.77 (m, 6H) | $^{13}$C NMR (CDCl$_3$) δ 176.16, 172.86, 170.27, 162.92, 160.26, 145.70, 144.01, 142.39, 109.60, 89.53, 76.13, 73.39, 56.18, 51.83, 44.09, 41.93, 36.34, 33.51, 30.06, 29.98, 27.99, 27.90, 27.45, 25.70, 25.68, 22.89, 22.19, 20.87, 18.74, 17.55 |
| F97 | — | (Neat) 3380, 2921, 1743, 1677, 1504, 1314, 1202 | HRMS-ESI (m/z) ([M]$^+$) calcd for C$_{30}$H$_{44}$N$_2$O$_8$, 560.3098; found, 560.3097 | $^1$H NMR (CDCl$_3$) δ 8.32 (d, J = 8.1 Hz, 1H), 8.28 (d, J = 5.3 Hz, 1H), 6.94 (d, J = 5.4 Hz, 1H), 5.74 (s, 2H), 4.96-4.81 (m, 1H), 4.57 (ddd, J = 10.8, 8.1, 7.0 Hz, 1H), 3.91 (s, 3H), 3.49 (dd, J = 9.6, 7.0 Hz, 1H), 3.37 (dd, J = 9.6, 6.8 Hz, 1H), 3.06-2.94 (m, 1H), 2.43-2.27 (m, 1H), 2.07 (s, 3H), 1.80-1.42 (m, 11H), 1.41 (d, J = 6.4 Hz, 3H), 1.37-0.69 (m, 9H), 0.63-0.49 (m, 2H), 0.28-0.16 (m, 2H) | $^{13}$C NMR (CDCl$_3$) δ 172.84, 170.27, 162.94, 160.24, 145.76, 143.92, 142.53, 109.56, 89.54, 84.40, 78.52, 75.41, 56.18, 51.84, 40.15, 38.32, 35.07, 34.60, 33.77, 32.35, 27.46, 26.70, 26.50, 26.17, 20.89, 18.81, 18.10, 11.15, 3.17, 2.94 |
| F98 | — | (Neat) 3382, 2939, 1746, 1678, 1508, 1314, 1203 | HRMS-ESI (m/z) ([M]$^+$) calcd for C$_{30}$H$_{37}$FN$_2$O$_8$, 572.2534; found, 572.2546 | $^1$H NMR (CDCl$_3$) δ 8.29 (d, J = 8.1 Hz, 1H), 8.27 (d, J = 5.4 Hz, 1H), 7.18-7.08 (m, 2H), 7.02-6.91 (m, 3H), 5.73 (s, 2H), 4.99-4.85 (m, 1H), 4.58 (ddd, J = 10.9, 8.1, 7.0 Hz, 1H), 3.90 (s, 3H), 3.58 (dd, J = 9.7, 7.0 Hz, 1H), 3.45 (dd, J = 9.7, 6.8 Hz, 1H), 3.21-3.14 (m, 1H), 3.14-3.05 (m, 1H), 2.40-2.25 (m, 2H), 2.06 (s, 3H), 1.89-1.76 (m, 1H), 1.64-1.50 (m, 2H), 1.47-1.36 (m, 1H), 1.46 (d, J = 6.5 Hz, 3H), 1.31-1.06 (m, 2H), 0.96-0.81 (m, 1H), 0.64-0.52 (m, 2H), 0.32-0.19 (m, 2H) | $^{13}$C NMR (CDCl$_3$) δ 172.69, 170.23, 162.95, 161.27 (d, J = 243.6 Hz), 160.22, 145.75, 143.88, 142.41, 136.32 (d, J = 3.2 Hz), 130.14 (d, J = 7.8 Hz), 115.11 (d, J = 21.0 Hz), 109.61, 89.46, 83.72, 78.77, 75.18, 56.17, 51.75, 46.16, 36.04, 33.62, 26.60, 20.85, 18.76, 18.08, 11.16, 3.14, 3.00 |
| F99 | — | (Neat) 3380, 2940, 1751, 1678, 1508, 1204 | HRMS-ESI (m/z) ([M]$^+$) calcd for C$_{32}$H$_{35}$FN$_2$O$_8$, 594.2377; found, 594.2395 | $^1$H NMR (CDCl$_3$) δ 8.33 (d, J = 8.0 Hz, 1H), 8.27 (d, J = 5.4 Hz, 1H), 7.36-7.26 (m, 2H), 7.11-6.89 (m, 8H), 5.74 (s, 2H), 5.18-5.06 (m, 1H), 4.64 (ddd, J = 11.0, 8.0, 6.9 Hz 1H), 4.39-4.28 (m, 1H), 3.90 (s, 3H), 3.02-2.91 (m, 1H), 2.43-2.29 (m, 2H), 2.14-1.99 (m, 1H), 2.07 (s, 3H), 1.74-1.62 (m, 2H), 1.62-1.46 (m, 1H), 1.34 (d, J = 6.4 Hz, 3H), 1.31-1.23 (m, 1H), 1.10-0.98 (m, 1H) | $^{13}$C NMR (CDCl$_3$) δ 172.70, 170.24, 162.97, 161.29 (d, J = 243.7 Hz) 160.25, 159.55, 145.75, 143.95, 142.35, 135.85 (d, J = 3.2 Hz), 130.10 (d, J = 7.8 Hz), 129.71, 121.25, 115.46, 115.10 (d, J = 21.1 Hz), 109.65, 89.46, 80.98, 74.59, 56.18, 51.84, 45.73, 36.10, 33.55, 26.79, 20.85, 18.94, 18.34 |
| F100 | — | (Neat) 3382, 2938, 1745, 1677, 1507, 1202 | HRMS-ESI (m/z) ([M]$^+$) calcd for C$_{29}$H$_{35}$FN$_2$O$_8$, 558.2377; found, 558.2390 | $^1$H NMR (CDCl$_3$) δ 8.29 (d, J = 8.5 Hz, 1H), 8.27 (d, J = 5.4 Hz, 1H), 7.17-7.07 (m, 2H), 7.02-6.90 (m, 3H), 6.03-5.88 (m, 1H), 5.74 (s, 2H), 5.33 (dq, J = 17.2, 1.6 Hz, 1H), 5.21 (dq, J = 10.4, 1.3 Hz, 1H), 4.99-4.86 (m, 1H), 4.59 (ddd, J = 10.9, 8.1, 7.0 Hz, 1H), 4.29 (ddt, J = 12.2, 5.6, 1.4 Hz, 1H), 4.11 (ddt, J = 12.1, 5.5, 1.4 Hz, 1H), 3.90 (s, 3H), 3.29-3.18 (m, 1H), 3.12-3.01 (m, 1H), 2.40-2.24 (m, | $^{13}$C NMR (CDCl$_3$) δ 172.71, 170.26, 162.96, 161.30 (d, J = 243.6 Hz), 160.24, 145.75, 143.93, 142.43, 136.27 (d, J = 3.3 Hz), 134.31, 130.14 (d, J = 7.7 Hz), 117.14, 115.12 (d, J = 21.1 Hz), 109.60, 89.50, 84.16, 75.04, 74.70, 56.18, 51.77, 45.99, 36.11, 33.63, 26.61, 20.88, 18.82, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 2H), 2.07 (s, 3H), 1.89-1.74 (m, 1H), 1.65-1.50 (m, 2H), 1.47 (d, J = 6.5 Hz, 3H), 1.47-1.34 (m, 1H), 1.28-1.14 (m, 1H), 0.97-0.78 (m, 1H) | 18.15 $^{19}$F NMR (CDCl$_3$) δ −117.47 |
| F101 | — | (Neat) 3381, 2937, 1745, 1677, 1508, 1372, 1203 | HRMS-ESI (m/z) ([M]$^+$) calcd for C$_{29}$H$_{37}$FN$_2$O$_8$, 560.2534; found, 560.2541 | $^1$H NMR (CDCl$_3$) δ 8.29 (d, J = 8.1 Hz, 1H), 8.26 (d, J = 5.4 Hz, 1H), 7.17-7.07 (m, 2H), 7.02-6.90 (m, 3H), 5.74 (s, 2H), 4.98-4.84 (m, 1H), 4.58 (ddd, J = 10.9, 8.1, 7.0 Hz, 1H), 3.90 (s, 3H), 3.73 (dt, J = 8.6, 6.5 Hz, 1H), 3.52 (dt, J = 8.7, 6.7 Hz, 1H), 3.21-3.11 (m, 1H), 3.11-3.01 (m, 1H), 2.41-2.25 (m, 2H), 2.06 (s, 3H), 1.86-1.72 (m, 1H), 1.70-1.51 (m, 4H), 1.46 (d, J = 6.4 Hz, 3H), 1.46-1.35 (m, 1H), 1.30-1.13 (m, 1H), 0.98 (t, J = 7.4 Hz, 3H), 0.94-0.79 (m, 1H) | $^{13}$C NMR (CDCl$_3$) δ 172.72, 170.24, 162.95, 161.27 (d, J = 243.5 Hz), 160.23, 145.75, 143.90, 142.43, 136.40 (d, J = 3.1 Hz), 130.13 (d, J = 7.7 Hz), 115.09 (d, J = 21.1 Hz), 109.60, 89.49, 83.92, 75.62, 75.19, 56.18, 51.77, 46.17, 36.00, 33.64, 26.61, 23.58, 20.86, 18.81, 18.09, 10.73 $^{19}$F NMR (CDCl$_3$) δ −117.52 |
| F102 | — | (Neat) 3382, 2957, 1744, 1677, 1508, 1369, 1203 | HRMS-ESI (m/z) ([M]$^+$) calcd for C$_{30}$H$_{39}$FN$_2$O$_8$, 574.2690; found, 574.2691 | $^1$H NMR (CDCl$_3$) δ 8.29 (d, J = 8.1 Hz, 1H), 8.27 (d, J = 5.4 Hz, 1H), 7.18-7.05 (m, 2H), 7.02-6.90 (m, 3H), 5.74 (s, 2H), 4.98-4.83 (m, 1H), 4.58 (ddd, J = 10.9, 8.1, 7.0 Hz, 1H), 3.90 (s, 3H), 3.56 (dd, J = 8.4, 6.3 Hz, 1H), 3.33 (dd, J = 8.4, 6.5 Hz, 1H), 3.19-3.10 (m, 1H), 3.10-3.01 (m, 1H), 2.41-2.24 (m, 2H), 2.07 (s, 3H), 1.97-1.71 (m, 2H), 1.63-1.51 (m 2H), 1.45 (d, J = 6.4 Hz, 3H), 1.45-1.34 (m, 1H), 1.29-1.14 (m, 1H), 0.97 (d, J = 6.8 Hz, 3H), 0.96 (d, J = 6.8 Hz, 3H), 0.93-0.79 (m, 1H) | $^{13}$C NMR (CDCl$_3$) δ 172.73, 170.27, 162.95, 161.28 (d, J = 243.5 Hz) 160.24, 145.75, 143.93, 142.44, 136.44 (d, J = 3.2 Hz), 130.13 (d, J = 7.8 Hz), 115.11 (d, J = 21.0 Hz), 109.58, 89.52 83.65, 80.70, 75.24, 56.18, 51.77, 46.31, 35.91, 33.66, 29.27, 26.56, 20.88, 19.53, 19.49, 18.84, 18.16 $^{19}$F NMR (CDCl$_3$) δ −117.53 |
| F103 | — | (Neat) 3382 2940, 1749, 1677, 1508, 1203 | HRMS-ESI (m/z) ([M]$^+$) calcd for C$_{28}$H$_{33}$F$_3$N$_2$O$_8$, 582.2189; found, 582.2191 | $^1$H NMR (CDCl$_3$) δ 8.29 (d, J = 8.4 Hz, 1H), 8.27 (d, J = 5.4 Hz, 1H), 7.18-7.05 (m, 2H), 7.03-6.89 (m, 3H), 5.94 (tt, J = 55.2, 3.9 Hz, 1H), 5.73 (s, 2H), 5.02-4.84 (m, 1H), 4.58 (ddd, J = 10.9, 8.1, 6.9 Hz, 1H), 4.06-3.91 (m, 1H), 3.90 (s, 3H), 3.86-3.72 (m, 1H), 3.32-3.21 (m, 1H), 3.11-2.98 (m, 1H), 2.44-2.24 (m, 2H), 2.06 (s, 3H), 1.92-1.76 (m, 1H), 1.68-1.38 (m, 3H), 1.47 (d, J = 6.4 Hz, 3H), 1.30-1.15 (m, 1H), 0.98-0.80 (m, 1H) | $^{13}$C NMR (CDCl$_3$) δ 172.59, 170.25, 162.98, 161.35 (d, J = 243.8 Hz), 160.25, 145.76, 143.94, 142.34, 135.86 (d, J = 3.2 Hz), 130.14 (d, J = 7.8 Hz), 115.19 (d, J = 21.1 Hz), 113.88 (t, J = 241.2 Hz), 109.65, 89.47, 85.53, 74.41, 72.60 (t, J = 27.6 Hz), 56.19, 51.74, 45.81, 35.93, 33.51, 26.57, 20.86, 18.86, 18.14 $^{19}$F NMR (CDCl$_3$) δ −117.21 |
| F104 | — | (Neat) 3379, 2943, 1732, 1677, 1507, 1201 | HRMS-ESI (m/z) ([M]+ calcd for C$_{32}$H$_{39}$FN$_2$O$_9$, 614.2640; found, 614.2649 | $^1$H NMR (CDCl$_3$) δ 8.29 (d, J = 7.8 Hz, 1H), 8.27 (d, J = 5.3 Hz, 1H), 7.12-7.02 (m, 2H), 7.02-6.90 (m, 3H), 5.73 (s, 2H), 5.11-4.94 (m, 2H), 4.62 (ddd, J = 11.0, 8.0, 7.0 Hz, 1H), 3.90 (s, 3H), 2.80-2.69 (m, 1H), 2.69-2.61 (m, 1H), 2.42-2.29 (m, 2H), 2.07 (s, 3H), 2.01-1.43 (m, 11H), 1.36 -1.16 (m, 2H), 1.29 (d, J = 5.6 Hz, 3H), 1.05-0.91 (m, 1H) | $^{13}$C NMR (CDCl$_3$) δ 176.11, 172.73, 170.27, 162.94, 161.35 (d, J = 244.0 Hz), 160.26, 145.71, 144.01, 142.33, 135.59 (d, J = 3.2 Hz) 130.07 (d, J = 7.8 Hz) 115.22 (d, J = 21.2 Hz), 109.63, 89.51, 75.54 73.16, 56.18, 51.75 44.16, 44.01, 35.93, 33.44, 30.06, 30.04, 26.82, 25.72, 25.70, 20.86, 18.73, 17.55 $^{19}$F NMR (CDCl$_3$) δ −117.11 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F105 | — | (Neat) 3380, 2940, 1734, 1677, 1508, 1201 | HRMS-ESI (m/z) ([M]$^+$) calcd for C$_{30}$H$_{37}$FN$_2$O$_9$, 588.2483; found, 588.2484 | $^1$H NMR (CDCl$_3$) δ 8.30 (d, J = 8.0 Hz, 1H), 8.26 (d, J = 5.3 Hz, 1H), 7.12-7.02 (m, 2H), 7.02-6.90 (m, 3H), 5.73 (s, 2H), 5.10-4.97 (m, 2H), 4.62 (ddd, J = 10.9, 8.0, 7.0 Hz, 1H), 3.91 (s, 3H), 2.65 (dd, J = 14.0, 3.6 Hz, 1H), 2.58 (hept, J = 7.0 Hz, 1H), 2.43-2.29 (m, 2H), 2.07 (s, 3H), 2.00-1.85 (m, 1H), 1.77-1.44 (m, 3H), 1.35-1.17 (m, 1H), 1.29 (d, J = 5.8 Hz, 3H), 1.22 (d, J = 7.1 Hz, 3H), 1.22 (d, J = 6.9 Hz, 3H); 1.06-0.91 (m, 1H) | $^{13}$C NMR (CDCl$_3$) δ 176.42, 172.70, 170.23, 162.94, 161.34 (d, J = 244.1 Hz), 160.25, 145.70, 143.98, 142.30, 135.54 (d, J = 3.2 Hz), 130.05 (d, J = 7.7 Hz), 115.20 (d, J = 21.2 Hz), 109.64, 89.46, 75.47, 73.07, 56.17, 51.73, 44.13, 35.84, 34.19, 33.40, 26.73, 20.84, 19.06, 18.97, 18.70, 17.48 $^{19}$F NMR (CDCl$_3$) δ −117.09 |
| F106 | — | — | ESIMS m/z 557.3 ([M + H]$^+$) | $^1$H NMR (CDCl$_3$) δ 8.29 (d, J = 8.3 Hz, 1H), 8.26 (d, J = 5.4 Hz, 1H), 7.32-7.25 (m, 2H), 7.23-7.13 (m, 3H), 6.94 (d, J = 5.4 Hz, 1H), 5.74 (s, 2H), 4.91 (dq, J = 9.3, 6.5 Hz, 1H), 4.58 (ddd, J = 10.9, 8.2, 7.0 Hz, 1H), 3.90 (s, 3H), 3.57 (dd, J = 8.4, 6.2 Hz, 1H), 3.34 (dd, J = 8.4, 6.5 Hz, 1H), 3.16 (t, J = 9.1 Hz, 1H), 3.11 (dd, J = 13.3, 3.2 Hz, 1H), 2.41-2.26 (m, 2H), 2.06 (s, 3H) 1.97-1.77 (m, 2H), 1.58 (tt, J = 8.6, 2.6 Hz, 2H), 1.46 (d, J = 6.4 Hz, 3H), 1.49-1.39 (m, 1H, overlapping), 1.27-1.13 (m, 1H), 0.97 (dd, J = 6.7, 5.4 Hz, 6H), 0.91-0.83 (m, 1H) | $^{13}$C NMR (CDCl$_3$) δ 172.76, 170.27, 162.95, 160.23, 145.75, 143.90, 142.47, 140.86, 128.87, 128.34, 125.88, 109.58, 89.52 83.71, 80.66, 75.29, 56.18, 51.79, 46.21, 36.74, 33.71, 29.28, 26.55, 20.88, 19.56, 19.50, 18.84, 18.18 |
| F107 | — | — | ESIMS m/z 555.4 ([M + H]$^+$) | $^1$H NMR (CDCl$_3$) δ 8.36-8.20 (m, 2H), 7.33-7.23 (m, 2H), 7.23-7.12 (m, 3H), 6.94 (d, J = 5.4 Hz, 1H), 5.73 (s, 2H), 4.93 (dq, J = 9.1, 6.4 Hz, 1H), 4.58 (ddd, J = 10.9, 8.1, 7.0 Hz, 1H), 3.90 (s, 3H), 3.59 (dd, J = 9.7, 7.0 Hz, 1H), 3.45 (dd, J = 9.7, 6.8 Hz, 1H), 3.28-3.04 (m, 2H), 2.42-2.23 (m, 2H), 2.06 (s, 3H), 1.89 (ddt, J = 12.2, 8.3, 3.9 Hz, 1H), 1.66-1.50 (m, 2H), 1.49-1.38 (m, overlapping, 1H), 1.46 (d, J = 6.4 Hz, 3H), 1.23-1.06 (m, 2H), 0.94-0.80 (m, 1H), 0.65-0.53 (m, 2H), 0.34-0.17 (m, 2H) | $^{13}$C NMR (CDCl$_3$) δ 172.73, 170.27, 162.95, 160.23, 145.75, 143.89, 142.45, 140.73, 128.89, 128.35, 125.90, 109.58, 89.50, 83.80, 78.76, 75.24, 56.18, 51.77, 46.07, 36.89, 33.70, 26.58, 20.88, 18.76, 18.11, 11.18, 3.16, 3.01 |
| F108 | — | — | ESIMS m/z 577.5 ([M + H]$^+$) | $^1$H NMR (CDCl$_3$) δ 8.31 (d, J = 8.0 Hz, 1H), 8.27 (d, J = 5.4 Hz, 1H), 7.35-7.21 (m, 3H), 7.21-7.08 (m, 3H), 7.06-6.91 (m, 4H), 5.74 (s, 2H), 5.12 (dq, J = 9.1, 6.5 Hz, 1H), 4.63 (ddd, J = 10.9, 8.1, 7.0 Hz, 1H), 4.36 (t, J = 8.9 Hz, 1H), 3.90 (s, 3H), 3.02 (dd, J = 13.4, 3.3 Hz, 1H), 2.46-2.29 (m, 2H), 2.16-2.08 (m, 1H), 2.06 (s, 3H), 1.76-1.63 (m, 2H), 1.63-1.49 (m, 1H), 1.35 (d, J = 6.5 Hz, 3H), 1.31-1.21 (m, 2H), 1.09-0.96 (m, 1H) | $^{13}$C NMR (75 MHz, CDCl3) δ 172.83, 170.35, 163.08, 160.35, 159.76, 145.85, 144.04, 142.52, 140.36, 129.81, 128.92, 128.43, 126.07, 121.32, 115.65, 109.75, 89.59, 81.26, 74.78, 56.28, 51.97, 45.79, 37.01, 33.72, 26.86, 20.97, 19.06, 18.49 |
| F109 | — | — | HRMS-ESI (m/z) [M + H]$^+$ calcd for C$_{29}$H$_{39}$N$_2$O$_8$, | $^1$H NMR (CDCl$_3$) δ 8.34-8.24 (m, 2H), 7.34-7.24 (m, 2H), 7.24-7.13 (m, 3H), 6.94 (d, J = 5.4 Hz, 1H), 5.73 (s, 2H), 4.91 (dq, J = 9.2, 6.4 Hz, | $^{13}$C NMR (CDCl$_3$) δ 172.78, 170.30, 162.97, 160.25, 145.77, 143.91, 142.49, 140.82, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | 543.2701; found, 543.2707 | 1H), 4.58 (ddd, J = 10.9, 8.1, 7.0 Hz, 1H), 3.90 (s, 3H), 3.78-3.70 (m, 1H), 3.57-3.48 (m, 1H), 3.22-3.14 (m, 1H), 3.11 (dd, J = 13.2, 3.3 Hz, 1H), 2.41-2.24 (m, 2H), 2.06 (s, 3H), 1.90-1.79 (m, 1H), 1.73-1.53 (m, 4H), 1.50-1.38 (m, 1H), 1.46 (d, J = 6.4 Hz, 3H) 1.27-1.15 (m, 1H), 0.98 (t, J = 7.4 Hz, 3H), 0.94-0.81 (m, 1H) | 128.89, 128.35, 125.89, 109.59, 89.51, 84.00, 75.61, 75.26, 56.18, 51.78, 46.08, 36.82, 33.70, 26.58, 23.60, 20.88, 18.80, 18.11 10.75. |
| F110 | — | — | ESIMS m/z 569.3 ([M + H]$^+$) | $^1$H NMR (CDCl$_3$) δ 8.29 (d, J = 8.1 Hz, 1H), 8.26 (d, J = 5.4 Hz, 1H), 7.35-7.23 (m, 2H), 7.23-7.12 (m, 3H), 6.93 (d, J = 5.4 Hz, 1H), 4.89 (dq, J = 9.1, 6.5 Hz, 1H), 4.56 (ddd, J = 11.1, 8.1, 6.7 Hz, 1H), 4.13 (ddd, J = 9.5, 4.7, 2.7 Hz, 1H), 3.90 (s, 3H), 3.40-3.24 (m, 1H), 3.20 (dd, J = 13.3, 3.3 Hz, 1H), 2.36-2.19 (m, 2H), 2.06 (s, 3H), 1.89-1.67 (m, 7H), 1.64-1.53 (m, 4H), 1.48 (d, J = 6.5 Hz, 3H), 1.45-1.36 (m, 1H), 1.23-1.06 (m, 2H), 1.00-0.83 (m, 2H) | $^{13}$C NMR (CDCl$_3$) δ 172.95, 170.26, 162.92, 160.23, 145.75, 143.91, 142.48, 141.13, 128.89, 128.34, 125.82, 109.57, 89.53, 83.85, 82.36, 75.69, 56.17, 52.01, 45.31, 36.92, 33.53, 32.84, 32.56, 29.70, 27.84, 23.03, 22.98, 20.87, 19.13, 18.37 |
| F111 | — | — | ESIMS m/z 529.3 ([M + H]$^+$) | $^1$H NMR (CDCl$_3$) δ 8.27 (t, J = 7.0 Hz, 2H), 7.24 (dt, J = 39.0, 7.6 Hz, 5H), 6.94 (d, J = 5.4 Hz, 1H), 5.73 (s, 2H), 4.91 (dq, J = 12.9, 6.8 Hz, 1H), 4.58 (dt, J = 10.7, 7.6 Hz, 1H), 3.90 (s, 3H), 3.82 (t, J = 7.8 Hz, 1H), 3.70-3.56 (m, 1H), 3.19 (t, J = 9.0 Hz, 1H), 3.10 (dd, J = 13.1, 3.6 Hz, 1H), 2.53-2.23 (m, 2H), 2.06 (s, 3H), 1.84 (qd, J = 8.0, 3.7 Hz, 1H), 1.58 (dt, J = 9.6, 5.1 Hz, 2H), 1.47 (t, J = 5.8 Hz, 4H), 1.25 (t, J = 6.3 Hz, 4H), 1.01-0.78 (m, 1H) | $^{13}$C NMR (CDCl$_3$) δ 172.76, 170.27, 162.95, 160.24, 145.76, 143.91, 142.47, 140.76, 128.88, 128.34, 125.90, 109.58, 89.52, 84.22, 75.21, 69.24, 56.18, 51.78, 45.97, 36.92, 33.71, 26.61, 20.88, 18.78, 18.04, 15.74 |
| F112 | — | — | ESIMS m/z 559.2 ([M + H]$^+$) | $^1$H NMR (CDCl$_3$) δ 8.31-8.24 (m, 2H), 7.31-7.25 (m, 2H), 7.23-7.14 (m, 3H), 6.93 (d, J = 5.4 Hz, 1H), 5.73 (s, 2H), 4.94 (dq, J = 9.2, 6.4 Hz, 1H), 4.58 (ddd, J = 10.9, 8.1, 7.0 Hz, 1H), 3.95 (ddd, J = 9.9, 6.0, 3.7 Hz, 1H), 3.90 (s, 3H), 3.72 (ddd, J = 10.4, 5.6, 3.4 Hz, 1H), 3.62-3.51 (m, 2H), 3.40 (s, 3H), 3.23 (t, J = 9.1 Hz, 1H), 3.19-3.09 (m, 1H), 2.42-2.24 (m, 2H), 2.06 (s, 3H), 1.96-1.85 (m, 1H), 1.63-1.53 (m, 2H), 1.48 (d, J = 6.4 Hz, 3H), 1.46-1.39 (m, 1H), 1.25-1.15 (m, 1H), 0.93-0.81 (m, 1H) | $^{13}$C NMR (CDCl$_3$) δ 172.70, 170.26, 162.94, 160.23, 145.75, 143.92, 142.46, 140.78, 128.91, 128.33, 125.88, 109.57, 89.52, 84.75, 75.06, 72.83, 72.16, 59.09, 56.18, 51.76, 45.85, 36.78, 33.70, 26.55, 20.88, 18.81, 18.17 |
| F113 | — | — | ESIMS m/z 563.6 ([M + H]$^+$) | $^1$H NMR (CDCl$_3$) δ 8.33 (d, J = 8.1 Hz, 1H), 8.28 (d, J = 5.4 Hz, 1H), 6.95 (d, J = 5.4 Hz, 1H), 5.74 (s, 2H), 4.87 (dq, J = 9.2, 6.4 Hz, 1H), 4.57 (ddd, J = 10.8, 8.2, 7.1 Hz, 1H), 3.91 (s, 3H), 3.46 (dd, J = 8.4, 6.1 Hz, 1H), 3.24 (dd, J = 8.4, 6.7 Hz, 1H), 2.98 (t, J = 8.8 Hz, 1H), 2.42-2.27 (m, 1H), 2.07 (s, 3H), 1.83 (dt, J = 13.2, 6.6 Hz, 1H), 1.77-1.55 (m, 8H), 1.41 (d, J = 6.3 Hz, 3H), 1.37- | $^{13}$C NMR (CDCl$_3$) δ 172.86, 170.26, 162.94, 160.24, 145.74, 143.91, 142.55, 109.56, 89.54, 84.33, 80.37, 75.48, 56.17, 51.87, 40.04, 38.15, 35.08, 34.60, 33.75, 32.27, 29.21, 27.47, 26.69, 26.52, 26.20, 20.87, 19.58, 19.47, 18.87, 18.16 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 1.11 (m, 8H), 1.01-0.87 (m, 8H), 0.77 (t, J = 11.2 Hz, 1H) | |
| F114 | — | — | HRMS-ESI (m/z) ([M]$^+$) calcd for C$_{33}$H$_{38}$N$_2$O$_9$, 606.2577; found, 606.2585 | $^1$H NMR (CDCl$_3$) δ 8.31 (d, J = 8.1 Hz, 1H), 8.28 (d, J = 5.4 Hz, 1H), 7.36-7.23 (m, 2H), 7.08-6.99 (m, 4H), 6.99-6.91 (m, 2H), 6.80 (d, J = 8.6 Hz, 2H), 5.74 (s, 2H), 5.12 (dq, J = 9.2, 6.4 Hz, 1H), 4.63 (ddd, J = 10.9, 8.0, 6.8 Hz, 1H), 4.33 (t, J = 8.9 Hz, 1H), 3.91 (s, 3H), 3.77 (s, 3H), 3.00-2.90 (m, 1H), 2.42-2.25 (m, 2H), 2.07 (s, 3H), 1.73-1.63 (m, 2H), 1.63-1.50 (m, 2H), 1.34 (d, J = 6.4 Hz, 3H), 1.33-1.17 (m, 1H), 1.06-0.97 (m, 1H) | $^{13}$C NMR (CDCl$_3$) δ 172.75, 170.30, 162.96, 160.25, 159.67, 157.83, 145.74, 143.97, 142.39, 132.22, 129.69, 121.18, 115.55, 113.73, 109.60, 89.52, 81.13, 74.71, 56.19, 55.20, 51.85, 45.83, 35.96, 33.65, 26.67, 20.89, 18.91, 18.39 |
| F115 | — | — | HRMS-ESI (m/z) ([M]$^+$) calcd for C$_{31}$H$_{40}$N$_2$O$_8$, 568.2785; found, 568.2786 | $^1$H NMR (CDCl$_3$) δ 8.35 (d, J = 8.0 Hz, 1H), 8.29 (d, J = 5.4 Hz, 1H), 7.35-7.25 (m, 2H), 6.99-6.90 (m, 4H), 5.75 (s, 2H), 5.07 (dq, J = 9.2, 6.5 Hz, 1H), 4.62 (ddd, J = 10.9, 8.0, 6.9 Hz, 1H), 4.25-4.12 (m, 1H), 3.91 (s, 3H), 2.41 (dtd, J = 13.7, 7.0, 1.4 Hz, 1H), 2.07 (s, 3H), 1.92-1.76 (m, 3H), 1.76-1.59 (m, 4H), 1.60-1.32 (m, 7H), 1.30 (d, J = 6.5 Hz, 3H), 1.20-1.06 (m, 1H), 1.08-0.90 (m, 2H) | $^{13}$C NMR (CDCl$_3$) δ 172.84, 170.26, 162.97, 160.26, 159.78, 145.75, 143.97, 142.46, 129.58, 120.93, 115.56, 109.61, 89.54, 81.67, 74.89, 56.19, 51.94, 42.05, 37.27, 36.85, 33.71, 33.66, 31.77, 27.59, 25.04, 20.88, 19.10, 18.39. |
| F116 | — | — | HRMS-ESI (m/z) ([M]$^+$) calcd for C$_{31}$H$_{40}$N$_2$O$_9$, 584.2734; found, 584.2744 | $^1$H NMR (CDCl$_3$) δ 8.42-8.15 (m, 2H), 7.09 (d, J = 8.6 Hz, 2H), 6.94 (d, J = 5.4 Hz, 1H), 6.83 (d, J = 8.6 Hz, 2H), 5.73 (s, 2H), 4.92 (dq, J = 9.1, 6.4 Hz, 1H), 4.58 (ddd, J = 10.9, 8.1, 7.0 Hz, 1H), 3.90 (s, 3H), 3.79 (s, 3H), 3.58 (dd, J = 9.7, 7.0 Hz, 1H), 3.45 (dd, J = 9.7, 6.8 Hz, 1H), 3.17 (t, J = 9.0 Hz, 1H), 3.08 (dd, J = 13.4, 3.4 Hz, 1H), 2.41-2.22 (m, 2H), 2.06 (s, 3H), 1.91-1.76 (m, 1H), 1.61-1.52 (m, 2H), 1.52-1.40 (m, 1H), 1.46 (d, J = 6.4 Hz, 3H), 1.23-1.17 (m, 1H), 1.17-1.07 (m, 1H), 0.91-0.77 (m, 1H), 0.64-0.54 (m, 2H), 0.29-0.21 (m, 2H) | $^{13}$C NMR (CDCl$_3$) δ 172.74, 170.28, 162.94, 160.23, 157.82, 145.75, 143.91, 142.46, 132.68, 129.74, 113.77, 109.57, 89.52, 83.80, 78.77, 75.25, 56.18, 55.23, 51.76, 46.21, 35.92, 33.72, 26.52, 20.88, 18.75, 18.10, 11.18, 3.16, 3.00 |
| F117 | — | — | HRMS-ESI (m/z) ([M]$^+$) calcd for C$_{29}$H$_{42}$N$_2$O$_8$, 546.2941; found, 546.2956 | $^1$H NMR (CDCl$_3$) δ 8.33 (d, J = 8.1 Hz, 1H), 8.28 (d, J = 5.3 Hz, 1H), 6.94 (d, J = 5.4 Hz, 1H), 5.74 (s, 2H), 4.89 (dq, J = 9.3, 6.4 Hz, 1H), 4.57 (dt, J = 10.8, 7.3 Hz, 1H), 3.91 (s, 3H), 3.50 (dd, J = 9.6, 7.0 Hz, 1H), 3.36 (dd, J = 9.6, 6.8 Hz, 1H), 3.01 (t, J = 8.9 Hz, 1H), 2.46-2.26 (m, 1H), 2.07 (s, 3H), 1.91-1.43 (m, 13H), 1.42 (d, J = 6.5 Hz, 3H), 1.36-1.26 (m, 1H), 1.18-0.92 (m, 4H), 0.60-0.49 (m, 2H), 0.21 (dt, J = 6.0, 4.5 Hz, 2H) | $^{13}$C NMR (CDCl$_3$) δ 172.85, 170.28, 162.94, 160.24, 145.75, 143.93, 142.52, 109.55, 89.56, 84.35, 78.54, 75.38, 56.18, 51.87, 42.35, 37.26, 36.89, 33.96, 33.77, 31.84, 27.51, 25.10, 25.07, 20.89, 18.96, 18.10, 11.14, 3.14, 2.94 |
| F118 | — | — | HRMS-ESI (m/z) ([M]$^+$) calcd for C$_{31}$H$_{42}$N$_2$O$_9$, 586.2890; found, 586.2905 | $^1$H NMR (CDCl$_3$) δ 8.28 (dd, J = 9.8, 6.7 Hz, 2H), 7.08 (d, J = 8.5 Hz, 2H), 6.94 (d, J = 5.4 Hz, 1H), 6.88-6.71 (m, 2H), 5.74 (s, 2H), 4.96-4.73 (m, 1H), 4.58 (ddd, J = 10.9, 8.1, 7.0 Hz, 1H), 3.90 (s, 3H), 3.79 (s, 3H), 3.56 (dd, J = 8.4, 6.2 | $^{13}$C NMR (CDCl$_3$) δ 172.78, 170.28, 162.96, 160.25, 157.82, 145.75, 143.92, 142.49, 132.83, 129.73, 113.77, 109.59, 89.53, 83.73, 80.65, 75.31, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | Hz, 1H), 3.34 (dd, J = 8.4, 6.5 Hz, 1H), 3.14 (t, J = 9.0 Hz, 1H), 3.07-2.99 (m, 1H), 2.41-2.20 (m, 2H), 2.06 (s, 3H), 1.95-1.84 (m, 1H), 1.84-1.65 (m, 2H), 1.66-1.52 (m, 2H), 1.45 (d, J = 6.4 Hz, 3H), 1.32-1.21 (m, 1H), 1.00-0.93 (m, 6H), 0.88-0.82 (m, 1H) | 56.18, 55.23, 51.81, 46.35, 35.79, 33.73, 31.60, 29.28, 26.53, 22.67, 20.88, 19.56, 19.50, 18.85, 18.18, 14.13 |
| F119 | — | — | HRMS-ESI (m/z) ([M]$^+$) calcd for C$_{30}$H$_{40}$N$_2$O$_9$, 572.2734; found, 572.2720 | $^1$H NMR (CDCl$_3$) δ 8.28 (dd, J = 8.8, 6.6 Hz, 2H), 7.08 (d, J = 8.5 Hz, 2H), 6.94 (d, J = 5.4 Hz, 1H), 6.83 (d, J = 8.6 Hz, 2H), 5.74 (s, 2H), 4.90 (dq, J = 9.2, 6.4 Hz, 1H), 4.58 (ddd, J = 10.9, 8.1, 7.0 Hz, 1H), 3.90 (s, 3H), 3.79 (s, 3H), 3.73 (dt, J = 8.7, 6.5 Hz, 1H), 3.52 (dt, J = 8.7, 6.7 Hz, 1H), 3.16 (t, J = 9.0 Hz, 1H), 3.04 (dd, J = 13.4, 3.3 Hz, 1H), 2.43-2.22 (m, 2H), 2.06 (s, 3H), 1.79 (ddq, J = 12.2, 7.4, 3.7 Hz, 1H), 1.70-1.52 (m, 5H), 1.45 (d, J = 6.4 Hz, 3H), 1.25-1.13 (m, 1H), 0.98 (t, J = 7.4 Hz, 3H), 0.93-0.81 (m, 1H) | $^{13}$C NMR (CDCl$_3$) δ 172.76, 170.27, 162.94, 160.23, 157.80, 145.74, 143.91, 142.47, 132.77, 129.72, 113.75, 109.57, 89.52, 84.00, 75.60, 75.26, 56.18, 55.23, 51.78, 46.21, 35.86, 33.73, 26.54, 23.60, 20.88, 18.79, 18.11, 10.75 |
| F120 | — | (Thin Film) 3379, 2954, 1744, 1677, 1505, 1202 | HRMS-ESI (m/z) ([M]$^+$) calcd for C$_{28}$H$_{38}$N$_2$O$_9$, 546.2577; found, 546.2602 | $^1$H NMR (CDCl$_3$) δ 8.31 (d, J = 8.1 Hz, 1H), 8.27 (d, J = 5.3 Hz, 1H), 7.30 (dd, J = 1.9, 0.9 Hz, 1H), 6.94 (d, J = 5.4 Hz, 1H), 6.28 (dd, J = 3.1, 1.9 Hz, 1H), 6.02 (d, J = 3.1 Hz, 1H), 5.74 (s, 2H), 4.92 (dq, J = 9.2, 6.4 Hz, 1H), 4.58 (ddd, J = 10.8., 8.0, 6.8, Hz, 1H), 3.90 (s, 3H), 3.50 (dd, J = 8.4, 6.5 Hz, 1H), 3.30 (dd, J = 8.4, 6.4 Hz, 1H), 3.14 (t, J = 9.0 Hz, 1H), 3.01 (dd, J = 14.7, 3.5 Hz, 1H), 2.52 (dd, J = 14.6, 11.2 Hz, 1H), 2.31 (dt, J = 12.6, 6.4 Hz, 1H), 2.07 (s, 3H), 2.01-1.91 (m, 1H), 1.87 (dt, J = 13.2, 6.6 Hz, 1H), 1.55 (dddd, J = 20.1, 12.2, 10.0, 5.2 Hz, 3H), 1.44 (d, J = 6.4 Hz, 3H), 1.36-1.20 (m, 1H), 1.06-0.95 (m, 1H), 0.94 (d, J = 6.7 Hz, 6H) | $^{13}$C NMR (CDCl$_3$) δ 172.78, 170.29, 162.93, 160.24, 154.69, 145.75, 143.93, 142.45, 141.01, 110.09, 109.56, 106.04, 89.54, 83.46, 80.26, 75.19, 56.18, 51.80, 43.22, 33.63, 29.34, 29.20, 27.89, 20.89, 19.49, 19.46, 18.85, 18.17 |
| F121 | — | — | HRMS-ESI (m/z) ([M]$^+$) calcd for C$_{29}$H$_{42}$N$_2$O$_9$, 562.2890; found, 562.2888 | $^1$H NMR (CDCl$_3$) δ 8.32 (d, J = 8.0 Hz, 1H), 8.28 (d, J = 5.3 Hz, 1H), 6.95 (d, J = 5.4 Hz, 1H), 5.74 (d, J = 0.8 Hz, 2H), 5.00 (dq, J = 9.4, 6.3 Hz, 1H), 4.85 (t, J = 9.1 Hz, 1H), 4.61 (ddd, J = 10.9, 7.9, 6.9 Hz, 1H), 3.91 (s, 3H), 2.57 (hept, J = 7.0 Hz, 1H), 2.39 (dtd, J = 13.2, 6.5, 1.9 Hz, 1H), 2.07 (s, 3H), 1.91-1.27 (m, 13H), 1.25 (d, J = 6.3 Hz, 3H), 1.19 (dd, J = 7.0, 1.6 Hz, 6H), 1.13-1.00 (m, 3H), 1.00-0.86 (m, 1H) | $^{13}$C NMR (CDCl$_3$) δ 176.47, 172.86, 170.29, 162.93, 160.27, 145.71, 144.03, 142.42, 109.59, 89.56, 76.08, 73.32, 56.18, 51.84, 40.64 37.00, 36.53, 34.29, 33.68, 33.57, 31.86, 27.31, 25.03, 25.02 20.87, 19.11, 18.95, 18.86, 17.50 |
| F122 | — | — | HRMS-ESI (m/z) ([M]$^+$) calcd for C$_{28}$H$_{42}$N$_2$O$_8$, 534.2941; found, 534.2945 | $^1$H NMR (CDCl$_3$) δ 8.33 (d, J = 8.1 Hz, 1H), 8.28 (d, J = 5.3 Hz, 1H), 6.95 (d, J = 5.4 Hz, 1H), 5.74 (s, 2H), 4.87 (dq, J = 9.2, 6.4 Hz, 1H), 4.57 (ddd, J = 10.8, 8.1, 6.9 Hz, 1H), 3.91 (s, 3H), 3.64 (dt, J = 8.7, 6.4 Hz, 1H), 3.44 (dt, J = 8.7, 6.7 Hz, 1H), 3.00 (t, J = 8.8 Hz, | $^{13}$C NMR (CDCl$_3$) δ 172.85, 170.24, 162.93, 160.23, 145.74, 143.89, 142.50, 109.58, 89.50, 84.55, 75.37, 75.32, 56.17, 51.87, 42.22, 37.25, 36.81, 33.92, 33.72, 31.77, 27.54, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 1H), 2.41-2.29 (m, 1H), 2.07 (s, 3H), 1.94-1.39 (m, 15H), 1.41 (d, J = 6.3 Hz, 3H), 1.37-1.22 (m, 1H), 1.17-0.98 (m, 3H), 0.94 (t, J = 7.4 Hz, 3H) | 25.08, 25.06, 23.53, 20.86, 18.98, 18.08, 10.72 |
| F123 | — | — | HRMS-ESI (m/z) ([M]+ calcd for C$_{29}$H$_{44}$N$_2$O$_8$, 548.3098; found, 548.3094 | $^1$H NMR (CDCl$_3$) δ 8.33 (d, J = 8.1 Hz, 1H), 8.28 (d, J = 5.4 Hz, 1H), 6.95 (d, J = 5.4 Hz, 1H), 5.74 (s, 2H), 4.87 (dq, J = 9.2, 6.4 Hz, 1H), 4.57 (ddd, J = 10.8, 8.1, 6.9 Hz, 1H), 3.91 (s, 3H), 3.47 (dd, J = 8.4, 6.1 Hz, 1H), 3.24 (dd, J = 8.4, 6.7 Hz, 1H), 2.98 (t, J = 8.8 Hz, 1H), 2.41-2.29 (m, 1H), 2.07 (s, 3H), 1.90-1.38 (m, 11H), 1.41 (d, J = 6.5 Hz, 3H), 1.37-1.21 (m, 2H), 1.17-0.96 (m, 5H), 0.92 (t, J = 6.8 Hz, 6H) | $^{13}$C NMR (CDCl$_3$) δ 172.86, 170.25, 162.93, 160.23, 145.74, 143.90, 142.52, 109.57, 89.53, 84.28, 80.39, 75.44, 56.17, 51.89, 42.25, 37.22, 36.72, 33.96, 33.74, 31.72, 29.20, 27.54, 25.09, 25.07, 20.87, 19.55, 19.44, 19.01, 18.15 |
| F124 | — | — | HRMS-ESI (m/z) ([M]+ calcd for C$_{26}$H$_{32}$N$_2$O$_8$, 500.2159; found, 500.2162 | $^1$H NMR (CDCl$_3$) δ 8.36 (d, J = 8.0 Hz, 1H), 8.28 (d, J = 5.4 Hz, 1H), 7.34-7.24 (m, 2H), 7.01-6.88 (m, 4H), 5.75 (s, 2H), 5.09 (dq, J = 9.1, 6.4 Hz, 1H), 4.63 (dt, J = 10.9, 7.1 Hz, 1H), 4.17 (t, J = 8.8 Hz, 1H), 3.91 (s, 3H), 2.41 (dt, J = 13.0, 6.6 Hz, 1H), 2.07 (s, 3H), 1.93 (dd, J = 9.2, 5.4 Hz, 1H), 1.80-1.61 (m, 3H), 1.40 (dt, J = 13.5, 10.7 Hz, 1H), 1.31 (d, J = 6.4 Hz, 3H), 1.29-1.24 (m, 1H), 1.01 (d, J = 6.9 Hz, 3H) | $^{13}$C NMR (CDCl$_3$) δ 172.85, 170.29, 162.96, 160.26, 159.68, 145.75, 143.97, 142.41, 129.76, 120.98, 115.48, 109.60, 89.54, 82.29, 74.69, 56.19, 51.95, 37.67, 33.62, 32.38, 20.89, 19.26, 18.30, 17.76 |
| F125 | 142-147 | — | HRMS-ESI (m/z) [M + H]$^+$ calcd for C$_{27}$H$_{35}$N$_2$O$_8$, 515.2388; found, 515.2390 | $^1$H NMR (CDCl$_3$) δ 8.34 (d, J = 8.0 Hz, 1H), 8.28 (d, J = 5.4 Hz, 1H), 7.40-7.28 (m, 5H), 6.95 (d, J = 5.4 Hz, 1H), 5.75 (s, 2H), 4.95 (dq, J = 9.2, 6.4 Hz, 1H), 4.72 (d, J = 10.8 Hz, 1H), 4.64-4.55 (m, 2H), 3.91 (s, 3H), 3.23 (t, J = 8.9 Hz, 1H), 2.37 (dt, J = 13.3, 6.7 Hz, 1H), 2.07 (s, 3H), 1.82-1.72 (m, 1H), 1.70-1.58 (m, 3H), 1.48 (d, J = 6.4 Hz, 3H), 1.41-1.30 (m, 1H), 1.18 (dt, J = 7.5, 3.5 Hz, 1H), 1.08 (d, J = 6.8 Hz, 3H) | $^{13}$C NMR (CDCl$_3$) δ 172.89, 170.32, 162.96, 160.25, 145.77, 143.94, 142.47, 138.05, 128.47, 127.82, 127.75, 109.58, 89.56, 85.30, 75.60, 75.20, 56.19, 51.89, 37.99, 33.71, 32.27, 20.90, 19.10, 18.22, 17.79 |
| F126 | — | — | ESIMS m/z 571 ([M + H]$^+$) | $^1$H NMR (CDCl$_3$) δ 8.25-8.16 (m, 2H), 7.06-6.94 (m, 4H), 6.86 (d, J = 5.4 Hz, 1H), 5.66 (s, 2H), 4.83 (dq, J = 9.3, 6.4 Hz, 1H), 4.50 (dt, J = 11.0, 7.5 Hz, 1H), 3.82 (s, 3H), 3.49 (dd, J = 8.4, 6.2 Hz, 1H), 3.26 (dd, J = 8.4, 6.5 Hz, 1H), 3.07 (t, J = 9.0 Hz, 1H), 2.99 (dd, J = 13.2, 3.1 Hz, 1H), 2.24 (s, 5H), 1.99 (s, 3H), 1.90-1.69 (m, 2H), 1.59-1.45 (m, 2H), 1.44-1.30 (m, 4H), 1.17-1.05 (m, 1H), 0.92-0.86 (m, 6H), 0.83-0.73 (m, 1H) | $^{13}$C NMR (CDCl$_3$) δ 171.71, 169.22, 161.90, 159.19, 144.70, 142.86, 141.42, 136.64, 134.27, 127.98, 127.68, 108.54, 88.47, 82.67, 79.59, 74.25, 55.13, 50.74, 45.17, 35.19, 32.67, 28.22, 25.46, 19.97, 19.83, 18.51, 18.45, 17.77, 17.13 |
| F127 | 55-60 | — | ESIMS m/z 569 ([M + H]$^+$) | $^1$H NMR (CDCl$_3$) δ 8.28 (d, J = 8.1 Hz, 1H), 8.26 (d, J = 5.4 Hz, 1H), 7.12-7.04 (m, 4H), 6.94 (d, J = 5.4 Hz, 1H), 5.73 (s, 1H), 4.92 (dq, J = 9.2, 6.4 Hz, 1H), 4.58 (ddd, J = 10.9, 8.2, 7.0 Hz, 1H), 3.90 (s, 3H), 3.59 (dd, J = 9.7, 7.0 Hz, 1H), 3.45 (dd, J = 9.7, 6.9 Hz, 1H), 3.17 (t, J = 9.1 Hz, 1H), 3.10 (dd, J = 13.3, 3.3 Hz, 1H), 2.40-2.23 (m, 5H), 2.06 (s, | $^{13}$C NMR (CDCl$_3$) δ 172.65, 170.17, 162.86, 160.14, 145.67, 143.80, 142.35, 137.47, 135.25, 128.95, 128.66, 109.51, 89.40, 83.70, 78.66, 75.16, 56.10, 51.68, 46.01, 36.30, 33.61, 26.44, 20.93, 20.79, 18.65, 18.02, 11.09, 3.07, |

TABLE 2-continued

Analytical Data

| Cmpd. No. | MP (°C.) | IR (cm$^{-1}$) | MASS | $^1$H NMR | $^{13}$C or $^{19}$F NMR |
|---|---|---|---|---|---|
| | | | | 3H), 1.94-1.79 (m, 1H), 1.65-1.39 (m, 5H), 1.33-1.08 (m, 3H), 0.92-0.82 (m, 2H), 0.65-0.54 (m, 2H), 0.25 (dtd, J = 5.5, 3.9, 3.5, 1.6 Hz, 2H) | 2.92 |
| F128 | — | — | HRMS-ESI (m/z) ([M + Na]$^+$) calcd for C$_{25}$H$_{37}$FN$_2$O$_8$Na, 535.2426; found, 535.2423 | $^1$H NMR (CDCl$_3$) δ 8.34 (d, J = 8.1 Hz, 1H), 8.28 (d, J = 5.4 Hz, 1H), 6.95 (d, J = 5.4 Hz, 1H), 5.74 (s, 2H), 4.90 (dq, J = 9.1, 6.4 Hz, 1H), 4.58 (ddt, J = 9.4, 5.9, 4.6 Hz, 2H), 4.50-4.39 (m, 1H), 3.91 (s, 3H), 3.45 (dd, J = 8.4, 6.6 Hz, 1H), 3.26 (dd, J = 8.4, 6.4 Hz, 1H), 3.14-3.02 (m, 1H), 2.36 (dt, J = 12.9, 6.7 Hz, 1H), 2.07 (s, 3H), 2.06-1.98 (m, 1H), 1.84 (dp, J = 13.4, 6.7 Hz, 1H), 1.78-1.60 (m, 4H), 1.57 (s, 1H), 1.42 (d, J = 6.4 Hz, 3H), 1.39-1.29 (m, 1H), 1.10 (dd, J = 14.3, 5.7 Hz, 1H), 0.92 (d, J = 6.8 Hz, 6H) | $^{13}$C NMR (CDCl$_3$) δ 170.35, 167.84, 160.52, 157.81, 143.31, 141.51, 140.02, 107.14, 87.11, 81.42, 81.36, 79.73, 77.78, 72.81, 53.74, 49.43, 37.34, 37.30, 31.13, 29.17, 28.98, 26.73, 26.26, 18.44, 17.02, 16.98, 16.74, 15.69 |
| F129 | — | — | HRMS-ESI (m/z) ([M + H]$^+$) calcd for C$_{33}$H$_{39}$N$_2$O$_9$, 607.2650; found, 607.2664 | $^1$H NMR (CDCl$_3$) δ 8.36 (d, J = 8.0 Hz, 1H), 8.29 (d, J = 5.4 Hz, 1H), 7.33-7.27 (m, 2H), 7.25-7.21 (m, 2H), 7.02-6.87 (m, 5H), 6.86-6.77 (m, 2H), 5.75 (s, 2H), 5.19-5.04 (m, 1H), 4.64 (dt, J = 10.9, 7.0 Hz, 1H), 4.29 (t, J = 8.7 Hz, 1H), 3.96 (t, J = 6.0 Hz, 2H), 3.91 (s, 3H), 2.41 (dt, J = 12.6, 6.4 Hz, 1H), 2.07 (s, 5H), 1.98-1.84 (m, 1H), 1.84-1.64 (m, 3H), 1.40 (q, J = 11.3 Hz, 1H), 1.32 (d, J = 6.5 Hz, 3H), 1.29-1.20 (m, 1H) | $^{13}$C NMR (CDCl$_3$) δ 171.99, 169.51, 162.20, 159.49, 158.57, 158.01, 144.98, 143.21, 141.63, 128.91, 128.61, 120.40, 119.82, 114.64, 113.68, 108.83, 88.76, 80.39, 74.00, 65.27, 55.41, 51.14, 39.45, 32.81, 29.76, 27.68, 20.11, 18.54, 17.56 |
| F130 | — | — | HRMS-ESI (m/z) ([M + H]$^+$) calcd for C$_{28}$H$_{37}$N$_2$O$_9$, 545.2494; found, 545.2519 | $^1$H NMR (CDCl$_3$) δ 8.36 (d, J = 8.0 Hz, 1H), 8.29 (d, J = 5.4 Hz, 1H), 7.33-7.27 (m, 2H), 6.98-6.91 (m, 4H), 5.75 (s, 2H), 5.08 (dq, J = 9.1, 6.5 Hz, 1H), 4.63 (dt, J = 10.9, 7.0 Hz, 1H), 4.25 (t, J = 8.8 Hz, 1H), 3.91 (s, 3H), 3.38 (t, J = 6.8 Hz, 2H), 3.26 (s, 3H), 2.41 (dt, J = 12.4, 6.3 Hz, 1H), 2.07 (s, 3H), 1.99-1.78 (m, 3H), 1.78-1.61 (m, 2H), 1.49 (ddt, J = 13.6, 10.1, 6.6 Hz, 1H), 1.44-1.33 (m, 1H), 1.30 (d, J = 6.5 Hz, 3H), 1.23-1.14 (m, 1H) | $^{13}$C NMR (CDCl$_3$) δ 172.77, 170.29, 162.97, 160.26, 159.47, 145.75, 143.99, 142.43, 129.62, 121.06, 115.39, 109.61, 89.54, 81.12, 74.83, 70.80, 58.44, 56.19, 51.90, 40.15, 33.63, 30.56, 28.14 20.89, 19.18, 18.35 |
| F131 | — | — | HRMS-ESI (m/z) [M + H]$^+$ calcd for C$_{26}$H$_{41}$N$_2$O$_8$S, 541.2578; found, 541.2581 | $^1$H NMR (CDCl$_3$) δ 8.34 (d, J = 8.1 Hz, 1H), 8.28 (d, J = 5.4 Hz, 1H), 6.94 (d, J = 5.4 Hz, 1H), 5.74 (s, 2H), 4.96-4.83 (m, 1H), 4.58 (dt, J = 10.8, 7.0 Hz, 1H), 3.91 (s, 3H), 3.45 (dd, J = 8.4, 6.5 Hz, 1H), 3.27 (dd, J = 8.4, 6.5 Hz, 1H), 3.04 (t, J = 8.7 Hz, 1H), 2.59 (ddd, J = 12.8, 9.7, 4.6 Hz, 1H), 2.49-2.41 (m, 1H), 2.41-2.31 (m, 1H), 2.10 (s, 3H), 2.07 (s, 3H), 1.94 (ddd, J = 11.9, 9.5, 6.9 Hz, 1H), 1.84 (dt, J = 13.2, 6.6 Hz, 1H), 1.80-1.60 (m, 3H), 1.52 (ddt, J = 13.9, 9.7, 4.7 Hz, 2H), 1.41 (d, J = 6.4 Hz, 3H), 1.34 (q, J = 11.1 Hz, 1H), 1.09-1.00 (m, 1H), 0.92 (dd, J = 6.7, 1.0 Hz, 6H) | $^{13}$C NMR (CDCl$_3$) δ 172.79, 170.28, 162.95, 160.25, 145.75, 143.95, 142.48, 109.57, 89.55, 83.95, 80.40, 75.34, 56.18, 51.86, 42.31, 33.59, 32.17, 29.99, 29.20, 27.81, 20.89, 19.49, 18.99, 18.14, 15.39 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F132 | — | — | HRMS-ESI (m/z) [M + Na]$^+$ calcd for C$_{26}$H$_{40}$O$_9$N$_2$Na, 547.2626; found, 547.2652 | $^1$H NMR (CDCl$_3$) δ 8.34 (d, J = 8.0 Hz, 1H), 8.28 (d, J = 5.4 Hz, 1H), 6.95 (d, J = 5.4 Hz, 1H), 5.74 (s, 2H), 4.88 (dq, J = 9.1, 6.4 Hz, 1H), 4.58 (dt, J = 10.8, 7.3 Hz, 1H), 3.91 (s, 3H), 3.42 (q, J = 7.6, 6.9 Hz, 3H), 3.32 (s, 3H), 3.32-3.26 (m, 1H), 3.05 (t, J = 8.8 Hz, 1H), 2.36 (dt, J = 13.2, 6.5 Hz, 1H), 2.07 (s, 3H), 2.02-1.91 (m, 1H), 1.84 (dq, J = 13.2, 6.6 Hz, 1H), 1.67 (tq, J = 20.9, 8.5, 6.2 Hz, 3H), 1.59-1.44 (m, 2H), 1.41 (d, J = 6.4 Hz, 3H), 1.33 (q, J = 11.2 Hz, 1H), 1.10-0.99 (m, 1H), 0.92 (dd, J = 6.7, 2.6 Hz, 6H) | $^{13}$C NMR (CDCl$_3$) δ 172.82, 170.27, 162.94, 160.25, 145.74, 143.94, 142.50, 109.57, 89.55, 84.05, 80.35, 75.38, 71.28, 58.49, 56.18, 51.88, 40.27, 33.65, 30.41, 29.17, 28.37, 20.88, 19.51, 19.43, 19.11, 18.15 |
| F133 | — | — | HRMS-ESI (m/z) [M + H]$^+$ calcd for C$_{25}$H$_{39}$O$_8$N$_2$, 495.2701; found, 495.2717 | $^1$H NMR (CDCl$_3$) δ 8.34 (d, J = 8.1 Hz, 1H), 8.28 (d, J = 5.4 Hz, 1H), 6.95 (d, J = 5.4 Hz, 1H), 5.74 (s, 2H), 4.88 (dq, J = 9.2, 6.4 Hz, 1H), 4.68-4.49 (m, 1H), 3.91 (s, 3H), 3.43 (dd, J = 8.4, 6.6 Hz, 1H), 3.27 (dd, J = 8.4, 6.4 Hz, 1H), 3.01 (t, J = 8.9 Hz, 1H), 2.35 (dt, J = 12.8, 6.9 Hz, 1H), 2.07 (s, 3H), 1.83 (dd, J = 13.2, 6.6 Hz, 1H), 1.80-1.69 (m, 2H), 1.65-1.47 (m, 2H), 1.41 (d, J = 6.4 Hz, 4H), 1.38-1.27 (m, 1H), 1.22 (ddd, J = 13.2, 10.8, 7.3 Hz, 1H), 1.05-0.95 (m, 1H), 0.91 (d, J = 6.8 Hz, 9H) | $^{13}$C NMR (CDCl$_3$) δ 172.88, 170.27, 162.94, 160.24, 145.75, 143.93, 142.53, 109.56, 89.56, 84.25, 80.41, 75.44, 56.17, 51.88, 45.22, 33.74, 29.18, 27.13, 23.27, 20.88, 19.49, 19.45, 18.81, 18.18, 11.96 |
| F134 | 71-75 | — | ESIMS m/z 591 ([M + H]$^+$) | $^1$H NMR (CDCl$_3$) δ 8.32 (d, J = 8.0 Hz, 1H), 8.27 (d, J = 5.4 Hz, 1H), 7.34-7.28 (m, 2H), 7.09-6.95 (m, 7H), 6.94 (d, J = 5.4 Hz, 1H), 5.74 (s, 2H), 5.12 (dq, J = 9.2, 6.4 Hz, 1H), 4.63 (ddd, J = 11.0, 8.1, 7.0 Hz, 1H), 4.34 (t, J = 8.9 Hz, 1H), 3.89 (s, 3H), 2.97 (dd, J = 13.4, 3.2 Hz, 1H), 2.43-2.27 (m, 5H), 2.15-2.02 (m, 4H), 1.77-1.48 (m, 2H), 1.35 (d, J = 6.5 Hz, 3H), 1.32-1.19 (m, 2H) | $^{13}$C NMR (CDCl$_3$) δ 172.65, 170.18, 162.89, 160.16, 159.61, 145.67, 143.86, 142.30, 137.00, 135.31, 129.60, 128.94, 128.60, 121.10, 115.48, 109.55, 89.40, 81.08, 74.61, 56.10, 51.77, 45.65, 36.33, 33.54, 26.58, 20.93, 20.79, 18.31, 14.05 |
| F135 | — | — | HRMS-ESI (m/z) [M + H]$^+$ calcd for C$_{27}$H$_{34}$O$_8$BrN$_2$, 593.1493; found, 593.1499 | $^1$H NMR (CDCl$_3$) δ 8.38 (d, J = 7.9 Hz, 1H), 8.28 (d, J = 5.4 Hz, 1H), 7.30 (dd, J = 8.6, 7.4 Hz, 2H), 7.07-6.87 (m, 4H), 5.74 (s, 2H), 5.11 (dq, J = 9.1, 6.5 Hz, 1H), 4.63 (dt, J = 10.9, 6.9 Hz, 1H), 4.24 (t, J = 8.7 Hz, 1H), 3.91 (s, 3H), 3.46 (ddd, J = 10.0, 7.3, 5.0 Hz, 1H), 3.41-3.28 (m, 1H), 2.50-2.36 (m, 1H), 2.20-1.99 (m, 5H), 1.93-1.75 (m, 2H), 1.70 (dt, J = 16.7, 7.1 Hz, 2H), 1.51-1.36 (m, 1H), 1.31 (d, J = 6.5 Hz, 3H), 1.27-1.15 (m, 1H) | $^{13}$C NMR (CDCl$_3$) δ 172.69, 170.27, 162.99, 160.26, 159.18, 145.79, 143.95, 142.33, 129.75, 121.33, 115.38, 109.69, 89.48, 80.92, 74.65, 56.22, 51.92, 41.32, 34.14, 33.39, 31.57, 28.20, 20.89, 19.20, 18.28 |
| F136 | — | — | HRMS-ESI (m/z) [M + H]$^+$ calcd for C$_{27}$H$_{35}$O$_8$N$_2$, 515.2388; found, 515.2393 | $^1$H NMR (CDCl$_3$) δ 8.36 (d, J = 8.0 Hz, 1H), 8.29 (d, J = 5.4 Hz, 1H), 7.30 (d, J = 7.7 Hz, 2H), 6.94 (dd, J = 7.2, 4.7 Hz, 4H), 5.75 (s, 2H), 5.21-5.02 (m, 1H), 4.63 (dt, J = 10.8, 7.5 Hz, 1H), 4.22 (t, J = 8.8 Hz, 1H), 3.91 (s, 3H), 2.41 (dt, J = 12.7, 7.1 Hz, 1H), 2.07 (s, 3H), 1.95-1.82 (m, 1H), 1.64 (dd, J = 10.5, 3.9 Hz, 4H), 1.47- | $^{13}$C NMR (CDCl$_3$) δ 172.82, 170.29, 162.97, 160.26, 159.68, 145.75, 143.98, 142.44, 129.59, 120.95, 115.41, 109.60, 89.55, 81.44, 74.84, 56.19, 51.91, 45.00, 33.68, 27.03, 23.53, 20.89, 18.85, 18.38, 11.88 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 1.34 (m, 1H), 1.30 (d, J = 6.5 Hz, 3H), 1.26-1.21 (m, 1H), 1.17 (s, 1H), 0.88 (t, J = 7.3 Hz, 3H) | |
| F137 | — | — | ESIMS m/z 627 ([M + H]$^+$) | $^1$H NMR (CDCl$_3$) δ 8.30 (d, J = 8.1 Hz, 1H), 8.26 (d, J = 5.4 Hz, 1H), 7.43-7.27 (m, 5H), 7.08 (td, J = 8.7, 6.7 Hz, 1H), 6.93 (d, J = 5.4 Hz, 1H), 6.81-6.72 (m, 2H), 5.73 (s, 2H), 4.98 (dq, J = 9.2, 6.4 Hz, 1H), 4.81 (d, J = 10.8 Hz, 1H), 4.64 (d, J = 10.9 Hz, 1H), 4.60 (dt, J = 10.9, 7.3 Hz, 1H), 3.89 (s, 3H), 3.40 (t, J = 9.0 Hz, 1H), 3.12-2.93 (m, 1H), 2.50 (dd, J = 13.6, 11.5 Hz, 1H), 2.39-2.27 (m, 1H), 2.06 (s, 3H), 1.94 (ddq, J = 12.2, 8.0, 3.9 Hz, 1H), 1.70-1.57 (m, 2H), 1.52 (d, J = 6.4 Hz, 3H), 1.49-1.38 (m, 1H), 1.30-1.17 (m, 1H), 1.01-0.90 (m, 1H) | $^{13}$C NMR (CDCl$_3$) δ 172.70, 170.27, 162.98, 162.96-159.98 (m), 161.13 (dd, J = 248.8, 13.1 Hz), 160.25, 145.77, 143.92, 142.40, 137.82, 131.60 (dd, J = 9.2, 6.7 Hz), 128.53, 127.91, 127.67, 123.17 (dd, J = 16.0, 3.8 Hz), 111.06 (dd, J = 20.7, 3.9 Hz), 109.64, 104.33-103.29 (m), 89.49, 83.96, 75.39, 74.97, 56.20, 51.79, 44.52, 33.59, 29.35, 27.15, 20.89, 18.89, 18.27 $^{19}$F NMR (CDCl$_3$) δ −113.32 (d, J = 6.4 Hz), −113.57 (d, J = 6.7 Hz) |
| F138 | — | — | HRMS-ESI (m/z) [M + H]$^+$ calcd for C$_{27}$H$_{33}$O$_8$N$_2$F$_2$, 551.2199; found, 551.2202 | $^1$H NMR (CDCl$_3$) δ 8.37 (d, J = 7.9 Hz, 1H), 8.29 (d, J = 5.4 Hz, 1H), 7.36-7.28 (m, 2H), 7.05-6.91 (m, 4H), 6.03-5.67 (m, 1H), 5.75 (s, 2H), 5.11 (dq, J = 9.1, 6.5 Hz, 1H), 4.72-4.56 (m, 1H), 4.24 (t, J = 8.7 Hz, 1H), 3.92 (s, 3H), 2.43 (dt, J = 12.9, 6.6 Hz, 1H), 2.09 (s, 1H), 2.07 (s, 3H), 2.06-1.95 (m, 1H), 1.94-1.75 (m, 3H), 1.73-1.62 (m, 1H), 1.41 (q, J = 11.3 Hz, 1H), 1.31 (d, J = 6.5 Hz, 3H), 1.29-1.24 (m, 1H) | $^{13}$C NMR (CDCl$_3$) δ 172.69, 170.29, 163.00, 160.27, 158.93, 145.77, 144.00, 142.31, 129.84, 121.56, 116.75, 115.26, 109.65, 89.51, 80.58, 74.49, 56.20, 51.91, 37.61, 35.77, 33.36, 29.42 20.88, 19.32, 18.26 |
| F139 | — | — | ESIMS m/z 625 ([M + H]$^+$) | $^1$H NMR (CDCl$_3$) δ 8.28 (d, J = 8.0 Hz, 1H), 8.25 (d, J = 5.3 Hz, 1H), 7.09 (d, J = 7.8 Hz, 2H), 7.03 (d, J = 8.1 Hz, 2H), 6.93 (d, J = 5.4 Hz, 1H), 5.72 (s, 2H), 4.89 (dq, J = 9.2, 6.4 Hz, 1H), 4.56 (dt, J = 10.9, 7.4 Hz, 1H), 3.88 (s, 3H), 3.79 (dt, J = 8.9, 6.1 Hz, 1H), 3.59 (dt, J = 8.8, 6.2 Hz, 1H), 3.17 (t, J = 9.0 Hz, 1H), 2.96 (dd, J = 13.3, 3.4 Hz, 1H), 2.41-2.12 (m, 7H), 2.05 (s, 3H), 1.91-1.76 (m, 3H), 1.68-1.36 (m, 6H), 1.28-1.12 (m, 1H), 0.92-0.79 (m, 1H) | $^{13}$C NMR (CDCl$_3$) δ 172.62, 170.16, 162.87, 160.15, 145.66, 143.82, 142.30, 137.20, 135.37, 128.99, 128.55, 127.06 (q, J = 276.1 Hz), 109.53, 89.37, 84.16, 74.79, 71.57, 56.08, 51.68, 45.79, 36.39, 33.52, 30.69 (q, J = 29.1 Hz), 26.57, 22.98 (q, J = 2.9 Hz), 20.90, 20.76, 18.71, 18.01 $^{19}$F NMR (CDCl$_3$) δ −66.35 |
| 140 | — | — | HRMS-ESI (m/z) [M + H]$^+$ calcd for C$_{29}$H$_{43}$O$_9$N$_2$, 563.2963; found, 563.2959 | $^1$H NMR (CDCl$_3$) δ 8.13 (d, J = 8.0 Hz, 1H), 8.07 (d, J = 5.4 Hz, 1H), 6.76 (d, J = 5.4 Hz, 1H), 5.53 (s, 2H), 4.69 (dt, J = 9.1, 6.4 Hz, 1H), 4.37 (dt, J = 10.7, 7.5 Hz, 1H), 3.71 (s, 3H), 3.26 (dt, J = 13.1, 6.7 Hz, 4H), 3.05 (dq, J = 6.5, 3.3 Hz, 2H), 2.88 (t, J = 8.9 Hz, 1H), 2.15 (dt, J = 13.2, 6.5 Hz, 1H), 1.86 (s, 3H), 1.80 (dp, J = 13.0, 4.8, 4.0 Hz, 1H), 1.59-1.39 (m, 3H), 1.39-1.25 (m, 2H), 1.22 (d, J = 6.4 Hz, 3H), 1.13 (q, J = 11.5 Hz, 1H), 0.95-0.77 (m, 3H), 0.43-0.23 (m, 4H), 0.00 (dq, J = 10.1, 5.2, 4.5 Hz, | $^{13}$C NMR (CDCl$_3$) δ 172.75, 170.21, 162.92, 160.21, 145.73, 143.86, 142.41, 109.60, 89.45, 83.98, 78.32, 75.39, 75.28, 69.04, 56.17, 51.80, 40.46, 33.60, 30.63, 28.16, 20.84, 19.00, 18.06, 11.07, 10.63, 3.14, 2.98, 2.92, 2.86 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F141 | 40-45 | — | ESIMS m/z 655 ([M + H]$^+$) | $^1$H NMR (CDCl$_3$) δ 8.29 (d, J = 8.1 Hz, 1H), 8.25 (d, J = 5.3 Hz, 1H), 7.31-7.23 (m, 2H), 7.23-7.07 (m, 4H), 6.93 (d, J = 5.4 Hz, 1H), 6.85-6.72 (m, 2H), 5.73 (s, 2H), 4.91 (dq, J = 9.2, 6.4 Hz, 1H), 4.57 (dt, J = 10.9, 7.5 Hz, 1H), 3.89 (s, 3H), 3.78 (dt, J = 8.8, 6.3 Hz, 1H), 3.57 (dt, J = 8.9, 6.5 Hz, 1H), 3.18 (t, J = 9.0 Hz, 1H), 2.98 (d, J = 12.8 Hz, 1H), 2.73 (td, J = 7.5, 4.0 Hz, 2H), 2.47 (dd, J = 13.5, 11.5 Hz, 1H), 2.31 (ddd, J = 13.2, 6.7, 4.9 Hz, 1H), 2.06 (s, 3H), 2.00-1.80 (m, 3H), 1.68-1.51 (m, 2H), 1.49-1.36 (m, 4H), 1.28-1.15 (m, 1H), 0.91 (ddt, J = 14.5, 6.4, 3.0 Hz, 1H) | $^{13}$C NMR (CDCl$_3$) δ 172.62, 170.17, 162.88, 161.27 (dd, J = 246.7, 12.2 Hz), 161.05 (dd, J = 248.0, 12.2 Hz), 160.15, 145.67, 143.83, 142.33, 141.66, 131.50 (dd, J = 9.3, 6.6 Hz), 128.29, 128.24, 125.79, 123.19 (dd, J = 16.0, 3.8 Hz), 110.96 (dd, J = 20.8, 3.7 Hz), 109.54, 103.97-103.18 (m), 89.40, 83.99, 74.96, 72.86, 56.10, 51.68, 44.45, 33.51, 32.33, 31.87, 29.30, 27.05, 20.79, 18.76, 18.04 $^{19}$F NMR (CDCl$_3$) δ −113.37 (d, J = 6.6 Hz), −113.58 (d, J = 7.5 Hz) |
| F142 | — | — | HRMS-ESI (m/z) [M + H]$^+$ calcd for C$_{31}$H$_{41}$O$_9$N$_2$, 585.2807; found, 585.2816 | $^1$H NMR (CDCl$_3$) δ 8.33 (d, J = 8.0 Hz, 1H), 8.27 (d, J = 5.4 Hz, 1H), 7.39-7.19 (m, 2H), 6.98-6.92 (m, 2H), 6.92-6.86 (m, 2H), 5.74 (s, 2H), 5.07-4.84 (m, 1H), 4.59 (dt, J = 10.7, 7.4 Hz, 1H), 4.16-3.96 (m, 2H), 3.90 (s, 3H), 3.49 (dd, J = 9.6, 7.3 Hz, 1H), 3.42 (dd, J = 9.6, 6.8 Hz, 1H), 3.14 (t, J = 8.8 Hz, 1H), 2.36 (dt, J = 13.2, 6.7 Hz, 1H), 2.19 (ddd, J = 15.0, 5.8, 2.3 Hz, 1H), 2.07 (s, 3H), 1.90-1.75 (m, 2H), 1.69 (dq, J = 21.9, 7.6, 7.0 Hz, 2H), 1.62-1.50 (m, 1H), 1.44 (d, J = 6.4 Hz, 3H), 1.34 (q, J = 11.5 Hz, 1H), 1.07 (dt, J = 12.1, 5.9 Hz, 2H), 0.60-0.49 (m, 2H), 0.21 (q, J = 4.9 Hz, 2H) | $^{13}$C NMR (CDCl$_3$) δ 172.76, 170.26, 162.96, 160.24, 158.86, 145.76, 143.92, 142.44, 129.41, 120.59, 114.48, 109.61, 89.51, 83.95, 78.24, 75.25, 66.18, 56.19, 51.83, 40.33, 33.61, 30.34, 28.17, 20.88, 19.10, 18.10, 11.09, 3.16, 2.94 |
| F143 | — | — | HRMS-ESI (m/z) [M + H]$^+$ calcd for C$_{21}$H$_{29}$O$_2$N$_8$, 437.1918; found, 437.1929 | $^1$H NMR (CDCl$_3$) δ 8.42 (d, J = 6.9 Hz, 1H), 8.27 (dt, J = 5.0, 2.6 Hz, 1H), 7.07-6.83 (m, 1H), 5.82-5.59 (m, 2H), 5.10-4.89 (m, 1H), 4.64-4.43 (m, 1H), 4.04-3.87 (m, 3H), 3.80 (s, 1H), 3.69 (dq, J = 8.7, 5.3, 4.7 Hz, 1H), 3.42 (dd, J = 8.2, 3.6 Hz, 1H), 2.38 (t, J = 11.9 Hz, 1H), 2.12-2.04 (m, 3H), 2.05-1.83 (m, 3H), 1.74 (d, J = 14.6 Hz, 1H), 1.64 (t, J = 12.7 Hz, 1H), 1.50 (d, J = 9.5 Hz, 2H), 1.46-1.32 (m, 4H) | $^{13}$C NMR (CDCl$_3$) δ 173.64, 170.23, 162.85, 160.26, 145.75, 143.93, 142.43, 109.60, 89.53, 86.83, 73.26, 67.69, 56.18, 53.28, 39.69, 36.09, 35.75, 32.41, 21.78, 20.85, 18.37 |
| F144 | 76-80 | — | ESIMS m/z 631 ([M + H]$^+$) | $^1$H NMR (CDCl$_3$) δ 8.28 (d, J = 7.9 Hz, 1H), 8.22 (d, J = 5.4 Hz, 1H), 7.58 (dd, J = 1.9, 0.6 Hz, 1H), 7.15 (dd, J = 3.4, 0.6 Hz, 1H), 7.02 (td, J = 8.5, 6.4 Hz, 1H), 6.92 (d, J = 5.4 Hz, 1H), 6.73-6.62 (m, 2H), 6.50 (dd, J = 3.5, 1.7 Hz, 1H), 5.70 (s, 2H), 5.18 (t, J = 9.2 Hz, 1H), 5.09 (dq, J = 9.5, 6.3 Hz, 1H), 4.60 (dt, J = 10.9, 7.4 Hz, 1H), 3.86 (s, 3H), 2.70 (dd, J = 13.9, 4.5 Hz, 1H), 2.49 (dd, J = 13.9, 10.2 Hz, 1H), 2.34 (ddt, J = 13.2, 7.4, 3.7 Hz, | $^{13}$C NMR (CDCl$_3$) δ 172.51, 170.12, 162.84, 161.37 (dd, J = 246.6, 11.6 Hz), 160.88 (dd, J = 247.6, 11.5 Hz), 160.13, 158.06, 146.83, 145.59, 143.86, 143.79, 142.14, 131.49 (dd, J = 9.5, 6.5 Hz), 122.36 (dd, J = 15.7, 3.8 Hz), 118.50, 111.88, 110.81 (dd, J = 21.0, 3.7 Hz), 109.55, 103.56 (t, J = |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1H), 2.18-2.07 (m, 1H), 2.03 (s, 3H), 1.73-1.51 (m, 3H), 1.29 (d, J = 6.3 Hz, 3H), 1.27-1.18 (m, 1H), 1.12-0.98 (m, 1H) | 25.7 Hz), 89.32, 76.33, 72.97, 56.06, 51.59, 42.51, 33.26, 29.97, 27.25, 20.72, 18.65, 17.38 $^{19}$F NMR (CDCl$_3$) δ −112.99 (d, J = 6.8 Hz), −113.49 (d, J = 6.9 Hz) |
| F145 | 48-53 | — | ESIMS m/z 593 ([M + H]⁺) | ¹H NMR (CDCl$_3$) δ 8.28 (d, J = 8.1 Hz, 1H), 8.25 (d, J = 5.4 Hz, 1H), 7.11 (td, J = 8.5, 6.5 Hz, 1H), 6.92 (d, J = 5.4 Hz, 1H), 6.82-6.71 (m, 2H), 5.72 (s, 2H), 4.89 (dq, J = 9.2, 6.4 Hz, 1H), 4.57 (ddd, J = 10.9, 8.1, 7.0 Hz, 1H), 3.88 (s, 3H), 3.54 (dd, J = 8.4, 6.2 Hz, 1H), 3.31 (dd, J = 8.4, 6.5 Hz, 1H), 3.15 (t, J = 9.0 Hz, 1H), 3.04-2.93 (m, 1H), 2.46 (dd, J = 13.5, 11.6 Hz, 1H), 2.30 (dtd, J = 13.1, 6.6, 1.9 Hz, 1H), 2.05 (s, 3H), 1.94-1.77 (m, 2H), 1.66-1.51 (m, 2H), 1.49-1.34 (m, 4H), 1.31-1.14 (m, 2H), 0.95 (d, J = 6.7 Hz, 3H), 0.94 (d, J = 6.7 Hz, 3H) | ¹³C NMR (CDCl$_3$) δ 172.33, 169.88, 162.58, 160.96 (dd, J = 246.6, 12.1 Hz), 160.77 (dd, J = 247.7, 11.9 Hz), 159.86, 145.37, 143.54, 142.06, 131.51-130.92 (m), 122.97 (dd, J = 16.0, 3.8 Hz), 110.65 (dd, J = 20.8, 3.9 Hz), 109.22, 103.94-102.92 (m), 89.12, 83.23, 80.04, 74.80, 55.80, 51.38, 44.35, 33.25, 28.85, 28.83, 26.71, 20.49, 19.10, 19.07, 18.47, 17.76 $^{19}$F NMR (CDCl$_3$) δ −113.49 (d, J = 6.7 Hz), −113.61 (d, J = 7.0 Hz) |
| F146 | — | — | HRMS-ESI (m/z) [M + H]⁺ calcd for C$_{27}$H$_{33}$N$_2$O$_8$, 513.2231; found, 513.2255 | ¹H NMR (CDCl$_3$) δ 8.35 (d, J = 7.9 Hz, 1H), 8.28 (d, J = 5.4 Hz, 1H), 7.26 (s, 2H), 6.93 (ddd, J = 7.8, 5.4, 4.2 Hz, 4H), 5.84-5.75 (m, 1H), 5.75 (s, 2H), 5.15 (dq, J = 9.1, 6.4 Hz, 1H), 5.04 (dt, J = 17.1, 1.3 Hz, 1H), 4.95 (d, J = 10.3 Hz, 1H), 4.64 (ddd, J = 11.0, 7.9, 6.7 Hz, 1H), 4.31 (t, J = 8.8 Hz, 1H), 3.91 (s, 3H), 2.59-2.46 (m, 1H), 2.46-2.34 (m, 1H), 2.07 (s, 3H), 1.90 (td, J = 14.5, 6.7 Hz, 1H), 1.83-1.68 (m, 2H), 1.47-1.36 (m, 2H), 1.34 (d, J = 6.4 Hz, 3H) | ¹³C NMR (CDCl$_3$) δ 172.84, 170.31, 162.97, 159.33, 145.75, 138.53, 129.49, 121.09, 116.19, 115.78, 109.61, 99.97, 89.55, 80.48, 74.48, 56.19, 51.95, 47.50, 33.61, 31.11, 20.89, 19.77, 18.33 |
| F147 | — | (Neat) 3383, 2928, 1746, 1677, 1493, 1207 | HRMS-ESI (m/z) ([M]⁺) calcd for C$_{32}$H$_{44}$N$_2$O$_8$, 584.3098; found, 584.3108 | ¹H NMR (CDCl$_3$) δ 8.41 (d, J = 8.0 Hz, 1H), 8.28 (d, J = 5.4 Hz, 1H), 7.33-7.23 (m, 2H), 7.00-6.89 (m, 4H), 5.82-5.72 (m, 2H), 5.14-5.01 (m, 1H), 4.62 (ddd, J = 10.8, 8.0, 6.9 Hz, 1H), 4.26-4.16 (m, 1H), 3.89 (s, 3H), 2.55 (hept, J = 7.0 Hz, 1H), 2.47-2.32 (m, 1H), 1.94-1.31 (m, 7H), 1.30 (d, J = 6.5 Hz, 3H), 1.28-1.04 (m, 4H), 1.14 (d, J = 7.0 Hz, 6H), 0.80 (d, J = 6.6 Hz, 3H), 0.79 (d, J = 6.6 Hz, 3H) | ¹³C NMR (CDCl$_3$) δ 176.24, 172.82, 162.94, 160.23, 159.72, 145.61, 144.17, 142.09, 129.57, 120.95, 115.50, 109.56, 89.88, 81.64, 74.86, 56.14, 51.91, 43.23, 36.41, 33.86, 33.65, 28.27, 27.88, 27.56, 23.04, 22.06, 18.94, 18.68, 18.40 |
| F148 | — | (Neat) 3379, 2925, 1743, 1677, 1504, 1209 | HRMS-ESI (m/z) ([M]⁺) calcd for C$_{30}$H$_{48}$N$_2$O$_8$, 564.3411; found, 564.3413 | ¹H NMR (CDCl$_3$) δ 8.39 (d, J = 8.1 Hz, 1H), 8.27 (d, J = 5.4 Hz, 1H), 6.94 (d, J = 5.3 Hz, 1H), 5.82-5.72 (m, 2H), 4.94-4.81 (m, 1H), 4.57 (ddd, J = 10.7, 8.1, 7.0 Hz, 1H), 3.89 (s, 3H), 3.46 (dd, J = 8.3, 6.3 Hz, 1H), 3.27 (dd, J = 8.4, 6.5 Hz, 1H), 3.07-2.94 (m, 1H), 2.55 (hept, J = 7.0 Hz, 1H), 2.42-2.27 (m, 1H), 1.94-1.43 (m, 7H), 1.41 (d, J = 6.4 Hz, 3H), 1.38-0.95 (m, 5H), 1.14 (d, J = 7.0 Hz, 6H), 0.95-0.81 (m, 12H) | ¹³C NMR (CDCl$_3$) δ 176.21, 172.86, 162.90, 160.21, 145.60, 144.11, 142.15, 109.51, 89.88, 84.32, 80.43, 75.43, 56.12, 51.86, 43.55, 36.55, 33.84, 33.70, 29.18, 28.11, 28.04, 27.56, 22.98, 22.28, 19.52, 19.46, 18.86, 18.67, 18.17 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| F149 | — | (Neat) 3382, 2927, 1745, 1678, 1505, 1374, 1210 | HRMS-ESI (m/z) ([M]⁺) calcd for $C_{30}H_{46}N_2O_8$, 562.3254; found, 562.3262 | ¹H NMR (CDCl₃) δ 8.38 (d, J = 8.1 Hz, 1H), 8.27 (d, J = 5.4 Hz, 1H), 6.94 (d, J = 5.4 Hz, 1H), 5.81-5.72 (m, 2H), 4.96-4.82 (m, 1H), 4.57 (ddd, J = 10.7, 8.1, 7.0 Hz, 1H), 3.89 (s, 3H), 3.58-3.31 (m, 2H), 3.09-2.97 (m, 1H), 2.55 (hept, J = 7.0 Hz, 1H), 2.40-2.29 (m, 1H), 1.86-1.45 (m, 6H), 1.42 (d, J = 6.4 Hz, 3H), 1.38-0.93 (m, 6H), 1.14 (d, J = 7.0 Hz, 6H), 0.90 (d, J = 6.6 Hz, 3H), 0.88 (d, J = 6.6 Hz, 3H), 0.62-0.50 (m, 2H), 0.27-0.15 (m, 1H) | ¹³C NMR (CDCl₃) δ 176.22, 172.83, 162.91, 160.22, 145.61, 144.12, 142.15, 109.51, 89.88, 84.36, 78.64, 75.39, 56.13, 51.83, 43.60, 36.44, 33.85, 33.72, 28.08, 27.35, 23.03, 22.22, 18.75, 18.67, 18.11, 11.13, 3.08, 3.01 |
| F150 | — | (Neat) 3385, 2950, 1746, 1679, 1506, 1377, 1253 | HRMS-ESI (m/z) ([M]⁺) calcd for $C_{30}H_{45}F_3N_2O_8$, 618.3128; found, 618.3154 | ¹H NMR (CDCl₃) δ 8.38 (d, J = 8.1 Hz, 1H), 8.27 (d, J = 5.3 Hz, 1H), 6.94 (d, J = 5.4 Hz, 1H), 5.81-5.72 (m, 2H), 4.93-4.81 (m, 1H), 4.57 (ddd, J = 10.7, 8.1, 7.0 Hz, 1H), 3.89 (s, 3H), 3.80-3.66 (m, 1H), 3.64-3.50 (m, 1H), 3.09-2.98 (m, 1H), 2.55 (hept, J = 7.0 Hz, 1H), 2.40-2.28 (m, 1H), 2.28-2.11 (m, 2H), 1.88-1.27 (m, 9H), 1.40 (d, J = 6.4 Hz, 3H), 1.27-0.92 (m, 4H), 1.14 (d, J = 7.0 Hz, 6H), 0.92-0.83 (m, 6H) | ¹³C NMR (CDCl₃) δ 176.24, 172.82, 162.93, 160.24, 145.61, 144.16, 142.13, 127.17 (q, J = 276.1 Hz), 109.52, 89.90, 84.85, 75.02, 71.55, 56.13, 51.85, 43.48, 36.49, 33.86, 33.66, 30.82 (q, J = 29.0 Hz), 28.20, 28.09, 27.47, 23.06 (dd, J = 6.5, 3.4 Hz), 22.97, 22.18, 18.84, 18.67, 18.14<br>¹⁹F NMR (CDCl₃) δ −66.43 |
| F151 | 122-124 | — | ESIMS m/z 585.5 ([M + H]⁺) | ¹H NMR (CDCl₃) δ 8.36 (d, J = 7.2 Hz, 1H), 8.31 (d, J = 5.4 Hz, 1H), 7.31-7.24 (m, 2H), 7.21-7.15 (m, 3H), 6.97 (d, J = 5.4 Hz, 1H), 5.76 (s, 2H), 5.04-4.92 (m, 1H), 4.60 (dd, J = 7.3, 3.8 Hz, 1H), 3.90 (s, 3H), 3.54 (dd, J = 8.3, 6.3 Hz, 1H), 3.39-3.30 (m, 1H), 3.20-3.10 (m, 2H), 2.62-2.49 (m, 1H), 2.40-2.28 (m, 1H), 2.00-1.80 (m, 3H), 1.75-1.62 (m, 1H), 1.56 (dd, J = 13.8, 7.4 Hz, 1H), 1.48-1.41 (m, 4H), 1.26 (dd, J = 8.1, 6.2 Hz, 1H), 1.22-1.17 (m, 1H), 1.15 (dd, J = 4.9, 2.1 Hz, 6H), 0.99-0.93 (m, 7H), 0.93-0.86 (m, 1H) | ¹³C NMR (CDCl₃) δ 176.39, 170.64, 162.92, 160.31, 145.61, 144.44, 142.06, 140.87, 128.87, 128.36, 125.91, 109.53, 89.99, 84.01, 80.55, 75.32, 56.17, 52.13, 45.78, 37.01, 33.87, 31.97, 29.26, 26.94, 19.55, 19.50, 18.69, 18.16, 17.44 |
| F152 | — | — | ESIMS m/z 583.6 ([M + H]⁺) | ¹H NMR (CDCl₃) δ 8.34 (d, J = 8.1 Hz, 1H), 8.25 (d, J = 5.4 Hz, 1H), 7.35-7.24 (m, 2H), 7.22-7.13 (m, 3H), 6.93 (d, J = 5.4 Hz, 1H), 5.82-5.68 (m, 2H), 4.93 (dq, J = 9.1, 6.4 Hz, 1H), 4.58 (ddd, J = 10.8, 8.1, 7.0 Hz, 1H), 3.88 (s, 3H), 3.59 (dd, J = 9.6, 7.0 Hz, 1H), 3.45 (dd, J = 9.7, 6.8 Hz, 1H), 3.26-3.07 (m, 2H), 2.54 (p, J = 7.0 Hz, 1H), 2.43-2.23 (m, 2H), 1.97-1.79 (m, 1H), 1.69-1.51 (m, 2H), 1.49-1.38 (m, overlapping, 1H), 1.46 (d, J = 6.4 Hz, 3H), 1.22-1.05 (m, 2H), 1.14 (d, overlapping, J = 7.0 Hz, 6H), 0.95-0.80 (m, 1H), 0.65-0.53 (m, 2H), 0.33-0.19 (m, 2H) | ¹³C NMR (75 MHz, CDCl₃) δ 176.36, 172.91, 163.12, 160.42, 145.79, 144.30, 142.34, 140.94, 128.54, 126.08, 109.74, 90.05, 84.04, 78.91, 75.41, 56.33, 54.04, 51.98, 46.25, 37.12, 34.06, 33.91, 29.49, 26.85, 19.02, 18.87, 18.32, 11.39, 3.35, 3.21 |
| F153 | — | — | HRMS-ESI (m/z) [M + H]⁺ | ¹H NMR (CDCl₃) δ 8.54 (d, J = 8.3 Hz, 1H), 8.34 (d, J = 5.4 Hz, 1H), 7.35-7.23 (m, 2H), | ¹³C NMR (CDCl₃) δ 172.72, 169.43, 162.36, 159.77, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | calcd for C$_{32}$H$_{43}$N$_2$O$_8$, 583.3014; found, 583.3013 | 7.00 (d, J = 5.5 Hz, 1H), 6.97-6.89 (m, 3H), 5.07 (dq, J = 9.1, 6.5 Hz, 1H), 4.60 (ddd, J = 10.9, 8.3, 6.9 Hz, 1H), 4.16 (t, J = 8.7 Hz, 1H), 3.90 (s, 3H), 3.81 (t, J = 6.6 Hz, 2H), 3.69 (dt, J = 9.2, 5.7 Hz, 1H), 3.41 (s, 3H), 2.99 (t, J = 6.6 Hz, 2H), 2.63 (t, J = 6.2 Hz, 1H), 2.37 (dt, J = 13.3, 6.6 Hz, 1H), 1.83 (dh, J = 16.6, 4.8, 4.2 Hz, 3H), 1.77-1.35 (m, 9H), 1.28 (d, J = 6.5 Hz, 3H), 1.18-1.07 (m, 1H), 0.98 (ddq, J = 15.6, 12.5, 7.9 Hz, 2H) | 159.44, 146.77, 141.48, 137.34, 129.58, 120.93, 115.56, 109.80, 81.67, 74.88, 67.71, 67.59, 58.87, 58.79, 56.33, 51.66, 42.02, 37.27, 36.85, 34.62, 33.87, 33.66, 31.77, 27.61, 25.05, 19.07, 18.38 |
| F154 | — | (Thin Film) 3381, 2942, 1745, 1678, 1506, 974 | HRMS-ESI (m/z) ([M]$^+$) calcd for C$_{31}$H$_{46}$N$_2$O$_8$, 574.3254; found, 674.3262 | $^1$H NMR (CDCl$_3$) δ 8.38 (d, J = 8.2 Hz, 1H), 8.27 (d, J = 5.3 Hz, 1H), 6.93 (d, J = 5.4 Hz, 1H), 5.81-5.61 (m, 2H), 4.89 (dd, J = 9.2, 6.3 Hz, 1H), 4.57 (dt, J = 11.0, 7.5 Hz, 1H), 3.89 (s, 3H), 3.50 (dd, J = 9.6, 7.0 Hz, 1H), 3.36 (dd, J = 9.6, 6.9 Hz, 1H), 3.01 (t, J = 9.0 Hz, 1H), 2.54 (p, J = 7.0 Hz, 1H), 2.36 (dd, J = 13.1, 6.8 Hz, 1H), 1.92-1.43 (m, 15H), 1.42 (d, J = 6.5 Hz, 3H), 1.35-1.19 (m, 2H), 1.14 (d, J = 7.0 Hz, 3H), 1.17-0.92 (m, 5H), 0.62-0.48 (m, 2H), 0.29-0.17 (m, 2H) | |
| F155 | | | HRMS-ESI (m/z) ([M]$^+$) calcd for C$_{28}$H$_{36}$N$_2$O$_8$, 528.2472; found, 528.2485 | $^1$H NMR (CDCl$_3$) 8.42 (d, J = 8.0 Hz, 1H), 8.28 (d, J = 5.4 Hz, 1H), 7.33-7.23 (m, 2H), 7.01-6.89 (m, 4H), 5.83-5.73 (m, 2H), 5.10 (dq, J = 9.1, 6.4 Hz, 1H), 4.68-4.55 (m 1H), 4.17 (t, J = 8.8 Hz, 1H), 3.89 (s, 3H), 2.55 (hept, J = 7.0 Hz, 1H), 2.40 (dt, J = 13.0, 6.6 Hz, 1H), 2.01-1.85 (m, 1H), 1.70 (dq, J = 16.8, 5.4, 4.7 Hz, 3H), 1.40 (dt, J = 13.5, 10.6 Hz, 1H), 1.31 (d, J = 6.4 Hz, 3H), 1.29-1.22 (m, 1H), 1.15 (d, J = 7.0 Hz, 6H), 1.01 (d, J = 6.9 Hz, 3H) | $^{13}$C NMR (CDCl$_3$) δ 176.26, 172.85, 162.94 160.24, 159.69, 145.62, 144.19, 142.08, 129.59, 120.99, 115.49, 109.55, 89.90, 82.30, 74.68, 56.14, 51.95, 37.67, 33.86, 33.63, 32.38, 19.27, 18.69, 18.31, 17.77 |
| F156 | — | — | HRMS-ESI (m/z) [M + H]$^+$ calcd for C$_{31}$H$_{47}$O$_9$N$_2$, 591.3276; found, 591.3280 | $^1$H NMR (CDCl$_3$) δ 8.19 (d, J = 8.0 Hz, 1H), 8.06 (d, J = 5.4 Hz, 1H), 6.75 (d, J = 5.4 Hz, 1H), 5.66-5.50 (m, 2H), 4.70 (dt, J = 9.1, 6.4 Hz, 1H), 4.37 (dt, J = 10.7, 7.4 Hz, 1H), 3.69 (s, 3H), 3.34-3.18 (m, 4H), 3.15-3.00 (m, 2H), 2.88 (t, J = 8.8 Hz, 1H), 2.34 (p, J = 7.0 Hz, 1H), 2.15 (dt, J = 13.1, 6.5 Hz, 1H), 1.81 (dp, J = 12.9, 4.8, 4.0 Hz, 1H), 1.48 (td, J = 18.9, 14.6, 5.7 Hz, 3H), 1.40-1.27 (m, 2H), 1.22 (d, J = 6.4 Hz, 3H), 1.13 (q, J = 11.3 Hz, 1H), 0.94 (d, J = 7.0 Hz, 6H), 0.91-0.75 (m, 3H), 0.44-0.26 (m, 4H), 0.10--0.06 (m, 4H) | $^{13}$C NMR (CDCl$_3$) δ 176.13, 172.72, 162.87, 160.17, 145.59, 144.05, 142.05, 109.54, 89.79, 83.98, 78.29, 75.36, 75.24, 69.01, 56.11, 51.78, 40.43, 33.79, 33.59, 30.63, 28.17, 19.01, 18.62, 18.04, 11.06, 10.61 3.12, 2.96, 2.90, 2.85 |
| F157 | 68-72 | | ESIMS m/z 659 ([M + H]$^+$) | $^1$H NMR (CDCl$_3$) δ 8.34 (d, J = 8.0 Hz, 1H), 8.22 (d, J = 5.3 Hz, 1H), 7.59 (dd, J = 1.7, 0.8 Hz, 1H), 7.15 (dd, J = 3.5, 0.8 Hz, 1H), 7.03 (td, J = 8.5, 6.4 Hz, 1H), 6.91 (d, J = 5.4 Hz, 1H), 6.74-6.63 (m, 2H), 6.50 (dd, J = 3.5, 1.7 Hz, 1H), 5.77- | $^{13}$C NMR (CDCl$_3$) δ 176.11, 172.53, 162.83, 161.40 (dd, J = 246.3, 11.4 Hz), 160.91 (dd, J = 247.6, 11.4 Hz), 160.13, 158.08, 146.84, 145.47, 144.12, |

TABLE 2-continued

Analytical Data

| Cmpd. No. | MP (°C.) | IR (cm$^{-1}$) | MASS | $^1$H NMR | $^{13}$C or $^{19}$F NMR |
|---|---|---|---|---|---|
| | | | | 5.70 (m, 2H), 5.19 (t, J = 9.2 Hz, 1H), 5.10 (dq, J = 9.5, 6.2 Hz, 1H), 4.61 (dt, J = 10.9, 7.5 Hz, 1H), 3.85 (s, 3H), 2.71 (dd, J = 13.9, 4.5 Hz, 1H), 2.57-2.46 (m, 2H), 2.35 (ddt, J = 13.2, 7.7, 3.3 Hz, 1H), 2.18-2.07 (m, 1H), 1.74-1.52 (m, 3H), 1.34-1.18 (m, 5H), 1.11 (d, J = 7.0 Hz, 6H) | 143.82, 141.83, 131.51 (dd, J = 9.3, 6.5 Hz), 122.39 (dd, J = 15.8, 3.7 Hz), 118.52, 111.90, 110.83 (dd, J = 21.0, 3.6 Hz), 109.50, 103.58 (t, J = 25.7 Hz), 89.72, 76.37, 72.98, 56.02, 51.61, 42.53, 33.72, 33.31, 30.00, 27.28, 18.68, 18.55, 17.41 $^{19}$F NMR (CDCl$_3$) δ −113.00 (d, J = 7.1 Hz), −113.49 (d, J = 6.7 Hz) |
| F158 | — | (Neat) 2926, 1746, 1678, 1494, 1208, 1098 | HRMS-ESI (m/z) ([M]$^+$) calcd for C$_{32}$H$_{44}$N$_2$O$_9$, 600.3047; found, 600.3070 | $^1$H NMR (CDCl$_3$) δ 8.37 (d, J = 8.0 Hz, 1H), 8.28 (d, J = 5.4 Hz, 1H), 7.35-7.23 (m, 2H), 6.99-6.91 (m, 4H), 5.82 (s, 2H), 5.14-5.01 (m, 1H), 4.67-4.54 (m, 1H), 4.25-4.17 (m, 1H), 4.10 (s, 2H), 3.90 (s, 3H), 3.59 (q, J = 7.0 Hz, 2H), 2.47-2.31 (m, 1H), 1.98-1.31 (m, 7H), 1.30 (d, J = 6.4 Hz, 3H), 1.27-1.03 (m, 4H), 1.23 (t, J = 7.0 Hz, 3H), 0.80 (d, J = 6.7 Hz, 3H), 0.79 (d, J = 6.6 Hz, 3H) | $^{13}$C NMR (CDCl$_3$) δ 172.79, 170.04, 162.91, 160.16, 159.70, 145.80, 143.89, 142.25, 129.57, 120.95, 115.48, 109.73, 89.50, 81.62, 74.86, 67.78, 67.16, 56.23, 51.90, 43.20, 36.39, 33.61, 28.26, 27.87, 27.58, 23.03, 22.05, 18.94, 18.39, 15.01 |
| F159 | — | (Neat) 2954, 1744, 1679, 1506, 1210, 1096 | HRMS-ESI (m/z) ([M]$^+$) calcd for C$_{30}$H$_{48}$N$_2$O$_9$, 580.3360; found, 580.3379 | $^1$H NMR (CDCl$_3$) δ 8.35 (d, J = 8.0 Hz, 1H), 8.27 (d, J = 5.4 Hz, 1H), 6.95 (d, J = 5.4 Hz, 1H), 5.82 (s, 2H), 4.94-4.81 (m, 1H), 4.63-4.49 (m, 1H), 4.10 (s, 2H), 3.90 (s, 3H), 3.59 (q, J = 7.0 Hz, 2H), 3.46 (dd, J = 8.4, 6.3 Hz, 1H), 3.27 (dd, J = 8.4, 6.5 Hz, 1H), 3.06-2.96 (m, 1H), 2.41-2.26 (m, 1H), 1.92-1.42 (m, 7H), 1.41 (d, J = 6.4 Hz, 3H), 1.38-0.95 (m, 5H), 1.23 (t, J = 7.0 Hz, 3H), 0.95-0.82 (m, 12H) | $^{13}$C NMR (CDCl$_3$) δ 172.83, 170.03, 162.86, 160.14, 145.78, 143.85, 142.34, 109.66, 89.53, 84.31, 80.43, 75.45, 67.78, 67.16, 56.20, 51.85, 43.53, 36.55, 33.68, 29.18, 28.11, 28.03, 27.58, 22.97, 22.28, 19.51, 19.46, 18.85, 18.17, 15.00 |
| F160 | — | (Neat) 3378, 2948, 1741, 1676, 1504, 1374, 1209 | HRMS-ESI (m/z) ([M]$^+$) calcd for C$_{30}$H$_{46}$N$_2$O$_9$, 578.3203; found, 578.3206 | $^1$H NMR (CDCl$_3$) δ 8.34 (d, J = 8.1 Hz, 1H), 8.27 (d, J = 5.5 Hz, 1H), 6.95 (d, J = 5.4 Hz, 1H), 5.82 (s, 2H), 4.95-4.82 (m, 1H), 4.55 (ddd, J = 10.7, 8.2, 7.0 Hz, 1H), 4.10 (s, 2H), 3.90 (s, 3H), 3.59 (q, J = 7.0 Hz, 2H), 3.51 (dd J = 9.7, 7.0 Hz, 1H), 3.38 (dd J = 9.7, 6.9 Hz, 1H), 3.09-2.97 (m, 1H), 2.40-2.27 (m, 1H), 1.84-1.45 (m, 6H), 1.42 (d, J = 6.4 Hz, 3H), 1.38-0.92 (m, 6H), 1.23 (t, J = 7.0 Hz, 3H), 0.90 (d, J = 6.6 Hz, 3H), 0.88 (d, J = 6.6 Hz, 3H), 0.62-0.50 (m, 2H), 0.28-0.16 (m, 2H) | $^{13}$C NMR (CDCl$_3$) δ 172.81, 170.04, 162.88, 160.15, 145.80, 143.85, 142.34, 109.66, 89.53, 84.36, 78.63, 75.41, 67.78, 67.17, 56.21, 51.83, 43.58, 36.43, 33.69, 28.07, 27.37, 23.03, 22.21, 18.75, 18.11, 15.00, 11.13 3.08, 3.01 |
| F161 | — | (Neat) 3378, 2933, 1742, 1677, 1504, 1374, 1128 | HRMS-ESI (m/z) ([M]$^+$) calcd for C$_{29}$H$_{46}$N$_2$O$_9$, 566.3203; found, 566.3237 | $^1$H NMR (CDCl$_3$) δ 8.34 (d, J = 8.1 Hz, 1H), 8.27 (d, J = 5.3 Hz, 1H), 6.94 (d, J = 5.4 Hz, 1H), 5.82 (s, 2H), 4.93-4.81 (m, 1H), 4.56 (ddd, J = 10.8, 8.1, 7.0 Hz, 1H), 4.10 (s, 2H), 3.90 (s, 3H), 3.69-3.57 (m, 1H), 3.59 (q, J = 7.0 Hz, 2H), 3.51-3.41 (m, 1H), 3.07- | $^{13}$C NMR (CDCl$_3$) δ 172.84, 170.04, 162.88, 160.16, 145.78, 143.88, 142.36, 109.66, 89.56, 84.58, 75.42, 67.79, 67.17, 56.21, 51.85, 43.52, 36.51, 33.71, 28.10, 27.52, 23.54, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 2.98 (m, 1H), 2.41-2.27 (m, 1H), 1.82-1.27 (m, 9H) 1.42 (d, J = 6.4 Hz, 3H), 1.27-0.95 (m, 4H), 1.23 (t, J = 7.0 Hz, 3H), 0.94 (t, J = 7.4 Hz, 3H), 0.89 (d, J = 6.6 Hz, 3H), 0.88 (d, J = 6.6 Hz, 3H) | 23.02, 22.22, 18.82, 18.12, 15.00, 10.70 |
| F162 | — | (Neat) 3377, 2950, 1744, 1678, 1505, 1314, 1130 | HRMS-ESI (m/z) ([M]$^+$) calcd for C$_{30}$H$_{45}$F$_3$N$_2$O$_9$, 634.3077; found, 634.3089 | $^1$H NMR (CDCl$_3$) δ 8.34 (d, J = 8.1 Hz, 1H), 8.27 (d, J = 5.4 Hz, 1H), 6.95 (d, J = 5.4 Hz 1H), 5.82 (s, 2H), 4.93-4.81 (m, 1H), 4.56 (ddd, J = 10.7, 8.0, 6.9 Hz, 1H), 4.10 (s, 2H), 3.90 (s, 3H), 3.79-3.69 (m, 1H), 3.63-3.52 (m, 1H), 3.59 (q, J = 7.0 Hz, 2H), 3.09-2.98 (m, 1H), 2.40-2.28 (m, 1H), 2.28-2.12 (m, 2H), 1.89-1.27 (m, 9H), 1.40 (d, J = 6.4 Hz, 3H), 1.27-0.94 (m, 4H), 1.23 (t, J = 7.0 Hz, 3H), 0.93-0.83 (m, 6H) | $^{13}$C NMR (CDCl$_3$) δ 172.80, 170.05, 162.90, 160.17, 145.79, 143.90, 142.31, 127.17 (q, J =, 275.9 Hz), 109.69, 89.55, 84.85, 75.05, 71.55, 67.79, 67.18, 56.21, 51.84, 43.46, 36.48, 33.64, 30.82 (q, J = 29.1 Hz), 28.20, 28.09, 27.48, 23.06 (q, J = 3.0 Hz), 22.96, 22.17, 18.84, 18.14, 15.00 $^{19}$F NMR (CDCl$_3$) δ −66.44 |
| F163 | — | (Neat) 3379, 2941, 1743, 1678, 1504, 1374, 1210 | HRMS-ESI (m/z) ([M]$^+$) calcd for C$_{27}$H$_{42}$N$_2$O$_9$, 538.2890; found, 538.2903 | $^1$H NMR (CDCl$_3$) δ 8.34 (d, J = 8.1 Hz, 1H), 8.27 (d, J = 5.3 Hz, 1H), 6.95 (d, J = 5.4 Hz, 1H), 5.82 (s, 2H), 4.92-4.80 (m, 1H), 4.62-4.50 (m, 1H), 4.10 (s, 2H), 3.90 (s, 3H), 3.59 (q, J = 7.0 Hz, 2H), 3.50 (s, 3H), 2.99-2.89 (m, 1H), 2.41-2.26 (m, 1H), 1.83-1.27 (m, 7H), 1.43 (d, J = 6.4 Hz, 3H) 1.27-0.92 (m, 4H), 1.23 (t, J = 7.0 Hz, 3H), 0.90 (d, J = 6.6 Hz, 3H), 0.88 (d, J = 6.6 Hz, 3H) | $^{13}$C NMR (CDCl$_3$) δ 172.77, 170.03, 162.87, 160.15, 145.78, 143.86, 142.32, 109.68, 89.51, 86.41, 75.14, 67.77, 67.15, 61.18, 56.21, 51.80, 43.53, 36.47, 33.67, 28.24, 28.14 27.26, 23.07, 22.16, 18.75, 18.05, 14.99 |
| F164 | — | (Neat) 3381, 2938, 1742, 1677, 1507, 1314, 1218 | HRMS-ESI (m/z) ([M]$^+$) calcd for C$_{32}$H$_{41}$FN$_2$O$_9$, 616.2796; found, 616.2815 | $^1$H NMR (CDCl$_3$) δ 8.30 (d, J = 8.1 Hz, 1H), 8.26 (d, J = 5.4 Hz, 1H), 7.17-7.09 (m, 2H), 7.02-6.91 (m, 3H), 5.81 (s, 2H), 4.99-4.84 (m, 1H), 4.56 (ddd, J = 10.9, 8.1, 7.0 Hz, 1H), 4.09 (s, 2H), 3.90 (s, 3H), 3.64-3.53 (m, 3H), 3.45 (dd, J = 9.7, 6.8 Hz, 1H), 3.17 (t, J = 9.0 Hz, 1H), 3.14-3.05 (m, 1H), 2.37-2.23 (m, 2H), 1.89-1.77 (m, 1H), 1.63-1.50 (m, 2H), 1.47-1.34 (m, 1H), 1.46 (d, J = 6.5 Hz, 3H), 1.32-1.05 (m, 2H), 1.22 (t, J = 7.0 Hz, 3H), 0.95-0.80 (m, 1H), 0.65-0.52 (m, 2H), 0.31-0.19 (m, 2H) | $^{13}$C NMR (CDCl$_3$) δ 172.66, 170.01, 162.89, 161.26 (d, J = 243.6 Hz), 160.14, 145.79, 143.83, 142.25, 136.32 (d, J = 3.2 Hz), 130.14 (d, J = 7.7 Hz), 115.10 (d, J = 21.0 Hz), 109.71, 89.48, 83.72, 78.75, 75.18, 67.76, 67.14, 56.21, 51.73, 46.13, 36.04, 33.60, 26.62, 18.77, 18.08, 14.99, 11.16, 3.13, 2.99 $^{19}$F NMR (CDCl$_3$) δ −117.49 |
| F165 | 68-70 | (Neat) 3379, 2938, 1744, 1676, 1507, 1206 | HRMS-ESI (m/z) ([M]$^+$) calcd for C$_{34}$H$_{39}$FN$_2$O$_9$, 638.2640; found, 638.2663 | $^1$H NMR (CDCl$_3$) δ 8.34 (d, J = 8.0 Hz, 1H), 8.27 (d, J = 5.4 Hz, 1H), 7.35-7.25 (m, 2H), 7.13-6.87 (m, 8H), 5.82 (s, 2H), 5.18-5.05 (m, 1H), 4.62 (ddd, J = 11.0, 8.1, 6.9 Hz, 1H), 4.38-4.29 (m, 1H), 4.10 (s, 2H), 3.90 (s, 3H), 3.59 (q, J = 7.0 Hz, 2H), 3.03-2.91 (m, 1H), 2.42 - 2.28 (m, 2H), 2.12-1.99 (m, 1H), 1.73-1.61 (m, 2H), 1.61-1.46 (m, 1H), 1.35 (d, J = 6.5 Hz, 3H), 1.30-1.23 (m, 1H), 1.22 (t, J = 7.0 Hz, 3H), 1.11-0.97 (m, 1H) | $^{13}$C NMR (CDCl$_3$) δ 172.67, 170.04, 162.92, 161.30 (d, J = 243.7 Hz), 160.17, 159.55, 145.80, 143.91, 142.21, 135.84 (d, J = 3.1 Hz), 130.10 (d, J = 7.7 Hz), 129.72, 121.25, 115.46, 115.11 (d, J = 21.1 Hz), 109.74, 89.50, 80.99, 74.62, 67.79, 67.16, 56.22, 51.82, 45.71, 36.11, 33.55, 26.81, 18.95, 18.35, 15.00 $^{19}$F NMR (CDCl$_3$) δ −117.34 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F166 | — | (Neat) 3377, 2939, 1743, 1676, 1507, 1220 | HRMS-ESI (m/z) ([M]$^+$) calcd for C$_{31}$H$_{39}$FN$_2$O$_9$, 602.2640; found, 602.2648 | $^1$H NMR (CDCl$_3$) δ 8.30 (d, J = 8.0 Hz, 1H), 8.26 (d, J = 5.3 Hz, 1H), 7.18-7.06 (m, 2H), 7.03-6.90 (m, 3H), 6.06-5.84 (m, 1H), 5.82 (s, 2H), 5.33 (dq, J = 17.2, 1.6 Hz, 1H), 5.21 (dq, J = 10.4, 1.3 Hz, 1H), 4.98-4.87 (m, 1H), 4.57 (ddd, J = 10.9, 8.1, 7.0 Hz, 1H), 4.29 (ddt, J = 12.3, 5.5, 1.4 Hz, 1H), 4.16-4.08 (m, 1H), 4.09 (s, 2H), 3.90 (s, 3H), 3.59 (q, J = 7.0 Hz, 2H), 3.30-3.18 (m, 1H), 3.12-3.01 (m, 1H), 2.41-2.24 (m, 2H), 1.89-1.75 (m, 1H), 1.63-1.51 (m, 2H), 1.47 (d, J = 6.4 Hz, 3H), 1.46-.36 (m, 1H), 1.28-1.14(m, 1H), 1.23 (t, J = 7.0 Hz, 3H), 0.97-0.81 (m, 1H) | $^{13}$C NMR (CDCl$_3$) δ 172.69, 170.04, 162.91, 161.33 (d, J = 243.6 Hz), 160.17, 145.80, 143.89, 142.27, 136.26 (d, J = 3.3 Hz), 134.30, 130.14 (d, J = 7.7 Hz), 117.15, 115.12 (d, J = 21.1 Hz), 109.70, 89.53, 84.16, 75.05, 74.70, 67.80, 67.18, 56.22, 51.76, 45.97, 36.11, 33.63, 26.63, 18.82, 18.16, 15.01 $^{19}$F NMR (CDCl$_3$) δ −117.46 |
| F167 | — | — | HRMS-ESI (m/z) ([M]$^+$) calcd for C$_{31}$H$_{41}$FN$_2$O$_9$, 604.2796; found, 604.2800 | $^1$H NMR (CDCl$_3$) δ 8.31 (d, J = 8.1 Hz, 1H), 8.26 (d, J = 5.4 Hz, 1H), 7.17-7.07 (m, 2H), 7.02-6.90 (m, 3H), 5.81 (s, 2H), 4.98-4.83 (m, 1H), 4.57 (ddd, J = 10.9, 8.1, 7.0 Hz, 1H), 4.09 (s, 2H), 3.90 (s, 3H), 3.73 (dt, J = 8.6, 6.5 Hz, 1H), 3.59 (q, J = 7.0 Hz, 2H), 3.52 (dt, J = 8.7, 6.7 Hz, 1H), 3.20-3.11 (m, 1H), 3.11-3.01 (m, 1H), 2.41-2.23 (m, 2H), 1.87-1.72 (m, 1H), 1.71-1.51 (m, 4H), 1.46 (d, J = 6.5 Hz, 3H), 1.46-1.35 (m, 1H), 1.30-1.14 (m, 1H), 1.23 (t, J = 7.0 Hz, 3H), 0.98 (t, J = 7.4 Hz, 3H), 0.94-0.79 (m, 1H) | $^{13}$C NMR (CDCl$_3$) δ 172.69, 170.03, 162.89, 161.27 (d, J = 243.6 Hz), 160.15, 145.80, 143.86, 142.27, 136.39 (d, J = 3.2 Hz), 130.13 (d, J = 7.7 Hz), 115.09 (d, J = 21.0 Hz), 109.70, 89.51, 83.92, 75.62, 75.21, 67.78, 67.16, 56.21, 51.75, 46.15, 36.00, 33.63, 26.63, 23.58, 18.81, 18.09, 15.00, 10.72 $^{19}$F NMR (CDCl$_3$) δ −117.52 |
| F168 | — | (Neat) 3380, 2956, 1742, 1677, 1507, 1375, 1220 | HRMS-ESI (m/z) ([M]$^+$) calcd for C$_{32}$H$_{43}$FN$_2$O$_9$, 618.2953; found, 618.2960 | $^1$H NMR (CDCl$_3$) δ 8.31 (d, J = 8.1 Hz, 1H), 8.26 (d, J = 5.3 Hz, 1H), 7.17-7.06 (m, 2H), 7.03-6.89 (m, 3H), 5.82 (s, 2H), 4.98-4.83 (m, 1H), 4.57 (ddd, J = 10.9, 8.1, 7.0 Hz, 1H), 4.09 (s, 2H), 3.90 (s, 3H), 3.59 (q, J = 7.0 Hz, 2H), 3.56 (dd, J = 8.4, 6.3 Hz, 1H), 3.33 (dd, J = 8.4, 6.5 Hz, 1H), 3.18-3.10 (m, 1H), 3.10-3.00 (m, 1H), 2.39-2.23 (m, 2H), 1.97-1.73 (m, 2H), 1.63-1.51 (m, 2H), 1.45 (d, J = 6.4 Hz, 3H), 1.45-1.33 (m, 1H), 1.29-1.14 (m, 1H), 1.23 (t, J = 7.0 Hz, 3H), 0.97 (d, J = 6.7 Hz, 3H), 0.96 (d, J = 6.7 Hz, 3H), 0.93-0.80 (m, 1H) | $^{13}$C NMR (CDCl$_3$) δ 172.70, 170.05, 162.90, 161.28 (d, J = 243.6 Hz), 160.16, 145.80, 143.89, 142.29, 136.43 (d, J = 3.2 Hz), 130.13 (d, J = 7.7 Hz), 115.11 (d, J = 21.1 Hz), 109.69, 89.54, 83.66, 80.69, 75.25, 67.79, 67.18, 56.22, 51.76, 46.29, 35.91, 33.65, 29.27, 26.59, 19.53, 19.49, 18.85, 18.17, 15.01 $^{19}$F NMR (CDCl$_3$) δ −117.52 |
| F169 | — | (Neat) 3379, 2940, 1745, 1678, 1508, 1220 | HRMS-ESI (m/z) ([M]$^+$) calcd for C$_{30}$H$_{37}$F$_3$N$_2$O$_9$, 626.2451; found, 626.2455 | $^1$H NMR (CDCl$_3$) δ 8.30 (d, J = 8.0 Hz, 1H), 8.26 (d, J = 5.4 Hz, 1H), 7.18-7.05 (m, 2H), 7.03-6.90 (m, 3H), 5.87 (tt, J = 55.1, 4.0 Hz, 1H), 5.81 (s, 2H), 5.00-4.87 (m, 1H), 4.56 (ddd, J = 10.9, 8.1, 7.0 Hz, 1H), 4.09 (s, 2H), 4.06-3.91 (m, 1H), 3.90 (s, 3H), 3.87-3.71 (m, 1H), 3.59 (q, J = 7.0 Hz, 2H), 3.31-3.22 (m, 1H), 3.10-2.99 (m, 1H), 2.44-2.23 (m, 2H), 1.92-1.76 (m, 1H), 1.68-1.36 (m, 3H), 1.47 (d, J = 6.5 Hz, 3H), 1.30-1.15 (m, 1H), 1.23 (t, J = 7.0 Hz, 3H), 0.96-0.81 (m, 1H) | $^{13}$C NMR (CDCl$_3$) δ 172.56, 170.04, 162.92, 161.35 (d, J = 243.8 Hz), 160.17, 145.81, 143.89, 142.19, 135.85 (d, J = 3.2 Hz), 130.14 (d, J = 7.8 Hz), 115.19 (d, J = 21.1 Hz), 113.88 (t, J = 241.2 Hz), 109.75, 89.49, 85.53, 74.42, 72.59 (t, J = 27.6 Hz), 67.78, 67.16, 56.22, 51.72, 45.79, 35.92, 33.50, 26.59, 18.86, 18.14, 15.00 $^{19}$F NMR (CDCl$_3$) δ |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F170 | — | (Neat) 3379, 2943, 1733, 1678, 1508, 1156 | HRMS-ESI (m/z) ([M]$^+$) calcd for C$_{34}$H$_{43}$FN$_2$O$_{10}$, 658.2902; found, 658.2905 | $^1$H NMR (CDCl$_3$) δ 8.30 (d, J = 8.0 Hz, 1H), 8.26 (d, J = 5.4 Hz, 1H), 7.12-7.02 (m, 2H), 7.01-6.91 (m, 3H), 5.81 (s, 2H), 5.10-4.97 (m, 2H), 4.60 (ddd, J = 10.9, 8.0, 7.0 Hz, 1H), 4.10 (s, 2H), 3.90 (s, 3H), 3.59 (q, J = 7.0 Hz, 2H), 2.81-2.69 (m, 1H), 2.66 (dd, J = 13.8, 3.8 Hz, 1H), 2.43-2.28 (m, 2H), 2.01-1.45 (m, 11H), 1.34-1.17 (m, 2H), 1.29 (d, J = 5.7 Hz, 3H), 1.23 (t, J = 7.0 Hz, 3H), 1.05-0.92 (m, 1H) | −117.21, −125.47 (d, J = 9.4 Hz, 2F) $^{13}$C NMR (CDCl$_3$) δ 176.11, 172.70, 170.06, 162.89, 161.36 (d, J = 244.0 Hz), 160.17, 145.75, 143.96, 142.18, 135.58 (d, J = 3.2 Hz), 130.06 (d, J = 7.7 Hz), 115.22 (d, J = 21.2 Hz), 109.72, 89.51, 75.54, 73.17, 67.78, 67.17, 56.22, 51.73, 44.14, 44.01 35.93, 33.43, 25.72, 25.69, 18.72 17.55, 15.00 $^{19}$F NMR (CDCl$_3$) δ −117.11 |
| F171 | 118-120 | (Neat) 3379, 2976, 2939, 1734, 1677, 1507, 1153 | HRMS-ESI (m/z) ([M]$^+$) calcd for C$_{32}$H$_{41}$FN$_2$O$_{10}$, 632.2745; found, 632.2746 | $^1$H NMR (CDCl$_3$) δ 8.30 (d, J = 7.9 Hz, 1H), 8.26 (d, J = 5.3 Hz, 1H), 7.13-7.02 (m, 2H), 7.02-6.90 (m, 3H), 5.81 (s, 2H), 5.12-4.96 (m, 2H), 4.68-4.54 (m, 1H), 4.10 (s, 2H), 3.90 (s, 3H), 3.59 (q, J = 7.0 Hz, 2H), 2.65 (dd, J = 14.0, 3.6 Hz, 1H), 2.58 (hept, J = 7.0 Hz, 1H), 2.45-2.26 (m, 2H), 2.00-1.85 (m, 1H), 1.77-1.43 (m, 3H), 1.29 (d, J = 5.6 Hz, 3H), 1.29-1.15 (m, 10H), 1.05-0.91 (m, 1H) | $^{13}$C NMR (CDCl$_3$) δ 176.44, 172.68, 170.05, 162.90, 161.35 (d, J = 244.0 Hz), 160.17, 145.75, 143.94, 142.17, 135.53 (d, J = 3.2 Hz), 130.05 (d, J = 7.8 Hz), 115.22 (d, J = 21.1 Hz), 109.74, 89.48, 75.48, 73.10, 67.77, 67.16, 56.22, 51.73, 44.11, 35.85, 34.21, 33.41, 26.76, 19.07, 18.98, 18.72, 17.49, 15.00 $^{19}$F NMR (CDCl$_3$) δ −117.07 |
| F172 | — | — | ESIMS m/z 601.7 ([M + H]$^+$) | $^1$H NMR (CDCl$_3$) δ 8.30 (d, J = 8.2 Hz, 1H), 8.26 (d, J = 5.3 Hz, 1H), 7.33-7.23 (m, 3H), 7.23-7.13 (m, 3H), 6.93 (d, J = 5.4 Hz, 1H), 5.81 (s, 2H), 4.91 (dq, J = 9.1, 6.4 Hz, 1H), 4.57 (dt, J = 10.9, 7.5 Hz, 1H), 4.09 (s, 2H), 3.90 (s, 3H), 3.65-3.51 (m, 3H), 3.34 (dd, J = 8.4, 6.5 Hz, 1H), 3.20-3.03 (m, 2H), 2.42-2.21 (m, 2H), 1.98-1.76 (m, 2H), 1.63-1.53 (m, 2H), 1.50-1.40 (m, overlapping, 1H), 1.46 (d, J = 6.4 Hz, 3H), 1.31-1.15 (m, 7H), 0.97 (dd, J = 6.7, 5.2 Hz, 6H), 0.92-0.80 (m, 2H) | $^{13}$C NMR (CDCl$_3$) δ 172.72, 170.04, 162.89, 160.15, 145.78, 143.87, 142.31, 140.85, 128.86, 128.34, 125.87, 109.67, 89.55, 83.71, 80.65, 75.30, 67.79, 67.18, 56.21, 51.77, 46.19, 36.73, 33.70, 29.70, 29.28, 26.56, 19.55, 19.50, 18.84, 18.18, 15.01 |
| F173 | — | — | ESIMS m/z 599.6 ([M + H]$^+$) | $^1$H NMR (CDCl$_3$) δ 8.29 (d, J = 8.1 Hz, 1H), 8.26 (d, J = 5.4 Hz, 1H), 7.38-7.23 (m, 2H), 7.23-7.15 (m, 3H), 6.93 (d, J = 5.4 Hz, 1H), 5.81 (s, 2H), 4.93 (dq, J = 9.0, 6.4 Hz, 1H), 4.57 (dt, J = 10.9, 7.5 Hz, 1H), 4.09 (s, 2H), 3.90 (s, 3H), 3.61-3.52 (m, 3H), 3.45 (dd, J = 9.7, 6.8 Hz 1H) 3.26-3.09 m, 2H), 2.44-2.22 (m, 2H), 1.89 (ddq, J = 12.0, 7.4, 3.7 Hz, 1H), 1.57 (ddd, J = 12.3, 6.4, 2.5 Hz, 2H), 1.51-1.40 (m, overlapping, 1H), 1.46 (d, J = 6.4 Hz, 3H), 1.32-1.18 (m, 3H), 1.17-1.10 (m, 1H), 0.96-0.78 (m, 2H), 0.64-0.51 (m, 2H), 0.26 (dd, J = 5.8, 3.7 Hz, 2H) | $^{13}$C NMR (CDCl$_3$) δ 172.70, 170.04, 162.89, 160.15, 145.79, 143.86, 142.30, 140.72, 128.88, 128.35, 125.90, 109.67, 89.53, 83.81, 78.75, 75.25, 67.79, 67.18, 56.21, 51.75, 46.05, 36.89, 33.69, 29.70, 26.60, 18.77, 18.11, 15.01, 11.17, 3.16, 3.01 |
| F174 | — | — | ESIMS m/z 587.5 | $^1$H NMR (CDCl$_3$) δ 8.30 (d, J = 8.1 Hz, 1H), 8.26 (d, J = 5.3 | $^{13}$C NMR (CDCl$_3$) δ 172.72, 170.04, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | ([M + H]$^+$) | Hz, 1H), 7.35-7.23 (m, 2H), 7.23-7.13 (m, 3H), 6.93 (d, J = 5.4 Hz, 1H), 5.81 (s, 2H), 4.91 (dq, J = 9.2, 6.4 Hz, 1H), 4.57 (ddd, J = 10.9, 8.2, 7.0 Hz, 1H), 4.09 (s, 2H), 3.89 (s, 3H), 3.74 (dt, J = 8.7, 6.6 Hz, 1H), 3.66-3.47 (m, 3H), 3.18 (t, J = 9.1 Hz, 1H), 3.11 (dd, J = 13.3, 3.4 Hz, 1H), 2.42-2.23 (m, 2H), 1.85 (ddt, J = 12.1, 8.2, 3.7 Hz, 1H), 1.70-1.53 (m, 4H), 1.51-1.40 (m, overlapping, 1H), 1.46 (d, J = 6.4 Hz, 3H), 1.36-1.11 (m, 4H), 0.98 (t, J = 7.4 Hz, 3H), 0.91-0.81 (m, 1H) | 162.89, 160.15, 145.79, 143.87, 142.31, 140.80, 128.87, 128.34, 125.88, 109.68, 89.54, 84.00, 75.60, 75.26, 67.79, 67.18, 56.21, 51.76, 46.06, 36.83, 33.70, 26.60, 23.59, 18.81, 18.11, 15.01, 10.74 |
| F175 | — | — | ESIMS m/z 607.6 ([M + H]$^+$) | $^1$H NMR (CDCl$_3$) δ 8.34 (d, J = 8.1 Hz, 1H), 8.27 (d, J = 5.3 Hz, 1H), 6.95 (d, J = 5.4 Hz, 1H), 5.82 (s, 2H), 4.87 (dq, J = 9.2, 6.3 Hz, 1H), 4.61-4.48 (m, 1H), 4.10 (s, 2H), 3.90 (s, 3H), 3.59 (q, J = 7.0 Hz, 2H), 3.46 (dd J = 8.4, 6.1 Hz 1H), 3.24 (dd, J = 8.4, 6.7 Hz, 1H), 2.98 (t, J = 8.8 Hz, 1H), 2.34 (dt, J = 13.2, 6.7 Hz, 1H), 1.83 (dp, J = 13.2, 6.6 Hz, 2H), 1.77-1.50 (m, 9H), 1.41 (d, J = 6.4 Hz, 3H), 1.39-1.11 (m, 10H), 1.02-0.92 (m, 8H), 0.76 (tt, J = 11.6, 6.3 Hz, 1H) | $^{13}$C NMR (CDCl$_3$) δ 172.83, 170.05, 162.88, 160.15, 145.79, 143.87, 142.35, 109.67, 89.54, 84.31, 80.37, 75.49, 67.78, 67.17, 56.21, 51.85, 40.03, 38.13, 35.08, 34.58, 33.73, 32.26, 29.20, 27.45, 26.69, 26.51, 26.20, 19.58, 19.46, 18.85, 18.16, 15.00 |
| F176 | — | — | HRMS-ESI (m/z) ([M]$^+$) calcd for C$_{33}$H$_{44}$N$_2$O$_9$, 612.3047; found, 612.3053 | $^1$H NMR (CDCl$_3$) δ 8.37 (d, J = 8.0 Hz, 1H), 8.28 (d, J = 5.3 Hz, 1H), 7.35-7.23 (m, 2H), 7.02-6.88 (m, 4H), 5.82 (s, 2H), 5.07 (dq, J = 9.2, 6.4 Hz, 1H), 4.61 (ddd, J = 10.8, 8.1, 7.0 Hz, 1H), 4.18 (t, J = 8.7 Hz, 1H), 4.10 (s, 2H), 3.90 (s, 3H), 3.59 (q, J = 7.0 Hz, 2H), 2.48-2.34 (m, 1H), 1.93-1.33 (m, 14H), 1.30 (d, J = 6.5 Hz, 3H), 1.27-1.19 (m, 3H), 1.20-1.06 (m, 1H), 1.07-0.90 (m, 2H) | $^{13}$C NMR (CDCl$_3$) δ 172.80, 170.06, 162.92, 160.18, 159.77, 145.80, 143.93, 142.30, 129.58, 120.94, 115.56, 109.71, 89.55, 81.66, 74.90, 67.80, 67.19, 56.23, 51.93, 42.03, 37.27, 36.85, 33.70, 33.66, 31.77, 27.62, 25.05, 19.11, 18.40, 15.02 |
| F177 | — | — | HRMS-ESI (m/z) ([M]$^+$) calcd for C$_{33}$H$_{44}$N$_2$O$_{10}$, 628.2996; found, 628.3010 | $^1$H NMR (CDCl$_3$) δ 8.29 (d, J = 8.2 Hz, 1H), 8.26 (d, J = 5.4 Hz, 1H), 7.09 (d, J = 8.6 Hz, 2H), 6.93 (d, J = 5.4 Hz, 1H), 6.83 (d, J = 8.6 Hz, 2H), 5.81 (s, 2H), 4.92 (dq, J = 9.2, 6.4 Hz, 1H), 4.56 (ddd, J = 10.9, 8.2, 7.0 Hz, 1H), 4.09 (s, 2H), 3.90 (s, 3H), 3.79 (s, 3H), 3.59 (q, J = 7.0 Hz, 3H), 3.45 (dd, J = 9.7, 6.8 Hz, 1H), 3.16 (t, J = 9.1 Hz, 1H), 3.08 (dd, J = 13.2, 3.3 Hz, 1H), 2.37-2.22 (m, 2H), 1.83 (ddt, J = 12.1, 8.4, 3.8 Hz, 1H), 1.67-1.51 (m, 3H), 1.46 (d, J = 6.4 Hz, 3H), 1.26-1.18 (m, 1H), 1.23 (t, J = 7.0 Hz, 3H), 1.17-1.05 (m, 1H), 0.87 (d, J = 15.1 Hz, 1H), 0.62-0.54 (m, 2H), 0.31-0.19 (m, 2H) | $^{13}$C NMR (CDCl$_3$) δ 172.71, 170.04, 162.89, 160.16, 157.83, 145.79, 143.88, 142.32, 132.68, 129.74, 113.78, 109.67, 89.55, 83.82, 78.76, 75.27, 67.80, 67.18, 56.21, 55.24, 51.76, 46.18, 35.93, 33.72, 26.56, 18.77, 18.11, 15.02, 11.18, 3.16, 3.01 |
| F178 | — | — | HRMS-ESI (m/z) ([M]$^+$) calcd for C$_{31}$H$_{46}$N$_2$O$_9$, 590.3203; found, | $^1$H NMR (CDCl$_3$) δ 8.34 (d, J = 8.0 Hz, 1H), 8.27 (d, J = 5.4 Hz, 1H), 6.94 (d, J = 5.4 Hz, 1H), 5.82 (d, J = 0.8 Hz, 2H), 4.89 (dq, J = 9.3, 6.4 Hz, 1H), 4.64-4.43 (m, 1H), 4.10 (s, 3H), 3.90 (s, 3H), 3.59 (q, J = | $^{13}$C NMR (CDCl$_3$) δ 172.82, 170.05, 162.89, 160.16, 145.80, 143.89, 142.36, 109.66, 89.58, 84.35, 78.54, 75.39, 67.80, 67.19, 56.21, |

| Cmpd. No. | MP (° C.) | IR (cm$^{-1}$) | MASS | $^1$H NMR | $^{13}$C or $^{19}$F NMR |
|---|---|---|---|---|---|
| | | | 590.3225 | 7.0 Hz, 2H), 3.50 (dd, J = 9.6, 7.0 Hz, 1H), 3.36 (dd, J = 9.6, 6.8 Hz, 1H), 3.00 (t, J = 8.9 Hz, 1H), 2.34 (dt, J = 13.3, 6.8 Hz, 1H), 1.93-1.45 (m, 12H), 1.42 (d, J = 6.5 Hz, 3H), 1.37-1.27 (m, 1H), 1.23 (t, J = 7.0 Hz, 3H), 1.15-0.90 (m, 4H), 0.62-0.50 (m, 2H), 0.21 (dt, J = 5.9, 4.5 Hz, 2H) | 51.86, 42.33, 37.26, 36.90, 33.96, 33.76, 31.84, 27.54, 25.10, 25.07, 18.97, 18.10, 15.01, 11.14, 3.14, 2.94 |
| F179 | — | — | HRMS-ESI (m/z) ([M]$^+$) calcd for C$_{33}$H$_{46}$N$_2$O$_{10}$, 630.3152; found, 630.3164 | $^1$H NMR (CDCl$_3$) δ 8.30 (d, J = 8.1 Hz, 1H), 8.26 (d, J = 5.3 Hz, 1H), 7.08 (d, J = 8.6 Hz, 2H), 6.94 (d, J = 5.4 Hz, 1H), 6.83 (d, J = 8.6 Hz, 2H), 5.81 (s, 2H), 4.91 (dq, J = 9.2, 6.4 Hz, 1H), 4.56 (ddd, J = 10.9, 8.1, 7.0 Hz, 1H), 4.09 (s, 2H) 3.89 (s, 3H), 3.78 (s, 3H), 3.66-3.50 (m, 3H), 3.34 (dd, J = 8.4, 6.5 Hz, 1H), 3.14 (t, J = 9.0 Hz, 1H), 3.04 (dd, J = 13.4, 3.2 Hz, 1H), 2.35-2.23 (m, 2H), 1.97-1.73 (m, 2H), 1.64-1.51 (m, 2H), 1.45 (d, J = 6.4 Hz, 3H), 1.30-1.13 (m, 5H), 0.97 (dd, J = 6.7, 5.2 Hz, 6H), 0.94-0.79 (m, 1H) | $^{13}$C NMR (CDCl$_3$) δ 172.73, 170.04, 162.88, 160.15, 157.80, 145.79, 143.87, 142.31, 132.81, 129.71, 113.76, 109.68, 89.54, 83.71, 80.63, 75.31, 67.79, 67.18, 56.22, 55.23, 51.77, 46.32, 35.78, 33.71, 29.27, 26.53, 19.55, 19.50, 18.84, 18.18, 15.02 |
| F180 | 50-55 | — | ESIMS m/z 613 ([M + H]$^+$) | $^1$H NMR (CDCl$_3$) δ 8.28 (d, J = 8.1 Hz, 1H), 8.25 (s, 1H), 7.12-7.03 (m, 4H), 6.93 (d, J = 5.4 Hz, 1H), 5.80 (s, 2H), 4.91 (dq, J = 9.2, 6.4 Hz, 1H), 4.55 (ddd, J = 10.9, 8.2, 7.0 Hz, 1H), 4.08 (s, 2H), 3.88 (s, 3H), 3.58 (q, J = 7.0 Hz, 2H), 3.58 (dd, J = 9.7, 7.0 Hz, 1H), 3.44 (dd, J = 9.7, 6.9 Hz, 1H), 3.16 (t, J = 9.1 Hz, 1H), 3.09 (dd, J = 13.2, 3.3 Hz, 1H), 2.39-2.21 (m, 5H), 1.93-1.80 (m, 1H), 1.63-1.51 (m, 2H), 1.51-1.40 (m, 4H), 1.30-1.07 (m, 5H), 0.90-0.80 (m, 1H), 0.61-0.54 (m, 2H), 0.28-0.20 (m, 2H) | $^{13}$C NMR (CDCl$_3$) δ 172.65, 169.98, 162.83, 160.09, 145.74, 143.80, 142.23, 137.49, 135.29, 128.98, 128.68, 109.63, 89.47, 83.74, 78.69, 75.20, 67.73, 67.11, 56.16, 51.69, 46.01, 36.33, 33.64, 26.49, 20.96, 18.69, 18.05, 14.96, 11.12, 3.10, 2.95 |
| F181 | — | — | HRMS-ESI (m/z) ([M + Na]$^+$) calcd for C$_{27}$H$_{41}$FN$_2$O$_9$Na, 579.2688; found 579.2694 | $^1$H NMR (CDCl$_3$) δ 8.35 (d, J = 8.1 Hz, 1H), 8.27 (d, J = 5.4 Hz, 1H), 6.94 (d, J = 5.5 Hz, 1H), 5.82 (s, 2H), 4.90 (dq, J = 9.1, 6.4 Hz, 1H), 4.64-4.51 (m, 2H), 4.51-4.39 (m, 1H), 4.10 (s, 2H), 3.90 (s, 3H), 3.59 (q, J = 7.0 Hz, 2H), 3.45 (dd, J = 8.4, 6.6 Hz, 1H), 3.26 (dd, J = 8.4, 6.4 Hz, 1H), 3.14-3.02 (m, 1H), 2.35 (dt, J = 12.9, 6.7 Hz, 1H), 2.15-1.96 (m, 1H), 1.83 (dq, J = 13.3, 6.7 Hz, 1H), 1.78-1.60 (m, 4H), 1.56 (s, 1H), 1.42 (d, J = 6.4 Hz, 3H), 1.39-1.29 (m, 1H), 1.23 (t, J = 7.0 Hz, 3H), 1.10 (dd, J = 14.0, 6.8 Hz, 1H), 0.96-0.89 (m, 6H) | $^{13}$C NMR (CDCl$_3$) δ 172.76, 170.06, 162.90, 160.18, 145.80, 143.91, 142.30, 109.69, 89.57, 83.86, 83.81, 82.17, 80.23, 75.26, 67.80, 67.19, 56.22, 51.86, 39.77, 39.73, 33.56, 31.62, 31.42, 29.17, 28.72 19.46, 19.42, 19.19, 18.14, 15.02 |
| F182 | — | — | HRMS-ESI (m/z) ([M + H]$^+$) calcd for C$_{35}$H$_{43}$N$_2$O$_{10}$, 651.2912; found, 651.2930 | $^1$H NMR (CDCl$_3$) δ 8.37 (d, J = 8.0 Hz, 1H), 8.28 (d, J = 5.4 Hz, 1H), 7.33-7.27 (m, 2H), 7.26-7.21 (m, 2H), 7.02-6.88 (m, 5H), 6.88-6.78 (m, 2H), 5.82 (s, 2H), 5.18-5.06 (m, 1H), 4.62 (dt, J = 10.9, 7.0 Hz, 1H), 4.29 (t, J = 8.7 Hz, 1H), 4.10 (s, 2H), 3.96 (t, J = 6.1 Hz, 2H), 3.91 (s, 3H), 3.59 | $^{13}$C NMR (CDCl$_3$) δ 172.74, 170.07, 162.93, 160.18, 159.35, 158.78, 145.80, 143.96, 142.24, 129.69, 129.39, 121.18, 120.61, 115.42, 114.46, 109.72, 89.56, 81.16, 74.79, 67.81, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | (q, J = 7.0 Hz, 2H), 2.40 (dt, J = 12.7, 6.7 Hz, 1H), 2.15-2.02 (m, 2H), 1.99-1.83 (m, 1H), 1.83 - 1.62 (m, 3H), 1.40 (q, J = 12.3, 11.7 Hz, 1H), 1.32 (d, J = 6.5 Hz, 3H), 1.23 (m, 4H) | 67.19, 66.05, 56.23, 51.90, 40.21, 33.58, 30.54, 28.47, 19.32, 18.34, 15.02 |
| F183 | — | — | HRMS-ESI (m/z) ([M + H]$^+$) calcd for C$_{30}$H$_{41}$N$_2$O$_{10}$, 589.2756; found, 589.2763 | $^1$H NMR (CDCl$_3$) δ 8.37 (d, J = 8.0 Hz, 1H), 8.28 (d, J = 5.4 Hz, 1H), 7.32-7.27 (m, 2H), 6.99-6.90 (m, 4H), 5.82 (s, 2H), 5.08 (dq, J = 9.1, 6.5 Hz, 1H), 4.61 (dt, J = 10.8, 7.0 Hz, 1H), 4.24 (t, J = 8.8 Hz, 1H), 4.10 (s, 2H), 3.91 (s, 3H), 3.59 (q, J = 7.0 Hz, 2H), 3.38 (t, J = 6.8 Hz, 2H), 3.26 (s, 3H), 2.40 (dt, J = 12.3, 6.7 Hz, 1H), 1.99-1.78 (m, 3H), 1.78-1.61 (m, 2H), 1.48 (ddd, J = 13.6, 9.9, 6.7 Hz, 1H), 1.39 (q, J = 11.0 Hz, 1H), 1.30 (d, J = 6.5 Hz, 3H), 1.23 (t, J = 7.0 Hz, 3H), 1.17 (d, J = 7.5 Hz, 1H) | $^{13}$C NMR (CDCl$_3$) δ 172.74, 170.07, 162.92, 160.18, 159.46, 145.80, 143.95, 142.27, 129.62, 121.06, 115.38, 109.71, 89.56, 81.12, 74.84, 70.80, 67.80, 67.19, 58.44, 56.23, 51.89, 40.13, 33.63, 30.56, 28.15, 19.18, 18.35, 15.02 |
| F184 | — | — | ESIMS m/z 527.3 ([M + H]$^+$) | $^1$H NMR (CDCl$_3$) δ 8.52 (d, J = 8.2 Hz, 1H), 8.34 (d, J = 5.4 Hz, 1H), 7.00 (d, J = 5.5 Hz, 1H), 4.89 (dq, J = 9.0, 6.4 Hz, 1H), 4.55 (tt, J = 10.9, 4.4 Hz, 2H), 4.48 (s, 2H), 4.44 (ddd, J = 7.7, 5.9, 2.6 Hz, 1H), 3.90 (d, J = 1.8 Hz, 3H), 3.73 (q, J = 7.0 Hz, 2H), 3.44 (dd, J = 8.4, 6.6 Hz, 1H), 3.26 (dd, J = 8.4, 6.4 Hz, 1H), 3.10-3.02 (m, 1H), 2.32 (dt, J = 12.9, 6.7 Hz, 1H), 2.13-1.97 (m, 1H), 1.84 (dp, J = 13.2, 6.6 Hz, 1H), 1.78-1.64 (m, 3H), 1.60-1.45 (m, 2H), 1.41 (d, J = 6.4 Hz, 3H), 1.37-1.31 (m, 1H), 1.29 (t, J = 7.0 Hz, 3H), 1.08 (dd, J = 12.1, 5.0 Hz, 1H), 0.92 (d, J = 6.6 Hz, 6H) | $^{13}$C NMR (CDCl$_3$) δ 172.65, 168.71, 162.20, 159.41, 146.89, 141.38, 137.00, 109.84, 83.85, 83.79, 82.15, 80.20, 75.24, 67.86, 67.36, 56.30, 51.57, 39.75, 33.73, 31.61, 31.42, 29.17, 28.70, 19.45, 19.41, 19.14, 18.11, 15.08 |
| F185 | — | — | ESIMS m/z 621.3 ([M + H]$^+$) | $^1$H NMR (CDCl$_3$) δ 8.54 (d, J = 8.2 Hz, 1H), 8.35 (d, J = 5.4 Hz, 1H), 7.35-7.27 (m, 2H), 7.25-7.20 (m, 2H), 7.01 (d, J = 5.5 Hz, 1H), 6.99-6.88 (m, 4H), 6.82 (dd, J = 8.7, 1.0 Hz, 2H), 5.11 (dq, J = 9.1, 6.4 Hz, 1H), 4.61 (ddd, J = 10.9, 8.2, 7.0 Hz, 1H), 4.48 (s, 2H), 4.28 (t, J = 8.7 Hz, 1H), 3.95 (t, J = 6.0 Hz, 2H), 3.90 (s, 3H), 3.73 (q, J = 7.0 Hz, 2H), 2.37 (dt, J = 12.9, 6.6 Hz, 1H), 2.07 (td, J = 9.0, 7.1, 3.6 Hz, 2H), 1.96-1.82 (m, 1H), 1.82-1.62 (m, 3H), 1.44-1.34 (m, 1H), 1.33-1.26 (m, 6H), 1.26-1.18(m, 1H) | $^{13}$C NMR (CDCl$_3$) δ 172.64, 168.72, 162.23, 159.43, 159.35, 158.78, 146.89, 141.35, 137.04, 129.69, 129.39, 121.19, 120.61, 115.42, 114.46, 109.87, 81.18, 74.77, 67.87, 67.37, 66.05, 56.31, 51.63, 40.21, 33.75, 30.54, 28.48, 19.29, 18.32, 15.08 |
| F186 | — | — | ESIMS (m/z) 559.3 ([M + H]$^+$) | $^1$H NMR (CDCl$_3$) δ 8.53 (d, J = 8.0 Hz, 1H), 8.35 (d, J = 5.4 Hz, 1H), 7.33-7.27 (m, 2H), 7.01 (d, J = 5.5 Hz, 1H), 6.94 (dd, J = 8.0, 3.2 Hz, 3H), 5.15-5.00 (m, 1H), 4.60 (dt, J = 10.8, 7.1 Hz, 1H), 4.48 (s, 2H), 4.23 (t, J = 8.8 Hz, 1H), 3.90 (s, 3H), 3.73 (q, J = 7.0 Hz, 2H), 3.37 (t, J = 6.6 Hz, 2H), 3.26 (s, 3H), 2.37 (dt, J = 13.0, 6.7 Hz, 1H), 1.98-1.76 (m, 3H), 1.76-1.61 (m, 2H), 1.56- | $^{13}$C NMR (CDCl$_3$) δ 172.64, 168.72, 162.21, 159.46, 146.88, 141.37, 129.62, 121.06, 115.39, 109.86, 81.14, 74.82, 70.81, 67.86, 67.36, 58.44, 56.30, 51.61, 40.12, 33.79, 30.57, 28.17, 19.16, 18.33, 15.07 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1.42 (m, 1H), 1.42-1.32 (m, 1H), 1.29 (dt, J = 7.0, 3.8 Hz, 6H), 1.18 (dd, J = 15.2, 7.5 Hz, 1H) | |
| F187 | — | — | HRMS-ESI (m/z) [M + Na]⁺ calcd for C$_{28}$H$_{44}$O$_{10}$N$_2$Na, 591.2888; found, 591.2914 | ¹H NMR (CDCl$_3$) δ 8.35 (d, J = 8.0 Hz, 1H), 8.27 (d, J = 5.4 Hz, 1H), 6.96 (d, J = 5.5 Hz, 1H), 5.82 (s, 2H), 4.88 (dq, J = 9.0, 6.4 Hz, 1H), 4.56 (dt, J = 10.8, 7.1 Hz, 1H), 4.10 (s, 2H), 3.90 (s, 3H), 3.59 (q, J = 7.0 Hz, 2H), 3.42 (q, J = 7.8, 7.2 Hz, 3H), 3.32 (s, 3H), 3.29 (dd, J = 8.1, 6.1 Hz, 1H), 3.05 (t, J = 8.8 Hz, 1H), 2.34 (dt, J = 13.2, 6.5 Hz, 1H), 1.97 (dtd, J = 10.8, 7.5, 3.2 Hz, 1H), 1.85 (dp, J = 13.2, 6.6 Hz, 1H), 1.67 (ddt, J = 27.8, 14.0, 6.7 Hz, 3H), 1.59-1.44 (m, 2H), 1.41 (d, J = 6.4 Hz, 3H), 1.33 (q, J = 11.3 Hz, 1H), 1.23 (t, J = 7.0 Hz, 3H), 1.10-1.00 (m, 1H), 0.92 (dd, J = 6.7, 2.5 Hz, 6H) | ¹³C NMR (CDCl$_3$) δ 172.76, 170.02, 162.86, 160.13, 145.79, 143.82, 142.27, 109.70, 89.47, 84.00, 80.30, 75.35, 71.21, 67.75, 67.13, 58.46, 56.21, 51.83, 40.21, 33.57, 30.37, 29.13, 28.33, 19.48, 19.40, 19.08, 18.12, 14.99 |
| F188 | — | — | HRMS-ESI (m/z) [M + Na]⁺ calcd for C$_{27}$H$_{42}$O$_{9}$N$_2$Na, 561.2783; found, 561.2802 | ¹H NMR (CDCl$_3$) δ 8.52 (d, J = 8.2 Hz, 1H), 8.34 (d, J = 5.4 Hz, 1H), 7.00 (d, J = 5.5 Hz, 1H), 4.94-4.82 (m, 1H), 4.54 (ddd, J = 10.8, 8.2, 7.0 Hz, 1H), 4.48 (s, 2H), 3.90 (s, 3H), 3.73 (q, J = 7.0 Hz, 2H), 3.41 (q, J = 7.4, 6.6 Hz, 3H), 3.32 (s, 3H), 3.32-3.26 (m, 1H), 3.03 (t, J = 8.8 Hz, 1H), 2.31 (dt, J = 13.2, 6.5 Hz, 1H), 1.96 (dtd, J = 10.6, 7.4, 3.1 Hz, 1H), 1.83 (dq, J = 13.3, 6.6 Hz, 1H), 1.75-1.63 (m, 2H), 1.62 (s, 1H), 1.56-1.44 (m, 2H), 1.40 (d, J = 6.4 Hz, 3H), 1.29 (m, 4H), 1.03 (dd, J = 13.3, 5.9 Hz, 1H), 0.91 (dd, J = 6.7, 2.7 Hz, 6H) | ¹³C NMR (CDCl$_3$) δ 172.70, 168.72, 162.18, 159.41, 146.88, 141.42, 137.00, 109.82, 84.04, 80.33, 75.38, 71.28, 67.86, 67.36, 58.51, 56.30, 51.58, 40.25, 33.82, 30.42, 29.17, 28.36, 19.51, 19.43, 19.07, 18.13, 15.08 |
| F189 | — | — | HRMS-ESI (m/z) [M + H]⁺ calcd for C$_{29}$H$_{39}$O$_{9}$N$_9$, 559.2650; found, 559.2654 | ¹H NMR (CDCl$_3$) δ 8.37 (d, J = 8.0 Hz, 1H), 8.28 (d, J = 5.3 Hz, 1H), 7.30 (d, J = 7.7 Hz, 2H), 6.94 (dd, J = 7.1, 4.6 Hz, 4H), 5.83 (s, 2H), 5.16-5.01 (m, 1H), 4.61 (dt, J = 10.8, 7.4 Hz, 1H), 4.22 (t, J = 8.8 Hz 1H), 4.10 (s, 2H), 3.91 (s, 3H), 3.59 (q, J = 7.0 Hz, 2H), 2.40 (dt, J = 12.5, 6.4 Hz, 1H), 1.95-1.78 (m, 1H), 1.77-1.59 (m, 4H), 1.38 (q, J = 12.7, 11.9 Hz, 1H), 1.30 (d, J = 6.4 Hz, 3H), 1.27-1.19 (m, 4H), 1.17 (s, 1H), 0.88 (t, J = 7.2 Hz, 3H) | ¹³C NMR (CDCl$_3$) δ 172.79, 170.07, 162.92, 160.18, 159.68, 145.80, 143.95, 142.29, 129.60, 120.95, 115.40, 109.70, 99.98, 89.57, 81.44, 74.86, 67.81, 67.19, 56.23, 51.89, 44.98, 33.68, 27.05, 23.53, 18.85, 18.38, 15.02, 11.88, 0.00 |
| F190 | — | — | ESIMS m/z 669 [M + H]⁺ | ¹H NMR (CDCl$_3$) δ 8.29 (d, J = 8.1 Hz, 1H), 8.25 (d, J = 5.4 Hz, 1H), 7.09 (d, J = 7.9 Hz, 2H), 7.03 (d, J = 8.0 Hz, 2H), 6.93 (d, J = 5.4 Hz, 1H), 5.80 (s, 2H), 4.89 (dq, J = 9.1, 6.4 Hz, 1H), 4.55 (dt, J = 10.9, 7.4 Hz, 1H), 4.08 (s, 2H), 3.88 (s, 3H), 3.80 (dt, J = 8.9, 6.1 Hz, 1H), 3.64-3.54 (m, 3H), 3.17 (t, J = 9.0 Hz, 1H), 2.96 (dd, J = 13.3, 3.4 Hz, 1H), 2.40-2.13 (m, 7H), 1.92-1.76 (m, 3H), 1.65-1.37 (m, 6H), 1.30-1.14 (m, 4H), 0.93-0.80 (m, | ¹³C NMR (CDCl$_3$) δ 172.62, 169.97, 162.83, 160.09, 145.73, 143.81, 142.18, 137.20, 135.41, 129.02, 128.58, 131.42-122.86 (m), 109.65, 89.44, 84.20, 74.83, 71.60, 67.71, 67.10, 56.15, 51.69, 45.80, 36.42, 33.56, 30.73 (q, J = 29.0 Hz), 26.62, 23.01 (q, J = 3.1 Hz), 20.93, 18.75, 18.05, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 1H) | 14.94<br>$^{19}$F NMR (CDCl$_3$) δ −66.35 |
| F191 | — | — | HRMS-ESI (m/z) [M + H]$^+$ calcd for C$_{31}$H$_{47}$O$_{10}$N$_2$, 607.3225; found, 607.3236 | $^1$H NMR (CDCl$_3$) δ 8.14 (d, J = 8.0 Hz, 1H), 8.07 (d, J = 5.4 Hz, 1H), 6.75 (d, J = 5.5 Hz, 1H), 5.61 (s, 2H), 4.69 (dq, J = 9.0, 6.4 Hz, 1H), 4.35 (dt, J = 10.7, 7.2 Hz, 1H), 3.89 (s, 2H), 3.70 (s, 3H), 3.39 (q, J = 7.0 Hz, 2H), 3.34-3.15 (m, 4H), 3.05 (dq, J = 6.5, 3.3 Hz, 2H), 2.88 (t, J = 8.9 Hz, 1H), 2.14 (dt, J = 13.2, 6.5 Hz, 1H), 1.90-1.72 (m, 1H), 1.48 (dtd, J = 21.5, 11.5, 10.3, 6.2 Hz, 3H), 1.40-1.26 (m, 2H), 1.22 (d, J = 6.4 Hz, 3H), 1.13 (q, J = 11.4 Hz, 1H), 1.02 (t, J = 7.0 Hz, 3H), 0.85 (dddd, J = 14.8, 6.8, 5.0, 3.5 Hz, 3H), 0.33 (tdd, J = 10.0, 4.9, 3.7 Hz, 4H), 0.00 (dtd, J = 10.2, 5.3, 4.7, 2.9 Hz, 4H) | $^{13}$C NMR (CDCl$_3$) δ 172.74, 170.02, 162.87, 160.13, 145.78, 143.84, 142.29, 109.69, 89.49, 84.00, 78.33, 75.41, 75.30, 69.06, 67.76, 67.14, 56.21, 51.80, 40.47, 33.62, 30.66, 28.20, 19.02, 18.07, 14.99, 11.08, 10.64, 3.15, 2.99, 2.92, 2.87 |
| F192 | — | — | HRMS-ESI (m/z) [M + H]$^+$ calcd for C$_{23}$H$_{33}$O$_9$N$_2$, 481.2181; found, 481.2183 | $^1$H NMR (CDCl$_3$) δ 8.43 (d, J = 7.5 Hz, 1H), 8.27 (dd, J = 5.3, 3.3 Hz, 1H), 6.96 (dd, J = 5.4, 1.7 Hz, 1H), 5.82 (d, J = 2.9 Hz, 2H), 4.99 (ddt, J = 12.6, 9.2, 4.7 Hz, 1H), 4.61-4.41 (m, 1H), 4.10 (d, J = 2.8 Hz, 2H), 3.90 (d, J = 2.7 Hz, 3H), 3.80 (td, J = 7.5, 6.5, 3.2 Hz, 1H), 3.69 (dq, J = 8.8, 5.5, 4.7 Hz, 1H), 3.59 (qd, J = 7.0, 2.7 Hz, 2H), 3.42 (tt, J = 6.6, 2.9 Hz, 1H), 2.47-2.31 (m, 1H), 2.15-1.82 (m, 3H), 1.75 (t, J = 14.0 Hz, 1H), 1.63 (t, J = 13.1 Hz, 1H), 1.57-1.46 (m, 2H), 1.41 (dt, J = 9.7, 4.8 Hz, 4H), 1.23 (td, J = 7.0, 3.0 Hz, 3H) | $^{13}$C NMR (CDCl$_3$) δ 173.60, 170.02, 162.79, 160.14, 145.80, 143.84, 142.28, 109.71, 89.47, 86.82, 73.26, 67.74, 67.68, 67.13, 56.21, 53.27, 39.67, 36.07, 35.73, 32.37, 21.77, 18.36, 14.98 |
| F193 | 70-75 | — | ESIMS m/z 675 ([M + H]$^+$) | $^1$H NMR (CDCl$_3$) δ 8.29 (d, J = 8.0 Hz, 1H), 8.22 (d, J = 5.4 Hz, 1H), 7.59 (dd, J = 1.7, 0.8 Hz, 1H), 7.15 (dd, J = 3.5, 0.8 Hz, 1H), 7.03 (td, J = 8.5, 6.4 Hz, 1H), 6.92 (d, J = 5.4 Hz, 1H), 6.73-6.63 (m, 2H), 6.50 (dd, J = 3.5, 1.7 Hz, 1H), 5.78 (s, 2H), 5.19 (t, J = 9.2 Hz, 1H), 5.09 (dq, J = 9.5, 6.2 Hz 1H), 4.59 (dt, J = 10.9, 7.4 Hz, 1H), 4.06 (s, 2H), 3.86 (s, 3H), 3.56 (q, J = 7.0 Hz, 2H), 2.70 (dd, J = 13.9, 4.5 Hz, 1H), 2.50 (dd, J = 13.9, 10.3 Hz, 1H), 2.39-2.29 (m, 1H), 2.18-2.07 (m, 1H), 1.74-1.51 (m, 3H), 1.30 (d, J = 6.3 Hz, 3H), 1.28-1.21 (m, 1H), 1.19 (t, J = 7.0 Hz, 3H), 1.11-0.99 (m, 1H) | $^{13}$C NMR (CDCl$_3$) δ 172.50, 169.95, 162.79, 161.38 (dd, J = 246.4, 11.5 Hz), 160.89 (dd, J = 247.5, 11.6 Hz), 160.05, 158.08, 146.84, 145.65, 143.82, 143.80, 142.02, 131.50 (dd, J = 9.4, 6.5 Hz) 122.36 (dd, J = 15.7, 111.89, 110.82 (dd, J = 21.0, 3.6 Hz), 109.65, 103.58 (t J = 25.7 Hz), 89.34, 76.34, 73.01, 67.65, 67.04, 56.11, 51.59, 42.51, 33.28, 29.98, 27.26, 18.66, 17.40, 14.88<br>$^{19}$F NMR R (CDCl$_3$) δ −112.99 (d, J = 6.8 Hz), −113.49 (d, J = 6.9 Hz) |
| F194 | — | — | HRMS-ESI (m/z) ([M]$^+$) calcd for C$_{30}$H$_{44}$N$_2$O$_8$, 560.3098; found, 560.3112 | $^1$H NMR (CDCl$_3$) δ 8.51 (d, J = 8.2 Hz, 1H), 8.33 (d, J = 5.4 Hz, 1H), 6.99 (d, J = 5.5 Hz, 1H), 4.88 (dq, J = 9.2, 6.4 Hz, 1H), 4.54 (ddd, J = 10.8, 8.4, 7.0 Hz, 1H), 3.89 (s, 3H), 3.81 (t, J = 6.6 Hz, 2H), 3.49 (dd, J = 9.6, 7.0 Hz, 1H), 3.41 (s, 3H), 3.39-3.28 (m, 2H), 3.05-2.93 (m, 3H), 2.31 (dt, J = | $^{13}$C NMR (CDCl$_3$) δ 172.72, 169.40, 162.31, 159.40, 146.75, 141.50, 137.29, 109.75, 84.34, 78.49, 75.34, 67.58, 58.77, 56.30, 51.57, 42.30, 37.25, 36.89, 34.62, 33.95, 33.92, 31.83, 27.54, 25.09, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | — | — | | 13.4, 6.8 Hz, 1H), 1.91-1.65 (m, 4H), 1.65-1.43 (m, 8H), 1.40 (d, J = 6.5 Hz, 3H), 1.37-1.23 (m, 1H), 1.15-0.91 (m, 4H), 0.61-0.51 (m, 2H), 0.21 (dt, J = 5.8, 4.6 Hz, 2H) | 25.06, 18.93, 18.06, 11.13, 3.12, 2.93 |
| F195 | — | — | HRMS-ESI (m/z) ([M]$^+$) calcd for C$_{32}$H$_{42}$N$_2$O$_9$, 598.2890; found, 589.2914 | $^1$H NMR (CDCl$_3$) δ 8.47 (d, J = 7.3 Hz, 1H), 8.31 (d, J = 5.4 Hz, 1H), 7.09 (d, J = 8.6 Hz, 2H), 6.98 (d, J = 5.5 Hz, 1H), 6.83 (d, J = 8.6 Hz, 2H), 4.91 (dq, J = 9.1, 6.4 Hz, 1H), 4.55 (ddd, J = 10.9, 8.4, 7.0 Hz, 1H), 3.88 (s, 3H), 3.81 (t, J = 6.6 Hz, 2H), 3.78 (s, 3H), 3.57 (dd, J = 9.7, 7.0 Hz, 1H), 3.44 (dd, J = 9.7, 6.8 Hz, 1H), 3.41 (s, 3H), 3.15 (t, J = 9.0 Hz, 1H), 3.07 (dd, J = 13.4, 3.3 Hz, 1H), 2.98 (t, J = 6.6 Hz, 2H), 2.35-2.20 (m, 2H), 1.87-1.77 (m, 1H), 1.61-1.47 (m, 2H), 1.48-1.37 (m, 1H), 1.45 (d, J = 6.4 Hz, 3H), 1.22-1.05 (m, 2H), 0.90-0.79 (m, 1H), 0.63-0.49 (m, 2H), 0.29-0.14 (m, 2H) | $^{13}$C NMR (CDCl$_3$) δ 172.61, 169.39, 162.32, 159.40, 157.82, 146.76, 141.45, 137.29, 132.66, 129.73, 113.77, 109.78, 83.79, 78.71, 75.22, 67.58, 58.78, 56.30, 55.22, 51.47, 46.17, 35.92, 34.62, 33.89, 26.55, 18.73, 18.08, 11.18, 3.16, 3.00 |
| F196 | — | — | HRMS-ESI (m/z) [M + H]$^+$ calcd for C$_{30}$H$_{43}$O$_8$N$_2$, 559.3014; found, 559.3016 | $^1$H NMR (CDCl$_3$) δ 8.50 (d, J = 7.7 Hz, 1H), 8.32 (d, J = 5.5 Hz, 1H), 6.98 (d, J = 5.5 Hz, 1H), 5.01-4.75 (m, 1H), 4.59 (dt, J = 10.6, 7.7 Hz, 1H), 3.90 (s, 3H), 3.54-3.37 (m, 4H), 3.25 (dq, J = 6.6, 3.3 Hz, 2H), 3.06 (t, J = 8.8 Hz, 1H), 2.34 (dt, J = 13.4, 6.5 Hz, 1H), 1.97 (tt, J = 8.2, 4.6 Hz, 2H), 1.77-1.60 (m, 3H), 1.57-1.45 (m, 2H), 1.41 (d, J = 6.4 Hz, 3H), 1.36-1.22 (m, 3H), 1.06 (ddt, J = 12.2, 8.6, 4.0 Hz, 5H), 0.60-0.47 (m, 4H), 0.30 - 0.14 (m, 4H) | $^{13}$C NMR (CDCl$_3$) δ 172.75, 172.47, 162.31, 159.44, 146.62, 141.81, 137.40, 109.66, 99.97, 84.00, 78.38, 75.48, 75.26, 69.12, 56.31, 51.46, 40.52, 33.93, 30.65, 28.15, 18.94, 18.06, 12.99, 11.09, 10.66, 9.31, 3.18, 3.02, 2.95, 2.88 |
| F197 | — | — | HRMS-ESI (m/z) [M + H]$^+$ calcd for C$_{29}$H$_{39}$N$_2$O$_8$, 543.2701; found, 543.2705 | $^1$H NMR (CDCl$_3$) δ 8.47 (d, J = 8.3 Hz, 1H), 8.32 (d, J = 5.4 Hz, 1H), 7.31-7.26 (m, 2H), 7.18 (tq, J = 7.4, 1.8 Hz, 3H), 6.98 (d, J = 5.4 Hz, 1H), 4.90 (dq, J = 9.2, 6.4 Hz, 1H), 4.56 (ddd, J = 10.9, 8.4, 7.0 Hz, 1H), 3.89 (s, 3H), 3.86-3.75 (m, 3H), 3.63 (dq, J = 8.9, 7.0 Hz, 1H), 3.41 (s, 3H), 3.22-3.13 (m, 1H), 3.09 (dd, J = 13.3, 3.4 Hz, 1H), 2.98 (t, J = 6.6 Hz, 2H), 2.35 (dd, J = 13.3, 11.6 Hz, 1H), 2.31-2.21 (m, 1H), 1.89-1.77 (m, 1H), 1.74-1.63 (m, 1H), 1.63-1.51 (m, 1H), 1.51-1.38 (m, 1H), 1.45 (d, J = 6.4 Hz, 3H), 1.25 (t, J = 7.0 Hz, 3H), 1.22-1.12 (m, 1H), 0.92-0.79 (m, 1H) | $^{13}$C NMR (CDCl$_3$) δ 172.64, 169.41, 162.33, 159.41, 146.76, 141.47, 140.75, 137.31, 128.87, 128.34, 125.89, 109.77, 84.20, 75.19, 69.21, 67.59, 58.79, 56.31, 51.49, 45.94, 36.91, 34.63, 33.89, 26.61, 18.75, 18.02, 15.73 |
| F198 | — | — | HRMS-ESI (m/z) [M + H]$^+$ calcd for C$_{30}$H$_{41}$N$_2$O$_8$, 557.2857; found, 557.2869 | $^1$H NMR (CDCl$_3$) δ 8.47 (d, J = 8.0 Hz, 1H), 8.32 (d, J = 5.4 Hz, 1H), 7.32-7.26 (m, 2H), 7.22-7.14 (m, 3H), 6.98 (d, J = 5.5 Hz, 1H), 4.90 (dq, J = 9.2, 6.4 Hz, 1H), 4.56 (ddd, J = 10.9, 8.4, 7.0 Hz, 1H), 3.89 (s, 3H), 3.81 (t, J = 6.6 Hz, 2H), 3.73 (dt, J = 8.8, 6.5 Hz, 1H), 3.52 (dt, J = 8.7, 6.7 Hz, 1H), 3.41 (s, 3H), 3.16 (t, J = | $^{13}$C NMR (CDCl$_3$) δ 172.64, 169.42, 162.33, 159.41, 146.75, 141.47, 140.80, 137.31, 128.87, 128.34, 125.89, 109.77, 83.99, 75.58, 75.24, 67.59, 58.79, 56.31, 51.49, 46.06, 36.83, 34.62, 33.89, 26.59, 23.60, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 9.0 Hz, 1H), 3.13-3.07 (m, 1H), 2.98 (t, J = 6.6 Hz, 2H), 2.35 (dd, J = 13.3, 11.7 Hz, 1H), 2.31-2.22 (m, 1H), 1.84 (ddq, J = 12.1, 7.6, 3.7 Hz, 1H), 1.73-1.51 (m, 4H), 1.51-1.36 (m, 1H), 1.45 (d, J = 6.4 Hz, 3H), 1.29-1.07 (m, 1H), 0.98 (t, J = 7.4 Hz, 3H), 0.92-0.82 (m, 1H) | 18.78, 18.09, 10.75 |
| F199 | — | — | ESIMS m/z 456.3 ([M + Na]$^+$) | $^1$H NMR (CDCl$_3$) δ 7.28 - 7.09 (m, 2H), 6.96-6.75 (m, 3H), 5.07 (d, J = 8.3 Hz, 1H), 5.02-4.88 (m, 1H), 4.21-4.02 (m, 2H), 2.27-2.07 (m, 1H), 1.81-1.29 (m, 7H), 1.36 (s, 9H), 1.29-0.91 (m, 3H), 1.21 (d, J = 6.4 Hz, 3H), 0.82-0.73 (m, 1H), 0.72 (d, J = 6.6 Hz, 3H), 0.71 (d, J = 6.7 Hz, 3H) | $^{13}$C NMR (CDCl$_3$) δ 172.32, 158.69, 153.90, 128.54, 119.93, 114.46, 80.59, 78.76, 73.72, 52.00, 42.14, 35.35, 33.09, 27.32, 27.21, 26.82, 26.56, 22.02, 21.02, 17.83, 17.39 |
| F200 | — | — | ESIMS m/z 436.4 ([M + Na]$^+$) | $^1$H NMR (CDCl$_3$) δ 5.06 (d, J = 8.3 Hz, 1H), 4.90-4.75 (m, 1H), 4.21-4.07 (m, 1H), 3.44 (dd, J = 8.4, 6.3 Hz, 1H), 3.25 (dd, J = 8.4, 6.5 Hz, 1H), 2.97 (t, J = 8.9 Hz, 1H), 2.28-2.11 (m, 1H), 1.83 (hept, J = 6.6 Hz, 1H), 1.75-1.41 (m, 8H), 1.44 (s, 9H), 1.39 (d, J = 6.4 Hz, 3H), 1.30-1.01 (m, 3H), 0.92 (d, J = 6.7 Hz, 3H), 0.91 (d, J = 6.7 Hz, 3H), 0.88 (d, J = 6.6 Hz, 3H), 0.87 (d, J = 6.6 Hz, 3H) | $^{13}$C NMR (CDCl$_3$) δ 173.40, 154.93, 84.31, 80.43, 79.76, 75.36, 52.97, 43.48, 36.53, 34.21, 29.18, 28.33, 28.10, 27.99, 27.55, 22.98, 22.27, 19.52, 19.46, 18.76, 18.19 |
| F201 | — | — | ESIMS m/z 434.4 ([M + Na]$^+$) | $^1$H NMR (CDCl$_3$) δ 5.08 (d, J = 8.1 Hz, 1H), 4.86-4.68 (m, 1H), 4.14-4.01 (m, 1H), 3.43 (dd, J = 9.6, 7.0 Hz, 1H), 3.29 (dd, J = 9.7, 6.9 Hz, 1H), 2.93 (t, J = 9.0 Hz, 1H), 2.20-2.04 (m, 1H), 1.71-1.37 (m, 7H), 1.37 (s, 9H), 1.34 (d, J = 6.5 Hz, 3H), 1.25-0.92 (m, 5H), 0.82 (d, J = 6.6 Hz, 3H), 0.81 (d, J = 6.7 Hz, 3H), 0.53-0.43 (m, 2H), 0.20-0.09 (m, 2H) | $^{13}$C NMR (CDCl$_3$) δ 173.35, 154.95, 84.37, 79.69, 78.61, 75.28, 52.97, 43.55, 36.43, 34.16, 28.35, 28.05, 27.38, 23.05, 22.22, 18.68, 18.14, 11.15, 3.10, 3.03 |
| F202 | — | (Neat) 2955, 1750, 1708, 1455, 1367, 1296, 1176, 1083 | ESIMS m/z 466.4 ([M + Na]$^+$) | $^1$H NMR (CDCl$_3$) δ 5.02-4.69 (m, 3H), 4.62-4.46 (m, 0.5H), 4.25-4.10 (m, 0.5H), 3.70-3.55 (m, 1H), 3.49-3.40 (m, 1H), 3.40-3.28 (m, 3H), 3.07-2.93 (m, 1H), 2.18-1.98 (m, 1H), 1.81-1.42 (m, 17H), 1.40 (d, J = 6.4 Hz, 3H), 1.35 -1.01 (m, 4H), 0.93 (t, J = 7.5 Hz, 3H), 0.91-0.83 (m, 7H) | — |
| F203 | 87-89 | — | ESIMS m/z 534.4 ([M + Na]$^+$) | $^1$H NMR (CDCl$_3$) δ 5.02-4.69 (m, 3H), 4.62-4.45 (m, 0.5H), 4.27-4.09 (m, 0.5H), 3.82-3.65 (m, 1H), 3.61-3.47 (m, 1H), 3.42-3.26 (m, 3H), 3.09-2.93 (m, 1H), 2.31-1.95 (m, 3H), 1.92-1.42 (m, 17H), 1.39 (d, J = 6.4 Hz, 3H), 1.33-1.00 (m, 4H), 1.00-0.81 (m, 7H) | $^{19}$F NMR (CDCl$_3$) δ −66.42-−66.63 (m, 3F) |
| F204 | — | (Neat) 2932, 1765, 1707, 1454, 1367, | HRMS-ESI (m/z) ([M]$^+$) calcd for C$_{26}$H$_{47}$NO$_6$, 469.3403; | $^1$H NMR (CDCl$_3$) δ 5.03-4.66 (m, 3H), 4.61-4.46 (m, 0.5H), 4.24-4.09 (m, 0.5H), 4.08-3.96 (m, 1H), 3.42-3.27 (m, 3H), 3.17-3.04 (m, 1H), 2.23-1.99 (m, 1H), 1.86- | — |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | 1296, 1173, 1083 | found, 469.3416 | 0.99 (m, 30H), 0.95-0.83 (m, 7H) | |
| F205 | — | (Neat) 2934, 1747, 1705, 1454, 1366, 1296, 1170, 1080 | HRMS-ESI (m/z) ([M]⁺) calcd for $C_{22}H_{41}NO_6$, 415.2934; found, 415.2943 | ¹H NMR (CDCl₃) δ 4.97-4.70 (m, 3H), 4.60-4.47 (m, 0.5H), 4.25-4.11 (m, 0.5H), 3.49 (s, 3H), 3.40-3.28 (m, 3H), 2.97-2.86 (m, 1H), 2.17-2.01 (m, 1H), 1.79-1.42 (m, 16H), 1.42 (d, J = 6.4 Hz, 3H), 1.31-1.07 (m, 3H), 0.99-0.82 (m, 7H) | — |
| F206 | — | (Neat) 2955, 1735, 1705, 1454, 1367, 1298, 1170 | HRMS-ESI (m/z) ([M]⁺) calcd for $C_{27}H_{47}NO_7$, 497.3353; found, 497.3368 | ¹H NMR (CDCl₃) δ 5.02-4.75 (m, 4H), 4.66-4.47 (m, 0.5H), 4.32-4.14 (m, 0.5H), 3.45-3.24 (m, 3H), 2.85-2.65 (m, 1H), 2.22-1.36 (m, 25H), 1.35-0.94 (m, 7H), 0.93-0.76 (m, 6H) | — |
| F207 | — | (Neat) 2937, 1748, 1714, 1509, 1367, 1220, 1160 | HRMS-ESI (m/z) ([M]⁺) calcd for $C_{25}H_{36}FNO_5$, 449.2578; found, 449.2586 | ¹H NMR (CDCl₃) δ 7.20-7.05 (m, 2H), 7.03-6.87 (m 2H), 5.14 (d, J = 8.3 Hz, 1H), 4.95-4.79 (m, 1H), 4.23-4.06 (m, 1H), 3.56 (dd, J = 9.7, 7.0 Hz, 1H), 3.43 (dd, J = 9.7, 6.8 Hz, 1H), 3.13-3.04 (m, 1H), 2.31 (dd, J = 13.4, 11.6 Hz, 1H), 2.23-2.09 (m, 1H), 1.86-1.72 (m, 1H), 1.61-1.31 (m, 5H), 1.45 (d, J = 6.5 Hz, 3H), 1.43 (s, 9H), 1.19-0.99 (m, 1H), 0.89-0.75 (m, 1H), 0.62-0.52 (m, 2H), 0.29-0.20 (m, 2H) | ¹³C NMR (CDCl₃) δ 173.20, 170.99, 161.24 (d, J = 243.7 Hz), 154.90, 136.32 (d, J = 3.2 Hz), 130.11 (d, J = 7.7 Hz), 115.07 (d, J = 21.0 Hz), 83.70, 79.67, 78.68, 75.01, 60.30, 52.87, 46.08, 36.00, 33.98, 28.27, 26.62, 20.95, 18.66, 18.07, 14.16, 11.15, 3.12, 2.97 ¹⁹F NMR R (CDCl₃) δ −117.40 |
| F208 | 75-77 | (Neat) 2936, 1714, 1509, 1368, 1163 | HRMS-ESI (m/z) ([M]⁺) calcd for $C_{24}H_{34}FNO_5$, 471.2421; found, 471.2430 | ¹H NMR (CDCl₃) δ 7.36 - 7.26 (m, 2H), 7.12-6.86 (m, 7H), 5.17-4.96 (m, 2H), 4.30 (t, J = 8.9 Hz, 1H), 4.26-4.16 (m, 1H), 2.95 (dd, J = 13.7, 3.5 Hz, 1H), 2.38-2.15 (m, 2H), 2.09-1.95 (m, 1H), 1.67-1.45 (m, 3H), 1.44 (s, 9H), 1.33 (d, J = 6.5 Hz, 3H), 1.18-0.90 (m, 2H) | ¹³C NMR (CDCl₃) δ 173.26, 161.31 (d, J = 243.8 Hz), 159.56, 154.89, 135.84 (d, J = 2.5 Hz) 130.09 (d, J = 7.8 Hz), 129.72, 121.26, 115.47, 115.11 (d, J = 21.1 Hz), 81.00, 79.93, 74.53, 52.94, 45.66, 36.09, 34.08, 28.33, 26.83, 18.83, 18.38 ¹⁹F NMR (CDCl₃) δ −117.34 |
| F209 | — | — | ESIMS m/z 502.3 ([M + Na]⁺) | ¹H NMR (CDCl₃) δ 7.18 - 7.04 (m, 2H), 7.01-6.88 (m, 2H), 5.94 (ddt, J = 17.3, 10.7, 5.5 Hz, 1H), 5.39-5.27 (m, 1H), 5.19 (dd, J = 10.4, 1.7 Hz, 1H), 4.96-4.72 (m, 3H), 4.63-4.48 (m, 0.5H), 4.28 (dd, J = 12.4, 5.3 Hz, 1H), 4.25-4.16 (m, 0.5H), 4.13-4.03 (m, 1H), 3.39-3.14 (m, 3H), 3.05 (dd, J = 13.3, 3.4 Hz, 1H), 2.33 (dd, J = 13.4, 11.6 Hz, 1H), 2.19-1.97 (m, 1H), 1.88-1.72 (m, 1H), 1.73-1.33 (m, 17H), 0.93- 0.77 (m, 1H) | ¹⁹F NMR (CDCl₃) δ −117.36, −117.46 |
| F210 | — | (Neat) 2936, 1746, 1701, 1509, 1366, 1297, 1177 | HRMS-ESI (m/z) ([M]⁺) calcd for $C_{26}H_{40}FNO_6$, 481.2840; found, 481.2842 | ¹H NMR (CDCl₃) δ 7.18 - 7.05 (m, 2H), 7.03-6.88 (m, 2H), 4.98-4.68 (m, 3H), 4.63-4.49 (m, 0.5H), 4.27-4.15 (m, 0.5H), 3.80-3.63 (m, 1H), 3.57-3.43 (m, 1H), 3.39-3.23 (m, 2H), 3.20-3.08 (m, 1H), 3.05 (dt, J = 13.5, 3.5 Hz, 1H), 2.98-2.86 (m, 1H), 2.32 (t, J = 12.5 Hz, 1H), 2.17- | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 2.00 (m, 1H), 1.94-1.32 (m, 19H), 0.97 (t, J = 7.4 Hz, 3H), 0.91-0.76 (m, 1H) | |
| F211 | — | (Neat) 2957, 1748, 1705, 1509, 1367, 1296, 1175 | HRMS-ESI (m/z) ([M]$^+$) calcd for C$_{27}$H$_{42}$FNO$_6$, 495.2996; found, 495.2993 | $^1$H NMR (CDCl$_3$) δ 7.17-7.03 (m, 2H), 7.02-6.87 (m, 2H), 5.03-4.66 (m, 2H), 4.65-4.49 (m, 0.5H), 4.29-4.13 (m, 0.5H), 3.61-3.48 (m, 1H), 3.39-3.23 (m, 3H), 3.19-2.99 (m, 2H), 2.97-2.87 (m, 1H), 2.39-2.24 (m, 1H), 2.21-1.22 (m, 20H), 1.08-0.75 (m, 7H) | — |
| F212 | — | (Neat) 2978, 2938, 1747, 1700, 1509, 1368, 1297, 1080 | HRMS-ESI (m/z) ([M]$^+$) calcd for C$_{25}$H$_{36}$F$_3$NO$_6$, 503.2495; found, 503.2499 | $^1$H NMR (CDCl$_3$) δ 7.16 - 7.04 (m, 2H), 7.02-6.89 (m, 2H), 5.86 (tt, J = 55.1, 4.0 Hz, 1H), 4.95-4.71 (m, 3H), 4.60-4.46 (m, 0.5H), 4.25-4.13 (m, 0.5H), 4.04-3.89 (m, 1H), 3.84-3.69 (m, 1H), 3.37-3.18 (m, 3H), 3.03 (dd, J = 13.3, 3.5 Hz, 1H), 2.41-2.30 (m, 1H), 2.19-1.99 (m, 1H), 1.88-1.75 (m, 1H), 1.72-1.32 (m, 17H), 0.93-0.75 (m, 1H) | $^{19}$F NMR (CDCl$_3$) δ −117.16, −117.27, −125.28--125.61 (m, 2F) |
| F213 | — | (Neat) 2954, 1734, 1703, 1509, 1368, 1297, 1167 | HRMS-ESI (m/z) ([M]$^+$) calcd for C$_{29}$H$_{42}$FNO$_7$, 535.2945; found, 535.2961 | $^1$H NMR (CDCl$_3$) δ 7.11-7.01 (m, 2H), 7.01-6.91 (m, 2H), 5.11-4.73 (m, 4H), 4.66-4.50 (m, 0.5H), 4.33-4.18 (m, 0.5H), 3.41-3.24 (m, 2.85-2.68 (m, 2H), 2.68-2.58 (m, 1H), 2.36 (dd, J = 13.7, 11.1 Hz, 1H), 2.22-2.02 (m, 1H), 2.01-1.37 (m, 21H), 1.34-1.20 (m, 3H), 1.03-0.88 (m, 1H) | $^{19}$F NMR (CDCl$_3$) δ −117.05, −117.18 |
| F214 | — | (Neat) 2976, 1737, 1704, 1510, 1367, 1297, 1177 | HRMS-ESI (m/z) ([M]$^+$) calcd for C$_{27}$H$_{40}$FNO$_7$, 509.2789; found, 509.2795 | $^1$H NMR (CDCl$_3$) δ 7.13 - 7.01 (m, 2H), 7.02-6.89 (m, 2H), 5.09-4.74 (m, 4H), 4.64-4.52 (m, 0.5H), 4.34-4.19 (m, 0.5H), 3.42-3.22 (m, 19 3H), 2.71-2.49 (m, 2H), 2.36 (dd, J = 13.8, 11.2 Hz, 1H), 2.23-2.01 (m, 1H), 1.98-1.82 (m, 1H), 1.78-1.37 (m, 14H), 1.35-1.13 (m, 8H), 1.03-0.85 (m, 1H) | $^{19}$F NMR (CDCl$_3$) δ −117.05, −117.17 |
| F215 | — | — | HRMS-ESI (m/z) ([M]$^+$) calcd for C$_{28}$H$_{37}$NO$_6$, 483.2621; found, 483.2600 | $^1$H NMR (CDCl$_3$) δ 7.30 (dd, J = 8.7, 7.3 Hz, 2H), 7.00 (td, J = 6.3, 3.0 Hz, 4H), 6.96 (t, J = 7.3 Hz, 2H), 6.79 (d, J = 8.6 Hz, 2H), 5.15-4.99 (m, 2H), 4.30 (t, J = 9.0 Hz, 1H), 4.26-4.14 (m, 1H), 3.76 (s, 3H), 2.93 (dd, J = 13.5, 3.3 Hz, 1H), 2.28 (dd, J = 13.5, 11.8 Hz, 1H), 2.23-2.16 (m, 1H), 2.00 (dt, J = 8.3, 3.9 Hz, 1H), 1.64-1.48 (m, 2H), 1.43 (s, 9H), 1.33 (d, J = 6.5 Hz, 3H), 1.15-1.02 (m, 1H), 1.00-0.87 (m, 1H) | $^{13}$C NMR (CDCl$_3$) δ 173.29, 159.66, 157.83, 154.89, 132.21, 129.67, 121.17, 115.54, 113.72, 81.13, 79.90, 74.60, 55.20, 52.94, 45.73, 35.93, 34.14, 28.32, 26.72, 18.80, 18.40 |
| F216 | — | (Thin Film) 2943, 2868, 1743, 1706, 1492, 1366, 1200, 1160 | HRMS-ESI (m/z) ([M]$^+$) calcd for C$_{26}$H$_{39}$NO$_5$, 445.2828; found, 445.2845 | $^1$H NMR (CDCl$_3$) δ 7.32-7.27 (m, 2H), 6.97-6.90 (m, 3H), 5.14-4.95 (m, 2H), 4.24-4.10 (m, 2H), 2.27 (dt, J = 13.6, 6.9 Hz, 1H), 1.88-1.73 (m, 3H), 1.74-1.58 (m, 4H), 1.55-1.46 (m, 4H), 1.44 (s, 9H), 1.41-1.34 (m, 2H), 1.28 (d, J = 6.5 Hz, 3H), 1.24-1.10 (m, 1H), 1.12-0.80 (m, 3H) | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F217 | — | — | ESIMS m/z 570 ([M + Na]$^+$) | $^1$H NMR (CDCl$_3$) δ 7.07-6.97 (m, 2H), 6.86-6.76 (m, 2H), 5.06-4.85 (m, 3H), 4.77 (d, J = 11.6 Hz, 1H), 3.78 (s, 3H), 3.38-3.26 (m, 3H), 2.74 (p, J = 8.0 Hz, 1H), 2.61 (dd, J = 13.7, 3.7 Hz, 1H), 2.31 (dd, J = 13.7, 11.1 Hz, 1H), 2.20-2.02 (m, 1H), 1.99-1.52 (m, 12H), 1.51-1.40 (m, 9H), 1.27 (d, J = 5.8 Hz, 3H), 1.15-1.04 (m, 1H), 1.00 (t, J = 7.5 Hz, 1H), 0.97-0.87 (m, 1H) | $^{13}$C NMR (CDCl$_3$) δ 176.26, 173.56, 157.94, 155.49, 131.94, 129.59, 113.80, 81.21, 75.54, 72.72, 58.52, 55.43, 55.22, 44.32, 44.04, 35.77, 30.09, 30.00, 29.58, 28.20, 26.48, 25.72, 25.70, 19.09, 17.56 |
| F218 | — | — | ESIMS m/z 566 ([M + Na]$^+$) | $^1$H NMR (CDCl$_3$) δ 7.10-7.00 (m, 2H), 6.88-6.76 (m, 2H), 4.97-4.82 (m, 2H), 4.81-4.71 (m, 1H), 4.55 (s, 1H), 4.19 (t, J = 9.6 Hz, 1H), 3.97-3.84 (m, 1H), 3.78 (s, 3H), 3.72 (dt, J = 9.1, 6.8 Hz, 1H), 3.37-3.26 (m, 3H), 3.14 (td, J = 8.9, 3.2 Hz, 1H), 2.97 (dd, J = 13.4, 3.5 Hz, 1H), 2.37-2.24 (m, 1H), 2.26-2.02 (m, 3H), 1.81-1.57 (m, 5H), 1.58-1.23 (m, 14H), 0.89-0.77 (m, 1H) | $^{19}$F NMR (CDCl$_3$) δ −89.52, −89.56 (d, J = 72.5 Hz) |
| F219 | — | — | HRMS-ESI (m/z) ([M]$^+$) calcd for C$_{24}$H$_{41}$NO$_5$, 423.2985; found, 423.2998 | $^1$H NMR (CDCl$_3$) δ 5.05 (d, J = 8.2 Hz, 1H), 4.94-4.77 (m, 1H), 4.14 (q, J = 8.1 Hz, 1H), 3.48 (dd, J = 9.6, 7.0 Hz, 1H), 3.34 (dd, J = 9.6, 6.9 Hz, 1H), 2.97 (t, J = 8.9 Hz, 1H), 2.21 (dt, J = 13.6, 7.0 Hz, 1H), 1.94-1.64 (m, 5H), 1.64-1.47 (m, 9H), 1.43 (s, 9H), 1.40 (d, J = 6.4 Hz, 2H), 1.19-0.98 (m, 4H), 0.91 (dd, J = 15.2, 7.9 Hz, 1H), 0.59-0.46 (m, 2H), 0.26-0.08 (m, 2H) | $^{13}$C NMR (CDCl$_3$) δ 173.37, 154.92, 84.35, 79.79, 78.53, 75.28, 52.97, 42.26, 37.26, 36.86, 34.29, 33.95, 31.82, 28.34, 27.59, 25.10, 25.07, 18.87, 18.11, 11.13, 3.14, 2.94 |
| F220 | — | — | HRMS-ESI (m/z) ([M]$^+$) calcd for C$_{28}$H$_{45}$NO$_7$, 507.3196; found, 507.3173 | $^1$H NMR (CDCl$_3$) δ 7.07 (dd, J = 8.7, 3.3 Hz, 2H), 6.86-6.77 (m, 2H), 4.92-4.73 (m, 2H), 4.23-4.11 (m, 1H), 3.81-3.76 (m, 3H), 3.54 (ddd, J = 8.5, 6.3, 2.3 Hz, 1H), 3.36-3.25 (m, 3H), 3.10 (td, J = 9.2, 3.1 Hz, 1H), 3.03 (dt, J = 13.4, 3.6 Hz, 1H), 2.91 (s, 1H), 2.33-2.20 (m, 1H), 1.89 (dp, J = 13.3, 6.8 Hz, 1H), 1.77 (s, 1H), 1.67-1.47 (m, 3H), 1.47-1.37 (m, 15H), 0.96 (t, J = 6.3 Hz, 6H), 0.85-0.76 (m, 1H) | $^{13}$C NMR (CDCl$_3$) δ 173.39, 157.80, 132.82, 129.69, 113.73, 83.74, 80.58, 55.25, 46.32, 46.28, 35.76, 30.07, 29.26, 28.38, 28.32, 28.25, 28.19, 26.54, 19.56, 19.50, 19.25, 19.12, 18.26, 18.18 |
| F221 | — | — | HRMS-ESI (m/z) ([M]$^+$) calcd for C$_{27}$H$_{43}$NO$_7$, 493.3040; found, 493.3018 | $^1$H NMR (CDCl$_3$) δ 7.12-7.03 (m, 2H), 6.86-6.77 (m, 2H), 4.89-4.73 (m, 3H), 4.28-4.11 (m, 1H), 3.78 (s, 3H), 3.71 (dtd, J = 8.4, 6.6, 1.8 Hz, 1H), 3.50 (dtd, J = 8.5, 6.7, 1.7 Hz, 1H), 3.30 (d, J = 14.0 Hz, 3H), 3.12 (td, J = 8.9, 3.7 Hz, 1H), 3.02 (dd, J = 13.4, 3.3 Hz, 1H), 2.27 (ddd, J = 13.3, 11.7, 6.2 Hz, 1H), 1.76 (s, 1H), 1.71-1.50 (m, 5H), 1.44 (dd, J = 10.8, 4.6 Hz, 14H), 0.97 (dd, J = 7.8, 6.9 Hz, 3H), 0.81 (s, 1H) | $^{13}$C NMR (CDCl$_3$) δ 173.30, 157.80, 132.75, 129.69, 113.73, 99.98, 88.37, 84.02, 83.98, 83.86, 81.11, 75.59, 75.52, 55.25, 46.20, 46.12, 35.86, 35.82, 28.32, 28.23, 26.56, 23.59, 19.21, 18.68, 18.18, 18.12, 10.75 |
| F222 | — | — | ESIMS m/z 446.2 [(M + Na)$^+$] | $^1$H NMR (CDCl$_3$) δ 7.29 (dd, J = 1.8, 0.9 Hz, 1H), 6.27 (dd, J = 3.1, 1.9 Hz, 1H), 6.00 (d, J = 3.2 Hz, 1H), 5.05 (d, J = 8.3 Hz, 1H), 4.87 (dq, J = 9.3, 6.1 Hz, 1H), 4.20-4.09 (m, 1H), | $^{13}$C NMR (CDCl$_3$) δ 173.31, 154.91, 154.68, 140.98, 110.07, 106.00, 83.49, 80.24, 75.08, 52.92, 43.13, 34.10, 32.07, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 3.48 (dd, J = 8.4, 6.5 Hz, 1H), 3.28 (dd, J = 8.4, 6.4 Hz, 1H), 3.10 (t, J = 9.0 Hz, 1H), 2.99 (dd, J = 14.5, 3.5 Hz, 1H), 2.48 (dd, J = 14.7, 11.3 Hz, 1H), 2.16 (dt, J = 13.5, 6.8 Hz, 1H), 1.88 (tdd, J = 16.7, 9.0, 3.6 Hz, 3H), 1.66 (dt, J = 11.8, 2.8 Hz, 1H), 1.53-1.47 (m, 1H), 1.43 (s, 9H), 1.46-1.40 (m, 4H), 1.10 (dt, J = 13.8, 10.8 Hz, 1H), 0.93 (d, J = 6.7 Hz, 6H) | 29.32, 29.19, 28.33, 26.23, 22.01, 19.47, 19.46, 18.78, 18.18 |
| F223 | — | — | ESIMS m/z 506 ([M + Na]⁺) | ¹H NMR (CDCl₃) δ 5.03-4.74 (m, 3H), 4.30-4.17 (m, 1H), 3.39-3.30 (m, 3H), 2.72-2.51 (m, 1H), 2.22-2.04 (m, 1H), 1.88-0.75 (m, 36H) | ¹³C NMR (CDCl₃) δ 182.04, 173.67, 36.98, 36.48, 35.09, 34.30, 33.68, 31.84, 28.24, 28.18, 25.04, 25.02, 22.53, 19.13, 18.95, 18.84, 18.79, 18.29, 17.51 |
| F224 | 144-145 | — | ESIMS m/z 400.2 [(M + Na)⁺] | ¹H NMR (CDCl₃) δ 7.32-7.24 (m, 2H), 6.94 (dd, J = 7.8, 6.5 Hz, 3H), 5.05 (m, 2H), 4.20 (dt, J = 10.8, 7.7 Hz, 1H), 4.13 (t, J = 8.8 Hz, 1H), 2.27 (dt, J = 12.8, 6.2 Hz, 1H), 1.90 (d, J = 7.0 Hz, 1H), 1.74-1.53 (m, 4H), 1.44 (s, 9H), 1.30 (d, J = 6.5 Hz, 3H), 1.25-1.17 (m, 1H), 0.99 (d, J = 6.9 Hz, 3H) | ¹³C NMR (CDCl₃) δ 173.36, 159.67, 154.90, 129.57, 120.98, 115.47, 82.27, 79.86, 74.59, 53.05, 37.61, 34.14, 32.37, 28.33, 19.15, 18.31, 17.74 |
| F225 | — | — | ESIMS m/z 292.2 [(M-tBoc + H)⁺] | ¹H NMR (CDCl₃) δ 7.50-7.04 (m, 5H), 5.06 (d, J = 7.9 Hz, 1H), 4.90 (m, 1H), 4.70 (d, J = 10.8 Hz, 1H), 4.58 (d, J = 10.8 Hz, 1H), 4.16 (m, 1H), 3.19 (t, J = 8.9 Hz, 1H), 2.3-2.14 (m, 1H), 1.83-1.67 (m, 1H), 1.66-.58 (m, 3H), 1.46 (d, J = 6.4 Hz, 3H), 1.44 (s, 9H), 1.23-1.08 (m, 2H), 1.06 (d, J = 6.8 Hz, 3H) | ¹³C NMR (CDCl₃) δ 173.39, 154.94, 128.46, 127.81, 127.73, 85.30, 79.81, 75.57, 75.09, 53.01, 37.92, 34.22, 32.29, 28.34, 19.01, 18.23, 17.77 |
| F226 | — | — | ESIMS m/z 500.3 ([M + Na]⁺) | ¹H NMR (CDCl₃) δ 7.31-7.26 (m, 2H), 7.23-7.15 (m, 3H), 4.80 (dd, J = 10.6, 7.9 Hz, 1H), 4.71 (dq, J = 9.4, 6.3 Hz, 1H), 3.50 (t, J = 9.0 Hz, 1H), 3.11 (dd, J = 13.4, 4.6 Hz, 1H), 2.47 (dd, J = 13.5, 10.4 Hz, 1H), 2.30-2.20 (m 1H), 1.98 (dddd, J = 13.1, 7.8, 5.2, 2.2 Hz, 1H), 1.76 (ddd, J = 10.1, 8.3, 4.5 Hz, 1H), 1.60 (dd, J = 10.3, 6.5 Hz, 2H), 1.54-1.45 (m, 20H), 1.45-1.39 (m, 2H), 1.26 (t, J = 7.1 Hz, 2H) | ¹³C NMR (CDCl₃) δ 171.03, 152.84, 140.62, 128.88, 128.47, 126.06, 82.69, 76.09, 74.83, 57.42, 47.48, 37.80, 30.66, 27.96, 27.34, 19.75, 18.25 |
| F227 | — | — | ESIMS m/z 458.3 ([M + Na]⁺) | ¹H NMR (300 MHz, CDCl₃) δ 7.31-7.20 (m, 2H), 7.19-7.07 (m, 3H), 5.12-4.98 (m, 1H), 4.88 (dq, J = 9.0, 6.4 Hz, 1H), 4.20-4.05 (m, 1H), 3.91 (ddd, J = 10.0, 5.7, 3.9 Hz, 1H), 3.74-3.62 (m, 1H), 3.60-3.48 (m, 2H), 3.37 (s, 3H), 3.24-3.05 (m, 3H), 2.31 (dd, J = 13.2, 11.6 Hz, 1H), 2.20-2.05 (m, 1H), 1.92-1.75 (m, 1H), 1.45 (d, J = 6.5 Hz, 3H), 1.40 (s, 9H), 1.55-1.30 (m, 2H, overlapping), 1.01 (q, J = 11.6 Hz, 1H), 0.84-0.68 (m, 1H) | ¹³C NMR (75 MHz, CDCl₃) δ 173.40, 155.11, 140.95, 129.06, 128.50, 128.46, 126.06, 84.91, 79.94, 75.12, 72.99, 72.34, 59.25, 53.09, 45.97, 36.94, 34.30, 28.52, 26.78, 18.91, 18.38 |
| F229 | 108-110 | — | ESIMS m/z 504 | ¹H NMR (CDCl₃) δ 7.41-7.26 (m, 5H), 7.07 (d, J = 7.9 | ¹³C NMR (CDCl₃) δ 173.32, 154.95, |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | ([M + Na]⁺) | Hz, 2H), 7.02 (d, J = 8.0 Hz, 2H), 5.04 (d, J = 8.3 Hz, 1H), 4.94 (dq, J = 9.2, 6.5 Hz, 1H), 4.79 (d, J = 10.8 Hz, 1H), 4.63 (d, J = 10.8 Hz, 1H), 4.17 (dt, J = 10.8, 7.5 Hz, 1H), 3.35 (t, J = 9.0 Hz, 1H), 3.10 (dd, J = 13.3, 3.3 Hz, 1H), 2.32 (dd, J = 13.3, 11.8 Hz, 1H), 2.30 (s, 3H), 2.22-2.11 (m, 1H), 1.89 (ddt, J = 12.1, 8.3, 3.8 Hz, 1H), 1.64-1.33 (m, 15H), 1.04 (qd, J = 10.5, 5.5 Hz, 1H), 0.88-0.77 (m, 1H) | 137.92, 137.48, 135.38, 129.06, 128.73, 128.56, 127.94, 127.77, 84.20, 79.83, 75.73, 75.03, 52.94, 45.88, 36.40, 34.18, 28.36, 26.68, 21.04, 18.76, 18.33 |
| F230 | 164-166 | — | ESIMS m/z 605 ([M + Na]⁺) | ¹H NMR (CDCl₃) δ 7.41-7.26 (m, 5H), 7.07 (d, J = 8.1 Hz, 2H), 7.03 (d, J = 8.0 Hz, 2H), 4.88-4.75 (m, 3H), 4.61 (d, J = 10.8 Hz, 1H), 3.35 (t, J = 9.1 Hz, 1H), 3.10 (dd, J = 13.3, 3.3 Hz, 1H), 2.40-2.28 (m, 4H), 2.22 (tt, J = 13.5, 7.2 Hz, 1H), 2.02-1.88 (m, 2H), 1.64-1.41 (m, 24H), 0.96-0.84 (m 1H) | ¹³C NMR (CDCl₃) δ 171.13, 152.83, 137.98, 137.51, 135.31, 129.01, 128.77, 128.54, 127.89, 127.76, 84.14, 82.64, 75.44, 75.21, 57.57, 45.77, 36.43, 30.83, 27.97, 26.84, 21.04, 19.67, 18.49 |
| F231 | — | — | ESIMS m/z 454.4 ([M + Na]⁺) | ¹H NMR (CDCl₃) δ 7.34-7.23 (m, 2H), 7.23-7.11 (m, 3H), 5.02 (d, J = 8.3 Hz, 1H), 4.88 (dq, J = 9.2, 6.4 Hz, 1H), 4.14 (ddt, J = 14.3, 8.9, 7.1 Hz, 1H), 3.57 (dd, J = 9.7, 7.0 Hz, 1H), 3.44 (dd, J = 9.7, 6.8 Hz, 1H), 3.21-3.08 (m, 2H), 2.32 (dd, J = 13.3, 11.7 Hz, 1H), 2.21-2.07 (m, 1H), 1.86 (tdd, J = 12.1, 6.7, 2.7 Hz, 1H), 1.66-1.25 (m, 18H), 1.17-0.99 (m, 2H), 0.84-0.75 (m, 1H), 0.65-0.53 (m, 2H), 0.24 (dtt, J = 4.9, 3.5, 1.8 Hz, 2H) | ¹³C NMR (CDCl₃) δ 173.26, 154.91, 140.72, 128.86, 128.34, 125.90, 83.80, 79.79, 78.74, 75.13, 52.87, 45.98, 36.85, 34.17, 31.59, 28.31, 26.62, 25.28, 22.65, 18.65, 18.12, 14.12, 11.16, 3.16, 3.00 |
| F232 | 110-114 | — | ESIMS m/z 570 ([M + Na]⁺) | ¹H NMR (CDCl₃) δ 7.12-7.03 (m, 4H), 4.82-4.69 (m, 2H), 3.52 (dd, J = 8.4, 6.3 Hz, 1H), 3.30 (dd, J = 8.4, 6.5 Hz, 1H), 3.11 (t, J = 9.1 Hz, 1H), 3.05 (dd, J = 13.2, 3.2 Hz, 1H), 2.36-2.13 (m, 5H), 2.01-1.77 (m, 3H), 1.48 (s, 24H), 0.96 (d, J = 6.7 Hz, 3H), 0.95 (d, J = 6.7 Hz, 3H), 0.91-0.79 (m, 1H) | ¹³C NMR (CDCl₃) δ 171.12, 152.82, 137.73, 135.23, 128.98, 128.75, 83.64, 82.58, 80.32, 75.37, 57.55, 46.00, 36.25, 30.81, 29.26, 27.96, 26.73, 21.02, 19.65, 19.56, 19.51, 18.36 |
| F233 | — | — | ESIMS m/z 456.4 ([M + Na]⁺) | ¹H NMR (CDCl₃) δ 7.32-7.23 (m, 2H), 7.22-7.12 (m, 3H), 5.01 (d, J = 8.3 Hz, 1H), 4.87 (dq, J = 9.3, 6.4 Hz, 1H), 4.24-4.05 (m, 1H), 3.55 (dd, J = 8.4, 6.2 Hz, 1H), 3.32 (dd, J = 8.4, 6.5 Hz 1H) 3.17-3.03 (m, 2H), 2.31 (dd, J = 13.2, 11.8 Hz, 1H), 2.16 (dt, J = 13.1, 6.8 Hz, 1H), 1.95-1.69 (m, 3H), 1.61-1.48 (m, 3H), 1.43-1.39 (m, 11H), 0.96 (dd, J = 6.8, 5.1 Hz, 6H), 0.90-0.73 (m, 2H) | ¹³C NMR (CDCl₃) δ 173.30, 154.92, 140.86, 128.84, 128.32, 125.87, 83.71, 80.65, 79.81, 75.19, 52.88, 46.10, 36.70, 34.19, 29.70, 29.26, 28.32, 26.60, 19.54, 19.49, 18.73, 18.19 |
| F234 | — | — | ESIMS m/z 418.3 ([M + H]⁺) | ¹H NMR (CDCl₃) δ 5.06 (d, J = 7.9 Hz, 1H), 4.91-4.78 (m, 1H), 4.15 (d, J = 11.0 Hz, 1H), 3.44 (dd, J = 8.4, 6.6 Hz, 1H), 3.25 (dd, J = 8.3, 6.5 Hz, 1H), 3.00 (t, J = 8.7 Hz, 1H), 2.57 (ddd, J = 14.3, 9.7, 4.6 Hz, 1H), 2.42 (ddd, J = 12.8, 9.1, 7.2 Hz, 1H), 2.27-2.15 (m, 1H), 2.09 (s, 3H), 1.93 (d, J = | ¹³C NMR (CDCl₃) δ 173.34, 99.99, 83.94, 80.39, 75.25, 52.96, 42.21, 34.10, 32.15, 29.93, 29.19, 28.33, 19.48, 18.89, 18.15, 15.37 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 7.0 Hz, 1H), 1.87-1.77 (m, 1H), 1.74-1.59 (m, 3H), 1.54-1.46 (m, 2H), 1.44 (s, 9H), 1.40 (d, J = 6.4 Hz, 3H), 1.26-1.10 (m, 1H), 0.95 (s, 1H), 0.95-0.89 (m, 6H) | |
| F235 | — | — | ESIMS m/z 412.3 [(M + Na)⁺] | ¹H NMR (CDCl₃) δ 5.07 (d, J = 8.1 Hz, 1H), 4.92-4.78 (m, 1H), 4.55 (td, J = 5.6, 3.2 Hz, 1H), 4.47-4.37 (m, 1H), 4.15 (dt, J = 10.7, 7.8 Hz, 1H), 3.43 (dd, J = 8.4, 6.6 Hz, 1H), 3.24 (dd, J = 8.4, 6.4 Hz, 1H), 3.09-2.96 (m, 1H), 2.22 (dt, J = 13.4, 6.7 Hz, 1H), 2.10-1.95 (m, 1H), 1.83 (dp, J = 13.2, 6.6 Hz, 1H), 1.67 (d, J = 7.9 Hz, 3H), 1.64-1.53 (m, 2H), 1.44 (s, 9H), 1.40 (d, J = 6.4 Hz, 3H), 1.17 (q, J = 11.6 Hz, 1H), 1.08-0.97 (m, 1H), 0.94-0.88 (m, 6H) | ¹³C NMR (CDCl₃) δ 173.30, 154.91, 83.83, 83.78, 82.14, 80.21, 79.82, 75.14, 52.97, 39.75, 34.06, 31.57, 31.37, 29.15, 28.69, 28.32, 19.44, 19.40, 19.07, 18.14 |
| F236 | 86-89 | — | ESIMS m/z 468 ([M + Na]⁺) | ¹H NMR (CDCl₃) δ 7.11-7.02 (m, 4H), 5.02 (d, J = 8.3 Hz, 1H), 4.94-4.81 (m, 1H), 4.14 (dt, J = 10.9, 7.5 Hz, 1H), 3.56 (dd, J = 9.7, 7.0 Hz, 1H), 3.43 (dd, J = 9.7, 6.8 Hz, 1H), 3.13 (t, J = 9.1 Hz, 1H), 3.08 (dd, J = 13.3, 3.4 Hz, 1H), 2.35-2.23 (m, 4H), 2.15 (dt, J = 12.8, 6.7 Hz, 1H), 1.83 (ddd, J = 12.1, 8.4, 3.9 Hz, 1H), 1.60-1.34 (m, 15H), 1.18-0.96 (m, 2H), 0.85-0.72 (m, 1H), 0.61-0.54 (m, 2H), 0.28-0.20 (m, 2H) | ¹³C NMR (CDCl₃) δ 173.21, 154.85, 137.49, 135.27, 128.97, 128.66, 83.74, 79.72, 78.68, 75.09, 52.81, 36.30, 34.13, 28.26, 26.50, 20.96, 18.57, 18.06, 11.11, 3.10, 2.94 |
| F237 | — | — | ESIMS m/z 452.0 ([M + Na]⁺) | ¹H NMR (CDCl₃) δ 7.31-7.24 (m, 2H), 7.23-7.12 (m, 3H), 4.84-4.69 (m, 1H), 3.70 (dt, J = 8.7, 6.6 Hz, 1H), 3.49 (dt, J = 8.6, 6.7 Hz, 1H), 3.21-3.02 (m, 2H), 2.89 (t, J = 7.6 Hz, 1H), 2.71 (dd, J = 8.2, 7.0 Hz, 1H), 2.34 (dd, J = 13.3, 11.7 Hz, 1H), 2.21 (ddt, J = 13.5, 10.6, 7.3 Hz, 1H), 2.01-1.77 (m, 2H), 1.70-1.53 (m, 4H), 1.48 (s, 18H), 1.44 (d, J = 6.4 Hz, 3H), 0.96 (t, J = 7.4 Hz, 3H), 0.92-0.79 (m, 1H) | ¹³C NMR (75 MHz, CDCl₃) δ171.29, 153.02, 141.05, 129.09, 128.60, 126.29, 126.02, 84.17, 82.76, 75.54, 75.47, 57.79, 46.07, 44.69, 37.08, 31.02, 29.95, 28.17, 27.13, 23.82, 19.91, 18.52, 10.97 |
| F238 | — | — | ESIMS m/z 468.2 ([M-Boc + Na]⁺) | ¹H NMR (CDCl₃) δ 7.31-7.23 (m, 2H), 7.23-7.12 (m, 3H), 4.82-4.65 (m, 1H), 4.16-4.06 (m, 1H), 3.30-3.13 (m, 1H), 2.88 (t, J = 7.6 Hz, 1H), 2.75-2.66 (m, 1H) 2.37-2.23 (m, 1H), 2.20-2.10 (m, 0H), 1.98-1.87 (m, 1H), 1.83-1.66 (m, 4H), 1.61-1.53 (m, 2H), 1.48 (s, 9H), 1.44 (d, J = 9.0 Hz, 2H), 0.99-0.80 (m, 1H) | ¹³C NMR (CDCl₃) δ 171.38, 152.94, 141.10, 128.59, 128.57, 128.41, 126.21, 125.88, 83.83, 82.67, 82.53, 75.93, 57.91, 45.36, 44.61, 39.36, 37.03, 32.98, 32.69, 30.89, 29.84, 28.06, 23.15, 23.09, 20.10, 18.68 |
| F239 | — | — | HRMS-ESI (m/z) ([M]⁺) calcd for C₂₆H₃₉NO₆, 461.2777; found, 261.2757 | ¹H NMR (CDCl₃) δ 7.07 (d, J = 8.6 Hz, 2H), 6.82 (d, J = 8.6 Hz, 2H), 5.00 (d, J = 8.4 Hz, 1H), 4.88 (dd, J = 9.1, 6.3 Hz, 1H), 4.21-4.08 (m, 1H), 3.78 (s, 3H), 3.56 (dd, J = 9.7, 7.0 Hz, 1H), 3.43 (dd, J = 9.6, 6.8 Hz, 1H), 3.13 (t, J = 9.1 Hz, 1H), 3.06 (dd, J = 13.4, 3.4 Hz, 1H), 2.26 (dd, J = 13.4, 11.7 Hz, 1H), 2.22-2.07 (m, 1H), 1.91-1.74 (m, 1H), 1.61- | ¹³C NMR (CDCl₃) δ 173.28, 157.83, 132.68, 129.72, 113.76, 83.81, 79.82, 78.76, 75.16, 55.24, 52.88, 46.11, 35.89, 34.22, 28.32, 26.57, 18.64, 18.11, 11.17, 3.16, 2.99 |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| | | | | 1.34 (m, 15H), 1.20-1.08 (m, 1H), 1.03 (q, J = 11.7 Hz, 1H), 0.98-0.71 (m, 1H), 0.65-0.48 (m, 2H), 0.27-0.15 (m, 2H) | |
| F240 | — | — | ESIMS m/z 484.3 ([M + H]⁺) | ¹H NMR (CDCl₃) δ 7.35-7.12 (m, 4H), 6.93 (p, J = 7.4 Hz, 4H), 6.86-6.76 (m, 2H), 5.15-4.98 (m, 2H), 4.33-4.15 (m, 2H), 3.94 (t, J = 6.6 Hz, 2H), 2.33-2.21 (m, 1H), 2.06 (dd, J = 16.4, 4.9 Hz, 2H), 1.93 (d, J = 12.6 Hz, 1H), 1.89-1.79 (m, 1H), 1.79-1.65 (m, 1H), 1.62 (d, J = 14.8 Hz, 1H), 1.44 (s, 9H), 1.31 (d, J = 6.5 Hz, 3H), 1.19 (dd, J = 25.8, 13.7 Hz, 2H) | ¹³C NMR (CDCl₃) δ 173.28, 159.34, 158.76, 129.68, 129.39, 121.17, 120.61, 115.40, 114.42, 99.98, 81.14, 74.68, 66.01, 53.01, 40.14, 34.11, 30.49, 28.33, 24.93, 19.20, 18.35 |
| F241 | — | — | ESIMS m/z 476.4 ([M + Na]⁺) | ¹H NMR (CDCl₃) δ 7.35-7.20 (m, 5H), 7.19-7.13 (m, 1H), 7.13-7.07 (m, 2H), 7.05-6.93 (m, 2H), 5.08 (dt, J = 9.2, 3.4 Hz, 2H), 4.77 (d, J = 2.6 Hz, 1H), 4.37 (qt, J = 5.6, 3.6 Hz, 1H), 4.31 (t, J = 9.0 Hz, 1H), 4.27-4.15 (m, 1H), 3.00 (dd, J = 13.3, 3.3 Hz, 1H), 2.33 (dd, J = 13.4, 11.8 Hz, 1H), 2.27-2.15 (m, 1H), 2.12-2.01 (m, 1H), 1.93-1.78 (m, 1H), 1.43 (s, 9H), 1.34 (d, J = 6.5 Hz, 3H), 1.16-1.04 (m, 1H), 1.01-0.84 (m, 1H) | ¹³C NMR (CDCl₃) δ 173.32, 159.66, 154.93, 140.25, 136.31, 129.70, 128.80, 128.32, 125.97, 121.22, 115.54, 81.14, 79.91, 74.60, 45.62, 36.87, 34.11, 28.33, 26.76, 18.83, 18.41 |
| F242 | — | — | ESIMS m/z 422.3 ([M + H]⁺) | ¹H NMR (CDCl₃) δ 7.27 (t, J = 8.0 Hz, 2H), 6.94 (dd, J = 7.7, 3.3 Hz, 3H), 5.10 (d, J = 8.1 Hz, 1H), 5.08-4.98 (m, 1H), 4.20 (q, J = 7.9, 6.9 Hz, 2H), 3.36 (t, J = 6.5 Hz, 2H), 3.25 (s, 3H), 2.27 (dt, J = 13.3, 6.8 Hz, 1H), 1.88 (ddt, J = 10.8, 6.9, 3.9 Hz, 2H), 1.83-1.71 (m, 1H), 1.70-1.61 (m, 1H), 1.60-1.52 (m, 1H), 1.44 (s, 10H), 1.28 (d, J = 6.5 Hz, 3H), 1.25-1.16 (m, 1H), 1.16-1.05 (m, 1H) | ¹³C NMR (CDCl₃) δ 173.28, 159.46, 154.90, 129.61, 121.05, 115.38, 81.12, 79.86, 74.71, 70.79, 58.42, 52.99, 40.09, 34.12, 30.53, 28.33, 28.15, 19.07, 18.36 |
| F243 | — | — | ESIMS m/z 402.3 ([M + H]⁺) | ¹H NMR (CDCl₃) δ 5.06 (d, J = 8.2 Hz, 1H), 4.83 (dq, J = 12.9, 6.4 Hz, 1H), 4.22 - 4.08 (m, 1H), 3.45-3.35 (m, 3H), 3.31 (s, 3H), 3.31-3.22 (m, 1H), 3.01 (t, J = 8.8 Hz, 1H), 2.21 (dt, J = 13.1, 6.4 Hz, 1H), 1.94 (dtd, J = 11.1, 7.6, 3.4 Hz 1H), 1.83 (dp, J = 13.3, 6.7 Hz, 1H), 1.63 (dd, J = 16.5, 6.0 Hz, 2H), 1.54 (d, J = 7.7 Hz, 1H), 1.43 (s, 11H), 1.40 (d, J = 6.4 Hz, 3H), 1.23-1.10 (m, 1H), 1.02-0.94 (m, 1H), 0.91 (dd, J = 6.7, 2.7 Hz, 6H) | ¹³C NMR (CDCl₃) δ 173.35, 154.92, 84.01, 80.35, 79.80, 75.29, 71.28, 58.50, 52.96, 40.24, 34.17, 30.37, 29.16, 28.33, 19.51, 19.42, 18.99, 18.16 |
| F244 | 63-68 | — | ESIMS m/z 490 ([M + Na]⁺) | ¹H NMR (CDCl₃) δ 7.36-7.26 (m, 2H), 7.06 (d, J = 7.8 Hz, 2H), 7.04-6.94 (m, 5H), 5.14-5.02 (m, 2H), 4.31 (t, J = 8.9 Hz, 1H), 4.21 (dt, J = 11.0, 7.6 Hz, 1H), 2.97 (dd, J = 13.4, 3.2 Hz, 1H), 2.36-2.17 (m, 5H), 2.11-2.00 (m, 1H), 1.67-1.41 (m, 12H), 1.34 (d, J = 6.5 Hz, 3H), 1.16-1.02 (m, 1H), 1.00-0.86 (m, | ¹³C NMR (CDCl₃) δ 173.24, 159.65, 154.86, 137.04, 135.36, 129.63, 128.97, 128.62, 121.14, 115.52, 81.13, 79.83, 74.56, 52.91, 45.59, 36.35, 34.09, 28.29, 26.68, 20.97, 18.76, 18.37 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F245 | — | (Neat) 2952, 1752, 1705, 1597, 1493, 1367, 1297, 1174 | HRMS-ESI (m/z) [M + H]$^+$ calcd for C$_{27}$H$_{43}$NO$_6$, 477.3090; found, 477.3086 | 1H) $^1$H NMR (CDCl$_3$) δ 7.33-7.21 (m, 2H), 6.99-6.84 (m, 3H), 5.10-4.78 (m, 3H), 4.65-4.51 (m, 0.5H), 4.30-4.10 (m, 1.5H), 3.42-3.29 (m, 3H), 2.24-2.02 (m, 1H), 1.92-1.33 (m, 16H), 1.28 (d, J = 6.4 Hz, 3H), 1.26-0.99 (m, 3H), 0.80 (d, J = 6.7 Hz, 3H), 0.79 (d, J = 6.5 Hz, 3H), 0.77-0.69 (m, 1H) | — |
| F246 | — | (Neat) 2954, 1747, 1704, 1454, 1366, 1296, 1174, 1143, 1084 | HRMS-ESI (m/z) [M + H]$^+$ calcd for C$_{25}$H$_{47}$NO$_6$, 457.3403; found, 457.3417 | $^1$H NMR (CDCl$_3$) δ 5.03-4.66 (m, 4H), 4.60-4.47 (m, 0.5H), 4.40-4.12 (m, 0.5H), 3.53-3.19 (m, 5H), 2.19-1.42 (m, 18H), 1.40 (d, J = 6.4 Hz, 3H), 1.31-1.04 (m, 3H), 0.99-0.81 (m, 13H) | — |
| F247 | | | ESIMS m/z, 372.3 ([M + H]$^+$) | $^1$H NMR (CDCl$_3$) δ 5.06 (d, J = 8.2 Hz, 1H), 4.83 (dd, J = 9.2, 6.5 Hz, 1H), 4.25-4.05 (m, 1H), 3.41 (dd, J = 8.4, 6.6 Hz, 1H), 3.25 (dd, J = 8.3, 6.5 Hz, 1H), 2.98 (t, J = 8.9 Hz, 1H), 2.21 (dt, J = 12.4, 6.2 Hz, 1H), 1.83 (dp, J = 13.2, 6.7 Hz, 1H), 1.70 (dt, J = 9.7, 4.7 Hz, 2H), 1.51 (dd, J = 15.4, 7.4 Hz, 1H), 1.44 (s, 10H), 1.39 (d, J = 6.4 Hz, 5H), 1.25-1.10 (m, 2H), 0.99-0.83 (m, 9H) | $^{13}$C NMR (CDCl$_3$) δ 173.40, 84.22, 80.41, 79.77, 75.35, 52.97, 45.17, 34.26, 29.17, 28.34, 27.10, 23.22, 19.49, 19.45, 18.70, 18.20, 11.94 |
| F248 | — | — | ESIMS m/z 502 ([M − H]$^−$) | $^1$H NMR (CDCl$_3$) δ 7.43-7.27 (m, 5H), 7.12-7.03 (m, 1H), 6.82-6.72 (m, 2H), 5.03 (d, J = 8.3 Hz, 1H), 4.95 (dq, J = 9.1, 6.4 Hz, 1H), 4.80 (d, J = 10.9 Hz, 1H), 4.63 (d, J = 10.9 Hz, 1H), 4.18 (dt, J = 10.9, 7.5 Hz, 1H), 3.38 (t, J = 9.0 Hz, 1H), 3.07-2.96 (m, 1H), 2.49 (dd, J = 13.5, 11.6 Hz, 1H), 2.19 (dt, J = 13.1, 6.9 Hz, 1H), 1.98-1.85 (m, 1H), 1.72-1.32 (m, 15H), 1.14-0.99 (m, 1H), 0.94-0.82 (m, 1H) | $^{13}$C NMR (CDCl$_3$) δ 173.22, 161.33 (dd, J = 246.9, 12.2 Hz), 161.09 (dd, J = 246.2, 10.5 Hz), 154.89, 137.75, 131.52 (dd, J = 9.0, 7.0 Hz), 128.50, 127.89, 127.63, 123.13 (dd, J = 15.4, 3.3 Hz), 111.02 (dd, J = 20.9, 3.7 Hz), 104.18-103.18 (m), 83.93, 79.83, 75.36, 74.84, 52.87, 44.42, 34.05, 29.26, 28.29, 27.17, 18.75, 18.24 $^{19}$F NMR (CDCl$_3$) δ −113.33 (d, J = 6.7 Hz), −113.62 (d, J = 6.7 Hz) |
| F249 | — | — | HRMS-ESI (m/z) [M + Na]$^+$ calcd for C$_{22}$H$_{32}$BrNNaO$_5$, 492.1356; found, 492.1352 | $^1$H NMR (CDCl$_3$) δ 7.39-7.27 (m, 2H), 7.03-6.82 (m, 3H), 5.18-4.99 (m, 2H), 4.21 (q, J = 8.7 Hz, 2H), 3.44 (ddd, J = 10.0, 7.4, 5.0 Hz, 1H), 3.33 (ddd, J = 9.9, 8.4, 6.9 Hz, 1H), 2.28 (dt, J = 13.0, 6.6 Hz, 1H), 2.10 (dtd, J = 12.6, 7.9, 4.5 Hz, 1H), 2.05-1.96 (m, 1H), 1.85-1.73 (m, 2H), 1.73-1.61 (m, 1H), 1.44 (s, 10H), 1.30 (d, J = 6.5 Hz, 3H), 1.28-1.20 (m, 1H), 1.20-1.09 (m, 1H) | $^{13}$C NMR (CDCl$_3$) δ 173.20, 159.18, 154.89, 129.74, 121.33, 115.37, 80.94, 79.95, 74.57, 53.02, 41.18, 34.13, 33.95, 31.54, 28.33, 19.13, 18.29 |
| F250 | — | — | ESIMS m/z 392.3 [(M + H)]$^+$ | $^1$H NMR (CDCl$_3$) δ 7.38-7.16 (m, 2H), 7.00-6.87 (m, 3H), 5.19-4.97 (m, 2H), 4.18 (t, J = 8.8 Hz, 2H), 2.27 (dt, J = 13.1, 6.7 Hz, 1H), 1.91-1.77 (m, 1H), 1.70-1.58 (m, 3H), 1.58-1.48 (m, 1H), 1.44 | $^{13}$C NMR (CDCl$_3$) δ 173.34, 159.68, 154.91, 129.58, 120.95, 115.40, 81.44, 79.86, 74.74, 53.00, 44.96, 34.20, 28.34, 27.85, 27.03, 26.85, |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | (s, 9H), 1.28 (d, J = 6.5 Hz, 3H), 1.25-1.14 (m, 2H), 1.12-1.01 (m, 1H), 0.86 (t, J = 7.3 Hz, 3H) | 23.50, 18.74, 18.40, 17.53, 13.61, 11.86 |
| F251 | — | — | ESIMS m/z 440.4 ([M + H]$^+$) | $^1$H NMR (CDCl$_3$) δ 5.06 (d, J = 8.1 Hz, 1H), 4.84 (dq, J = 12.9, 6.4 Hz, 1H), 4.14 (dt, J = 10.6, 7.7 Hz, 1H), 3.49-3.37 (m, 4H), 3.25 (dt, J = 6.8, 3.2 Hz, 2H), 3.04 (t, J = 8.8 Hz, 1H), 2.28-2.15 (m, 1H), 1.98 (dtd, J = 10.7, 7.5, 3.1 Hz, 1H), 1.71-1.55 (m, 3H), 1.55-1.46 (m, 2H), 1.43 (s, 9H), 1.41 (d, J = 6.4 Hz, 3H), 1.23-1.10 (m, 1H), 1.05 (dddd, J = 14.9, 10.0, 5.9, 2.4 Hz, 2H), 1.00-0.90 (m, 1H), 0.60-0.45 (m, 4H), 0.25-0.15 (m, 4H) | $^{13}$C NMR (CDCl$_3$) δ 173.29, 154.90, 121.90, 84.01, 79.78, 78.35, 75.44, 75.22, 69.10, 52.93, 40.47, 34.18, 30.66, 28.32, 18.92, 18.09, 11.08, 10.64, 3.16, 3.00, 2.93, 2.87 |
| F253 | — | — | ESIMS m/z 626 ([M + Na]$^+$) | $^1$H NMR (CDCl$_3$) δ 7.41-7.27 (m, 5H), 7.09 (td, J = 8.7, 6.8 Hz, 1H), 6.82-6.71 (m, 2H), 4.87-4.76 (m, 2H), 4.61 (d, J = 10.9 Hz, 1H), 3.37 (t, J = 9.1 Hz, 1H), 3.06-2.96 (m, 1H), 2.50 (dd, J = 13.5, 11.6 Hz, 1H), 2.31-2.16 (m, 1H), 2.03-1.89 (m, 1H), 1.70-1.39 (m, 26H), 1.02-0.91 (m, 1H) | $^{13}$C NMR (CDCl$_3$) δ 171.04, 161.32 (dd, J = 246.7, 12.2 Hz), 162.52-159.74 (m), 152.83, 137.85, 131.74-131.38 (m), 128.50, 127.87, 127.65, 123.51-122.90 (m), 111.34-110.66 (m), 103.61 (t, J = 25.7 Hz), 83.90, 82.65, 75.04, 75.02, 57.50, 44.32, 30.74, 29.22, 27.95, 27.43, 19.71, 18.43 $^{19}$F NMR (CDCl$_3$) δ −113.52 (d, J = 6.8 Hz), −113.69 (d, J = 6.5 Hz) |
| F254 | 108-115 | — | ESIMS m/z 570 ([M + Na]$^+$) | $^1$H NMR (CDCl$_3$) δ 7.41-7.27 (m, 5H), 7.07 (td, J = 8.7, 6.4 Hz, 1H), 6.82-6.70 (m, 2H), 5.01-4.85 (m, 2H), 4.80 (d, J = 10.9 Hz, 2H), 4.62 (d, J = 10.9 Hz, 1.5H), 4.29-4.15 (m, 0.5H), 3.45-3.25 (m, 4H), 3.08-2.91 (m, 1H), 2.50 (t, J = 12.5 Hz, 1H), 2.21-2.02 (m, 1H), 2.00-1.86 (m, 1H), 1.78-1.34 (m, 16H), 1.00-0.83 (m, 1H) | $^{19}$F NMR (CDCl$_3$) δ −113.13−−113.46 (m), −113.58−−113.82 (m) |
| F255 | — | — | ESIMS m/z 563 ([M + NH$_4$]$^+$) | $^1$H NMR (CDCl$_3$) δ 7.09 (dd, J = 8.0, 3.1 Hz, 2H), 7.03 (dd, J = 8.0, 3.3 Hz, 2H), 4.97-4.66 (m, 3H), 3.78 (dd, J = 9.4, 5.3 Hz, 1H), 3.58 (dt, J = 8.8, 6.2 Hz, 1H), 3.30 (d, J = 14.2 Hz, 1H), 3.22-3.07 (m, 1H), 2.99-2.84 (m, 3H), 2.70 (dd, J = 8.2, 7.0 Hz, 1H), 2.40-2.12 (m, 6H), 1.93-1.73 (m, 4H), 1.73-1.35 (m, 16H), 0.90-0.75 (m, 1H) | $^{19}$F NMR (CDCl$_3$) δ −66.37 |
| F256 | — | — | ESIMS m/z 598 ([M + H]$^+$) | $^1$H NMR (CDCl$_3$) δ 7.36-7.05 (m, 6H), 6.85-6.71 (m, 2H), 4.99-4.68 (m, 2H), 4.54 (d, J = 9.0 Hz, 0.5H), 4.24-4.14 (m, 0.5H), 3.77 (q, J = 6.8 Hz, 1H), 3.61-3.50 (m, 1H), 3.31 (d, J = 13.4 Hz, 3H), 3.15 (td, J = 8.9, 4.1 Hz, 1H), 3.02-2.88 (m, 2H), 2.73 (td, J = 7.5, 4.2 Hz, 2H), 2.47 (t, J = 12.5 Hz, 1H), 2.17-2.01 (m, 1H), 2.00-1.77 (m, 3H), 1.75-1.34 (m, 14H), 0.95-0.79 (m, 1H) | $^{19}$F NMR (CDCl$_3$) δ −113.14 - −113.49 (m), −113.52 - −113.90 (m) |

TABLE 2-continued

Analytical Data

| Cmpd. No. | MP (° C.) | IR (cm⁻¹) | MASS | ¹H NMR | ¹³C or ¹⁹F NMR |
|---|---|---|---|---|---|
| F257 | — | — | ESIMS m/z 484.3 ([M + Na]⁺) | ¹H NMR (CDCl₃) δ 7.30-7.24 (m, 2H), 6.97-6.90 (m, 1H), 6.90-6.85 (m, 2H), 5.05 (d, J = 8.2 Hz, 1H), 4.95-4.79 (m, 1H), 4.28 - 4.09 (m, 1H), 4.00 (td, J = 7.3, 6.4, 2.3 Hz, 2H), 3.55-3.35 (m, 2H), 3.10 (t, J = 8.9 Hz, 1H), 2.31-2.10 (m, 2H), 1.87-1.75 (m, 1H), 1.75-1.58 (m, 3H), 1.50 (d, J = 11.8 Hz, 1H), 1.46-1.39(m, 12H), 1.16 (q, J = 11.7 Hz, 1H), 1.11-0.95 (m, 2H), 0.54 (ddd, J = 8.0, 5.3, 3.8 Hz, 2H), 0.24-0.16 (m, 2H) | ¹³C NMR (CDCl₃) δ 173.27, 158.83, 154.90, 129.42, 120.60, 114.44, 83.91, 79.84, 78.29, 75.17, 66.15, 52.91, 40.31, 34.15, 30.28, 28.32, 28.12, 18.95, 18.10, 11.07, 3.16, 2.92 |
| F258 | — | — | ESIMS m/z 336.2 ([M + Na]⁺) | ¹H NMR (CDCl₃) δ 5.16 (d, J = 7.5 Hz, 1H), 4.95 (dq, J = 9.5, 6.2 Hz, 1H), 4.11 (ddd, J = 12.5, 7.9, 5.2 Hz, 1H), 3.80 (ddd, J = 8.6, 7.2, 3.6 Hz, 1H), 3.68 (td, J = 9.0, 5.4 Hz, 1H), 3.39 (dd, J = 9.5, 6.5 Hz, 1H), 2.31-2.18 (m, 1H), 2.05 (dddd, J = 11.8, 8.7, 5.4, 3.6 Hz, 1H), 1.98-1.79 (m, 2H), 1.75-1.64 (m, 1H), 1.64-1.55 (m, 1H), 1.53-1.46 (m, 2H), 1.44 (s, 9H), 1.40 (d, J = 6.3 Hz, 3H), 1.24 (ddd, J = 18.0, 11.7, 4.8 Hz, 1H) | ¹³C NMR (CDCl₃) δ 174.15, 154.82, 86.81, 79.86, 73.23, 67.71, 54.40, 39.68, 36.07, 35.75, 33.00, 28.34, 21.72, 18.37 |
| F259 | — | — | — | ¹H NMR (CDCl₃) δ 7.34-7.19 (m, 2H), 7.02-6.86 (m, 3H), 5.76 (ddd, J = 17.2, 10.3, 8.0 Hz, 1H), 5.17-5.06 (m, 2H), 5.03 (d, J = 17.1 Hz, 1H), 4.94 (d, J = 10.4 Hz, 1H), 4.28 (t, J = 8.8 Hz, 1H), 4.25-4.17 (m, 1H), 2.56-2.41 (m, 1H), 2.27 (dt, J = 13.5, 6.6 Hz, 1H), 1.85 (td, J = 14.6, 7.1 Hz, 1H), 1.75 (dt, J = 14.8, 7.3 Hz, 1H), 1.65 (s, 1H), 1.44 (s, 9H), 1.33 (d, J = 6.4 Hz, 3H), 1.31-1.17 (m, 2H) | ¹³C NMR (CDCl₃) δ 173.35, 159.33, 138.51, 129.49, 121.10, 116.18, 115.78, 99.98, 80.46, 74.39, 53.05, 47.47, 34.13, 31.07, 28.34, 19.66, 18.36 |
| F260 | 45-48 | — | ESIMS m/z 552 ([M + H]⁺) | ¹H NMR (CDCl₃) δ 7.60 (d, J = 1.5 Hz, 1H), 7.17 (d, J = 3.5 Hz, 1H), 7.09-6.96 (m, 1H), 6.77-6.63 (m, 2H), 6.52 (dd, J = 3.4, 1.7 Hz, 1H), 5.19 (q, J = 8.2, 7.2 Hz, 1H), 5.04 (dq, J = 12.5, 6.5 Hz, 1H), 4.90 (t, J = 8.7 Hz, 1H), 4.80 (d, J = 11.5 Hz, 1H), 4.58 (t, J = 9.0 Hz, 0.5H), 4.26 (t, J = 7.8 Hz, 0.5H), 3.32 (d, J = 12.2 Hz, 3H), 2.70 (dd, J = 13.9, 4.5 Hz, 1H), 2.52 (dd, J = 13.9, 10.1 Hz, 1H), 2.25-2.00 (m, 2H), 1.87-1.52 (m, 4H), 1.45 (s, 9H), 1.30 (d, J = 6.3 Hz, 3H), 1.13-0.96 (m, 1H) | ¹⁹F NMR (CDCl₃) δ −112.78--113.23 (m), −113.37--113.71 (m) |
| F261 | — | — | ESIMS m/z 536 ([M + H]⁺) | ¹H NMR (CDCl₃) δ 7.22-7.05 (m, 1H), 6.84-6.71 (m, 2H), 4.83 (dq, J = 34.5, 9.9 Hz, 3H), 4.56 (d, J = 9.0 Hz, 0.5H), 4.20 (dd, J = 12.0, 6.7 Hz, 0.5H), 3.54 (t, J = 7.3 Hz, 1H), 3.47-3.37 (m, 0.5H), 3.37-3.25 (m, 3H), 3.20-3.09 (m, 1H), 3.03-2.85 (m, 2H), 2.71 (t, J = 7.6 Hz, 0.5H), | ¹⁹F NMR (CDCl₃) δ −113.49 (d, J = 43.3 Hz), −113.74 (d, J = 31.5 Hz) |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 2.47 (td, J = 13.1, 12.3, 4.8 Hz, 1H), 2.17-1.99 (m, 1H), 1.99-1.76 (m, 1H), 1.74-1.32 (m, 16H), 1.04-0.77 (m, 7H) | |
| F262 | 161-163 | (Neat) 3394, 2953, 1747, 1597, 1492, 1225 | HRMS-ESI (m/z) [M + H]$^+$ calcd for C$_{20}$H$_{32}$NO$_3$, 334.2377; found, 334.2382 | $^1$H NMR (CDCl$_3$) δ 8.62 (bs, 3H), 7.26-7.08 (m, 2H), 6.94-6.73 (m, 3H), 5.06-4.84 (m, 1H), 4.22-3.92 (m, 2H), 2.64-2.39 (m, 1H), 1.89-0.91 (m, 13H), 0.90-0.59 (m, 7H) | $^{13}$C NMR (CDCl$_3$) δ 170.45, 159.55, 129.60, 121.07, 115.42, 81.29, 75.78, 52.60, 43.19, 36.23, 31.23, 28.22, 27.80, 27.31, 23.01, 22.02, 18.48, 18.33 |
| F263 | 186-188 | (Neat) 3369, 2955, 1746, 1642, 1475, 1225 | HRMS-ESI (m/z) [M + H]$^+$ calcd for C$_{18}$H$_{36}$NO$_3$, 314.2690; found, 314.2690 | $^1$H NMR (CDCl$_3$) δ 8.64 (bs, 3H), 4.94-4.69 (m, 1H), 4.15-3.94 (m, 1H), 3.51-3.36 (m, 1H), 3.31-3.17 (m, 1H), 3.03-2.88 (m, 1H), 2.64-2.39 (m, 1H), 1.93-1.33 (m, 9H), 1.41 (d, J = 6.2 Hz, 3H), 1.33-0.98 (m, 3H), 0.98-0.77 (m, 12H) | $^{13}$C NMR (CDCl$_3$) δ 170.38, 84.06, 80.53, 76.38, 52.45, 43.53, 36.38, 31.27, 29.16, 28.03, 27.95, 27.23, 22.95, 22.23, 19.48, 19.43, 18.34, 18.08 |
| F264 | 205-207 | (Neat) 3375, 2953, 1746, 1634, 1454, 1233, 1076 | HRMS-ESI (m/z) [M + H]$^+$ calcd for C$_{18}$H$_{34}$NO$_3$, 312.2533; found, 312.2532 | $^1$H NMR (CDCl$_3$) δ 8.63 (bs, 3H), 4.91-4.75 (m, 1H), 4.18-3.91 (m, 1H), 3.56-3.30 (m, 2H), 3.05-2.91 (m, 1H), 2.61-2.38 (m, 1H), 1.85-1.32 (m, 7H), 1.42 (d, J = 6.3 Hz, 3H), 1.32-0.98 (m, 5H), 0.96-0.79 (m, 6H), 0.60-0.50 (m, 2H), 0.26-0.15 (m, 2H) | $^{13}$C NMR (CDCl$_3$) δ 170.35, 84.09, 78.76, 76.31, 52.42, 43.57, 43.54, 36.26, 31.27, 27.98, 27.08, 23.00, 22.16, 18.21, 18.01, 11.09, 3.08, 2.98 |
| F265 | 200-202 | (Neat) 3411, 2955, 2872, 1748, 1478, 1209 | HRMS-ESI (m/z) [M + H]$^+$ calcd for C$_{17}$H$_{34}$NO$_3$, 300.2533; found, 300.2532 | $^1$H NMR (CDCl$_3$) δ 8.67 (bs, 3H), 4.96-4.65 (m, 1H), 4.14-3.90 (m, 1H), 3.69-3.55 (m, 1H), 3.51-3.37 (m, 1H), 3.04-2.89 (m, 1H), 2.61-2.41 (m, 1H), 1.85-1.32 (m, 9H), 1.43 (t, J = 8.5 Hz, 3H), 1.30-0.98 (m, 4H), 0.93 (t, J = 7.4 Hz, 3H), 0.90-0.81 (m, 6H) | $^{13}$C NMR (CDCl$_3$) δ 170.32, 84.33, 76.49, 75.55, 52.41, 43.47, 36.37, 31.41, 28.04, 27.28, 23.53, 23.01, 22.19, 18.32, 18.04, 10.69 |
| F266 | 215-217 | (Neat) 3369, 1744, 1635, 1453, 1252 | HRMS ESI (m/z) [M + H]$^+$ calcd for C$_{18}$H$_{33}$F$_3$NO$_3$, 368.2407; found, 368.2418 | $^1$H NMR (CDCl$_3$) δ 8.73 (bs, 3H), 4.91-4.77 (m, 1H), 4.03-3.89 (m, 1H), 3.81-3.63 (m, 1H), 3.61-3.48 (m, 1H), 3.04-2.94 (m, 1H), 2.59-2.45 (m, 1H), 2.29-2.08 (m, 2H), 1.87-1.43 (m, 9H), 1.40 (d, J = 6.4 Hz, 3H), 1.31 - 0.90 (m, 4H), 0.90-0.83 (m, 6H) | $^{13}$C NMR (CDCl$_3$) δ 170.41, 127.08 (q, J = 277 Hz), 84.51, 76.13 71.66, 52.43, 43.44, 3 36.32, 31.17, 30.72 (q, J = 31 Hz), 28.09, 27.98, 27.17, 23.01 (q, J = 3.2 Hz), 22.89, 22.08, 18.30, 18.01 $^{19}$F NMR (CDCl$_3$) δ −66.49 |
| F267 | — | (Neat) 2952, 1746, 1453, 1208, 1054 | HRMS-ESI (m/z) [M + H]$^+$ calcd for C$_{19}$H$_{36}$NO$_3$, 326.2690; found, 326.2687 | $^1$H NMR (CDCl$_3$) δ 8.69 (bs, 3H), 4.88-4.73 (m, 1H), 4.11-3.89 (m, 2H), 3.17-2.98 (m, 1H), 2.96-2.46 (m, 2H), 1.89-0.96 (m, 21H), 0.95-0.81 (m, 6H) | — |
| F268 | 218-220 | (Neat) 2932, 2874, 1751, 1580, 1481, 1211 | HRMS-ESI (m/z) [M + H]$^+$ calcd for C$_{15}$H$_{30}$NO$_3$, 272.2220; found, 272.2222 | $^1$H NMR (CDCl$_3$) δ 8.70 (bs, 3H), 4.91-4.71 (m, 1H), 4.12-3.91 (m, 1H), 3.49 (s, 3H), 2.98-2.83 (m, 1H), 2.61-2.40 (m, 1H), 1.88-1.35 (m, 7H), 1.43 (d, J = 6.4 Hz, 3H), 1.30-1.02 (m, 4H), 0.95-0.80 (m, 6H) | — |
| F269 | — | (Neat) 3404, 2952, 1732, 1453, 1383, 1149 | HRMS-ESI (m/z) [M + H]$^+$ calcd for C$_{20}$H$_{36}$NO$_4$, 354.2639; found, 354.2655 | $^1$H NMR (CDCl$_3$) δ 8.70 (bs, 3H), 5.09-4.90 (m, 1H), 4.90-4.76 (m, 1H), 4.15-3.95 (m, 1H), 2.84-2.65 (m, 2H), 2.64-2.47 (m, 1H), 2.01-1.36 (m, 14H), 1.35-0.91 (m, 7H), 0.91-0.76 (m, 6H) | $^{13}$C NMR (CDCl$_3$) δ 176.09, 170.16, 75.71, 74.41, 52.33, 44.02, 43.59, 41.80, 36.15, 30.04, 29.94, 29.92, 27.90, 25.80, 25.67, 25.66, 22.84, 22.13, 18.20, 17.43 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F271 | 222-224 | (Neat) 2923, 2877, 1746, 1508, 1218, 1073 | HRMS-ESI (m/z) [M + H]$^+$ calcd for C$_{20}$H$_{29}$FNO$_3$, 350.2126; found, 350.2130 | $^1$H NMR (CDCl$_3$) δ 8.54 (bs, 3H), 7.14-7.03 (m, 2H), 7.01-6.89 (m, 2H), 4.91-4.72 (m, 1H), 4.11-3.89 (m 1H), 3.58-3.48 (m, 1H), 3.46-3.35 (m, 1H), 3.16-2.96 (m, 2H), 2.51-2.34 (m, 1H), 2.34-2.18 (m, 1H), 1.86-1.68 (m, 1H), 1.66-1.24 (m, 4H), 1.39 (d, J = 6.5 Hz, 3H), 1.18-1.01 (m, 1H), 0.84-0.68 (m, 1H), 0.65-0.51 (m, 2H), 0.30-0.17 (m, 2H) | $^{19}$F NMR (CDCl$_3$) δ −117.24 |
| F272 | 196-198 | — | HRMS-ESI (m/z) [M + H]$^+$ calcd for C$_{22}$H$_{27}$FNO$_3$, 372.1969; found, 372.1979 | $^1$H NMR (CDCl$_3$) δ 8.58 (bs, 3H), 7.34-7.25 (m, 2H), 7.06-6.86 (m, 7H), 5.09-4.92 (m, 1H), 4.32-4.18 (m, 1H), 4.16-3.97 (m, 1H), 2.97-2.85 (m, 1H), 2.59-2.41 (m, 1H), 2.34-2.21 (m, 1H), 2.07-1.91 (m, 1H), 1.76-1.37 (m, 4H), 1.27 (d, J = 6.4 Hz, 3H), 1.00-0.81 (m, 1H) | $^{13}$C NMR (CDCl$_3$) δ 170.26, 161.32 (d, J = 244.1 Hz), 159.34, 135.46 (d, J = 3.2 Hz), 130.03 (d, J = 7.9 Hz), 129.79, 121.46, 115.38, 115.18 (d, J = 20.9 Hz), 80.66, 75.74, 52.43, 45.39, 36.01, 31.13, 26.78, 18.38, 18.21 $^{19}$F NMR (CDCl$_3$) δ −117.02 |
| F273 | 210-212 | (Neat) 3378, 2937, 1743, 1601 1508, 1218 | HRMS-ESI (m/z) [M + H]$^+$ calcd for C$_{19}$H$_{27}$FNO$_3$, 336.1969; found, 336.1970 | $^1$H NMR (CDCl$_3$) δ 8.56 (bs, 3H), 7.15-7.01 (m, 2H), 7.01-6.86 (m, 2H), 6.03-5.83 (m, 1H), 5.33 (d, J = 17.2 Hz, 1H), 5.22 (d, J = 10.4 Hz, 1H), 4.92-4.74 (m, 1H), 4.25 (dd, J = 12.1, 5.5 Hz, 1H), 4.16-3.88 (m, 2H), 3.82-3.58 (m, 1H), 3.24-3.09 (m, 1H), 3.09-2.93 (m, 1H), 2.55-2.35 (m, 1H), 2.35-2.16 (m, 1H), 1.87-1.70 (m, 1H), 1.70-1.28 (m, 6H), 0.89-0.67 (m, 1H) | $^{13}$C NMR (75 MHz, CDCl$_3$) δ 170.33, 161.39 (d, J = 244.0 Hz), 136.02 (d, J = 3.1 Hz), 134.25, 130.16 (d, J = 7.5 Hz), 117.36, 115.25 (d, J = 21.1 Hz), 83.99, 76.11, 74.89, 52.40, 45.75, 36.12, 31.17, 26.73, 18.38, 18.09 |
| F274 | 215-217 | (Neat) 3385, 2934, 2876, 1742, 1508, 1215 | HRMS-ESI (m/z) [M + H]$^+$ calcd for C$_{19}$H$_{29}$FNO$_3$, 338.2126; found, 338.2126 | $^1$H NMR (CDCl$_3$) δ 8.64 (bs, 3H), 7.22-6.74 (m, 4H), 4.99-4.66 (m, 1H), 4.05-3.57 (m, 3H), 3.57-3.39 (m, 1H), 3.16-2.92 (m, 2H), 2.85-2.67 (m, 1H), 2.57-2.36 (m, 1H), 2.36-2.16 (m, 1H), 1.86-1.25(m, 8H), 0.97 (t, J = 7.4 Hz, 3H), 0.89-0.63 (m, 1H) | — |
| F275 | 163-165 | (Neat) 2956, 2875, 1748, 1509, 1221 | HRMS-ESI (m/z) [M + H]$^+$ calcd for C$_{20}$H$_{31}$FNO$_3$, 352.2282; found, 352.2282 | $^1$H NMR (CDCl$_3$) δ 8.60 (bs, 3H), 7.24-6.79 (m, 4H), 5.04-4.67 (m, 2H), 4.12-3.84 (m, 1H), 3.59-3.46 (m, 1H), 3.38-3.21 (m, 1H), 3.18-2.93 (m, 2H), 2.56-2.36 (m, 1H), 2.36-2.17 (m, 1H), 1.99-1.80(m, 1H), 1.80-1.29 (m, 7H), 1.05-0.67 (m, 7H) | — |
| F276 | 204-206 | (Neat) 2942, 2882, 1740, 1509, 1216 | HRMS-ESI (m/z) [M + H]$^+$ calcd for C$_{18}$H$_{25}$F$_3$NO$_3$, 360.1781; found, 360.1786 | $^1$H NMR (CD3OD) δ 7.27-7.16 (m, 2H), 7.08-6.96 (m, 2H), 5.99 (tt, J = 55.1, 3.7 Hz, 1H), 5.02-4.92 (m, 1H), 4.09-3.81 (m, 3H), 3.79-3.57 (m, 1H), 3.45-3.38 (m, 1H), 3.17-3.06 (m, 1H), 2.45 (dd, J = 13.5, 11.5 Hz, 1H), 2.29-2.14 (m, 1H), 1.92-1.75 (m, 1H), 1.75-1.57 (m, 2H), 1.52 (d, J = 6.4 Hz, 3H), 1.41-1.27 (m, 1H), 0.99-0.81 (m, 1H) | $^{19}$F NMR (CDCl$_3$) δ −113.38, −121.92 (2F) |
| F277 | 200-202 | (Neat) 3376, 2954, 1733, 1635 1509, | HRMS-ESI (m/z) [M + H]$^+$ calcd for C$_{22}$H$_{31}$FNO$_4$, 392.2232; | $^1$H NMR (CDCl$_3$) δ 8.63 (bs, 3H), 7.09-7.00 (m, 2H), 7.00-6.89 (m, 2H), 5.06-4.87 (m, 2H), 4.14-3.93 (m, 1H), 2.81-2.57 (m, 2H), 2.57-2.40 (m, 1H), 2.40-2.25 (m, 1H), 2.03- | $^{19}$F NMR (CDCl$_3$) δ −116.96 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F278 | 193-195 | 1220 (Neat) 3375, 2972, 1735, 1635, 1509, 1219 | found, 392.2236 HRMS-ESI (m/z) [M + H]$^+$ calcd for C$_{20}$H$_{29}$FNO$_4$, 366.2075; found, 366.2077 | 1.41 (m, 11H), 1.38-1.14 (m, 5H), 0.99-0.78 (m, 1H) $^1$H NMR (CDCl$_3$) δ 8.63 (bs, 3H), 7.08-6.99 (m, 2H), 6.99-6.90 (m, 2H), 5.10-4.82 (m, 2H), 4.12-3.91 (m, 1H), 2.69-2.38 (m, 3H), 2.31 (dd, J = 13.8, 11.1 Hz, 1H), 1.99-1.80 (m, 1H), 1.76-1.40 (m, 3H), 1.33-1.12 (m, 10H), 0.97-0.78 (m, 1H) | $^{13}$C NMR (CDCl$_3$) δ 176.43, 170.09, 161.39 (d, J = 244.2 Hz), (d, J = 244.2 Hz), 135.23 (d, J = 3.2 Hz), 130.02 (d, J = 7.7 Hz), 115.27 (d, J = 21.3 Hz), 75.11, 74.26, 52.24, 43.84, 35.77, 34.17, 33.62, 26.65, 19.07, 18.97, 18.82, 17.36 $^{19}$F NMR (CDCl$_3$) δ −116.88 |
| F279 | — | — | ESIMS m/z 334.4 ([M + H]$^+$) | $^1$H NMR (CD$_3$OD) δ 7.31 - 7.22 (m, 2H), 7.21-7.13 (m, 3H), 3.98-3.83 (m, 1H), 3.77-3.70 (m, 1H), 3.66 (q, J = 5.5, 5.0 Hz, 1H), 3.61-3.53 (m, 1H), 3.41 (dd, J = 8.5, 6.4 Hz, 1H), 3.23 (t, J = 8.9 Hz, 1H), 3.10 (dd, J = 13.3, 3.4 Hz, 1H), 2.47-2.30 (m, 1H), 2.20 (qd, J = 8.4, 7.5, 5.0 Hz, 1H), 1.89 (dt, J = 13.2, 6.6 Hz, 1H), 1.84-1.74 (m, 1H), 1.64 (dp, J = 8.5, 3.2, 2.8 Hz, 2H), 1.48 (d, J = 6.4 Hz, 4H), 1.36-1.24 (m, 2H), 0.98 (dd, J = 6.7, 3.6 Hz, 6H), 0.95-0.79 (m, 2H) | $^{13}$C NMR (CD$_3$OD) δ 171.46, 141.99, 129.89, 129.46, 127.06, 84.74, 81.69, 77.66, 53.00, 47.35, 37.69, 32.11, 30.51, 28.03, 19.88, 19.83, 19.45, 18.49 |
| F280 | — | — | ESIMS m/z 333.4 ([M + H]$^+$) | $^1$H NMR (CD$_3$OD) δ 7.33-7.22 (m, 2H), 7.22-7.11 (m, 3H), 3.91 (dd, J = 10.9, 7.1 Hz, 1H), 3.66-3.59 (m, 2H), 3.51 (dd, J = 9.9, 6.8 Hz, 1H), 3.30-3.23 (m, 2H), 3.15 (dd, J = 13.1, 3.3 Hz, 1H), 2.39 (dd, J = 13.3, 11.6 Hz, 1H), 2.20 (ddt, J = 12.6, 8.6, 4.6 Hz, 1H), 1.80 (ddt, J = 12.0, 7.9, 4.0 Hz, 1H), 1.63 (dq, J = 9.5, 5.3, 4.4 Hz, 2H), 1.56-1.40 (m, 4H), 1.40-1.25 (m, 1H), 1.12 (dddd, J = 14.9, 6.9, 5.9, 2.7 Hz, 1H), 0.94-0.77 (m, 1H), 0.64-0.47 (m, 2H), 0.32-0.17 (m, 2H) | $^{13}$C NMR (CDCl$_3$) δ 173.98, 144.51, 132.44, 131.98, 129.58, 87.29, 82.26, 80.13, 70.67, 55.51, 49.75 40.33, 34.61 30.63, 21.94, 20.95, 14.60, 6.06 |
| F281 | — | — | ESIMS m/z 354.3 ([M + H]$^+$) | $^1$H NMR (CDCl$_3$) δ 8.66 (s, 3H), 7.35-7.27 (m, 2H), 7.25-7.11 (m, 3H), 7.07 (d, J = 7.3 Hz, 2H), 7.03-6.93 (m, 3H), 5.04 (s, 1H), 4.47-4.34 (m, 1H), 4.29 (s, 1H), 3.77 (dddd, J = 5.9, 4.6, 2.8, 1.8 Hz, 1H), 3.68-3.60 (m, 1H), 2.97 (d, J = 12.2 Hz, 1H), 2.31 (t, J = 12.3 Hz, 1H), 2.07 (s, 1H), 1.92-1.77 (m, 2H), 1.73-1.36 (m, 4H), 0.96-0.83 (m, 1H) | — |
| F282 | — | — | HRMS-ESI (m/z) [M + H]$^+$ calcd for C$_{19}$H$_{30}$NO$_3$, 320.222; found, 320.2218 | $^1$H NMR (CDCl$_3$) δ 8.58 (s, 3H), 7.29-7.23 (m, 2H), 7.20-7.09 (m, 3H), 4.88-4.76 (m, 1H), 4.03-3.91 (m, 1H), 3.55-3.43 (m, 1H), 3.16-2.98 (m, 2H), 2.49-2.38 (m, 1H), 2.29 (dd, J = 13.2, 11.8 Hz, 1H), 1.87-1.73 (m, 1H), 1.70-1.50 (m, 5H), 1.50-1.36 (m, 2H), 1.41 (d, J = 6.5 Hz, 3H), 0.97 (t, J = 7.4 Hz, 3H), 0.79-0.69 (m, 1H) | $^{13}$C NMR (CDCl$_3$) δ 170.16, 140.43, 128.76, 128.37, 125.96, 83.70, 76.33, 75.68, 52.19, 45.95, 36.74, 31.33, 26.28, 23.58, 18.18, 17.97, 10.74 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F283 | — | — | ESIMS m/z 347.4 ([M + H]$^+$) | $^1$H NMR (CDCl$_3$) δ 8.57 (s, 3H), 7.36-7.20 (m, 2H), 7.20-7.05 (m, 3H), 4.94-4.66 (m, 1H), 4.22-3.89 (m, 2H), 3.37-3.07 (m, 2H), 2.87 (t, J = 7.6 Hz, 1H), 2.70 (dd, J = 8.2, 7.0 Hz, 1H), 2.54-2.33 (m, 1H), 2.33-2.11 (m, 1H), 1.87-1.64 (m, 7H), 1.43 (br s, 4H), 1.26 (br s, 3H), 0.93-0.70 (m, 1H) | — |
| F284 | — | — | HRMS-ESI (m/z) [M + H]$^+$ calcd for C$_{18}$H$_{28}$NO$_3$, 306.2064; found, 306.2062 | $^1$H NMR (CDCl$_3$) δ 8.55 (s, 3H), 7.29-7.22 (m, 2H), 7.20-7.10 (m, 3H), 4.81 (dq, J = 9.4, 6.4 Hz, 1H), 4.05-3.91 (m, 1H), 3.78 (dq, J = 8.8, 6.9 Hz, 1H), 3.59 (dq, J = 8.9, 7.0 Hz, 1H), 3.15-3.07 (m, 1H) 3.07-3.00 (m, 1H), 2.47-2.37 (m, 1H), 2.35-2.24 (m, 1H), 1.84-1.71 (m, 1H), 1.61-1.48 (m, 2H), 1.47-1.35 (m, 2H), 1.40 (d, J = 6.5 Hz, 3H), 1.24 (t, J = 6.9 Hz, 3H), 0.79-0.65 (m, 1H) | $^{13}$C NMR (CDCl$_3$) δ 170.22, 140.40, 128.77, 128.37, 125.96, 83.92, 76.21, 69.30, 52.22, 45.84 36.83, 31.26, 26.29, 18.15, 17.89, 15.72 |
| F285 | — | — | ESIMS m/z 336.2 ([M + H]$^+$) | 1H NMR (300 MHz, CD$_3$OD) δ 7.35-7.22 (m, 2H), 7.17 (d, J = 7.4 Hz, 3H), 4.84 (d, J = 1.0 Hz, 1H), 3.92 (dt, J = 10.0, 4.8 Hz, 2H), 3.74 (dq, J = 10.8, 5.5, 5.0 Hz, 1H), 3.65 (s, 3H), 3.55 (t, J = 4.3 Hz, 2H), 3.37 (s, 3H), 3.34-3.25 (m, 1H), 3.16 (dd, J = 13.2, 3.3 Hz, 1H), 2.38 (t, J = 12.4 Hz, 1H), 2.31-2.17 (m, 1H), 1.88-1.73 (m, 1H), 1.72-1.56 (m, 2H), 1.49 (d, J = 6.3 Hz, 4H), 1.39-1.24 (m, 1H), 0.91-0.76 (m, 1H) | 13C NMR (75 MHz, CD3OD) δ 170.26, 140.88, 128.80, 128.26, 125.84, 84.19, 76.24, 72.70, 72.14, 66.97, 58.07, 51.86, 45.94, 36.51, 30.93, 26.79, 18.27, 17.31 |
| F287 | — | — | HRMS-ESI (m/z) ([M]$^+$) calcd for C$_{23}$H$_{29}$NO$_4$, 383.2097; found, 383.2075 | $^1$H NMR (CD$_3$OD) δ 7.33 (ddd, J = 9.8, 5.9, 2.2 Hz, 2H), 7.14-7.03 (m, 4H), 6.98 (t, J = 7.3 Hz, 1H), 6.83 (d, J = 8.6 Hz, 2H), 5.14 (dq, J = 9.7, 6.4 Hz, 1H), 4.47 (t, J = 8.9 Hz, 1H), 3.98 (dd, J = 10.9, 7.1 Hz, 1H), 3.76 (s, 3H), 2.92 (dd, J = 13.5, 3.4 Hz, 1H), 2.37 (dd, J = 13.4, 11.6 Hz, 1H), 2.26 (ddd, J = 11.9, 7.4, 4.2 Hz, 1H), 2.03 (ddd, J = 10.5, 7.3, 3.6 Hz, 1H), 1.75 (d, J = 9.3 Hz, 2H), 1.62 (tt, J = 13.4, 6.6 Hz, 1H), 1.37 (d, J = 6.4 Hz, 4H), 1.01 (d, J = 14.8 Hz, 1H) | 13C NMR (CD$_3$OD) δ 170.13, 159.60, 158.13, 131.91, 129.39, 129.32, 120.97, 115.15, 113.45, 80.41, 75.60, 54.21, 51.63, 45.69, 35.49, 30.78, 26.56, 18.02, 17.21 |
| F288 | — | — | HRMS-ESI (m/z) ([M]$^+$) calcd for C$_{21}$H$_{31}$NO$_3$, 345.2304; found, 345.2287 | $^1$H NMR (CDCl$_3$) δ 8.76 (s, 3H), 7.31-7.22 (m, 2H), 6.99-6.84 (m, 3H), 5.03 (p, J = 6.6 Hz, 1H), 4.26-3.96 (m, 2H), 3.71 (s, 3H), 2.64-2.51 (m, 1H), 2.04-1.59 (m, 6H), 1.59-1.31 (m, 5H), 1.28 (d, J = 6.3 Hz, 3H), 1.08-0.88 (m, 3H) | $^{13}$C NMR (CDCl$_3$) δ 170.30, 159.58, 129.62, 121.09, 115.49, 81.25, 76.00, 67.09, 52.45, 42.05, 37.15, 36.76, 33.63, 31.73, 31.41, 27.29, 25.04, 18.51, 18.32 |
| F289 | — | (Thin Film) 2946, 2871, 1733, 1512, 1246, 1177 | HRMS-ESI (m/z) ([M]$^+$) calcd for C$_{23}$H$_{33}$NO$_5$, 403.2359; found, 403.2347 | $^1$H NMR (CDCl$_3$) δ 8.67 (s, 3H), 6.99 (d, J = 8.2 Hz, 2H), 6.80 (d, J = 7.9 Hz, 2H), 4.97 (s, 1H), 3.78 (s, 3H), 2.73 (p, J = 7.8 Hz, 1H), 2.59 (d, J = 12.9 Hz, 1H), 2.49 (s, 1H), 2.28 (t, J = 12.3 Hz, 1H), 1.98-1.70 (m, 10H), 1.65-1.57 (m, 4H), 1.30-1.24 (m, 3H), 1.15 (s, 1H), 0.87 (s, 1H) | — |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| F290 | — | — | ESIMS m/z 400 ([M + H]$^+$) | $^1$H NMR (CDCl$_3$) δ 8.64 (s, 3H), 7.03 (d, J = 8.3 Hz, 2H), 6.81 (d, J = 8.4 Hz, 2H), 4.89-4.79 (m, 1H), 3.99-3.85 (m, 2H), 3.78 (s, 3H), 3.11 (t, J = 9.0 Hz, 1H), 2.96 (d, J = 12.7 Hz, 1H), 2.51-2.36 (m, 1H), 2.33-2.09 (m, 3H), 1.75 (s, 1H), 1.73-1.58 (m, 6H), 1.46-1.39 (m, 4H), 0.81-0.72 (m, 1H) | $^{19}$F NMR (CDCl$_3$) δ −89.67--89.77 (m) |
| F291 | — | — | HRMS-ESI (m/z) ([M]$^+$) calcd for C$_{21}$H$_{31}$NO$_4$, 361.2253; found, 361.2245 | $^1$H NMR (CDCl$_3$) δ 8.82-8.25 (br s, 3H), 7.12-6.95 (m, 2H), 6.87-6.76 (m, 2H), 4.85 (dd, J = 9.1, 6.2 Hz, 1H), 3.98-3.89 (m, 1H), 3.78 (s, 3H), 3.55 (dd, J = 9.7, 7.0 Hz, 1H), 3.42 (dd, J = 9.7, 6.8 Hz, 1H), 3.19-2.97 (m, 2H), 2.51-2.37 (m, 1H), 2.24 (t, J = 12.5 Hz, 1H), 1.87-1.73 (m, 2H), 1.59-1.38 (m, 3H), 1.42 (d, J = 6.4 Hz, 3H), 1.11 (td, J = 7.4, 3.8 Hz, 1H), 0.79-0.68 (m, 1H), 0.62-0.43 (m, 2H), 0.24 (dq, J = 7.3, 4.5, 3.1 Hz, 2H) | $^{13}$C NMR (CDCl$_3$) δ 170.10, 157.88, 132.29, 129.64, 113.85, 83.49, 78.87, 76.43, 55.26, 52.16, 46.07, 35.85, 31.47, 26.25, 18.13, 17.98, 11.15, 3.18, 3.01 |
| F292 | — | (Thin Film) 3411, 2943, 2869, 1746, 1233, 1070 | HRMS-ESI (m/z) ([M]$^+$) calcd for C$_{19}$H$_{33}$NO$_3$, 323.2460; found, 323.2471 | $^1$H NMR (CDCl$_3$) δ 8.79-8.60 (br s, 3H), 4.96-4.71 (m, 1H), 4.10-3.73 (m, 1H), 3.48 (dd, J = 9.6, 7.0 Hz, 1H), 3.34 (dd, J = 9.6, 6.9 Hz, 1H), 2.95 (t, J = 8.9 Hz, 1H), 2.68-2.43 (m, 1H), 1.87-1.48 (m, 12H), 1.49-1.29 (m, 2H), 1.42 (d, J = 6.3 Hz, 3H), 1.07 (dt, J = 12.6, 6.8 Hz, 3H), 0.97-0.81 (m, 1H), 0.59-0.48 (m, 2H), 0.25-0.16 (m, 2H) | — |
| F293 | — | — | HRMS-ESI (m/z) ([M]$^+$) calcd for C$_{21}$H$_{33}$NO$_4$, 363.2410; found, 363.2396 | $^1$H NMR (CDCl$_3$) δ 8.61 (br s, 3H), 7.03 (d, J = 8.3 Hz, 2H), 6.87-6.68 (m, 2H), 4.85 (td, J = 27.2, 23.8, 14.0 Hz, 1H), 3.96 (s, 1H), 3.78 (s, 3H), 3.56-3.47 (m, 1H), 3.31 (t, J = 7.6 Hz, 1H), 3.08 (t, J = 9.0 Hz, 1H), 3.03-2.95 (m, 1H), 2.76 (br s, 1H), 2.55-2.37 (br s, 1H), 2.23 (t, J = 12.5 Hz, 1H), 2.14-1.99 (m, 1H), 1.88 (dt, J = 13.1, 6.6 Hz, 1H), 1.67-1.34 (m, 6H), 0.96 (dd, J = 6.7, 5.2 Hz, 6H), 0.76 (s, 1H) | $^{13}$C NMR (CDCl$_3$) δ 170.15, 157.86, 132.41, 129.62, 113.87, 113.84, 83.42, 83.33, 80.77, 55.26, 46.21, 35.67, 29.25, 19.52, 19.47, 18.23, 18.15, 18.07 |
| F294 | — | — | HRMS-ESI (m/z) ([M]$^+$) calcd for C$_{20}$H$_{31}$NO$_4$, 349.2253; found, 349.2234 | $^1$H NMR (CDCl$_3$) δ 8.61 (s, 3H), 7.03 (d, J = 8.5 Hz, 2H), 6.88-6.66 (m, 2H), 4.93-4.75 (m, 1H), 3.96 (d, J = 8.1 Hz, 1H), 3.78 (s, 3H), 3.49 (dt, J = 8.7, 6.7 Hz, 1H), 3.09 (t, J = 9.1 Hz, 1H), 3.00 (d, J = 10.9 Hz, 1H), 2.44 (dd, J = 13.3, 6.6 Hz, 1H), 2.24 (t, J = 12.5 Hz, 1H), 1.77 (d, J = 23.7 Hz, 3H), 1.68-1.51 (m, 3H), 1.43 (t, J = 7.1 Hz, 5H), 0.97 (t, J = 7.4 Hz, 3H), 0.74 (d, J = 14.8 Hz, 1H) | $^{13}$C NMR (CDCl$_3$) δ 170.13, 157.86, 132.36, 129.63, 113.82, 83.68, 75.71, 67.09, 55.25, 52.16, 46.08, 35.78, 31.44, 26.23, 23.57, 18.16, 17.97, 10.73 |
| F295 | — | (Thin Film) 2956, 2876, 1746, 1536, 1231, 1207 | HRMS-ESI (m/z) ([M]$^+$) calcd for C$_{18}$H$_{29}$NO$_4$, 323.2097; found, 323.2107 | $^1$H NMR (CDCl$_3$) δ 8.63 (s, 3H), 7.29 (d, J = 1.7 Hz, 1H), 6.26 (dd, J = 3.1, 1.8 Hz, 1H), 5.99 (d, J = 3.0 Hz, 1H), 4.89-4.82 (m, 1H), 3.98 (s, 1H), 3.47 (t, J = 7.5 Hz, 1H), 3.28 (t, J = 7.4 Hz, 1H), 3.10 (td, J = 8.9, 4.7 Hz, 1H), 3.01-2.92 | $^{13}$C NMR (CDCl$_3$) δ 170.21, 154.29, 141.09, 110.13, 106.15, 83.19, 80.39, 76.34, 69.65, 52.33, 43.11, 31.32, 29.28, 29.19, 27.72, 19.47, 19.44, 18.08 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | (m, 1H), 2.53-2.37 (m, 2H), 2.05 (s, 1H), 1.88 (dp, J = 19.7, 7.9, 6.9 Hz, 2H), 1.60 (d, J = 18.9 Hz, 4H), 1.49-1.36 (m, 3H), 0.93 (d, J = 6.6 Hz, 6H) | |
| F296 | — | (Thin Film) 3392, 2943, 2871, 1736, 1455, 1187, 1153, 1063 | HRMS-ESI (m/z) ([M]$^+$) calcd for C$_{19}$H$_{33}$NO$_4$, 339.2410; found, 339.2409 | $^1$H NMR (CDCl$_3$) δ 8.70 (s, 3H), 5.01-4.92 (m, 1H), 4.86-4.74 (m, 1H), 4.05 (s, 1H), 3.76-3.66 (m, 1H), 2.63-2.49 (m, 1H), 1.81-0.83 (m, 26H) | — |
| F297 | — | (Thin Film) 3390, 2942, 2869, 1744, 1453, 1230, 1095, 729 | HRMS-ESI (m/z) ([M]$^+$) calcd for C$_{18}$H$_{33}$NO$_3$, 311.2460; found, 311.2466 | $^1$H NMR (CDCl$_3$) δ 8.71 (s, 1H), 4.92-4.78 (m, 1H), 3.69-3.57 (m, 1H), 3.47-3.37 (m, 1H), 2.95 (t, J = 8.9 Hz, 1H), 2.86-2.79 (m, 1H), 2.57-2.50 (m, 1H), 1.86-1.31 (m, 19H), 1.15-0.96 (m, 4H), 0.93 (t, J = 7.3 Hz, 3H) | — |
| F298 | — | — | HRMS-ESI (m/z) ([M]$^+$) calcd for C$_{19}$H$_{35}$NO$_3$, 325.2617; found, 325.2619 | $^1$H NMR (CDCl$_3$) δ 8.68 (s, 3H), 4.89-4.75 (m, 1H), 3.99 (s, 1H), 3.84-3.61 (m, 3H), 3.50-3.41 (m, 1H), 3.27-3.18 (m, 2H), 2.93 (t, J = 8.8 Hz, 1H), 2.85-2.79 (m, 1H), 2.52 (s, 1H), 1.91-1.71 (m, 3H), 1.65-1.47 (m, 5H), 1.15-0.85 (m, 14H) | $^{13}$C NMR (CDCl$_3$) δ 170.29, 128.37, 83.94, 80.52, 42.30, 37.10, 37.06, 36.60, 33.91, 31.65, 29.16, 25.09, 25.05, 19.48, 19.37, 18.43, 18.28, 18.11, 18.06 |
| F299 | — | — | ESIMS m/z 278.2 ([M + H]$^+$) | — | — |
| F300 | — | — | ESIMS m/z 292.2 ([M + H]$^+$) | — | — |
| F301 | — | — | ESIMS m/z 334.4 ([M + H]$^+$) | $^1$H NMR (CD$_3$OD) δ 7.31-7.22 (m, 2H), 7.21-7.13 (m, 3H), 3.98-3.83 (m, 1H), 3.77-3.70 (m, 1H), 3.66 (q, J = 5.5, 5.0 Hz, 1H), 3.61-3.53 (m, 1H), 3.41 (dd, J = 8.5, 6.4 Hz, 1H), 3.23 (t, J = 8.9 Hz, 1H), 3.10 (dd, J = 13.3, 3.4 Hz, 1H), 2.47-2.30 (m, 1H), 2.20 (qd, J = 8.4, 7.5, 5.0 Hz, 1H), 1.89 (dt, J = 13.2, 6.6 Hz, 1H), 1.84-1.74 (m, 1H), 1.64 (dp, J = 8.5, 3.2, 2.8 Hz, 2H), 1.48 (d, J = 6.4 Hz, 4H), 1.36-1.24 (m, 2H), 0.98 (dd, J = 6.7, 3.6 Hz, 6H), 0.95-0.79 (m, 2H) | $^{13}$C NMR (CD$_3$OD) δ 171.46, 141.99, 129.89, 129.46, 127.06, 84.74, 81.69, 77.66, 53.00, 47.35, 37.69, 32.11, 30.51, 28.03, 19.88, 19.83, 19.45, 18.49 |
| F302 | — | — | ESIMS m/z 348 ([M + H]$^+$) | $^1$H NMR (CDCl$_3$) δ 8.54 (s, 3H), 7.18-6.88 (m, 4H), 4.83 (s, 1H), 4.30-3.82 (m, 1H), 3.62-3.43 (m, 1H), 3.43-3.21 (m, 1H), 3.23-2.90 (m, 2H), 2.31 (s, 5H), 1.83 (d, J = 41.6 Hz, 2H), 1.68 -1.15 (m 7H), 0.96 (t, J = 5.9 Hz, 6H), 0.81-0.60 (m, 1H) | $^{13}$C NMR (CDCl$_3$) δ 170.32, 137.33, 135.36, 129.08, 128.67, 83.50, 80.81, 76.36, 52.63, 46.21, 36.20, 31.43, 29.28, 26.16, 21.04, 19.58, 19.52, 18.35, 18.22 |
| F303 | — | — | ESIMS m/z 290.2 ([M + H]$^+$) | $^1$H NMR (DMSO-d$_6$) δ 8.40 (s, 3H), 4.91-4.71 (m, 1H), 4.56 (d, J = 4.7 Hz, 1H), 4.43 (t, J = 6.0 Hz, 1H), 3.88 (dd, J = 10.4, 6.9 Hz, 1H), 3.42 (dd, J = 8.6, 6.6 Hz, 1H), 3.26 (dd, J = 8.6, 6.4 Hz, 1H), 3.09 (t, J = 8.6 Hz, 1H), 2.13 (dd, J = | $^{13}$C NMR (DMSO-d$_6$) δ 170.43, 83.07, 82.65, 81.46, 78.94, 75.34, 51.12, 30.33, 28.51, 27.71, 19.14, 19.11, 17.96, 17.75 |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 13.2, 6.5 Hz, 1H), 2.05-1.85 (m, 1H), 1.86-1.48 (m, 5H), 1.45-1.27 (m, 5H), 0.87 (d, J = 6.7 Hz, 6H) | |
| F304 | 210 (dec) | — | ESIMS m/z 346 ([M + H]$^+$) | $^1$H NMR (CD$_3$OD) δ 7.08 (s, 4H), 4.87 (s, 1H), 4.13-3.42 (m, 3H), 3.30 (d, J = 19.1 Hz, 1H), 3.08 (s, 1H), 2.29 (s, 5H), 1.57 (q, J = 58.8, 55.9 Hz, 8H), 1.13 (s, 1H), 0.85 (d, J = 11.7 Hz, 1H), 0.56 (s, 2H), 0.27 (s, 2H) | $^{13}$C NMR (CD$_3$OD) δ 171.19, 138.52, 136.24, 129.92, 129.76, 84.73, 79.80, 77.27, 53.39, 47.04, 37.36, 32.14, 27.85, 21.08, 19.65, 18.63, 11.98, 3.64, 3.63 |
| F305 | — | — | ESIMS m/z 384.9 ([M + H]$^+$) | — | — |
| F306 | — | — | ESIMS m/z 321.9 ([M + H]$^+$) | — | — |
| F307 | — | — | ESIMS m/z 318.5 ([M + H]$^+$) | — | — |
| F308 | 200-210 (dec) | — | ESIMS m/z 368 ([M + H]$^+$) | $^1$H NMR (CD$_3$OD) δ 7.44-6.80 (m, 9H), 5.14 (s, 1H), 4.46 (s, 1H), 3.63 (s, 4H), 2.86 (s, 1H), 2.60-1.14 (m, 12H), 0.96 (s, 1H) | $^{13}$C NMR (CD$_3$OD) d 171.05, 160.65, 137.89, 136.19, 130.75, 129.87, 129.75, 122.14, 117.03, 81.89, 76.55, 68.05, 46.67, 37.46, 32.38, 27.71, 21.05, 20.12, 18.85 |
| F309 | — | — | ESIMS (m/z) 302.3 ([M + H]$^+$) | — | — |
| F310 | — | — | ESIMS m/z 272.2 ([M + H]$^+$) | — | — |
| F311 | 233-237 | — | ESIMS m/z 404 ([M + H]$^+$) | 1H NMR (CD$_3$OD) δ 7.44-7.25 (m, 5H), 7.24-7.15 (m, 1H), 6.92-6.82 (m, 2H), 4.96 (dq, J = 9.4, 6.5 Hz, 1H), 4.81 (d, J = 11.1 Hz, 1H), 4.66 (d, J = 11.2 Hz, 1H), 3.96 (dd, J = 10.9, 7.1 Hz, 1H), 3.49 (t, J = 8.9 Hz, 1H), 3.04 (dd, J = 13.7, 3.5 Hz, 1H), 2.51 (dd, J = 13.6, 11.4 Hz, 1H), 2.34-2.20 (m, 1H), 1.88 (ddq, J = 12.1, 8.0, 3.9 Hz, 1H), 1.74-1.60 (m, 2H), 1.53 (d, J = 6.4 Hz, 3H), 1.50-1.40 (m, 1H), 1.35 (dtd, J = 13.3, 10.4, 3.2 Hz, 1H), 0.92 (ddt, J = 14.7, 6.7, 3.4 Hz, 1H) | $^{13}$C NMR (101 MHz, CD$_3$OD) δ 171.39, 162.92 (d, J = 245.6, 12.2 Hz), d162.52 (dd, J = 246.5, 12.1 Hz), 139.36, 133.26 (dd, J = 9.5, 6.7 Hz), 129.44, 128.93, 128.88, 124.57 (dd, J = 15.9, 3.9 Hz), 112.10 (dd, J = 20.9, 3.9 Hz), 105.04-103.87 (m), 84.75, 77.35, 76.41, 52.98, 45.56, 32.02, 30.42, 28.52, 19.46, 18.50 $^{19}$F NMR (CD$_3$OD) δ 61.08 (d, J = 6.4 Hz), 60.97 (d, J = 6.5 Hz) |
| F312 | — | — | ESIMS (m/z) 370.1 ([M + H]$^+$) | — | — |
| F313 | — | — | ESIMS m/z 292.2 [(M + H)$^+$] | — | — |
| F314 | — | — | ESIMS m/z 328.5 ([M + H]$^+$) | — | — |
| F315 | — | — | ESIMS m/z 340.3 ([M + H]$^+$) | — | — |
| F316 | — | — | ESIMS m/z 402 ([M + H]$^+$) | $^1$H NMR (CDCl$_3$) δ 7.31-7.23 (m, 1H), 7.21-7.12 (m, 2H), 7.08 (d, J = 7.7 Hz, 2H), 6.99 (d, J = 7.8 Hz, 2H), 4.98-4.73 (m, 1H), 3.84-3.72 (m, 1H), 3.57 (q, J = 6.9 Hz, 1H), 3.11 (dt, J = 8.5, 5.5 Hz, 1H), 2.92 (d, J = 13.4 Hz, 1H), 2.75 (s, 1H), 2.58-2.39 (m, 1H), | $^{19}$F NMR (CDCl$_3$) δ −66.34 (d, J = 3.6 Hz) |

TABLE 2-continued

Analytical Data

| Cmpd. No. | MP (° C.) | IR (cm$^{-1}$) | MASS | $^1$H NMR | $^{13}$C or $^{19}$F NMR |
|---|---|---|---|---|---|
| | | | | 2.38-2.09 (m, 5H), 1.83 (tt, J = 15.7, 7.5 Hz, 3H), 1.72-1.31 (m, 5H), 0.87-0.64 (m, 1H) | |
| F317 | 190-195 (dec) | — | ESIMS m/z 432 ([M + H]$^+$) | $^1$H NMR (CDCl$_3$) δ 7.34-7.14 (m, 5H), 7.08 (q, J = 7.9 Hz, 1H), 6.87-6.71 (m, 2H), 4.98-4.77 (m, 1H), 3.83-3.71 (m, 1H), 3.61-3.48 (m, 1H), 3.21-3.07 (m, 1H), 3.02-2.88 (m, 1H), 2.73 (dp, J = 12.2, 3.9 Hz, 3H), 2.57-2.35 (m, 2H), 2.08-1.30 (m, 10H), 0.83 (p, J = 11.1, 8.5 Hz, 1H) | $^{19}$F NMR (CDCl$_3$) δ −113.07 (dd, J = 44.4, 6.6 Hz), −113.76 (dd, J = 21.5, 6.6 Hz) |
| F318 | — | — | ESIMS m/z 362.3 ([M + H]$^+$) | — | — |
| F319 | — | — | ESIMS m/z 214.2 ([M + H]$^+$) | — | — |
| F320 | — | — | ESIMS m/z 290.2 ([M + H]$^+$) | — | — |
| F321 | 67-73 | — | ESIMS m/z 370 ([M + H]$^+$) | $^1$H NMR (CD$_3$OD) δ 7.19-7.10 (m, 1H), 6.98-6.81 (m, 2H), 3.94 (dd, J = 10.8, 7.3 Hz, 1H), 3.65 (s, 3H), 3.57 (ddd, J = 8.5, 6.2, 2.6 Hz, 1H), 3.37 (dd, J = 8.5, 6.4 Hz, 1H), 3.24 (td, J = 8.9, 2.7 Hz, 1H), 3.16-2.99 (m, 1H), 2.87-2.68 (m, 1H), 2.51 (td, J = 14.2, 13.8, 11.6 Hz, 1H), 2.43-2.21 (m, 1H), 1.95-1.25 (m, 9H), 1.05 (dd, J = 5.4, 3.3 Hz, 1H), 0.96 (d, J = 6.7 Hz, 3H), 0.96 (d, J = 6.7 Hz, 3H) | $^{13}$C NMR (CD$_3$OD) δ 171.35, 162.87 (dd, J = 245.7, 12.4 Hz), 163.88-161.09 (m), 133.43-133.07 (m), 124.58 (dd, J = 16.1, 4.1 Hz), 112.10 (dd, J = 20.8, 3.9 Hz), 104.41 (t, J = 26.1 Hz), 84.49, 81.38, 77.43, 52.92, 47.12, 45.69, 32.01, 30.33, 19.84, 19.81, 19.38, 18.54, 18.42 $^{19}$F NMR (CD$_3$OD) δ 61.22 (d, J = 6.5 Hz), 61.11 (d, J = 6.6 Hz) |
| F322 | 218-222 dec. | — | ESIMS m/z 480 ([M + H]$^+$) | $^1$H NMR (CD$_3$OD) δ 7.79 (dd, J = 1.6, 0.6 Hz, 1H), 7.28-7.22 (m, 1H), 7.19 (q, J = 8.3 Hz, 1H), 6.79 (t, J = 8.9 Hz, 2H), 6.66-6.60 (m, 1H), 5.22-5.11 (m, 2H), 4.04 (dd, J = 10.9, 7.2 Hz, 1H), 2.72 (dd, J = 13.9, 5.1 Hz, 1H), 2.56 (dd, J = 13.9, 9.6 Hz, 1H), 2.35 (dt, J = 13.3, 6.9 Hz, 1H), 2.18 (dq, J = 9.0, 4.5 Hz, 1H), 1.90-1.60 (m, 3H), 1.44 (q, J = 12.3, 11.8 Hz, 1H), 1.31 (d, J = 5.7 Hz, 3H), 1.12-0.99 (m, 1H) | $^{13}$C NMR (CD$_3$OD) δ 171.31, 163.00 (dd, J = 245.7, 11.9 Hz), 162.37 (dd, J = 246.5, 11.9 Hz), 159.59, 148.98, 144.99, 133.20 (dd, J = 9.6, 6.4 Hz), 123.73 (dd, J = 15.7, 3.8 Hz), 120.22, 113.23, 112.04 (dd, J = 21.2, 3.7 Hz), 104.43 (t, J = 26.1 Hz), 77.44, 75.47, 52.89, 43.74, 31.98, 31.03, 28.52, 19.19, 17.75 $^{19}$F NMR (CD$_3$OD) δ 61.51 (d, J = 6.8 Hz), 60.95 (d, J = 6.8 Hz) |

*$^1$H NMR were run at 400 MHz unless noted otherwise
*$^{13}$C NMR were run at 101 MHz unless noted otherwise
*$^{19}$F NMR were run at 376 MHz unless noted otherwise

TABLE 3

Biological Testing Rating Scale
Rating Table for Fungal Pathogens

| % Control | Rating |
|---|---|
| 80-100 | A |
| More than 0-Less than 80 | B |
| Not Tested | C |
| No activity noticed in this bioassay | D |

TABLE 4

Biological Activity - Disease Control in High and Low Volume Applications

| | PUCCRT* | | | | SEPTTR* | | | |
|---|---|---|---|---|---|---|---|---|
| | 1 DP* | | 3 DC* | | 1 DP* | | 3 DC* | |
| | Rate | | | | Rate | | | |
| Cmpd. No. | 121.5 g/H* | 100 ppm* | 121.5 g/H* | 100 ppm* | 121.5 g/H* | 100 ppm* | 121.5 g/H* | 100 ppm* |
| F1 | C | A | C | B | C | A | C | A |
| F2 | C | A | C | B | C | A | C | A |
| F3 | C | A | C | A | C | A | C | A |
| F4 | C | A | C | A | C | A | C | A |
| F5 | C | A | C | B | C | A | C | A |
| F6 | C | A | C | A | C | A | C | A |
| F7 | C | A | C | B | C | A | C | A |
| F8 | C | A | C | A | C | A | C | A |
| F9 | C | A | C | A | C | A | C | A |
| F10 | A | A | B | A | A | A | A | A |
| F11 | C | A | C | B | C | A | C | A |
| F12 | C | B | C | A | C | A | C | A |
| F13 | C | D | C | B | C | A | C | A |
| F14 | C | A | C | A | C | A | C | A |
| F15 | C | A | C | A | C | A | C | A |
| F16 | C | A | C | B | C | A | C | B |
| F17 | C | A | C | B | C | A | C | A |
| F18 | C | A | C | B | C | A | C | A |
| F19 | C | A | C | A | C | A | C | A |
| F20 | C | A | C | B | C | A | C | A |
| F21 | C | A | C | A | C | B | C | B |
| F22 | C | A | C | A | C | A | C | A |
| F23 | C | A | C | A | C | A | C | A |
| F24 | C | A | C | A | C | A | C | A |
| F25 | C | A | C | D | C | A | C | B |
| F26 | C | A | C | B | C | A | C | A |
| F27 | C | A | C | A | C | A | C | A |
| F28 | C | A | C | D | C | A | C | B |
| F29 | C | C | C | C | C | C | C | C |
| F30 | C | A | C | A | C | A | C | A |
| F31 | C | A | C | A | C | A | C | A |
| F32 | C | A | C | B | C | A | C | A |
| F33 | C | A | C | A | C | A | C | A |
| F34 | C | A | C | A | C | A | C | A |
| F35 | C | B | C | D | C | A | C | D |
| F36 | C | A | C | D | C | A | C | D |
| F37 | C | B | C | B | C | A | C | D |
| F38 | C | A | C | A | C | A | C | D |
| F39 | C | A | C | A | C | A | C | B |
| F40 | C | A | C | B | C | B | C | B |
| F41 | C | A | C | B | C | A | C | A |
| F42 | C | A | C | A | C | A | C | A |
| F43 | C | A | C | A | C | A | C | A |
| F44 | C | A | C | A | C | A | C | A |
| F45 | C | A | C | A | C | A | C | A |
| F46 | C | A | C | A | C | B | C | A |
| F47 | C | A | C | A | C | A | C | A |
| F48 | C | A | C | A | C | A | C | A |
| F49 | C | A | C | B | C | A | C | A |
| F50 | C | A | C | A | C | A | C | A |
| F51 | C | A | C | B | C | A | C | B |
| F52 | C | A | C | A | C | A | C | A |
| F53 | C | A | C | A | C | A | C | B |
| F54 | C | A | C | A | C | B | C | A |
| F55 | C | A | C | D | C | A | C | B |
| F56 | C | A | C | B | C | A | C | B |
| F57 | C | A | C | A | C | A | C | B |
| F58 | C | A | C | A | C | D | C | D |
| F59 | A | A | D | A | A | A | B | A |
| F60 | A | A | D | A | A | A | D | A |
| F61 | C | A | C | B | C | A | C | D |
| F62 | A | A | B | A | A | A | A | A |
| F63 | A | A | A | A | A | A | A | A |
| F64 | A | A | A | A | A | A | A | A |
| F65 | A | A | B | A | A | A | A | A |
| F66 | B | A | B | A | A | A | B | A |
| F67 | A | A | A | A | A | A | A | A |
| F68 | A | A | B | A | A | A | A | A |
| F69 | A | A | A | A | A | A | A | A |
| F70 | A | A | A | A | A | A | A | A |
| F71 | A | A | B | A | A | A | A | A |
| F72 | A | A | B | A | A | A | A | A |
| F73 | A | A | A | A | A | A | A | A |
| F74 | A | A | B | A | A | A | A | A |
| F75 | A | A | B | A | A | A | A | A |
| F76 | A | C | A | C | A | C | A | C |
| F77 | A | A | A | A | A | A | A | A |
| F78 | A | A | A | A | A | A | A | A |
| F79 | C | A | C | A | C | A | C | A |
| F80 | A | A | A | A | A | A | A | A |
| F81 | A | A | A | A | A | A | A | A |
| F82 | A | A | A | A | A | A | A | A |
| F83 | A | A | A | A | B | A | B | D |
| F84 | A | A | A | A | B | A | D | A |
| F85 | A | C | A | C | B | C | D | C |
| F86 | A | C | A | C | A | C | A | C |
| F87 | A | C | A | C | A | C | A | C |
| F88 | A | C | A | C | A | C | A | C |
| F89 | A | A | B | A | A | A | A | A |
| F90 | A | A | A | A | A | A | A | A |
| F91 | A | A | A | A | A | A | A | A |
| F92 | A | A | A | A | A | A | A | A |
| F93 | A | A | B | A | A | A | A | A |
| F94 | C | A | C | A | C | A | C | A |
| F95 | A | A | B | A | A | A | B | A |
| F96 | A | A | B | A | A | A | A | A |
| F97 | A | A | A | A | A | A | A | A |
| F98 | A | A | A | A | A | A | A | A |
| F99 | A | A | B | A | A | A | A | A |
| F100 | A | A | B | A | A | A | A | A |
| F101 | A | A | A | A | A | A | A | A |
| F102 | A | A | B | A | A | A | A | A |
| F103 | A | A | A | A | A | A | A | A |
| F104 | A | A | B | A | A | A | A | A |
| F105 | A | D | A | A | A | A | A | A |
| F106 | A | A | A | A | A | A | A | A |
| F107 | A | A | A | A | A | A | A | A |
| F108 | A | A | B | A | A | A | A | A |
| F109 | A | A | A | A | A | A | A | A |
| F110 | A | A | A | A | A | A | A | A |
| F111 | A | C | A | C | A | C | A | C |
| F112 | A | C | A | C | A | C | A | C |
| F113 | A | A | A | A | A | A | A | A |
| F114 | A | A | B | A | A | A | A | A |
| F115 | A | A | B | A | A | A | A | A |
| F116 | A | A | A | A | A | A | A | A |
| F117 | A | A | A | A | A | A | A | A |
| F118 | A | A | A | A | A | A | A | A |
| F119 | A | A | A | A | A | A | A | A |
| F120 | A | C | D | C | A | C | B | C |
| F121 | A | A | A | A | A | A | A | A |

TABLE 4-continued

Biological Activity - Disease Control in High and Low Volume Applications

| | PUCCRT* | | | | SEPTTR* | | | |
|---|---|---|---|---|---|---|---|---|
| | 1 DP* | | 3 DC* | | 1 DP* | | 3 DC* | |
| | Rate | | | | Rate | | | |
| Cmpd. No. | 121.5 g/H* | 100 ppm* | 121.5 g/H* | 100 ppm* | 121.5 g/H* | 100 ppm* | 121.5 g/H* | 100 ppm* |
| F122 | A | A | A | A | A | A | A | A |
| F123 | A | A | B | A | A | A | A | A |
| F124 | A | A | A | A | A | A | A | A |
| F125 | A | A | A | A | A | A | A | A |
| F126 | A | A | B | A | A | A | A | A |
| F127 | C | A | C | A | C | A | C | A |
| F128 | A | A | A | A | A | A | A | A |
| F129 | A | A | B | A | A | A | A | A |
| F130 | A | A | A | A | A | A | A | B |
| F131 | A | A | A | A | B | A | A | A |
| F132 | A | A | A | A | A | A | A | A |
| F133 | A | A | A | A | A | A | A | A |
| F134 | C | A | C | A | C | A | C | A |
| F135 | C | A | C | A | C | A | C | A |
| F136 | A | A | A | A | A | A | A | A |
| F137 | A | A | B | A | A | A | A | A |
| F138 | A | A | A | A | A | A | A | A |
| F139 | A | A | B | A | A | A | A | A |
| F140 | A | A | A | A | B | A | B | B |
| F141 | A | A | D | B | A | A | B | A |
| F142 | A | A | A | A | A | A | B | A |
| F143 | A | A | A | A | B | B | D | B |
| F144 | A | C | D | C | A | C | B | C |
| F145 | A | C | A | C | A | C | A | C |
| F146 | A | C | A | C | A | C | A | C |
| F147 | A | A | B | A | A | A | A | A |
| F148 | A | A | A | A | A | A | A | A |
| F149 | A | A | A | A | A | A | A | A |
| F150 | A | A | A | A | A | A | A | A |
| F151 | A | A | A | A | A | A | A | A |
| F152 | A | A | A | A | A | A | A | A |
| F153 | A | A | B | A | A | A | A | A |
| F154 | A | A | A | A | A | A | A | A |
| F155 | A | A | A | A | A | A | A | A |
| F156 | A | A | A | A | B | B | B | B |
| F157 | A | C | B | C | A | C | D | C |
| F158 | A | A | B | A | A | A | A | A |
| F159 | A | A | B | A | A | A | A | A |
| F160 | A | A | A | A | A | A | A | A |
| F161 | A | A | A | A | A | A | A | A |
| F162 | A | A | B | A | A | A | A | A |
| F163 | B | A | B | B | A | A | B | A |
| F164 | A | A | B | A | A | A | A | A |
| F165 | A | A | B | A | A | A | A | A |
| F166 | A | A | A | A | A | A | A | A |
| F167 | A | A | A | A | A | A | A | A |
| F168 | A | A | A | A | A | A | A | A |
| F169 | A | A | A | A | A | A | A | B |
| F170 | A | A | B | A | A | A | A | A |
| F171 | A | A | B | A | A | A | A | A |
| F172 | A | A | A | A | A | A | A | A |
| F173 | A | A | A | A | A | A | A | A |
| F174 | A | A | A | A | A | A | A | A |
| F175 | A | A | B | A | A | A | B | A |
| F176 | A | A | B | A | A | A | A | A |
| F177 | A | A | A | A | A | A | A | A |
| F178 | A | A | B | A | A | A | A | A |
| F179 | A | A | A | A | A | A | A | A |
| F180 | A | A | B | A | A | A | A | A |
| F181 | A | A | A | A | A | A | A | A |
| F182 | A | A | B | A | A | A | A | A |
| F183 | A | A | A | A | A | A | A | A |
| F184 | C | A | C | A | C | A | C | A |
| F185 | C | A | C | A | C | A | C | A |
| F186 | C | A | C | A | C | A | C | A |
| F187 | A | A | A | A | A | A | A | A |
| F188 | A | A | A | A | A | A | A | A |
| F189 | A | A | A | A | A | A | A | A |
| F190 | A | A | B | D | A | A | A | A |
| F191 | A | A | A | A | B | A | B | D |
| F192 | A | A | A | A | D | D | D | D |
| F193 | A | C | D | C | A | C | B | C |
| F194 | A | A | B | A | A | A | A | A |
| F195 | A | A | B | A | A | A | A | A |
| F196 | A | A | A | A | B | A | B | B |
| F197 | A | C | A | C | A | C | A | C |
| F198 | A | C | A | C | A | C | A | C |

*PUCCRT—Wheat Brown Rust (*Puccinia triticina*)
*SEPTTR—Wheat Leaf Blotch (*Septoria tritici*)
*1 DP—1 Day Protectant
*3 DC—3 Day Curative

TABLE 5

Biological Activity - Disease Control at 100 ppm

| Compound Number | ALTESO* | CERCBE* | COLLLA* 1 DP* | ERYSCI* | ERYSGH* |
|---|---|---|---|---|---|
| F64 | A | A | A | A | A |
| F67 | A | A | A | B | A |
| F70 | B | A | A | A | A |
| F78 | B | A | A | B | B |
| F80 | B | A | A | D | B |
| F81 | B | A | A | B | B |
| F82 | D | A | A | D | B |
| F86 | B | A | A | D | B |
| F87 | A | A | A | B | A |
| F88 | A | A | A | A | A |
| F92 | A | A | A | A | B |
| F96 | A | A | A | A | B |
| F98 | A | A | A | A | A |
| F101 | A | A | A | A | A |
| F102 | C | C | A | C | B |
| F106 | A | A | A | A | A |
| F107 | A | A | A | A | A |
| F108 | D | A | A | D | B |
| F109 | A | A | A | A | A |
| F110 | C | C | C | C | A |
| F113 | A | A | C | A | A |
| F114 | D | A | A | D | C |
| F117 | A | A | A | A | A |
| F118 | B | A | A | B | C |
| F119 | B | A | A | A | C |
| F126 | B | A | A | A | C |
| F128 | A | A | A | B | B |
| F130 | B | B | A | B | B |
| F138 | D | A | A | D | B |
| F144 | A | B | A | B | D |
| F145 | A | A | A | A | A |
| F146 | A | A | A | D | B |
| F151 | A | A | A | A | A |
| F152 | A | A | A | A | A |
| F157 | A | A | A | D | D |
| F161 | A | A | A | A | A |
| F164 | A | A | A | A | A |
| F166 | D | D | C | D | C |

TABLE 5-continued

Biological Activity - Disease Control at 100 ppm

| Compound. Number | ALTESO* | CERCBE* | COLLLA* 1 DP* | ERYSCI* | ERYSGH* |
|---|---|---|---|---|---|
| F167 | A | A | A | A | A |
| F168 | D | D | A | D | A |
| F172 | A | A | A | A | A |
| F173 | A | A | A | A | A |
| F174 | A | A | A | A | A |
| F175 | A | A | C | B | A |
| F181 | A | B | A | B | B |
| F183 | B | B | A | B | B |
| F193 | A | A | A | D | B |
| 198 | A | A | A | A | A |

*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*ERYSCI—Powdery Mildew of Cucumber (*Erysiphe cichoracearum*)
*ERYSGH—Barley Powdery Mildew (*Blumeria graminis* f.sp. *hordei*; Synonym: *Erysiphe graminis* f.sp. *hordei*)
1 DP—1 Day Protectant

TABLE 6

Biological Activity - Disease Control at 100 ppm

| Compound. Number | ERYSGT* | LEPTNO* | PYRIOR* | RHYNSE* 1 DP* | UNCINE* | VENTIN* |
|---|---|---|---|---|---|---|
| F64 | C | A | A | A | A | B |
| F67 | C | A | A | A | B | B |
| F70 | C | A | A | A | A | B |
| F78 | C | A | A | A | B | B |
| F80 | C | C | A | D | B | B |
| F81 | C | C | A | A | A | B |
| F82 | C | C | A | B | B | B |
| F86 | C | A | A | A | A | B |
| F87 | C | A | A | A | A | C |
| F88 | C | A | A | A | A | C |
| F92 | C | A | A | A | A | A |
| F96 | C | A | A | A | A | B |
| F98 | C | A | A | A | A | B |
| F101 | C | C | A | A | A | D |
| F102 | C | C | C | C | B | C |
| F106 | A | A | A | A | A | B |
| F107 | C | C | A | A | B | C |
| F108 | C | A | A | A | A | B |
| F109 | C | A | A | A | A | A |
| F110 | C | A | A | A | A | B |
| F113 | C | C | A | A | B | C |
| F114 | C | C | A | A | C | C |
| F117 | C | A | A | A | A | A |
| F118 | C | C | A | A | C | C |
| F119 | C | C | A | A | C | C |
| F126 | C | C | A | A | C | C |
| F128 | C | A | A | B | A | B |
| F130 | C | A | A | A | B | B |
| F138 | C | C | A | B | B | B |
| F144 | C | A | C | A | B | A |
| F145 | C | A | C | A | A | A |
| F146 | C | A | A | A | A | A |
| F151 | A | A | A | C | C | B |
| F152 | C | C | A | A | B | C |
| F157 | C | A | C | A | A | B |
| F161 | C | A | A | A | A | A |
| F164 | C | A | A | A | A | A |
| F166 | C | C | D | D | C | D |
| F167 | C | C | A | A | A | A |
| F168 | C | C | D | D | A | D |
| F172 | C | A | A | A | B | B |
| F173 | C | C | A | A | B | C |
| F174 | C | A | A | A | A | A |
| F175 | C | C | A | A | B | C |

TABLE 6-continued

Biological Activity - Disease Control at 100 ppm

| Compound. Number | ERYSGT* | LEPTNO* | PYRIOR* | RHYNSE* 1 DP* | UNCINE* | VENTIN* |
|---|---|---|---|---|---|---|
| F181 | C | A | A | B | B | D |
| F183 | C | A | A | A | A | B |
| F193 | C | A | A | A | B | A |
| F198 | C | A | A | A | A | C |

*ERYSGT—Wheat Powdery Mildew (*Blumeria graminis* f.sp. *tritici*; Synonym: *Erysiphe graminis* f.sp. *tritici*)
*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*VENTIN—Apple Scab (*Venturia inaequalis*)
*1 DP—1 Day Protectant

TABLE 7

Biological Activity - Disease Control at 25 ppm

| Compound Number | PHAKPA* 1DP* | PHAKPA* 3DC* |
|---|---|---|
| F63 | A | A |
| F64 | A | A |
| F67 | A | B |
| F70 | A | B |
| F76 | A | A |
| F78 | A | A |
| F80 | A | B |
| F81 | A | A |
| F82 | A | A |
| F86 | A | B |
| F91 | A | A |
| F92 | A | A |
| F93 | A | B |
| F96 | A | B |
| F98 | A | A |
| F101 | A | B |
| F106 | A | B |
| F107 | A | A |
| F109 | A | B |
| F113 | A | B |
| F117 | A | A |
| F118 | A | B |
| F119 | A | B |
| F121 | A | B |
| F124 | A | A |
| F128 | A | A |
| F130 | A | A |
| F132 | A | A |
| F138 | A | A |
| F144 | B | D |
| F145 | A | B |
| F146 | A | A |
| F149 | A | B |
| F151 | A | A |
| F152 | A | A |
| F155 | A | A |
| F157 | B | D |
| F160 | A | A |
| F161 | A | A |
| F164 | A | B |
| F166 | A | B |
| F167 | A | B |
| F168 | A | B |
| F172 | A | B |
| F173 | A | A |
| F174 | A | B |
| F181 | A | A |

TABLE 7-continued

Biological Activity - Disease Control at 25 ppm

| Compound Number | PHAKPA* 1DP* | PHAKPA* 3DC* |
|---|---|---|
| F183 | A | A |
| F187 | A | A |
| F189 | A | A |
| 193 | B | B |

*PHAKPA—Asian Soybean Rust (*Phakopsora pachyrhizi*)
*1DP—1 Day Protectant
*3DC—3 Day Curative

What is claimed is:

1. A method for the control and/or the prevention of fungal growth comprising the steps of:
   applying a fungicidally effective amount of at least one compound of Formula I

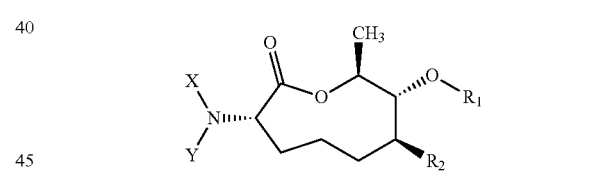

wherein:
X is H, C(O)R$_3$, or CH$_2$OR$_3$;
Y is H, C(O)R$_3$, or Q;
Q is

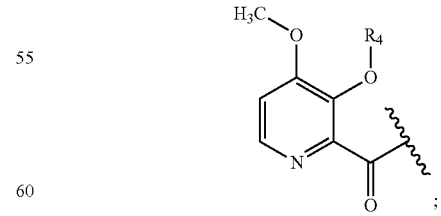

R$_1$ is chosen from H, alkyl, alkenyl, aryl, —Si(R$_5$)$_3$, or —C(O)R$_6$, each optionally substituted with 0, 1 or multiple R$_6$;
R$_2$ is chosen from CH$_2$R$_8$, aryl, alkyl, or alkenyl, each optionally substituted with 0, 1, or multiple R$_6$;

$R_3$ is chosen from alkyl, alkoxy, benzyl, or benzyloxy, each optionally substituted with 0, 1, or multiple $R_5$;

$R_4$ is chosen from H, —C(O)$R_7$ or —$CH_2OC(O)R_7$;

$R_5$ is chosen from alkyl, halo, or alkoxy;
$R_6$ is chosen from alkyl, alkenyl, halo, haloalkyl, alkoxy, aryl, heteroaryl, heterocyclyl, thioalkyl, or —C(O)$R_5$;
$R_7$ is chosen from alkyl or alkoxy, each optionally substituted with 0, 1, or multiple $R_6$;
$R_8$ is chosen from H, alkyl, alkenyl, aryl, thioalkyl, or heteroaryl, each optionally substituted with 0, 1, or multiple $R_6$;
to one or more selected from the group consisting of:
a plant, an area adjacent to a plant, soil adapted to support growth of a plant, and a seed adapted to produce a plant.

2. The method according to claim 1, wherein X and Y are independently chosen from H, C(O)$R_3$, or $CH_2OR_3$.

3. The method according to claim 2, wherein $R_1$ is chosen from alkyl, alkenyl, aryl, —Si$(R_5)_3$, or —C(O)$R_6$, each optionally substituted with 0, 1 or multiple $R_6$.

4. The method according to claim 3, wherein $R_2$ is chosen from $CH_2R_8$, aryl, or alkyl, each optionally substituted with 0, 1, or multiple $R_6$.

5. The method according to claim 4, wherein $R_8$ is chosen from alkyl, alkenyl, aryl, or heteroaryl, each optionally substituted with 0, 1, or multiple $R_6$.

6. The method according to claim 1, wherein X is H and Y is Q.

7. The method according to claim 6, wherein $R_1$ is chosen from H, alkyl, alkenyl, aryl, —Si$(R_5)_3$, or —C(O)$R_6$, each optionally substituted with 0, 1 or multiple $R_6$.

8. The method according to claim 7, wherein $R_2$ is chosen from $CH_2R_8$, aryl, alkyl, or alkenyl, each optionally substituted with 0, 1, or multiple $R_6$.

9. The method according to claim 8, wherein $R_8$ is chosen from H, alkyl, alkenyl, aryl, or heteroaryl, each optionally substituted with 0, 1, or multiple $R_6$.

10. The method according to claim 9, wherein $R_4$ is H, —C(O)$R_7$ or —$CH_2OC(O)R_7$.

11. The method according to claim 10, wherein $R_4$ is chosen from —C(O)$R_7$ or —$CH_2OC(O)R_7$.

12. The method according to claim 11, wherein $R_7$ is chosen from alkyl or alkoxy, each optionally substituted with 0, 1, or multiple $R_6$.

13. The method according to claim 1 wherein:

at least one compound of said Formula I is applied in combination with a phytologically acceptable carrier material.

14. The method according to claim 13 wherein:

the compound of Formula I is admixed with a phytologically acceptable carrier material.

15. The method according to claim 14 wherein:

the compound of Formula I is applied in combination with at least one agriculturally active ingredient selected from the group consisting of: fungicides, insecticides, nematocides, miticides, arthropodicides, bactericides and combinations thereof.

16. The method according to claim 15 wherein:

the compound of Formula I is admixed with at least one agriculturally active ingredient selected from the group consisting of: fungicides, insecticides, nematocides, miticides, arthropodicides, bactericides and combinations thereof.

17. The method according to claim 1, wherein the compound of Formula I is suitable for the control of at least one fungal pathogen selected from the group consisting of: *Mycosphaerella graminicola*; anamorph: *Septoria tritici, Puccinia triticina, Puccinia striiformis, Venturia inaequalis, Ustilago maydis, Uncinula necator, Rhynchosporium secalis, Magnaporthe grisea, Phakopsora pachyrhizi, Leptosphaeria nodorum, Blumeria graminis f.* sp. *tritici, Blumeria graminis f.* sp. *hordei, Erysiphe cichoracearum, Glomerella lagenarium, Cercospora beticola, Alternaria solani*, and *Pyrenophora teres.*

18. The method according to claim 1, wherein the compound of Formula I is suitable for the control of a fungal pathogen comprising *Septoria tritici, Puccinia triticina, Phakopsora pachyrhizi.*

19. The method according to claim 16, wherein the compound of Formula I is suitable for the control of at least one fungal pathogen selected from the group consisting of: *Mycosphaerella graminicola*; anamorph: *Septoria tritici, Puccinia triticina, Puccinia striiformis, Venturia inaequalis, Ustilago maydis, Uncinula necator, Rhynchosporium secalis, Magnaporthe grisea, Phakopsora pachyrhizi, Leptosphaeria nodorum, Blumeria graminis f.* sp. *tritici, Blumeria graminis f.* sp. *hordei, Erysiphe cichoracearum, Glomerella lagenarium, Cercospora beticola, Alternaria solani*, and *Pyrenophora teres.*

20. The method according to claim 16, wherein the compound of Formula I is suitable for the control of a fungal pathogen comprising *Septoria tritici, Puccinia triticina*, and *Phakopsora pachyrhizi.*

* * * * *